US007314874B2

(12) United States Patent
Zhu et al.

(10) Patent No.: US 7,314,874 B2
(45) Date of Patent: Jan. 1, 2008

(54) BENZAMIDES AND RELATED INHIBITORS OF FACTOR XA

(75) Inventors: Bing-Yan Zhu, Palo Alto, CA (US); Penglie Zhang, Foster City, CA (US); Wenrong Huang, Cupertino, CA (US); Robert M. Scarborough, deceased, late of Half Moon Bay, CA (US)

(73) Assignee: Millennium Pharmaceuticals, Inc., Cambrdige, MA (US)

( * ) Notice: Subject to any disclaimer, the term of this patent is extended or adjusted under 35 U.S.C. 154(b) by 0 days.

(21) Appl. No.: 10/942,733

(22) Filed: Sep. 15, 2004

(65) Prior Publication Data
US 2005/0261346 A1    Nov. 24, 2005

Related U.S. Application Data

(63) Continuation of application No. 10/687,334, filed on Oct. 15, 2003, now Pat. No. 6,835,739, which is a continuation of application No. 10/126,976, filed on Apr. 22, 2002, now abandoned, which is a continuation of application No. 09/794,225, filed on Feb. 28, 2001, now Pat. No. 6,376,515, which is a continuation-in-part of application No. 09/663,420, filed on Sep. 15, 2000, now Pat. No. 6,844,367.

(60) Provisional application No. 60/185,746, filed on Feb. 29, 2000.

(51) Int. Cl.
C07D 401/02    (2006.01)
A61K 31/44     (2006.01)

(52) U.S. Cl. .............................. 514/235.5; 514/252.13; 514/318; 514/341; 514/352; 514/617; 544/124; 544/360; 546/193; 546/272.9; 546/309; 564/156

(58) Field of Classification Search .............. 546/304, 546/193, 309, 272.9; 514/352, 235.5, 252.13, 514/318, 617, 341; 544/124, 360; 564/156
See application file for complete search history.

(56) References Cited

U.S. PATENT DOCUMENTS

| 2,095,619 | A |   | 10/1937 | Stoesser |         |
|-----------|---|---|---------|----------|---------|
| 4,514,416 | A |   | 4/1985  | Fujii et al. | 549/442 |
| 4,912,001 | A |   | 3/1990  | Kouno et al. | 430/71 |
| 4,971,957 | A |   | 11/1990 | Tsutsumi et al. | 514/79 |
| 5,569,768 | A |   | 10/1996 | Boyd et al. | 548/253 |
| 5,576,343 | A |   | 11/1996 | Nagahara et al. | 514/422 |
| 5,872,115 | A |   | 2/1999  | Binet et al. | 514/211 |
| 6,140,351 | A |   | 10/2000 | Arnaiz et al. | 514/336 |
| 6,376,515 | B2 | * | 4/2002 | Zhu et al. | 514/318 |

FOREIGN PATENT DOCUMENTS

| CH | 520657 | * | 3/1972 |
| EP | 077534 | * | 4/1983 |
| EP | 540 051 A1 |  | 5/1993 |
| EP | 0 937 711 A1 |  | 8/1999 |
| GB | 2220206 A | * | 1/1990 |
| JP | 59-181257 |  | 10/1984 |
| JP | 418675 |  | 7/1992 |
| JP | 11302177 |  | 11/1999 |
| WO | 96/28427 |  | 9/1996 |
| WO | 97/29067 |  | 8/1997 |
| WO | 98/06694 |  | 2/1998 |
| WO | 98/09630 |  | 3/1998 |
| WO | 98/28269 |  | 7/1998 |
| WO | 98/28282 |  | 7/1998 |
| WO | 98/57934 |  | 12/1998 |
| WO | 99/00121 |  | 1/1999 |
| WO | 99/00126 |  | 1/1999 |
| WO | 99/00127 |  | 1/1999 |
| WO | 99/00128 |  | 1/1999 |
| WO | 99/32477 |  | 7/1999 |
| WO | WO99/42439 A1 |  | 8/1999 |
| WO | 00/34237 |  | 6/2000 |
| WO | 00/34238 |  | 6/2000 |
| WO | 00/34258 |  | 6/2000 |
| WO | 00/34260 |  | 6/2000 |
| WO | 00/34261 |  | 6/2000 |
| WO | 00/34268 |  | 6/2000 |
| WO | 00/34269 |  | 6/2000 |
| WO | 00/39118 |  | 7/2000 |

OTHER PUBLICATIONS

Michael R. Wiley et al., "Structure-Based Design of Potent, Amidine-Derived Inhibitors of Factor Xa: Evaluation of Selectively, Anticoagulant Activity, and Antithrombotic Activity", *J. Med. Chem.*, vol. 43, pp. 883-899 (2000).
Ying K. Yee et al., "$N^2$-Aroylanthranilamide Inhibitors of Human Factor Xa", *J. Med. Chem.*, vol. 43, pp. 873-882 (2000).
David K. Herron et al., "1,2-Dibenzamidobenzene Inhibitors of Human Factor Xa", *J. Med. Chem.*, vol. 43, pp. 859-872 (2000).
W. E. Bachmann et al., "Reduction by Magnesium + Magnesium Halide, XIII. The Reaction Between Epoxy Ketones and Grignard Reagents", *Journal of the American Chemical Society*, vol. 56, No. 7, pp. 1559-1560 (1934).
Takashi Keumi et al., "2-(Trifluoromethylsulfonyloxy)pyridine as a Reagent for the Ketone Synthesis from Carboxylic Acids and Aromatic Hydrocarbons", *Bull. Chem. Soc. Jpn.*, vol. 61, No. 2, pp. 455-459 (1988).
"Dictionary of Organic Compounds, 5th Ed., vol. 5," Chapman and Hall, New York, NY, US (1982), compounds T-00160, T-00161, T-00162, p. 5119 (1982).
Herbert J. Sipe, Jr. et al., "An Improved Synthesis of Aryl Sulfones", *Synthesis*, No. 3, pp. 283-284 (1984).

(Continued)

*Primary Examiner*—Zinna N. Davis
(74) *Attorney, Agent, or Firm*—Foley & Lardner LLP

(57) ABSTRACT

Novel benzamide compounds including their pharmaceutically acceptable isomers, salts, hydrates, solvates and pro-drug derivatives having activity against mammalian factor Xa are described. Compositions containing such compounds are also described. The compounds and compositions are useful in vitro or in vivo for preventing or treating coagulation disorders.

10 Claims, No Drawings

OTHER PUBLICATIONS

Richard Kuhn et al., "Addition von Maleinsaure-anhydrid an Polyene. (Uber konjugierte Doppelbindungen, XIV," *Berichte Der Deutschen Chemischen Gesellschaft*, vol. 63, pp. 2662-2679 (1930).

John D. Young et al., "Interannular Interactions in Para-Substituted Diphenylmethane Anion Radicals," *J. Am. Chem. Soc.*, 94:25, Dec. 1972.

Hitomi Suzuki et al., "Selective Reduction with Lithium Aluminum Hydride/Diphosphorus Tetraiodide. A Mild Conversion of Aromatic Ketones to Parent Hydrocarbons," *Chemistry Letters*, pp. 909-910, 1983.

St. Goldschmidt and P. Modderman, "Biphenyl Derivatives II. Basic 4-Biphenyl Compounds," *Recueil*, 69, 1109-1117 (1950).

W. F. Cockburn et al., "Molecular Rearrangement of Tertiary Amines. Part I.," *J. Chem. Soc.*, No. 8, pp. 3340-3346 (1960).

Hamilton, A., "Intra- and Intermolecular Hydrogen Bonding Control of Supermolecular Structure," *NATO ASI Ser.*, Ser. C. (Computational Approaches In Supramolecular Chemistry) vol. 426, 101-8, (1994).

El-Nagdy, S., *Asian J. Chem.* 2(4):368-78 (1990).

Kulkarni, *J. Indian Chem. Soc.* 61(8):720-1 (1984).

Hey, D., *J. Chem. Soc.* 16, 1513-18 (1967).

El-Zanfally, S., *Egypt. J. Pharm. Sci.* vol. 17(1), 29-34 (1978).

Bing-Yan Zhu et al., *Annual Reports in Medicinal Chemistry*, 35, pp. 83-102 (2000).

\* cited by examiner

BENZAMIDES AND RELATED INHIBITORS OF FACTOR XA

FIELD OF THE INVENTION

This invention relates to novel compounds which are potent and highly selective inhibitors of isolated factor Xa or when assembled in the prothrombinase complex. These compounds show selectivity for factor Xa versus other proteases of the coagulation (e.g. thrombin, fVIIa, fIXa) or the fibrinolytic cascades (e.g. plasminogen activators, plasmin). In another aspect, the present invention relates to novel monoamidino-containing compounds, their pharmaceutically acceptable salts, and pharmaceutically acceptable compositions thereof which are useful as potent and specific inhibitors of blood coagulation in mammals. In yet another aspect, the invention relates to methods for using these inhibitors as therapeutic agents for disease states in mammals characterized by coagulation disorders.

BACKGROUND OF THE INVENTION

Hemostasis, the control of bleeding, occurs by surgical means, or by the physiological properties of vasoconstriction and coagulation. This invention is particularly concerned with blood coagulation and ways in which it assists in maintaining the integrity of mammalian circulation after injury, inflammation, disease, congenital defect, dysfunction or other disruption. Although platelets and blood coagulation are both involved in thrombus formation, certain components of the coagulation cascade are primarily responsible for the amplification or acceleration of the processes involved in platelet aggregation and fibrin deposition.

Thrombin is a key enzyme in the coagulation cascade as well as in hemostasis. Thrombin plays a central role in thrombosis through its ability to catalyze the conversion of fibrinogen into fibrin and through its potent platelet activation activity. Direct or indirect inhibition of thrombin activity has been the focus of a variety of recent anticoagulant strategies as reviewed by Claeson, G., "Synthetic Peptides and Peptidomimetics as Substrates and Inhibitors of Thrombin and Other Proteases in the Blood Coagulation System", Blood Coag. Fibrinol. 5, 411-436 (1994). Several classes of anticoagulants currently used in the clinic directly or indirectly affect thrombin (i.e. heparins, low-molecular weight heparins, heparin-like compounds and coumarins).

A prothrombinase complex, including Factor Xa (a serine protease, the activated form of its Factor X precursor and a member of the calcium ion binding, gamma carboxyglutamyl (Gla)-containing, vitamin K dependent, blood coagulation glycoprotein family), converts the zymogen prothrombin into the active procoagulant thrombin. Unlike thrombin, which acts on a variety of protein substrates as well as at a specific receptor, factor Xa appears to have a single physiologic substrate, namely prothrombin. Since one molecule of factor Xa may be able to generate up to 138 molecules of thrombin (Elodi et al., *Thromb. Res.* 15, 617-619 (1979)), direct inhibition of factor Xa as a way of indirectly inhibiting the formation of thrombin may be an efficient anticoagulant strategy. Therefore, it has been suggested that compounds which selectively inhibit factor Xa may be useful as in vitro diagnostic agents, or for therapeutic administration in certain thrombotic disorders. see e.g., WO 94/13693.

Polypeptides derived from hematophagous organisms have been reported which are highly potent and specific inhibitors of factor Xa. U.S. Pat. No. 4,588,587 describes anticoagulant activity in the saliva of the Mexican leech, *Haementeria officinalis*. A principal component of this saliva was shown to be the polypeptide factor Xa inhibitor, antistasin (ATS), by Nutt, E. et al., "The Amino Acid Sequence of Antistasin, a Potent Inhibitor of Factor Xa Reveals a Repeated Internal Structure", J. Biol. Chem., 263, 10162-10167 (1988). Another potent and highly specific inhibitor of Factor Xa, called tick anticoagulant peptide (TAP), has been isolated from the whole body extract of the soft tick *Ornithidoros moubata*, as reported by Waxman, L., et al., "Tick Anticoagulant Peptide (TAP) is a Novel Inhibitor of Blood Coagulation Factor Xa" Science, 248, 593-596 (1990).

Factor Xa inhibitory compounds which are not large polypeptide-type inhibitors have also been reported including: Tidwell, R. R. et al., "Strategies for Anticoagulation With Synthetic Protease Inhibitors. Xa Inhibitors Versus Thrombin Inhibitors", Thromb. Res., 19, 339-349 (1980); Turner, A. D. et al., "p-Amidino Esters as Irreversible Inhibitors of Factor IXa and Xa and Thrombin", Biochemistry, 25, 4929-4935 (1986); Hitomi, Y. et al., "Inhibitory Effect of New Synthetic Protease Inhibitor (FUT-175) on the Coagulation System", Haemostasis, 15, 164-168 (1985); Sturzebecher, J. et al., "Synthetic Inhibitors of Bovine Factor Xa and Thrombin. Comparison of Their Anticoagulant Efficiency", Thromb. Res., 54, 245-252 (1989); Kam, C. M. et al., "Mechanism Based Isocoumarin Inhibitors for Trypsin and Blood Coagulation Serine Proteases: New Anticoagulants", Biochemistry, 27, 2547-2557 (1988); Hauptmann, J. et al., "*Comparison* of the Anticoagulant and Antithrombotic Effects of Synthetic Thrombin and Factor Xa Inhibitors", Thromb. Haemost., 63, 220-223 (1990); and the like.

Others have reported Factor Xa inhibitors which are small molecule organic compounds, such as nitrogen containing heterocyclic compounds which have amidino substituent groups, wherein two functional groups of the compounds can bind to Factor Xa at two of its active sites. For example, WO 98/28269 describes pyrazole compounds having a terminal C(=NH)—NH$_2$ group; WO 97/21437 describes benzimidazole compounds substituted by a basic radical which are connected to a naphthyl group via a straight or branched chain alkylene, —C(=O) or —S(=O)$_2$ bridging group; WO 99/10316 describes compounds having a 4-phenyl-N-alkylamidino-piperidine and 4-phenoxy-N-alkylamidino-piperidine group connected to a 3-amidinophenyl group via a carboxamidealkyleneamino bridge; and EP 798295 describes compounds having a 4-phenoxy-N-alkylamidino-piperidine group connected to an amidinonaphthyl group via a substituted or unsubstituted sulfonamide or carboxamide bridging group.

There exists a need for effective therapeutic agents for the regulation of hemostasis, and for the prevention and treatment of thrombus formation and other pathological processes in the vasculature induced by thrombin such as restenosis and inflammation. In particular, there continues to be a need for compounds which selectively inhibit factor Xa or its precursors. Compounds that have different combinations of bridging groups and functional groups than compounds previously discovered are needed, particularly compounds which selectively or preferentially bind to Factor Xa. Compounds with a higher degree of binding to Factor Xa than to thrombin are desired, especially those compounds having good bioavailability and/or solubility.

SUMMARY OF THE INVENTION

As discussed above, a number of non-peptide, specific, factor Xa inhibitors have been described either in the scientific or patent literature (Zhu and Scarborough, Ann. Rep. Med. Chem. 35: 83-102 (2000)). Most of these compounds rely on the interaction of P1 and P4 elements of the inhibitor compounds with the S1 and S4 sub-sites on the factor Xa enzyme. In general, it has been described that P1 elements utilize a highly charged benzamidine functionality in order to interact with the S1 pocket of the factor Xa enzyme. Furthermore, substitution on the benzamidine nitrogens either by alkylation or cyclization (cyclic amidines) of these previously described inhibitors is detrimental to their interaction with the enzyme at the S1 pocket. In the present application, a novel series of inhibitors of factor Xa which do not utilize a S1-interacting benzamidine but utilize a neutral P1 species are described. In addition the compounds also utilize a substituted benzamidine or a cyclic amidine as a P4 element which can each interact with the S4 sub-site of factor Xa enzyme. Surprisingly, the inhibitors of this invention with modified amidine elements are not only of high potency in vitro, but also have excellent pharmacological and pharmaceutical properties in vivo. These are results that would not have been predicted for such structures.

Accordingly, the present invention relates to novel compounds which inhibit factor Xa, their pharmaceutically acceptable isomers, salts, hydrates, solvates and prodrug derivatives, and pharmaceutically acceptable compositions thereof which have particular biological properties and are useful as potent and specific inhibitors of blood coagulation in mammals. In another aspect, the invention relates to methods of using these inhibitors as diagnostic reagents or as therapeutic agents for disease states in mammals characterized by undesired thrombosis or which have coagulation disorders, such as in the treatment or prevention of any thrombotically mediated acute coronary or cerebrovascular syndrome, any thrombotic syndrome occurring in the venous system, any coagulopathy, and any thrombotic complications associated with extracorporeal circulation or instrumentation, and for the inhibition of coagulation in biological samples.

In certain embodiments, this invention relates to novel compounds which are potent and highly selective inhibitors of isolated factor Xa when assembled in the prothrombinase complex. These compounds show selectivity for factor Xa versus other proteases of the coagulation cascade (e.g. thrombin, etc.) or the fibrinolytic cascade, and are useful as diagnostic reagents as well as antithrombotic agents.

In one embodiment, the present invention relates to a compound according to the formula (I):

A-Q-D-E-G-J-X                        (I)

where:
A is selected from:
(a) $C_1$-$C_6$-alkyl;
(b) $C_3$-$C_8$-cycloalkyl;
(c) —N($R^1$,$R^2$), N($R^1$,$R^2$)—C(=N$R^3$)—, N($R^1$,$R^2$)—C(=N$R^3$)—N($R^4$)—, $R^1$—C(=N$R^3$)—, $R^1$—C(=N$R^3$)—N($R^4$)—;
(d) phenyl, which is independently substituted with 0-2 R substitutuents;
(e) naphthyl, which is independently substituted with 0-2 R substitutuents; and
(f) a monocyclic or fused bicyclic heterocyclic ring system having from 5 to 10 ring atoms, wherein 1-4 ring atoms of the ring system are selected from N, O and S, and wherein the ring system may be substituted with 0-2 R substitutuents;

R is selected from:
H, halo, —CN, —$CO_2R^1$, —C(=O)—N($R^1$, $R^2$), —($CH_2$)$_m$—$CO_2R^1$, —($CH_2$)$_m$—C(=O)—N($R^1$, $R^2$), —$NO_2$, —$SO_2$N($R^1$, $R^2$), —$SO_2R^1$, —($CH_2$)$_m$N$R^1R^2$, —($CH_2$)$_m$—C(=N$R^3$)—$R^1$, —($CH_2$)$_m$—C(=N$R^3$)—N($R^1$,$R^2$), —($CH_2$)$_m$—N($R^4$)—C(=N$R^3$)—N($R^1$,$R^2$), —($CH_2$)$_m$N$R^1$— group appended to a 3 to 6 membered heterocyclic ring containing from 1-4 heteroatoms selected from N, O and S, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$CF_3$, —$OR^2$, and a 5-6 membered heterocyclic system containing from 1-4 heteroatoms selected from N, O and S, wherein from 1-4 hydrogen atoms on the heterocyclic system may be independently replaced with a member selected from the group consisting of halo, —$C_1$-$C_4$-alkyl, —$C_{1-4}$alkyl-CN, —$C_{2-6}$alkenyl, —$C_{2-6}$alkynyl, —$C_{3-8}$cycloalkyl, —$C_{0-4}$alkyl$C_{3-8}$cycloalkyl and —$NO_2$;

m is an integer of 0-2;

$R^1$, $R^2$, $R^3$ and $R^4$ are independently selected from the group consisting of:
H, —$OR^5$, —N(—$R^5$, —$R^6$), —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$CO_{0-4}$alkylphenyl and —$C_{0-4}$alkylnaphthyl, wherein from 1-4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl $C_{3-8}$cycloalkyl, —CN, and —$NO_2$; or
$R^1$ and $R^2$, or $R^2$ and $R^3$ taken together can form a 3-8 membered cycloalkyl or a heterocyclic ring system, wherein the heterocyclic ring system may have from 3 to 10 ring atoms, with 1 to 2 rings being in the ring system and contain from 1-4 heteroatoms selected from N, O and S, wherein from 1-4 hydrogen atoms on the heterocyclic ring system may be independently replaced with a member selected from the group consisting of halo, $C_1$-$C_4$-alkyl, —CN —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl and —$NO_2$;

$R^5$ and $R^6$ are independently selected from the group consisting of:
H, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$alkylphenyl and —$C_{0-4}$alkylnaphthyl, wherein from 1-4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, and —$NO_2$; or
$R^5$ and $R^6$ taken together can form a 3-8 membered cycloalkyl or a heterocyclic ring system, wherein the heterocyclic ring system may have from 3 to 10 ring atoms, with 1 to 2 rings being in the ring system and contain from 1-4 heteroatoms selected from N, O and S, wherein from 1-4 hydrogen atoms on the heterocyclic ring system may be independently replaced with a member selected from the group consisting of halo, —$C_1$-$C_4$-alkyl, —CN —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl and —$NO_2$;

Q is a member selected from the group consisting of:
a direct link, —CH$_2$—, —C(=O)—, —O—, —N(R$^7$)—, —N(R$^7$)CH$_2$—, —CH$_2$N(R$^7$)—, —C(=NR$^7$)—, —C(=O)—N(R$^7$)—, —N(R$^7$)—C(=O)—, —S—, —SO—, —SO$_2$—, —SO$_2$—N(R$^7$)— and —N(R$^7$)—SO$_2$—;

R$^7$ is selected from:
H, —C$_{1-4}$alkyl, —C$_{2-6}$alkenyl, —C$_{2-6}$alkynyl, C$_{3-8}$cycloalkyl, —C$_{0-4}$alkylC$_{3-8}$cycloalkyl, —C$_{0-4}$alkylphenyl and —C$_{0-4}$alkylnaphthyl, wherein from 1-4 hydrogen atoms on the ring atoms of the phenyl and naphthyl moieties may be independently replaced with a member selected from the group consisting of halo, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —CN, and —NO$_2$;

D is a direct link or is a member selected from the group consisting of:
(a) phenyl, which is independently substituted with 0-2 R$^{1a}$ substitutuents;
(b) naphthyl, which is independently substituted with 0-2 R$^{1a}$ substitutuents; and
(c) a monocyclic or fused bicyclic heterocyclic ring system having from 5 to 10 ring atoms, wherein 1-4 ring atoms of the ring system are selected from N, O and S, and wherein the ring system may be subsituted from 0-2 R$^{1a}$ substitutuents;

R$^{1a}$ is selected from:
halo, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —CN, —NO$_2$, —(CH$_2$)$_n$NR$^{2a}$R$^{3a}$, —(CH$_2$)$_n$CO$_2$R$^{2a}$, —(CH$_2$)$_n$CONR$^{2a}$R$^{3a}$, —SO$_2$NR$^{2a}$R$^{3a}$, —SO$_2$R$^{2a}$, —CF$_3$, —OR$^{2a}$, and a 5-6 membered aromatic heterocyclic system containing from 1-4 heteroatoms selected from N, O and S, wherein from 1-4 hydrogen atoms on the aromatic heterocyclic system may be independently replaced with a member selected from the group consisting of halo, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —CN and —NO$_2$;

R$^{2a}$ and R$^{3a}$ are independently selected from the group consisting of:
H, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —C$_{0-4}$alkylphenyl and —C$_{0-4}$alkylnaphthyl, wherein from 1-4 hydrogen atoms on the ring atoms of the phenyl and naphthyl moieties may be independently replaced with a member selected from the group consisting of halo, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —CN and —NO$_2$;

n is an integer of 0-2;

E is a direct link or a member selected from the group consisting of:
—C$_{1-2}$-alkyl-, —O—, —S—, —SO—, —SO$_2$—, —C$_{0-1}$-alkyl-C(=O), —C$_{0-1}$-alkyl-C(=O)—N(—R$^8$)—C$_{0-1}$-alkyl-, —C$_{0-1}$-alkyl-N(—R$^8$)—C(=O)—C$_{0-1}$-alkyl-, —N(—R$^8$)—C(=O)—N(—R$^8$)— and —C$_{0-1}$-alkyl-N(—R$^8$)—;

R$^8$ is a member selected from the group consisting of:
H; —C$_{1-4}$-alkyl; —C$_{0-4}$-alkylaryl; —C$_{0-4}$-alkyl-heteroaryl; —C$_{1-4}$-alkyl-C(=O)—OH, —C$_{1-4}$-alkyl-C(=O)—O—C$_{1-4}$-alkyl, and —C$_{1-4}$-alkyl-C(=O)—N(—R$^{2b}$, —R$^{3b}$);

R$^{2b}$ and R$^{3b}$ are each a member independently selected from the group consisting of:
H, —C$_{1-4}$-alkyl, —C$_{0-4}$-alkyl-aryl; —C$_{0-4}$-alkyl-heterocyclic group, and R$^{2b}$ and R$^{3b}$ together with the N atom to which they are attached can form a 5-8 membered heterocyclic ring containing 1-4 heteroatoms selected from N, O and S, wherein the heterocyclic ring may be substituted with 0-2 R$^{1c}$ groups;

R$^{1c}$ is a member selected from the group consisting of:
Halo; —C$_{1-4}$-alkyl; —CN, —NO$_2$; —C(=O)—N(—R$^{2c}$, —R$^{3c}$); —C(=O)—OR$^{2c}$; —(CH$_2$)$_q$—N(—R$^{2c}$, R$^{3c}$); —SO$_2$—N(—R$^{2c}$, —R$^{3c}$); —SO$_2$R$^{2c}$; —CF$_3$ and —(CH$_2$)$_q$—OR$^{2c}$;

R$^{2c}$ and R$^{3c}$ are each independently a member selected from the group consisting of:
H; —C$_{1-4}$-alkyl and —C$_{1-4}$-alkyl-aryl;

q is an integer of 0-2;

G is a member selected from the group consisting of:
(a) C$_2$-alkenyl or C$_{3-8}$-cycloalkenyl, wherein the alkenyl and cycloalkenyl attachment points are the alkenyl carbon atoms and wherein the —C$_2$-alkenyl or —C$_{3-8}$-cycloalkenyl are substituted with 0-4 R$^{1d}$ groups;
(b) a phenylene group wherein the ring carbon atoms of the phenylene group are substituted with 0-4 R$^{1d}$ groups;
(c) a 3-8 membered a saturated, partially unsaturated or aromatic monocyclic-heterocyclic ring system containing 1-4 heteroatoms selected from N, O and S, wherein 0-2 ring atoms of the heterocyclic ring may be substituted with 0-4 R$^{1d}$ groups; and,
(d) an 8-10 membered fused heterocyclic bicyclic ring system, containing 1-4 heteroatoms selected from N, O and S, wherein 0-2 ring atoms of the fused bicyclic ring system may be substituted with 0-4 R$^{1d}$ groups;

R$^{1d}$ is a member selected from the group consisting of:
H, halo; C$_{1-6}$-alkyl, carbocylic aryl, —CN; —NO$_2$; —(CH$_2$)$_{0-6}$—NR$^{2d}$R$^{3d}$; —SO$_2$NR$^{2d}$R$^{3d}$; —SO$_2$R$^{2d}$; —CF$_3$; —(CH$_2$)$_{0-6}$—OR$^{2d}$; —OH, —OC$_{1-6}$alkyl, —O—(CH$_2$)$_{1-6}$—OR$^{2d}$; —O—(CH$_2$)$_{1-6}$—C(=O)—O—R$^{2d}$; —O—(CH$_2$)$_{1-6}$—C(=O)—N(R$^{2d}$,R$^{3d}$); —N(R$^{5a}$)—(CH$_2$)$_{1-6}$—OR$^{2d}$; —N(R$^{5a}$)—(CH$_2$)$_{1-6}$—N(R$^{2da}$,R$^{3d}$); —C(=O)—N(R$^{2d}$,R$^{3d}$); —N(R$^{5a}$)—(CH$_2$)$_{1-6}$—C(=O)—N(R$^{2d}$,R$^{3d}$); —N(—(CH$_2$)$_{1-6}$—OR$^{2d}$)$_2$; —N(R$^{5a}$)—(CH$_2$)$_{1-6}$—OR$^{2d}$; —N(R$^{5a}$)C(=O)—R$^d$; —N(R$^{5a}$)—SO$_2$—R$^{2d}$; —(CH$_2$)$_{0-6}$—C(=O)—O—R$^{2d}$; —(CH$_2$)$_{0-6}$—C(=O)—N(R$^{2d}$,R$^{3d}$); —(CH$_2$)$_{0-6}$—C(=NR$^{2d}$)—N(R$^{3d}$,R$^{4d}$); —(CH$_2$)$_{0-6}$—N(R$^{5a}$)C(=NR$^{2d}$)—N(R$^{3d}$R$^{4d}$); a —(CH$_2$)$_{0-6}$—N(R$^{3d}$)C$_{5-6}$ membered saturated, partially unsaturated or aromatic heterocyclic ring containing 1-4 heteroatoms selected from N, O and S, and a —(CH$_2$)$_{0-6}$-5-6 membered saturated, partially unsaturated or aromatic heterocyclic ring containing 1-4 heteroatoms selected from N, O and S;

R$^{5a}$, R$^{2d}$, R$^{3d}$ and R$^{4d}$ are each independently a member selected from the group consisting of:
H, C$_{1-6}$-alkyl and C$_{1-6}$-alkylaryl, —CN; —NO$_2$; carbocylic aryl, —CN; —NO$_2$; or R$^{2d}$ and R$^{3d}$ taken together with the N atoms they are independently attached form a 5-7 membered saturated, partially unsaturated or aromatic heterocyclic ring; or R$^{3d}$ and R$^{4d}$ taken together with the N atom to which they are attached form a 5-8 membered saturated, partially unsaturated or aromatic heterocyclic ring containing 1-4 heteroatoms selected from N, O and S;

J is a direct link or is a member selected from the group consisting of:
—N(—R$^9$)—C(=O)—; —C(=O)—N(—R$^9$)—; —O—; —S—; —SO—; —SO$_2$—; —CH$_2$—; —N(—R$^9$)—; and —N(—R$^9$)—SO$_2$—;

$R^9$ is a member selected from the group consisting of:
  H; —$C_{1-4}$-alkyl; —$C_{0-4}$-alkyl-carbocyclic aryl; —$(CH_2)_{0-4}$-5-6 membered saturated, partially unsaturated or aromatic heterocyclic ring containing 1-4 heteroatoms selected from N, O and S; —$(CH_2)_{1-6}$—C(=O)—O—$C_{1-4}$-alkyl; and —$(CH_2)_{1-6}$—C(=O)—N($R^{6a},R^{6b}$);
$R^{6a}$ and $R^{6b}$ are each a member independently selected from the group consisting of:
  H and —$C_{1-6}$-alkyl;
X is a member selected from the group consisting of:
  (a) phenyl substituted with 0-3 $R^{1e}$ groups;
  (b) naphthyl substituted with 0-3 $R^{1e}$ groups and
  (c) a 6-membered aromatic heterocyclic ring system containing 1-3 N atoms and having 0-3 ring atoms substituted with 0-3 $R^{1e}$ groups; and
  (d) an 8-10 membered fused aromatic heterocyclic bicyclic ring system containing 1-4 heteroatoms selected from N, O and S and 0-3 ring atoms of the fused heterocyclic bicyclic ring system are substituted with 0-3 $R^{1e}$ groups;
$R^{1e}$ is a member independently selected from the group consisting of:
  Halo; $CF_3$; —$C_{1-4}$-alkyl; carbocyclic aryl; —$C_{0-2}$-alkyl-CN; —O—$R^{2e}$; —$C_{0-2}$-alkyl-C(=O)—O—$R^{2e}$; —$C_{0-2}$-alkyl-C(=O)—N($R^{2e}$, $R^{3e}$); —$C_{0-2}$-alkyl-$NO_2$; —$C_{0-2}$-alkyl-N($R^{2e}$, $R^{3e}$); —$C_{0-2}$-alkyl-$SO_2$—N($R^{2e}$, $R^{3e}$); —$C_{0-2}$-alkyl-$SO_2$—$R^{2e}$; trihaloalkyl; —O—$C_{0-2}$-alkyl-O—$R^{2e}$; —$C_{0-2}$-alkyl-O—$R^{2e}$; —O—$C_{1-4}$-alkyl-C(=O)—N($R^{2e}$, $R^{3e}$); —O—$C_{1-4}$-alkyl-C(=O)—O—$R^{2e}$; —$C_{0-2}$-alkyl-N($R^{2e}$—C(=O)—$R^{3e}$; —$C_{0-2}$-alkyl-N(—$R^{2e}$)—$SO_2$—$R^{3e}$; —$CH_2$—N($R^{2e}$)—C(=O)—$R^{3e}$; —$CH_2$—N($R^{2e}$)—$SO_2$—$R^{3e}$; —$(CH_2)_{0-6}$—$NR^{2e}R^{3e}$; —C(=O)—N($R^{2e}$, $R^{3e}$); —N(—$(CH_2)_{1-6}$—$OR^{2e}$)$_2$; —N($R^{10}$)—$(CH_2)_{1-6}$—$OR^{2e}$; —N($R^{10}$)—C(=O)—$R^{2e}$; —N($R^{10}$)—$SO_2$—$R^{2e}$; —C(=N($R^{10}$))—N($R^{2e},R^{3e}$); and a —$(CH_2)_{0-6}$-5-6 membered saturated, partially unsaturated or aromatic heterocyclic ring containing 1-4 heteroatoms selected from N, O and S;
$R^{10}$, $R^{2e}$ and $R^{3e}$ are each independently a member selected from the group consisting of:
  H; —$C_{1-4}$-alkyl; —$C_{0-2}$-alkyl-O—$R^{1g}$; —$C_{0-2}$-alkyl-N(—$R^{1g}$, —$R^{2g}$); —$C_{1-4}$-alkyl-carbocyclic aryl; —$C_{1-4}$-alkyl-heterocyclic; and $R^{10}$ and $R^{2e}$, or $R^{2e}$ and $R^{3e}$ together with the N atom to which they are attached can form 5-8 membered heterocyclic ring containing 1-4 heteroatoms selected from N, O and S which can be substituted with 0-2 $R^{1g}$ groups;
$R^{1g}$ and $R^{2g}$ are indepedently a member selected from the group of:
  H; halo; —$C_{1-4}$-alkyl, a carbocyclic aryl group; a saturated, partially unsaturated or aromatic heterocyclic group; —CN; —C(=O)—N($R^{3g}$)$R^{4g}$; —C(=O)—$OR^{3g}$; —$NO_2$; —$(CH_2)_p$—$NR^{3g}R^{4g}$; —$SO_2NR^{3g}R^{4g}$; —$SO_2R^{3g}$; —$CF_3$; and —$(CH_2)_pOR^{3g}$;
p is an integer of 0-2;
$R^{3g}$ and $R^{4g}$ are each independently selected from the group consisting of:
  H; $C_{1-4}$-alkyl and —$C_{0-4}$-alkyl-carbocyclic aryl;
  and all pharmaceutically acceptable isomers, salts, hydrates, solvates and prodrug derivatives thereof.

In certain aspects of this invention, compounds are provided which are useful as diagnostic reagents. In another aspect, the present invention includes pharmaceutical compositions comprising a pharmaceutically effective amount of the compounds of this invention and a pharmaceutically acceptable carrier. In yet another aspect, the present invention includes methods comprising using the above compounds and pharmaceutical compositions for preventing or treating disease states characterized by undesired thrombosis or disorders of the blood coagulation process in mammals, or for preventing coagulation in stored blood products and samples. Optionally, the methods of this invention comprise administering the pharmaceutical composition in combination with an additional therapeutic agent such as an antithrombotic and/or a thrombolytic agent and/or an anticoagulant.

DETAILED DESCRIPTION OF THE INVENTION

Definitions

In accordance with the present invention and as used herein, the following terms are defined with the following meanings, unless explicitly stated otherwise.

The term "alkenyl" refers to a trivalent straight chain or branched chain unsaturated aliphatic radical. The term "alkinyl" (or "alkynyl") refers to a straight or branched chain aliphatic radical that includes at least two carbons joined by a triple bond. If no number of carbons is specified alkenyl and alkinyl each refer to radicals having from 2-12 carbon atoms.

The term "alkyl" refers to saturated aliphatic groups including straight-chain, branched-chain and cyclic groups having the number of carbon atoms specified, or if no number is specified, having up to 12 carbon atoms. The term "cycloalkyl" as used herein refers to a mono-, bi-, or tricyclic aliphatic ring having 3 to 14 carbon atoms and preferably 3 to 7 carbon atoms.

As used herein, the terms "carbocyclic ring structure" and "$C_{3-16}$ carbocyclic mono, bicyclic or tricyclic ring structure" or the like are each intended to mean stable ring structures having only carbon atoms as ring atoms wherein the ring structure is a substituted or unsubstituted member selected from the group consisting of: a stable monocyclic ring which is aromatic ring ("aryl") having six ring atoms; a stable monocyclic non-aromatic ring having from 3 to 7 ring atoms in the ring; a stable bicyclic ring structure having a total of from 7 to 12 ring atoms in the two rings wherein the bicyclic ring structure is selected from the group consisting of ring structures in which both of the rings are aromatic, ring structures in which one of the rings is aromatic and ring structures in which both of the rings are non-aromatic; and a stable tricyclic ring structure having a total of from 10 to 16 atoms in the three rings wherein the tricyclic ring structure is selected from the group consisting of: ring structures in which three of the rings are aromatic, ring structures in which two of the rings are aromatic and ring structures in which three of the rings are non-aromatic. In each case, the non-aromatic rings when present in the monocyclic, bicyclic or tricyclic ring structure may independently be saturated, partially saturated or fully saturated. Examples of such carbocyclic ring structures include, but are not limited to, cyclopropyl, cyclobutyl, cyclopentyl, cyclohexyl, adamantyl, cyclooctyl, [3.3.0]bicyclooctane, [4.3.0]bicyclononane, [4.4.0]bicyclodecane (decalin), 2.2.2]bicyclooctane, fluorenyl, phenyl, naphthyl, indanyl, adamantyl, or tetrahydronaphthyl (tetralin). Moreover, the ring structures described herein may be attached to one or more indicated pendant groups via any carbon atom which results in a stable structure. The term "substituted" as used in conjunction with carbocyclic ring structures means that hydrogen atoms attached to the ring carbon atoms of ring structures described herein may be substituted by one or more of the substituents indicated for that structure if such substitution(s) would result in a stable compound.

The term "aryl" which is included with the term "carbocyclic ring structure" refers to an unsubstituted or substituted aromatic ring, substituted with one, two or three substituents selected from loweralkoxy, loweralkyl, loweralkylamino, hydroxy, halogen, cyano, hydroxyl, mercapto, nitro, thioalkoxy, carboxaldehyde, carboxyl, carboalkoxy and carboxamide, including but not limited to carbocyclic aryl, heterocyclic aryl, and biaryl groups and the like, all of which may be optionally substituted. Preferred aryl groups include phenyl, halophenyl, loweralkylphenyl, napthyl, biphenyl, phenanthrenyl and naphthacenyl.

The term "arylalkyl" which is included with the term "carbocyclic aryl" refers to one, two, or three aryl groups having the number of carbon atoms designated, appended to an alkyl group having the number of carbon atoms designated. Suitable arylalkyl groups include, but are not limited to, benzyl, picolyl, naphthylmethyl, phenethyl, benzyhydryl, trityl, and the like, all of which may be optionally substituted.

As used herein, the term "heterocyclic ring" or "heterocyclic ring system" is intended to mean a substituted or unsubstituted member selected from the group consisting of stable monocyclic ring having from 5-7 members in the ring itself and having from 1 to 4 hetero ring atoms selected from the group consisting of N, O and S; a stable bicyclic ring structure having a total of from 7 to 12 atoms in the two rings wherein at least one of the two rings has from 1 to 4 hetero atoms selected from N, O and S, including bicyclic ring structures wherein any of the described stable monocyclic heterocyclic rings is fused to a hexane or benzene ring; and a stable tricyclic heterocyclic ring structure having a total of from 10 to 16 atoms in the three rings wherein at least one of the three rings has from 1 to 4 hetero atoms selected from the group consisting of N, O and S. Any nitrogen and sulfur atoms present in a heterocyclic ring of such a heterocyclic ring structure may be oxidized. Unless indicated otherwise the terms "heterocyclic ring" or "heterocyclic ring system" include aromatic rings, as well as non-aromatic rings which can be saturated, partially saturated or fully saturated non-aromatic rings. Also, unless indicated otherwise the term "heterocyclic ring system" includes ring structures wherein all of the rings contain at least one hetero atom as well as structures having less than all of the rings in the ring structure containing at least one hetero atom, for example bicyclic ring structures wherein one ring is a benzene ring and one of the rings has one or more hetero atoms are included within the term "heterocyclic ring systems" as well as bicyclic ring structures wherein each of the two rings has at least one hetero atom. Moreover, the ring structures described herein may be attached to one or more indicated pendant groups via any hetero atom or carbon atom which results in a stable structure. Further, the term "substituted" means that one or more of the hydrogen atoms on the ring carbon atom(s) or nitrogen atom(s) of the each of the rings in the ring structures described herein may be replaced by one or more of the indicated substituents if such replacement(s) would result in a stable compound. Nitrogen atoms in a ring structure may be quaternized, but such compounds are specifically indicated or are included within the term "a pharmaceutically acceptable salt" for a particular compound. When the total number of O and S atoms in a single heterocyclic ring is greater than 1, it is preferred that such atoms not be adjacent to one another. Preferably, there are no more that 1 O or S ring atoms in the same ring of a given heterocyclic ring structure.

Examples of monocylic and bicyclic heterocylic ring systems, in alphabetical order, are acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl. Preferred heterocyclic ring structures include, but are not limited to, pyridinyl, furanyl, thienyl, pyrrolyl, pyrazolyl, pyrrolidinyl, imidazolyl, indolyl, benzimidazolyl, 1H-indazolyl, oxazolinyl, or isatinoyl. Also included are fused ring and spiro compounds containing, for example, the above heterocyclic ring structures.

As used herein the term "aromatic heterocyclic ring system" has essentially the same definition as for the monocyclic and bicyclic ring systems except that at least one ring of the ring system is an aromatic heterocyclic ring or the bicyclic ring has an aromatic or non-aromatic heterocyclic ring fused to an aromatic carbocyclic ring structure.

The terms "halo" or "halogen" as used herein refer to Cl, Br, F or I substituents. The term "haloalkyl", and the like, refer to an aliphatic carbon radicals having at least one hydrogen atom replaced by a Cl, Br, F or I atom, including mixtures of different halo atoms. Trihaloalkyl includes trifluoromethyl and the like as preferred radicals, for example.

The term "methylene" refers to —$CH_2$—.

The term "pharmaceutically acceptable salts" includes salts of compounds derived from the combination of a compound and an organic or inorganic acid. These compounds are useful in both free base and salt form. In practice, the use of the salt form amounts to use of the base form; both acid and base addition salts are within the scope of the present invention.

"Pharmaceutically acceptable acid addition salt" refers to salts retaining the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

"Biological property" for the purposes herein means an in vivo effector or antigenic function or activity that is directly or indirectly performed by a compound of this invention that are often shown by in vitro assays. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it.

In the compounds of this invention, carbon atoms bonded to four non-identical substituents are asymmetric. Accordingly, the compounds may exist as diastereoisomers, enantiomers or mixtures thereof. The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using the same techniques or by other methods known in the art. Each of the asymmetric carbon atoms, when present in the compounds of this invention, may be in one of two configurations (R or S) and both are within the scope of the present invention.

PREFERRED EMBODIMENTS

The invention provides a compound according to the formula (I):

A-Q-D-E-G-J-X     (I)

where:
A is selected from:
(a) $C_1$-$C_6$-alkyl;
(b) $C_3$-$C_8$-cycloalkyl;
(c) —N($R^1$,$R^2$), N($R^1$,$R^2$)—C(=$NR^3$)—, N($R^1$,$R^2$)—C(=$NR^3$)—N($R^4$)—, $R^1$—C(=$NR^3$)—, $R^1$—C(=$NR^3$)—N($R^4$)—;
(d) phenyl, which is independently substituted with 0-2 R substitutuents;
(e) naphthyl, which is independently substituted with 0-2 R substituents; and
(f) a monocyclic or fused bicyclic heterocyclic ring system having from 5 to 10 ring atoms, wherein 1-4 ring atoms of the ring system are selected from N, O and S, and wherein the ring system may be substituted with 0-2 R substitutuents;

R is selected from:
H, halo, —CN, —$CO_2R^1$, —C(=O)—N($R^1$, $R^2$), —$(CH_2)_m$—$CO_2R^1$, —$(CH_2)_m$—C(=O)—N($R^1$, $R^2$), —$NO_2$, —$SO_2N(R^1, R^2)$, —$SO_2R^1$, —$(CH_2)_mNR^1R^2$, —$(CH_2)_m$—C(=$NR^3$)—$R^1$, —$(CH_2)_m$—C(=$NR^3$)—N($R^1$,$R^2$)—$(CH_2)_m$—N($R^4$)—C(=$NR^3$)—N($R^1$,$R^2$), —$(CH_2)_mNR^1$—$C_{3\text{-}6}$heterocyclics, $C_{1\text{-}4}$alkyl, $C_{2\text{-}6}$alkenyl, $C_{2\text{-}6}$alkynyl, $C_{3\text{-}8}$cycloalkyl, $C_{0\text{-}4}$alkyl$C_{3\text{-}8}$cycloalkyl, —$CF_3$, —$OR^2$, and a 5-6 membered heterocyclic system containing from 1-4 heteroatoms selected from N, O and S, wherein from 1-4 hydrogen atoms on the heterocyclic system may be independently replaced with a member selected from the group consisting of halo, $C_1$-$C_4$-alkyl, CN—$C_{1\text{-}4}$alkyl, —$C_{2\text{-}6}$alkenyl, —$C_{2\text{-}6}$alkynyl, —$C_{3\text{-}8}$cycloalkyl, —$C_{0\text{-}4}$alkyl$C_{3\text{-}8}$cycloalkyl and —$NO_2$;

m is an integer of 0-2;
$R^1$, $R^2$, $R^3$ and $R^4$ are independently selected from the group consisting of:
H, —$OR^5$, —N(—$R^5$, —$R^6$), —$C_{1\text{-}4}$alkyl, —$C_{2\text{-}6}$alkenyl, —$C_{2\text{-}6}$alkynyl, —$C_{3\text{-}8}$cycloalkyl, —$C_{0\text{-}4}$alkyl$C_{3\text{-}8}$cycloalkyl, —$C_{0\text{-}4}$alkylphenyl and —$C_{0\text{-}4}$alkylnaphthyl, wherein from 1-4 hydrogen atoms on the ring atoms of the phenyl and naphthyl moieties may be independently replaced with a member selected from the group consisting of halo, —$C_{1\text{-}4}$alkyl, —$C_{2\text{-}6}$alkenyl, —$C_{2\text{-}6}$alkynyl, —$C_{3\text{-}8}$cycloalkyl, —$C_{0\text{-}4}$alkyl$C_{3\text{-}8}$cycloalkyl, —CN, and —$NO_2$; or $R^1$ and $R^2$, or $R^2$ and $R^3$ taken together can form a 3-8 membered cycloalkyl or a heterocyclic ring system, wherein the heterocyclic ring system may have from 3 to 10 ring atoms, with 1 to 2 rings being in the ring system and contain from 1-4 heteroatoms selected from N, O and S, wherein from 1-4 hydrogen atoms on the heterocyclic ring system may be independently replaced with a member selected from the group consisting of halo, $C_1$-$C_4$-alkyl, —CN —$C_{1\text{-}4}$alkyl, —$C_{2\text{-}6}$alkenyl, —$C_{2\text{-}6}$alkynyl, —$C_{3\text{-}8}$cycloalkyl, —$C_{0\text{-}4}$alkyl$C_{3\text{-}8}$cycloalkyl and —$NO_2$;

$R^5$ and $R^6$ are independently selected from the group consisting of:
H, —$C_{1\text{-}4}$alkyl, —$C_{2\text{-}6}$alkenyl, —$C_{2\text{-}6}$alkynyl, —$C_{3\text{-}8}$cycloalkyl, —$C_{0\text{-}4}$alkyl$C_{3\text{-}8}$cycloalkyl, —$C_{0\text{-}4}$alkylphenyl and —$C_{0\text{-}4}$alkylnaphthyl, wherein from 1-4 hydrogen atoms on the ring atoms of the phenyl and naphthyl moieties may be independently replaced with a member selected from the group consisting of halo, —$C_{1\text{-}4}$alkyl, —$C_{2\text{-}6}$alkenyl, —$C_{2\text{-}6}$alkynyl, —$C_{3\text{-}8}$cycloalkyl, —$C_{0\text{-}4}$alkyl$C_{3\text{-}8}$cycloalkyl, —CN, and —$NO_2$; or $R^5$ and $R^6$ taken together can form a 3-8 membered cycloalkyl or a heterocyclic ring system, wherein the heterocyclic ring system may have from 3 to 10 ring atoms, with 1 to 2 rings being in the ring system and contain from 1-4 heteroatoms selected from N, O and S, wherein from 1-4 hydrogen atoms on the heterocyclic ring system may be independently replaced with a member selected from the group consisting of halo, $C_1$-$C_4$-alkyl, —CN —$C_{1\text{-}4}$alkyl, —$C^{2\text{-}6}$alkenyl, —$C_{2\text{-}6}$alkynyl, —$C_{3\text{-}8}$cycloalkyl, —$C_{0\text{-}4}$alkyl$C_{3\text{-}8}$cycloalkyl and —$NO_2$;

Q is a member selected from the group consisting of:
a direct link, —$CH_2$—, —C(=O)—, —O—, —N($R^7$)—, —N($R^7$)$CH_2$—, —$CH_2$N($R^7$)—, —C(=$NR^7$)—, —C(=O)—N($R^7$)—, —N($R^7$)—C(=O)—, —S—, —SO—, —$SO_2$—, —$SO_2$—N($R^7$)— and —N($R^7$)—$SO_2$—;

$R^7$ is selected from:

H, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$alkylphenyl and —$C_{0-4}$alkylnaphthyl, wherein from 1-4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, and —$NO_2$;

D is a direct link or is a member selected from the group consisting of:
 (a) phenyl, which is independently substituted with 0-2 $R^{1a}$ substitutuents;
 (b) naphthyl, which is independently substituted with 0-2 $R^{1a}$ substitutuents; and
 (c) a monocyclic or fused bicyclic heterocyclic ring system having from 5 to 10 ring atoms, wherein 1-4 ring atoms of the ring system are selected from N, O and S, and wherein the ring system may be subsituted from 0-2 $R^{1a}$ substitutuents;

$R^{1a}$ is selected from:

halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, —$NO_2$, —$(CH_2)_n NR^{2a}R^{3a}$, —$(CH_2)_n CO_2 R^{2a}$, —$(CH_2)_n CONR^{2a}R^{3a}$, —$SO_2 NR^{2a}R^{3a}$, —$SO_2 R^{2a}$, —$CF_3$, —$OR^{2a}$, and a 5-6 membered aromatic heterocyclic system containing from 1-4 heteroatoms selected from N, O and S, wherein from 1-4 hydrogen atoms on the aromatic heterocyclic system may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN and —$NO_2$;

$R^{2a}$ and $R^{3a}$ are independently selected from the group consisting of:

H, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$alkylphenyl and —$C_{0-4}$alkylnaphthyl, wherein from 1-4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN and —$NO_2$;

n is an integer of 0-2;

E is a direct link or a member selected from the group consisting of:

—$C_{1-2}$-alkyl-, —O—, —S—, —SO—, —$SO_2$—, —$C_{0-1}$-alkyl-C(=O)—, —$C_{0-1}$-alkyl-C(=O)—N($R^8$)—$C_{0-1}$-alkyl-, —$C_{0-1}$alkyl-N($R^8$)—C(=O)—$C_{0-1}$-alkyl-, —N($R^8$)—C(=O)—N($R^8$)— and —$C_{0-1}$-alkyl-N($R^8$)—;

$R^8$ is a member selected from the group consisting of:

H; —$C_{1-4}$-alkyl; —$C_{1-4}$-alkylaryl; —$C_{1-4}$-alkyl-heteroaryl; —$C_{1-4}$-alkyl-C(=O)—OH, —$C_{1-4}$-alkyl-C(=O)—O—$C_{1-4}$-alkyl, and —$C_{1-4}$-alkyl-C(=O)—N(—$R^{2b}$, —$R^{3b}$);

$R^{2b}$ and $R^{3b}$ are each a member independently selected from the group consisting of:

H, —$C_{1-4}$-alkyl, —$C_{0-4}$-alkyl-aryl; —$C_0 O_4$-alkyl-heterocyclic group, and $R^{2b}$ and $R^{3b}$ together with the N atom to which they are attached can form a 5-8 membered heterocyclic ring containing 1-4 heteroatoms selected from N, O and S, wherein the heterocyclic ring may be substituted with 0-2 $R^{1c}$ groups;

$R^{1c}$ is a member selected from the group consisting of:

Halo; —$C_{1-4}$-alkyl; —CN, —$NO_2$; —C(=O)—N(—$R^{2c}$, $R^{3c}$); —C(=O)—$OR^{2c}$; —$(CH_2)_q$—N(—$R^{2c}$, —$R^{3c}$); —$SO_2$—N(—$R^{2c}$, —$R^{3c}$); —$SO_2 R^{2c}$; —$CF_3$ and —$(CH_2)_q$—$OR^{2c}$;

$R^{2c}$ and $R^{3c}$ are each independently a member selected from the group consisting of:

H; —$C_{1-4}$-alkyl and —$C_{1-4}$-alkyl-aryl;

q is an integer of 0-2;

G is a member selected from the group consisting of:
 (a) $C_2$-alkenyl or $C_{3-8}$-cycloalkenyl, wherein the alkenyl and cycloalkenyl attachment points are the alkenyl carbon atoms and wherein $C_2$-alkenyl or $C_{3-8}$-cycloalkenyl are substituted with 0-4 $R^{1d}$ groups;
 (b) a phenylene group wherein the ring carbon atoms of the phenylene group are substituted with 0-4 $R^{1d}$ groups;
 (c) a 3-8 membered a saturated, partially unsaturated or aromatic monocyclic-heterocyclic ring system containing 1-4 heteroatoms selected from N, O and S, wherein 0-4 ring atoms of the heterocyclic ring may be substituted with 0-4 $R^{1d}$ groups; and,
 (d) an 8-10 membered fused heterocyclic bicyclic ring system, containing 1-4 heteroatoms selected from N, O and S, wherein 0-4 ring atoms of the fused bicyclic ring system may be substituted with 0-4 $R^{1d}$ groups;

$R^{1d}$ is a member selected from the group consisting of:

H, halo; $C_{1-6}$-alkyl, carbocylic aryl, —CN; —$NO_2$; —$(CH_2)_{0-6}$—$NR^{2d}R^{3d}$; —$SO_2 NR^{2d}R^{3d}$; —$SO_2 R^{2d}$; —$CF_3$; $(CH_2)_{0-6}$—$OR^{2d}$; —OH, —$OC_{1-6}$alkyl, —O—$(CH_2)_{1-6}OR^{2d}$; —O—$(CH_2)_{1-6}$—C(=O)—O—$R^{2d}$; —O—$(CH_2)_{1-6}$—C(=O)—N($R^{2d},R^{3d}$); —N($R^{5a}$)—$(CH_2)_{1-6}$—$OR^{2d}$; —N($R^{5a}$)—$(CH_2)_{1-6}$—N($R^{2d},R^{3d}$); —C(=O)—N($R^{2d},R^{3d}$); —N($R^{5a}$)—$(CH_2)_{1-6}$—C(=O)—N($R^{2d},R^{3d}$); —N(—$(CH_2)_{1-6}$—$OR^{2d})_2$; —N($R^{5a}$)—$(CH_2)_{1-6}$—$OR^{2d}$; —N($R^{5a}$)—C(=O)—$R^{2d}$; —N($R^{5a}$)—$SO_2$—$R^{2d}$; —$(CH_2)_{0-6}$—C(=O)—O—$R^{2d}$; —$(CH_2)_{0-6}$—C(=O)—N($R^{2d},R^{3d}$); —$(CH_2)_{0-6}$—C(=$NR^{2d}$)—N($R^{3d},R^{4d}$); —$(CH_2)_{0-6}$—N($R^{5a}$)C(=$NR^{2d}$)N($R^{3d}R^{4d}$); and —$(CH_2)_{0-6}$—N(—$R^{3d}$)— group attached directly by its nitrogen atom to a carbon atom of a 5 to 6 membered saturated, partially unsaturated or aromatic heterocyclic ring containing 1-4 heteroatoms selected from N, O and S, and a —$(CH_2)_{0-6}$— group attached to a 5-6 membered saturated, partially unsaturated or aromatic heterocyclic ring containing 1-4 heteroatoms selected from N, O and S;

$R^{5a}$, $R^{2d}$, $R^{3d}$ and $R^{4d}$ are each independently a member selected from the group consisting of:

H, $C_{1-6}$-alkyl and $C_{1-6}$-alkylaryl, —CN; —$NO_2$; carbocylic aryl, —CN; —$NO_2$; or $R^{2d}$ and $R^{3d}$ taken together with the N atoms ther are independently attached form a 5-7 membered saturated, partially unsaturated or aromatic heterocyclic ring; or $R^{3d}$ and $R^{4d}$ taken together with the N atom to which they are attached form a 5-8 membered saturated, partially unsaturated or aromatic heterocyclic ring containing 1-4 heteroatoms selected from N, O and S;

J is a direct link or is a member selected from the group consisting of:

—N(—$R^9$)—C(=O)—; —C(=O)—N(—$R^9$)—; —O—; —S—; —SO—; —$SO_2$—; —$CH_2$—; —N(—$R^9$)—; and —N(—$R^9$)—$SO_2$—;

$R^9$ is a member selected from the group consisting of:
  H; —$C_{1-4}$-alkyl; —$C_{0-4}$-alkyl-carbocyclic aryl; —$(CH_2)_{0-4}$-5-6 membered saturated, partially unsaturated or aromatic heterocyclic ring containing 1-4 heteroatoms selected from N, O and S; —$(CH_2)_{1-6}$—C(=O)—O-$C_{1-4}$-alkyl; and —$(CH_2)_{1-6}$—C(=O)—N($R^{6a},R^{6b}$);

$R^{6a}$ and $R^{6b}$ are each a member independently selected from the group consisting of:
  H and —$C_{1-6}$-alkyl;

X is a member selected from the group consisting of:
  (a) phenyl substituted with 0-3 $R^{1e}$ groups;
  (b) naphthyl substituted with 0-3 $R^{1e}$ groups;
  (c) a 6-membered aromatic heterocyclic ring system containing 1-3 N atoms and having 0-3 ring atoms substituted with 0-3 $R^{1e}$ groups; and
  (d) an 8-10 membered fused aromatic heterocyclic bicyclic ring system containing 1-4 heteroatoms selected from N, O and S and 0-3 ring atoms of the fused heterocyclic bicyclic ring system are substituted with 0-3 $R^{1e}$ groups;

$R^{1e}$ is a member independently selected from the group consisting of:
  Halo; $CF_3$; —$C_{1-4}$-alkyl; carbocyclic aryl; —$C_{0-2}$-alkyl-CN; —O—$R^{2e}$; —$C_{0-2}$-alkyl-C(=O)—O—$R^{2e}$; —$C_{0-2}$-alkyl-C(=O)—N($R^{2e},R^{3e}$); —$C_{0-2}$-alkyl-$NO_2$; —$C_{0-2}$-alkyl-N($R^{2e},R^{3e}$); —$C_{0-2}$-alkyl-$SO_2$—N($R^{2e}$, $R^{3e}$); —$CO_{0-2}$-alkyl-$SO_2$—$R^{2e}$; trihaloalkyl; —O—$C_{0-2}$-alkyl-O—$R^{2e}$; —$C_{0-2}$-alkyl-O—$R^{2e}$; —O—$C_{1-4}$-alkyl-C(=O)—N($R^{2e},R^{3e}$); —O—$C_{1-4}$-alkyl-C(=O)—O—$R^{2e}$; —$C_{0-2}$-alkyl-N($R^{2e}$)—C(=O)—$R^{3e}$; —$C_{0-2}$-alkyl-N(—$R^{2e}$)—$SO_2$—$R^{3e}$; —$CH_2$—N($R^{2e}$)—C(=O)—$R^{3e}$; —$CH_2$—N($R^{2e}$)—$SO_2$—$R^{3e}$; —$(CH_2)_{0-6}$—$NR^{2e}R^{3e}$; —C(=O)—N($R^{2e}R^{3e}$); —N(—$(CH_2)_{1-6}$—$OR^{2e}$)$_2$; —N($R^{10}$)—$(CH_2)_{1-6}$—$OR^{2e}$; —N($R^{10}$)—C(=O)—$R^{2e}$; —N($R^{10}$)$SO_2$—$R^{2e}$; —C(=N($R^{10}$))—N($R^{2e},R^{3e}$); and a —$(CH_2)_{0-6}$-5-6 membered saturated, partially unsaturated or aromatic heterocyclic ring containing 1-4 heteroatoms selected from N, O and S;

$R^{10}$, $R^{2e}$ and $R^{3e}$ are each independently a member selected from the group consisting of:
  H; —$C_{1-4}$-alkyl; —$C_{0-2}$-alkyl-O—$R^{1g}$; —$C_{0-2}$-alkyl-N(—$R^{1g}$—$R^{2g}$); —$C_{1-4}$-alkyl-carbocyclic aryl; —$C_{1-4}$-alkyl-heterocyclic; and $R^{10}$ and $R^{2e}$, or $R^{2e}$ and $R^{3e}$ together with the N atom to which they are attached can form 5-8 membered heterocyclic ring containing 1-4 heteroatoms selected from N, O and S which can be substituted with 0-2 $R^{1g}$ groups;

$R^{1g}$ and $R^{2g}$ are independently a member selected from the group of:
  H; halo; —$C_{1-4}$-alkyl, a carbocyclic aryl group; a saturated, partially unsaturated or aromatic heterocyclic group; —CN; —C(=O)—N($R^{3g}$)$R^{4g}$; —C(=O)—$OR^{3g}$; —$NO_2$; —$(CH_2)_p$—$NR^{3g}R^{4g}$; —$SO^2NR^{3g}R^{1g}$; —$SO_2R^{3g}$; —$CF_3$; and —$(CH_2)_pOR^{3g}$;

p is an integer of 0-2; and $R^{3g}$ and $R^{4g}$ are each independently selected from the group consisting of:
  H; $C_{1-4}$-alkyl and —$C_{0-4}$-alkyl-carbocyclic aryl;
  and all pharmaceutically acceptable isomers, salts, hydrates, solvates and prodrug derivatives thereof.

A preferred embodiment of formula I are compounds of formula (Ia):

A-Q-D-E-G-J-X (Ia)

where:
A is selected from:
  (a) $C_1$-$C_6$-alkyl;
  (b) $C_3$-$C_8$-cycloalkyl;
  (c) —N($R^1,R^2$), N($R^1,R^2$)—C(=$NR^3$)—, N($R^1,R^2$)—C(=$NR^3$)—N($R^4$)—, $R^1$—C(=$NR^3$)—, $R^1$—C(=$NR^3$)—N($R^4$)—;
  (d) phenyl, which is independently substituted with 0-2 R substitutuents;
  (e) naphthyl, which is independently substituted with 0-2 R substitutuents; and
  (f) monocyclic or fused bicyclic heterocyclic ring system having from 5 to 10 ring atoms, wherein 1-4 ring atoms of the ring system are selected from N, O and S, and wherein the ring system may be substituted with 0-2 R substitutuents;

R is selected from:
  H, halo, —CN, —$CO_2R^1$, —C(=O)—N($R^1$, $R^2$), —$(CH_2)_m$—$CO_2R^1$, —$(CH_2)_m$—C(=O)—N($R^1$, $R^2$), —$NO_2$, —$SO_2N(R^1, R^2)$, —$SO_2R^1$, —$(CH_2)_mNR^1R^2$, ($CH_2)_m$—C(=$NR^3$)—$R^1$; —$(CH_2)_m$—C(=$NR^3$)—N($R^1,R^2$), —$(CH_2)_m$—N($R^4$)—C(=$NR^3$)—N($R^1,R^2$), —$(CH_2)_mNR^1$— group attached to a 3-6 membered heterocyclic ring having from 1 to 3 heteroatoms selected from the group consisting of N, O and S, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$CF_3$, —$OR^2$, and a 5-6 membered heterocyclic aromatic or partially saturated system, including imidazoline, containing from 1-4 heteroatoms selected from N, O and S, wherein from 1-4 hydrogen atoms on the heterocyclic system may be independently replaced with a member selected from the group consisting of halo, -methyl, —$C_2$-$C_4$-alkyl, —CN, —$C_{2-6}$alkenyl, —$C_{2-6}$alkynyl, —$C_{3-8}$cycloalkyl, —$C_{0-4}$alkyl$C_{3-8}$cycloalkyl and —$NO_2$;

m is an integer of 0-2;

$R^1$, $R^2$, $R^3$ and $R^4$ are independently selected from the group consisting of:
  H, —$OR^5$, —N(—$R^5$, —$R^6$), —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$alkylphenyl and —$C_{0-4}$alkylnaphthyl, wherein from 1-4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, and —$NO_2$; or $R^1$ and $R^2$, or $R^2$ and $R^3$ taken together can form a 3-8 membered cycloalkyl or a heterocyclic ring system, wherein the heterocyclic ring system may have from 3 to 10 ring atoms, with 1 to 2 rings being in the ring system and contain from 1-4 heteroatoms selected from N, O and S, wherein from 1-4 hydrogen atoms on the heterocyclic ring system may be independently replaced with a member selected from the group consisting of halo, $C_1$-$C_4$-alkyl, —CN—$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl and —$NO_2$;

$R^5$ and $R^6$ are independently selected from the group consisting of:
  H, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$alkylphenyl and —$C_{0-4}$alkylnapnthyl, wherein from 1-4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, and —NO$_2$; or R$^5$ and R$^6$ taken together can form a 3-8 membered cycloalkyl or a heterocyclic ring system, wherein the heterocyclic ring system may have from 3 to 10 ring atoms, with 1 to 2 rings being in the ring system and contain from 1-4 heteroatoms selected from N, O and S, wherein from 1-4 hydrogen atoms on the heterocyclic ring system may be independently replaced with a member selected from the group consisting of halo, $C_1$-$C_4$-alkyl, —CN —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl and —NO$_2$;

Q is a member selected from the group consisting of:
a direct link, —CH$_2$—, —C(=O)—, —O—, —NH—, —NMe-, —NHCH$_2$—, —NMeCH$_2$—, —CH$_2$NH—, —C(=NH)—, —C(=O)—NH—, —NH—C(=O)—, —CH$_2$NMe-, —C(=NMe)—;

D is a direct link or is a member selected from the group consisting of:
(a) phenyl, which is independently substituted with 0-2 R$^{1a}$ substitutuents;
(b) naphthyl, which is independently substituted with 0-2 R$^{1a}$ substitutuents; and
a monocyclic or fused bicyclic heterocyclic ring system having from 5 to 10 ring atoms, wherein 1-4 ring atoms of the ring system are selected from N, O and S, and wherein the ring system may be subsituted from 0-2 R$^{1a}$ substitutuents;

R$^{1a}$ is selected from:
halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, —NO$_2$, —(CH$_2$)NR$^{2a}$R$^{3a}$, —(CH$_2$)$_n$CO$_2$R$^{2a}$, —(CH$_2$)$_n$CONR$^{2a}$R$^{3a}$, —SO$_2$NR$^{2a}$R$^{3a}$, —SO$_2$R$^{2a}$, —CF$_3$, —OR$^{2a}$, and a 5-6 membered aromatic heterocyclic system containing from 1-4 heteroatoms selected from N, O and S, wherein from 1-4 hydrogen atoms on the aromatic heterocyclic system may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN and —NO$_2$;

R$^{2a}$ and R$^{3a}$ are independently selected from the group consisting of:
H, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$alkylphenyl and —$C_{0-4}$alkylnaphthyl, wherein from 1-4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN and —NO$_2$;

n is an integer of 0-2;

E is a member selected from the group consisting of:
a direct link, —O—, —NH—, —CH$_2$NH—, —NHCH$_2$—, —NMe-, —NH—C(=O)—NH—, —C(=O)—NH—, —NH—C(=O)—;

G is a member selected from the group consisting of:
(a) a C$_2$-alkenyl group or a $C_{3-8}$-cycloalkenyl group, wherein the alkenyl group and cycloalkenyl group attachment points are the alkenyl carbon atoms and wherein the C$_2$-alkenyl group or $C_{3-8}$-cycloalkenyl group is substituted with 0-4 R$^{1d}$ groups;
(b) a phenylene group wherein the ring carbon atoms of the phenylene group are substituted with 0-4 R$^{1d}$ groups;
(c) a 3-8 membered a saturated, partially unsaturated or aromatic monocyclic-heterocyclic ring system containing 1-4 heteroatoms selected from N, O and S, wherein 0-4 ring atoms of the heterocyclic ring may be substituted with 0-4 R$^{1d}$ groups; and,
(d) an 8-10 membered fused heterocyclic bicyclic ring system, containing 1-4 heteroatoms selected from N, O and S, wherein 0-4 ring atoms of the fused bicyclic ring system may be substituted with 0-4 R$^{1d}$ groups;

R$^{1d}$ is a member selected from the group consisting of:
H, halo; $C_{1-6}$-alkyl, carbocylic aryl, —CN; —NO$_2$; —(CH$_2$)$_{0-6}$—NR$^{2d}$R$^{3d}$; —SO$_2$NR$^{2d}$R$^{3d}$; —SO$_2$R$^{2d}$; —CF$_3$; —(CH$_2$)$_{0-6}$—OR$^{2d}$; —OH, —OC$_{1-6}$alkyl, —O—(CH$_2$)$_{1-6}$—OR$^{2d}$; —O—(CH$_2$)$_{1-6}$—C(=O)—O—R$^{2d}$; —O—(CH$_2$)$_{1-6}$—C(=O)—N(R$^{2d}$,R$^{3d}$); —N(R$^{5a}$)—(CH$_2$)$_{1-6}$—OR$^{2d}$; —N(R$^{5a}$)—(CH$_2$)$_{1-6}$—N(R$^{2d}$R$^{3d}$); —C(=O)N(R$^{2d}$R$^{3d}$); —N(R$^{5a}$)—(CH$_2$)$_{1-6}$—C(=O)—N(R$^{2d}$,R$^{3d}$); —N(—(CH$_2$)$_{1-6}$—OR$^{2d}$)$_2$; —N(R$^{5a}$)—(CH$_2$)$_{1-6}$—OR$^{2d}$; —N(R$^{5a}$)—C(=O)—R$^{2d}$; —N(R$^{5a}$)—SO$_2$—R$^{2d}$; —(CH$_2$)$_{0-6}$—C(=O)—O—R$^{2d}$; —(CH$_2$)$_{0-6}$—C(=O)—N(R$^{2d}$,R$^{3d}$); —(CH$_2$)$_{0-6}$—C(=NR$^{2d}$)—N(R$^{3d}$,R$^{4d}$); —(CH$_2$)$_{0-6}$—N(R$^{5a}$)C(=NR$^{2d}$)—N(R$^{3d}$,R$^{4d}$); and a —(CH$_2$)$_{0-6}$N(R$^{3d}$) group which is attached via the nitrogen atom to a carbon atom of a 5 to 6 membered saturated, partially unsaturated or aromatic heterocyclic ring containing 1-4 heteroatoms selected from N, O and S, and a —(CH$_2$)$_{0-6}$— group attached to a 5-6 membered saturated, partially unsaturated or aromatic heterocyclic ring containing 1-4 heteroatoms selected from N, O and S;

R$^{5a}$, R$^{2d}$, R$^{3d}$ and R$^{4d}$ are each independently a member selected from the group consisting of:
H, $C_{1-6}$-alkyl and $C_{1-6}$-alkylaryl, —CN; —NO$_2$; carbocylic aryl, —CN; —NO$_2$; or
R$^{2d}$ and R$^{3d}$ taken together with the N atoms ther are independently attached form a 5-7 membered saturated, partially unsaturated or aromatic heterocyclic ring; or
R$^{3d}$ and R$^{4d}$ taken together with the N atom to which they are attached form a 5-8 membered saturated, partially unsaturated or aromatic heterocyclic ring containing 1-4 heteroatoms selected from N, O and S;

J is a member selected from the group consisting of:
a direct link, —O—, —NH—, —NMe-, —C(=O)—NH—, —NH—C(=O)—;

X is a member selected from the group consisting of:
(a) phenyl substituted with 0-3 R$^{1e}$ groups;
(b) naphthyl substituted with 0-3 R$^{1e}$ groups and
(c) a 6-membered aromatic heterocyclic ring system containing 1-3 N atoms and having 0-3 ring atoms substituted with 0-3 R$^{1e}$ groups; and
(d) an 8-10 membered fused aromatic heterocyclic bicyclic ring system containing 1-4 heteroatoms selected from N, O and S and 0-3 ring atoms of the fused heterocyclic bicyclic ring system are substituted with 0-3 R$^{1e}$ groups;

R$^{1e}$ is a member independently selected from the group consisting of:
Halo; CF$_3$; —$C_{1-4}$-alkyl; carbocyclic aryl; —$C_{0-2}$-alkyl-CN; —O—R$^{2e}$; —$C_{0-2}$-alkyl-C(=O)—O—R$^{2e}$; —$C_{0-2}$-alkyl-C(=O)—N(R$^{2e}$, R$^{3e}$); —$C_{0-2}$-alkyl-NO$_2$; —$C_{0-2}$-alkyl-N(R$^{2e}$, R$^{3e}$); —$C_{0-2}$-alkyl-S$_{0-2}$—N(R$^2$, R$^{3e}$); —CO$_2$-alkyl-SO$_2$—R$^{2e}$; trihaloalkyl; O—$C_{0-2}$-alkyl-O—R$^{2e}$; —$C_{0-2}$-alkyl-O—R$^{2e}$; —O—$C_{1-4}$-alkyl-C(=O)—N(R$^{2e}$, R$^{3e}$); —$C_{1-4}$-alkyl-C(=O)—O—R$^{2e}$; —$C_{0-2}$-alkyl-N(R$^{2e}$)—C(=O)—R$^{3e}$; —$C_{0-2}$-alkyl-N(—R$^{2e}$)—SO$_2$—R$^{3e}$;

—CH$_2$—N(R$^{2e}$)—C(=O)—R$^{3e}$; —CH$_2$—N(R$^{2e}$)—SO$_2$—R$^{3e}$; —(CH$_2$)$_{0-6}$—NR$^{2e}$R$^{3e}$; —C(=O)—N(R$^{2e}$, R$^{3e}$); —N(—(CH$_2$)$_{1-6}$—OR$^{2e}$)$_2$; —N(R$^{10}$)—(CH$_2$)$_{1-6}$—OR$^{2e}$; —N(R$^{10}$)—C(=O)—R$^{2e}$; —N(R$^{10}$)—SO$_2$—R$^{2e}$; —C(=N(R$^{10}$))—N(R$^{2e}$,R$^{3e}$); and a —(CH$_2$)$_{0-6}$-5-6 membered saturated, partially unsaturated or aromatic heterocyclic ring containing 1-4 heteroatoms selected from N, O and S;

R$^{10}$, R$^{2e}$ and R$^{3e}$ are each independently a member selected from the group consisting of:

H; —C$_{1-4}$-alkyl; —C$_{0-2}$-alkyl-O—R$^{1g}$; —C$_{0-2}$-alkyl-N(—R$^{1g}$, —R$^{2g}$); —C$_{1-4}$-alkyl-carbocyclic aryl; —C$_{1-4}$-alkyl-heterocyclic; and R$^{10}$ and R$^{2e}$, or R$^2$ and R$^{3e}$ together with the N atom to which they are attached can form 5-8 membered heterocyclic ring containing 1-4 heteroatoms selected from N, O and S which can be substituted with 0-2 R$^{1g}$ groups;

R$^{1g}$ and R$^{2g}$ are independently a member selected from the group of:

H; halo; —C$_{1-4}$-alkyl, a carbocyclic aryl group; a saturated, partially unsaturated or aromatic heterocyclic group; —CN; —C(=O)—N(R$^{3g}$,R$^{4g}$); —C(=O)—OR$^{3g}$; —NO$_2$; —(CH$_2$)$_p$—NR$^{3g}$R$^{4g}$; —SO$_2$NR$^{3g}$R$^{4g}$; —SO$_2$R$^{3g}$; —CF$_3$; and —(CH$_2$)$_p$OR$^{3g}$;

p is an integer of 0-2; and

R$^{3g}$ and R$^{4g}$ are each independently selected from the group consisting of:

H; C$_{1-4}$-alkyl and —C$_{0-4}$-alkyl-carbocyclic aryl;

and all pharmaceutically acceptable isomers, salts, hydrates, solvates and prodrug derivatives thereof.

Another preferred embodiment of formula I are compounds of formula (Ib):

A-Q-D-E-G-J-X    (Ib)

where:

A is selected from:
(a) C$_1$-C$_6$-alkyl;
(b) C$_3$-C$_8$-cycloalkyl;
(c) —N(R$^1$,R$^2$), N(R$^1$,R$^2$)—C(=NR$^3$)—, N(R$^1$,R$^2$)—C(=NR$^3$)—N(R$^4$)—, R$^1$—C(=NR$^3$)—, R$^1$—C(=NR$^3$)—N(R$^4$)—;
(d) phenyl, which is independently substituted with 0-2 R substitutuents;
(e) naphthyl, which is independently substituted with 0-2 R substitutuents;
(f) a monocyclic or fused bicyclic ring system having from 5 to 10 ring atoms, wherein 1-4 ring atoms of the ring system are selected from N, O and S, and wherein the ring system may be substituted with 0-2 R substitutuents;

R is selected from:

H, halo, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —CF$_3$, —CN, —(CH$_2$)$_m$—CO$_2$R$^1$, —(CH$_2$)$_m$—C(=O)—N(R$^1$, R$^2$), —(CH$_2$)$_m$—C(=S)—N(R$^1$, R$^2$), —NO$_2$, —(CH$_2$)$_m$—SO$_2$N(R$^1$,R$^2$), —(CH$_2$)$_m$—SO$_2$R$^1$, —(CH$_2$)$_m$NR$^1$R$^2$, —(CH$_2$)$_m$OR$^1$, —(CH$_2$)$_m$—C(=NR$^3$)—R$^1$, —(CH$_2$)$_m$—C(=NR$^3$)—N(R$^1$,R$^2$), —(CH$_2$)$_m$—N(R$^4$)—C(=NR$^3$)—N(R$^1$,R$^2$), and a 3-8 membered cyclic system containing from 1-4 heteroatoms selected from N, O and S, wherein from 1-4 hydrogen atoms on the heterocyclic ring system may be independently replaced with a member selected from the group consisting of halo, C$_1$-C$_4$-alkyl, —CN —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl and —NO$_2$;

m is an integer of 0-2;

R$^1$, R$^2$, R$^3$ and R$^4$ are independently selected from the group consisting of:

H, —(CH$_2$)$_{0-4}$OR$^5$, —(CH$_2$)$_{0-4}$—CO$_2$R$^5$, —(CH$_2$)$_{0-4}$N(—R$^5$, —R$^6$), —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —C$_{0-4}$alkylaryl and —C$_{0-4}$alkylheteroaryl, and a 3-8 membered cyclic system containing from 1-4 heteroatoms selected from N, O and S, wherein from 1-4 hydrogen atoms on the heterocyclic ring system may be independently replaced with a member selected from the group consisting of halo, C$_1$-C$_4$-alkyl, —CN —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl and —NO$_2$; or R$^1$ and R$^2$, or R$^2$ and R$^3$ taken together can form a 3-8 membered cycloalkyl or a heterocyclic ring system, wherein the heterocyclic ring system may have from 3 to 10 ring atoms, with 1 to 2 rings being in the ring system and contain from 1-4 heteroatoms selected from N, O and S, where the hydrogen atoms on the heterocyclic ring system may be independently replaced with a member selected from the group consisting of halo, C$_1$-C$_4$-alkyl, —CN, —CO$_2$R$^5$, —OH, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl and —NO$_2$;

R$^5$ and R$^6$ are independently selected from the group consisting of:

H, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —C$_{0-4}$alkylaryl and —C$_{0-4}$alkylheteroaryl, wherein from 1-4 hydrogen atoms on the ring atoms of the phenyl and naphthyl moieties may be independently replaced with a member selected from the group consisting of halo, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —CN, and —NO$_2$; or R$^5$ and R$^6$ taken together can form a 3-8 membered cycloalkyl or a heterocyclic ring system, wherein the heterocyclic ring system may have from 3 to 10 ring atoms, with 1 to 2 rings being in the ring system and contain from 1-4 heteroatoms selected from N, O and S, wherein from 1-4 hydrogen atoms on the heterocyclic ring system may be independently replaced with a member selected from the group consisting of halo, —C$_1$-C$_4$-alkyl, —CN—C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl and —NO$_2$;

Q is a member selected from the group consisting of:

a direct link, —CH$_2$—, —C(=O)—, —O—, —N(R$^7$)—, —N(R$^7$)CH$_2$—, —CH$_2$N(R$^7$)—, —C(=NR$^7$)—, —C(=O)—N(R$^7$)—, —N(R$^7$)—C(=O)—, —S—, —SO—, —SO$_2$—, —SO$_2$—N(R$^7$)— and —N(R$^7$)—SO$_2$—; preferably, Q is a member selected from the group consisting of: a direct link, —CH$_2$—, —C(=O)—, —O—, —NH—, —NMe-, —NHCH$_2$—, —NMeCH$_2$—, —CH$_2$NH—, —C(=NH)—, —C(=O)—NH—, —NH—C(=O)—, —CH$_2$NMe-, —C(=NMe)—;

R$^7$ is selected from:

H; —C$_{1-4}$-alkyl; —C$_{0-4}$-alkylaryl; —C$_{0-4}$-alkyl-heteroaryl; —C$_{1-4}$-alkyl-O—C$_{1-4}$-alkyl, —C$_{1-4}$-alkyl-N(—C$_{1-4}$-alkyl, —C$_{1-4}$-alkyl); —C$_{1-4}$-alkyl-C(=O)—O—C$_{1-4}$-alkyl, and —C$_{1-4}$-alkyl-C(=O)—N(—C$_{1-4}$-alkyl, —C$_{1-4}$-alkyl);

D is a direct link or is a member selected from the group consisting of:
  (a) phenyl, which is independently substituted with 0-2 $R^{1a}$ substitutuents;
  (b) naphthyl, which is independently substituted with 0-2 $R^{1a}$ substitutuents; and
  (c) a monocyclic or fused bicyclic heterocyclic ring system having from 5 to 10 ring atoms, wherein 1-4 ring atoms of the ring system are selected from N, O and S, and wherein the ring system may be subsituted from 0-2 $R^{1a}$ substitutuents;

$R^{1a}$ is selected from:
  halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, —$NO_2$, —$(CH_2)_n OR^{2a}$, —$(CH_2)_n NR^{2a}R^{3a}$, —$(CH_2)_n CO_2 R^{2a}$, —$(CH_2)_n CONR^{2a}R^{3a}$, —$SO_2 NR^{2a}R^{3a}$, —$SO_2 R^{2a}$, —$CF_3$, and a 5-6 membered aromatic heterocyclic system containing from 1-4 heteroatoms selected from N, O and S, wherein from 1-4 hydrogen atoms on the aromatic heterocyclic system may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN and —$NO_2$, $R^{2a}$ and $R^{3a}$ are independently selected from the group consisting of:
  H, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —$C_{0-4}$alkylaryl and —$C_{0-4}$alkylheteroaryl, wherein from 1-4 hydrogen atoms on the ring atoms of the phenyl and naphthyl moieties may be independently replaced with a member selected from the group consisting of halo, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN and —$NO_2$;

n is an integer of 0-2;

E is a direct link or a member selected from the group consisting of:
  —$C_{1-2}$-alkyl-, —S—, —SO—, —$SO_2$—, —O—$C_{0-1}$-alkyl-, —$C_{0-1}$-alkyl-O—, —$C_{0-1}$-alkyl-N(—$R^8$)—, —N(—$R^8$)—$C_{0-1}$-alkyl-, —$C_{0-1}$-alkyl-C(=O)—N(—$R^8$)—$C_{0-1}$-alkyl, —$C_{0-1}$-alkyl-N(—$R^8$)—C(=O)—$C_{0-1}$-alkyl-, and —$C_{0-1}$-alkyl-N($R^8$)—C(=O)—N(—$R^8$)—$C_{0-1}$-alkyl-; preferably, E is a member selected from the group consisting of: a direct link, —O—, —NH—, —$CH_2$NH—, —$NHCH_2$—, —$CH_2$O—, —$OCH_2$—, —NMe-, —NH—C(=O)—NH—, —$CH_2$—NH—C(=O)—NH—, —C(=O)—NH—, —NH—C(=O)—; —C(=O)—NMe-, —NMe-C(=O)—;

$R^8$ is a member selected from the group consisting of:
  H; —$C_{1-4}$-alkyl; —$C_{0-4}$-alkylaryl; —$C_{0-4}$-alkyl-heteroaryl; —$C_{1-4}$-alkyl-$OR^{2b}$, —$C_{1-4}$-alkyl-N(—$R^{2b}$, —$R^{3b}$); —$C_{1-4}$-alkyl-C(=O)—$OR^{2b}$; —$C_{1-4}$-alkyl-C(=O)—N(—$R^{2b}$, —$R^{3b}$); —$C_{0-4}$-alkyl-C(=O)—$R^{2b}$; and —$C_{0-4}$-alkyl-$SO_2$—$R^{2b}$;

$R^{2b}$ and $R^{3b}$ are each a member independently selected from the group consisting of:
  H, —$C_{1-4}$-alkyl, —$C_{1-4}$-alkyl-$CO_2$—$C_{0-4}$-alkyl, —$C_{0-4}$-alkyl-aryl; —$C_{0-4}$-alkyl-heterocyclic group, and $R^{2b}$ and $R^{3b}$ together with the N atom to which they are attached can form a 5-8 membered heterocyclic ring containing 1-4 heteroatoms selected from N, O and S, wherein the heterocyclic ring may be substituted with 0-2 $R^{1c}$ groups;

$R^{1c}$ is a member selected from the group consisting of:
  Halo; —$C_{1-4}$-alkyl; —CN, —$NO_2$; —C(=O)—N(—$R^{2c}$, —$R^{3c}$); —C(=O)—$OR^{2c}$; —$(CH_2)_q$—N(—$R^{2c}$, —$R^{3c}$); —$SO_2$—N(—$R^{2c}$; —$R^{3c}$); —$SO_2 R^{2c}$; —$CF_3$ and —$(CH_2)_q$—$OR^{2c}$;

$R^{2c}$ and $R^{3c}$ are each independently a member selected from the group consisting of:
  H; —$C_{1-4}$-alkyl and —$C_{1-4}$-alkyl-aryl;

q is an integer of 0-2;

G is a member selected from the group consisting of:
  (a) $C_2$-alkenyl or $C_{3-8}$-cycloalkenyl, wherein the alkenyl and cycloalkenyl attachment points are the alkenyl carbon atoms and wherein the —$C_2$-alkenyl or —$C_{3-8}$-cycloalkenyl are substituted with 0-4 $R^{1d}$ groups;
  (b) a phenylene group wherein the ring carbon atoms of the phenylene group are substituted with 0-4 $R^{1d}$ groups;
  (c) a 3-8 membered a saturated, partially unsaturated or aromatic monocyclic ring system containing 1-4 heteroatoms selected from N, O and S, wherein 0-2 ring atoms of the heterocyclic ring may be substituted with 0-4 $R^{1d}$ groups; and,
  (d) an 8-10 membered fused cyclic system, containing 0-4 heteroatoms selected from N, O and S, wherein 0-2 ring atoms of the fused bicyclic ring system may be substituted with 0-4 $R^{1d}$ groups;

$R^{1d}$ is a member selected from the group consisting of:
  H, halo; —$CF_3$; —$OCF_3$, —$OCF_2H$, —$OCFH_2$, —$OCH_2CF_3$, —$OCF_2CF_3$, $C_{1-6}$-alkyl, carbocyclic aryl, —CN; —$NO_2$; —$(CH_2)_{0-6}$-$NR^{2d}R^{3d}$; —$(CH_2)_{0-6}$—$OR^{2d}$; —OH, —$OC_{1-6}$alkyl, —O—$(CH_2)_{1-6}OR^{2d}$; —O—$(CH_2)_{1-6}$—$NR^{2d}R^{3d}$; —N($R^{5a}$)—$(CH_2)_{1-6}$—$OR^{2d}$; —N($R^{5a}$)—$(CH_2)_{1-6}$—N($R^{2d},R^{3d}$); —$(CH_2)_{0-6}$—C(=O)—O—$R^{2d}$; —$(CH_2)_{0-6}$—C(=O)—N($R^{2d},R^{3d}$); —O—$(CH_2)_{1-6}$—C(=O)—O—$R^{2d}$; —O—$(CH_2)_{1-6}$—C(=O)—N($R^{2d},R^{3d}$); —N($R^{5a}$)—$(CH_2)_{1-6}$—C(=O)—O—$R^{2d}$; —N($R^{5a}$)—$(CH_2)_{1-6}$—C(=O)—N($R^{2d},R^{3d}$); —N(—$(CH_2)_{1-6}$—$OR^{2d}$)$_2$; —N(—$(CH_2)_{1-6}$—N($R^{2d},R^{3d}$))$_2$; —$(CH_2)_{0-6}$—$SO_2 NR^{2d}R^{3d}$; —$(CH_2)_{0-6}$—$SO_2 R^{2d}$; —$(CH_2)_{0-6}$—N($R^{5a}$)—C(=O)—$R^{2d}$; —$(CH_2)_{0-6}$—N($R^{5a}$)—$SO_2$—$R^{2d}$, —$(CH_2)_{0-6}$—C(=$NR^{2d}$)—N($R^{3d},R^{4d}$); —$(CH_2)_{0-6}$—N($R^{5a}$)C(=$NR^{2d}$)—N($R^{3d},R^{4d}$); —$(CH_2)_{0-6}$—N($R^{5a}$)C(=$NR^{2d}$)—$R^{4d}$; —O—$(CH_2)_{1-6}$—$SO_2 NR^{2d}R^{3d}$; —O—$(CH_2)_{1-6}$—$SO_2 R^{2d}$; —O—$(CH_2)_{1-6}$—N($R^{5a}$)—C(=O)—$R^{2d}$; —O—$(CH_2)_{1-6}$—N($R^{5a}$)—$SO_2$—$R^{2d}$, —O—$(CH_2)_{1-6}$—C(=$NR^{2d}$)—N($R^{3d},R^{4d}$); —O—$(CH_2)_{1-6}$—N($R_{5a}$)C(=$NR^{2d}$)—N($R^{3d},R^{4d}$); —O—$(CH_2)_{1-6}$—N($R^{5a}$)C(=$NR^{2d}$)—$R^{4d}$; —N($R^{5d}$)—$(CH_2)_{1-6}SO_2 NR^{2d}R^{3d}$; —N($R^{5d}$)—$(CH_2)_{1-6}$—$SO_2 R^{2d}$; —N($R^{5d}$)—$(CH_2)_{1-6}$—N($R^{5a}$)—C(=O)—$R^{2d}$; —N($R^{5d}$)—$(CH_2)_{1-6}$—N($R^{5a}$)—$SO_2$—$R^{2d}$, —N($R^{5d}$)—$(CH_2)_{1-6}$—C(=$NR^{2d}$)—N($R^{3d},R^{4d}$); —N($R^{5d}$)—$(CH_2)_{1-6}$—N($R^{5a}$)C(=$NR^{2d}$)—N($R^{3d},R^{4d}$); —N($R^{5d}$)—$(CH_2)_{1-6}$—N($R^{5a}$)C(=$NR^{2d}$)—$R^{4d}$; and a 3-8 membered cyclic system containing from 1-4 heteroatoms selected from N, O and S, wherein from 1-4 hydrogen atoms on the heterocyclic ring system may be independently replaced with a member selected from the group consisting of halo, $C_1$-$C_4$-alkyl, —CN—$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl and —$NO_2$;

$R^{5a}$, $R^{2d}$, $R^{3d}$, $R^{4d}$ and $R^{5d}$ are each independently a member selected from the group consisting of:

H, $C_{1-6}$-alkyl and $C_{1-6}$alkylaryl, —CN; —NO$_2$; or $R^{2d}$ and $R^{3d}$, or $R^{3d}$ and $R^{4d}$ taken together with the N atoms they are independently attached form a 3-8 membered saturated, partially unsaturated or aromatic heterocyclic ring;

J is a direct link or is a member selected from the group consisting of:

—N(—R$^9$)—C(=O)—; —C(=O)—N(—R$^9$)—; —O—; —S—; —SO—; —SO$_2$—; —SO2N(R9)—, —CH$_2$—; —N(—R$^9$)—; and —N(—R$^9$)—SO$_2$—; preferably, J is a member selected from the group consisting of: a direct link, —O—, —SO2—, —SO2NH—, —NH—, —NMe-, —C(=O)—NH—, —NH—C(=O)—;

$R^9$ is a member selected from the group consisting of:

H; —C$_{1-4}$-alkyl; —C$_{0-4}$-alkylaryl; —C$_{0-4}$-alkyl-heteroaryl; —C$_4$-alkyl-OR$^{6a}$, —C$_{1-4}$-alkyl-N(—R$^{6a}$, —R$^{6b}$); —C$_{1-4}$-alkyl-C(=O)—OR$^{6a}$, and —C$_{1-4}$-alkyl-C(=O)—N(—R$^{6a}$, —R$^{6b}$);

$R^{6a}$ and $R^{6b}$ are each a member independently selected from the group consisting of:

H and —C$_{1-6}$-alkyl;

X is a member selected from the group consisting of:

(a) phenyl substituted with 0-3 R$^{1e}$ groups;

(b) naphthyl substituted with 0-3 R$^{1e}$ groups and (c) a 6-membered aromatic heterocyclic ring system containing 1-3 N atoms and having 0-3 ring atoms substituted with 0-3 R$^{1e}$ groups; and (d) an 8-10 membered fused bicyclic ring system containing 1-4 heteroatoms selected from N, O and S and 0-3 ring atoms of the fused heterocyclic bicyclic ring system are substituted with 0-3 R$^{1e}$ groups;

R$^{1e}$ is a member independently selected from the group consisting of:

Halo; CF$_3$; —C$_{1-4}$-alkyl; carbocyclic aryl; —C$_{0-2}$-alkyl-CN; —O—R$^{2e}$; —C$_{0-2}$-alkyl-C(=O)—O—R$^{2e}$; —C$_{0-2}$-alkyl-C(=O)—N(R$^{2e}$, R$^{3e}$); —C$_{0-2}$-alkyl-NO$_2$; —C$_{0-2}$-alkyl-N(R$^{2e}$, R$^{3e}$); —C$_{0-2}$-alkyl-SO$_2$—N(R$^{2e}$, R$^{3e}$); —C$_{0-2}$-alkyl-SO$_2$—R$^{2e}$; trihaloalkyl; —O—C$_{0-2}$-alkyl-O—R$^{2e}$; —C$_{0-2}$-alkyl-O—R$^{2e}$; —O—C$_{1-4}$-alkyl-C(=O)—N(R$^{2e}$, R$^{3e}$); —O—C$_{1-4}$-alkyl-C(=O)—O—R$^{2e}$; —C$_{0-2}$-alkyl-N(R$^{2e}$)—C(=O)—R$^{3e}$; —C$_{0-2}$-alkyl-N(—R$^{2e}$)—SO$_2$—R$^{3e}$; —CH$_2$—N(R$^{2e}$)—C(=O)—R$^{3e}$; —CH$_2$—N(R$^{2e}$)—SO$_2$—R$^{3e}$; —(CH$_2$)$_{0-6}$—NR$^{2e}$R$^{3e}$; —C(=O)—N(R$^{2e}$, R$^{3e}$); —N(—(CH$_2$)$_{1-6}$—OR$^{2e}$)$_2$; —N(R$^{10}$)—(CH$_2$)$_{1-6}$—OR$^{2e}$; —N(R$^{10}$)—C(=O)—R$^{2e}$; —N(R$^{10}$)—SO$_2$—R$^{2e}$; —C(=N(R$^{10}$))—N(R$^{2e}$,R$^{3e}$); and a —(CH$_2$)$_{0-6}$-5-6 membered saturated, partially unsaturated or aromatic heterocyclic ring containing 1-4 heteroatoms selected from N, O and S;

R$^{10}$, R$^{2e}$ and R$^{3e}$ are each independently a member selected from the group consisting of:

H; —C$_{1-4}$-alkyl; —C$_{0-2}$-alkyl-O—R$^{1g}$; —C$_{0-2}$-alkyl-N(—R$^{1g}$, —R$^{2g}$); —C$_{1-4}$-alkyl-carbocyclic aryl; —C$_{1-4}$-alkyl-heterocyclic; and R$^{10}$ and R$^{2e}$, or R$^{2e}$ and R$^{3e}$ together with the N atom to which they are attached can form 5-8 membered heterocyclic ring containing 1-4 heteroatoms selected from N, O and S which can be substituted with 0-2 R$^{1g}$ groups;

R$^{1g}$ and R$^{2g}$ are independently a member selected from the group of:

H; halo; —C$_{1-4}$-alkyl, a carbocyclic aryl group; a saturated, partially unsaturated or aromatic heterocyclic group; —CN; —C(=O)—N(R$^{3g}$)R$^{4g}$; —C(=O)—OR$^{3g}$; —NO$_2$; —(CH$_2$)$_p$—NR$^{3g}$R$^{4g}$; —SO$_2$NR$^{3g}$R$^{4g}$; —SO$_2$R$^{3g}$; —CF$_3$; and —(CH$_2$)$_p$OR$^{3g}$;

p is an integer of 0-2;

R$^{3g}$ and R$^{4g}$ are each independently selected from the group consisting of:

H; C$_{1-4}$-alkyl and —C$_{0-4}$-alkyl-carbocyclic aryl;

and all pharmaceutically acceptable isomers, salts, hydrates, solvates and prodrug derivatives thereof.

Another preferred embodiment of formula I are compounds of formula (Ic):

A-Q-D-E-G-J-X    (Ic)

where:

A is a member selected from the group consisting of:

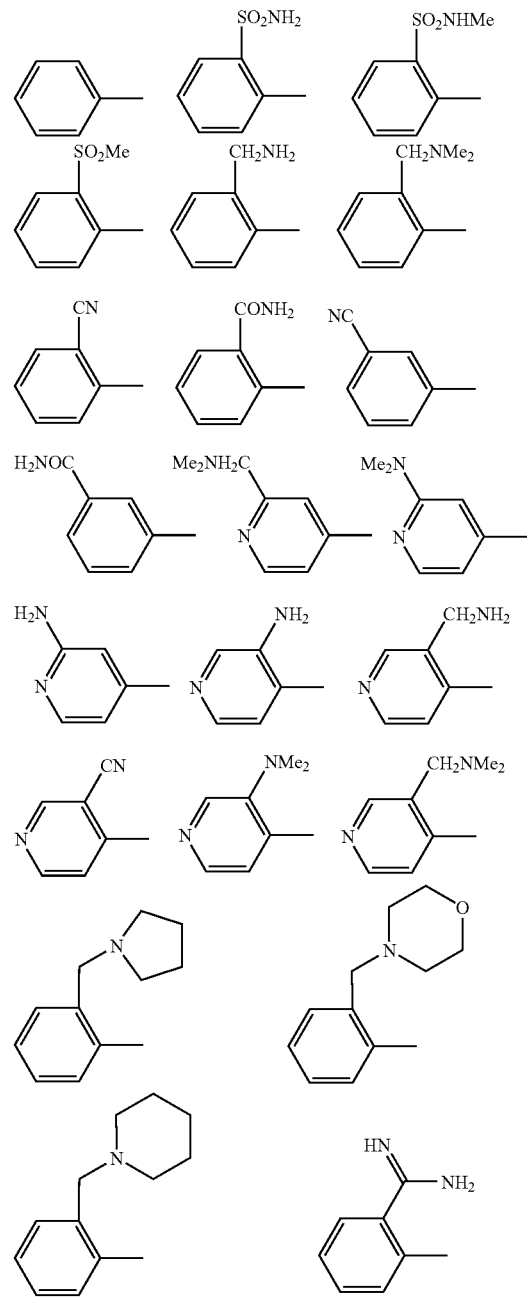

-continued
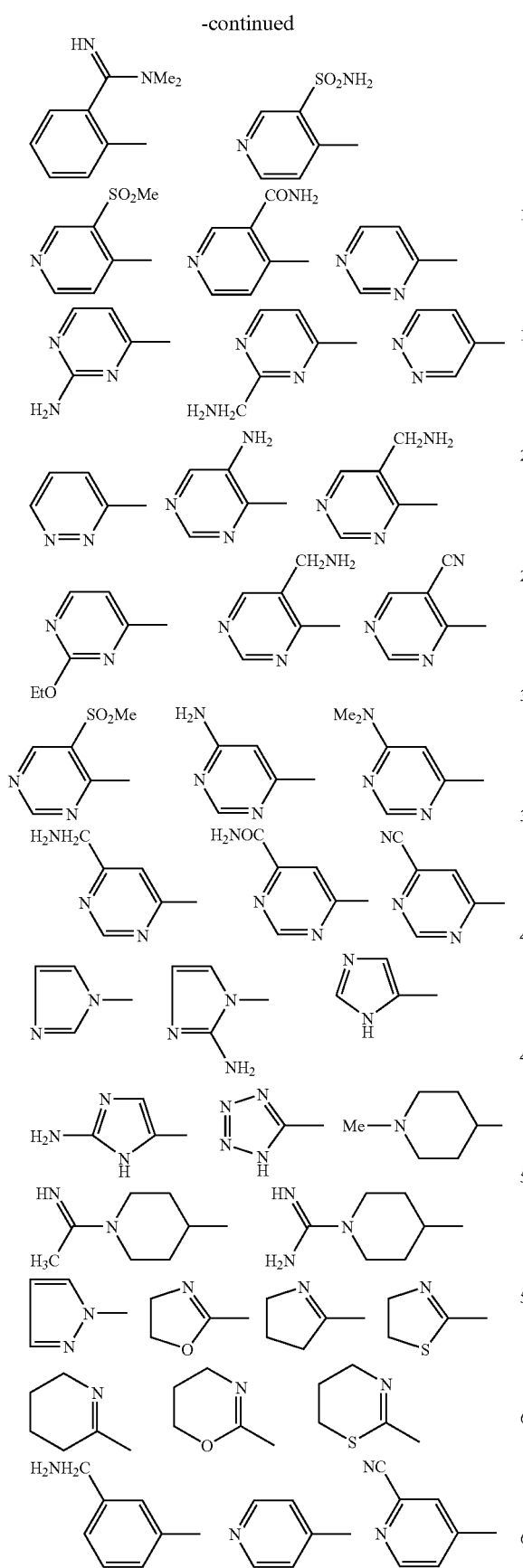
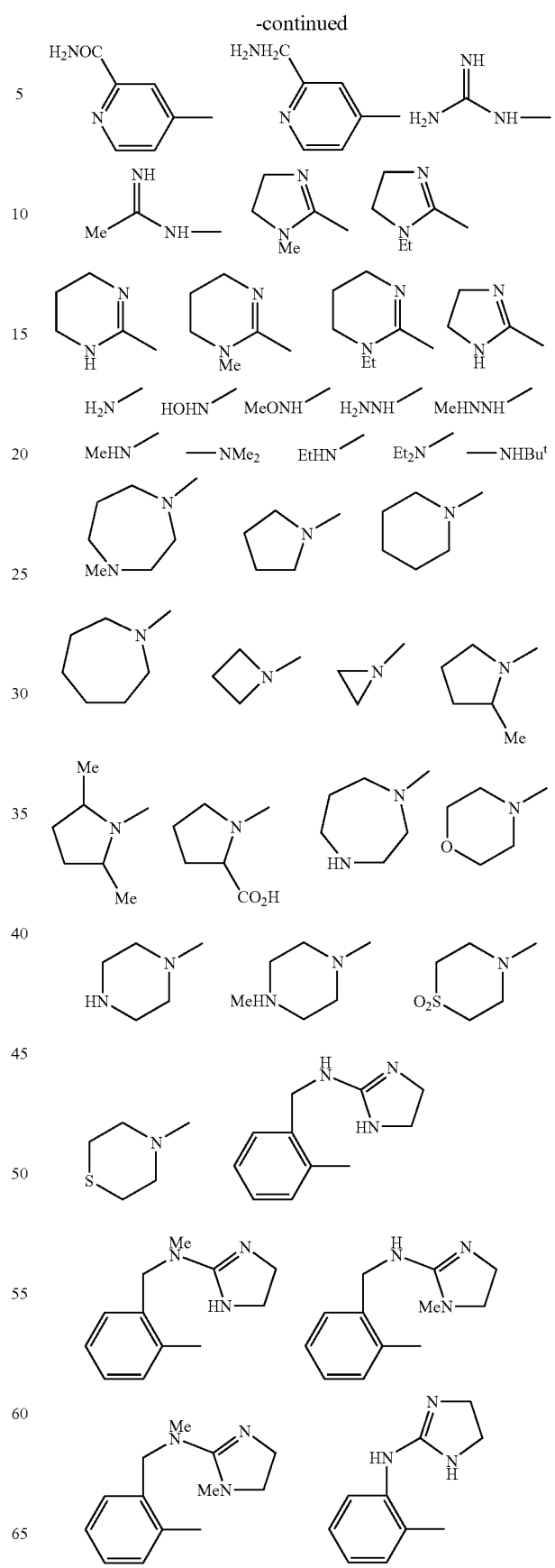

-continued
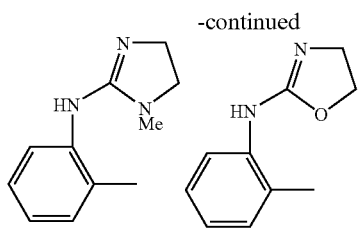
Q is a member selected from the group consisting of:
a direct link, —C(=O)—, —NH—, —NMe-, —NHCH₂—, —NMeCH₂—, —C(=NH)—, —C(=NMe)—;
D is a direct link or is a member selected from the group consisting of:
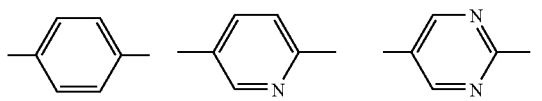
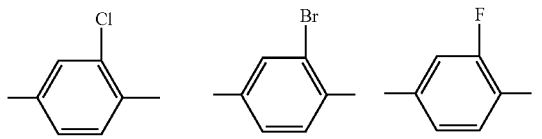
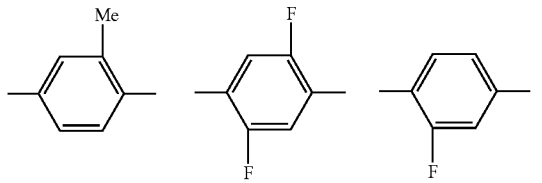
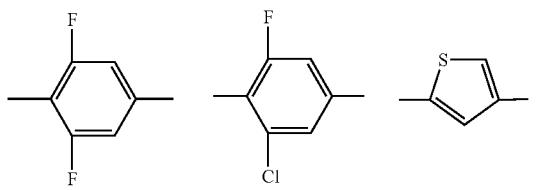
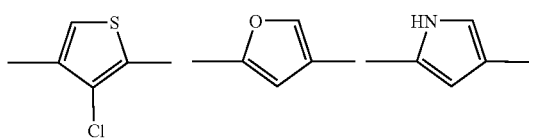
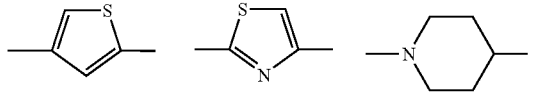
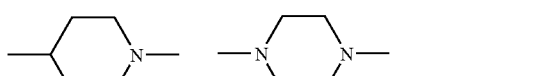
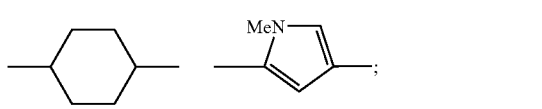
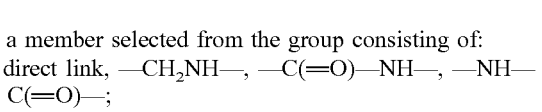
E is a member selected from the group consisting of:
a direct link, —CH₂NH—, —C(=O)—NH—, —NH—C(=O)—;
G is a member selected from the group consisting of:
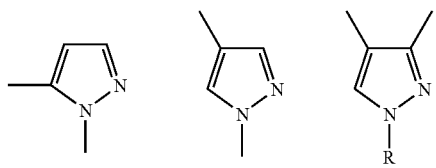
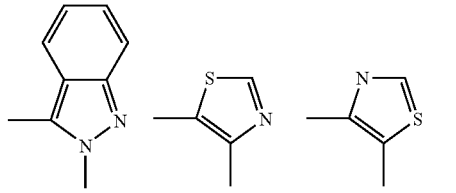
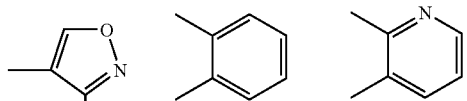
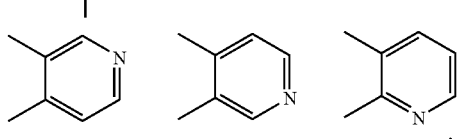
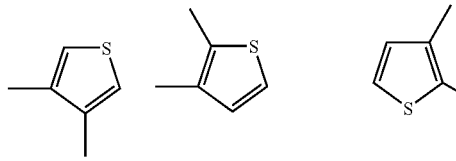
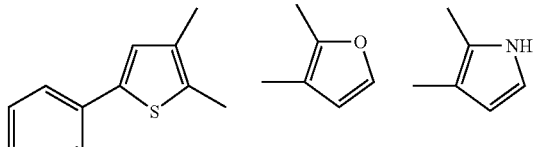
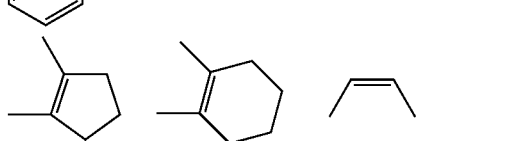
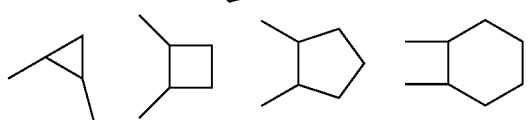
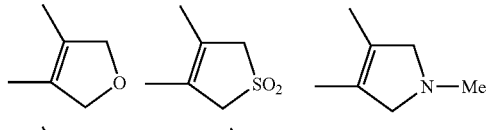
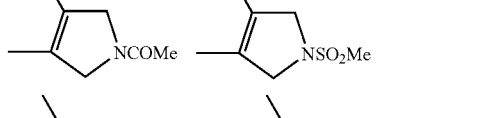
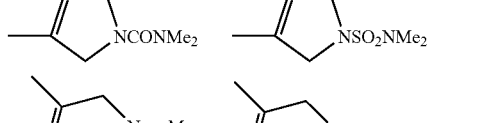
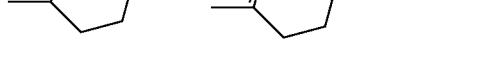

-continued

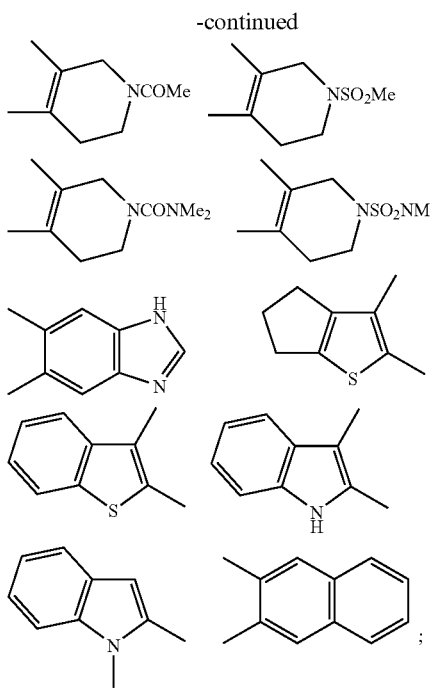

G is substituted by 0-4 $R^{1d}$ groups and each $R^{1d}$ group is independently selected from the group consisting of:

H, —$CH_3$, —$CF_3$, —Cl, —F, —Br, —$NH_2$, —$NMe_2$, —OH, —OMe, —$NHSO_2Me$, —$NO_2$, —CN, —C(=O)—OMe, —$CO_2H$, —$CONH_2$, —$SO_2NH_2$, —$SO_2CH_3$, —NHC(=O)Me, —C(=O)N(-Me)$_2$, —$CH_2NH_2$, —$CH_2N(-Me)_2$, —$CH_2OH$, —$OCH_2CO_2H$, —$OCH_2C(=O)$—OMe, —$OCH_2C(=O)$—$NH_2$ and —$OCH_2C(=O)N(-Me)_2$.

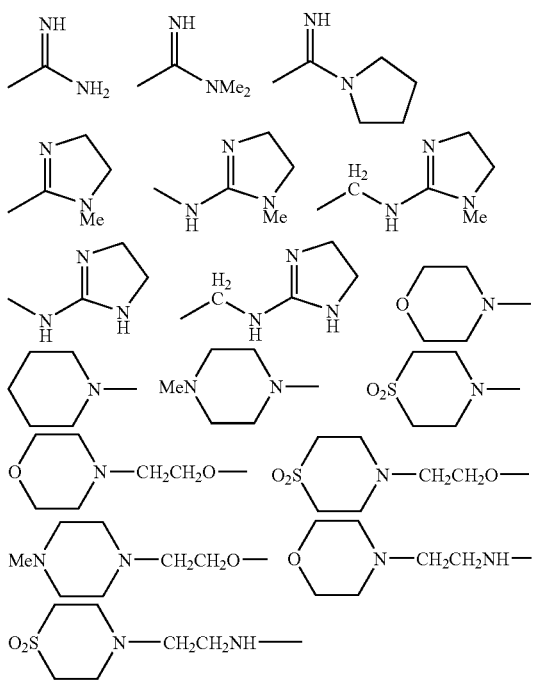

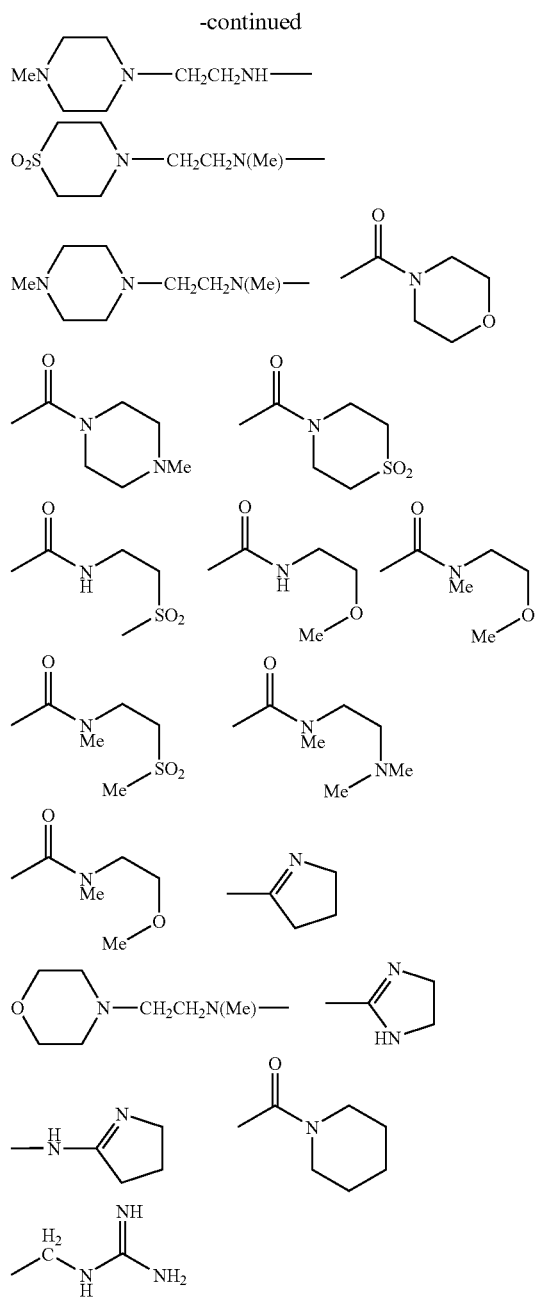

J is a member selected from the group consisting of:
a direct link, —O—, —NH—, —C(=O)—NH— and —NH—C(=O)—;

X is a member selected from the group consisting of:

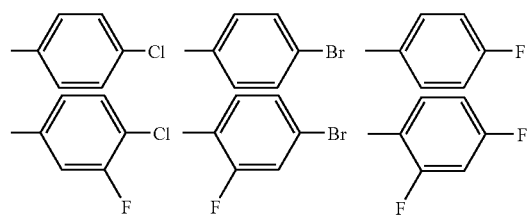

-continued
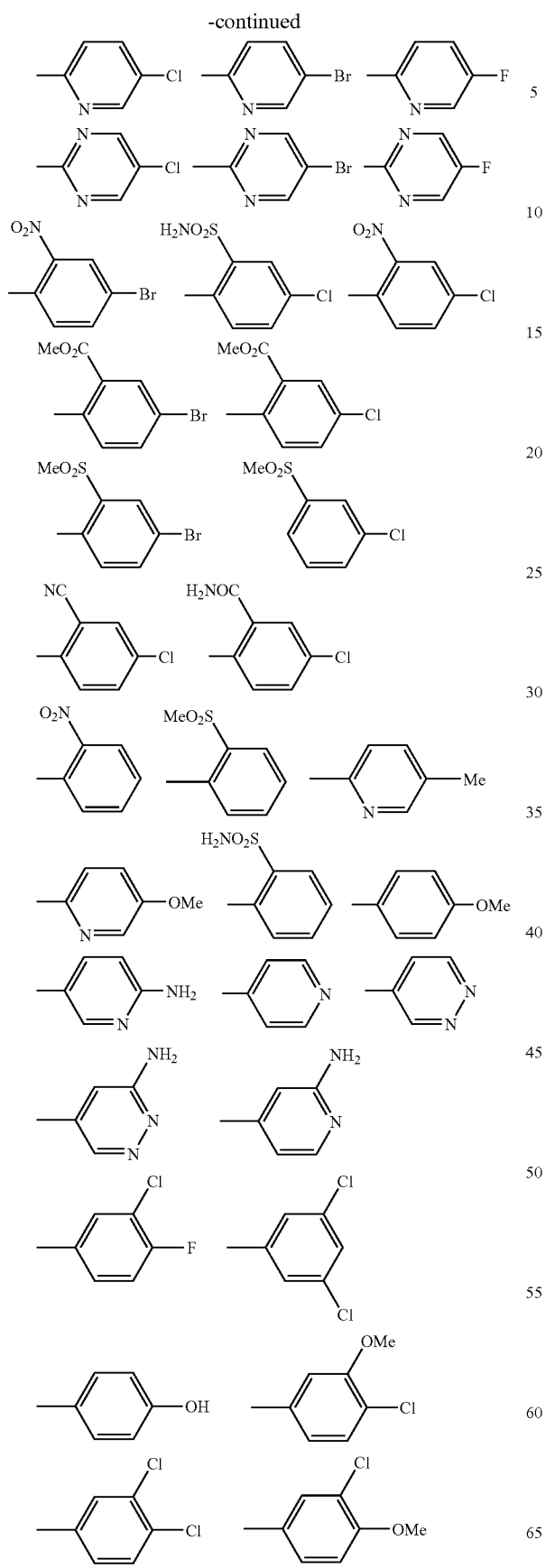
-continued
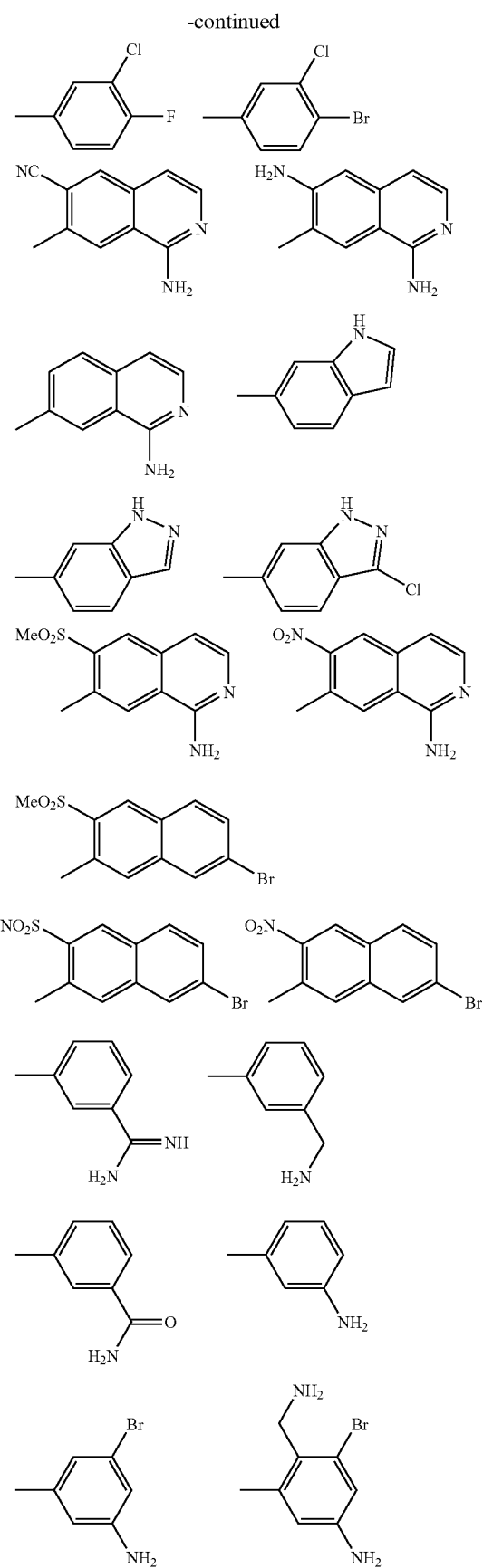

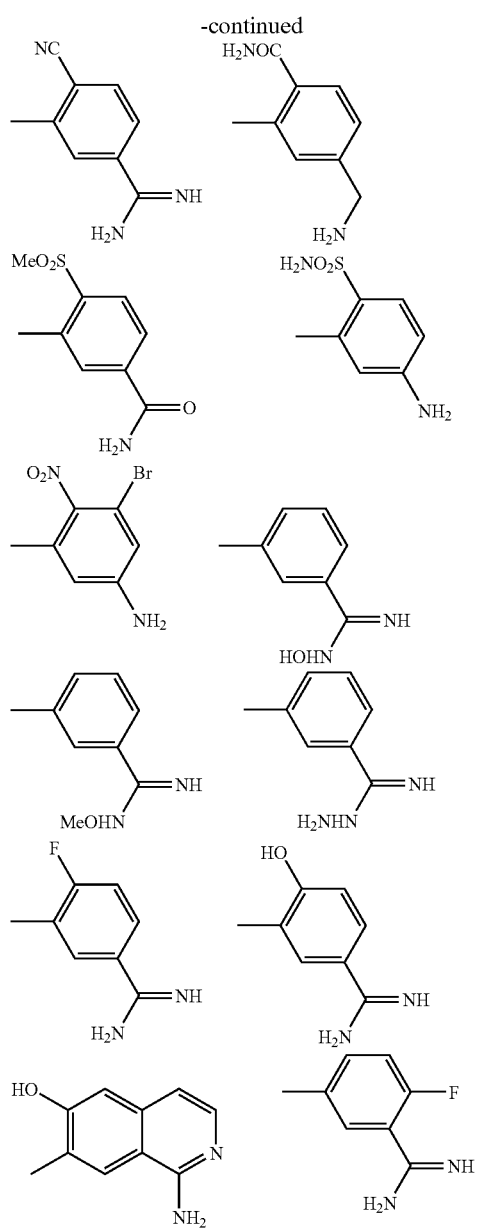

and all pharmaceutically acceptable isomers, salts, hydrates, solvates and prodrug derivatives thereof.

Still another preferred embodiment of the invention are compounds of the following formula (II):

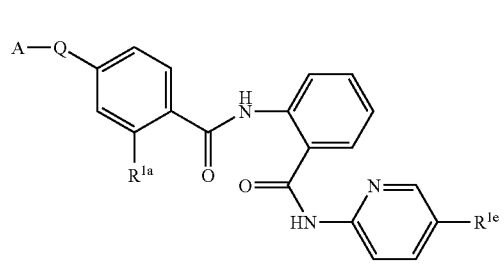

where:
$R^{1a}$ is a member selected from the group consisting of:
H, —F, —Cl and —Br;

$R^{1e}$ is a member selected from the group consisting of:
H, —F, —Cl, —Br, —OMe, —OH, -Me, —CF and —CH$_2$NH$_2$; and A-Q is a member selected from the group consisting of:

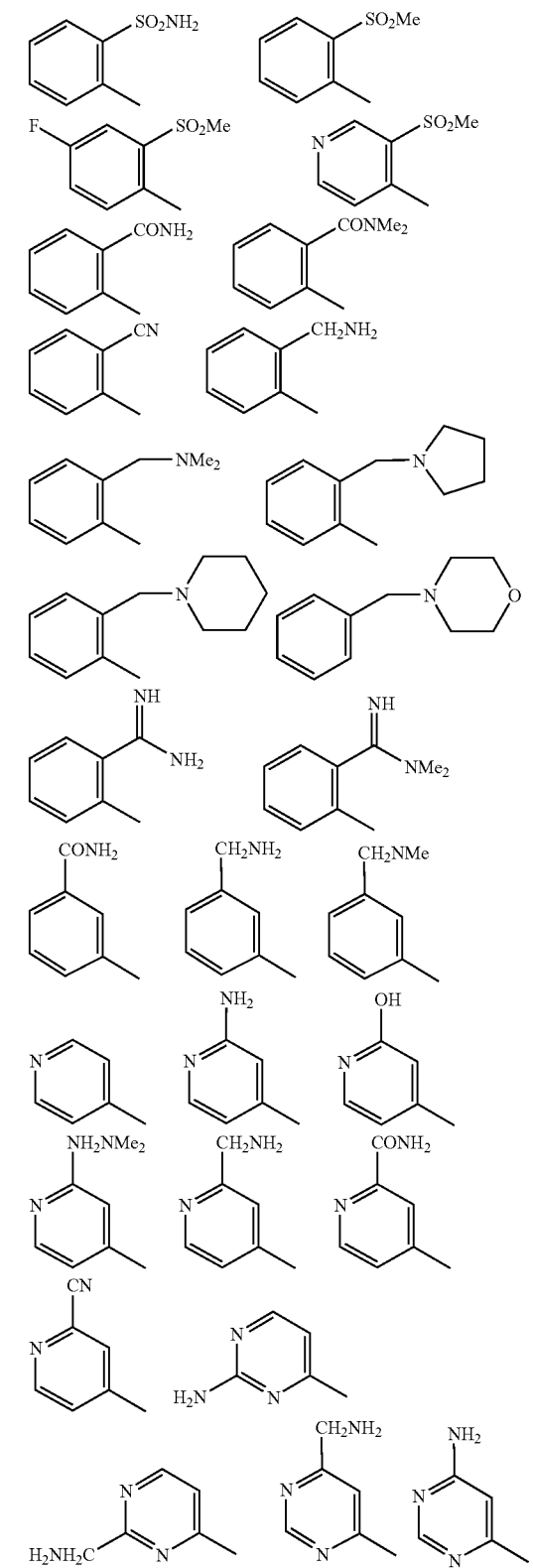

-continued

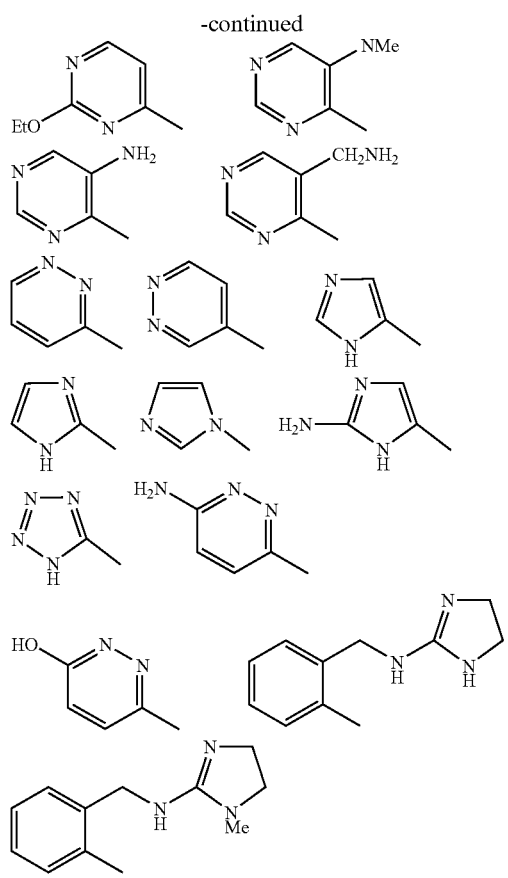

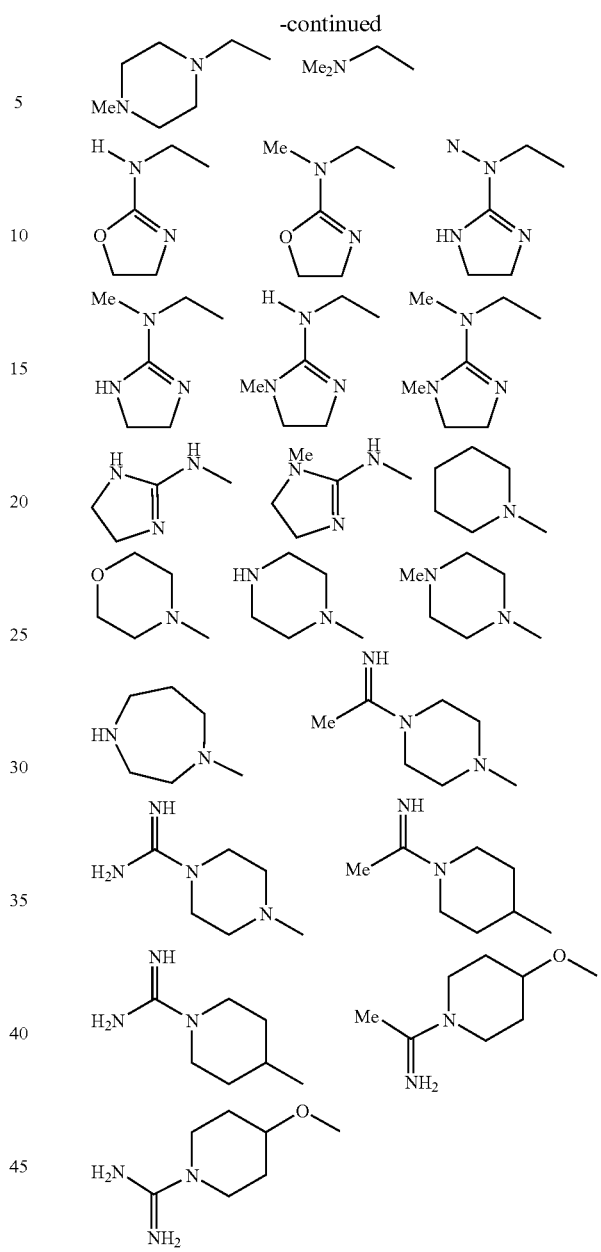

and all pharmaceutically acceptable isomers, salts, hydrates, solvates and prodrug derivatives thereof.

Still another preferred embodiment the invention are compounds of formula (III):

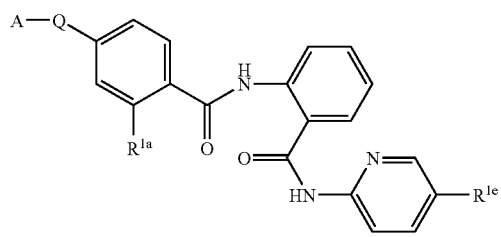

(III)

where:
R$^{1a}$ is a member selected from the group consisting of: H, —F, —Cl and —Br;
R$^{1e}$ is a member selected from the group consisting of: H, —F, —Cl, —Br, —OMe, —OH, -Me, —CF$_3$ and —CH$_2$NH$_2$; and
A-Q is a member selected from the group consisting of:

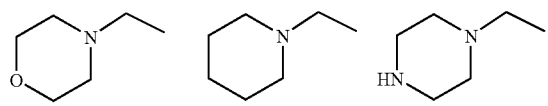

and all pharmaceutically acceptable isomers, salts, hydrates, solvates and prodrug derivatives thereof.

Another further preferred embodiment of the invention are compounds according to the formula (IV):

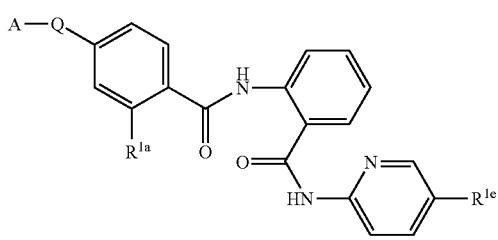

(IV)

where:

$R^{1a}$ is a member selected from the group consisting of:
 H, —F, —Cl and —Br;

$R^{1e}$ is a member selected from the group consisting of:
 H, —F, —Cl, —Br, —OMe, —OH, -Me, —CF$_3$ and —CH$_2$NH$_2$;

A-Q is a member selected from the group consisting of:

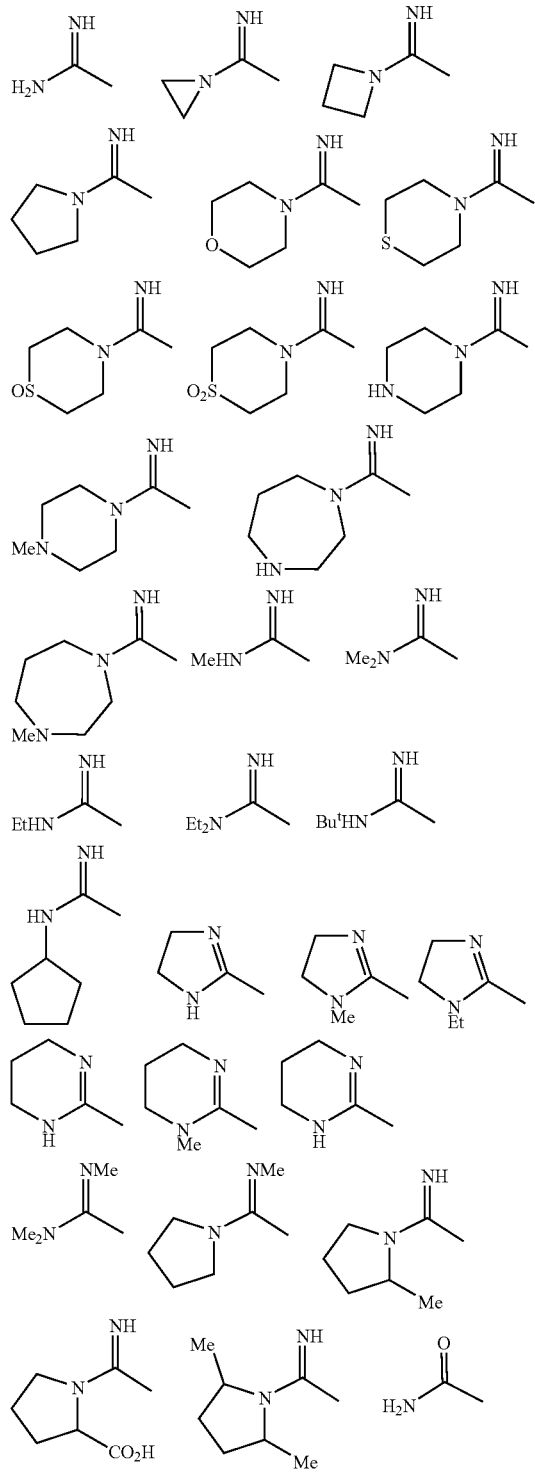

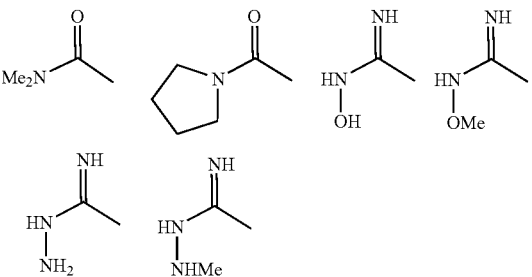

and all pharmaceutically acceptable isomers, salts, hydrates, solvates and prodrug derivatives thereof.

Still another preferred embodiment of the invention are compounds of formula (V):

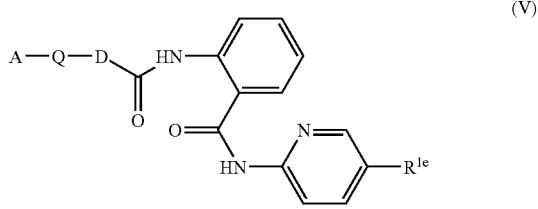

(V)

where:

$R^{1e}$ is a member selected from the group consisting of:
 H, —F, —Cl, —Br, —OMe, —OH, -Me, —CF$_3$ and —CH$_2$NH$_2$;

A-Q is a member selected from the group consisting of:

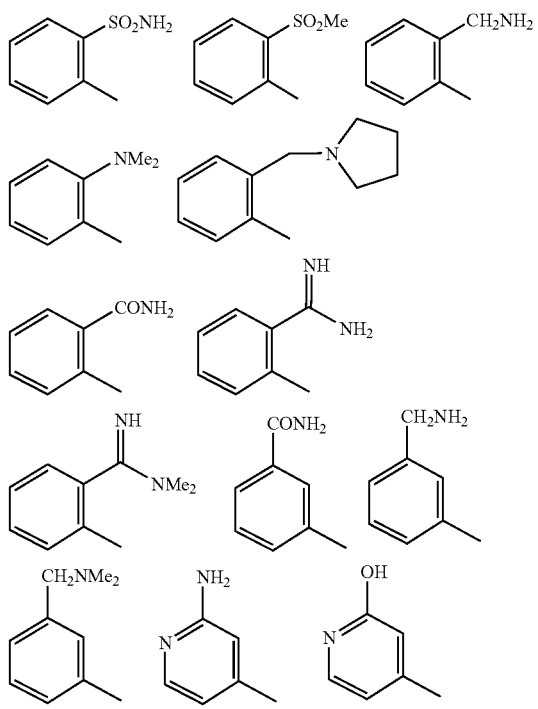

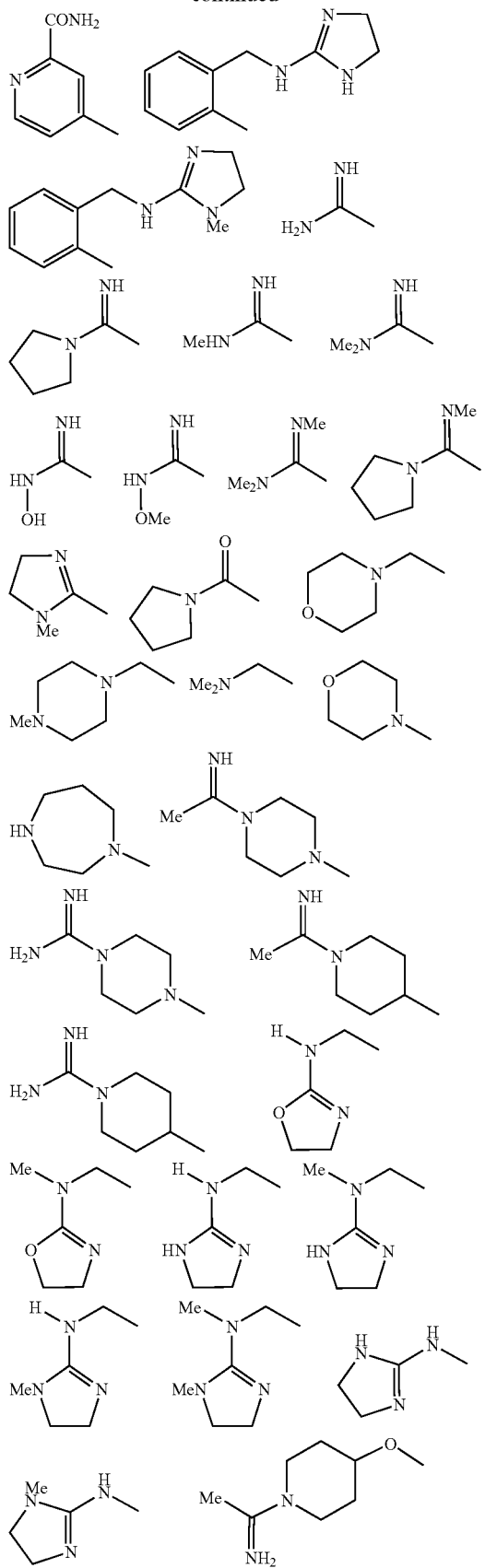
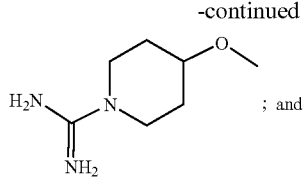
D is a member selected from the group consisting of:

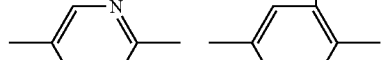
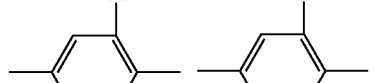
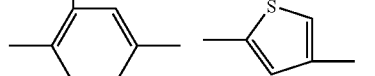
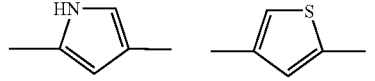
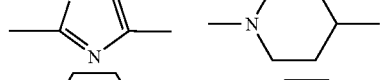

and all pharmaceutically acceptable isomers, salts, hydrates, solvates and prodrug derivatives thereof.

In another preferred embodiment, the present invention provides a compound according to the formula:

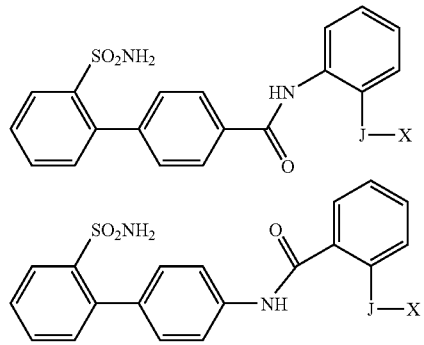

where:

J is a member selected from the group consisting of:
—NHC(=O)—, —C(=O)NH—;

X is a member selected from the group consisting of:

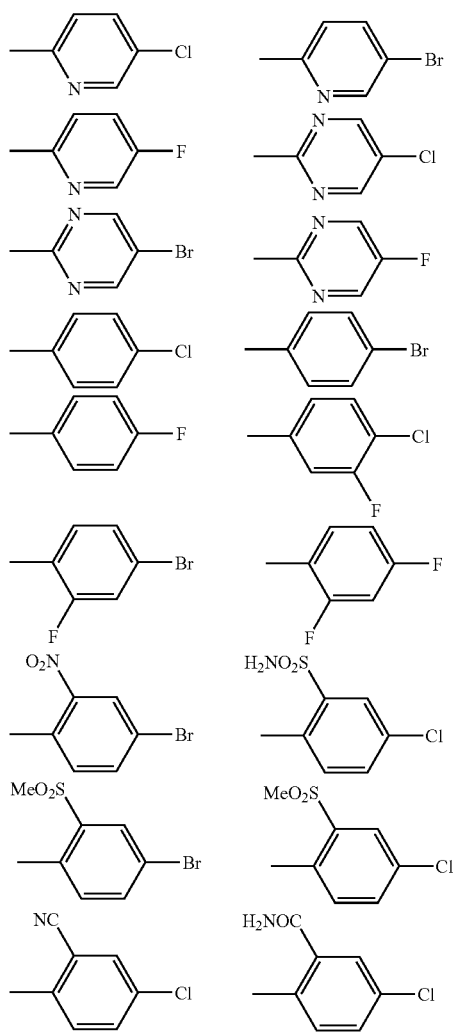

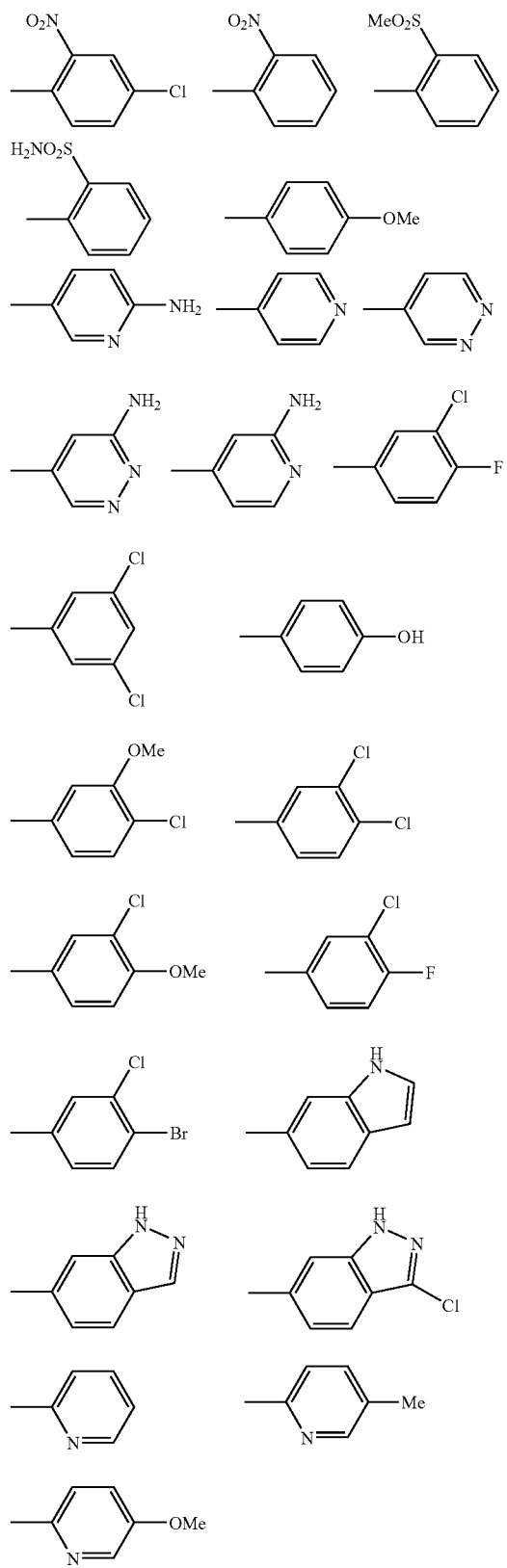

and all pharmaceutically acceptable isomers, salts, hydrates, solvates and prodrug derivatives thereof.

In another embodiment the present invention provides a compound according to the formula:

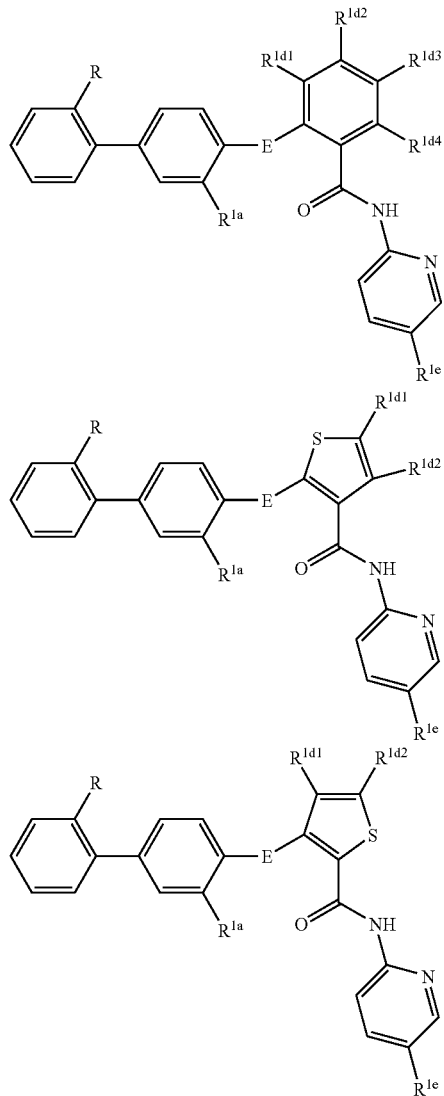

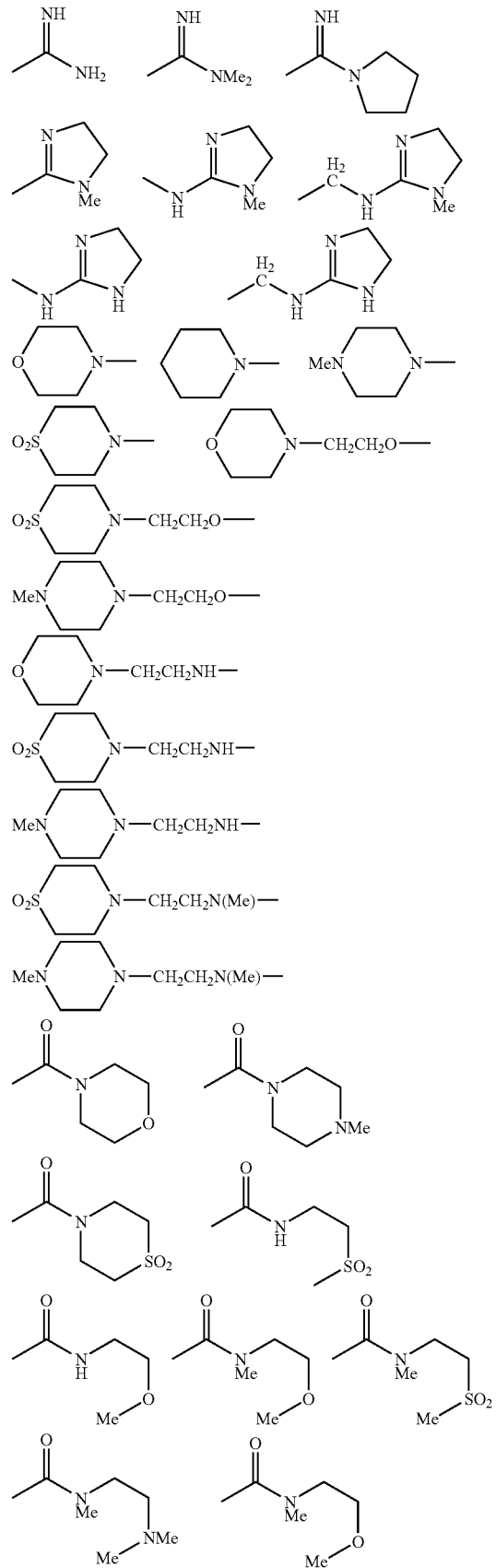

wherein:
R is a member selected from the group of:
—SO₂—NH₂ and —SO₂Me;
R¹ᵃ is a member selected from the group of:
H, —F, —Cl and Br;
E is a member selected from the group consisting of:
—NHC(=O)— and —C(=O)NH—;
R¹ᵈ¹, R¹ᵈ², and R¹ᵈ⁴ are independently a member selected from the group of:
H, —F, —Cl, —Br, -Me, —NO₂, —OH, —OMe, —NH₂, —NHAc, —NHSO₂Me, —CH₂OH and —CH₂NH₂;
R¹ᵈ³ is a member selected from the group of:
H, —CH₃, —CF₃, —Cl, —F, —Br, —NH₂, —N(-Me)₂, —OH, —OMe, —NHSO₂Me, —NO₂, —CN, —C(=O)—OMe, —CO₂H, —C(=O)—NH₂, —SO₂NH₂, —SO₂CH₃, —NHC(=O)-Me, —C(=O)—N(-Me)₂, —CH₂NH₂, —CH₂—N(-Me)₂, —CH₂OH, —OCH₂CO₂H, —OCH₂C(=O)—OMe, —OCH₂C(=O)—NH₂, and —OCH₂C(=O)—N(-Me)₂,

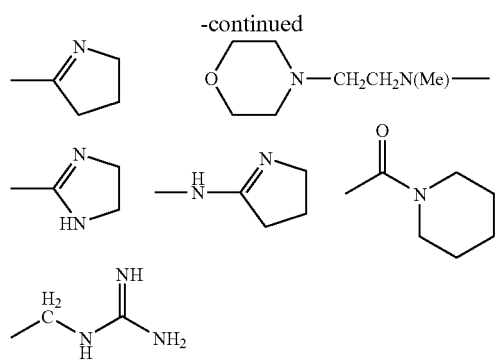

$R^{1e}$ is a member selected from the group of:
F, —Cl, —Br, —OH, -Me and —OMe,
and all pharmaceutically acceptable isomers, salts, hydrates, solvates and prodrug derivatives thereof.

In another further preferred embodiment, the present invention provides a compound according to the formula:

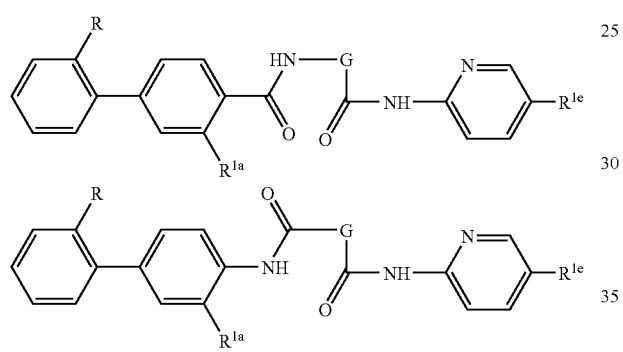

wherein:
R is a member selected from the group consisting of:
—SO$_2$NH$_2$, —SO$_2$Me;
$R^{1a}$ is a member selected from the group consisting of:
H, —F, —Cl and Br;
$R^{1e}$ is a member selected from the group consisting of:
H, —F, —Cl, —Br, —OMe, —OH, -Me, —CF$_3$ and —CH$_2$NH$_2$; and
G is a member selected from the group consisting of:

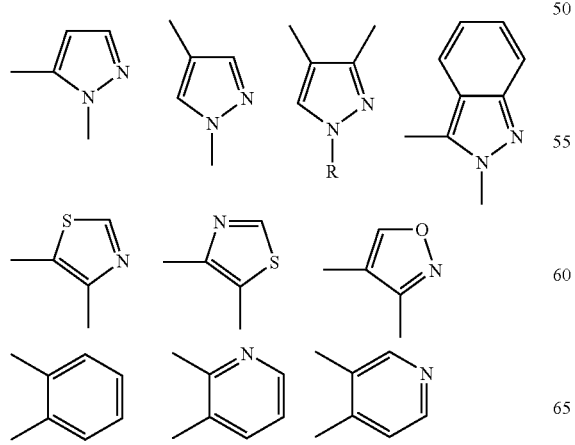

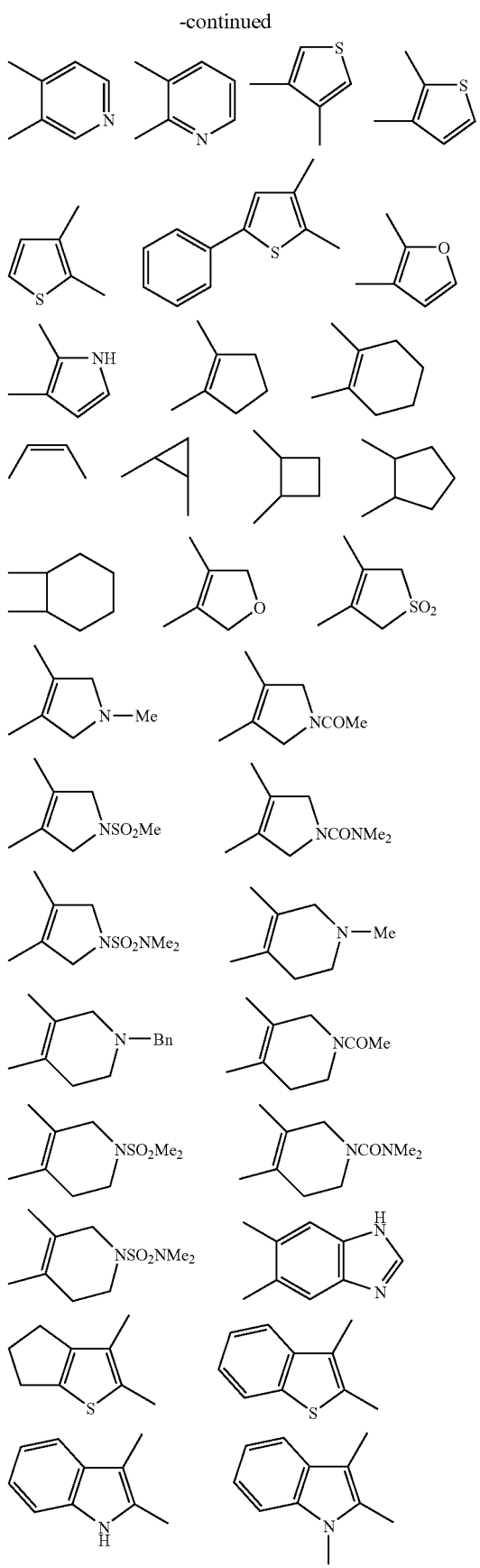

-continued

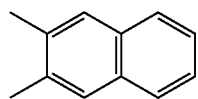

wherein each G group may be substituted by 0-4 $R^{1d}$ groups and each such $R^{1d}$ group is independently selected from the group consisting of:

H, —$CH_3$, —$CF_3$, —Cl, —F, —Br, —$NH_2$, —N(-Me)$_2$, —OH, —OMe, —$NHSO_2Me$, —$NO_2$, —CN, —C(=O)—OMe, —$CO_2H$, —C(=O)—$NH_2$, —$SO_2NH_2$, —$SO_2CH_3$, —NH—C(=O)-Me, —C(=O)—N(-Me)$_2$, —$CH_2NH_2$, —$CH_2$—N(-Me)$_2$, —$CH_2OH$, —$OCH_2CO_2H$, —$OCH_2CO_2Me$, —$OCH_2C(=O)$—$NH_2$, —$OCH_2C(=O)$—N(-Me)$_2$.

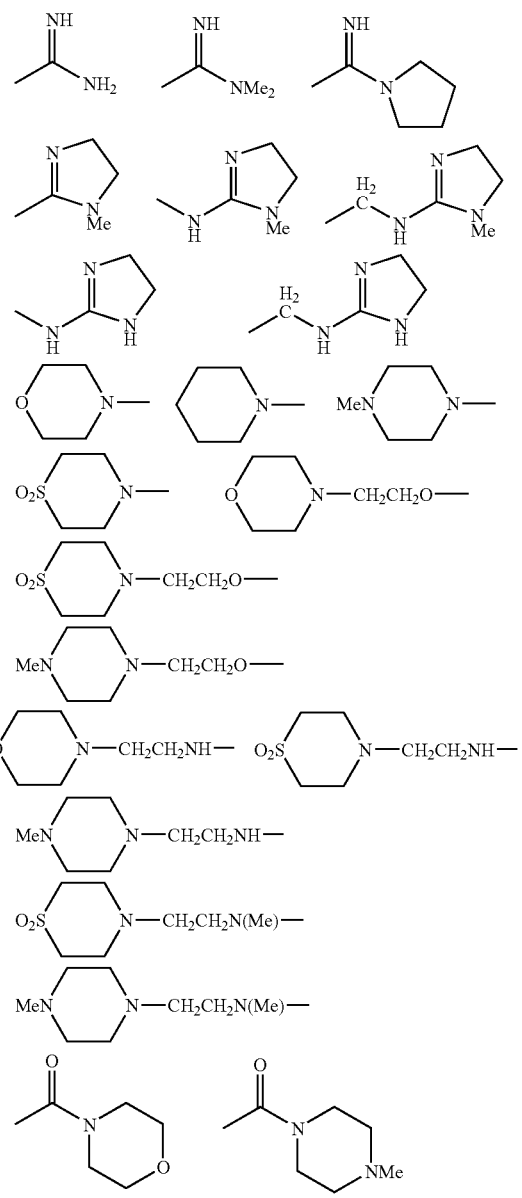

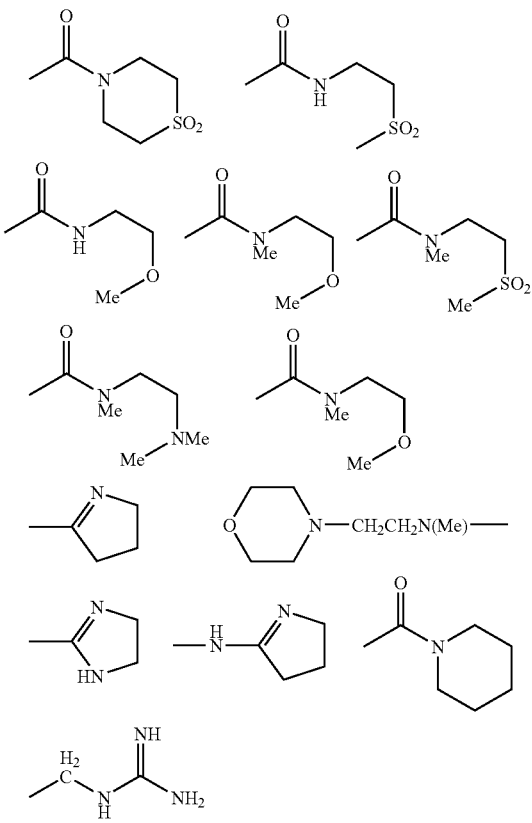

and all pharmaceutically acceptable isomers, salts, hydrates, solvates and prodrug derivatives thereof.

In another further preferred embodiment the present invention provides a compound according to the formula:

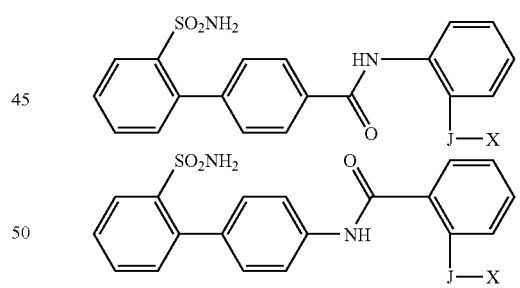

wherein:

J-X are collectively a member selected from the group consisting of:

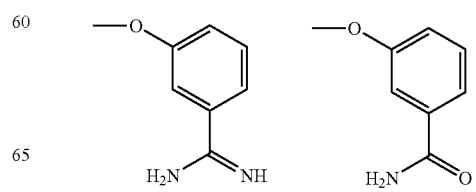

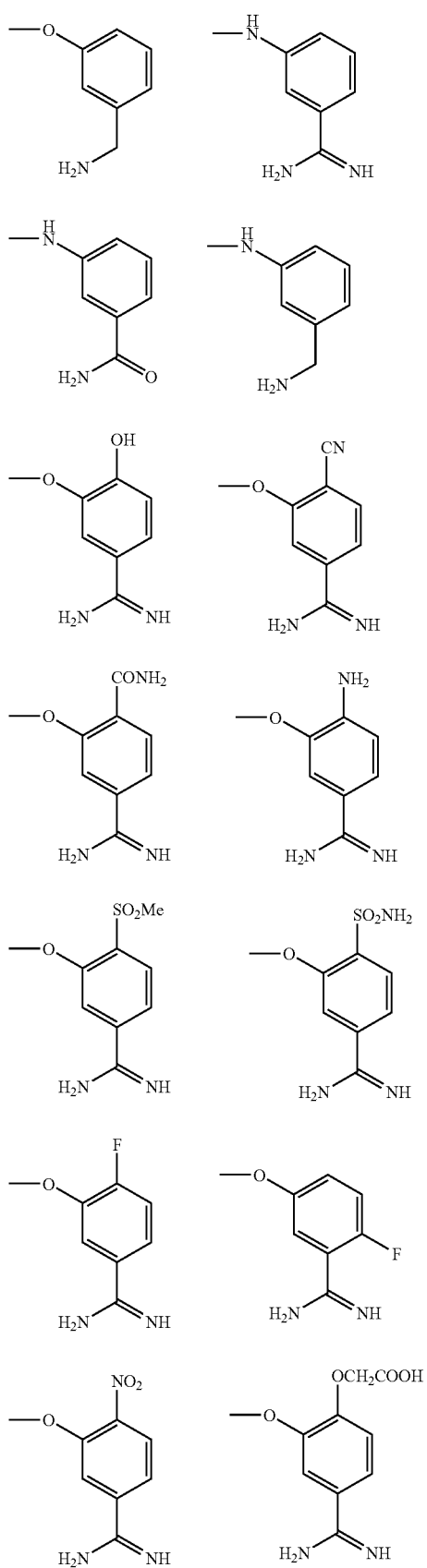
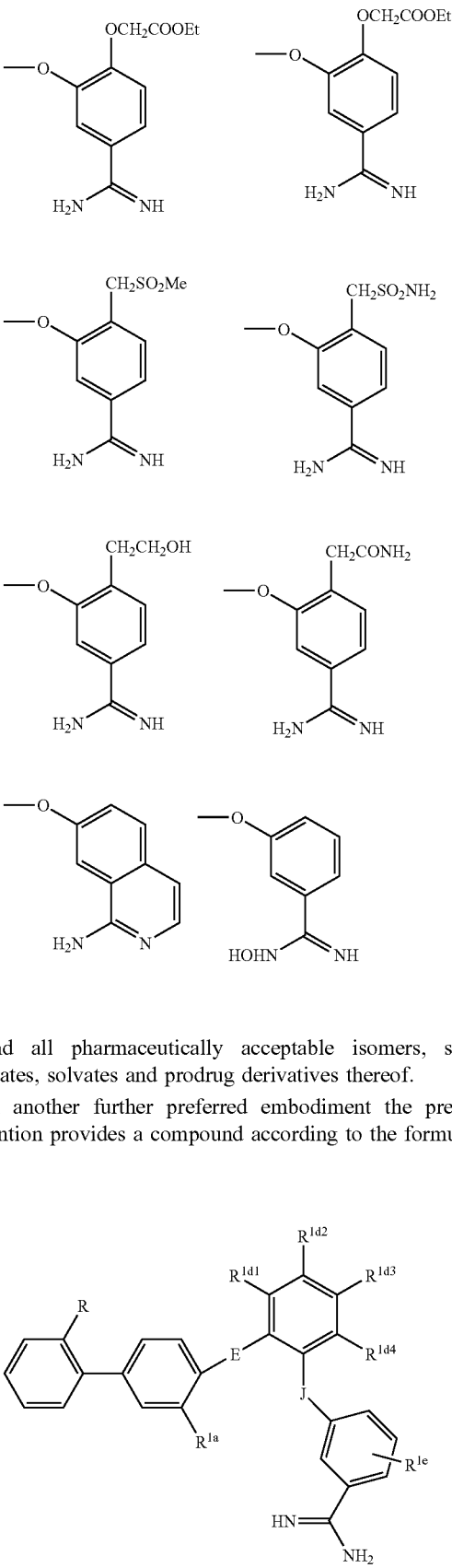
and all pharmaceutically acceptable isomers, salts, hydrates, solvates and prodrug derivatives thereof.
In another further preferred embodiment the present invention provides a compound according to the formula:
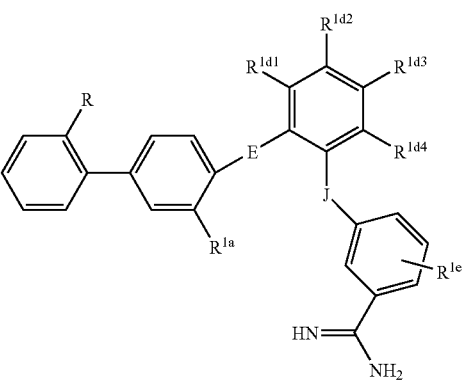

-continued

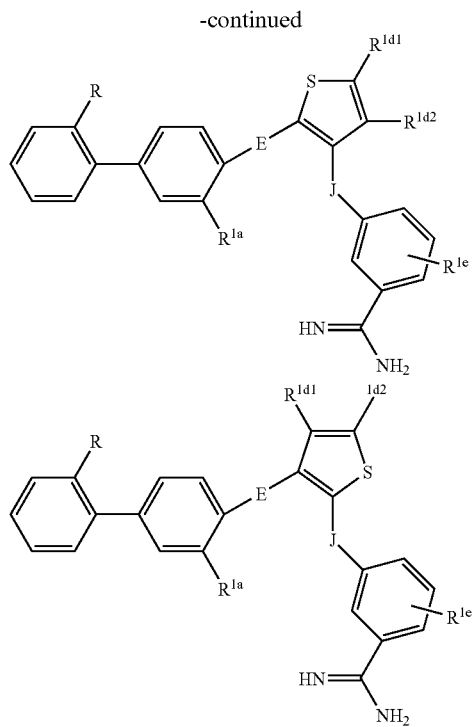

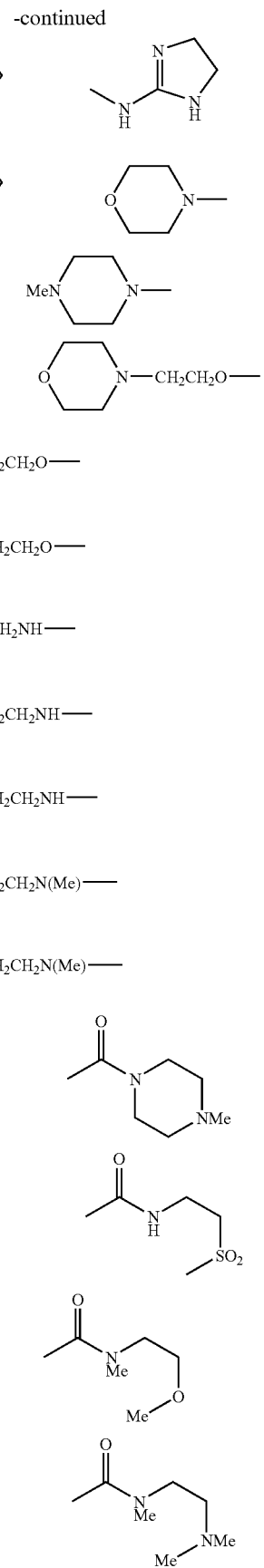

wherein:

R is a member selected from the group of:
—SO$_2$NH$_2$, and —SO$_2$Me;

R$^{1a}$ is a member selected from the group of:
H, —F, —Cl and Br;

E is a member selected from the group consisting of:
—NHC(=O)— and —C(=O)NH—;

J is a member selected from the group consisting of:
—NHC(=O)— and —C(=O)NH—, O;

R$^{1d1}$, $^{R1d2}$, and R$^{1d4}$ are independently a member selected from the group of:
H, —F, —Cl, —Br, -Me, —NO$_2$, —OH, —OMe, —NH$_2$, —NHAc, —NHSO$_2$Me, —CH$_2$OH, —CH$_2$NH$_2$;

R$_{1d3}$ is a member selected from the group of:
H, —CH$_3$, —CF$_3$, —Cl, —F, —Br, —NH$_2$, —N(-Me)$_2$, —OH, —OMe, —NHSO$_2$Me, —NO$_2$, —CN, —CO$_2$Me, —CO$_2$H, —C(=O)—NH$_2$, —SO$_2$NH$_2$, —SO$_2$CH$_{13}$, —NHC(=O)-Me, —C(=O)—N(-Me)$_2$, —CH$_2$NH$_2$, —CH$_2$—N(-Me)$_2$, —CH$_2$OH, —OCH$_2$CO$_2$H, —OCH$_2$C(=O)—OMe, —OCH$_2$C(=O)—NH$_2$, —OCH$_2$C(=O)—N(-Me)$_2$,

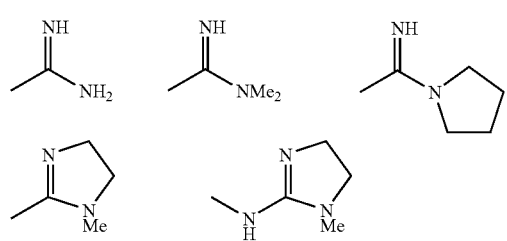

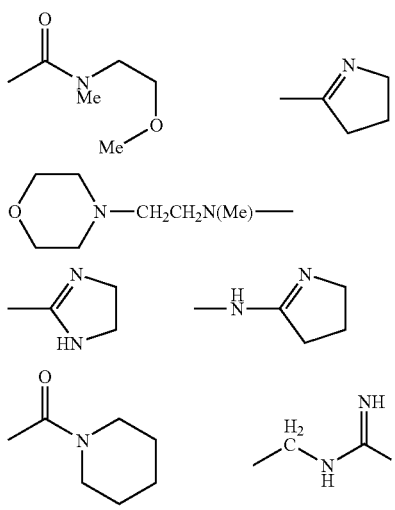

$R^{1e}$ is a member selected from the group of:

F, —Cl, —Br, —OH, -Me and —OMe;

and all pharmaceutically acceptable isomers, salts, hydrates, solvates and prodrug derivatives thereof.

In another preferred embodiment, the present invention provides a compound of the following formulae, which illustrate the compounds having preferred substituents for G, particularly when G is a pyrazole ring structure.

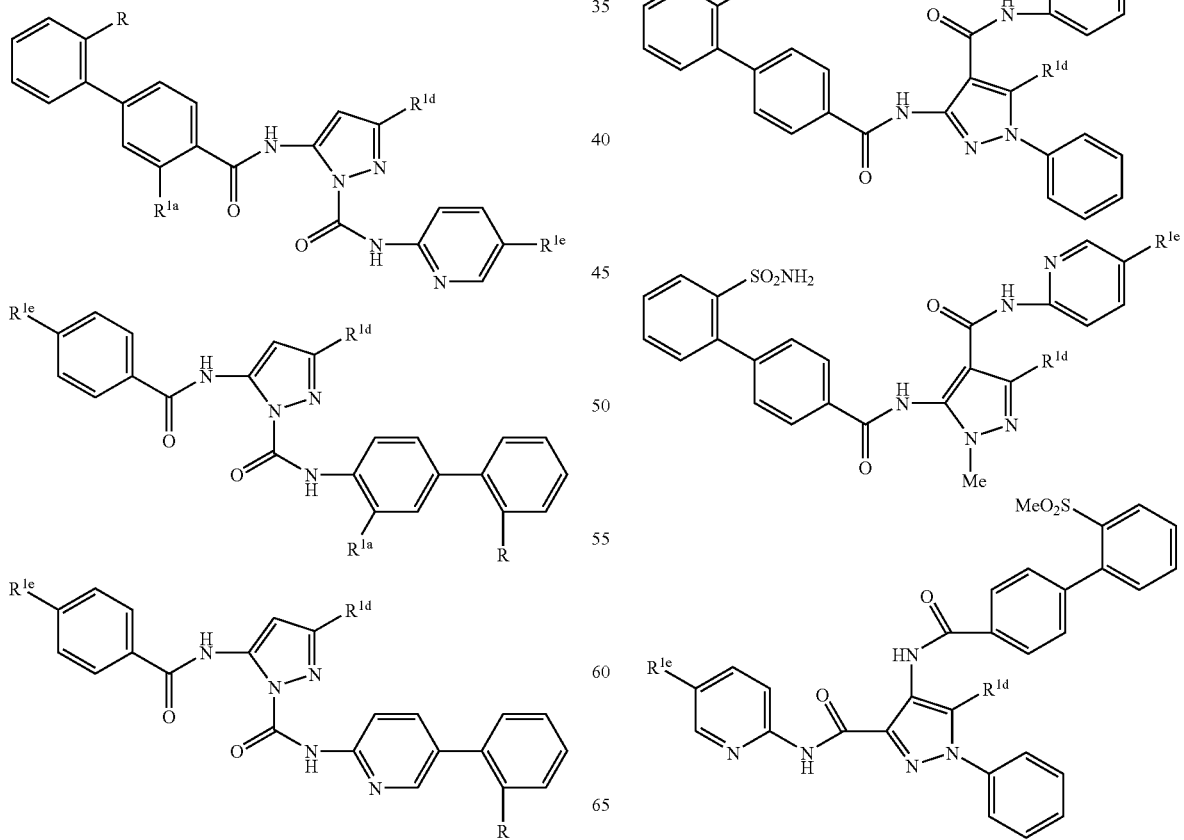

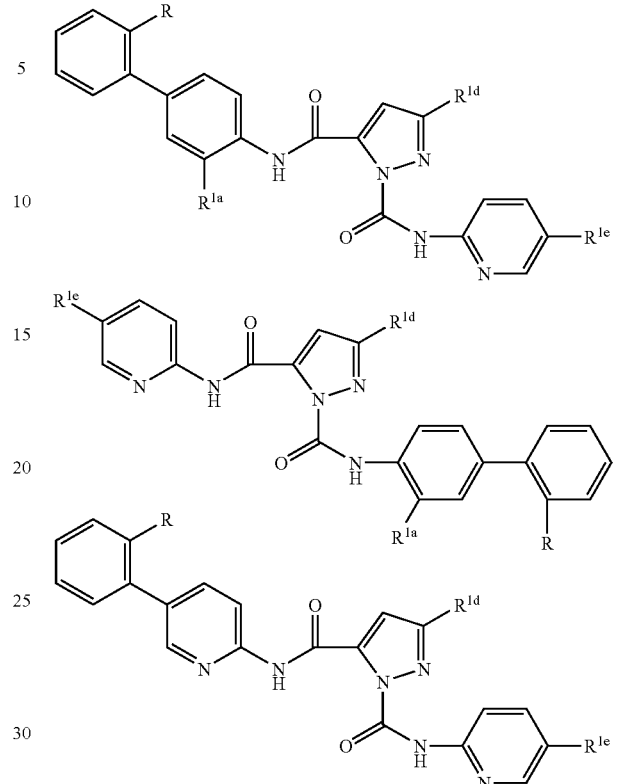

-continued

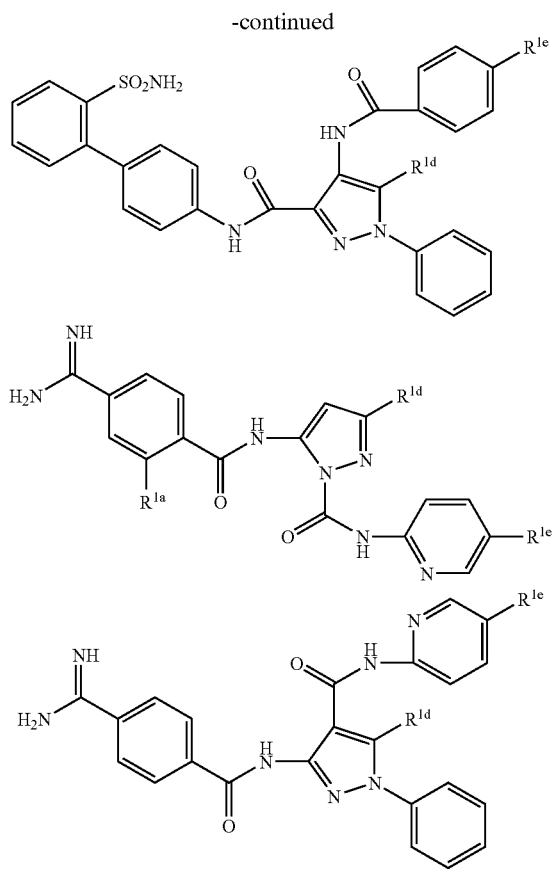

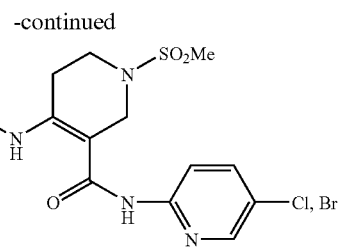

wherein:
A-Q taken together are a member selected from the group consisting of:

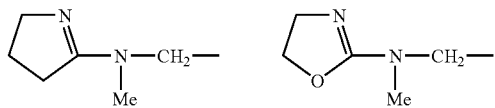

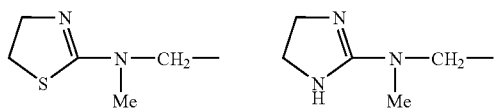

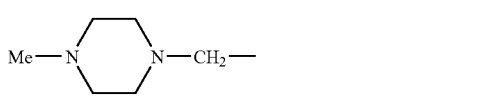

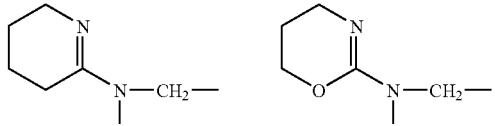

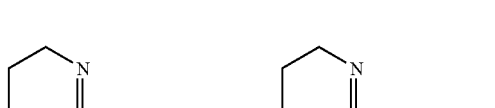


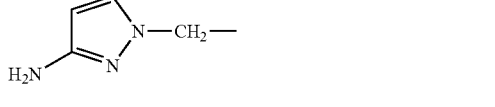

wherein:
R is a member selected from the group of:
   —SO$_2$—NH$_2$, and —SO$_2$Me;
R$^{1a}$ is a member selected from the group of:
   H, —F, —Cl and Br;
R$^{1d}$ is a member selected from the group consisting of:
   —H, —CH$_3$, —CF$_3$, —CN, —SO$_2$NH$_2$ and —SO$_2$CH$_3$; and
R$^{1e}$ is a member selected from the group of:
   —Cl and —Br;
and all pharmaceutically acceptable isomers, salts, hydrates, solvates and prodrug derivatives thereof.

In another preferred embodiment, the present invention provides a compound of the following formulae, which illustrate the compounds having preferred substituents for A-Q taken collectively when the remainder of the compound structure has the one of the following two formulae:

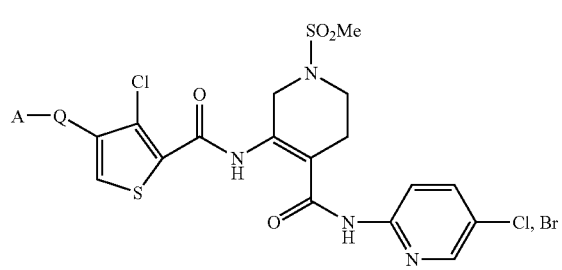

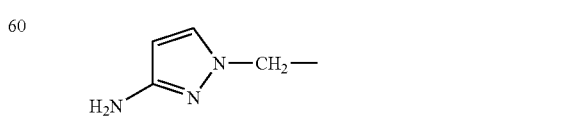

and all pharmaceutically acceptable isomers, salts, hydrates, solvates and pro drug derivatives thereof.

In another preferred embodiment the present invention provides a compound according to the formula:

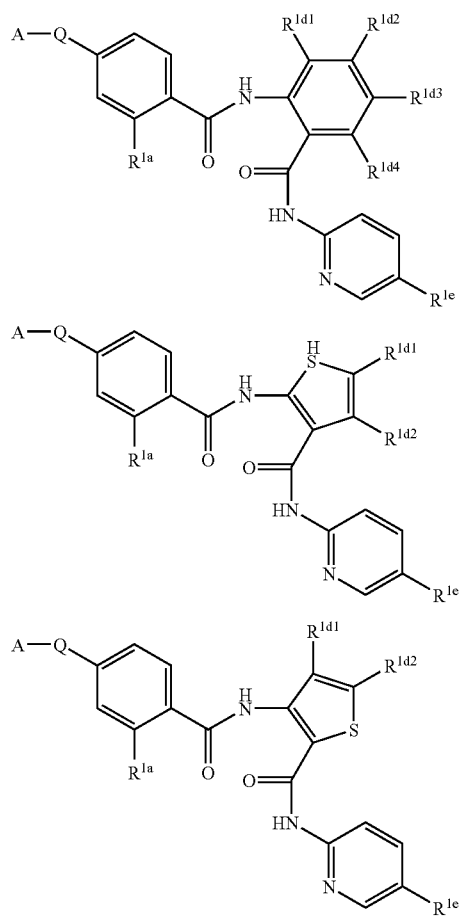

wherein:
A-Q is a member selected from the group of:

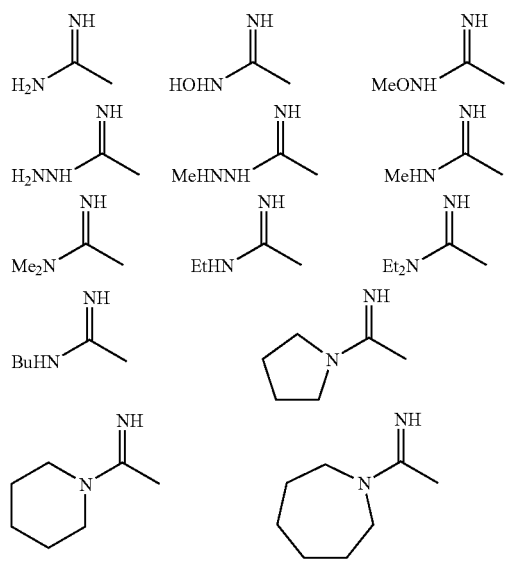

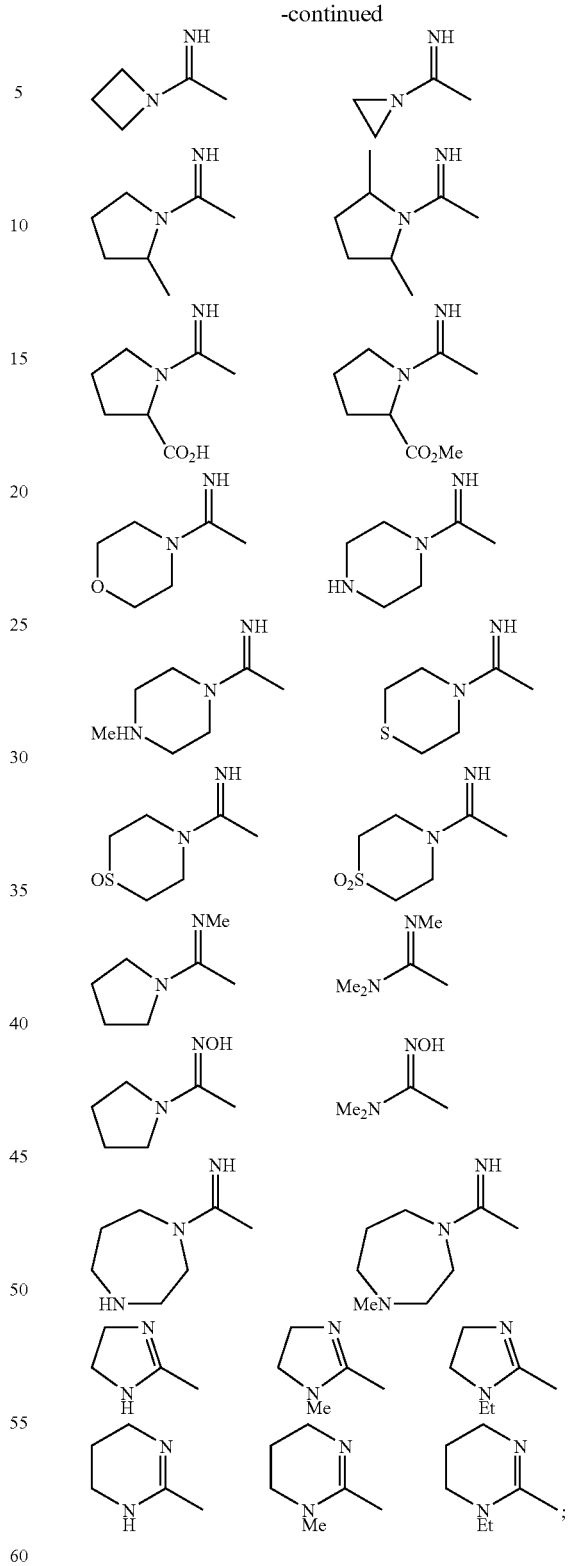

where A-Q may optionally be further substituted with at least one Z' group, where each Z' group is independently a $C_1$-$C_6$ alkyl, preferably a $C_1$-$C_3$ alkyl group, most preferably a methyl group and where each Z' group may optionally be substituted with a hydroxyl, carboxylic acid or carboxylic acid $C_1$-$C_6$ ester group, preferably a hydroxyl, carboxylic acid or carboxylic acid $C_1$-$C_3$ ester group, and most preferably, a hydroxyl, carboxylic acid or carboxylic acid methyl ester;

$R^{1a}$ is a member selected from the group of:
H, —F, —Cl and Br;

$R^{1d1}$, $R^{1d2}$, and $R^{1d4}$ are independently a member selected from the group of:
H, —F, —Cl, —Br, -Me, —$NO_2$, —OH, —OMe, —$NH_2$, —NHAc, —$NHSO_2Me$, —$CH_2OH$, —$CH_2NH_2$ $R^{1d3}$ is a member selected from the group of:
H, —$CH_3$, —$CF_3$, —Cl, —F, —Br, —$NH_2$, —N(-Me)$_2$, —OH, —OMe, —$NHSO_2Me$, —$NO_2$, —CN, —C(=O)—OMe, —$CO_2H$, —C(=O)—$NH_2$, —$SO_2NH_2$, —$SO_2CH_3$, —NHC(=O)-Me, —C(=O)—N(Me)$_2$, —$CH_2NH_2$, —$CH_2$—N(-Me)$_2$, —$CH_2OH$, —$OCH_2CO_2H$, —$OCH_2C(=O)$—OMe, —$OCH_2C(=O)$—$NH_2$, —$OCH_2C(=O)$—N(-Me)$_2$,

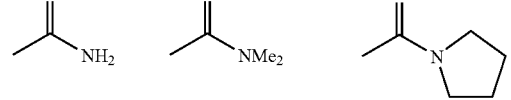
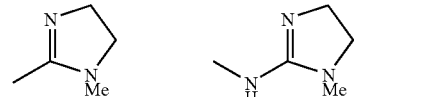
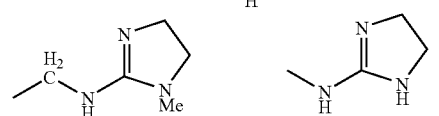
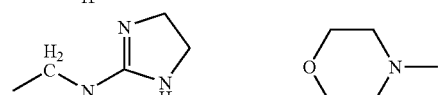
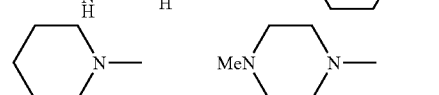
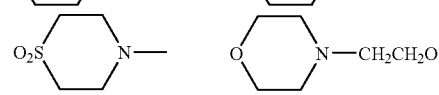

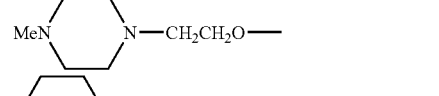
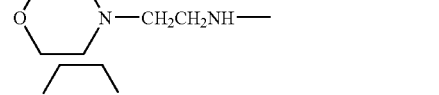
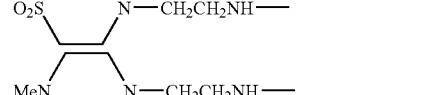
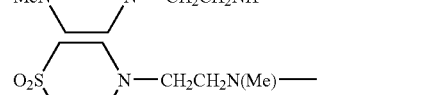
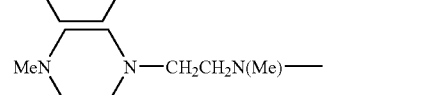

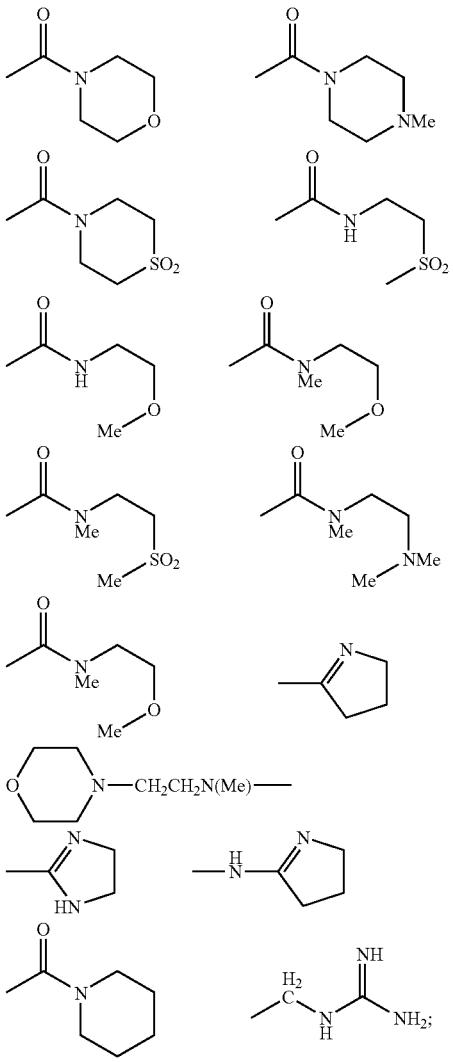

$R^{1e}$ is a member selected from the group of:
F, —Cl, —Br, —OH, -Me and —OMe;

and all pharmaceutically acceptable isomers, salts, hydrates, solvates and prodrug derivatives thereof.

In another embodiment, the invention provides a compound of formula VI:

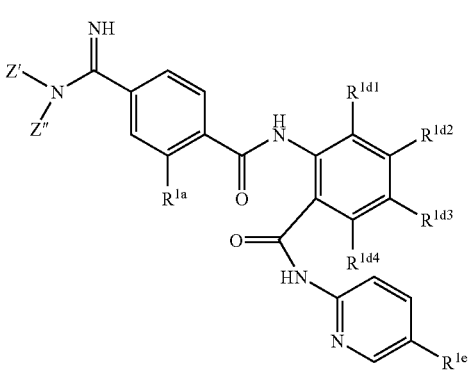

(VI)

and all pharmaceutically acceptable isomers, salts, hydrates, solvates and prodrug derivatives thereof.

In formula VI:
- Z' and Z" are each independently a $C_1$-$C_6$ alkyl, preferably a $C_1$-$C_3$ alkyl group, most preferably a methyl group; where Z' and Z" may be optionally substituted with a hydroxyl, carboxylic acid or carboxylic acid $C_1$-$C_6$ ester group, preferably a hydroxyl, carboxylic acid or carboxylic acid $C_1$-$C_3$ ester group, and most preferably, a hydroxyl, carboxylic acid or carboxylic acid methyl ester;
- $R^{1a}$ is a member selected from the group of H, —F, —Cl and Br;
- $R^{1d2}$ and $R^{1d4}$ are each H;
- $R^{1d1}$ and $R^{1d3}$ are each independently a member selected from the group of H, —Cl, —F, —Br, —OH and —OMe; and
- $R^{1e}$ is a member selected from the group of —F, —Cl, —Br, —OH, -Me and —OMe.

Examples of suitable compounds of formula VI, as described above, include, but are not limited to:

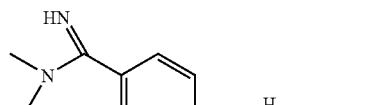

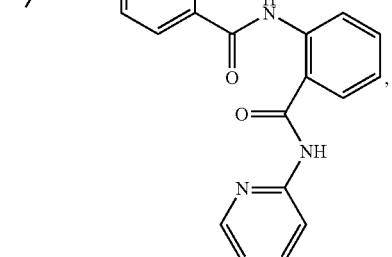

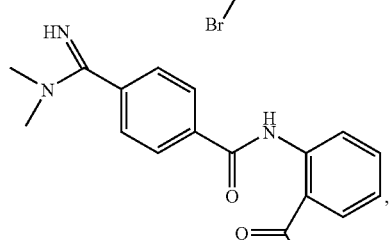

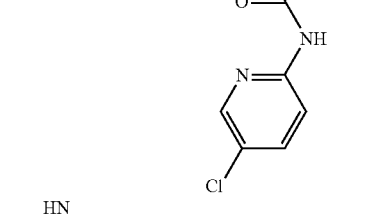

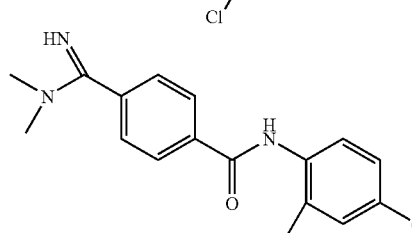

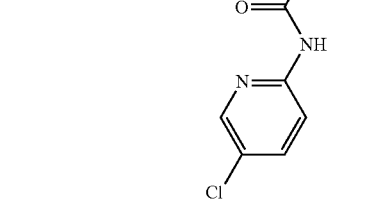

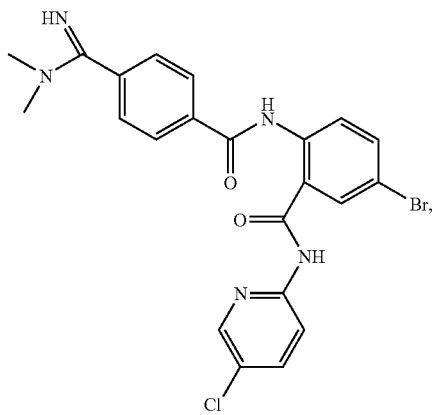

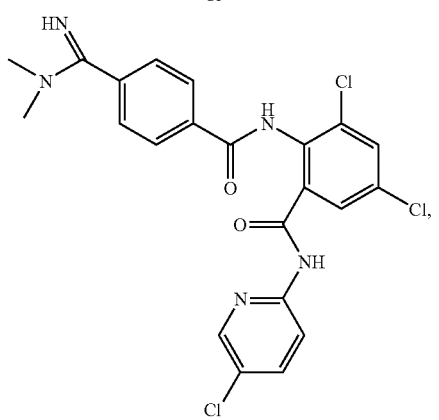

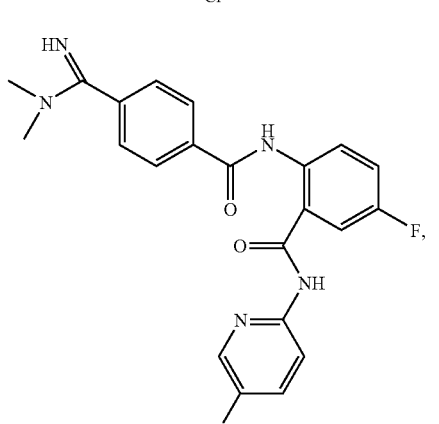

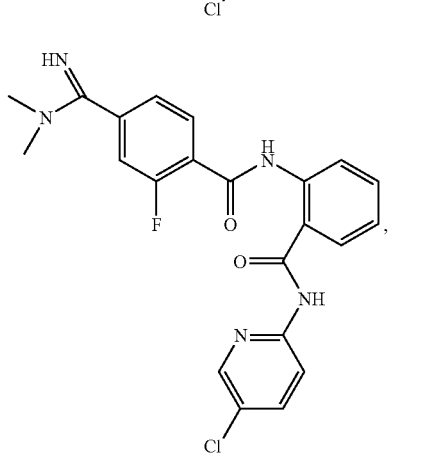

-continued
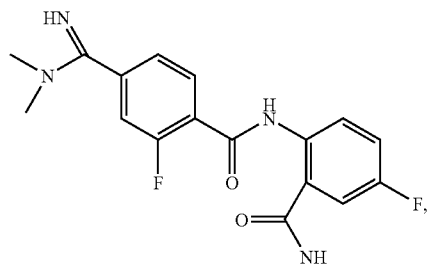
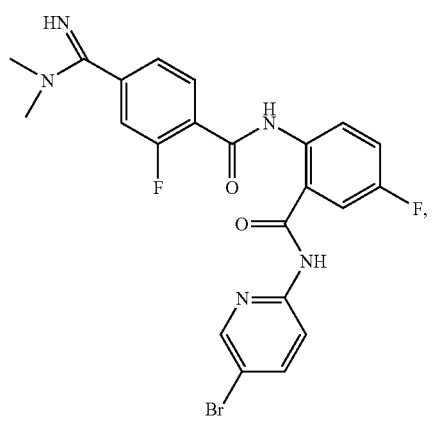
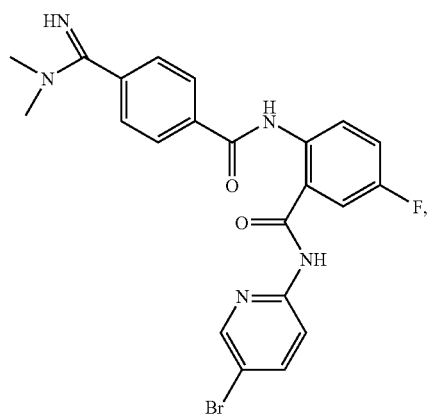
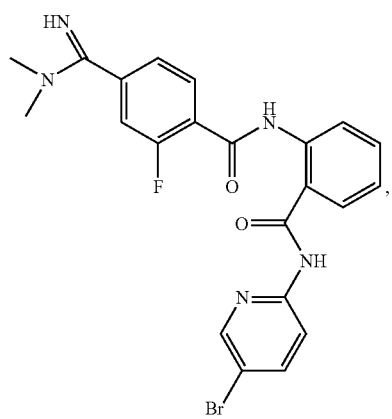
-continued
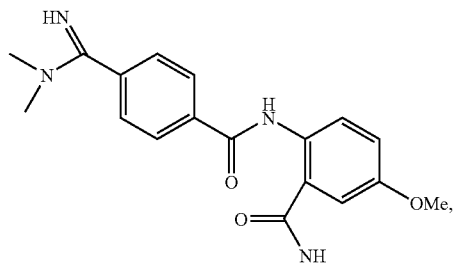
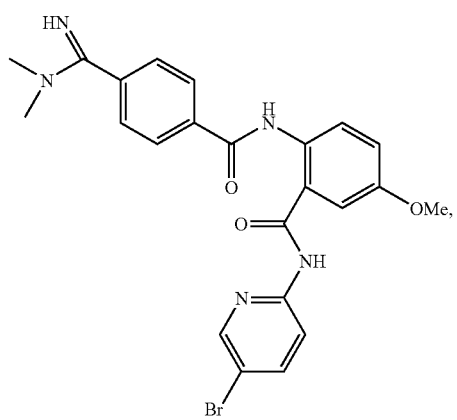
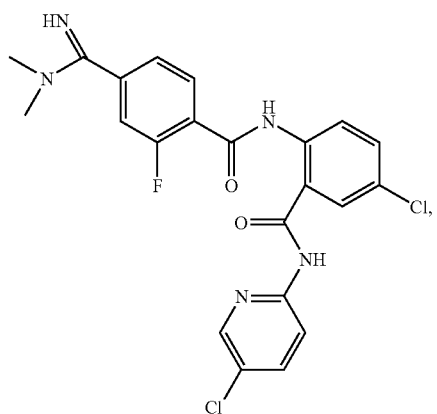
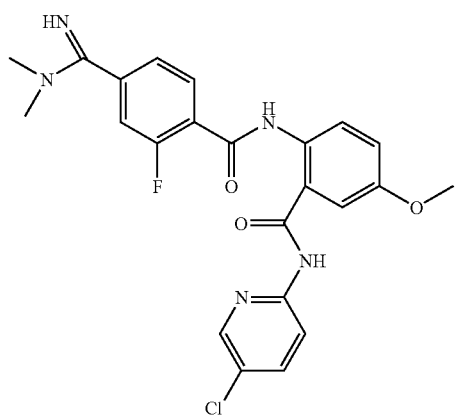

-continued

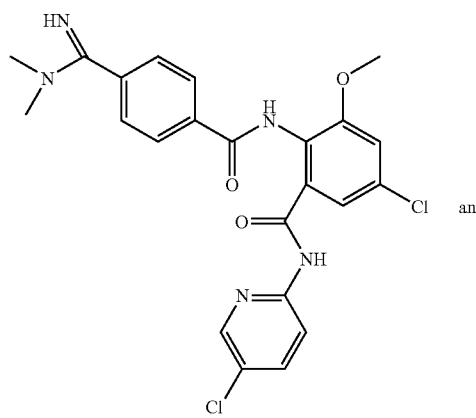

and

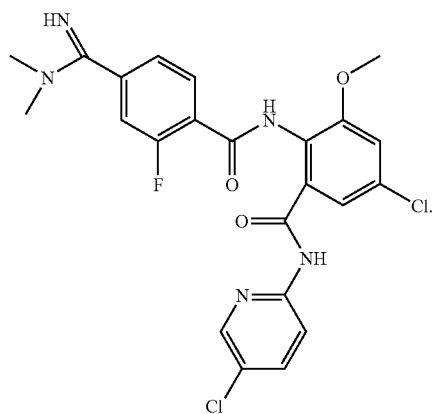

In another embodiment, the invention further provides a compound of formula VII:

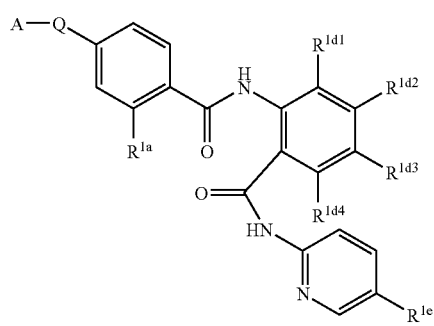 (VII)

and all pharmaceutically acceptable isomers, salts, hydrates, solvates and prodrug derivatives thereof.

In formula VII:

A-Q is a member selected from the group of:

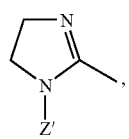 , 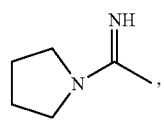 ,

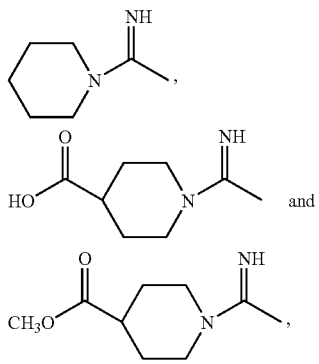

where Z' is as described above;

$R^{1a}$ is a member selected from the group of H, —F, —Cl and Br;

$R^{1d2}$ and $R^{1d4}$ are each H;

$R^{1d1}$ is $R^{1d3}$ are each independently a member selected from the group of H, —Cl, —F, —Br, —OH and —OMe;

$R^{1e}$ is a member selected from the group of —F, —Cl, —Br, —OH, -Me and —OMe.

Examples of suitable compounds of formula VII, as described above, include, but are not limited to:

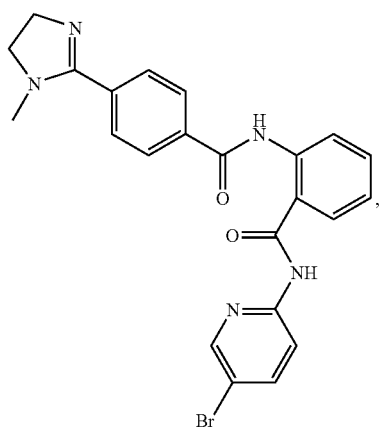

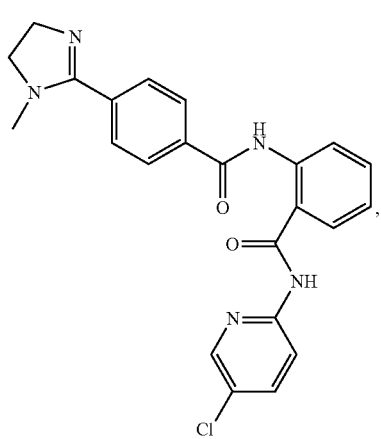

-continued
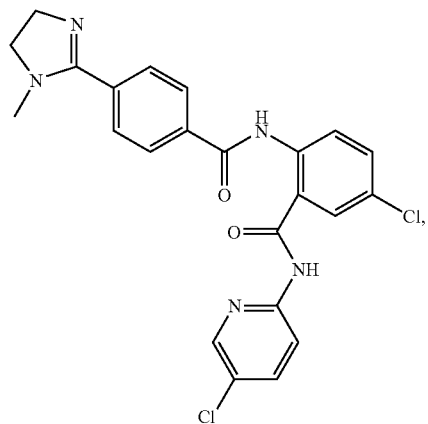
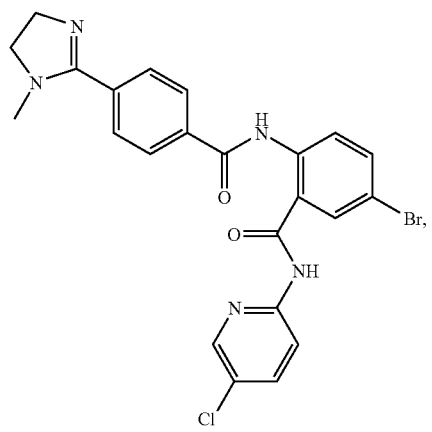
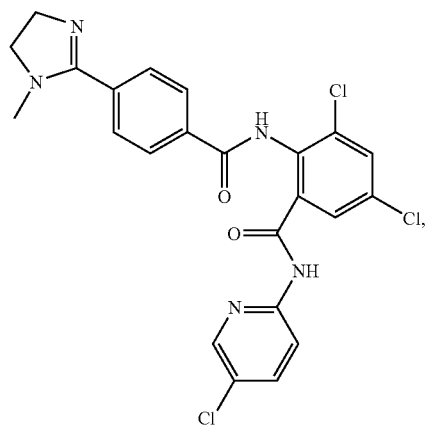
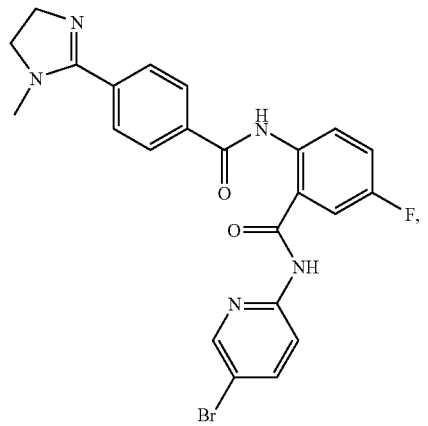
-continued
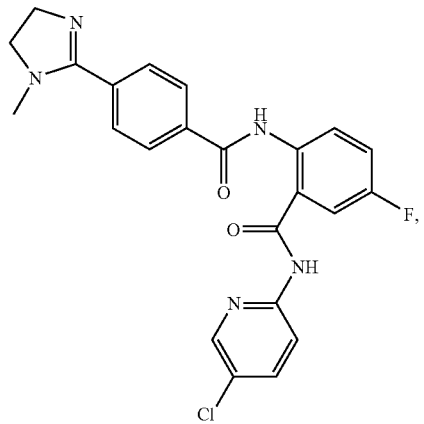
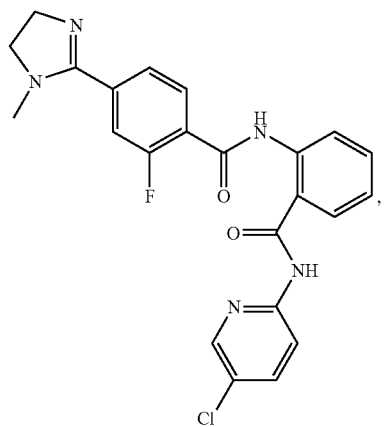
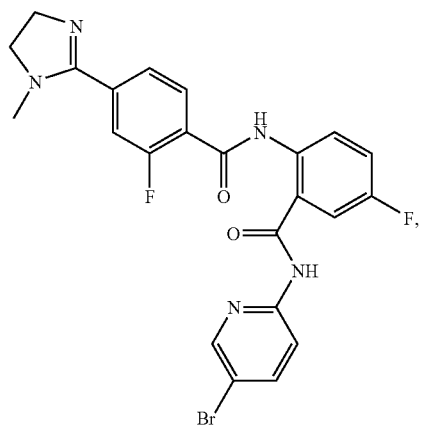
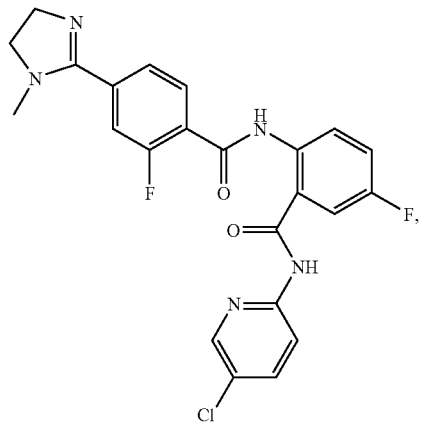

-continued
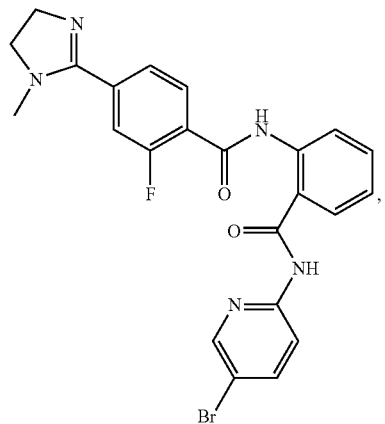
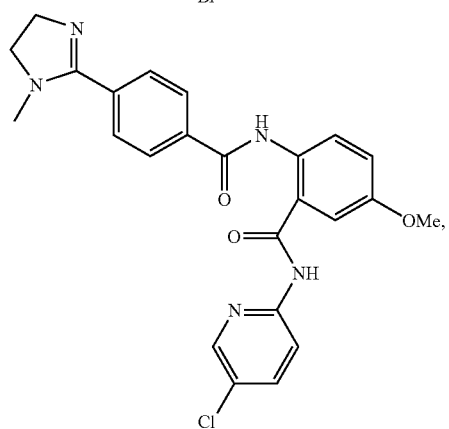
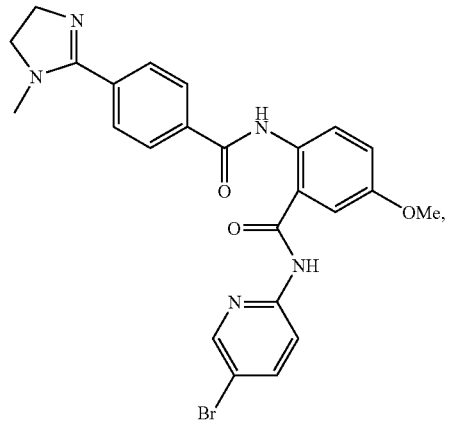
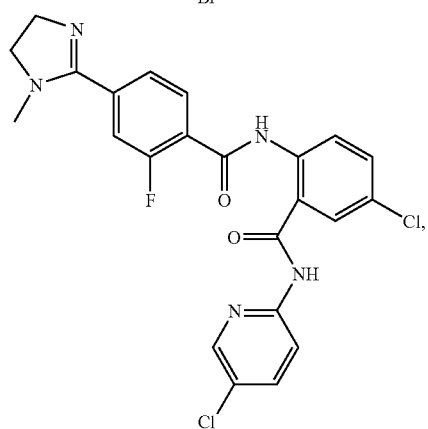
-continued
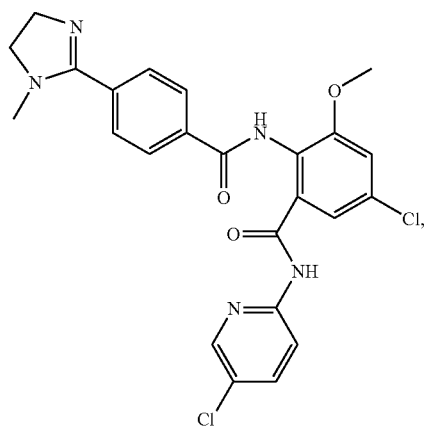
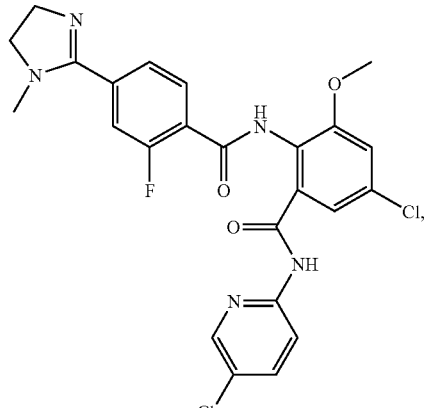
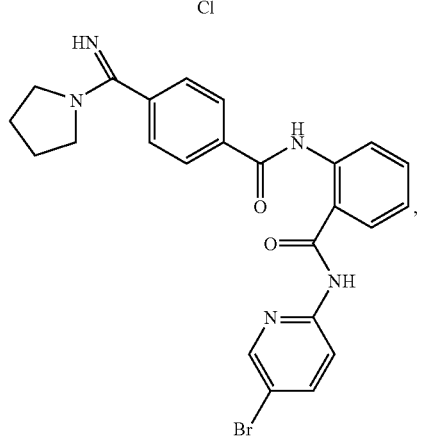
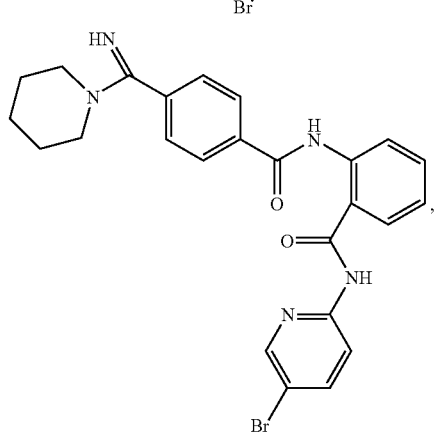

-continued
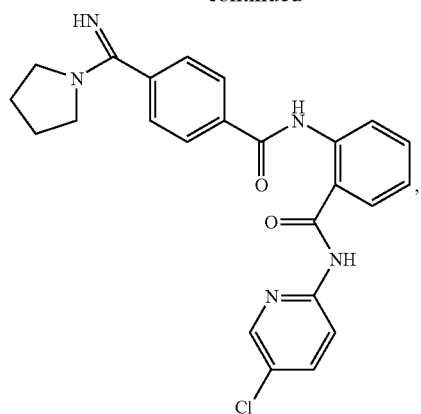
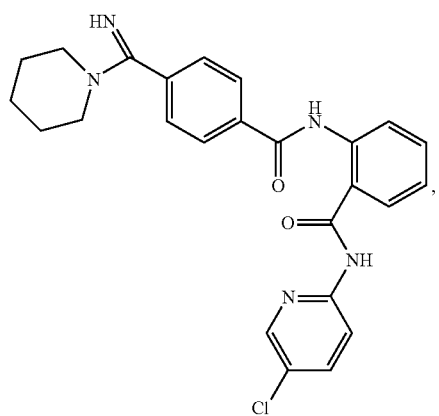
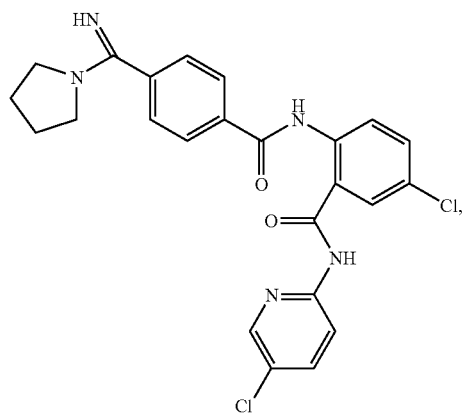
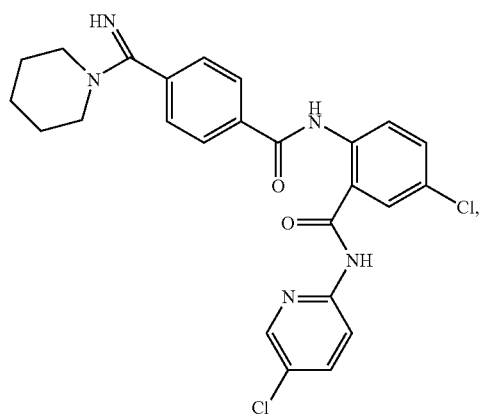
-continued
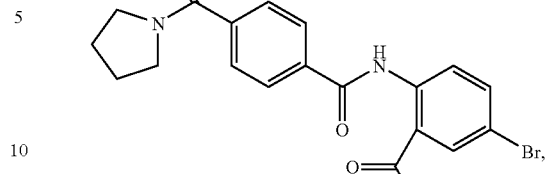
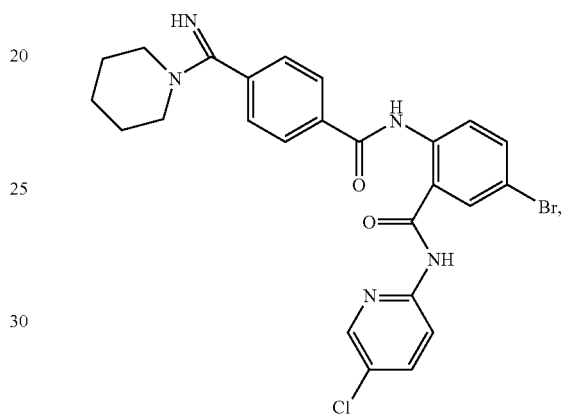
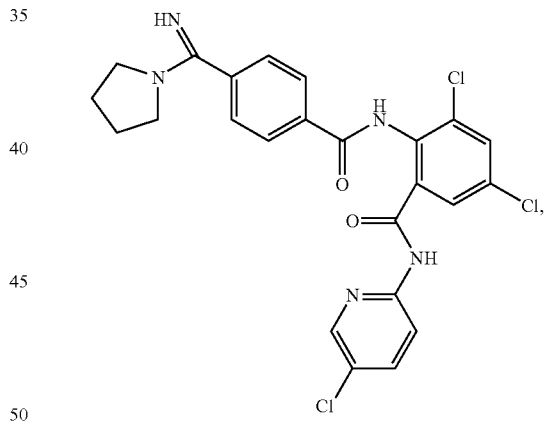
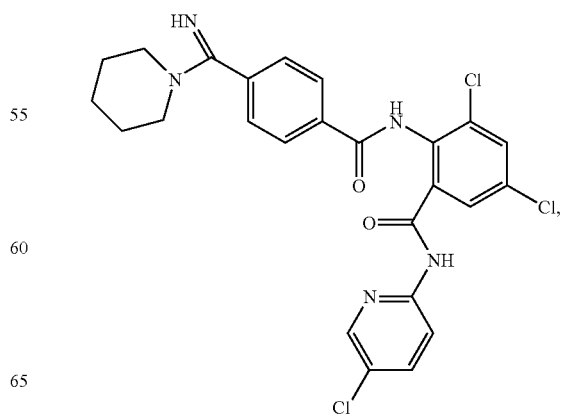

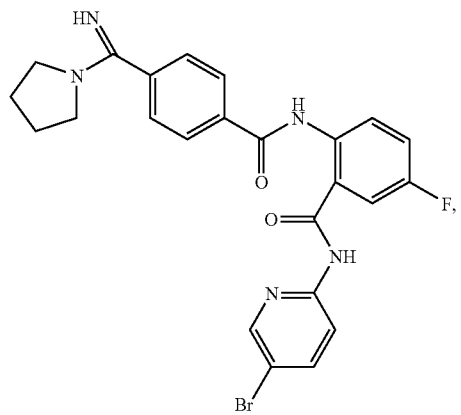
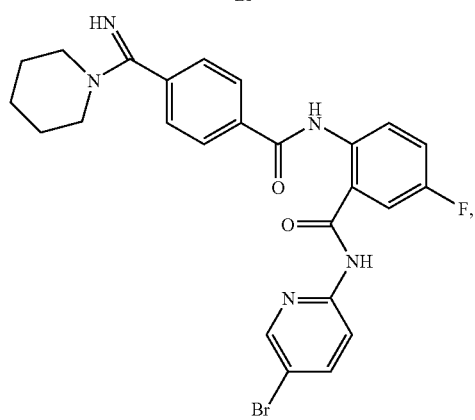
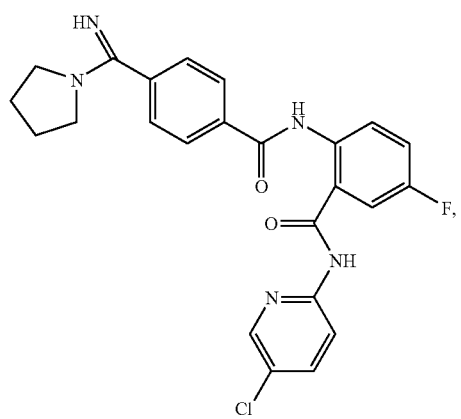
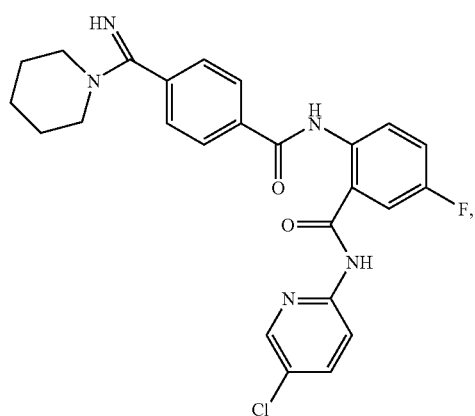
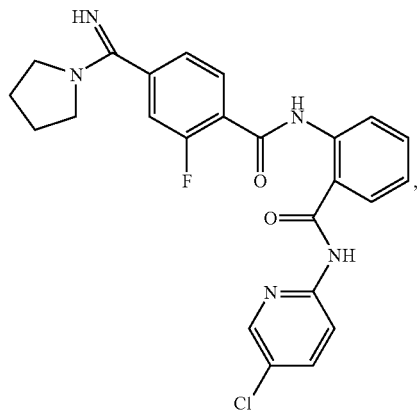
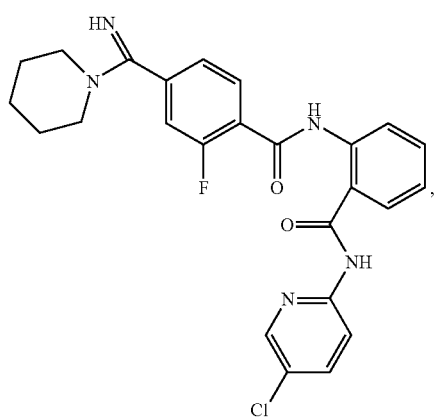
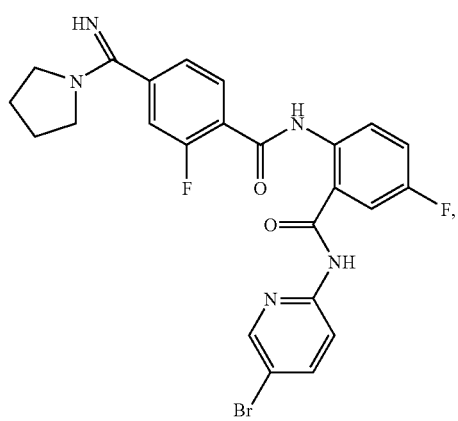
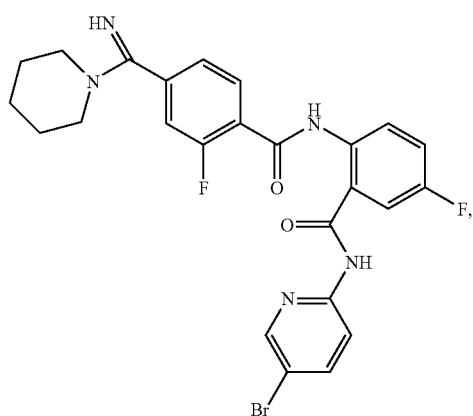

-continued
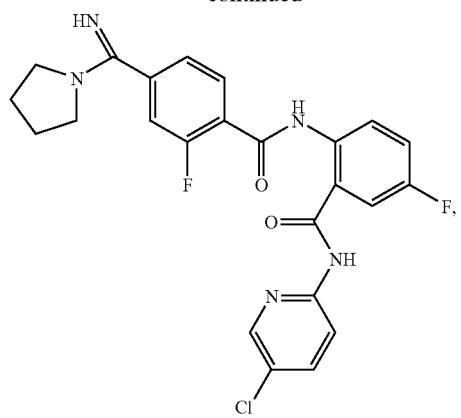
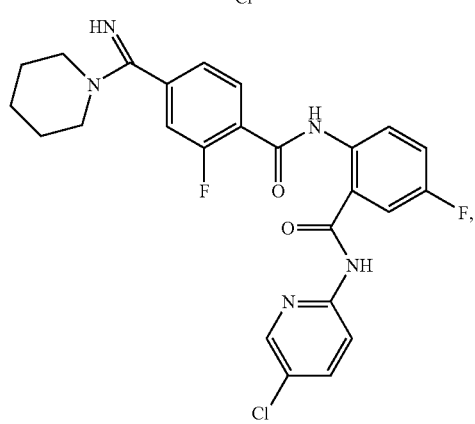
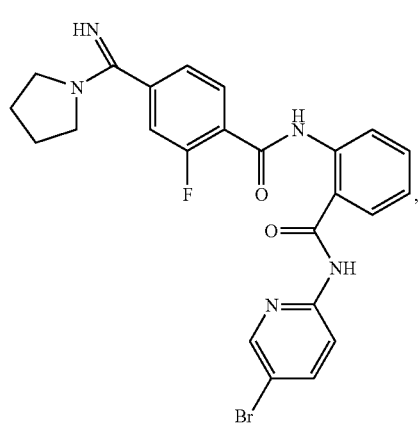
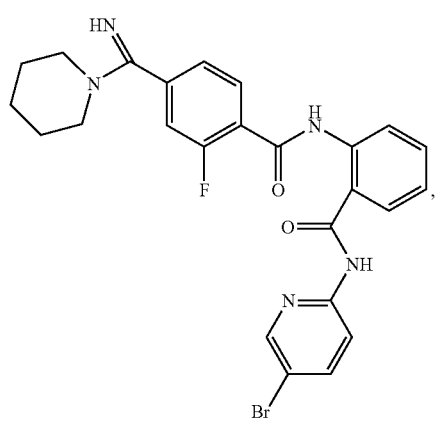
-continued
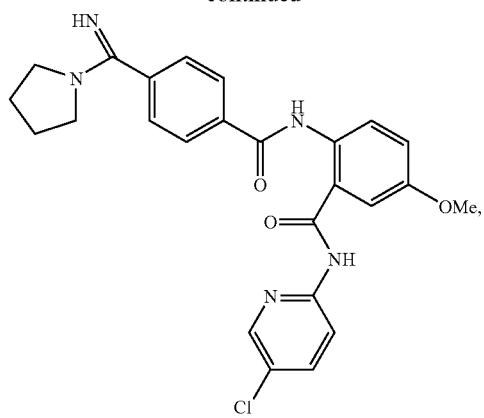
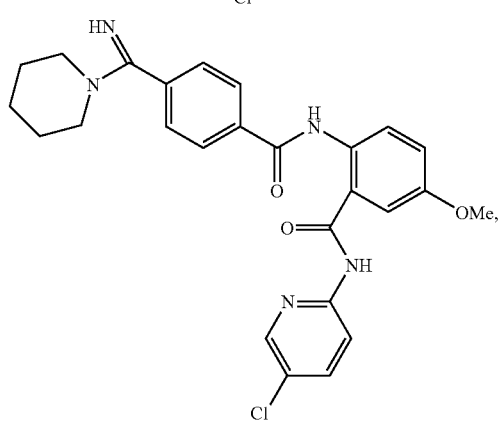
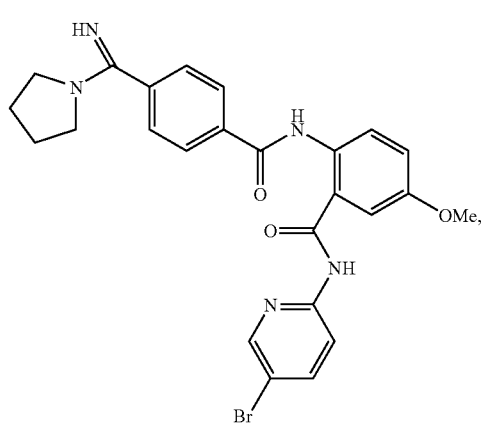
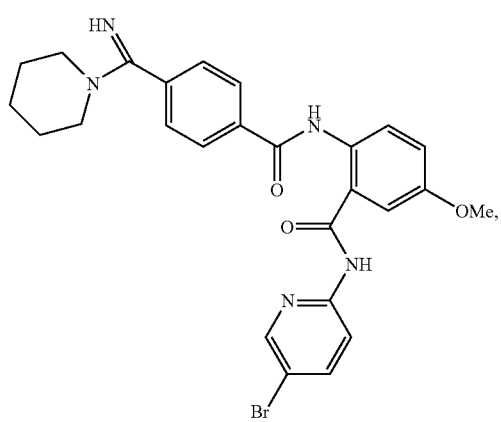

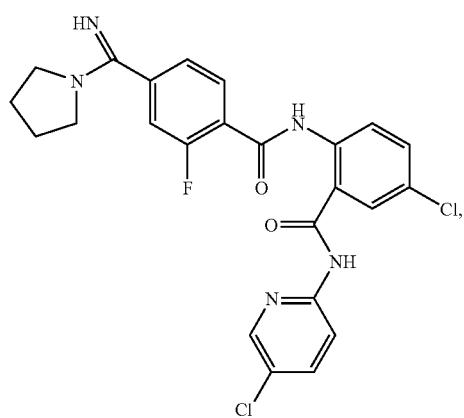
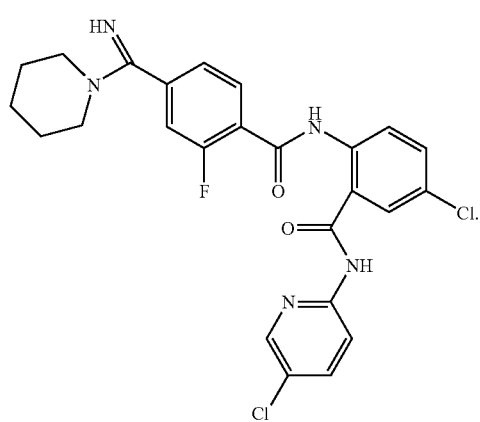
In another further preferred embodiment the present invention provides the following compounds:
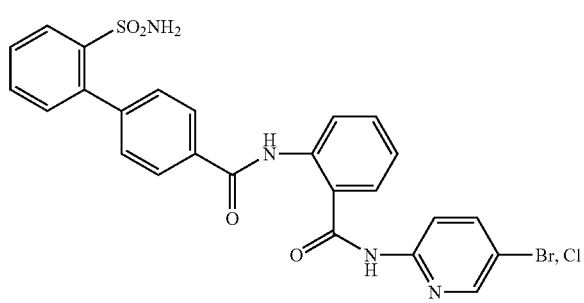
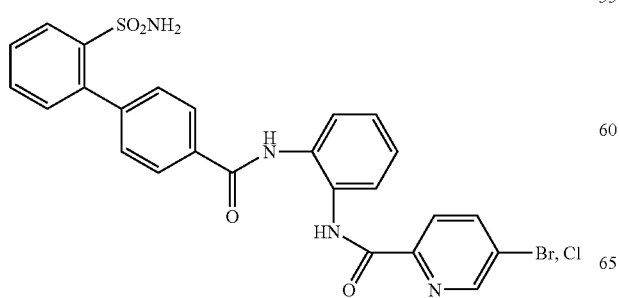
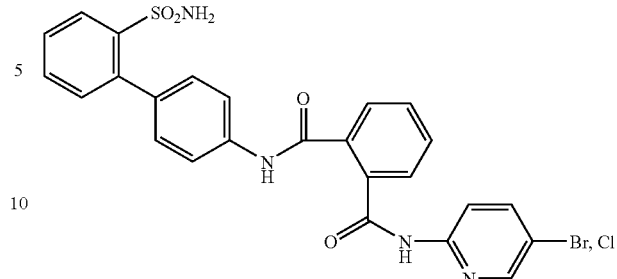
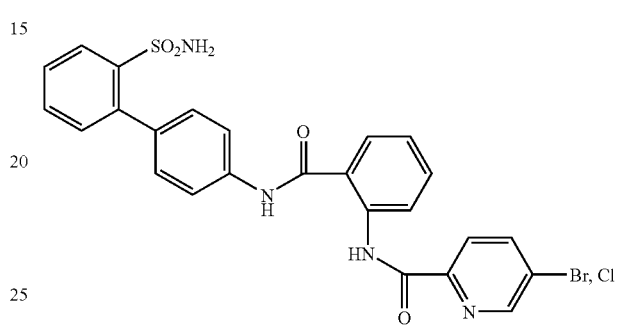
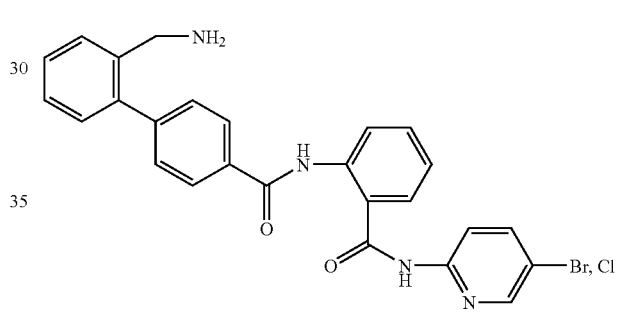
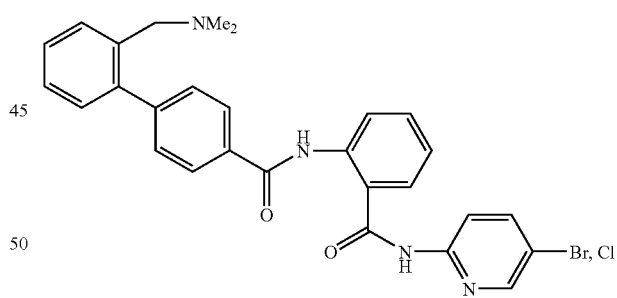
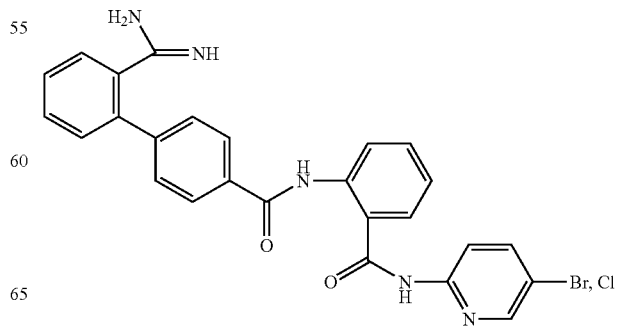

-continued
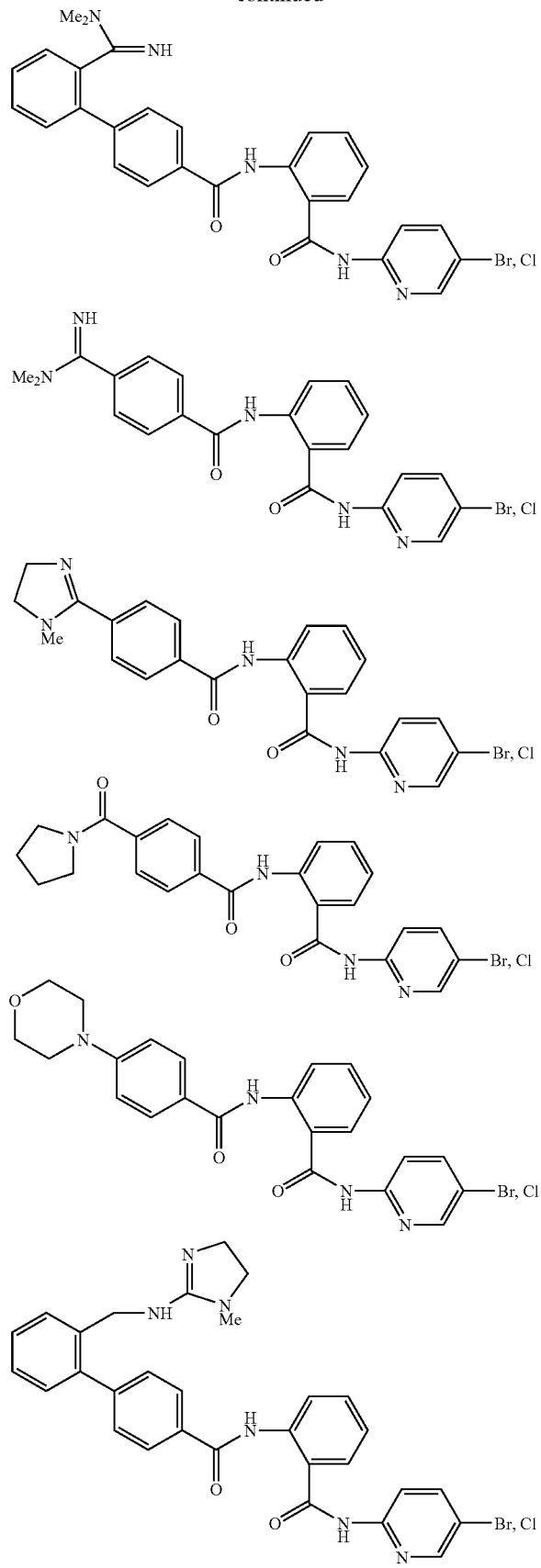
-continued
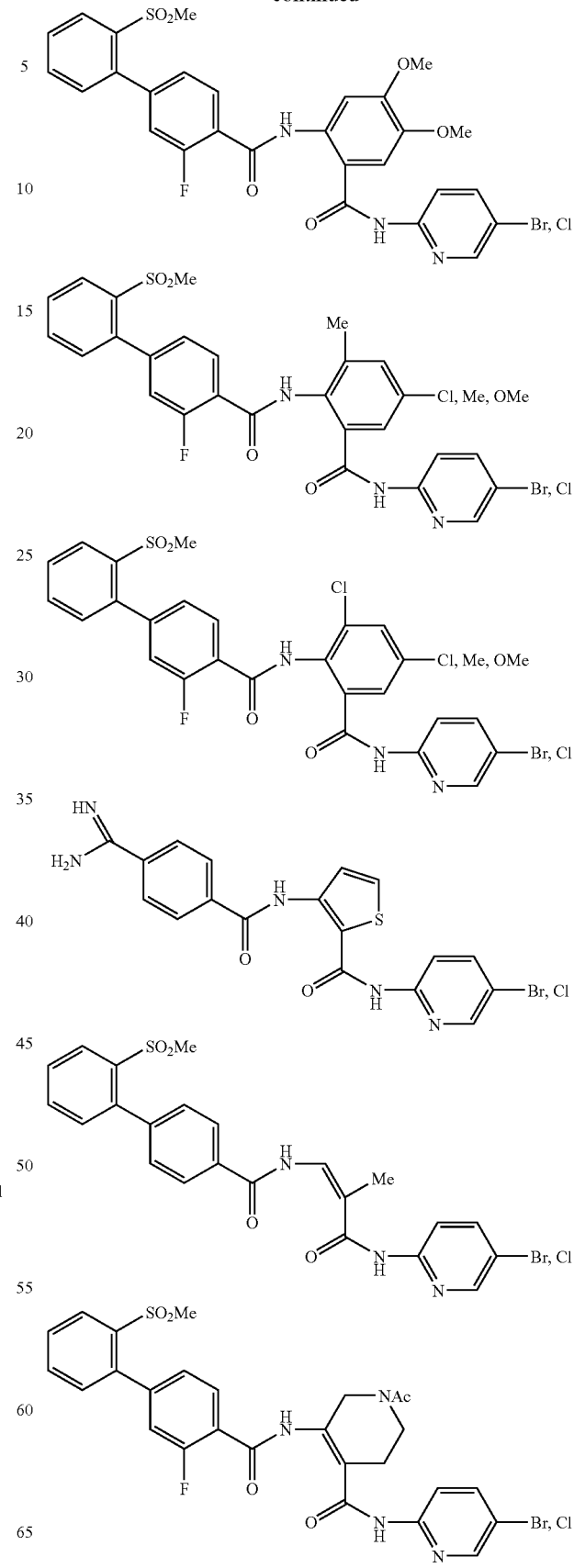

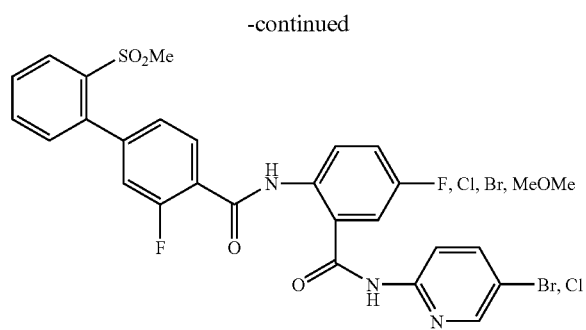
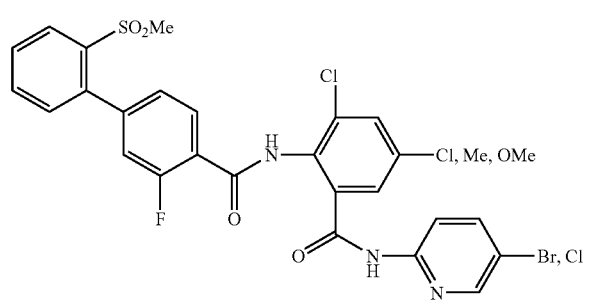
and all pharmaceutically acceptable isomers, salts, hydrates, solvates and prodrug derivatives thereof.
In another further preferred embodiment the present invention provides the following compounds:
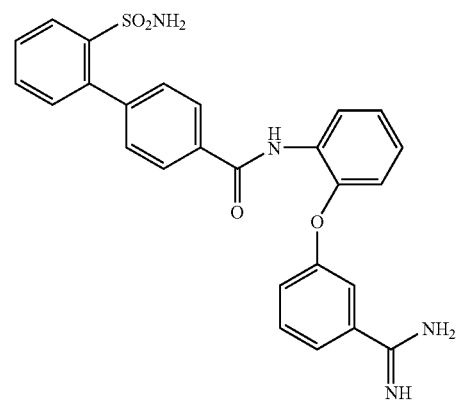
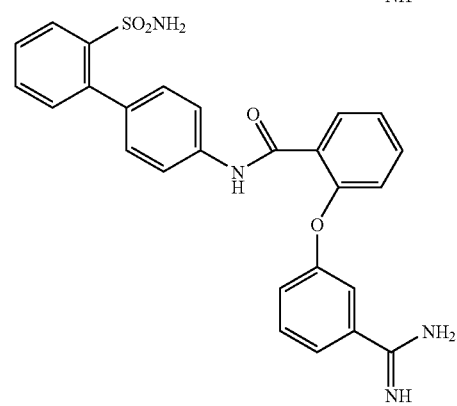
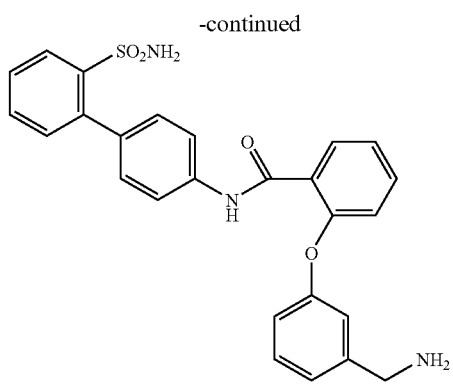
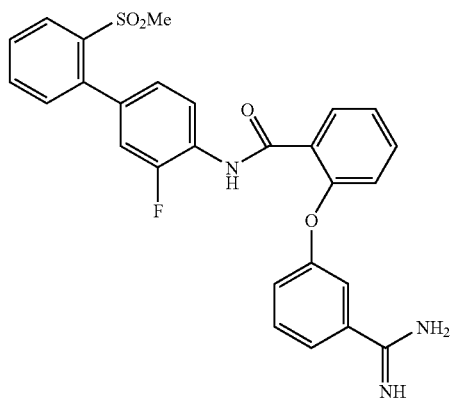
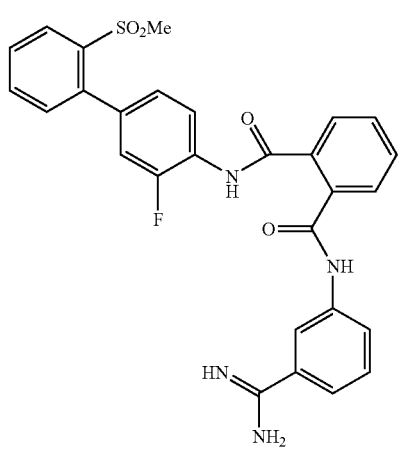

-continued
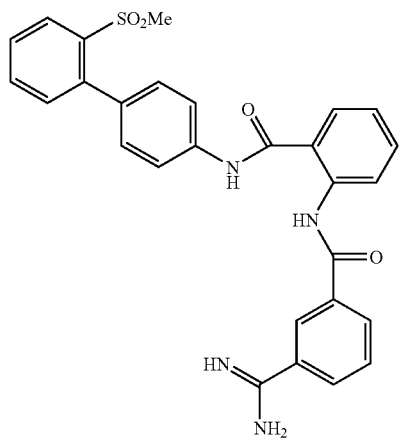
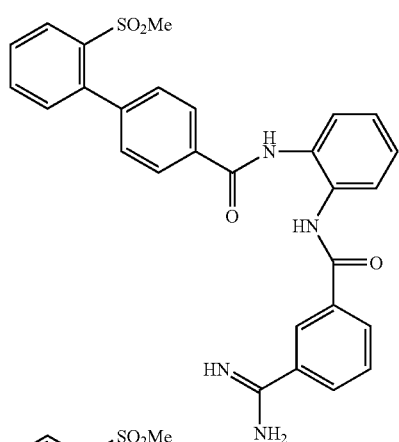
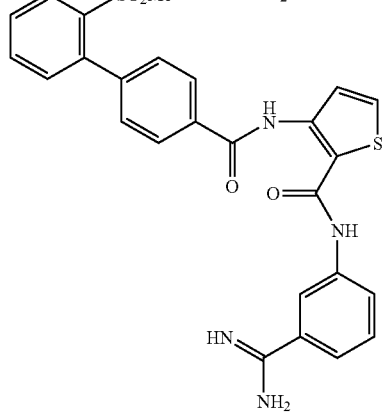
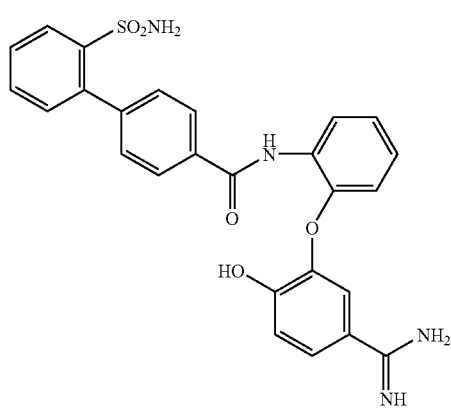
-continued
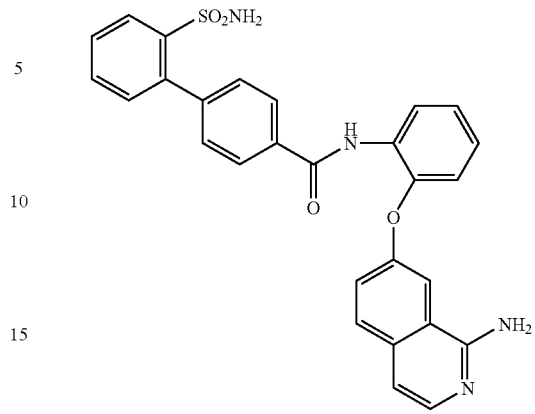
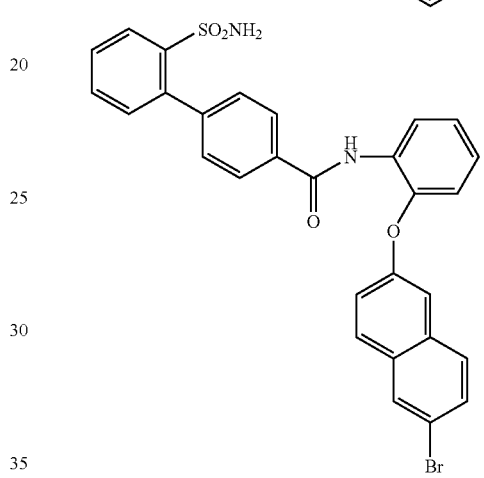
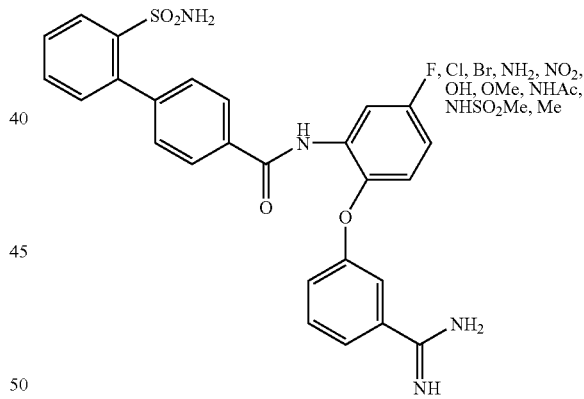
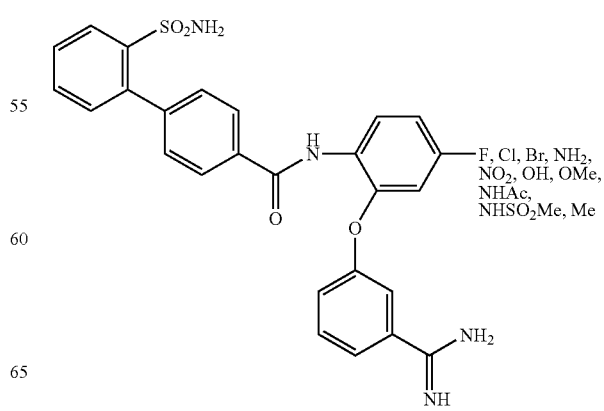

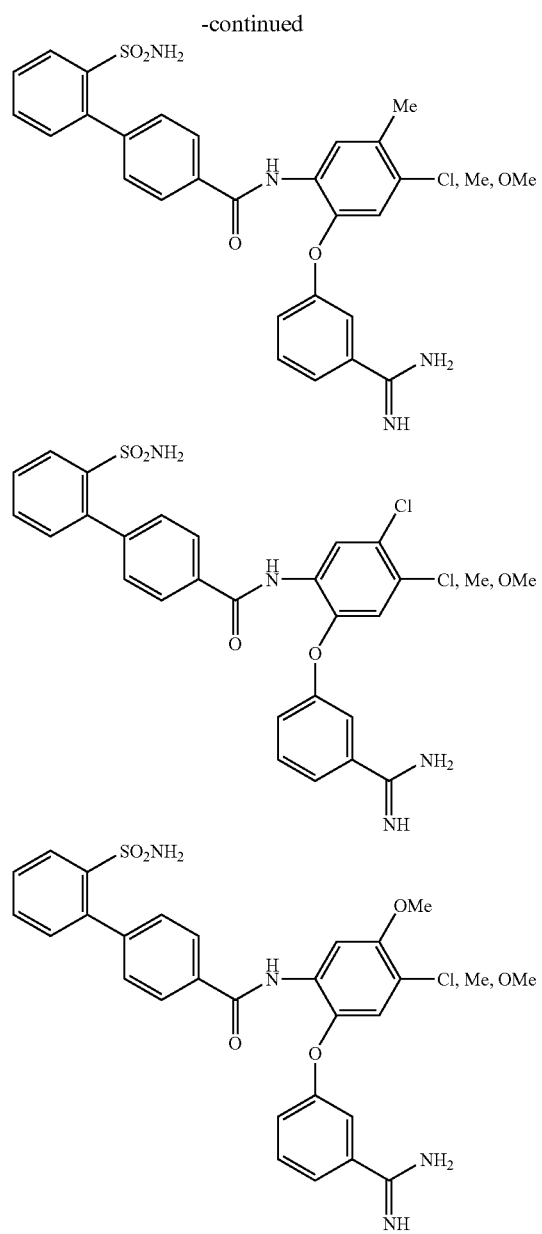
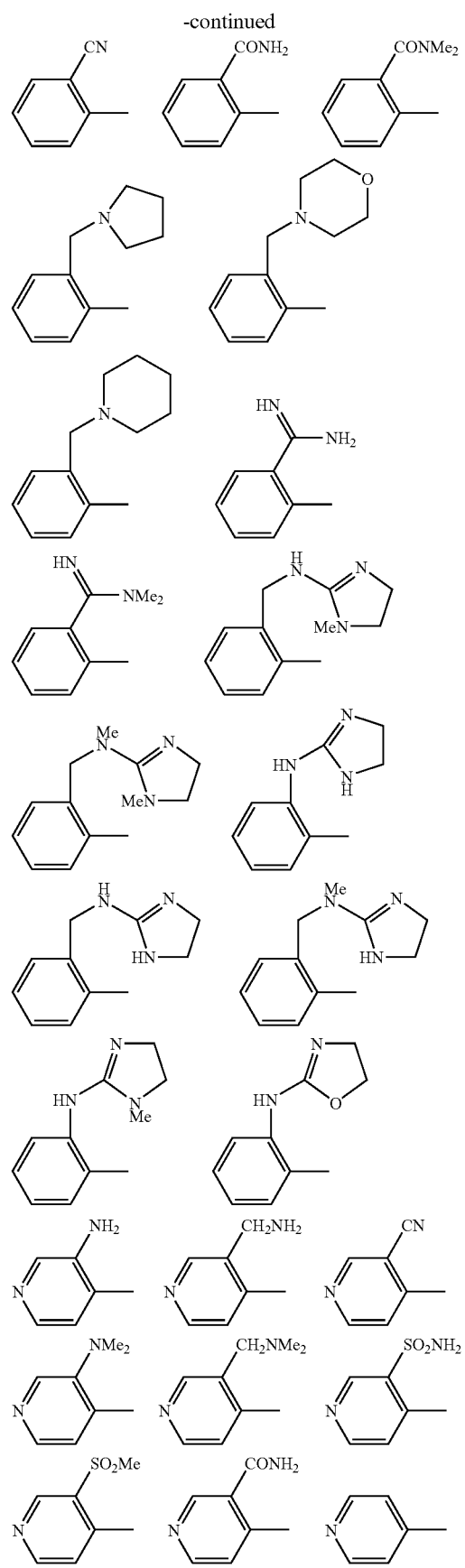
and all pharmaceutically acceptable isomers, salts, hydrates, solvates and prodrug derivatives thereof.
The invention also provides compounds of formula Ib, as set forth above, wherein:
A is a member selected from the group consisting of:
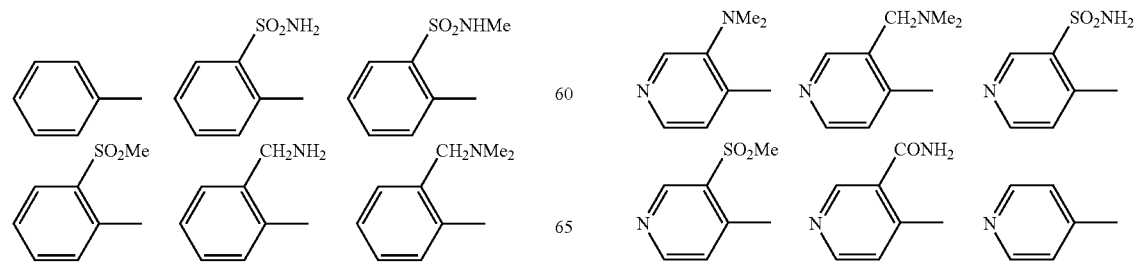

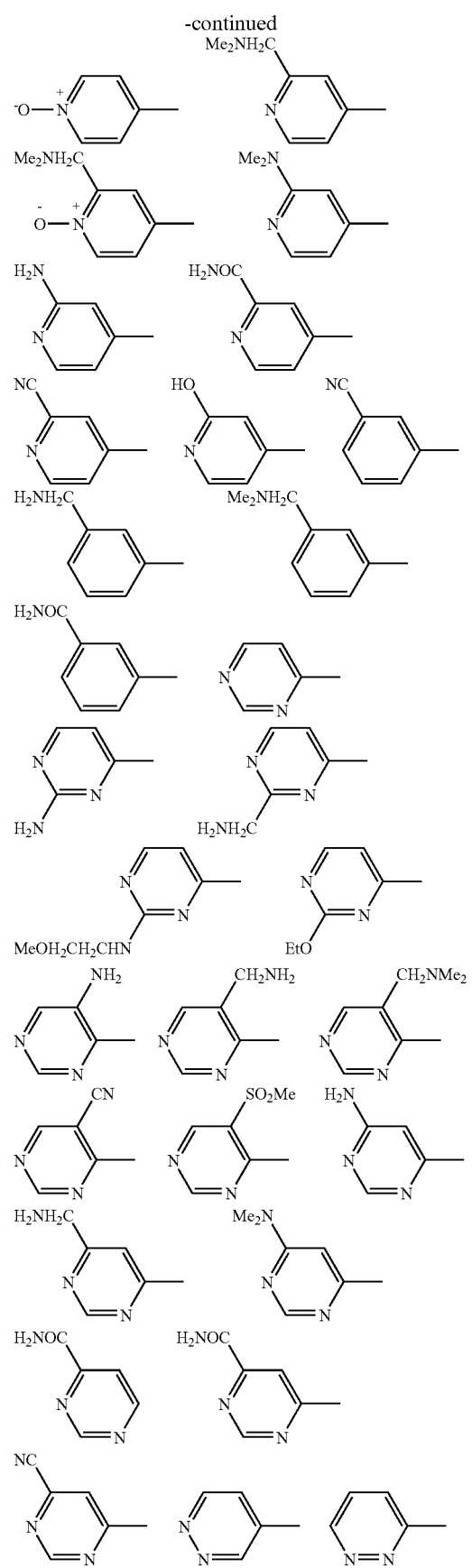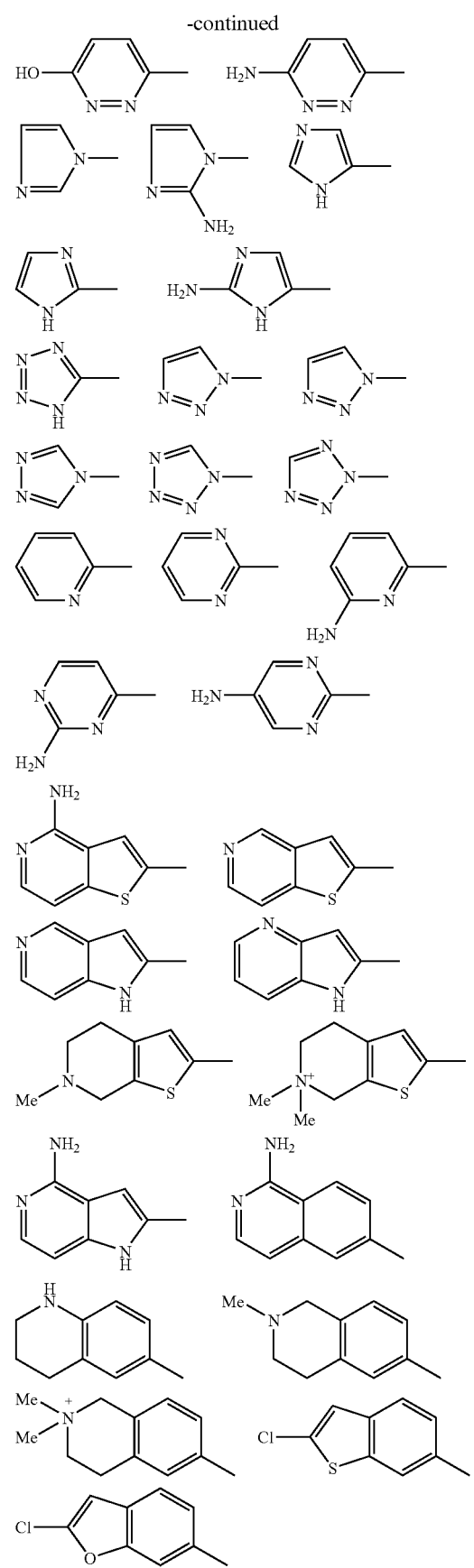

-continued
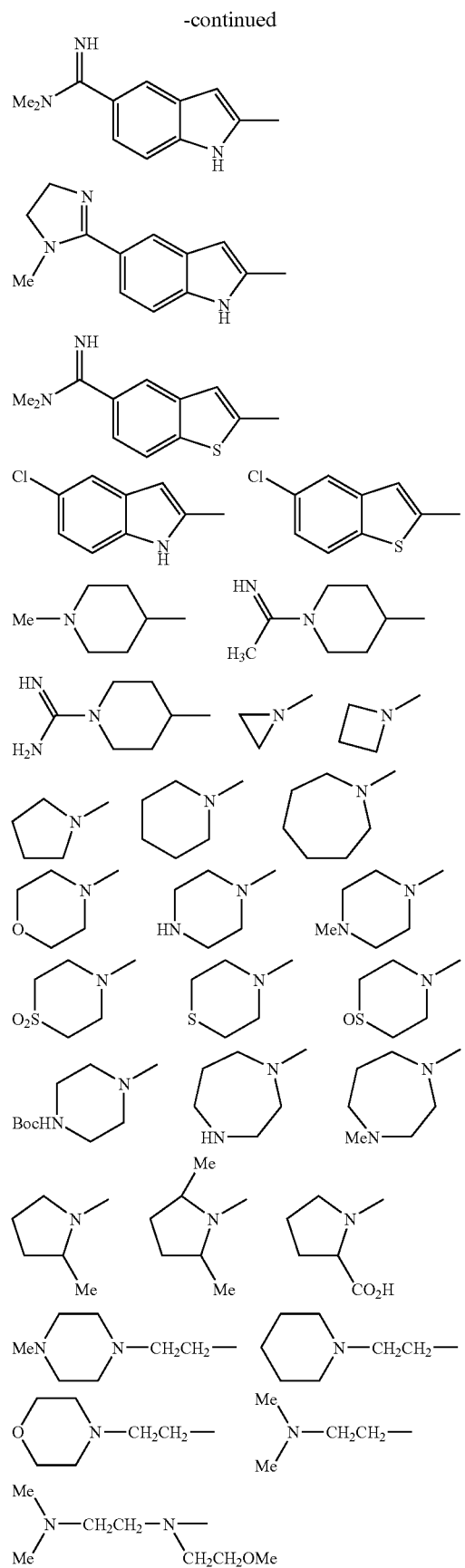
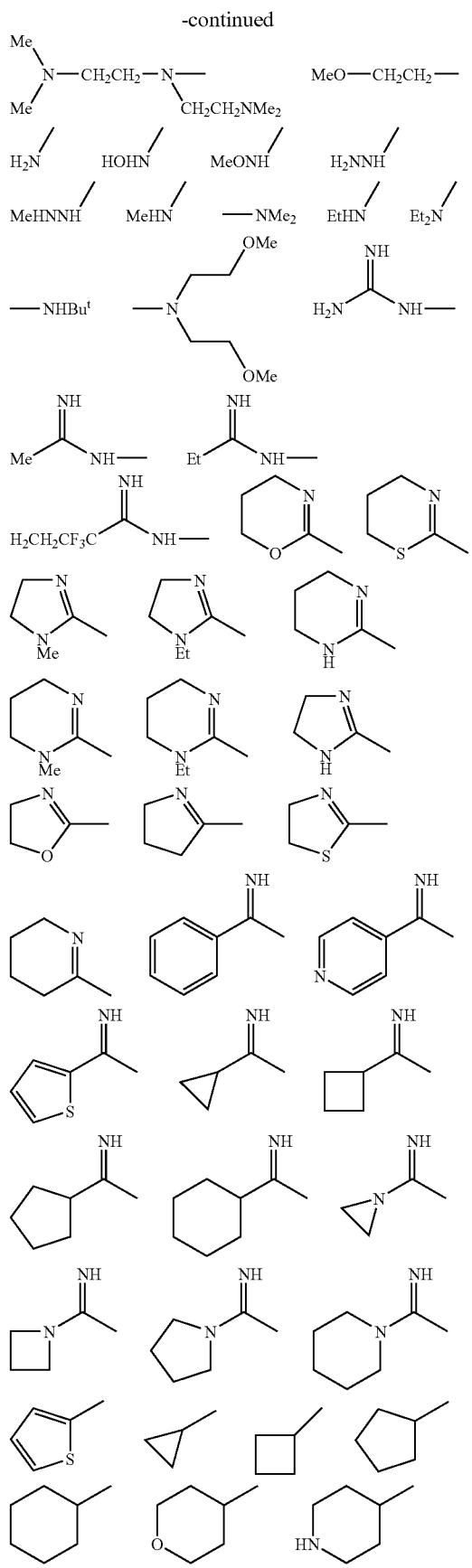

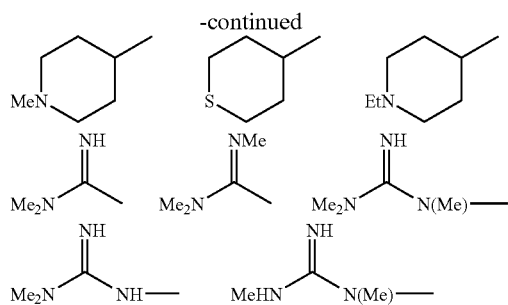
Q is a member selected from the group consisting of:
 a direct link, —CH$_2$—, C(=O)—, —NH—, —N(Me)—, —NHCH$_2$—, —N(Me)CH$_2$—; —C(=NH)—, —C(=NMe)—;
D is a direct link or is a member selected from the group consisting of:
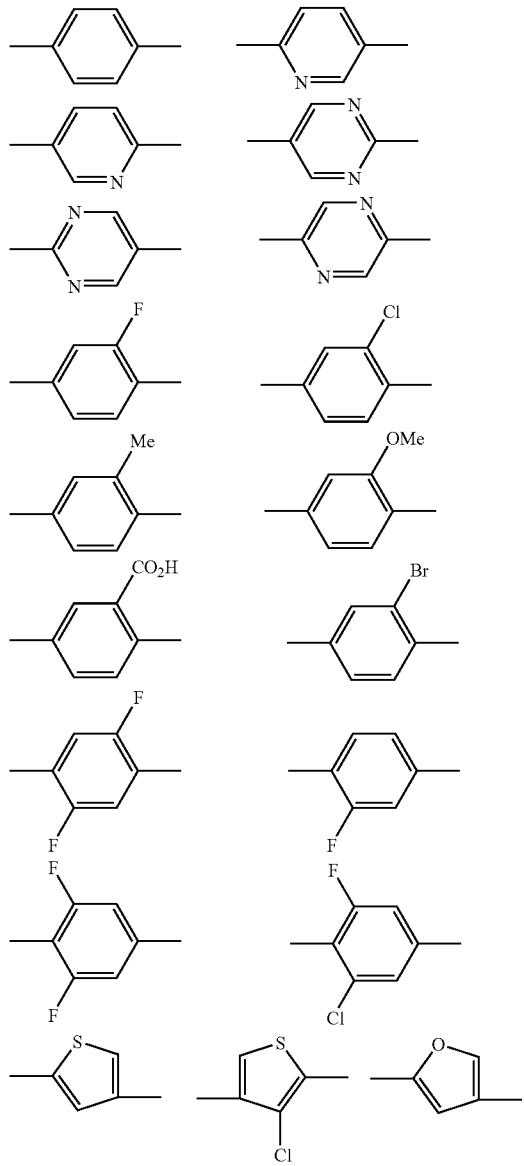
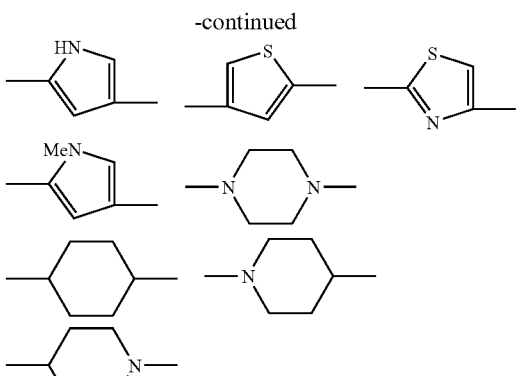
E is a member selected from the group consisting of:
 a direct link, —CH$_2$NH—, —NHCH$_2$—, —CH$_2$O—, —OCH$_2$—, —CH$_2$NH—, —CONH—, —NHCO—, —CONMe-, —NMeCO—;
G is a member selected from the group consisting of:
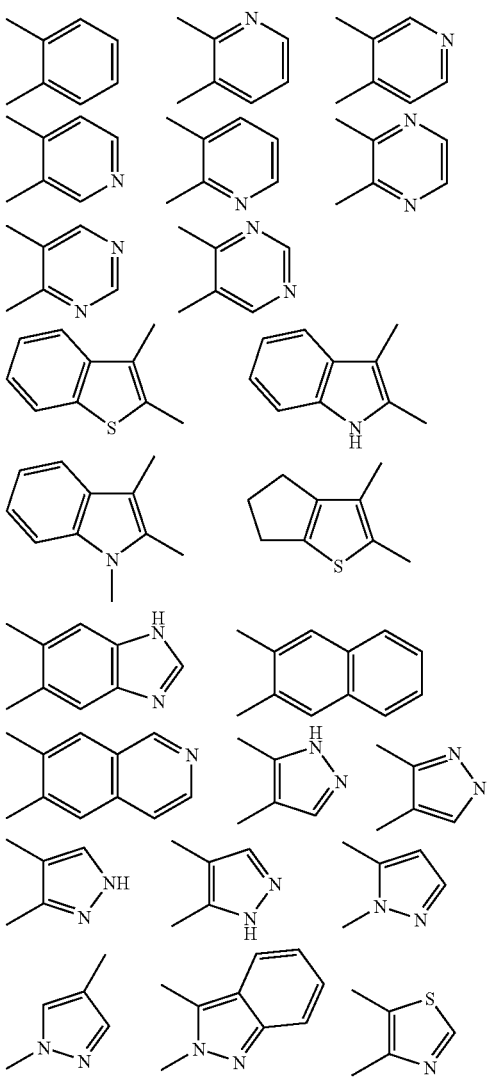

-continued

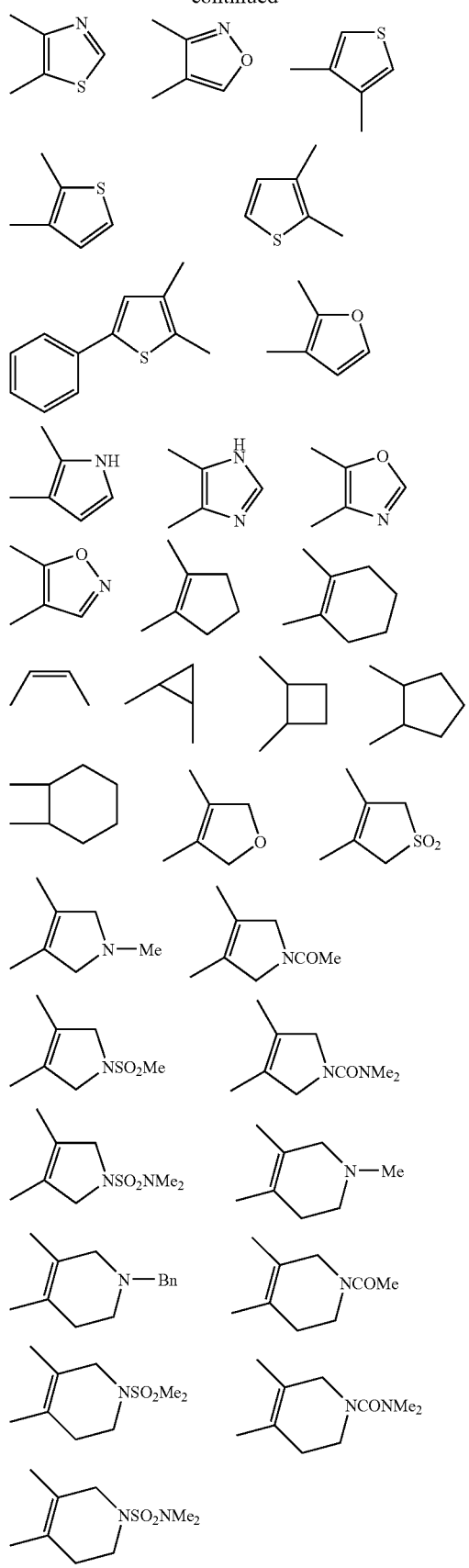

G is substituted by 0-4 $R^{1d}$ groups and each $R^{1d}$ group is independently selected from the group consisting of:

H, -Me, —F, —Cl, —Br, aryl, heteroaryl, —$NH_2$, —$NMe_2$, —NHMe, —$NHSO_2Me$, —NHCOMe, —$CH_3$, —$CF_3$, —OH, —$OCH_3$, —$SCH_3$, —$OCF_3$, —$OCH_2F$, —$OCHF_2$, —$OCH_2CF_3$, —$OCF_2CF_3$, —$NO_2$, —CN, —$CO_2H$, —$CO_2Me$, —$CO_2Et$, —$CONH_2$, —CONHMe, —$CONMe_2$, —$SO_2NH_2$, —$SO_2CH_3$, —$SO_2NMe_2$, —$CH_2OH$, —$CH_2NH_2$, —$CH_2NHMe$, —$CH_2NMe_2$, —$OCH_2CO_2H$, —$OCH_2CO_2Me$, —$OCH_2CO_2Et$, —$OCH_2CONH_2$, —$OCH_2CONMe_2$, —$OCH_2CONHMe$, —$OCH_2CH_2OMe$, —$OCH_2CH_2OEt$, —$OCH_2CH_2NH_2$, —$OCH_2CH_2NHMe$, —$OCH_2CH_2NMe_2$, —$NHCH_2CH_2OMe$, —$SCH_2CH_2OMe$, —$SO_2CH_2CH_2OMe$, —$OCH_2CH_2SO_2Me$, —$NHCH_2CH_2NHMe$, —$NHCH_2CH_2NMe_2$, —$N(CH_2CH_2OH)_2$, —$N(CH_2CH_2OMe)_2$, —$NHCH_2CO_2H$, —$NHCH_2CO_2Et$, —$NHCH_2CO_2Et$, —$NHCH_2CONH_2$, —$NHCH_2CONMe_2$, —$NHCH_2CONHMe$, —$N(CH_3)CH_2CO_2H$, —$N(CH_3)CH_2CO_2Et$, —(NMe)CH2COOH, —N(Me)CH2CONH2, —N(Me)CH2CH2NMe2, —N(Me)CH2CH2OMe, —NHCH2CH2OMe,

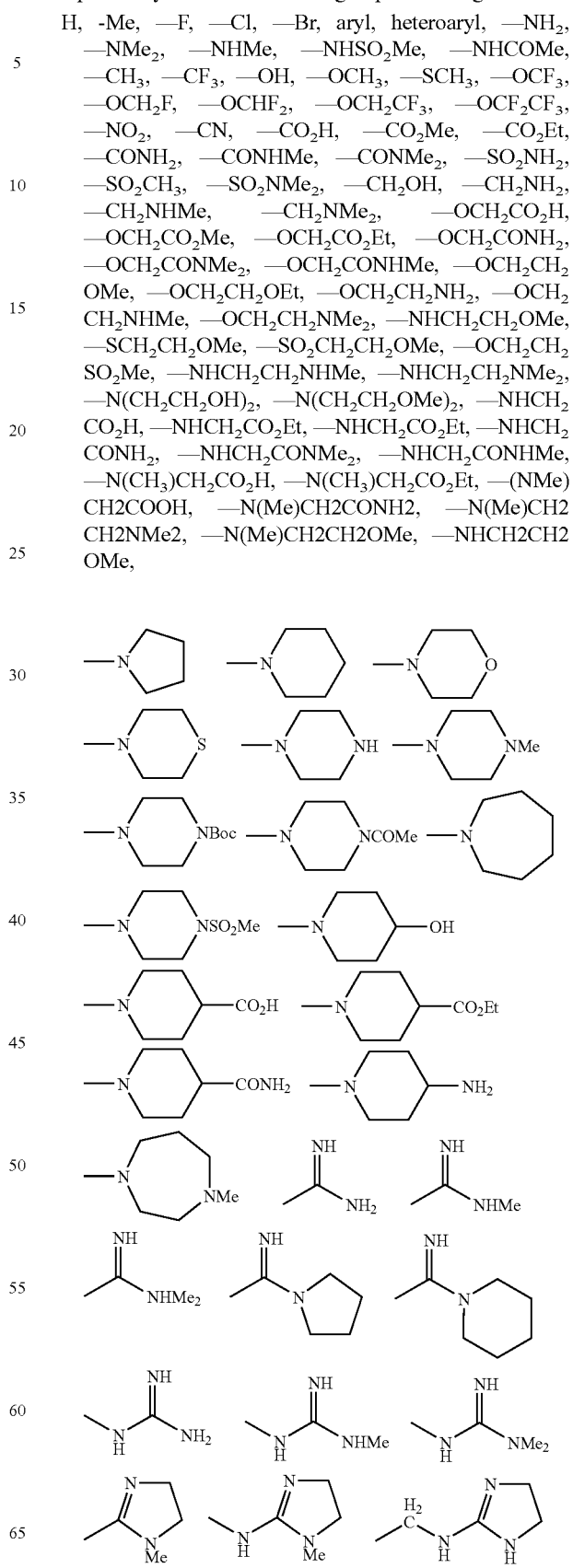

-continued
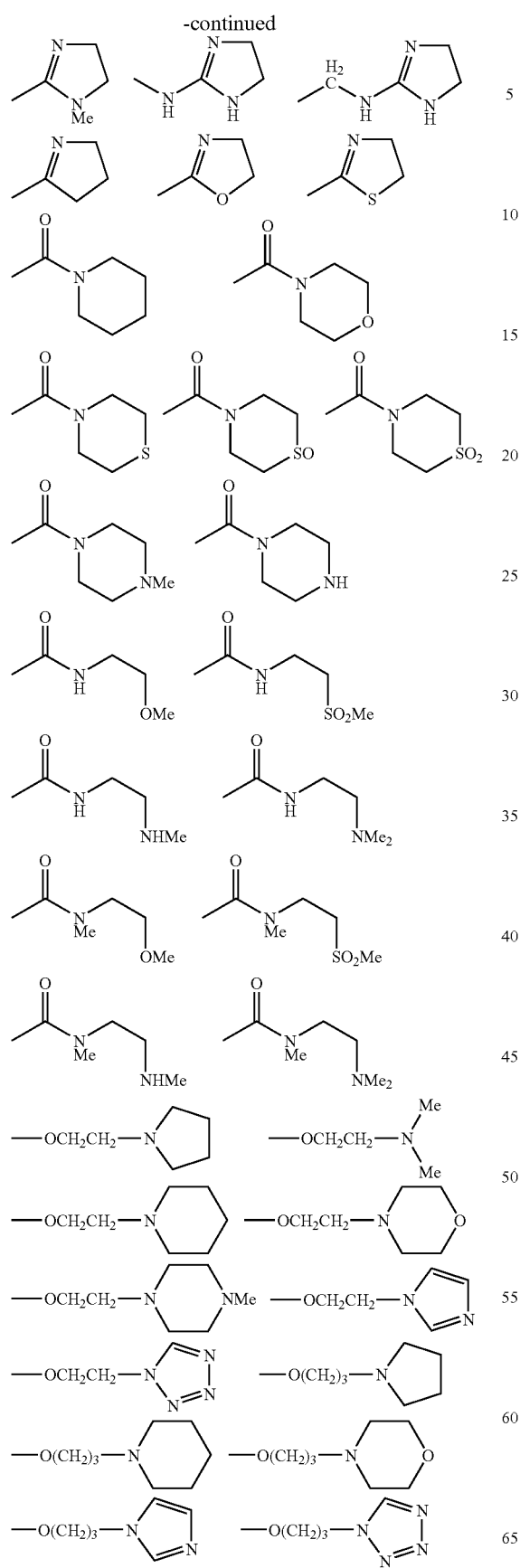
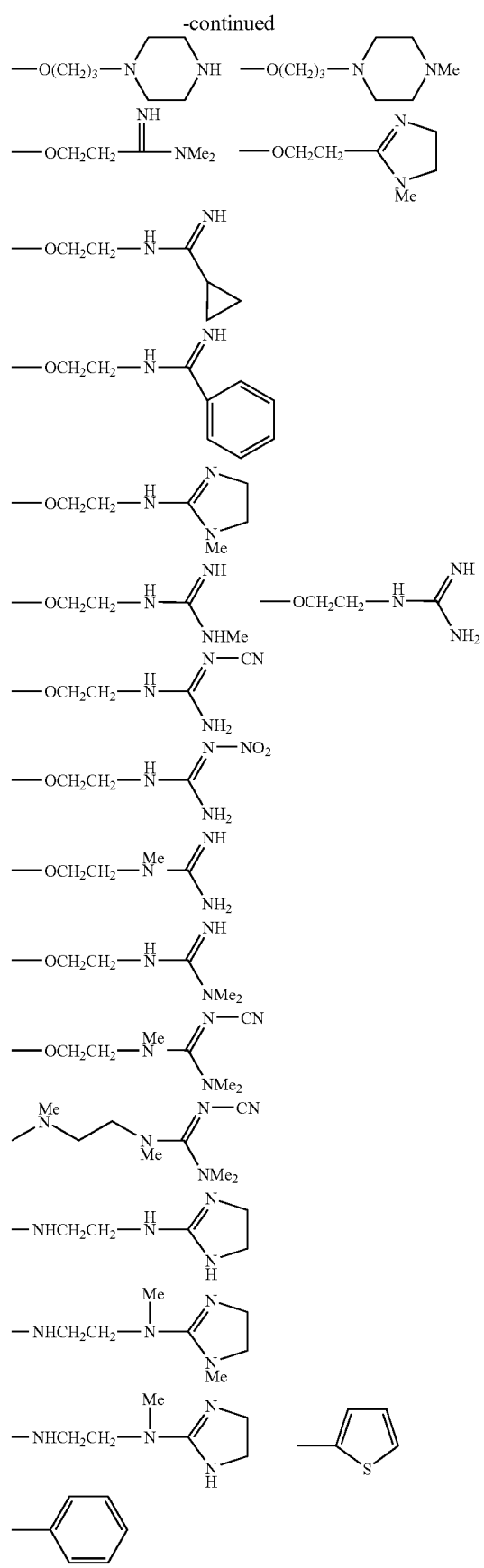

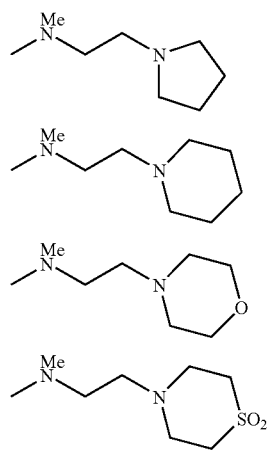
J is a member selected from the group consisting of:
a direct link, —SO2—, —CO—, —O—, —NH—, —C(=O)—NH— and —NH—C(=O)—;
X is a member selected from the group consisting of:
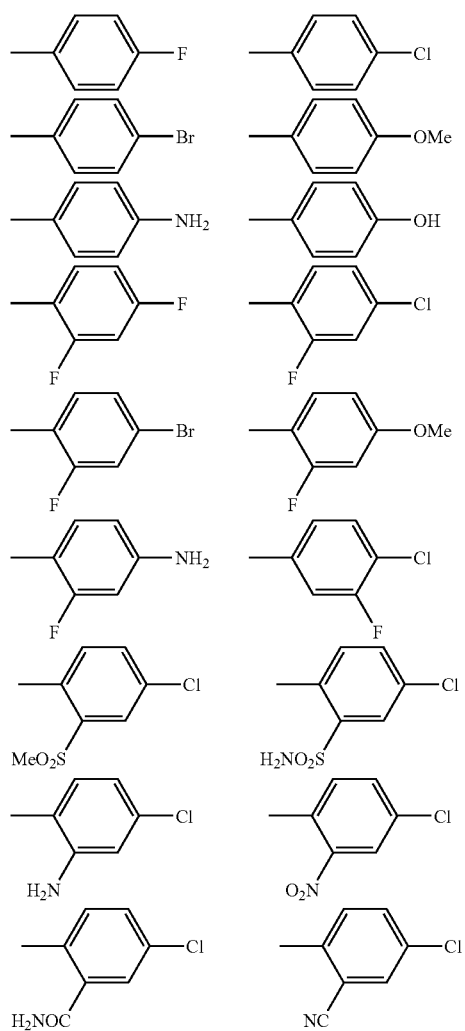
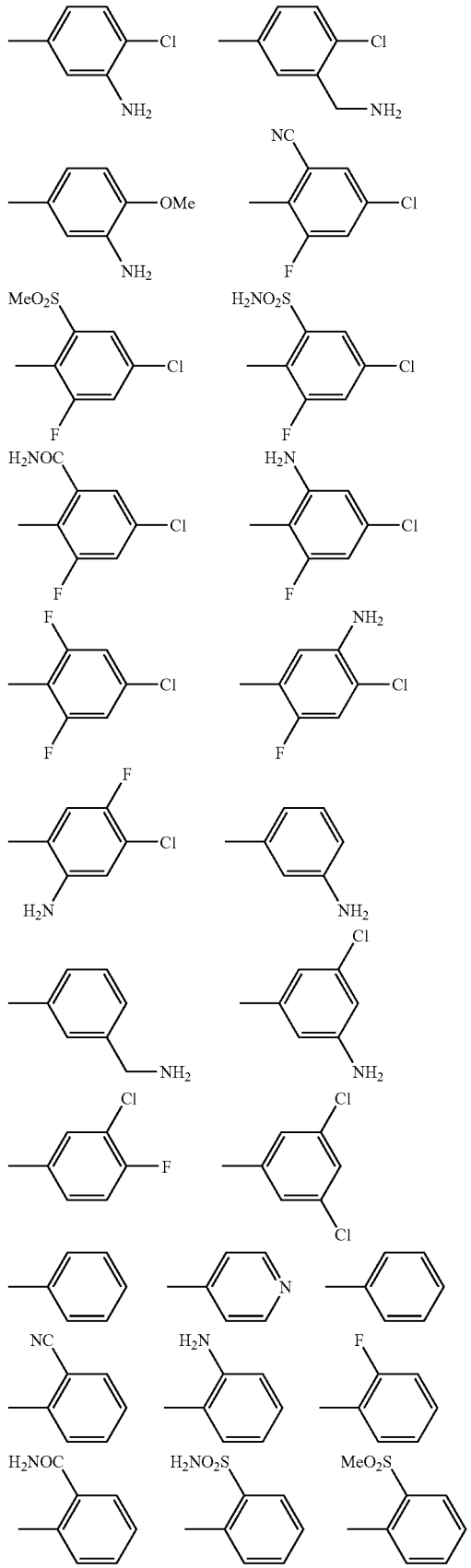

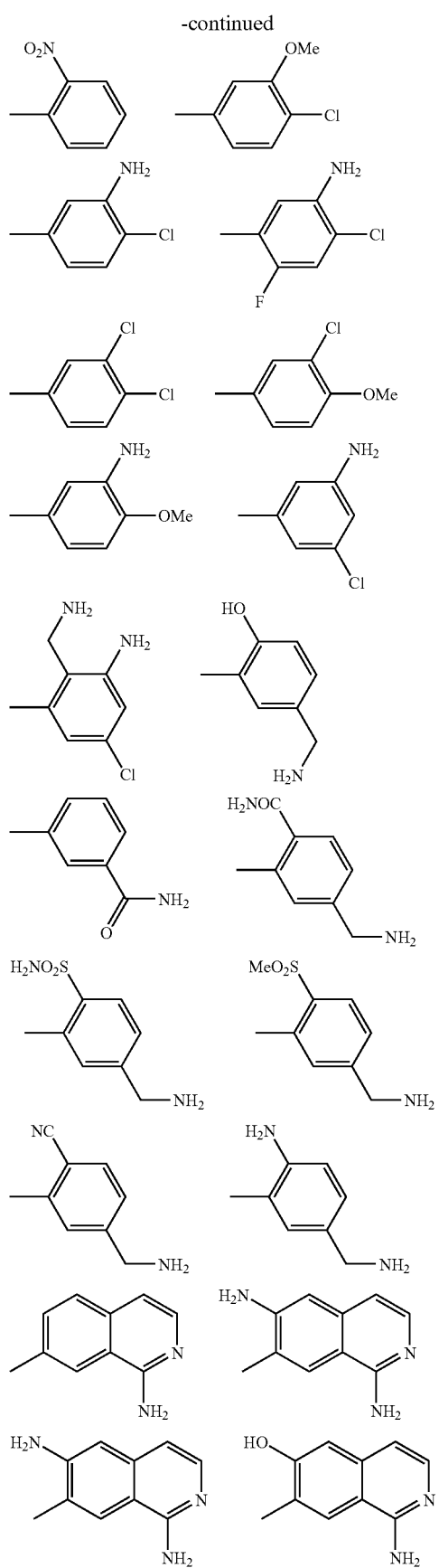
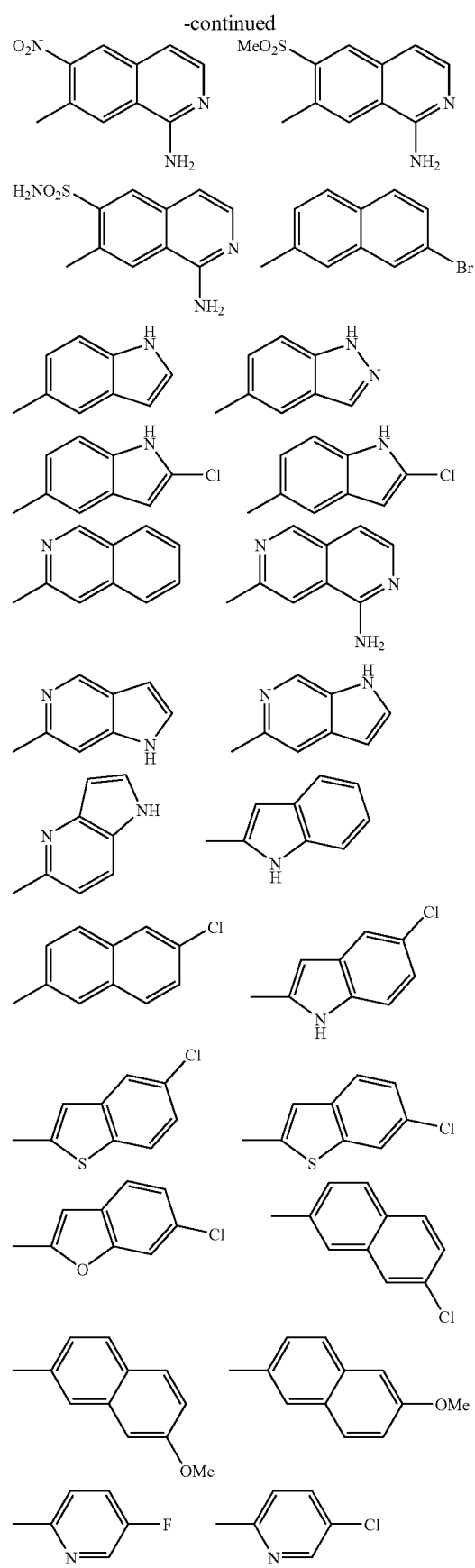

-continued
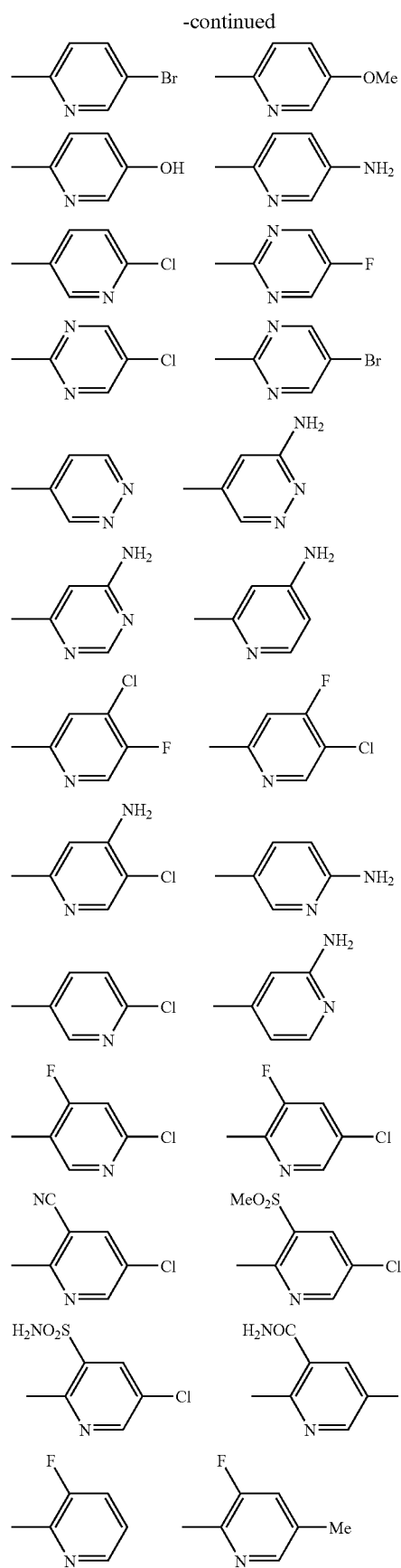
-continued
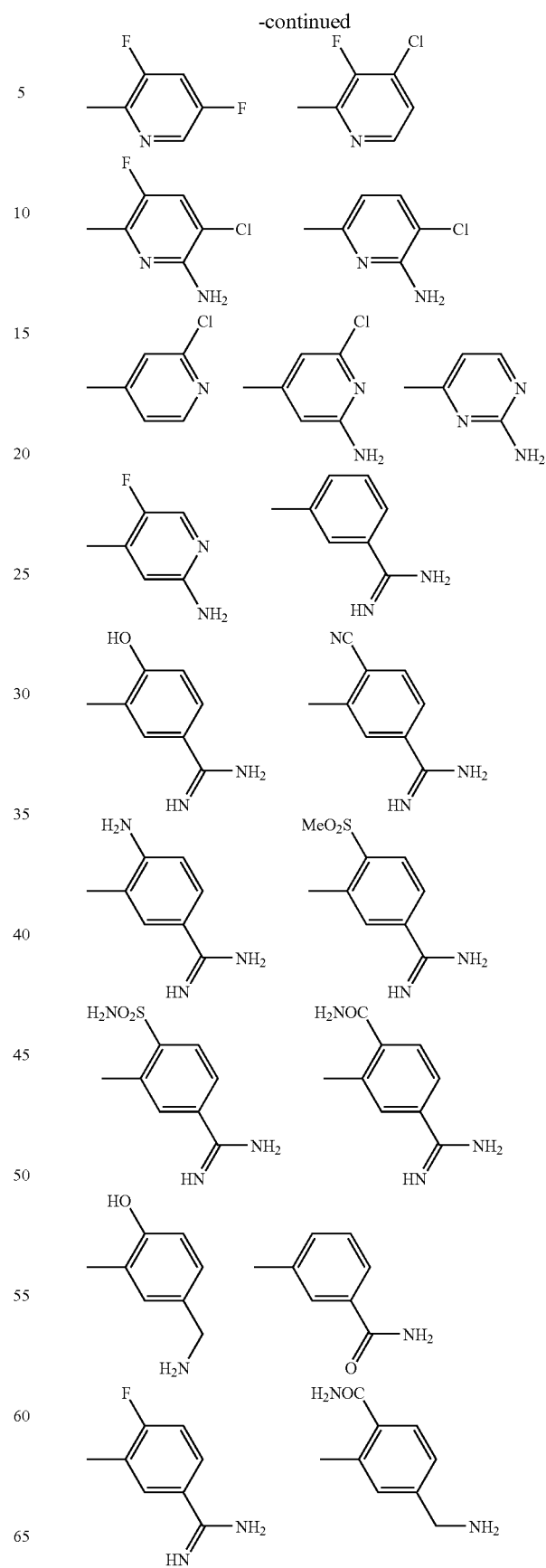

-continued

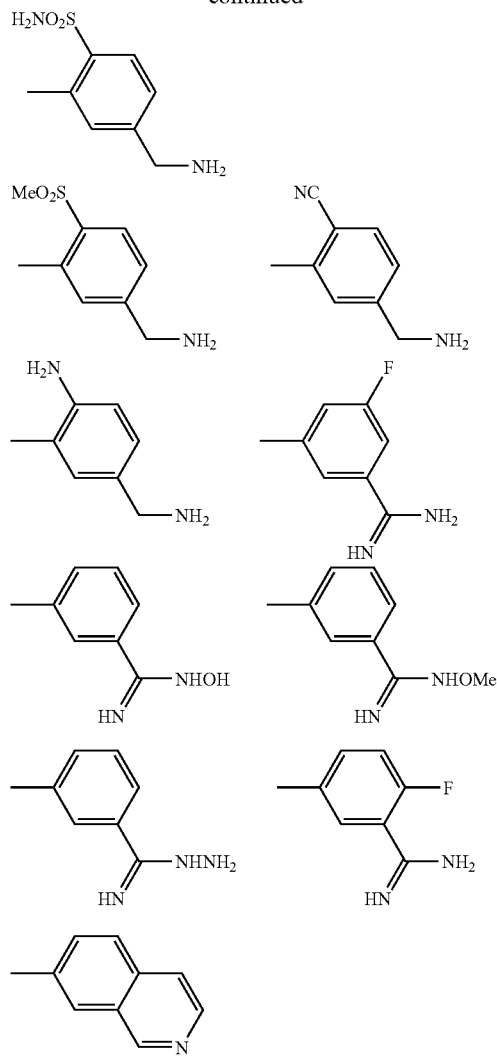

and all pharmaceutically acceptable isomers, salts, hydrates, solvates and prodrug derivatives thereof.

The invention provides compound of formula Ib, as described above, having the following structure:

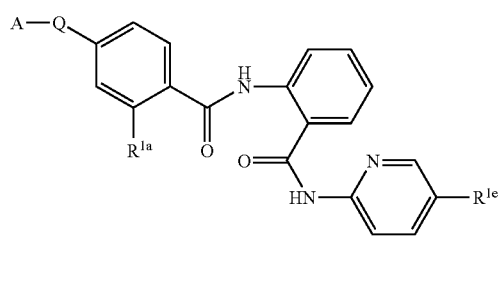

where:
$R^{1a}$ is a member selected from the group consisting of:
 H, —F, —Cl and —Br;
$R^{1e}$ is a member selected from the group consisting of:
 H, —F, —Cl, —Br, —OMe, —OH, -Me, —CF$_3$ and —CH$_2$NH$_2$; and A-Q is a member selected from the group consisting of:

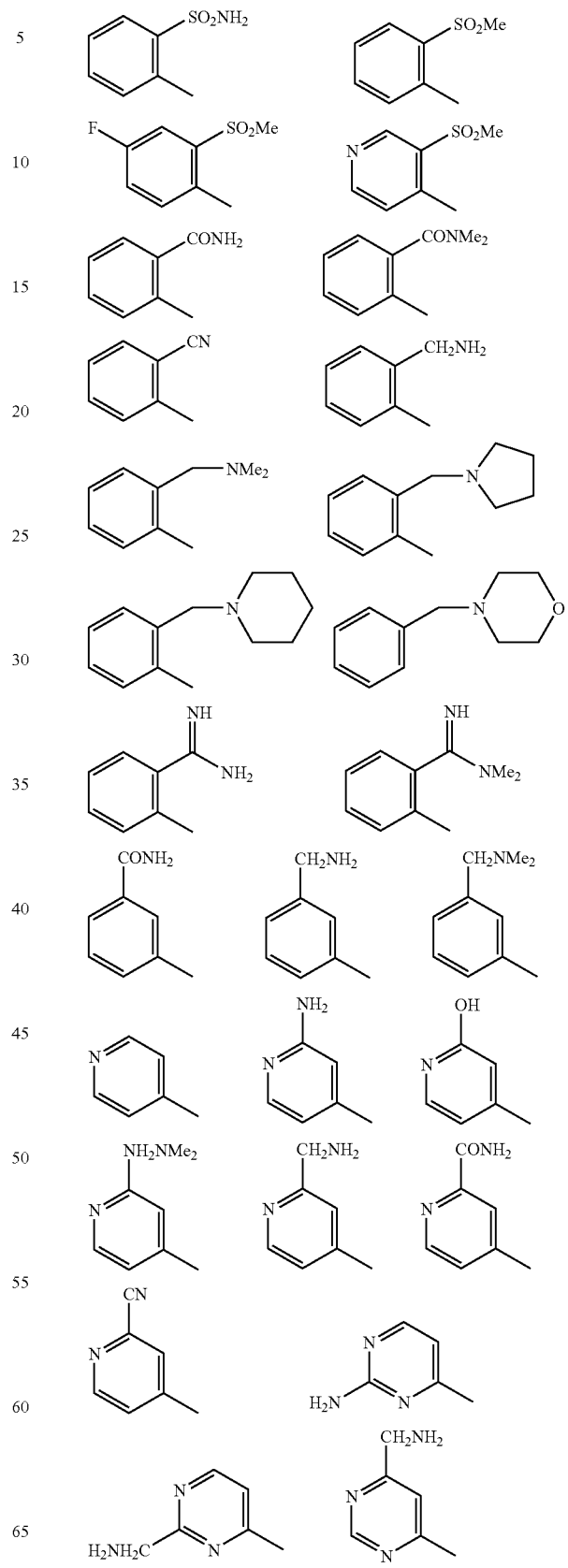

-continued

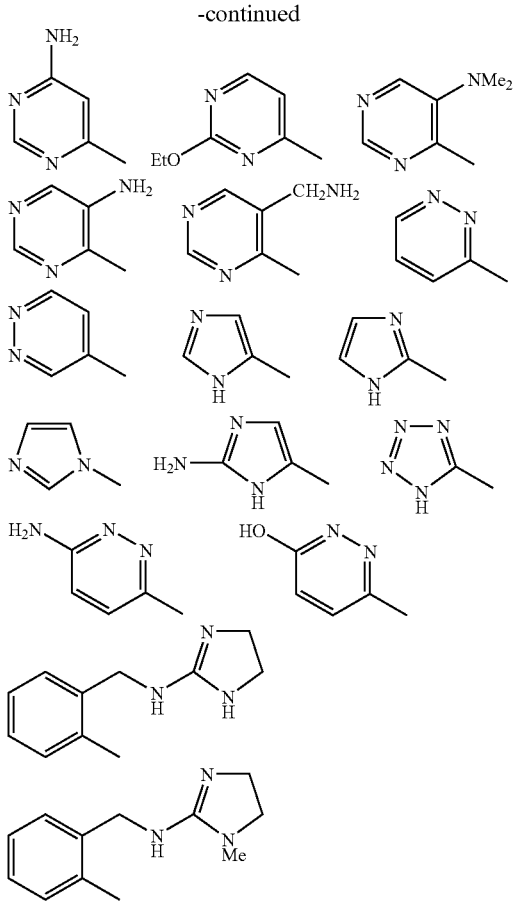

and all pharmaceutically acceptable isomers, salts, hydrates, solvates and prodrug derivatives thereof.

The invention provides compound of formula Ib, having the following structure:

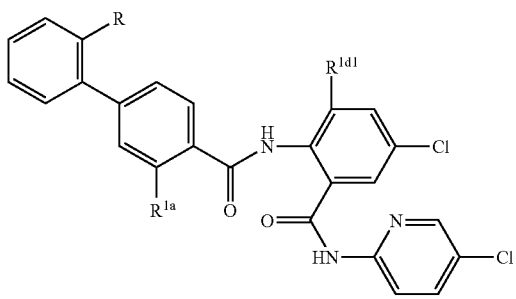

wherein:
R is a member selected from the group consisting of:
—$SO_2Me$, —$SO_2NH_2$, —$CH_2NH_2$, —$CH_2N(CH_3)_2$;
$R^{1a}$ is a member selected from the group consisting of:
H, —F;
$R^{1d1}$ is a member selected from the group consisting of:
H, -Me, —F, —Cl, —Br, aryl, heteroaryl, —$NH_2$, —$NMe_2$, —NHMe, —$NHSO_2Me$, —NHCOMe, —$CH_3$, —$CF_3$, —OH, —$OCH_3$, —$SCH_3$, —$OCF_3$, —$OCH_2F$, —$OCHF_2$, —$OCH_2CF_3$, —$OCF_2CF_3$, —$NO_2$, —CN, —$CO_2H$, —$CO_2Me$, —$CO_2Et$, —$CONH_2$, —CONHMe, —$CONMe_2$, —$SO_2NH_2$, —$SO_2CH_3$, —$SO_2NMe_2$, —$CH_2OH$, —$CH_2NH_2$, —$CH_2NHMe$, —$CH_2NMe_2$, —$OCH_2CO_2H$, —$OCH_2CO_2Me$, —$OCH_2CO_2Et$, —$OCH_2CONH_2$, —$OCH_2CONMe_2$, —$OCH_2CONHMe$, —$OCH_2CH_2OMe$, —$OCH_2CH_2OEt$, —$OCH_2CH_2NH_2$, —$OCH_2CH_2NHMe$, —$OCH_2CH_2NMe_2$, —$NHCH_2CH_2OMe$, —$SCH_2CH_2OMe$, —$SO_2CH_2CH_2OMe$, —$OCH_2CH_2SO_2Me$, —$NHCH_2CH_2NHMe$, —$NHCH_2CH_2NMe_2$, —$N(CH_2CH_2OH)_2$, —$N(CH_2CH_2OMe)_2$, —$NHCH_2CO_2H$, —$NHCH_2CO_2Et$, —$NHCH_2CO_2Et$, —$NHCH_2CONH_2$, —$NHCH_2CONMe_2$, —$NHCH_2CONHMe$, —$N(CH_3)CH_2CO_2H$, —$N(CH_3)CH_2CO_2Et$, —(NMe)$CH2COOH$, —N(Me)CH2CONH2, —N(Me)CH2CH2NMe2, —N(Me)CH2CH2OMe, —NHCH2CH2OMe,

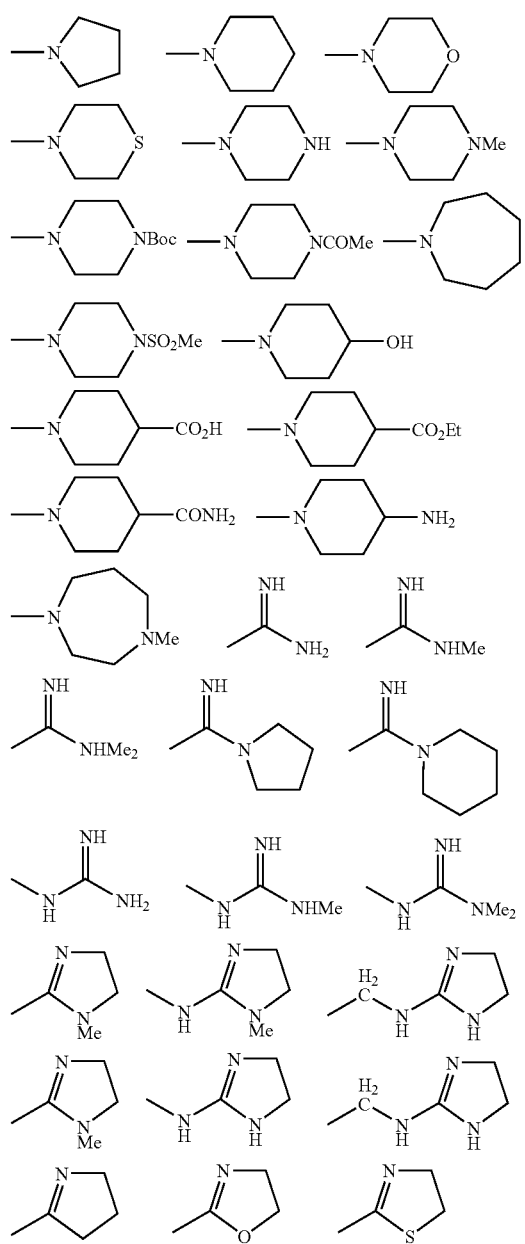

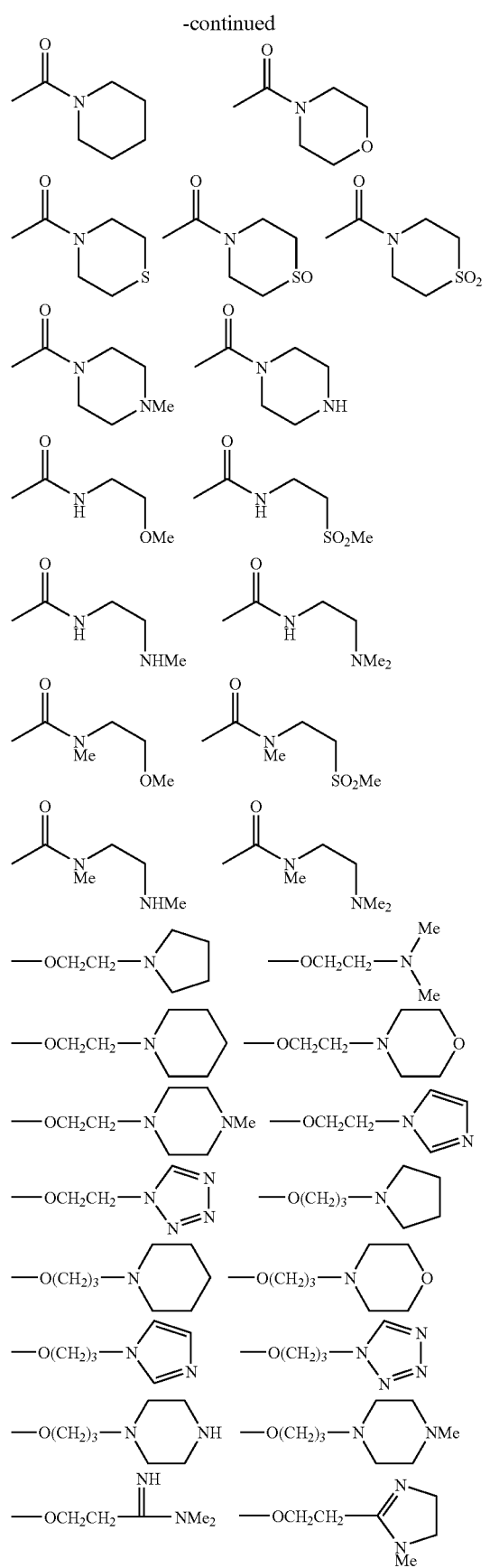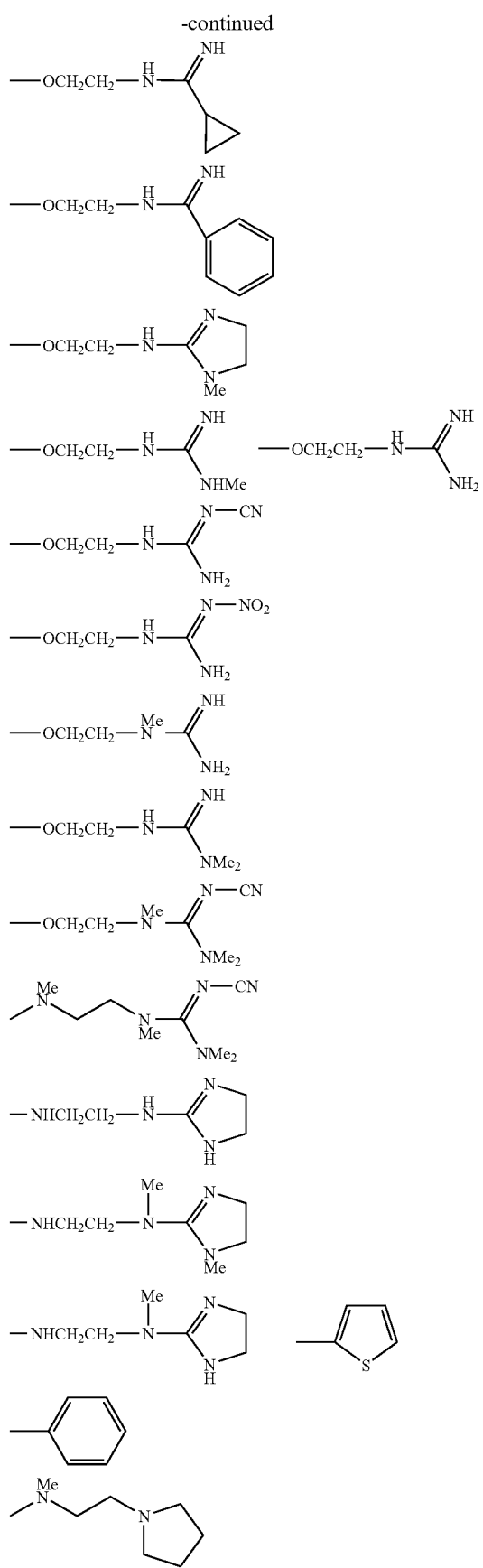

-continued

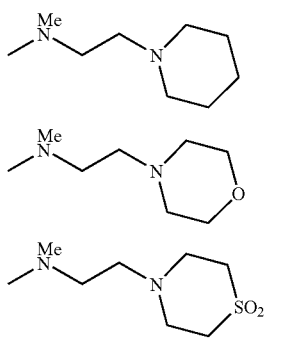

and all pharmaceutically acceptable isomers, salts, hydrates, solvates and prodrug derivatives thereof.

The invention provides compound of formula Ib, as described above, having the following structure:

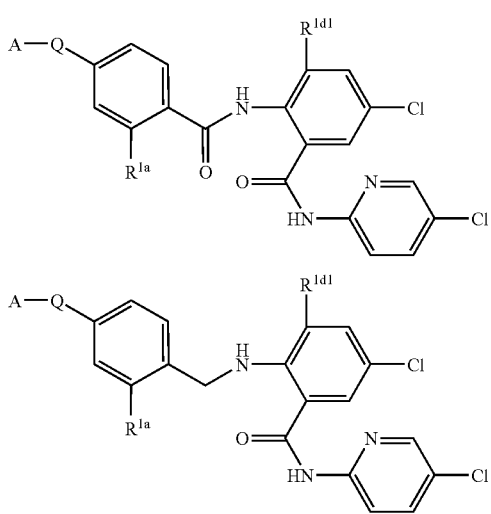

wherein:
A-Q is a member selected from the group consisting of:

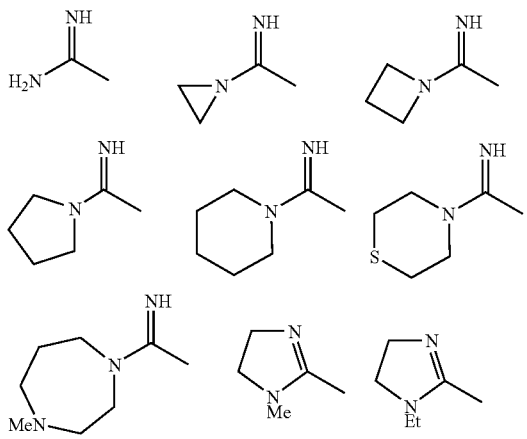

-continued

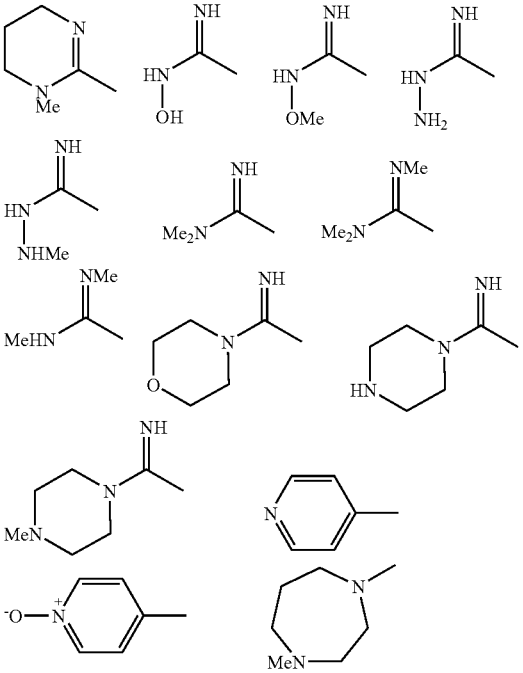

$R^{1a}$ is a member selected from the group consisting of:
H, —F;

$R^{1d1}$ is a member selected from the group consisting of:
H, -Me, —F, —Cl, —Br, aryl, heteroaryl, —NH$_2$, —NMe$_2$, —NHMe, —NHSO$_2$Me, —NHCOMe, —CH$_3$, —CF$_3$, —OH, —OCH$_3$, —SCH$_3$, —OCF$_3$, —OCH$_2$F, —OCHF$_2$, —OCH$_2$CF$_3$, —OCF$_2$CF$_3$, —NO$_2$, —CN, —CO$_2$H, —CO$_2$Me, —CO$_2$Et, —CONH$_2$, —CONHMe, —CONMe$_2$, —SO$_2$NH$_2$, —SO$_2$CH$_3$, —SO$_2$NMe$_2$, —CH$_2$OH, —CH$_2$NH$_2$, —CH$_2$NHMe, —CH$_2$NMe$_2$, —OCH$_2$CO$_2$H, —OCH$_2$CO$_2$Me, —OCH$_2$CO$_2$Et, —OCH$_2$CONH$_2$, —OCH$_2$CONMe$_2$, —OCH$_2$CONHMe, —OCH$_2$CH$_2$OMe, —OCH$_2$CH$_2$OEt, —OCH$_2$CH$_2$NH$_2$, —OCH$_2$CH$_2$NHMe, —OCH$_2$CH$_2$NMe$_2$, —NHCH$_2$CH$_2$OMe, —SCH$_2$CH$_2$OMe, —SO$_2$CH$_2$CH$_2$OMe, —OCH$_2$CH$_2$SO$_2$Me, —NHCH$_2$CH$_2$NHMe, —NHCH$_2$CH$_2$NMe$_2$, —N(CH$_2$CH$_2$OH)$_2$, —N(CH$_2$CH$_2$OMe)$_2$, —NHCH$_2$CO$_2$H, —NHCH$_2$CO$_2$Et, —NHCH$_2$CO$_2$Et, —NHCH$_2$CONH$_2$, —NHCH$_2$CONMe$_2$, —NHCH$_2$CONHMe, —N(CH$_3$)CH$_2$CO$_2$H, —N(CH$_3$)CH$_2$CO$_2$Et, —(NMe)CH2COOH, —N(Me)CH2CONH2, —N(Me)CH2CH2NMe2, —N(Me)CH2CH2OMe, —NHCH2CH2OMe,

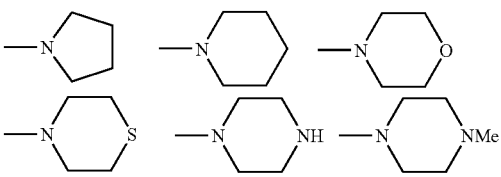

-continued
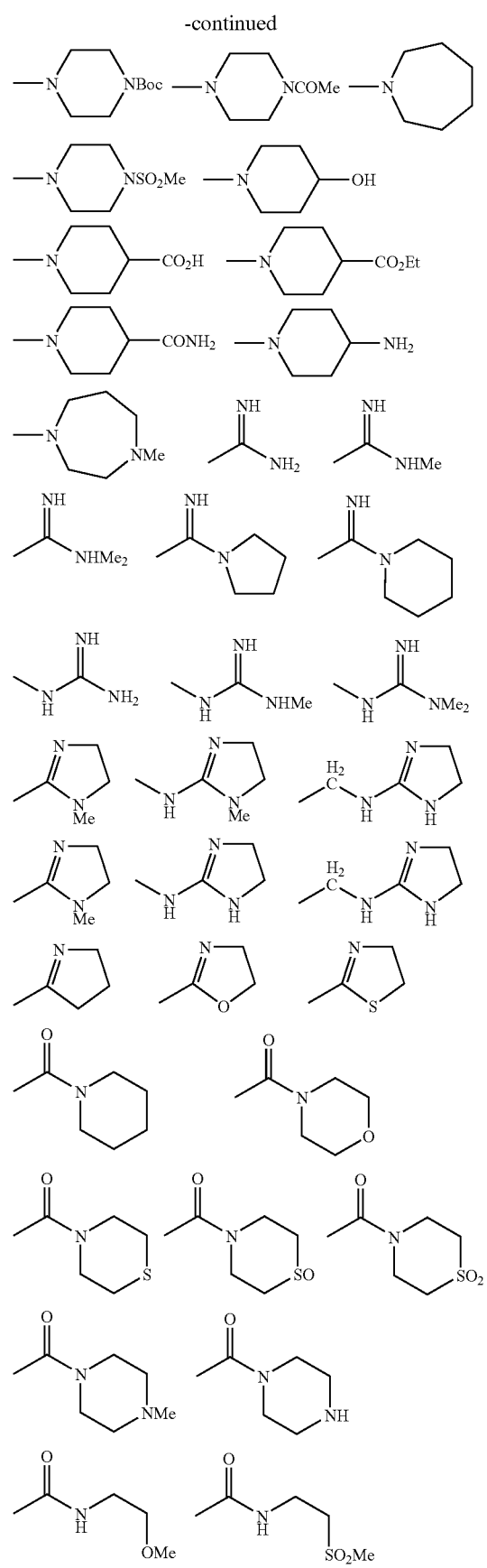

113
-continued
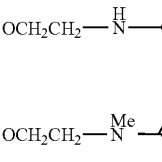
and all pharmaceutically acceptable isomers, salts, hydrates, solvates and prodrug derivatives thereof.
114
The invention provides compound of formula Ib, as described above, having the following structure:
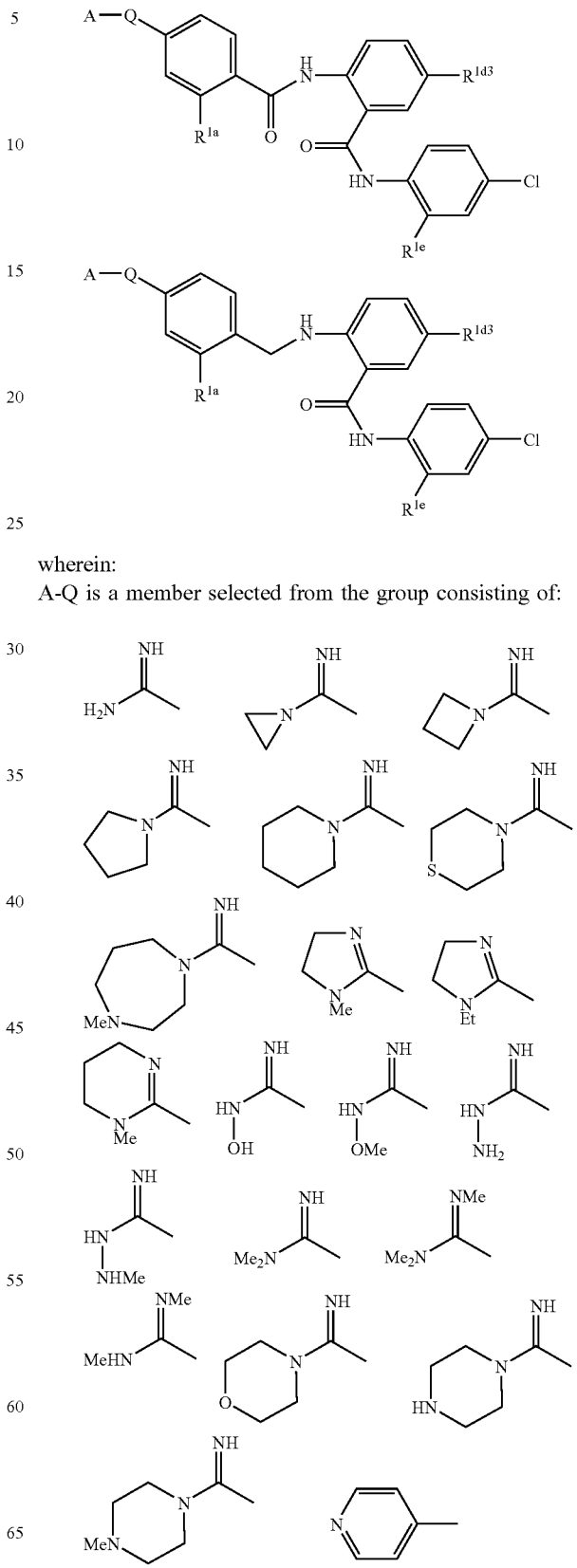
wherein:
A-Q is a member selected from the group consisting of:

-continued

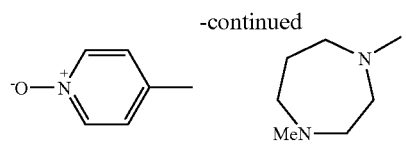

$R^{1a}$ is a member selected from the group consisting of:
H, —F;

$R^{1e}$ is a member selected from the group consisting of:
H, —F, —SO₂Me, —SO₂NH₂, —CN, —CONH₂, —CH₂NH₂, —CH₂NMe₂;

$R^{1d3}$ is a member selected from the group consisting of:
H, -Me, —F, —Cl, —Br, aryl, heteroaryl, —NH₂, —NMe₂, —NHMe, —NHSO₂Me, —NHCOMe, —CH₃, —CF₃, —OH, —OCH₃, —SCH₃, —OCF₃, —OCH₂F, —OCHF₂, —OCH₂CF₃, —OCF₂CF₃, —NO₂, —CN, —CO₂H, —CO₂Me, —CO₂Et, —CONH₂, —CONHMe, —CONMe₂, —SO₂NH₂, —SO₂CH₃, —SO₂NMe₂, —CH₂OH, —CH₂NH₂, —CH₂NHMe, —CH₂NMe₂, —OCH₂CO₂H, —OCH₂CO₂Me, —OCH₂CO₂Et, —OCH₂CONH₂, —OCH₂CONMe₂, —OCH₂CONHMe, —OCH₂CH₂OMe, —OCH₂CH₂OEt, —OCH₂CH₂NH₂, —OCH₂CH₂NHMe, —OCH₂CH₂NMe₂, —NHCH₂CH₂OMe, —SCH₂CH₂OMe, —SO₂CH₂CH₂OMe, —OCH₂CH₂SO₂Me, —NHCH₂CH₂NHMe, —NHCH₂CH₂NMe₂, —N(CH₂CH₂OH)₂, —N(CH₂CH₂OMe)₂, —NHCH₂CO₂H, —NHCH₂CO₂Et, —NHCH₂CO₂Et, —NHCH₂CONH₂, —NHCH₂CONMe₂, —NHCH₂CONHMe, —N(CH₃)CH₂CO₂H, —N(CH₃)CH₂CO₂Et, —(NMe)CH2COOH, —N(Me)CH2CONH2, —N(Me)CH2CH2NMe2, —N(Me)CH2CH2OMe, —NHCH2CH2OMe,

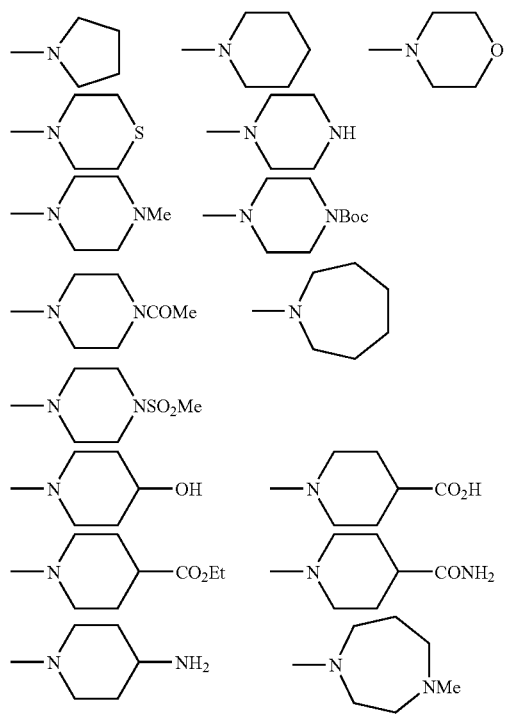
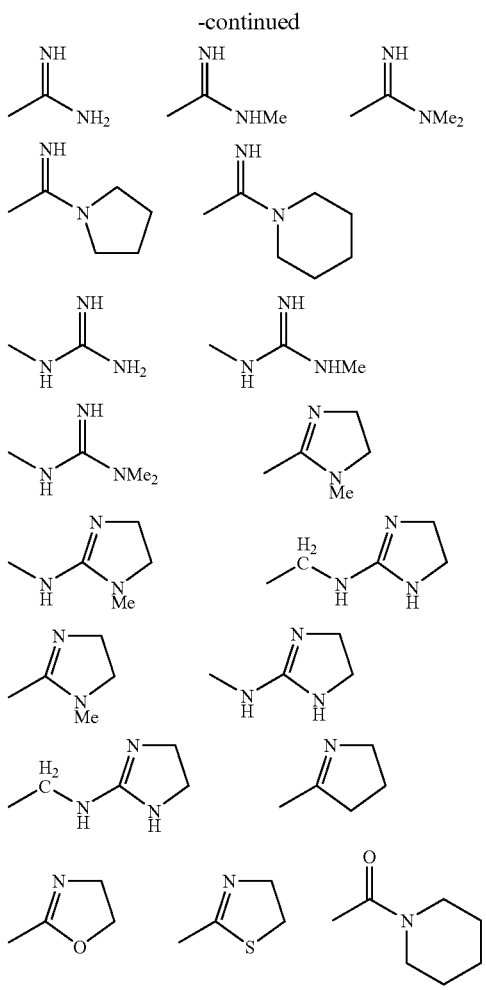
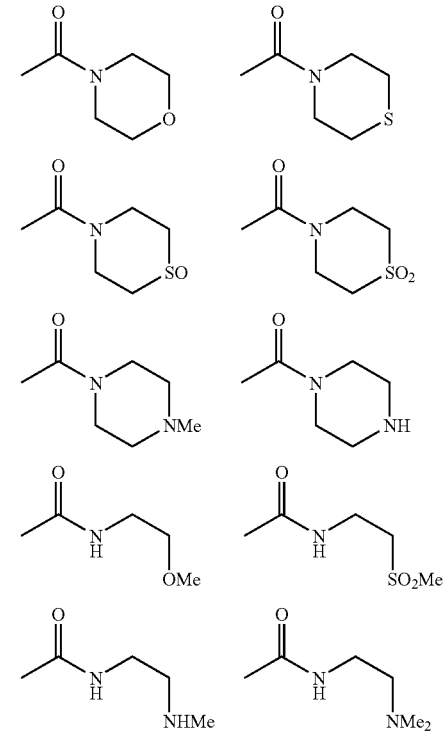

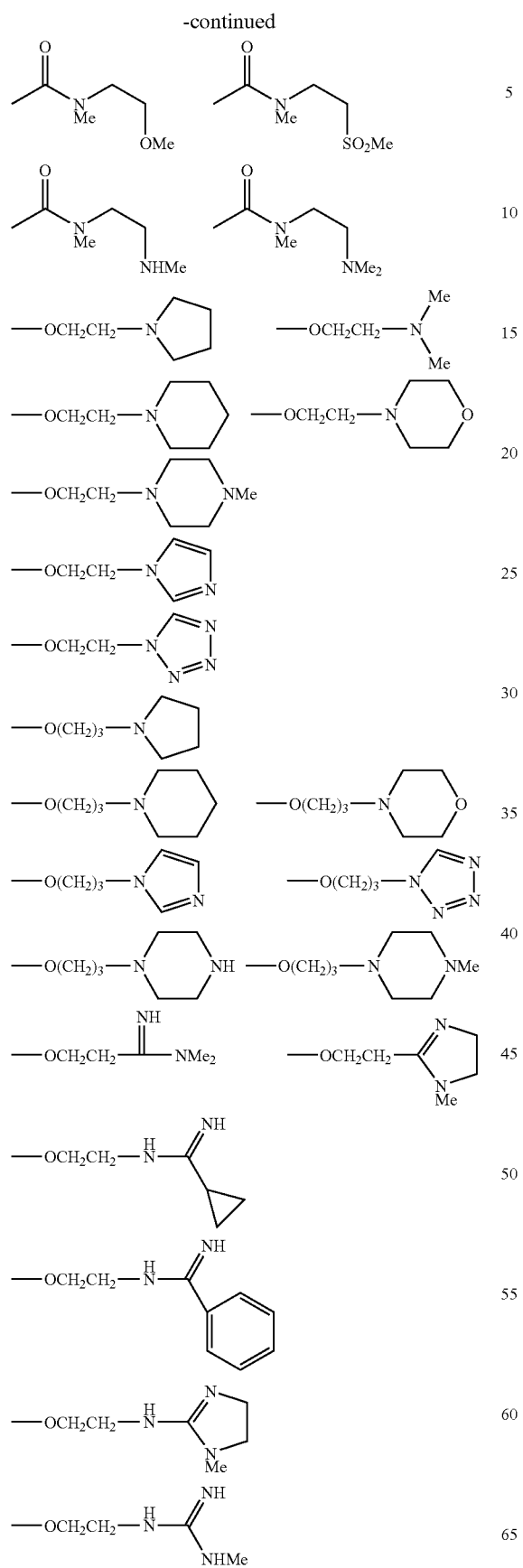
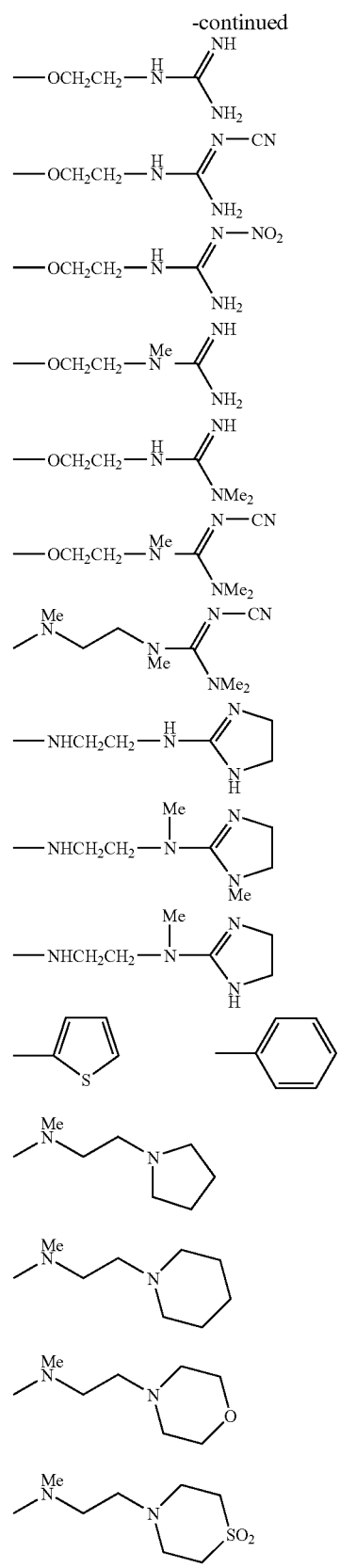
and all pharmaceutically acceptable isomers, salts, hydrates, solvates and prodrug derivatives thereof.

The invention provides compound of formula Ib, as described above, having the following structure:

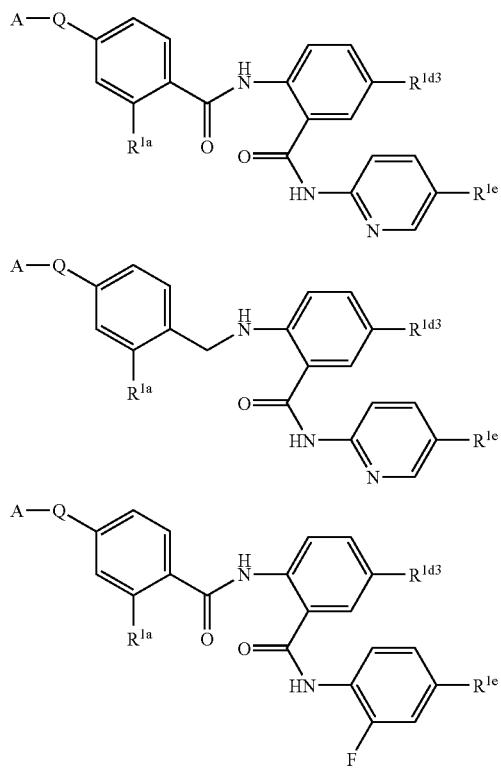

wherein:
A-Q is a member selected from the group consisting of:

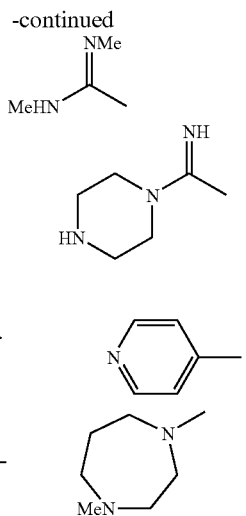

$R^{1a}$ is a member selected from the group consisting of:
  H, —F;
$R^{1e}$ is a member selected from the group consisting of:
  —Cl, —Br;
$R^{1d3}$ is a member selected from the group consisting of:
  H, F, Cl, Br, —OCH$_3$, —OCF$_3$, —OCH$_2$F, —OCHF$_2$, —OCH$_2$CF$_3$, —OCF$_2$CF$_3$;

and all pharmaceutically acceptable isomers, salts, hydrates, solvates and prodrug derivatives thereof.

The invention provides compound of formula Ib, as described above, having the following structure:

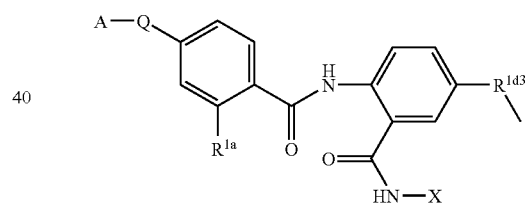

wherein:
A-Q is a member selected from the group consisting of:

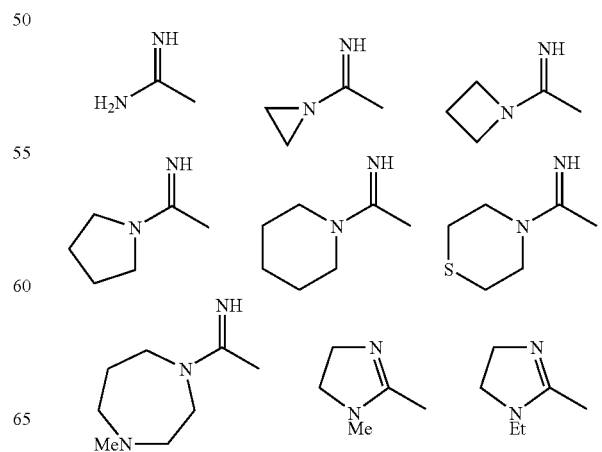

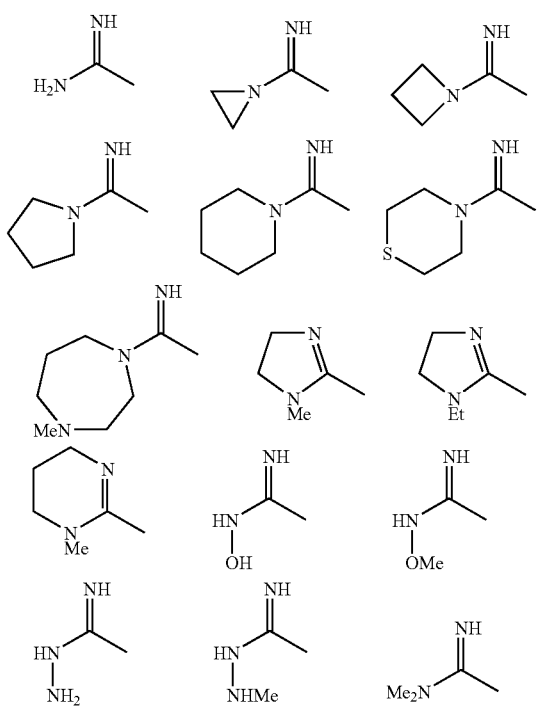

-continued

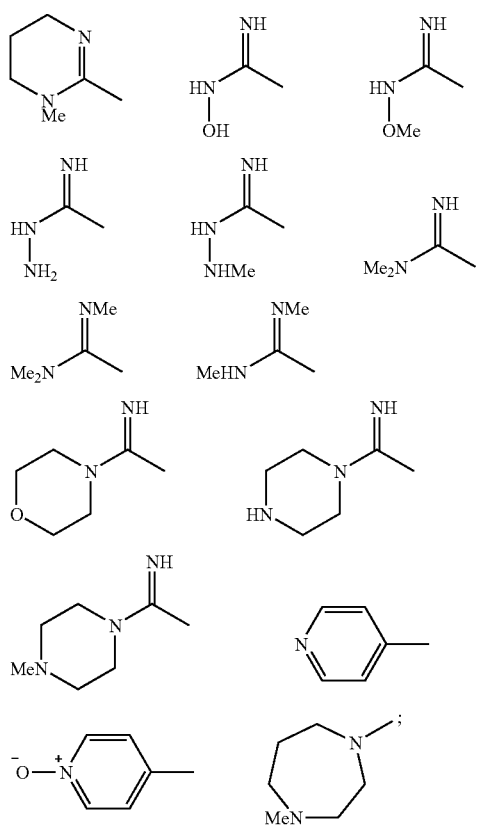

$R^{1a}$ is a member selected from the group consisting of:
H, —F;

$R^{1a3}$ is a member selected from the group consisting of:
H, —F, —Cl, —Br, —OCH$_3$, —OCF$_3$, —OCH$_2$F, —OCHF$_2$, —OCH$_2$CF$_3$, —OCF$_2$CF$_3$, —NHSO$_2$Me, —NHAc, —SO$_2$Me, —SO$_2$NH$_2$;

X is a member selected from the group consisting of:

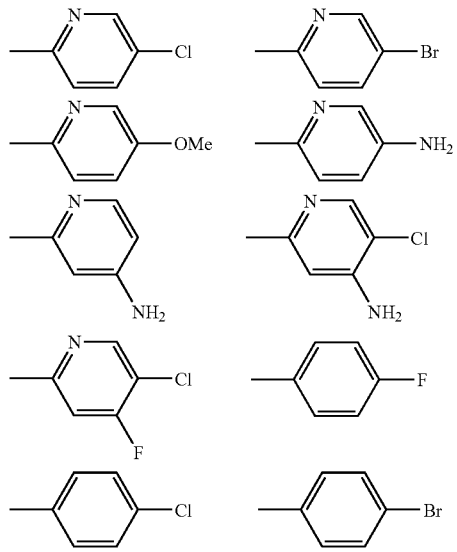

-continued

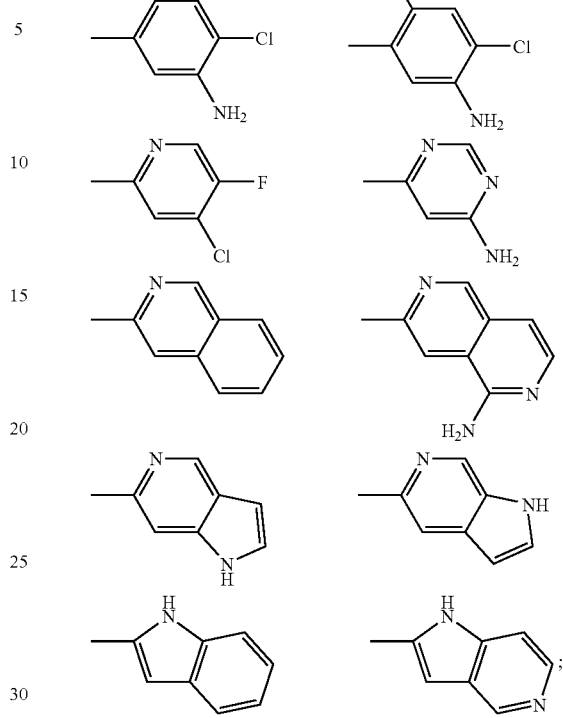

and all pharmaceutically acceptable isomers, salts, hydrates, solvates and prodrug derivatives thereof.

The invention provides compound of formula Ib, as described above, having the following structure:

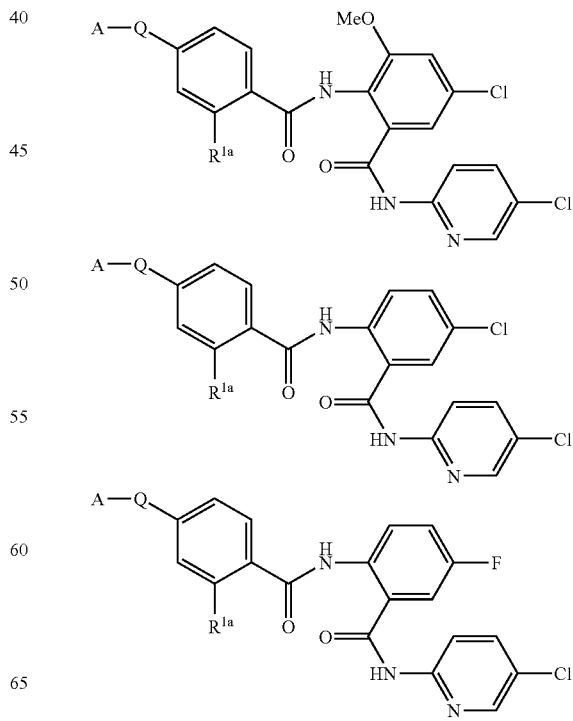

wherein:
A-Q is a member selected from the group consisting of:
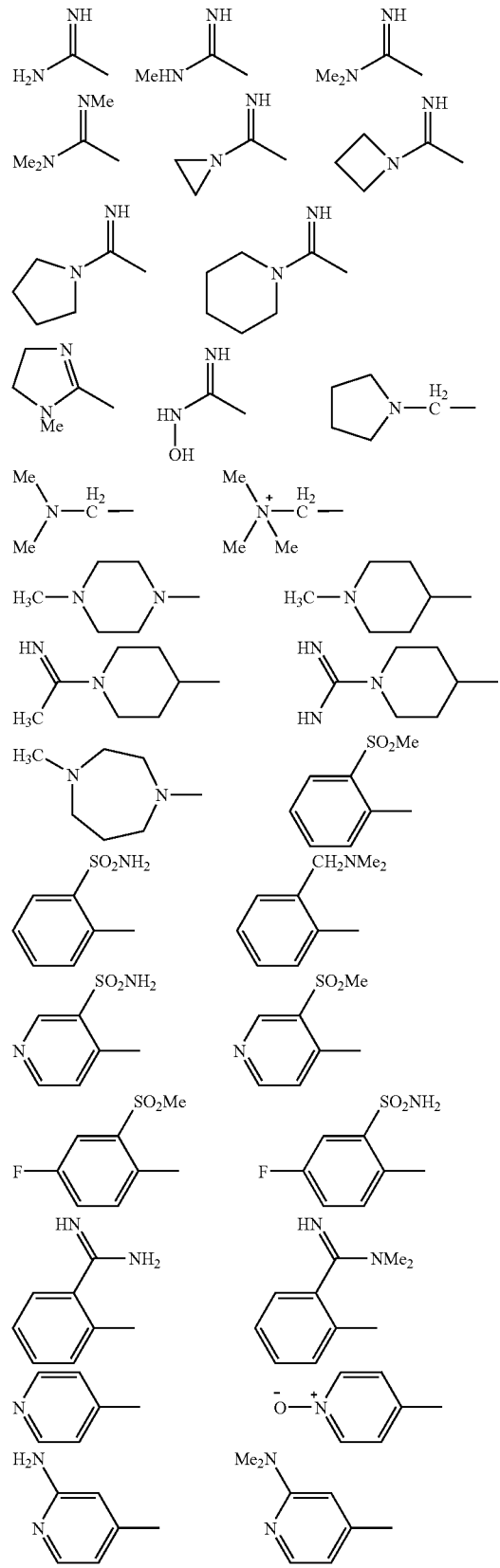
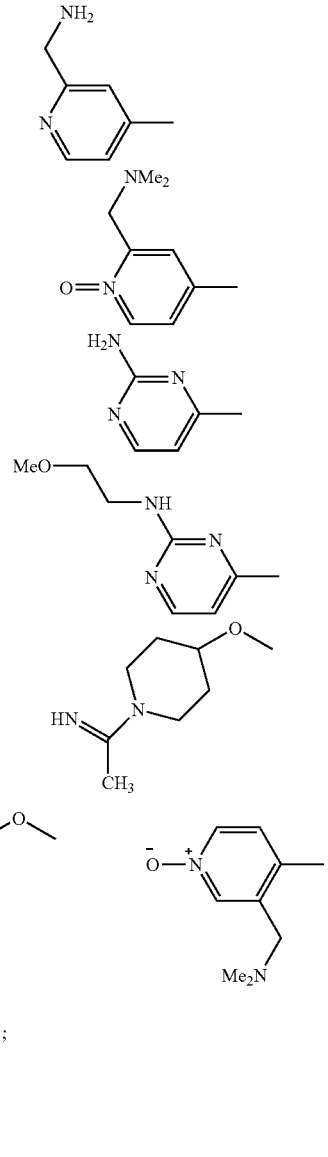
$R^{1a}$ is a member selected from the group consisting of:
H, —F;
and all pharmaceutically acceptable isomers, salts, hydrates, solvates and prodrug derivatives thereof.
The invention provides compound of formula Ib, as described above, having the following structure:
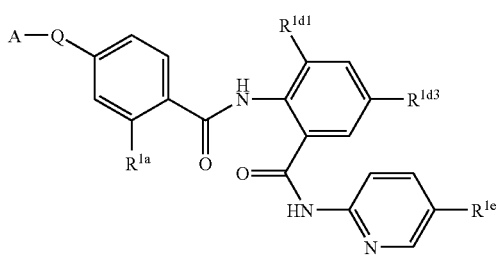

wherein:

R$^{1a}$ is a member selected from the group consisting of:
H, —F;

R$^{1d1}$ is a member selected from the group consisting of:
H, —OMe;

R$^{1d3}$ is a member selected from the group consisting of:
H, —F, —Cl, —Br, —OMe, —OCF$_3$;

R$^{1e}$ is a member selected from the group consisting of:
H, —F, —Cl, —Br;

A-Q is a member selected from the group consisting of:

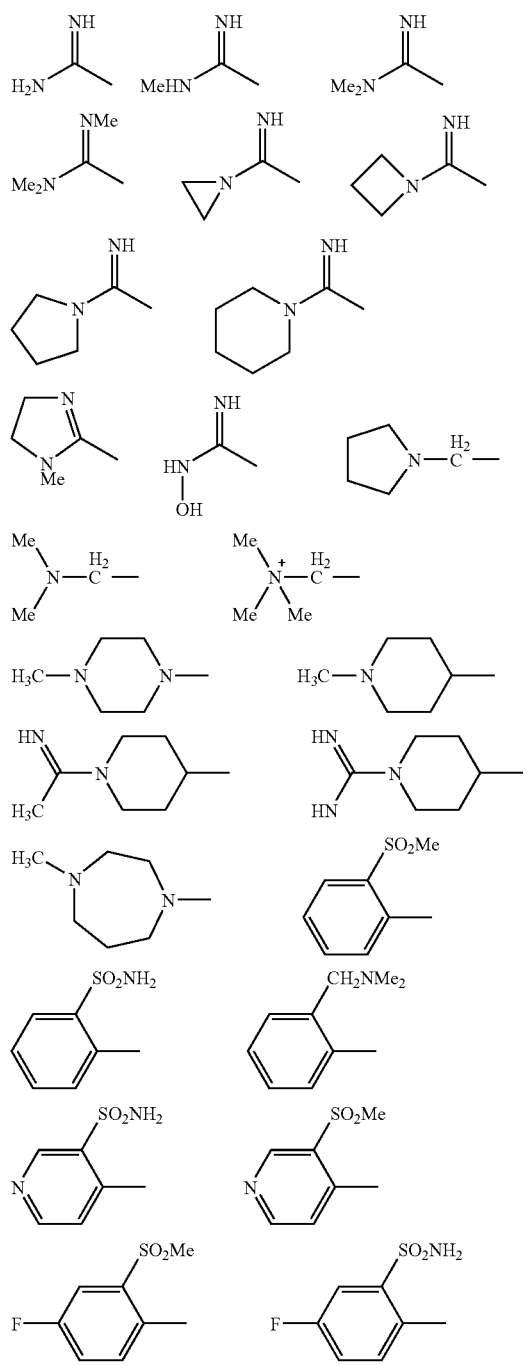

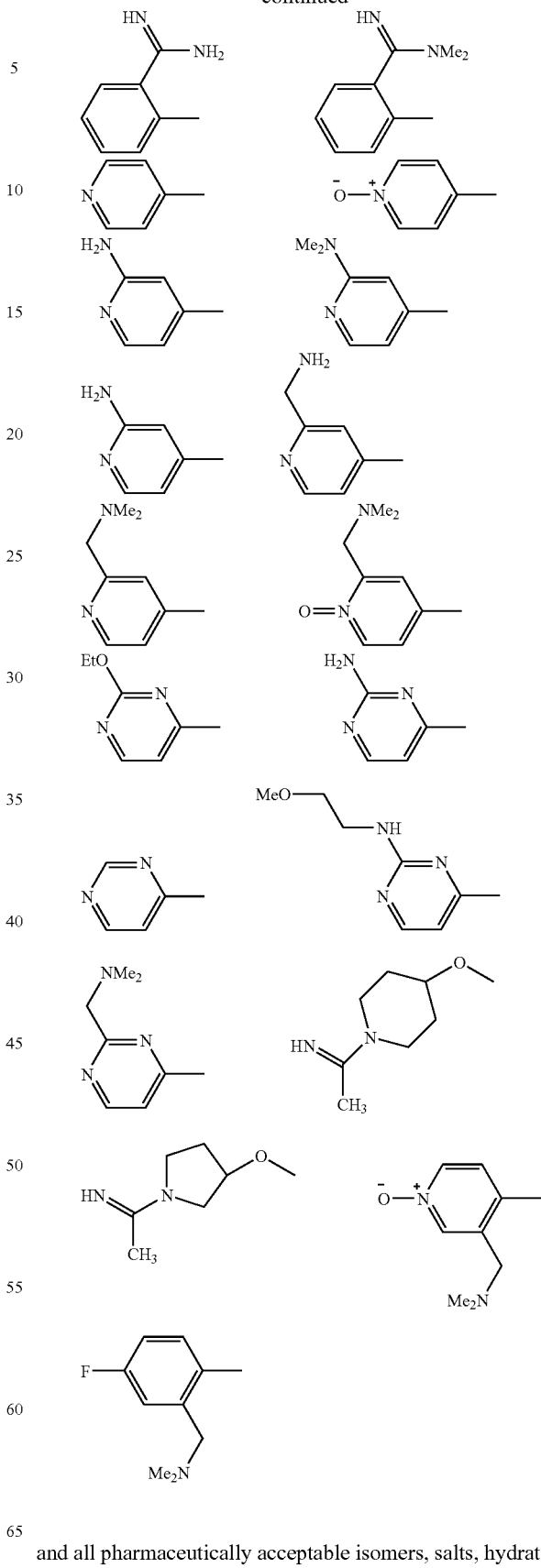

and all pharmaceutically acceptable isomers, salts, hydrates, solvates and prodrug derivatives thereof.

The invention provides compound of formula Ib, as described above, having the following structure:

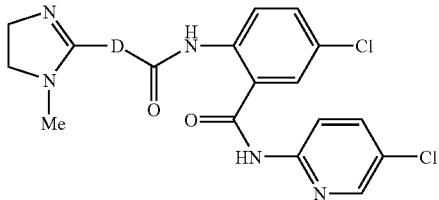

wherein:
D is a member selected from the group consisting of:

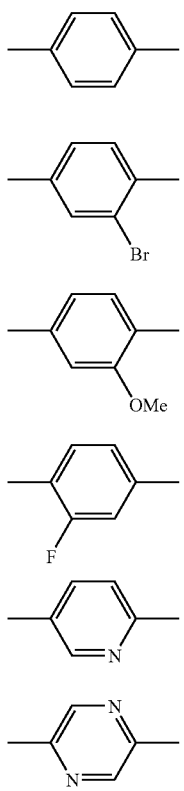

and all pharmaceutically acceptable isomers, salts, hydrates, solvates and prodrug derivatives thereof.

The invention provides compound of formula Ib, as described above, having the following structure:

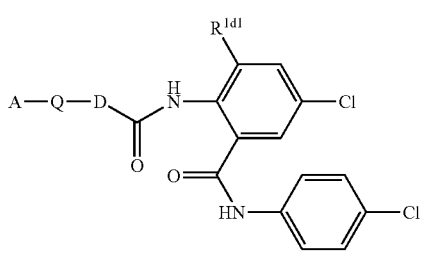

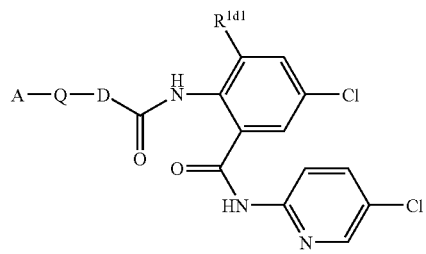

wherein:
$R^{1d1}$ is H or —OMe;
A-Q-D is a member selected from the group consisting of:

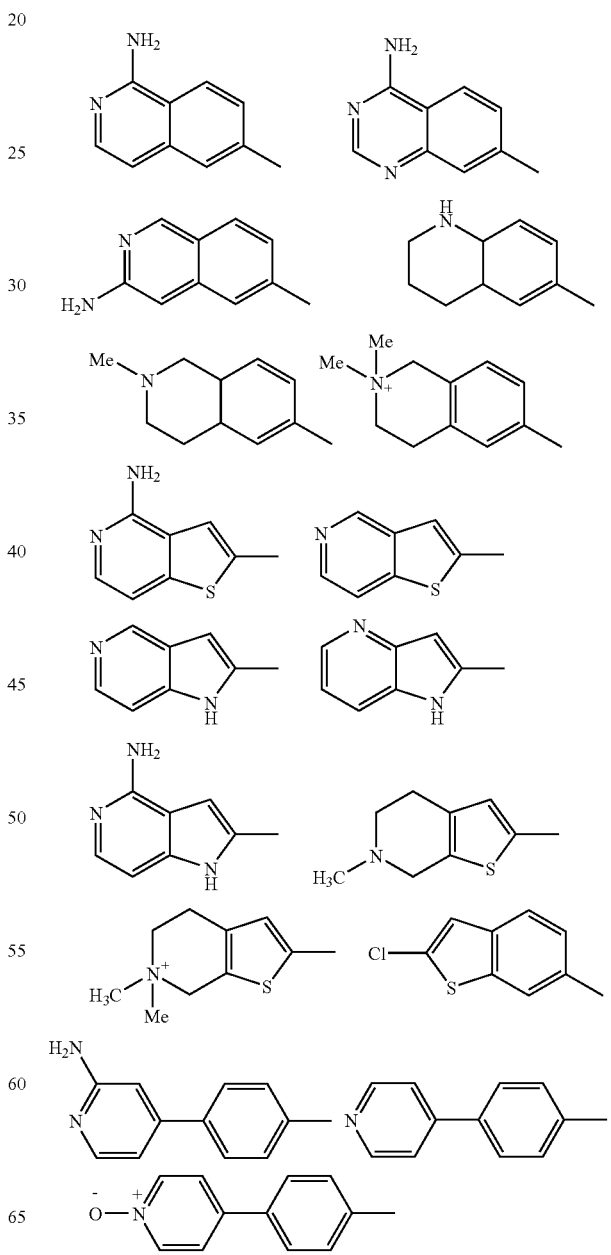

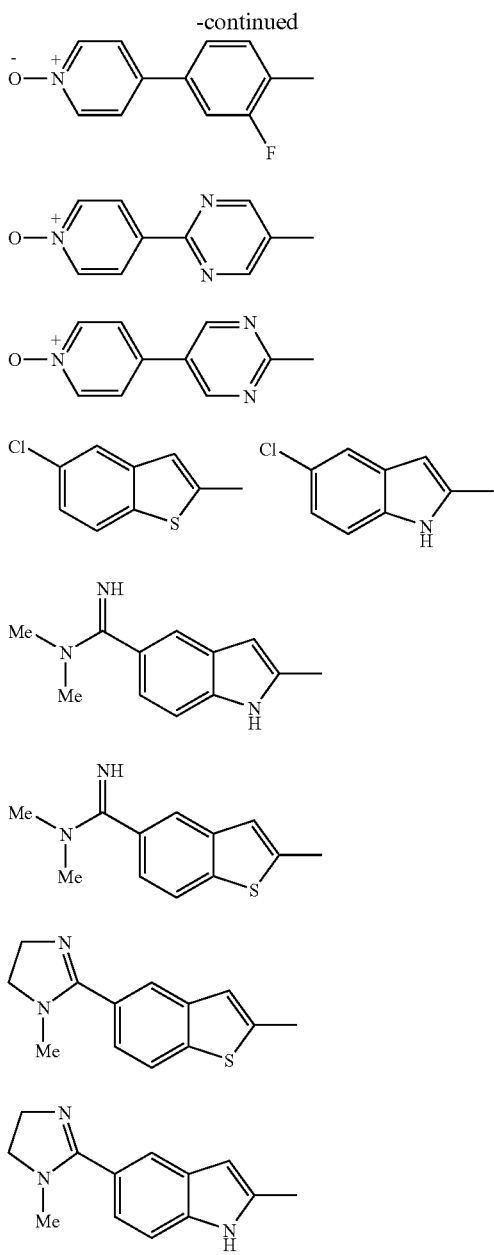
and all pharmaceutically acceptable isomers, salts, hydrates, solvates and prodrug derivatives thereof.
The invention provides compound of formula Ib, as described above, having the following structure:
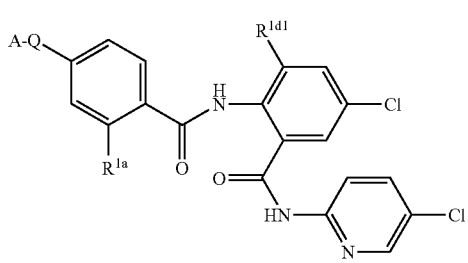
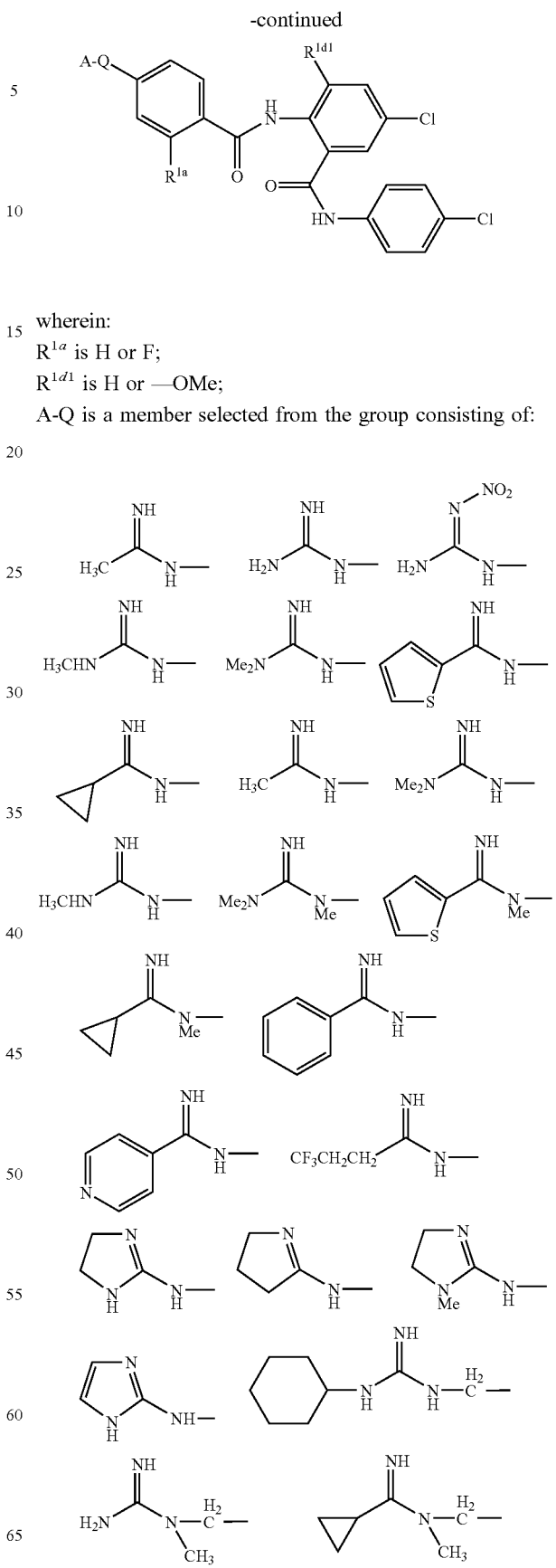
wherein:
$R^{1a}$ is H or F;
$R^{1d1}$ is H or —OMe;
A-Q is a member selected from the group consisting of:

131

-continued

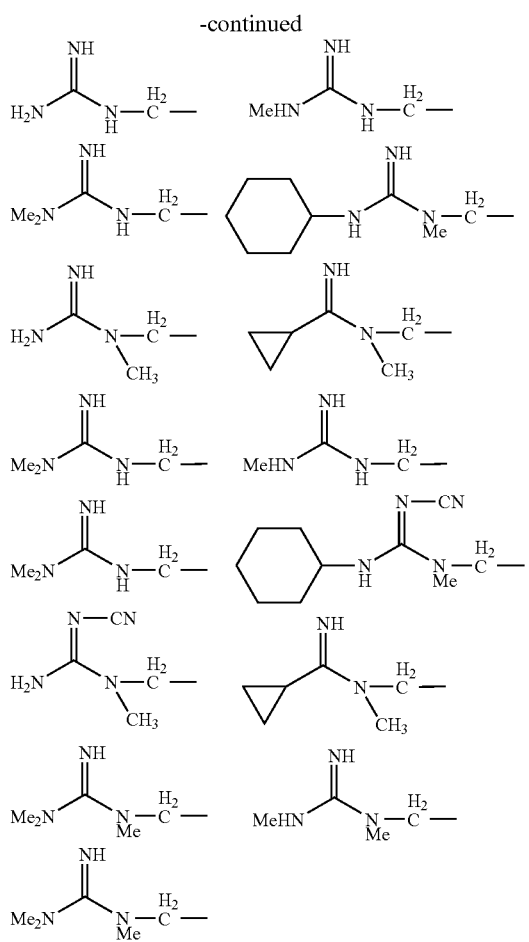

and all pharmaceutically acceptable isomers, salts, hydrates, solvates and prodrug derivatives thereof.

The invention provides compound of formula Ib, as described above, having the following structure:

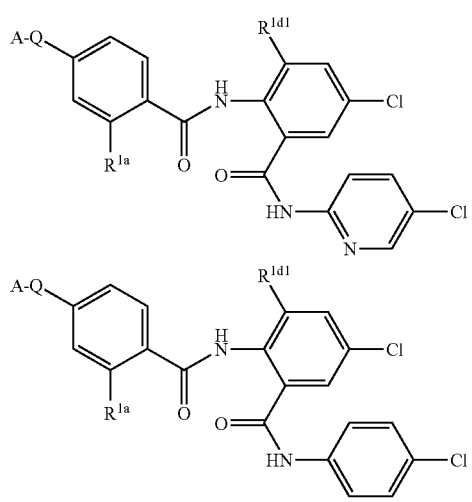

wherein:
R$^{1a}$ is H or F;
R$^{1d1}$ is H or —OMe;

132

A-Q is a member selected from the group consisting of:

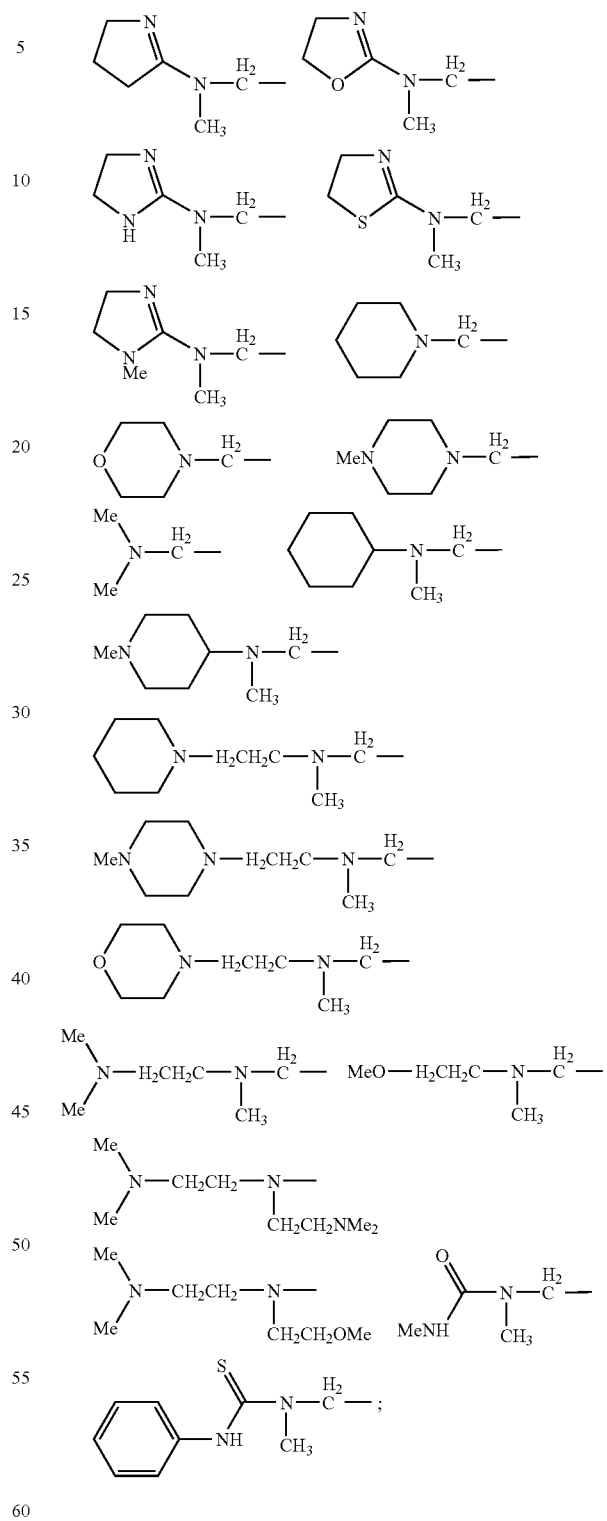

and
R$^{1a}$ is a member selected from the group consisting of: H, —F, and all pharmaceutically acceptable isomers, salts, hydrates, solvates and prodrug derivatives thereof.

The invention provides compound of formula Ib, as described above, having the following structure:

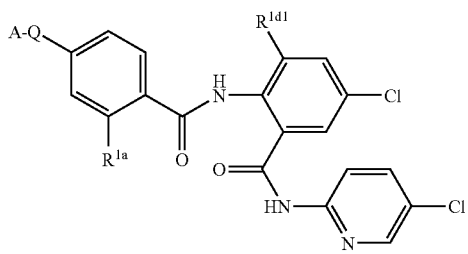

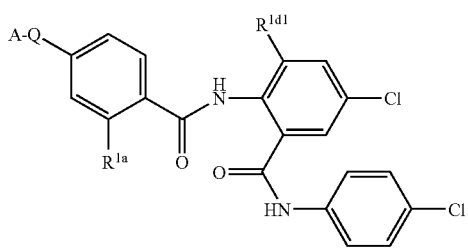

wherein:
$R^{1a}$ is H or F;
$R^{1d1}$ is H or —OMe; and
A-Q is a member selected from the group consisting of:

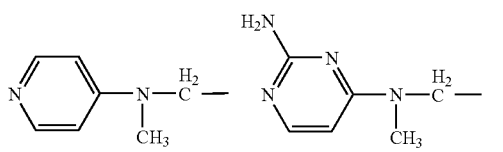

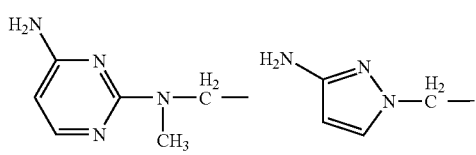

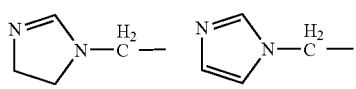

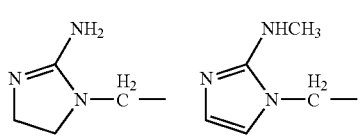

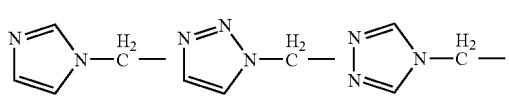

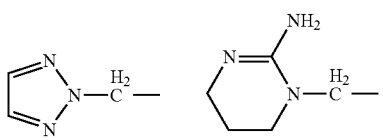

and all pharmaceutically acceptable isomers, salts, hydrates, solvates and prodrug derivatives thereof.

The invention provides compound of formula Ib, as described above, having the following structure:

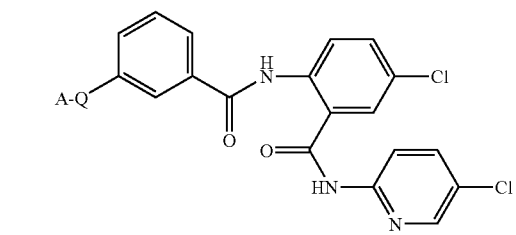

wherein:
A-Q is a member selected from the group consisting of:

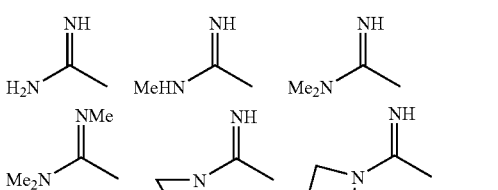

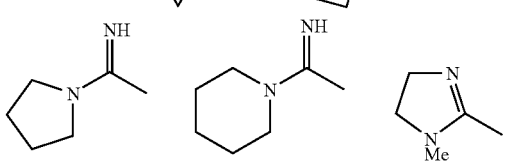

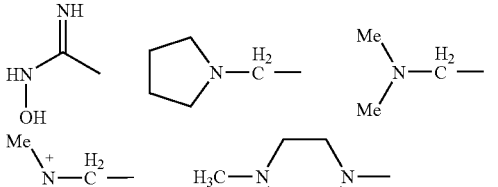

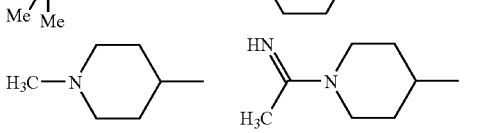

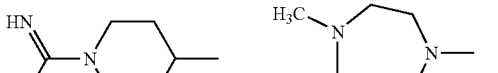

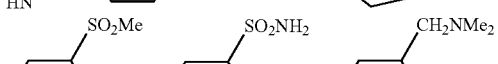

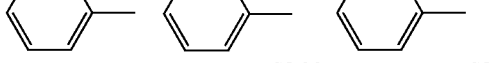

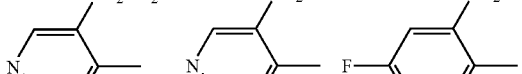

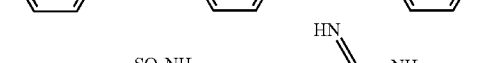

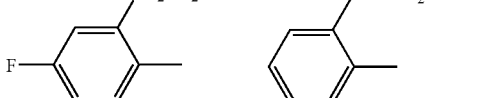

-continued
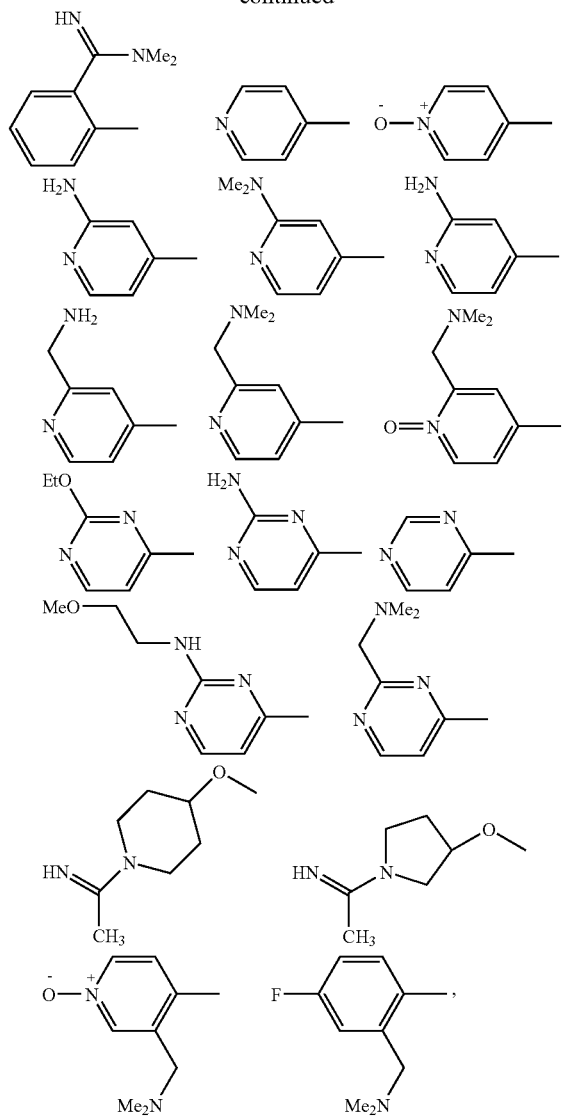
and all pharmaceutically acceptable isomers, salts, hydrates, solvates and prodrug derivatives thereof.
The invention provides compound of formula Ib, as described above, having the following structure:
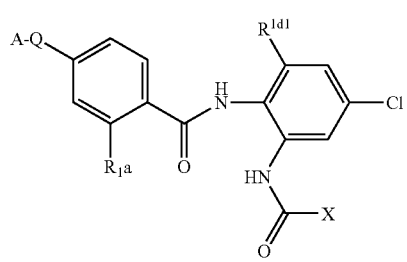
wherein:
$R^{1a}$ is H or F;
$R^{1d1}$ is H or —OMe;
A-Q is a member selected from the group consisting of:
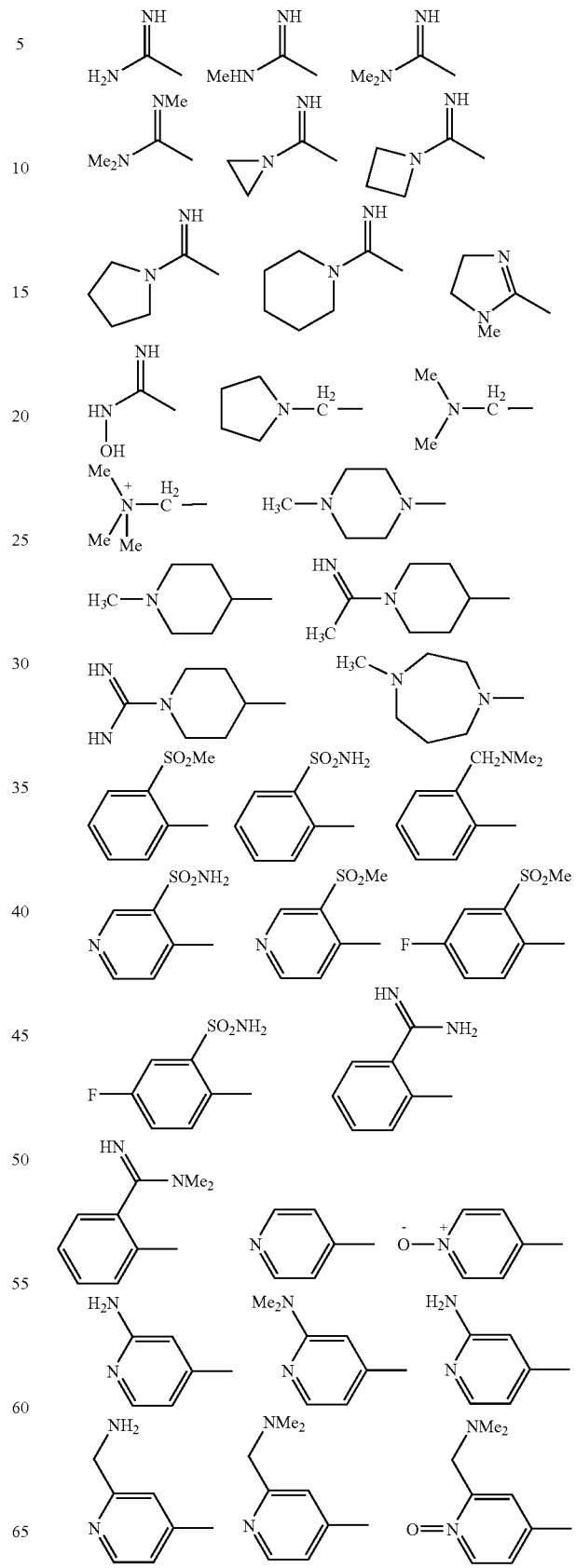

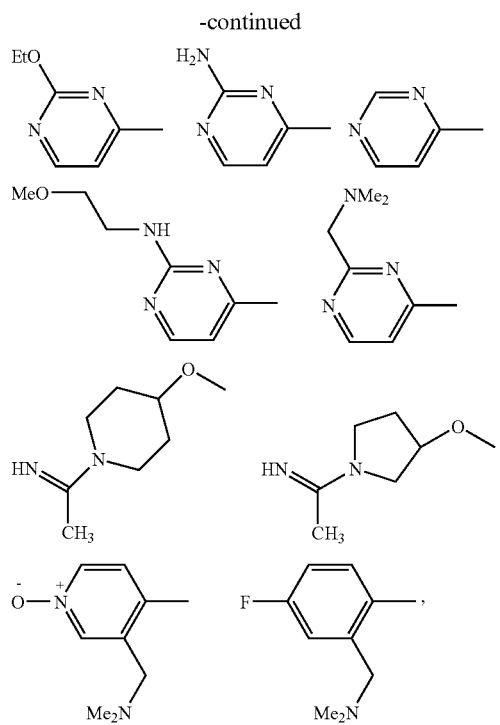
and X is a member selected from the group consisting of:
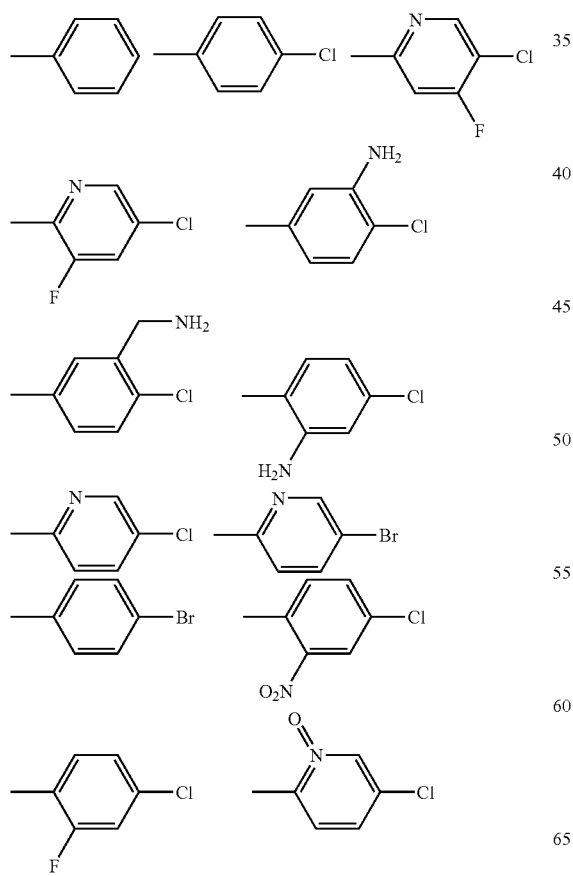
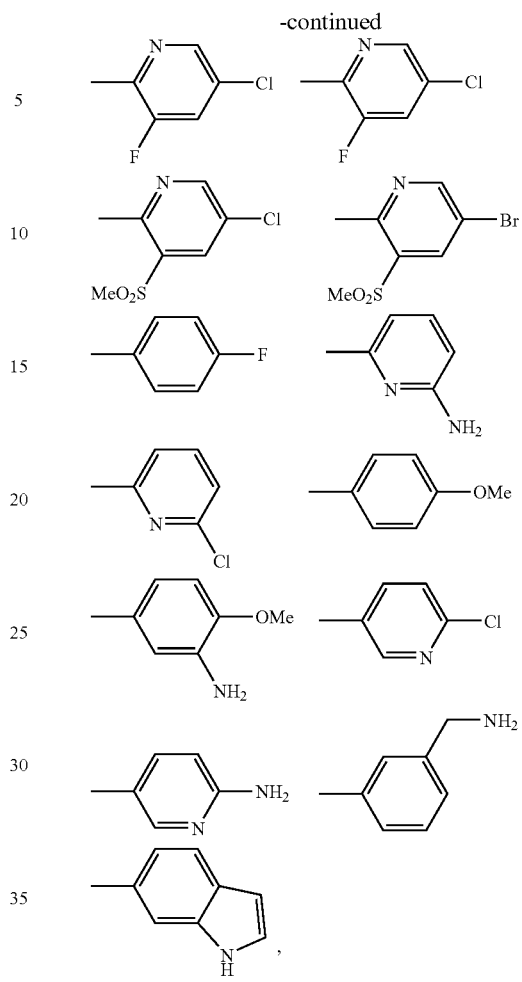
and all pharmaceutically acceptable isomers, salts, hydrates, solvates and prodrug derivatives thereof.
The invention provides compound of formula Ib, as describe above, having the following structure:
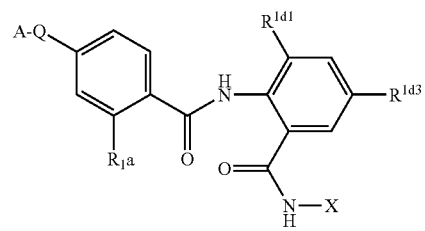
wherein:
R1a is H or F;
A-Q is a member selected from the group consisting of:
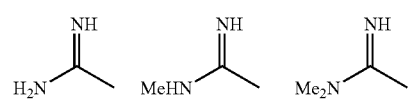

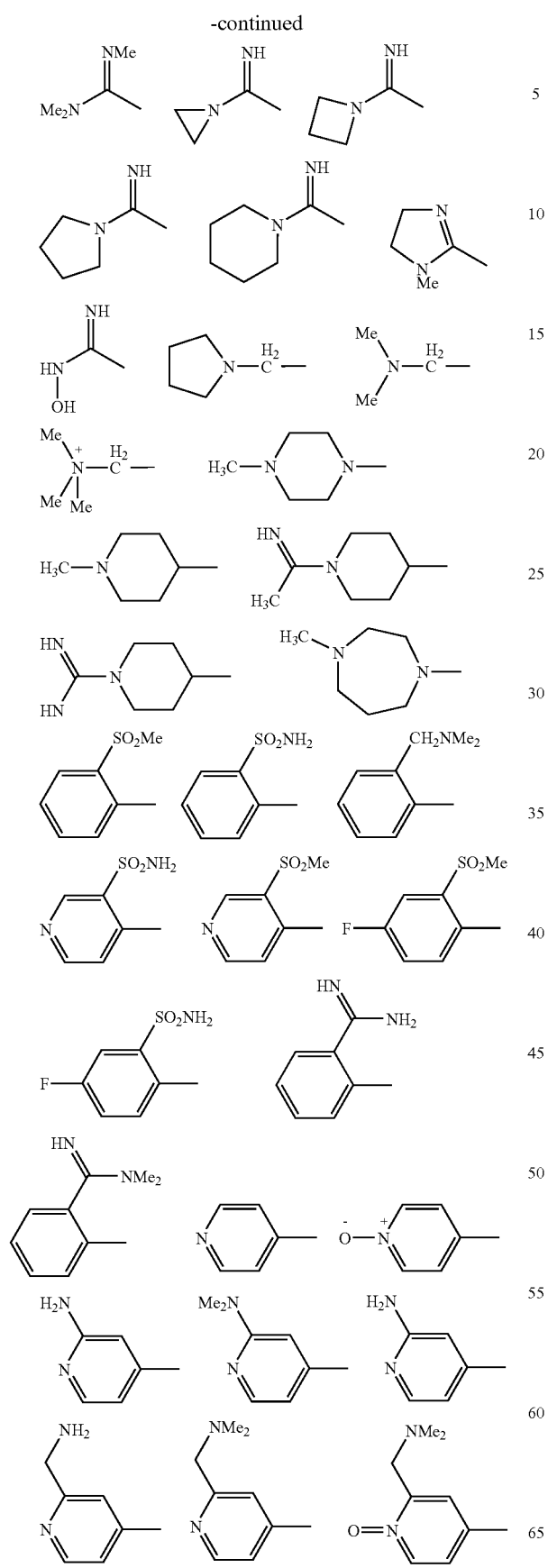

$R^{1d1}$ is a member selected from the group consisting of:

H, —F, —Cl, —Br, aryl, heteroaryl, —NH$_2$, —NMe$_2$, —NHMe, —NHSO$_2$Me, —NHCOMe, —CH$_3$, —CF$_3$, —OH, —OCH$_3$, —SCH$_3$, —OCF$_3$, —OCH$_2$F, —OCHF$_2$, —OCH$_2$CF$_3$, —OCF$_2$CF$_3$, —NO$_2$, —CN, —CO$_2$H, —CO$_2$Me, —CO$_2$Et, —CONH$_2$, —CONHMe, —CONMe$_2$, —SO$_2$NH$_2$, —SO$_2$CH$_3$, —SO$_2$NMe$_2$, —CH$_2$OH, —CH$_2$NH$_2$, —CH$_2$NHMe, —CH$_2$NMe$_2$, —OCH$_2$CO$_2$H, —OCH$_2$CO$_2$Me, —OCH$_2$CO$_2$Et, —OCH$_2$CONH$_2$, —OCH$_2$CONMe$_2$, —OCH$_2$CONHMe, —OCH$_2$CH$_2$OMe, —OCH$_2$CH$_2$OEt, —OCH$_2$CH$_2$NH$_2$, —OCH$_2$CH$_2$NHMe, —OCH$_2$CH$_2$NMe$_2$, —NHCH$_2$CH$_2$OMe, —SCH$_2$CH$_2$OMe, —SO$_2$CH$_2$CH$_2$OMe, —OCH$_2$CH$_2$SO$_2$Me, —NHCH$_2$CH$_2$NHMe, —NHCH$_2$CH$_2$NMe$_2$, —N(CH$_2$CH$_2$OH)$_2$, —N(CH$_2$CH$_2$OMe)$_2$, —NHCH$_2$CO$_2$H, —NHCH$_2$CO$_2$Et, —NHCH$_2$CO$_2$Et, —NHCH$_2$CONH$_2$, —NHCH$_2$CONMe$_2$, —NHCH$_2$CONHMe, —N(CH$_3$)CH$_2$CO$_2$H, —N(CH$_3$)CH$_2$CO$_2$Et, —(NMe)CH2COOH, —N(Me)CH2CONH2, —N(Me)CH2CH2NMe2, —N(Me)CH2CH2OMe, —NHCH2CH2OMe,

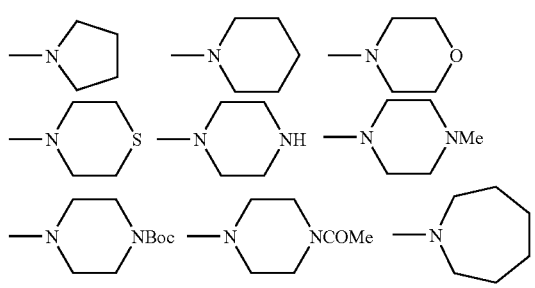

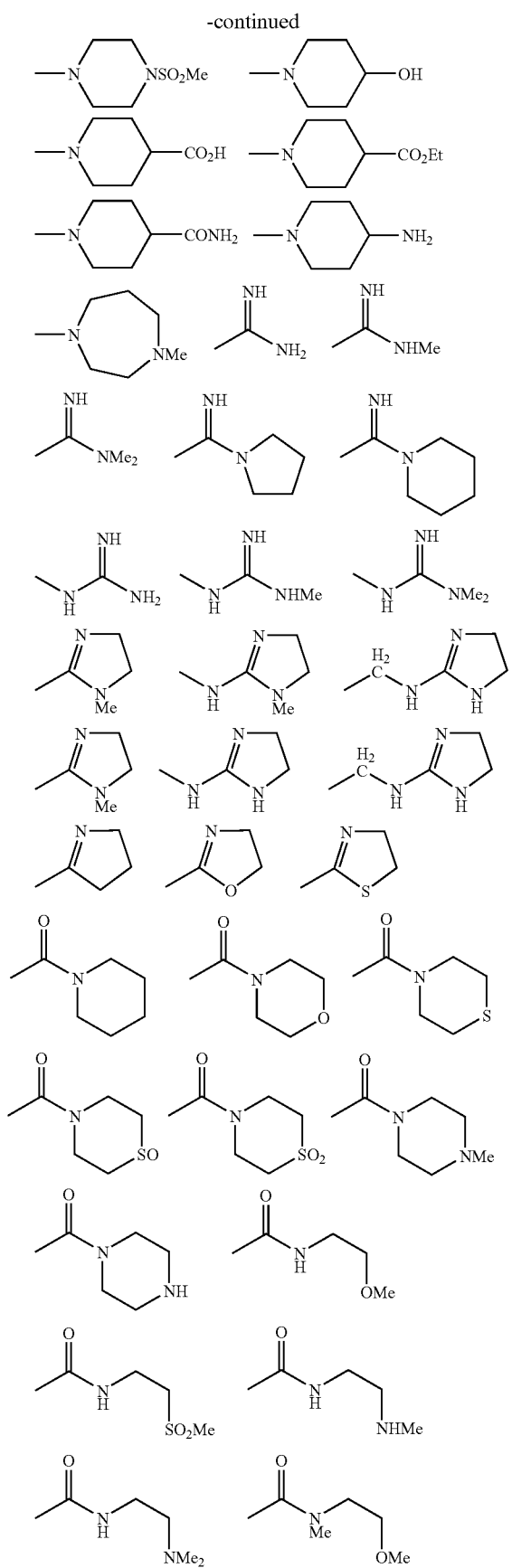
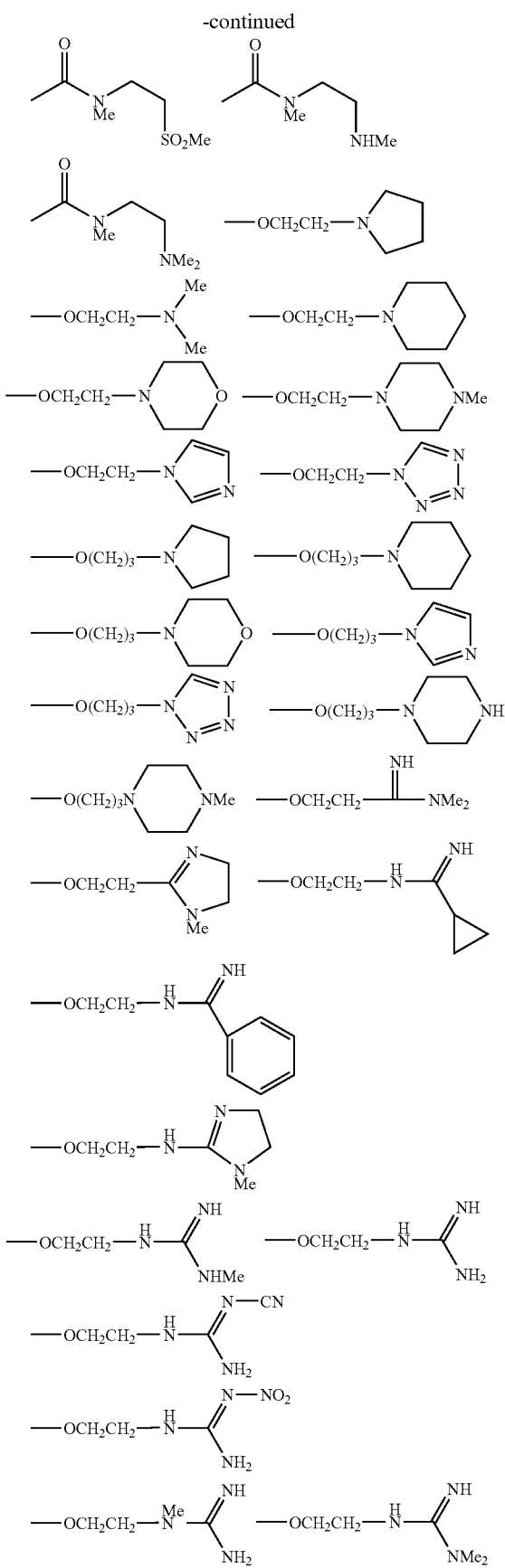

-continued
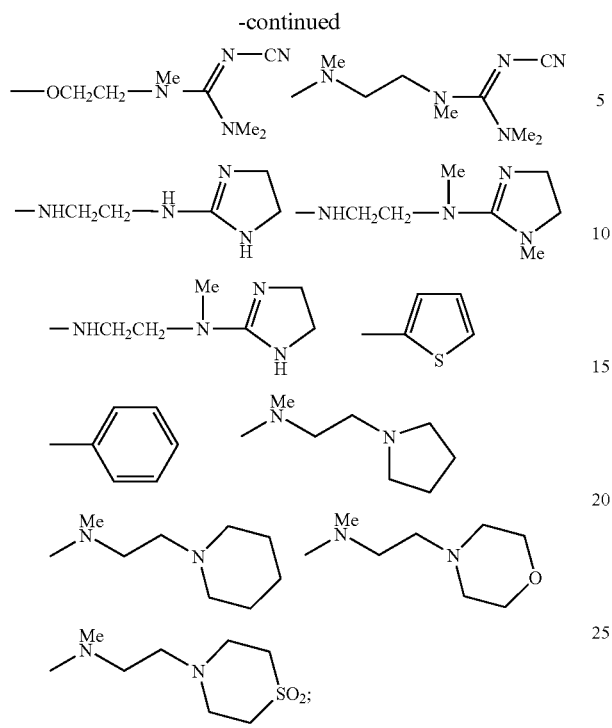
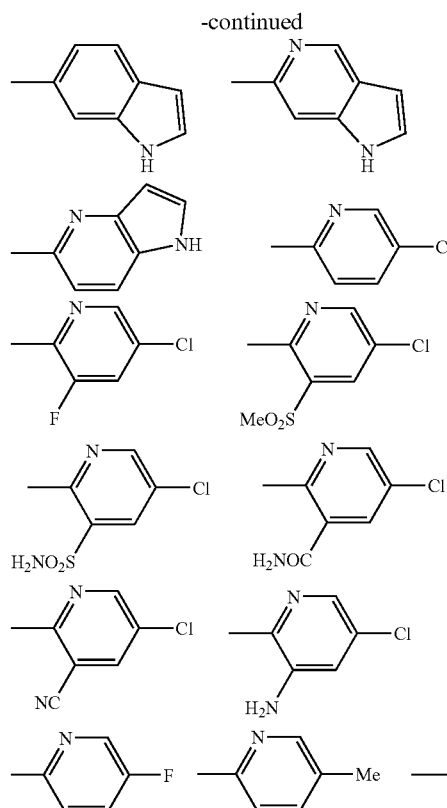
$R^{1d3}$ is a member selected from the group consisting of:
H, —F, —Cl, —Br, —OCH$_3$, —OCF$_3$, —OCH$_2$F, —OCHF$_2$, —OCH$_2$CF$_3$, —OCF$_2$CF$_3$; and
X is a member selected from the group consisting of:
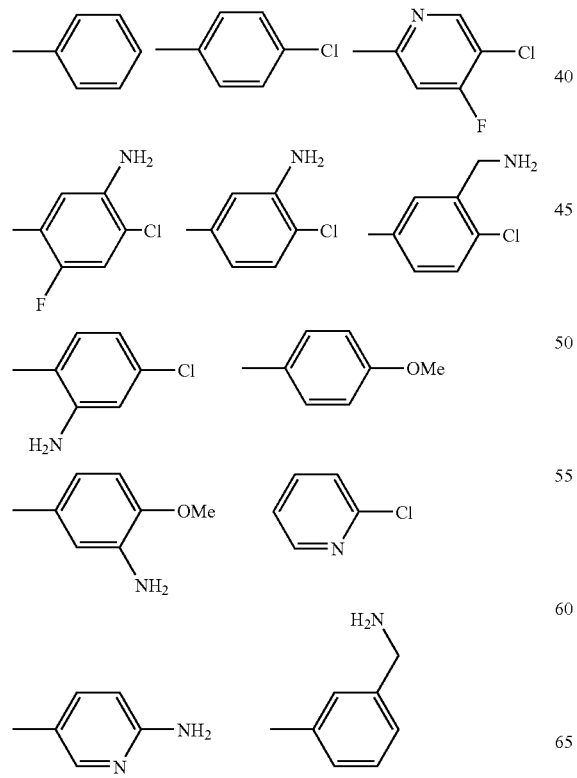
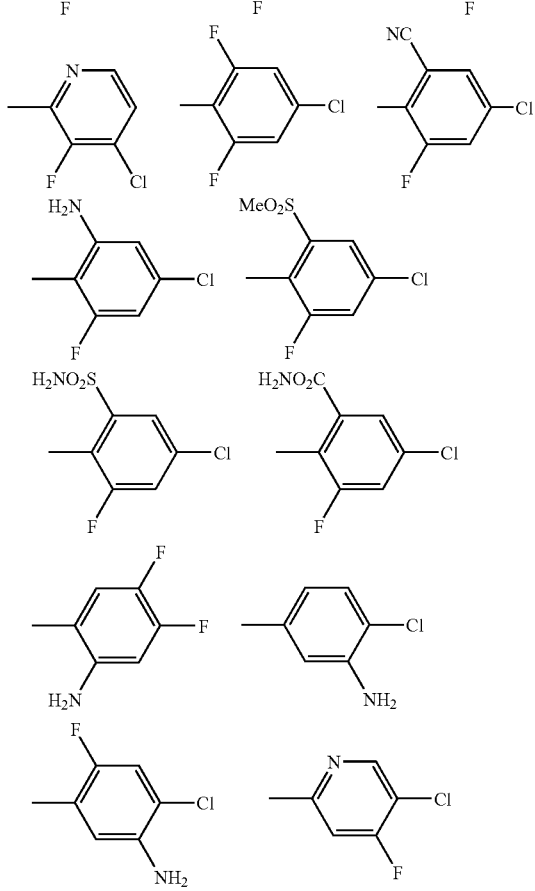

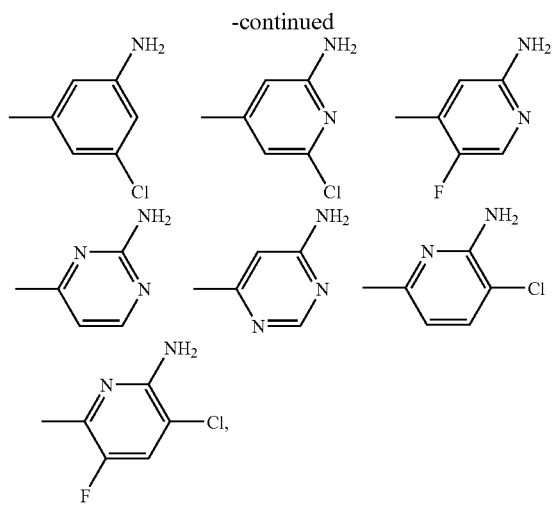
and all pharmaceutically acceptable isomers, salts, hydrates, solvates and prodrug derivatives thereof.
The invention provides compound of formula Ib, as described above, having the following structure:
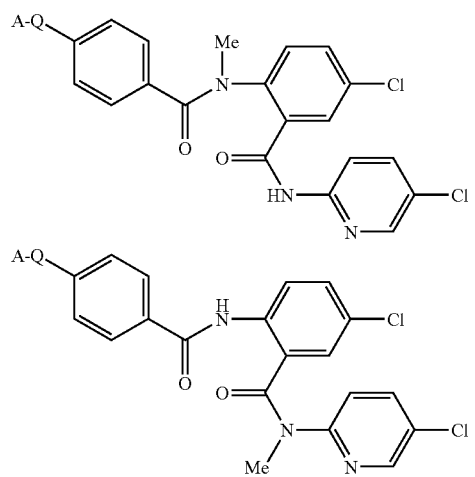
wherein:
A-Q is a member selected from the group consisting of:
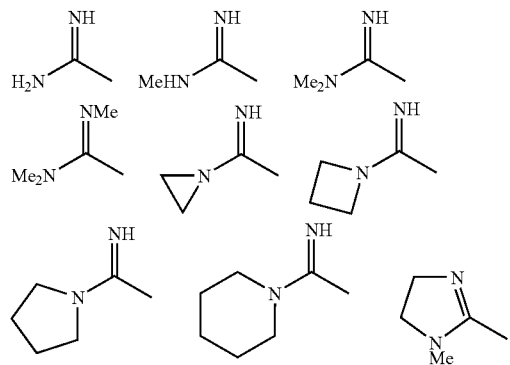
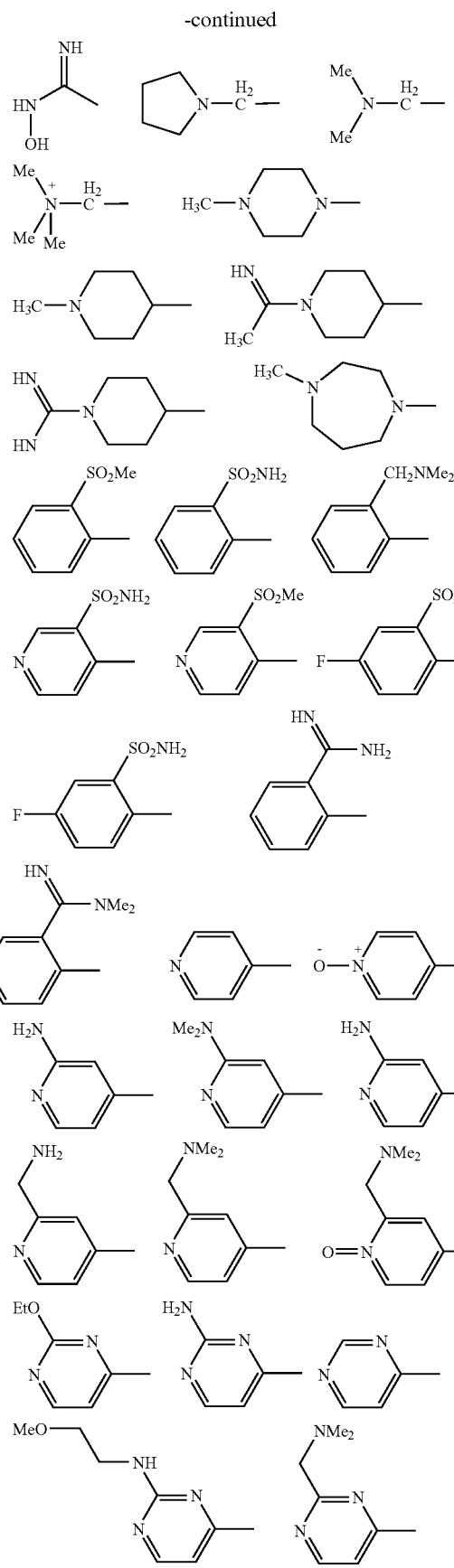

-continued
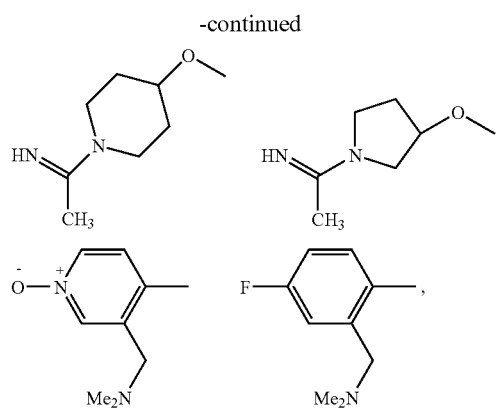
and all pharmaceutically acceptable isomers, salts, hydrates, solvates and prodrug derivatives thereof.
The invention provides compound of formula Ib, as described above, having the following structure:
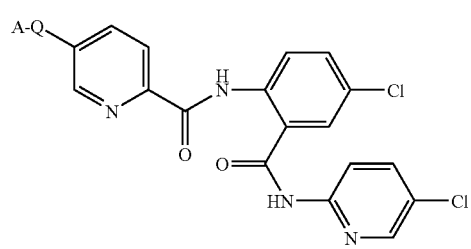
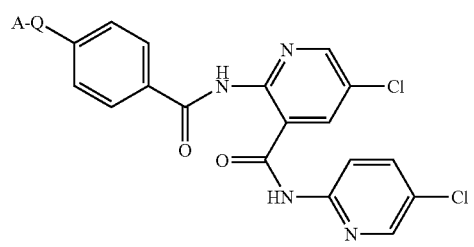
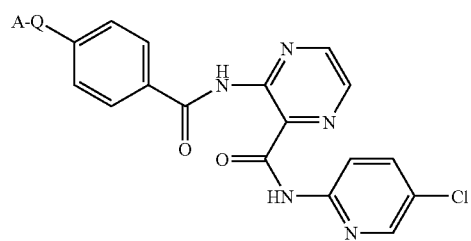
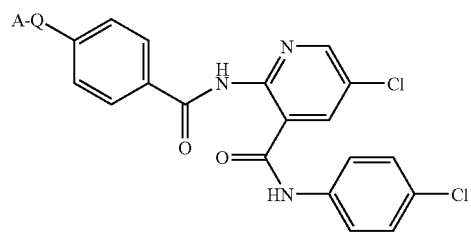
-continued
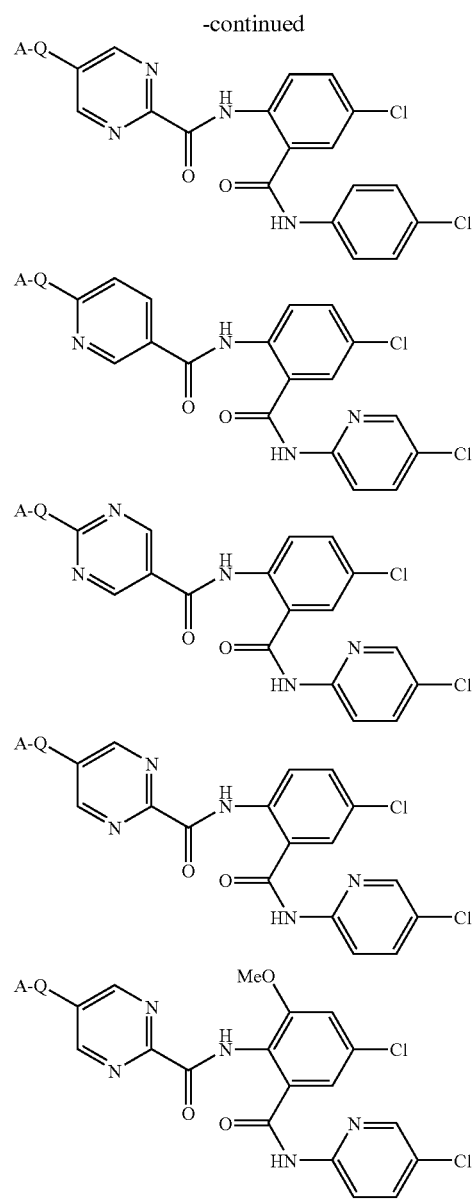
wherein:
A-Q is a member selected from the group consisting of:
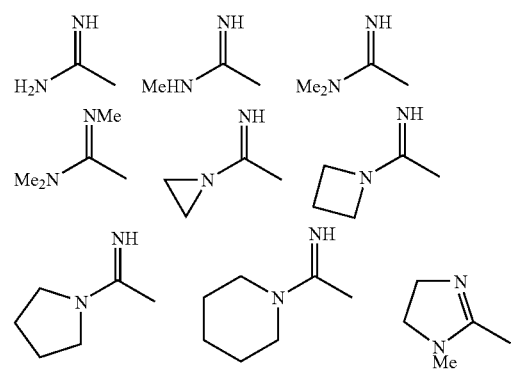

and all pharmaceutically acceptable isomers, salts, hydrates, solvates and prodrug derivatives thereof.

The invention provides compound of formula Ib, as described above, having the following structure:

wherein:
$R^{1a}$ is H or F;
A-Q is a member selected from the group consisting of:

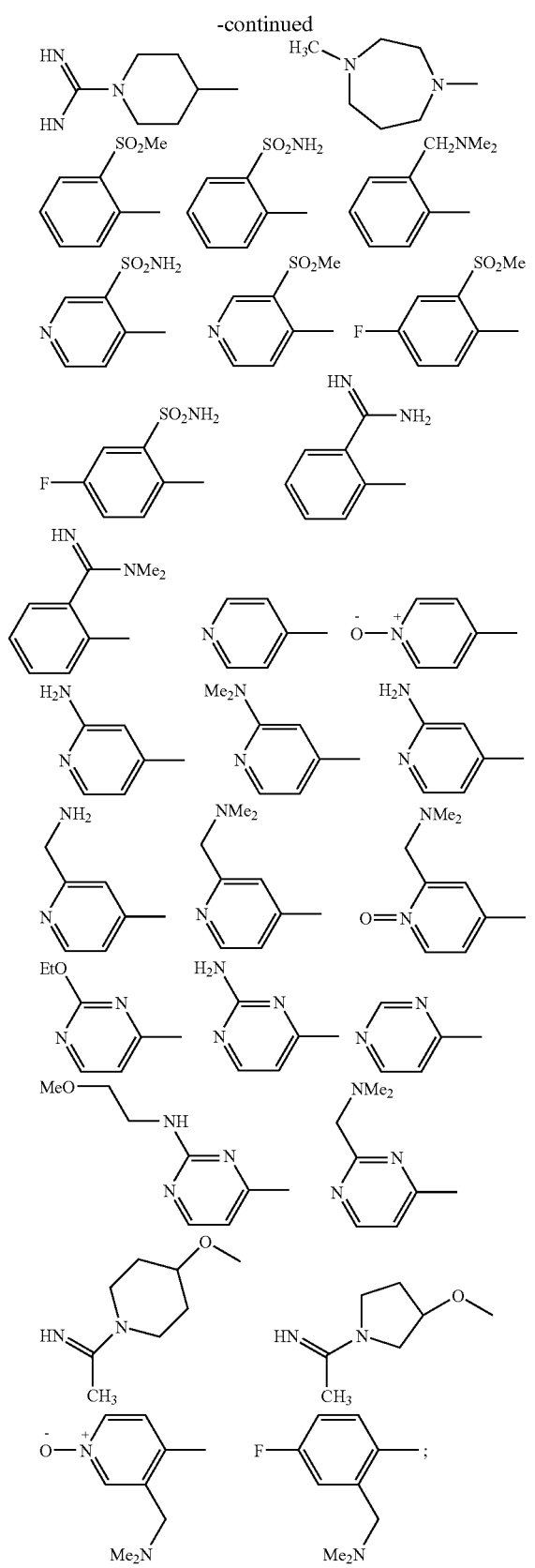
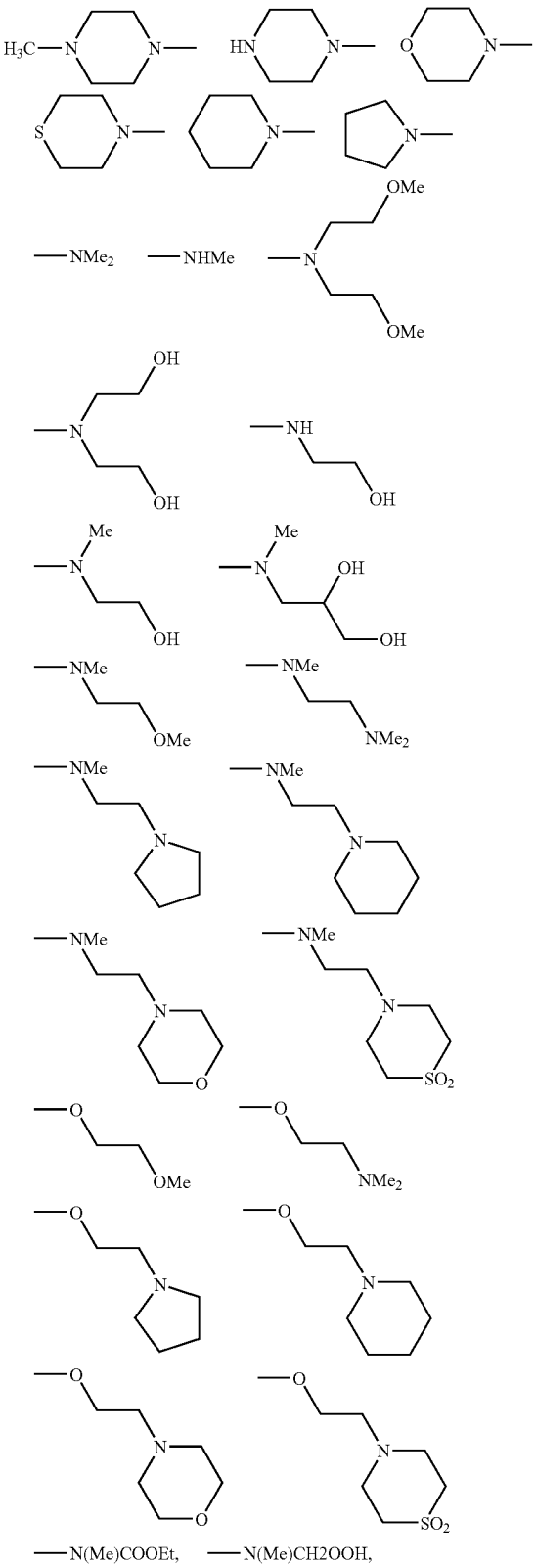
$R^{1d1}$ is a member selected from the group consisting of: H, OMe, Cl, F, OCF$_3$,
and all pharmaceutically acceptable isomers, salts, hydrates, solvates and prodrug derivatives thereof.

The invention provides compound of formula Ib, as described above, having the following structure:

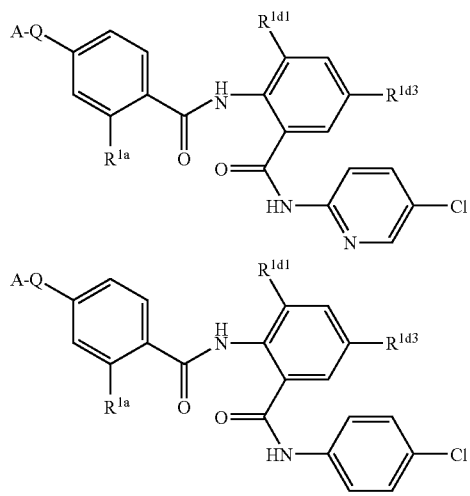

wherein:
R1a is H or F;
A-Q is a member selected from the group consisting of:

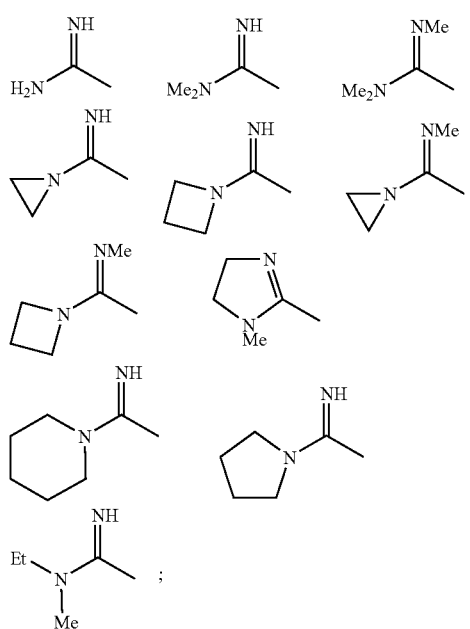

$R^{1d1}$ is a member selected from the group consisting of:
H, —F, —Cl, —Br, —OMe, —OCF$_3$, —OH, —NMe$_2$, —OCH$_2$CO$_2$Et, —OCH$_2$CO$_2$H;

$R^{1d3}$ is a member selected from the group consisting of:

H, —F, —Cl, —Br, —OMe, —OCF$_3$, —OH, —NMe$_2$, —OCH$_2$CO$_2$Et, —OCH$_2$CO$_2$H, —OCF$_2$H, —OCFH$_2$, —OCF$_2$CF$_3$, —OCH$_2$CH$_3$,

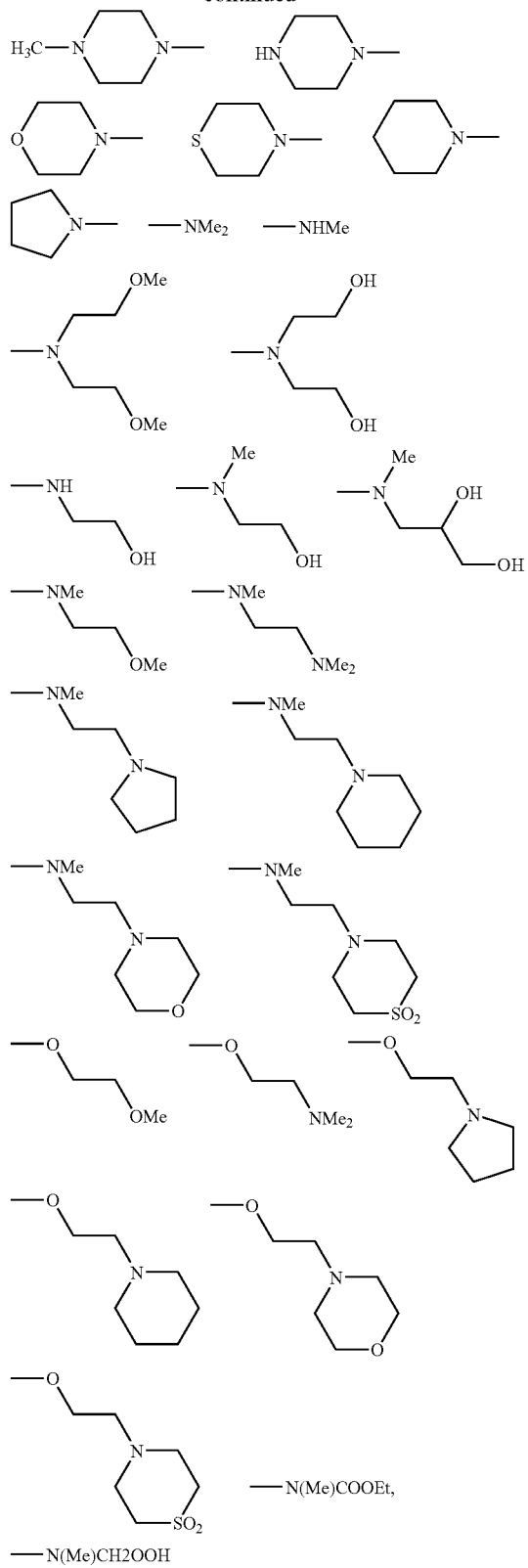

and all pharmaceutically acceptable isomers, salts, hydrates, solvates and prodrug derivatives thereof.

The invention provides compound of formula Ib, as described above, having the following structure:

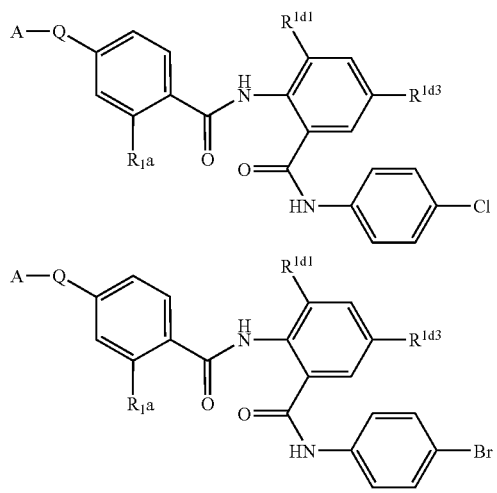

wherein:
R$^{1a}$ is H or F;
A-Q is a member selected from the group consisting of:

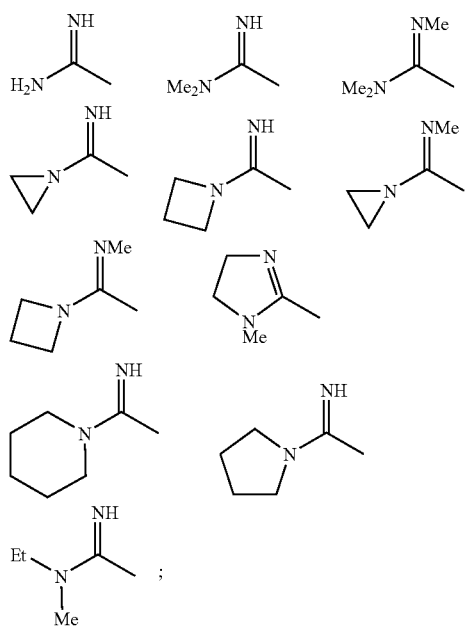

R$^{1d3}$ is a member selected from the group consisting of:

H, —F, —Cl, —Br, —OMe, —OCF$_3$, —OH, —NMe$_2$, —OCH$_2$CO$_2$Et, —OCH$_2$CO$_2$H,

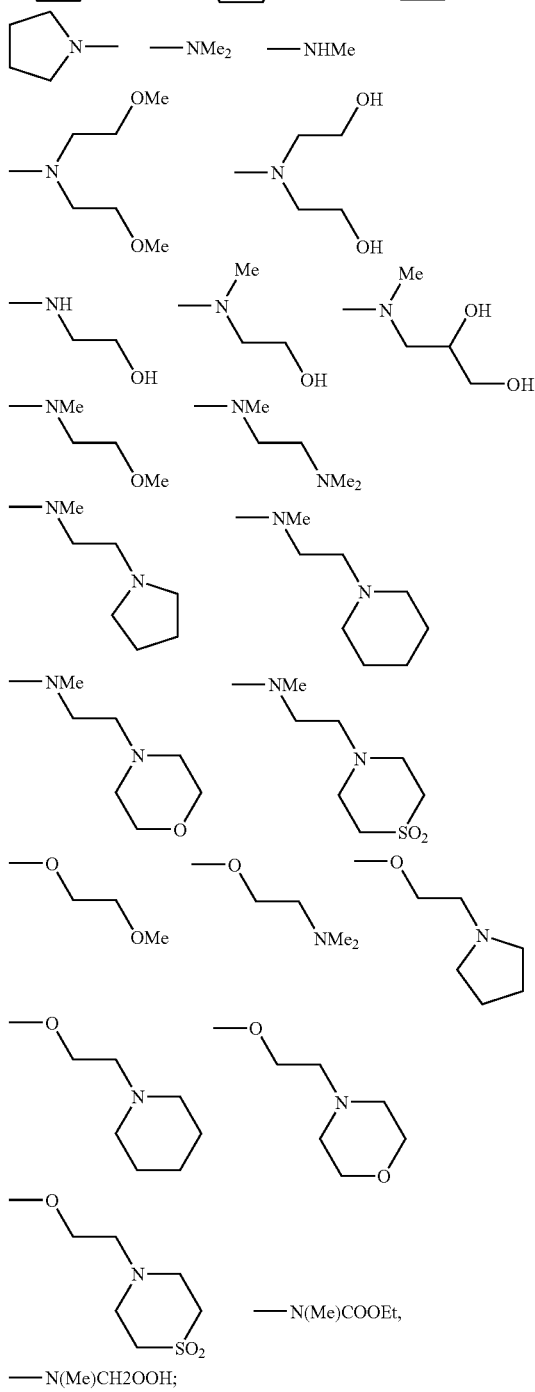

R$^{1d3}$ is a member selected from the group consisting of:
H, —F, —Cl, —Br, —OMe, —OCF$_3$, —OH, —NMe$_2$, —OCH$_2$CO$_2$Et, —OCH$_2$CO$_2$H, —OCF$_2$H, —OCFH$_2$, —OCF$_2$CF$_3$, —OCH$_2$CH$_3$, and all pharmaceutically acceptable isomers, salts, hydrates, solvates and prodrug derivatives thereof.

The invention provides compound of formula Ib, as described above, having the following structure:

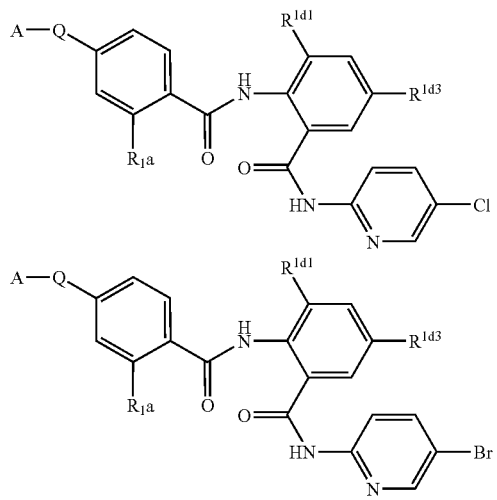

wherein:
$R^{1a}$ is H or F;
$R^{1d1}$ is selected from H, —OMe, —NMe$_2$,

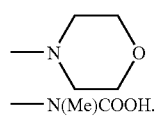  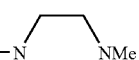

—N(Me)COOH.   —N(Me)COOEt;

$R^{1d3}$ is Cl or Br;
A-Q is a member selected from the group consisting of:

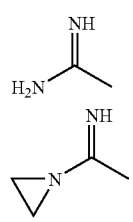 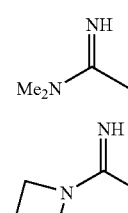 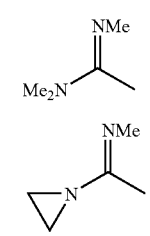

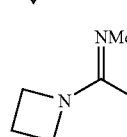 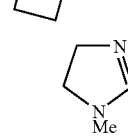

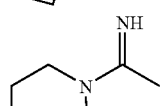 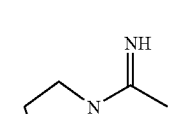

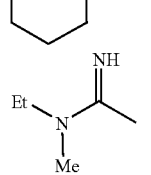

and all pharmaceutically acceptable isomers, salts, hydrates, solvates and prodrug derivatives thereof.

The invention provides compound of formula Ib, as described above, having the following structure:

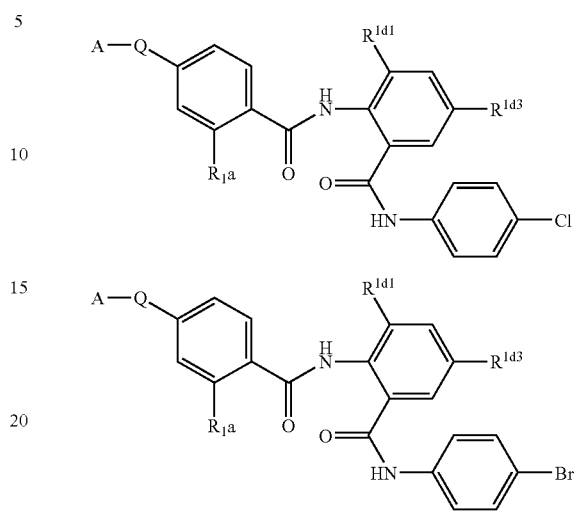

wherein:
$R^{1a}$ is H or F;
$R^{1d1}$ is selected from H, —OMe, —NMe$_2$,

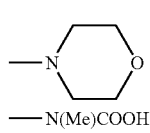 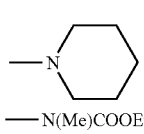 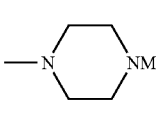

—N(Me)COOH,   —N(Me)COOEt;

$R^{1d3}$ is Cl or Br;
A-Q is a member selected from the group consisting of:

 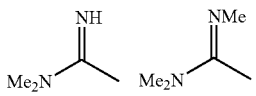

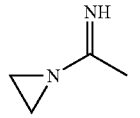 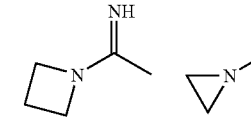

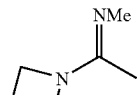 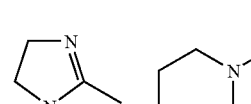

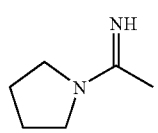 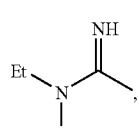

and all pharmaceutically acceptable isomers, salts, hydrates solvates and prodrug derivatives thereof.

The invention provides compound of formula Ib, as described above, having the following structure:

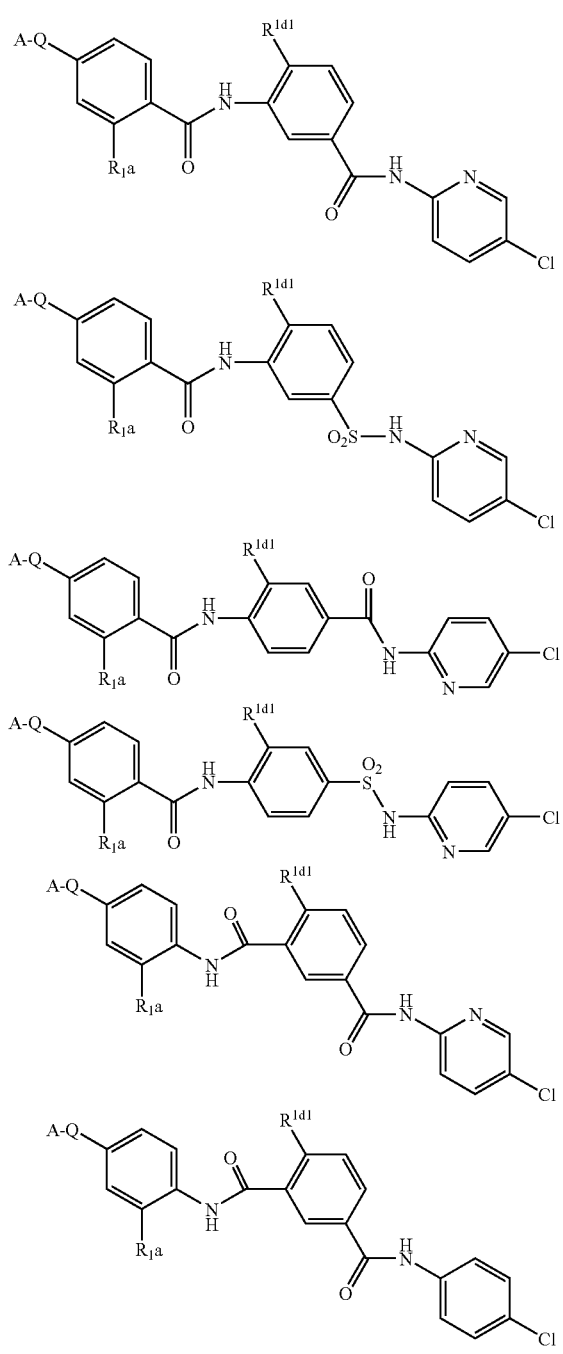

wherein:
$R^{1a}$ is H or F;
$R^{1d1}$ is selected from H, —OMe, —NMe$_2$,

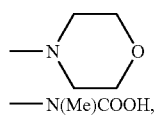

—N(Me)COOH, —N(Me)COOEt

A-Q is a member selected from the group consisting of:

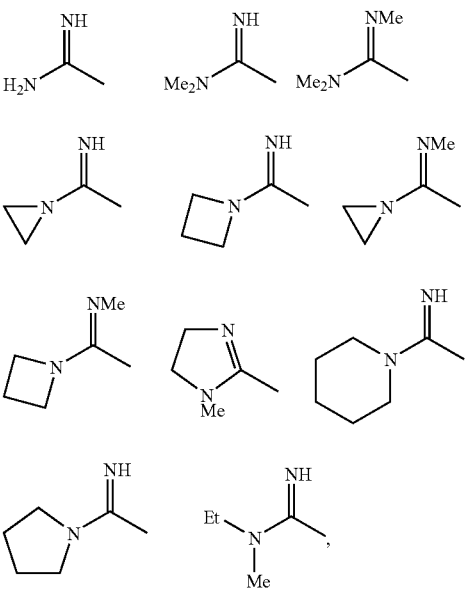

and all pharmaceutically acceptable isomers, salts, hydrates, solvates and prodrug derivatives thereof.

The invention provides compound of formula Ib, as described above, having the following structure:

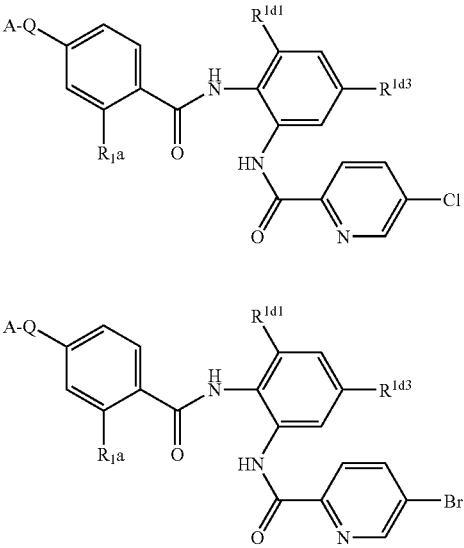

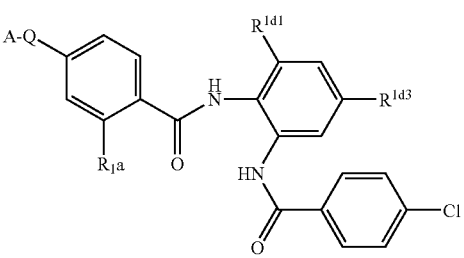

-continued

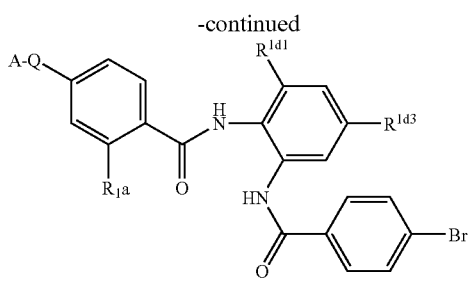

wherein:
R$^{1a}$ is H or F;
R$^{1d1}$ selected from H, —OMe, —NMe$_2$,

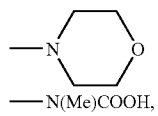 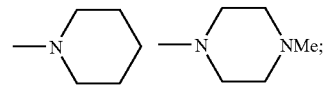

R$^{1d3}$ is —Cl or —Br;
A-Q is a member selected from the group consisting of:

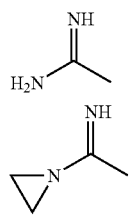 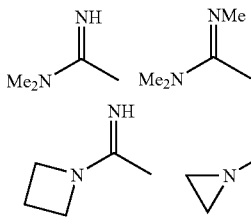 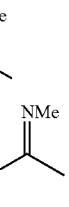
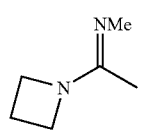 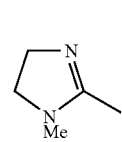 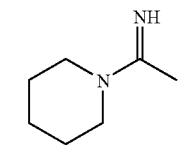
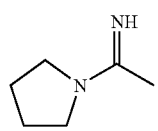 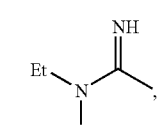

and all pharmaceutically acceptable isomers, salts, hydrates, solvates and prodrug derivatives thereof.

The invention provides a compound of formula Ib, as described above, having the following structure:

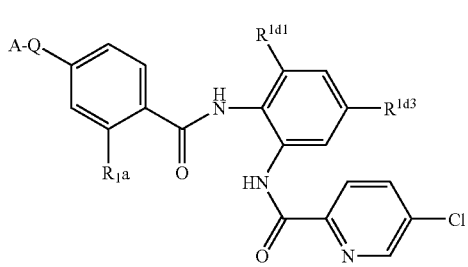

-continued

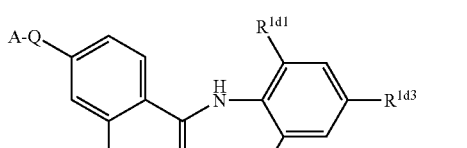

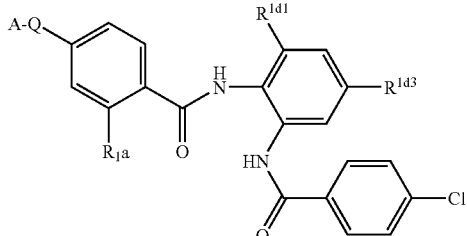

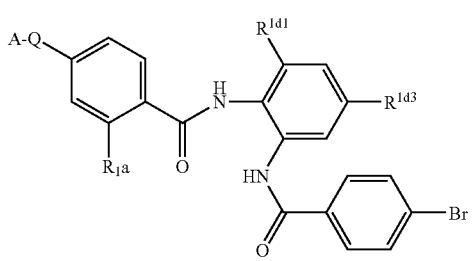

wherein:
R$^{1a}$ is H or F;
R$^{1d1}$ is selected from H, —OMe, —NMe$_2$,

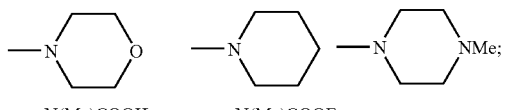

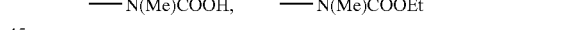

and
R$^{1d3}$ is —Cl or —Br;
A-Q is a member selected from the group consisting of:

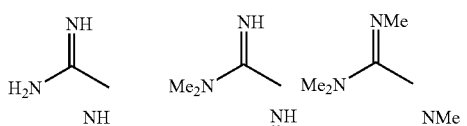

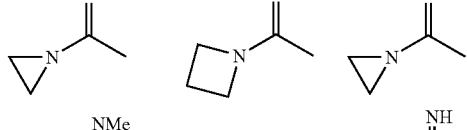

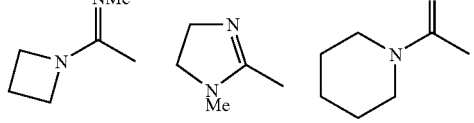

-continued

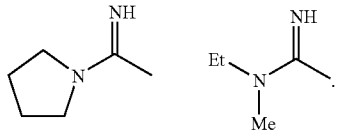

and all pharmaceutically acceptable isomers, salts, hydrates, solvates and prodrug derivatives thereof.

The invention provides compound of formula Ib, as described above, having the following structure:

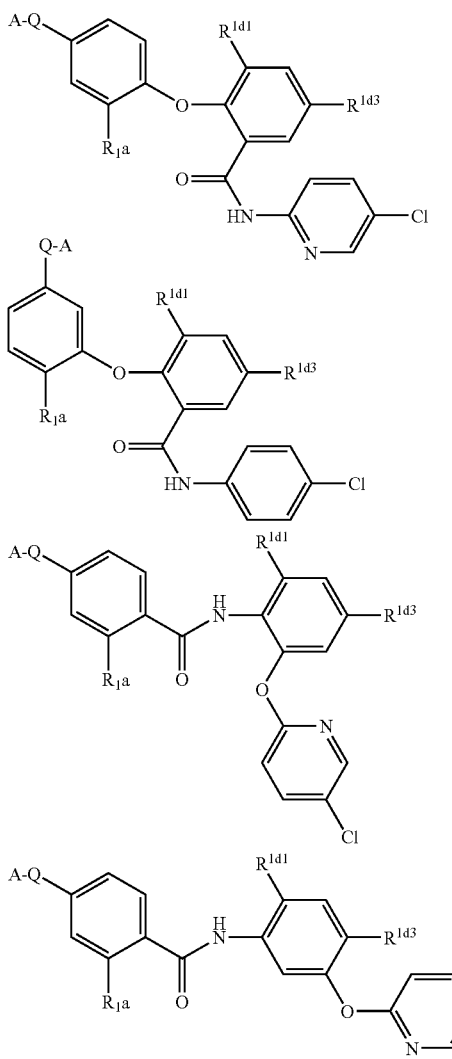

wherein:
$R^{1a}$ is H or F;
$R^{1d1}$ is selected from H, —OMe, —NMe$_2$,

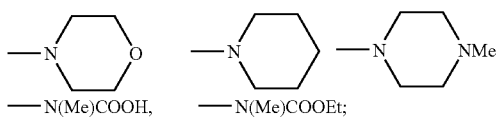

and
$R^{1d3}$ is —Cl or —Br;

A-Q is a member selected from the group consisting of:

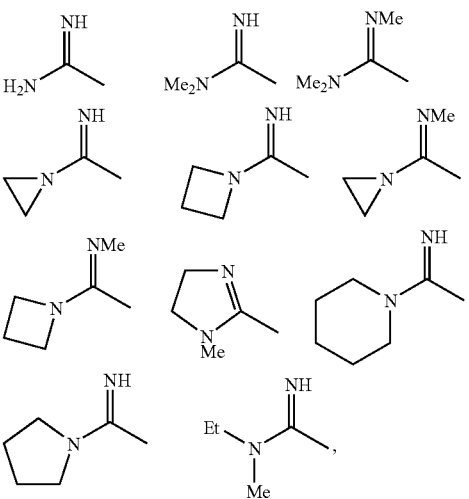

and all pharmaceutically acceptable isomers, salts, hydrates, solvates and prodrug derivatives thereof.

The invention provides compound of formula Ib, as described above, having the following structure:

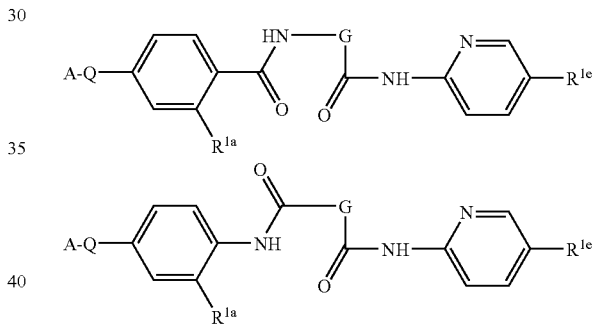

wherein:
A-Q is a member selected from the group consisting of:

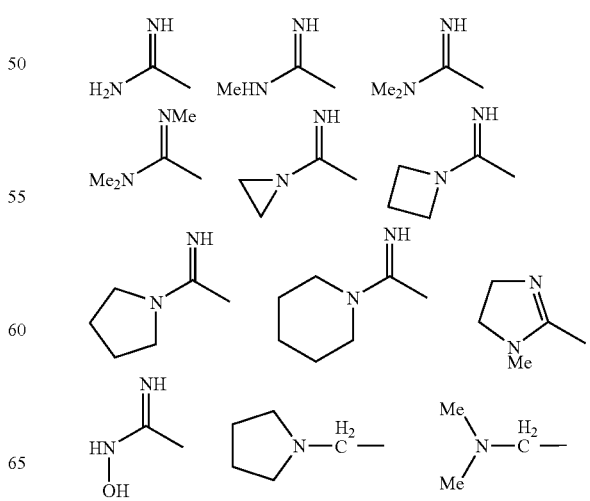

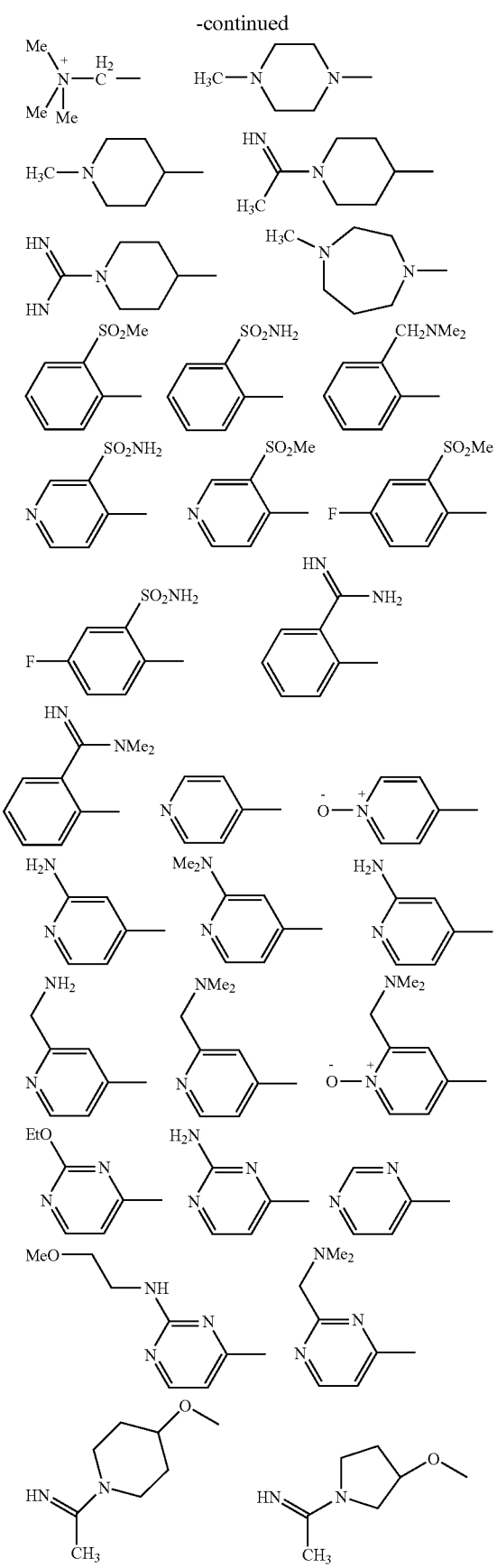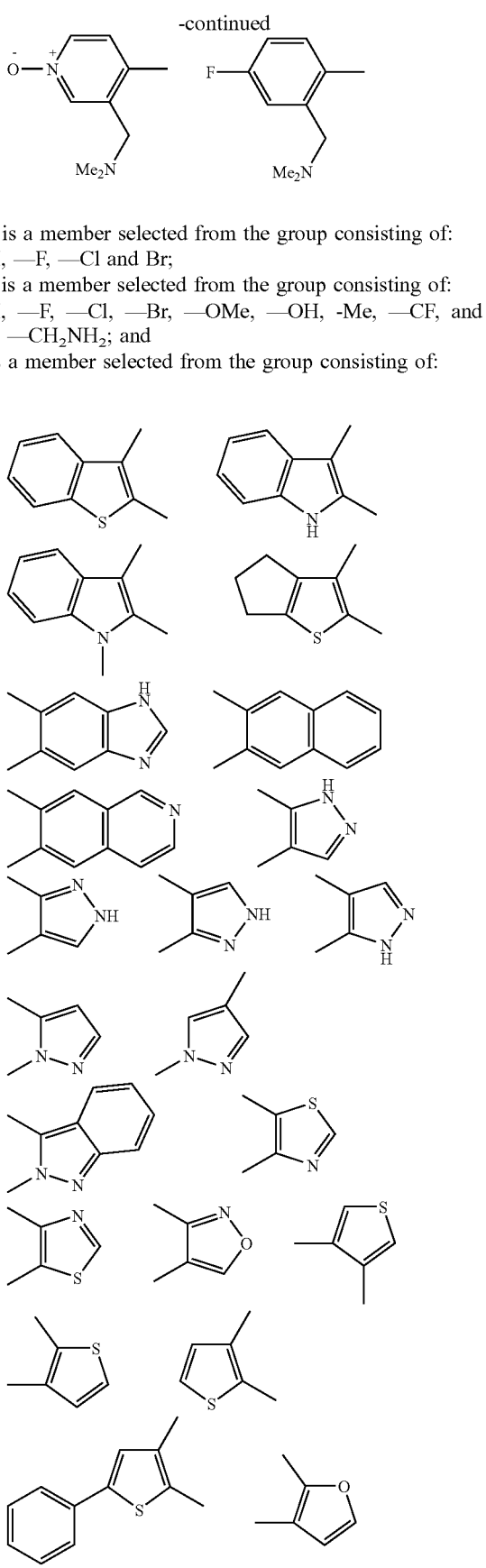
$R^{1a}$ is a member selected from the group consisting of:
H, —F, —Cl and Br;
$R^{1e}$ is a member selected from the group consisting of:
H, —F, —Cl, —Br, —OMe, —OH, -Me, —CF, and —CH$_2$NH$_2$; and
G is a member selected from the group consisting of:

-continued

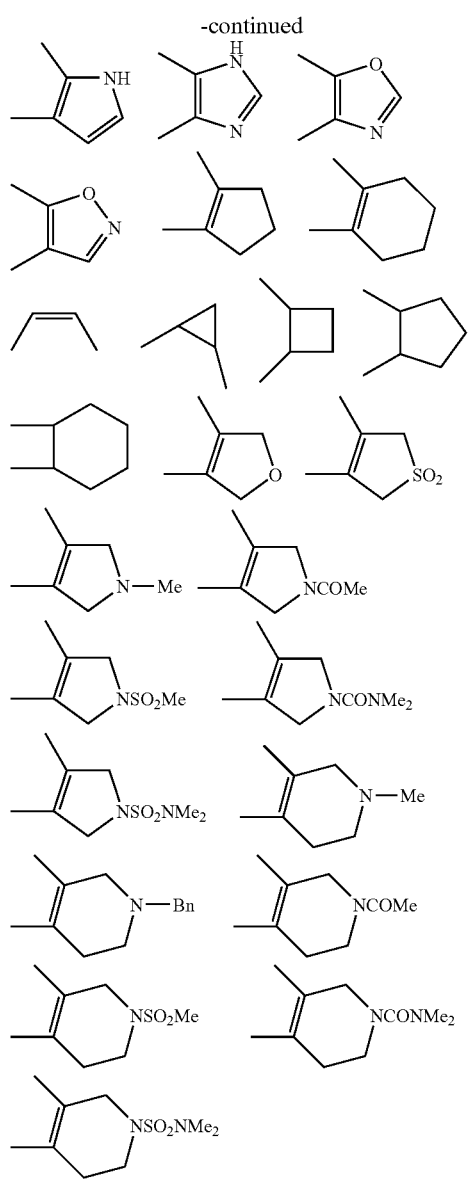

wherein each G group is substituted by 0-4 $R^{1d}$ groups and each such $R^{1d}$ group is independently selected from the group consisting of:

H, -Me, —F, —Cl, —Br, aryl, heteroaryl, —NH$_2$, —NMe$_2$, —NHMe, —NHSO$_2$Me, —NHCOMe, —CH$_3$, —CF$_3$, —OH, —OCH$_3$, —SCH$_3$, —OCF$_3$, —OCH$_2$F, —OCHF$_2$, —OCH$_2$CF$_3$, —OCF$_2$CF$_3$, —NO$_2$, —CN, —CO$_2$H, —CO$_2$Me, —CO$_2$Et, —CONH$_2$, —CONHMe, —CONMe$_2$, —SO$_2$NH$_2$, —SO$_2$CH$_3$, —SO$_2$NMe$_2$, —CH$_2$OH, —CH$_2$NH$_2$, —CH$_2$NHMe, —CH$_2$NMe$_2$, —OCH$_2$CO$_2$H, —OCH$_2$CO$_2$Me, —OCH$_2$CO$_2$Et, —OCH$_2$CONH$_2$, —OCH$_2$CONMe$_2$, —OCH$_2$CONHMe, —OCH$_2$CH$_2$OMe, —OCH$_2$CH$_2$OEt, —OCH$_2$CH$_2$NH$_2$, —OCH$_2$CH$_2$NHMe, —OCH$_2$CH$_2$NMe$_2$, —NHCH$_2$CH$_2$OMe, —SCH$_2$CH$_2$OMe, —SO$_2$CH$_2$CH$_2$OMe, —OCH$_2$CH$_2$SO$_2$Me, —NHCH$_2$CH$_2$NHMe, —NHCH$_2$CH$_2$NMe$_2$, —N(CH$_2$CH$_2$OH)$_2$, —N(CH$_2$CH$_2$OMe)$_2$, —NHCH$_2$CO$_2$H, —NHCH$_2$CO$_2$Et, —NHCH$_2$CO$_2$Et, —NHCH$_2$CONH$_2$, —NHCH$_2$CONMe$_2$, —NHCH$_2$CONHMe, —N(CH$_3$)CH$_2$CO$_2$H, —N(CH$_3$)CH$_2$CO$_2$Et, —(NMe)CH2COOH, —N(Me)CH2CONH2, —N(Me)CH2CH2NMe2, —N(Me)CH2CH2OMe, —NHCH2CH$_2$OMe,

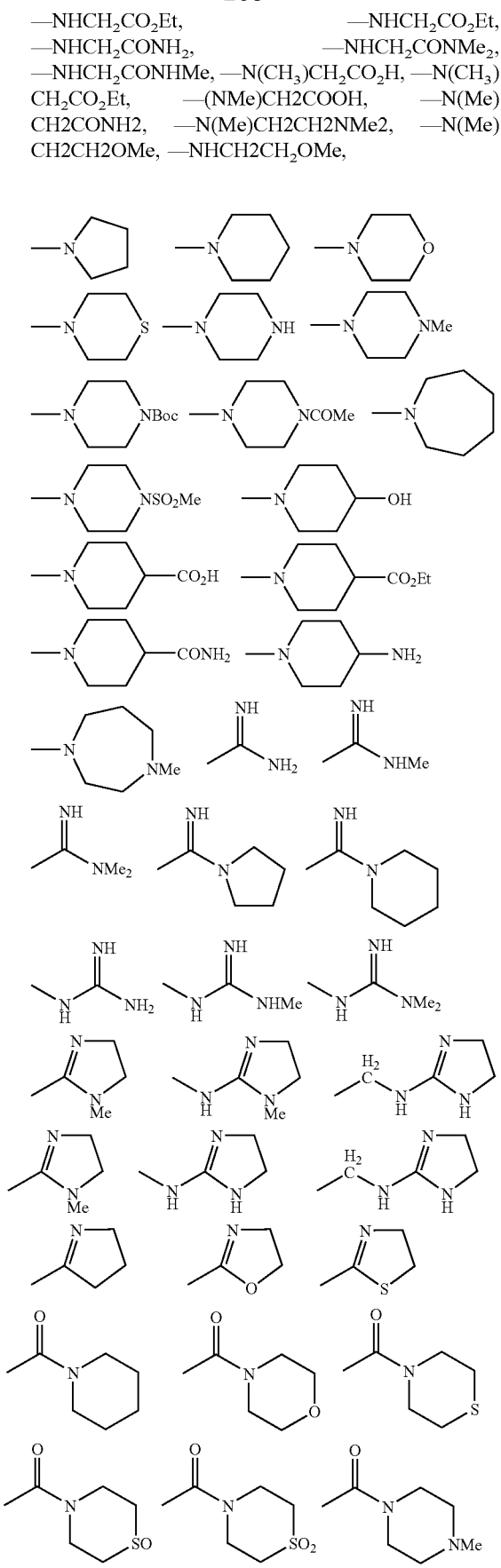

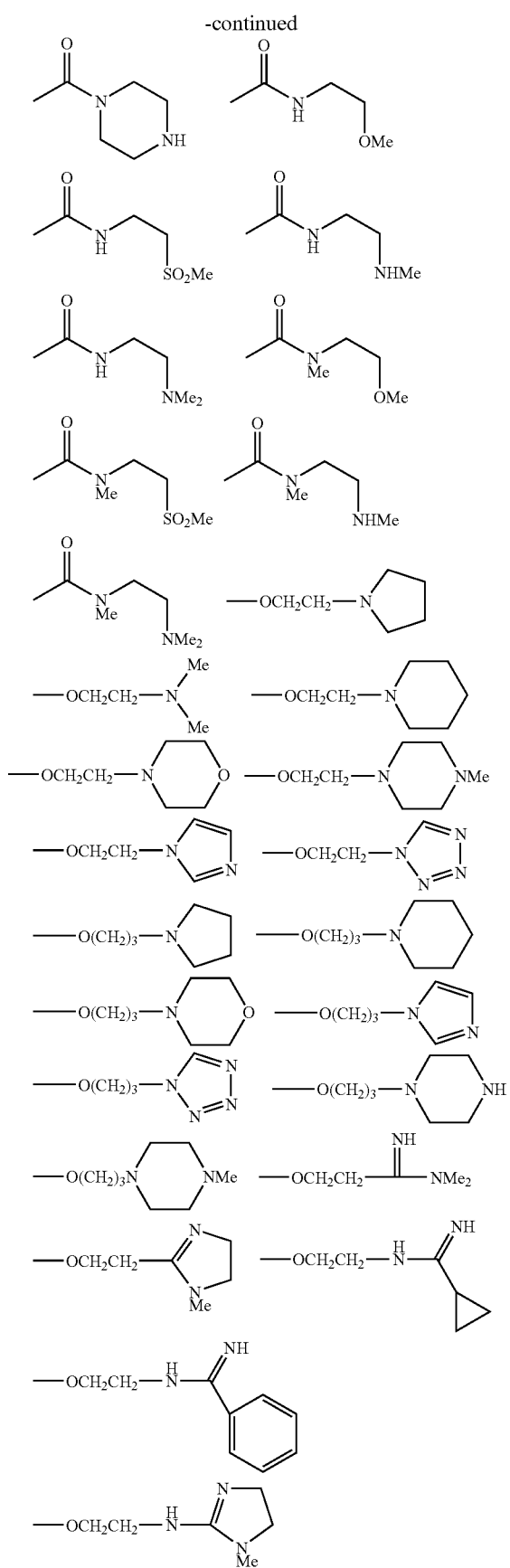
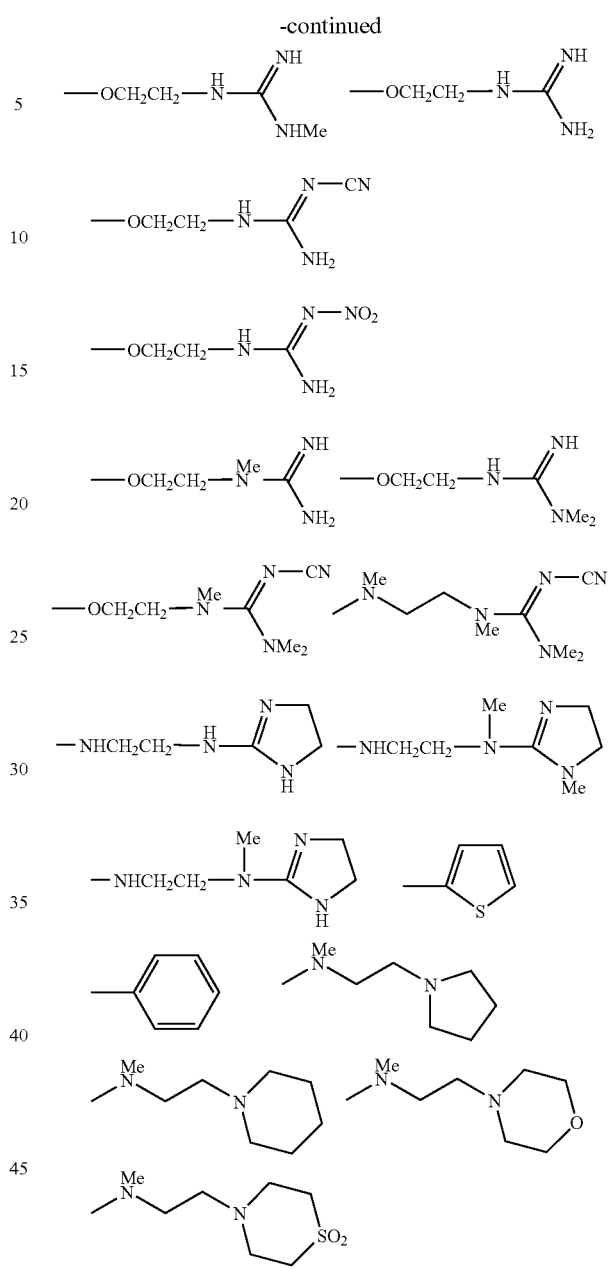
and all pharmaceutically acceptable isomers, salts, hydrates, solvates and prodrug derivatives thereof.
The invention provides compound of formula Ib, as described above, having the following structure:
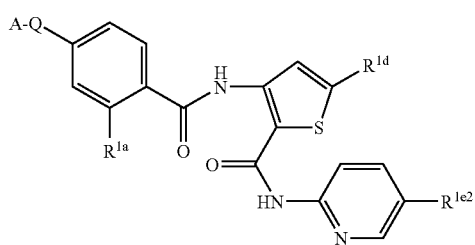

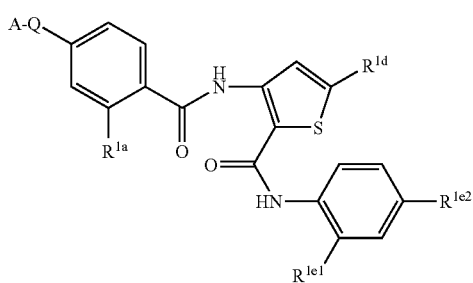

wherein:
A-Q is a member selected from the group of:

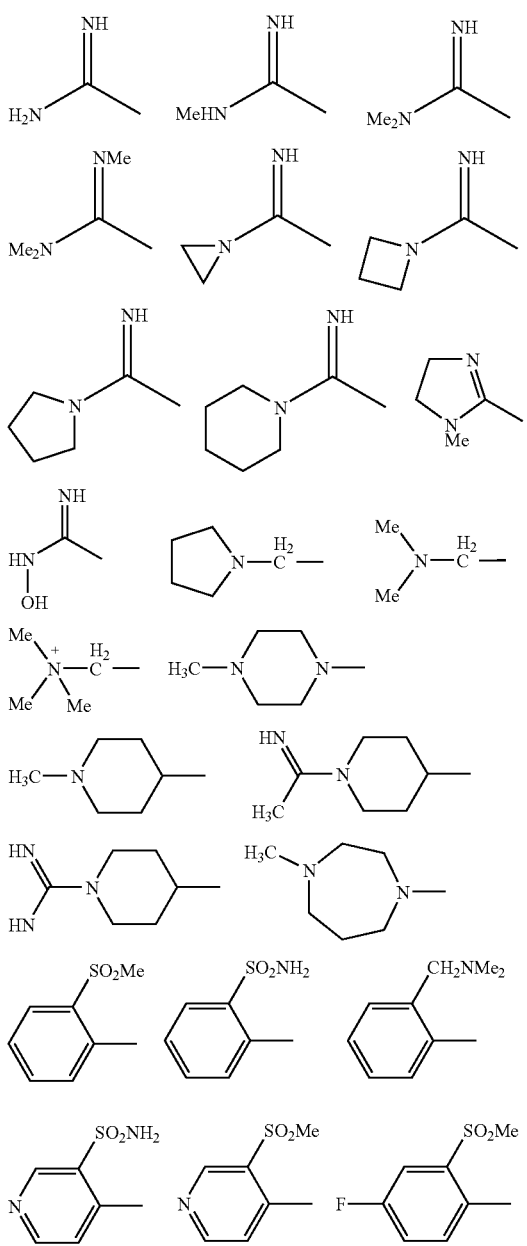

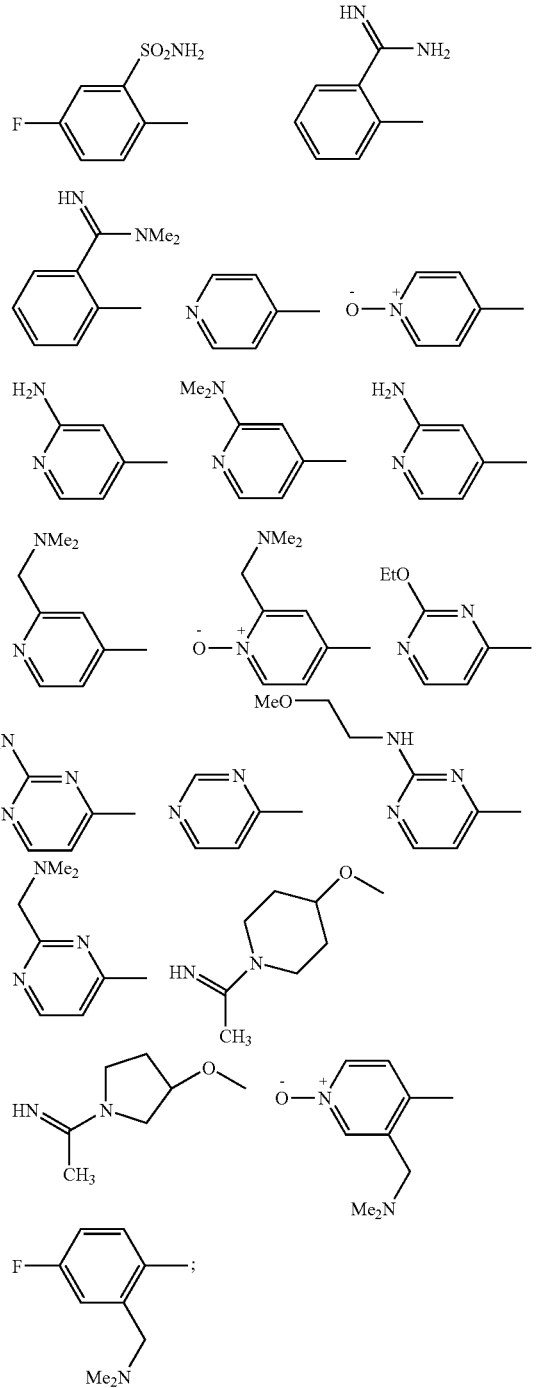

$R^{1a}$ is a member selected from the group of:
H, —F, —Cl, —Br;
$R^{1d}$ is a member selected from the group of:
H, —F, —Cl, —Br, —OMe;
$R^{1e1}$ is a member selected from the group of:
H, —F, —Cl, —Br, —NH$_2$, —CH$_2$NH$_2$, —OMe, —OH, —CN, —SO$_2$Me, —SO$_2$NH$_2$; and
$R^{1e2}$ is a member selected from the group of:
H, —F, —Cl, —Br, —NH$_2$,
and all pharmaceutically acceptable isomers, salts, hydrates, solvates and prodrug, derivatives thereof.

The invention provides compound of formula Ib, as described above, having the following structure:
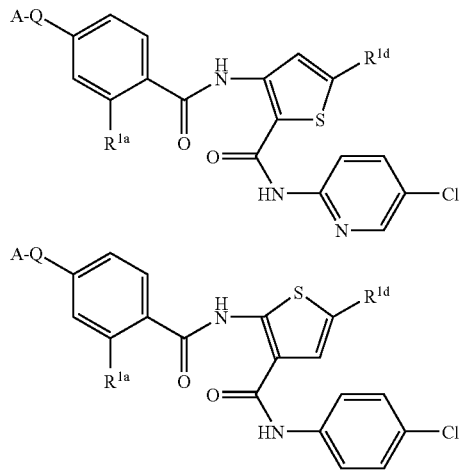
wherein:
A-Q is a member selected from the group of:
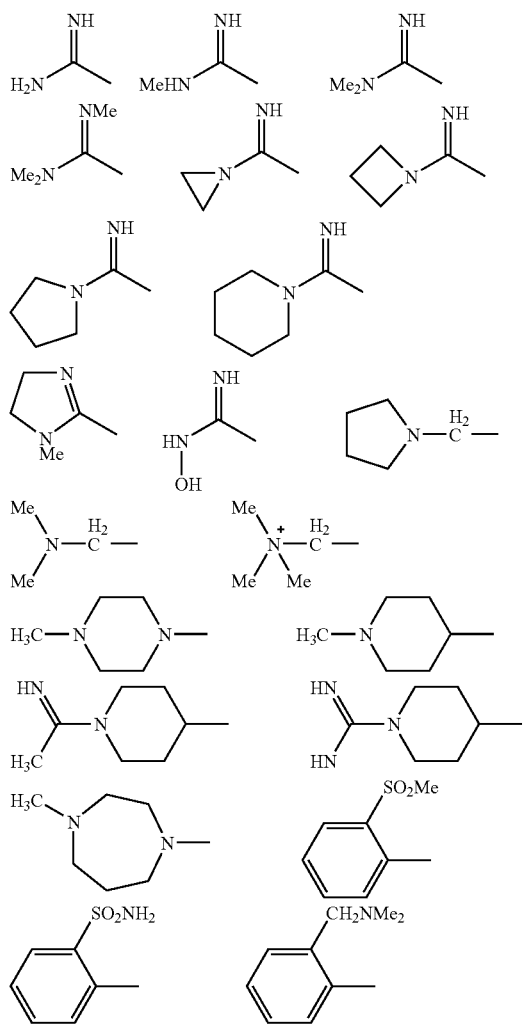
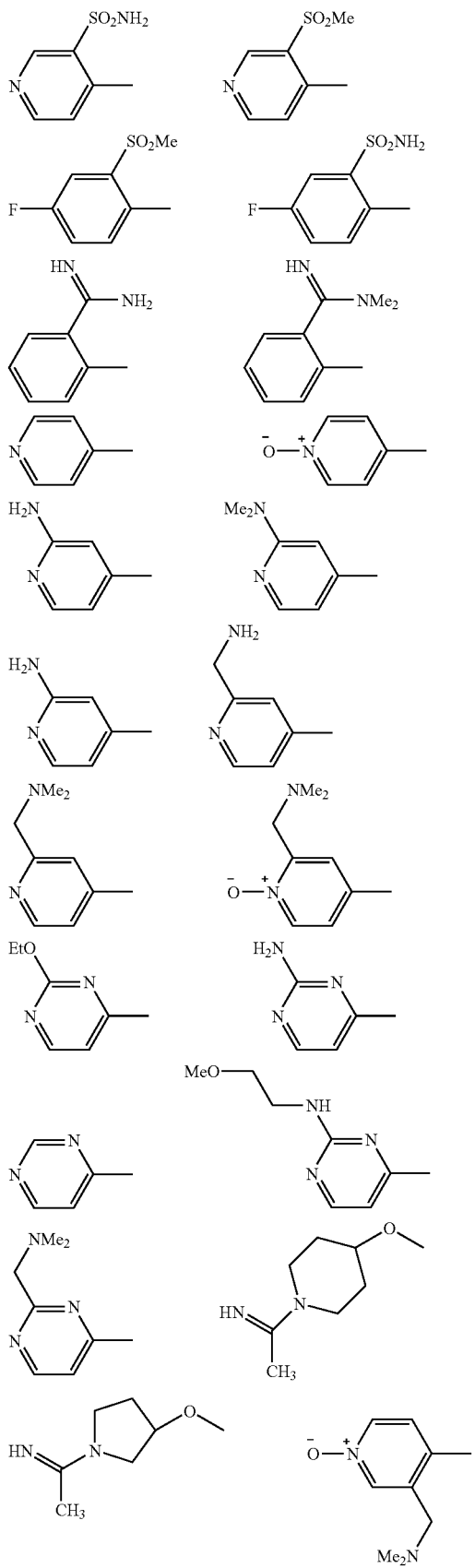

-continued

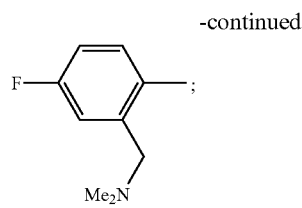

$R^{1a}$ is a member selected from the group of:
H, —F, —Cl and Br; and
$R^{1d}$ is a member selected from the group of:
H, —F, —Cl, —Br, —OMe, and all pharmaceutically acceptable isomers, salts, hydrates, solvates and prodrug derivatives thereof.

The invention provides compound of formula Ib, as described above, having the following structure:

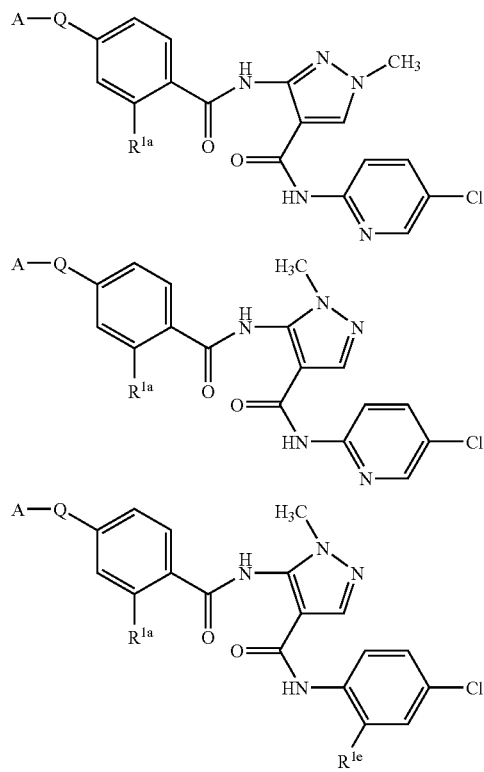

wherein:
A-Q is a member selected from the group of:

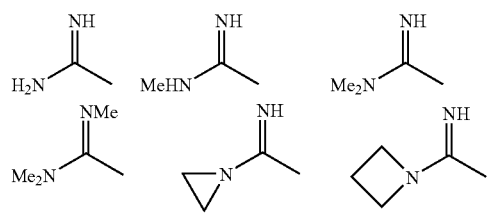

-continued

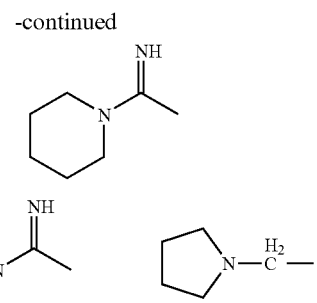

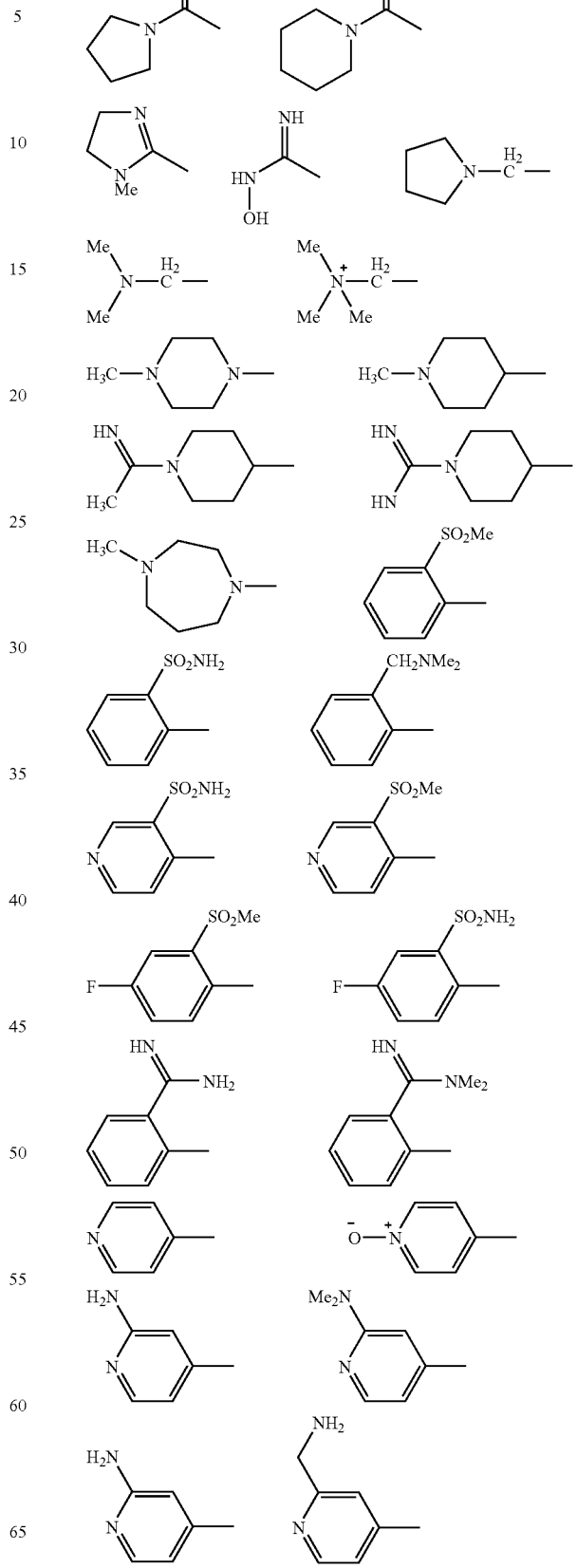

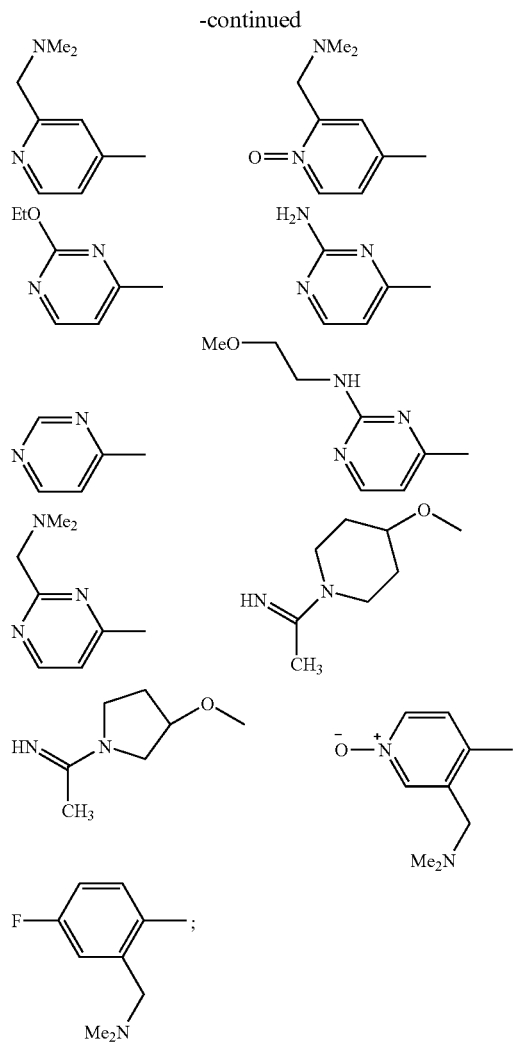
$R^{1a}$ is a member selected from the group of:
  H, —F, —Cl and Br; and
$R^{1e}$ is a member selected from the group of:
  H, —F, —Cl, —Br, —NH$_2$, —CH$_2$NH$_2$, —OMe, —OH, —CN, —SO$_2$Me, —SO$_2$NH$_2$.
and all pharmaceutically acceptable isomers, salts, hydrates, solvates and prodrug derivatives thereof.
The invention provides compound of formula Ib, as described above, having the following structure:
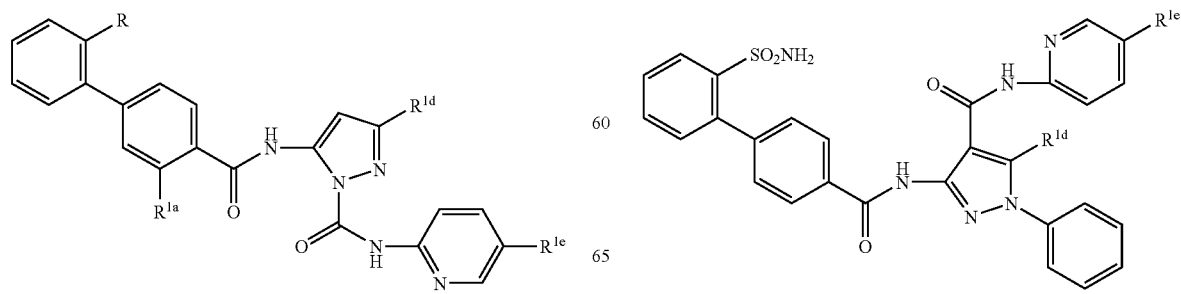
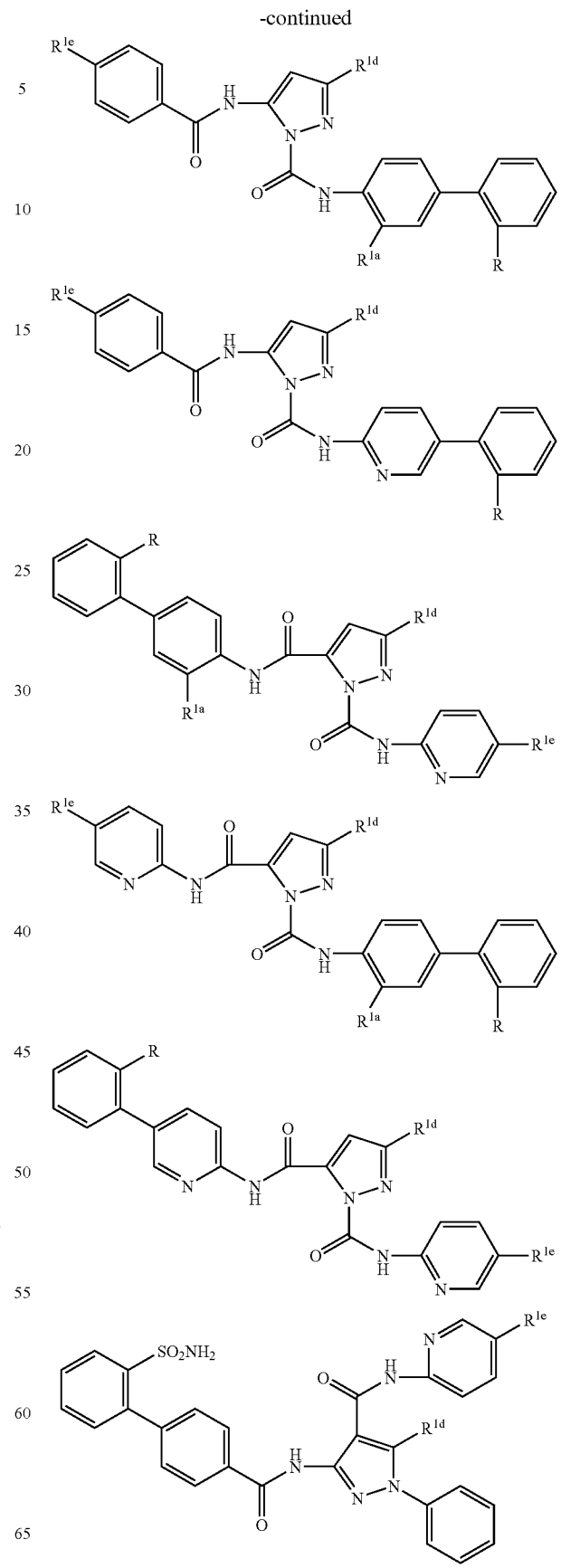

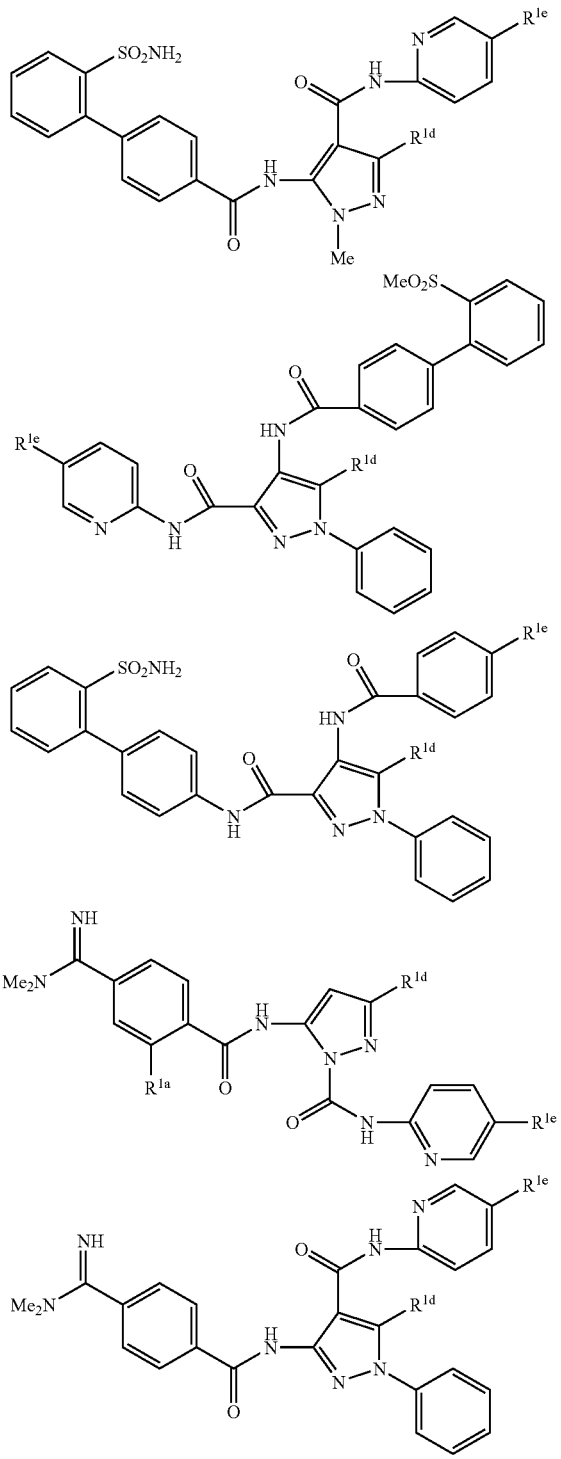

wherein:
R is a member selected from the group of:
—SO$_2$NH$_2$, —SO$_2$Me, —CH$_2$NMe$_2$;
R$^{1a}$ is a member selected from the group of:
H, —F, —Cl, —Br;
R$^{1d}$ is a member selected from the group of:
H, —F, —Cl, —Br, —CN, CF$_3$, —CH$_3$, —SO$_2$NH$_2$, —SO$_2$Me; and R$^{1e}$ is a member selected from the group of:
—Cl, —Br, and all pharmaceutically acceptable isomers, salts, hydrates, solvates and prodrug derivatives thereof.

The invention provides compound of formula Ib, as described above, having the following structure:

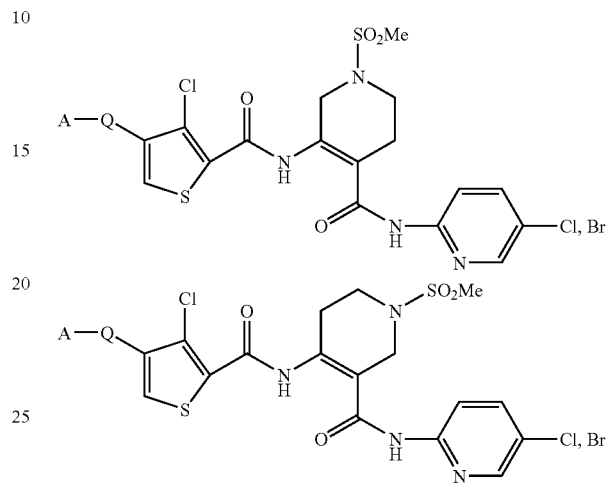

wherein:
A-Q taken together are a member selected from the group consisting of:

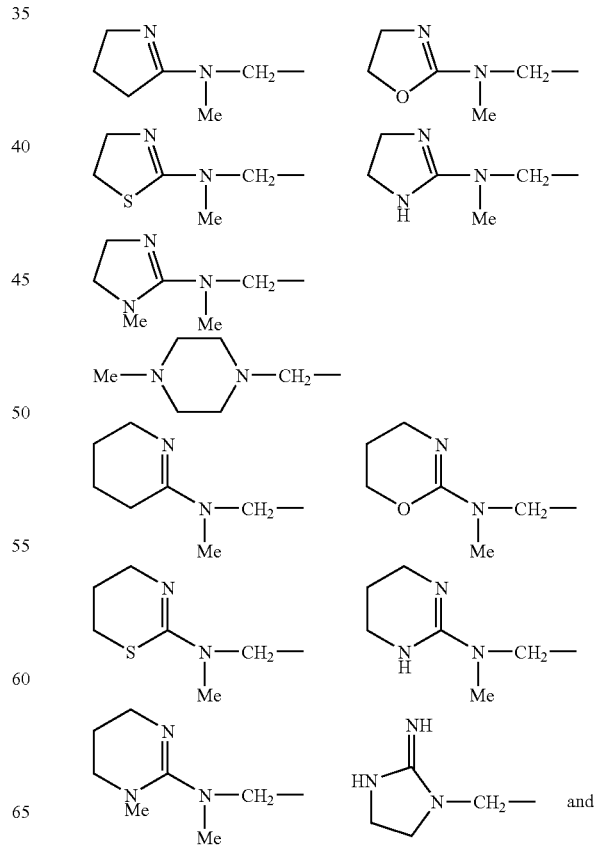

-continued
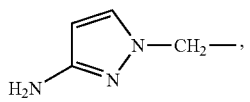
and all pharmaceutically acceptable isomers, salts, hydrates, solvates and prodrug derivatives thereof.
The invention provides compound of formula Ib, as described above, having the following structure:
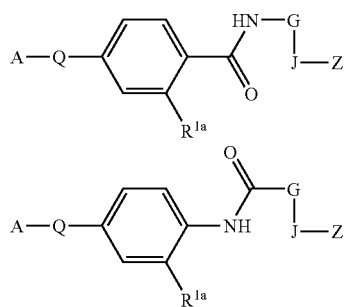
wherein:
A-Q is a member selected from the group consisting of:
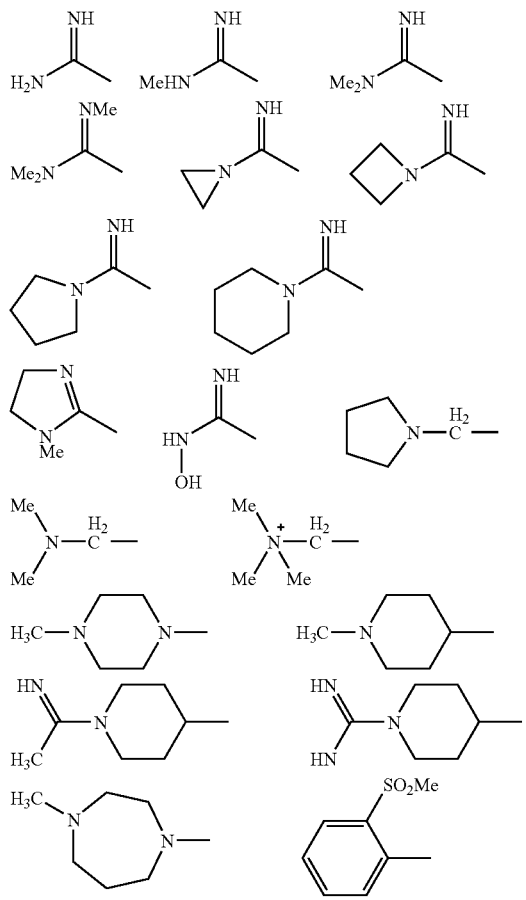
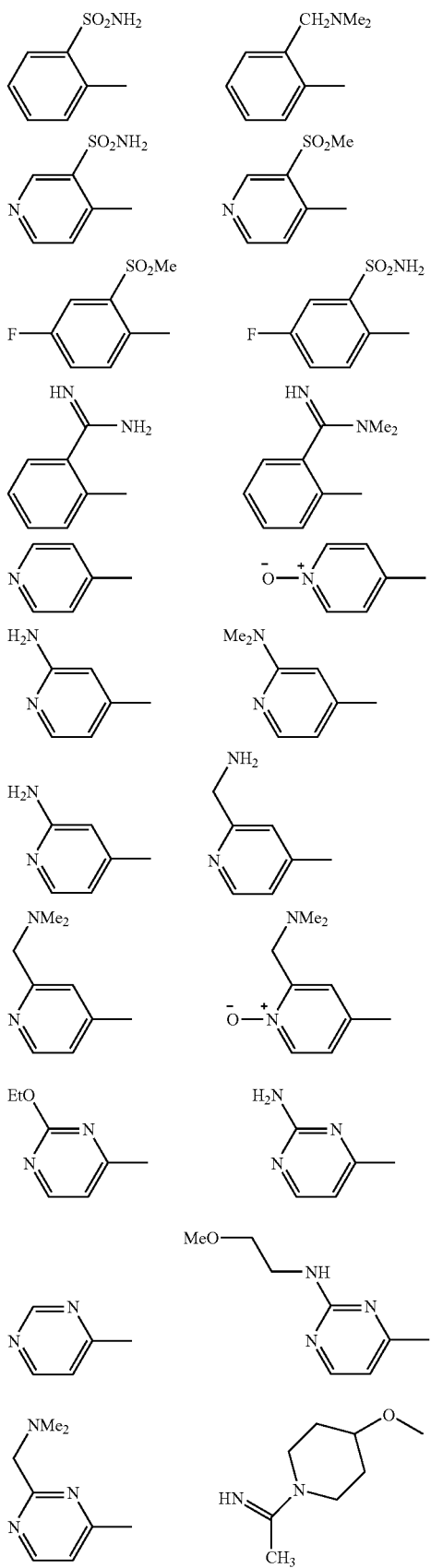

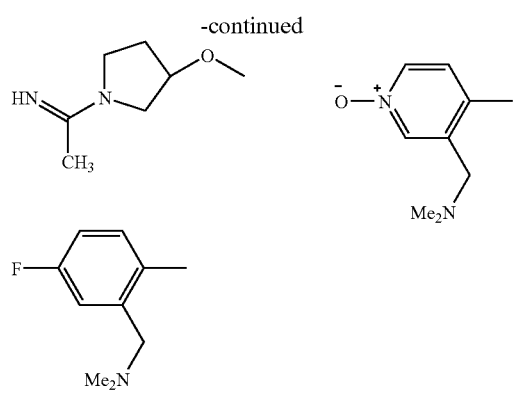
$R^{1a}$ is a member selected from the group consisting of: H, —F, —Cl and Br;
G is a member selected from the group consisting of:
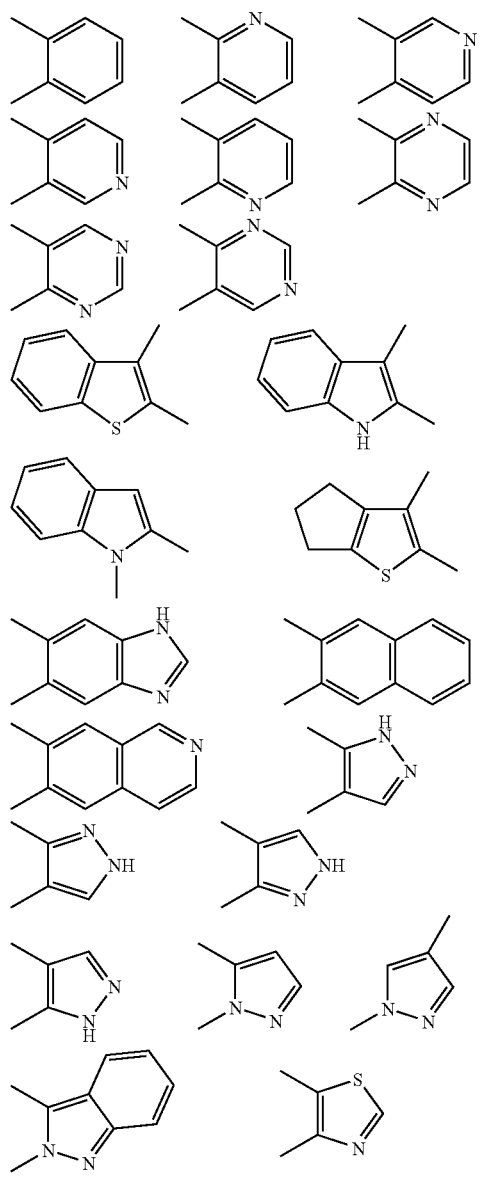
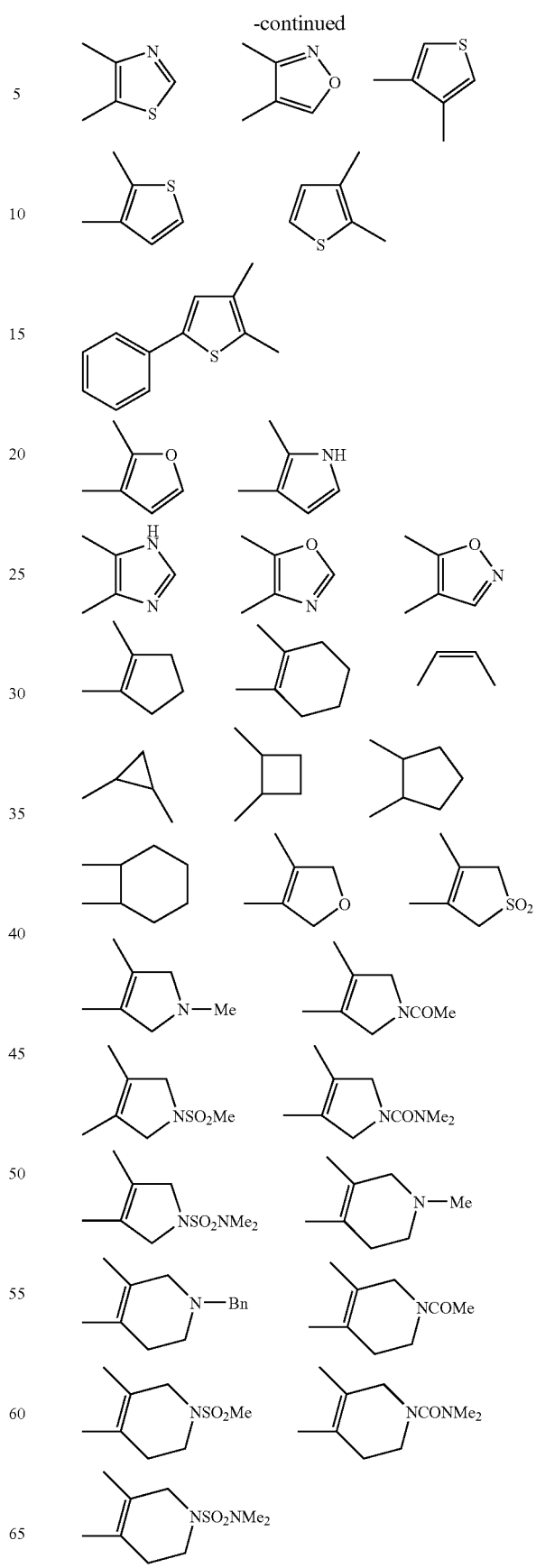

wherein each G group is substituted by 0-4 $R^{1d}$ groups and each such $R^{1d}$ group is independently selected from the group consisting of:

H, -Me, —F, —Cl, —Br, aryl, heteroaryl, —$NH_2$, —$NMe_2$, —NHMe, —$NHSO_2Me$, —NHCOMe, —$CH_3$, —$CF_3$, —OH, —$OCH_3$, —$SCH_3$, —$OCF_3$, —$OCH_2F$, —$OCHF_2$, —$OCH_2CF_3$, —$OCF_2CF_3$, —$NO_2$, —CN, —$CO_2H$, —$CO_2Me$, —$CO_2Et$, —$CONH_2$, —CONHMe, —$CONMe_2$, —$SO_2NH_2$, —$SO_2CH_3$, —$SO_2NMe_2$, —$CH_2OH$, —$CH_2NH_2$, —$CH_2NHMe$, —$CH_2NMe_2$, —$OCH_2CO_2H$, —$OCH_2CO_2Me$, —$OCH_2CO_2Et$, —$OCH_2CONH_2$, —$OCH_2CONMe_2$, —$OCH_2CONHMe$, —$OCH_2CH_2OMe$, —$OCH_2CH_2OEt$, —$OCH_2CH_2NH_2$, —$OCH_2CH_2NHMe$, —$OCH_2C_2NMe_2$, —$NHCH_2CH_2OMe$, —$SCH_2CH_2OMe$, —$SO_2CH_2CH_2OMe$, —$OCH_2CH_2SO_2Me$, —$NHCH_2CH_2NHMe$, —$NHCH_2CH_2NMe_2$, —$N(CH_2CO_2OH)_2$, —$N(CH_2CH_2Me)_2$, —$NHCH_2CO_2H$, —$NHCH_2CO_2Et$, —$NHCH_2CO_2Et$, —$NHCH_2CONH_2$, —$NHCH_2CONMe_2$, —$NCH_2CONHMe$, —$N(CH_3)CH_2CO_2H$, —$N(CH_3)CH_2CO_2Et$, —(NMe)$CH_2COOH$, —N(Me)CH2CONH2, —N(Me)CH2CH2NMe2, —N(Me)CH2CH2OMe, —NHCH2CH$_2$OMe,

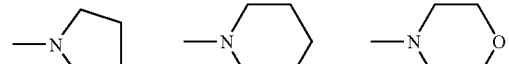
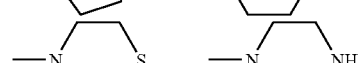
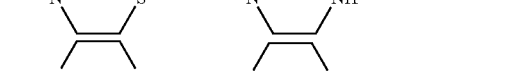
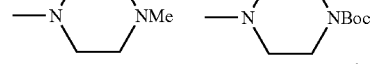
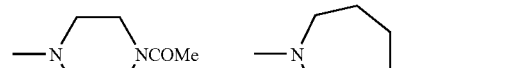
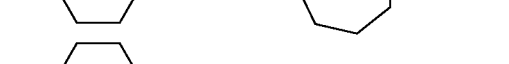
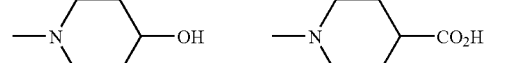
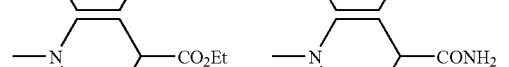
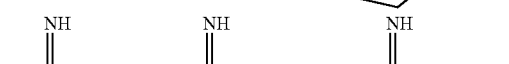
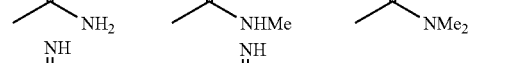
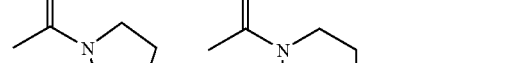
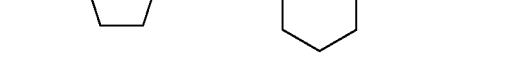

-continued

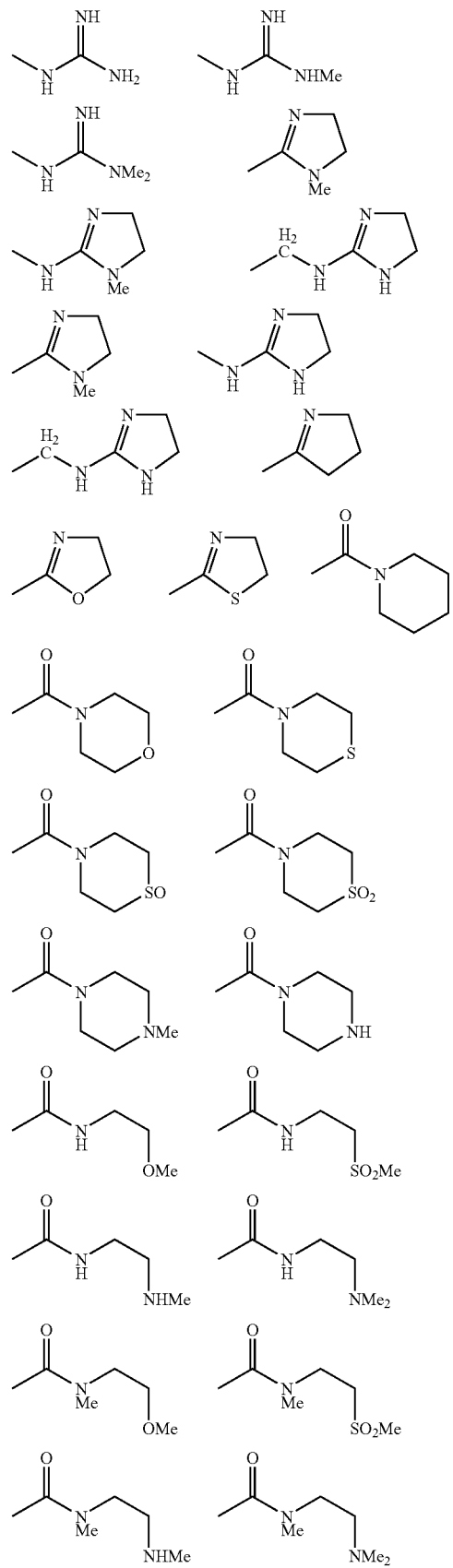

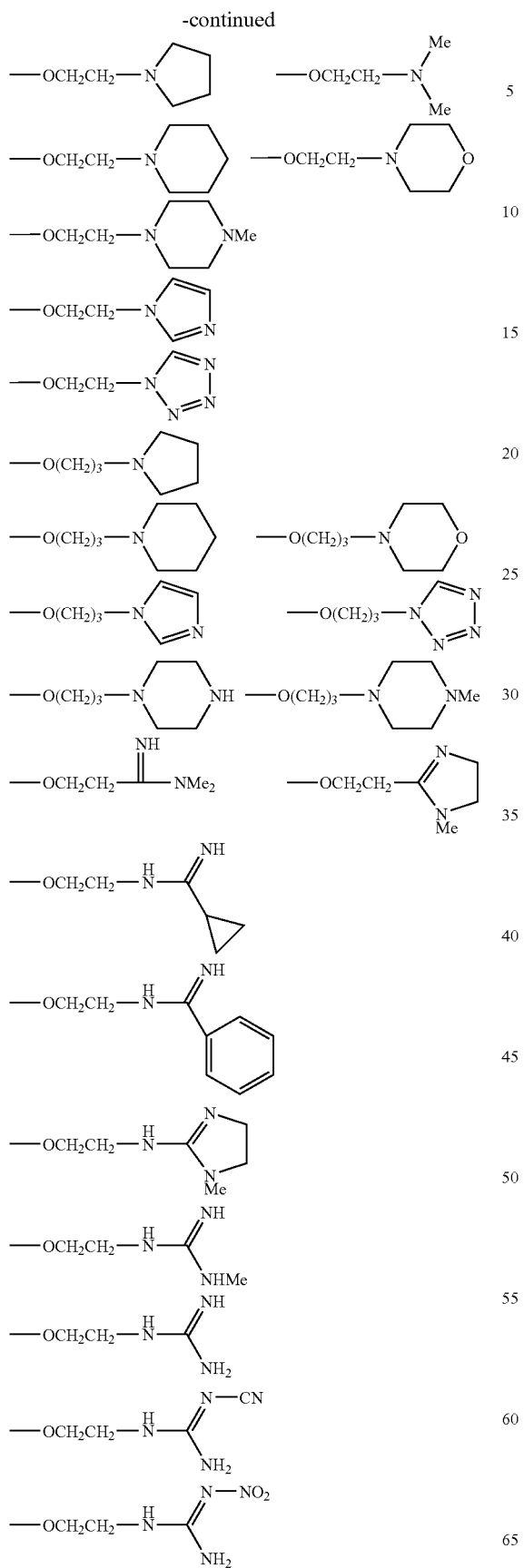
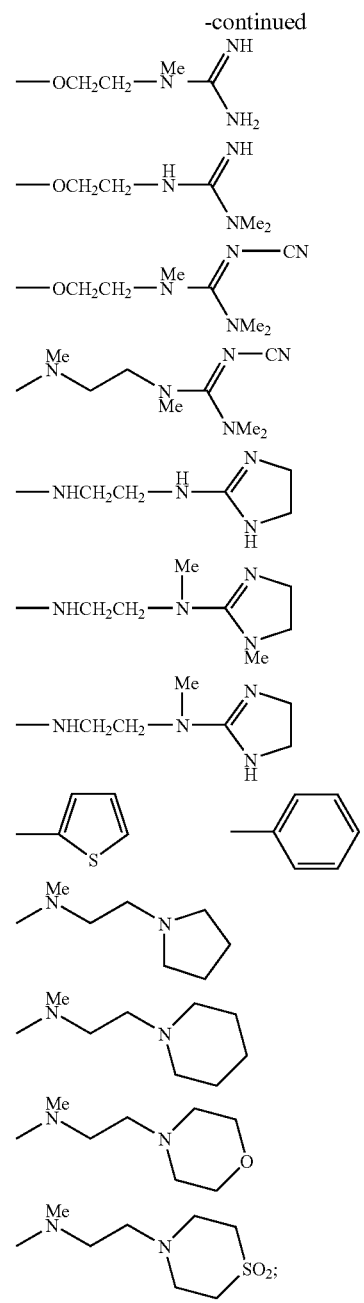
J is a member selected from the group consisting of:
—CONH—, —NHCO—, —O—, —NH—, —NMe-, —CONMe-, —NMeCO—; and
X is a member selected from the group consisting of:
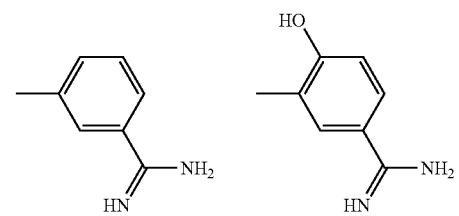

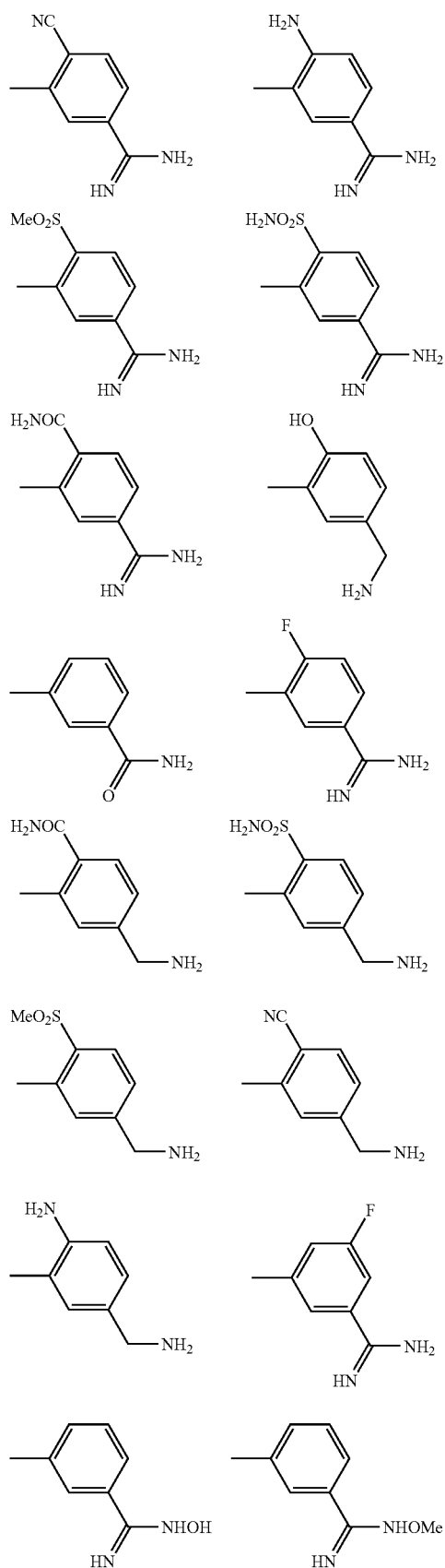
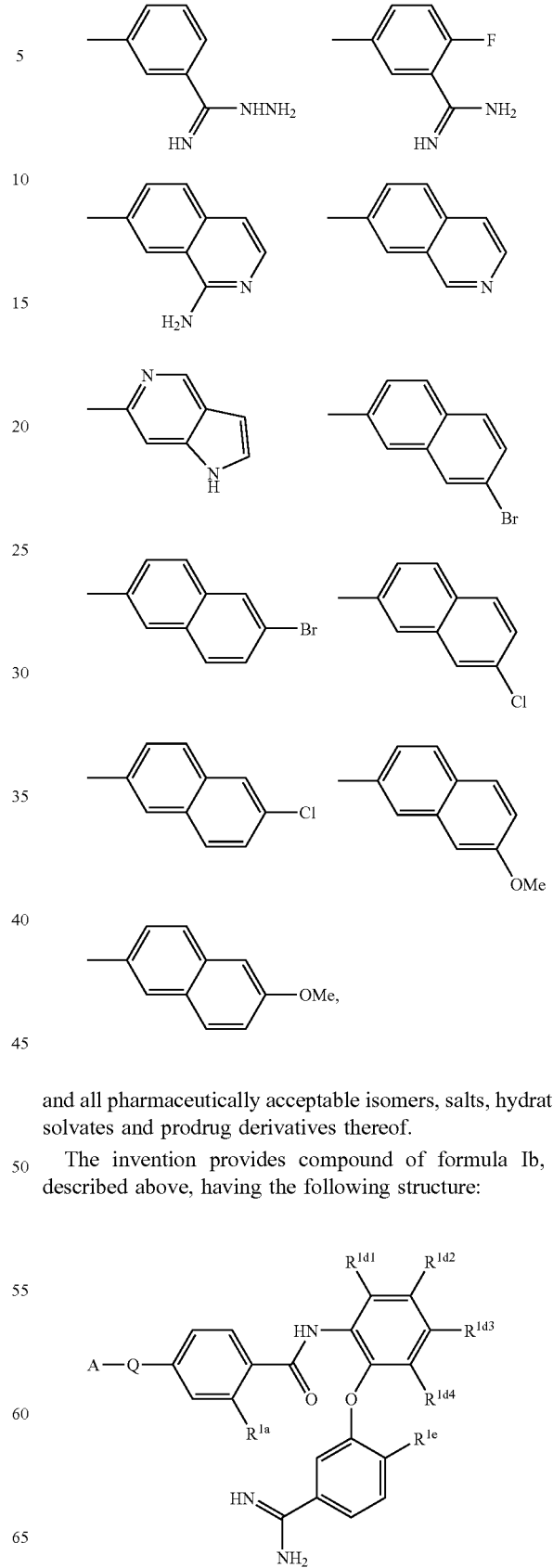
and all pharmaceutically acceptable isomers, salts, hydrates, solvates and prodrug derivatives thereof.
The invention provides compound of formula Ib, as described above, having the following structure:
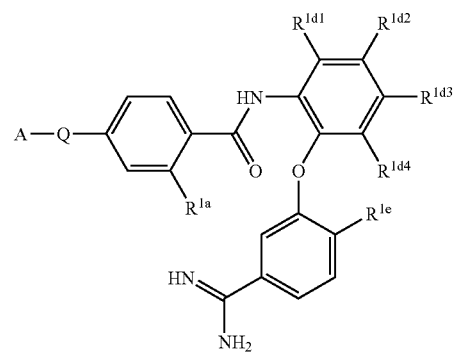

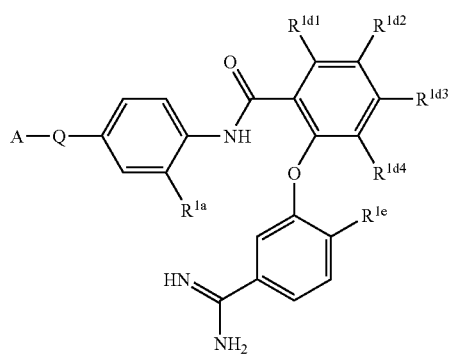
wherein:
A-Q is a member selected from the group of:
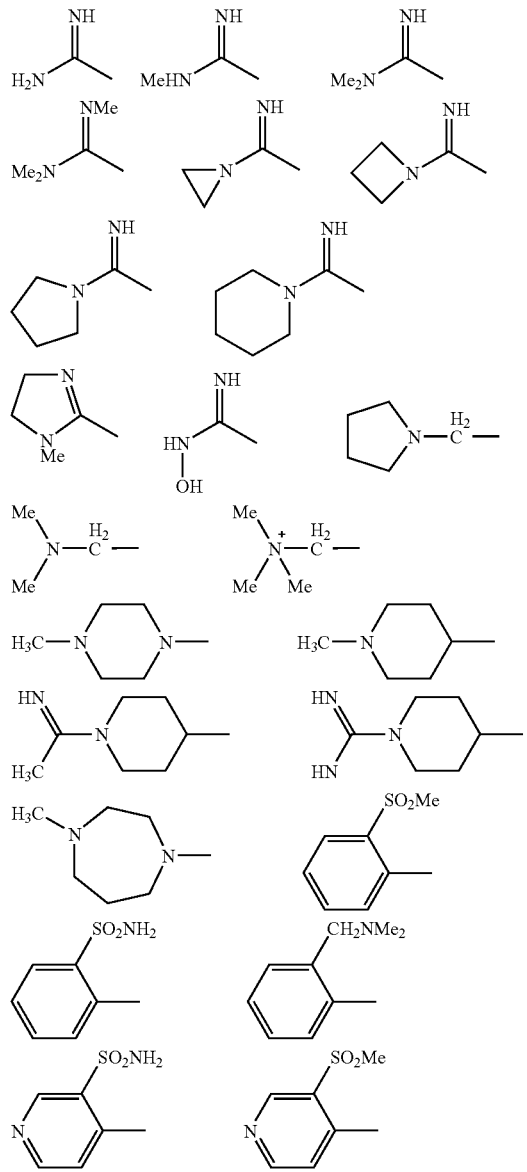
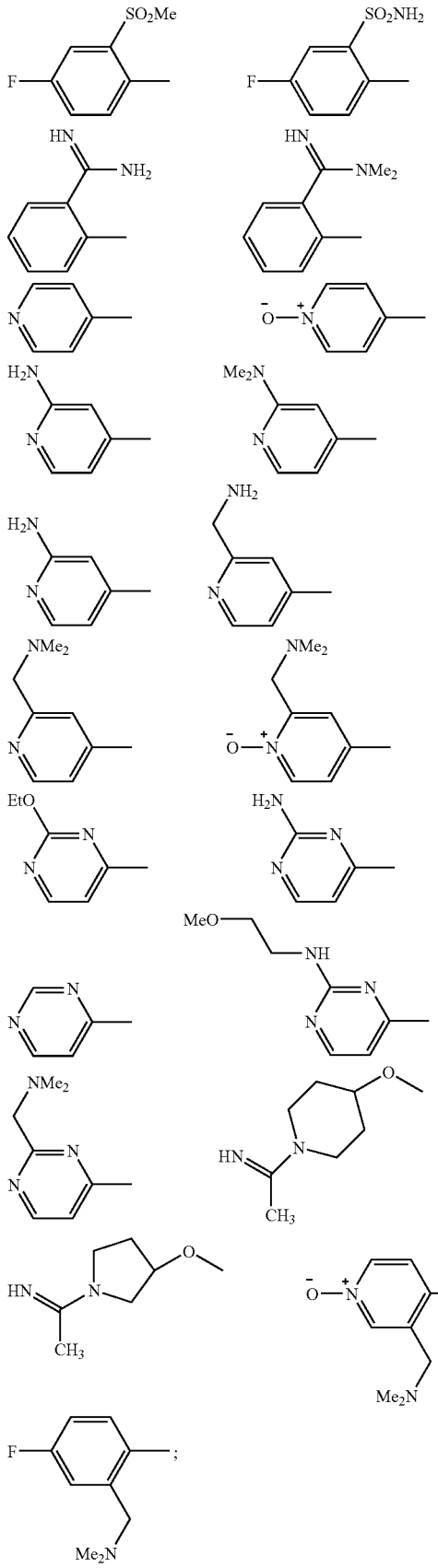

$R^{1a}$ is a member selected from the group of:
  H, —F, —Cl, —Br;
$R^{1d1}$, $R^{1d2}$, $R^{1d3}$ and $R^{1d4}$ is independently a member selected from the group of:
  H, —F, —Cl, —Br, —NO$_2$, —NH$_2$, —NHMe, —NMe$_2$, —NHAc, —NHSO$_2$Me, —SO$_2$Me, —CO$_2$H, —CO$_2$Me, —OH, —OMe, —N(Me)CO$_2$H, —N(Me)CO$_2$Et and

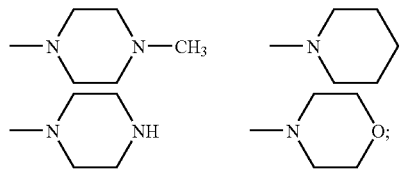

and
$R^{1e}$ is a member selected from the group of:
  H, —OH, and all pharmaceutically acceptable isomers, salts, hydrates, solvates and prodrug derivatives thereof.

The invention provides compound of formula Ib, as described above, having the following structure:

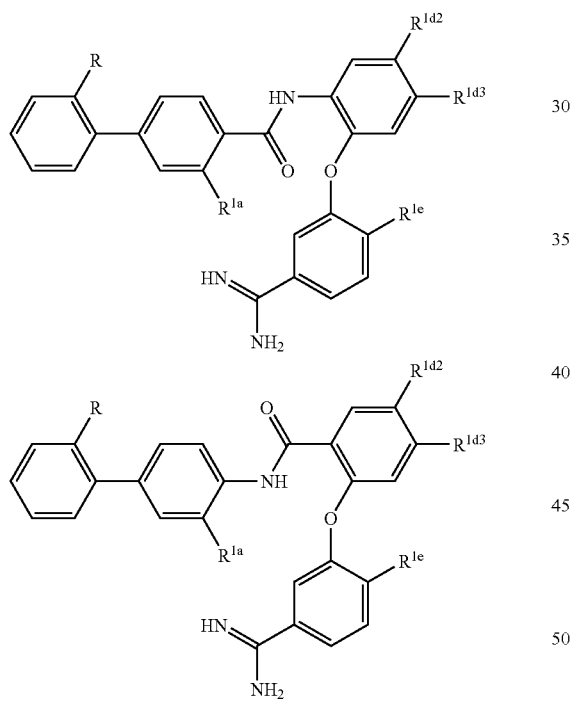

R is a member selected from the group of:
  —SO$_2$Me, —SO$_2$NH$_2$, —CH$_2$NH$_2$, —CH$_2$N(CH$_3$)$_2$;
$R^{1a}$ is a member selected from the group of:
  H, —F;
$R^{1d2}$ and $R^{1d3}$ is independently a member selected from the group of:
  H, —F, —Cl, —Br, —NO$_2$, —NH$_2$, —NHMe, —NMe$_2$, —NHAc, —NHSO$_2$Me, —SO$_2$Me, —CO$_2$H, —CO$_2$Me, —OH, —OMe; and
$R^{1e}$ is a member selected from the group of:
  H, —OH, and all pharmaceutically acceptable isomers, salts, hydrates, solvates and prodrug derivatives thereof.

The invention provides compound of formula Ib, as described above, having the following structure:

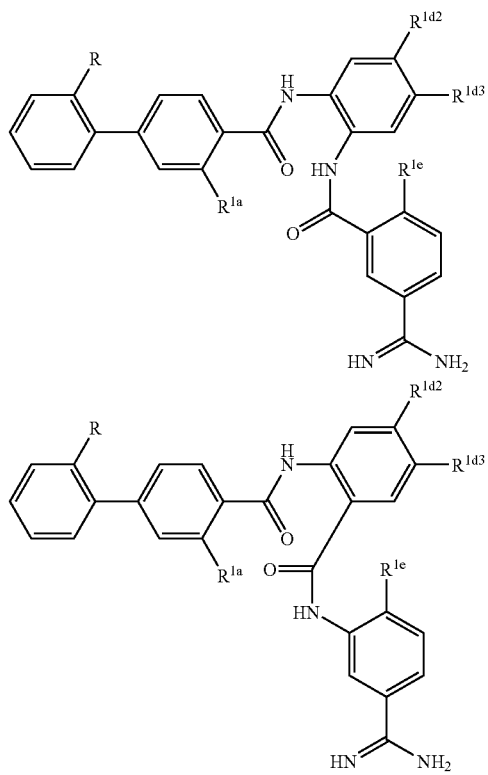

wherein:
R is a member selected from the group of:
  —SO$_2$Me, —SO$_2$NH$_2$, —CH$_2$NH$_2$, —CH$_2$N(CH$_3$)$_2$;
$R^{1a}$ is a member selected from the group of:
  H, —F;
$R^{1d2}$ and $R^{1d3}$ is independently a member selected from the group of:
  H, —F, —Cl, —Br, —NO$_2$, —NH$_2$, —NHMe, —NMe$_2$, —NHAc, —NHSO$_2$Me, —SO$_2$Me, —CO$_2$H, —CO$_2$Me, —OH, —OMe; and
$R^{1e}$ is a member selected from the group of:
  H, —OH, and all pharmaceutically acceptable isomers, salts, hydrates, solvates and prodrug derivatives thereof.

The invention provides compound of formula Ib, as described above, having the following structure:

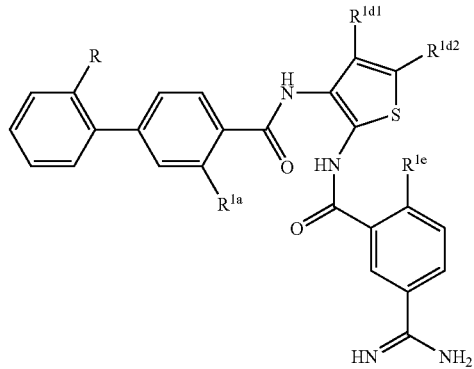

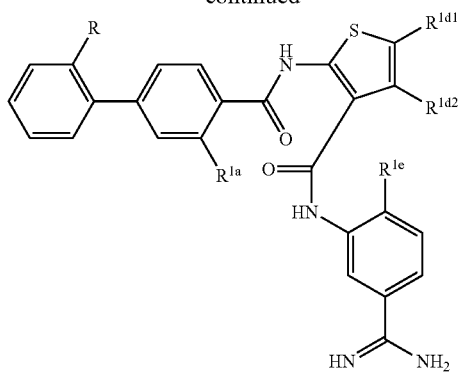

R is a member selected from the group of:
—SO₂Me, —SO₂NH₂, —CH₂NH₂, —CH₂N(CH₃)₂;
$R^{1a}$ is a member selected from the group of:
H, —F;
$R^{1d1}$ and $R^{1d2}$ is independently a member selected from the group of:
H, —F, —Cl, —Br, —OMe; and
$R^{1e}$ is a member selected from the group of:
H, —OH, and all pharmaceutically acceptable isomers, salts, hydrates, solvates and prodrug derivatives thereof.

The following preferred embodiments of the present invention illustrate compounds wherein the central aromatic ring structure is divalent phenylene, however divalent 6 membered heteroaromatic rings having from 1 to 3 nitrogen atoms may be substituted for the bivalent phenylene structure. Further the terminal aromatic ring substituted which is substituted by a $R^{1e}$ group as illustrated below in the preferred embodiments is either a phenyl or a 2-pyridyl group, however other 6 membered heteroaromatic rings having from 1 to 3 nitrogen atoms can be substituted for either the phenyl or 2-pyridyl. Moreover, 2 to 3 additional $R^{1e}$ groups other than hydrogen may each be independently substituted for a hydrogen atom attached to a ring carbon on the terminal rings illustrated or substituted for the illustrated terminal ring structure.

A preferred embodiment of the invention provides a compound of formula VIII:

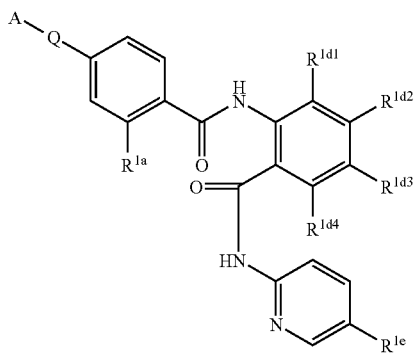

(VIII)

wherein:
$R^{1a}$ is a member selected from the group of H, —F, —Cl and Br;

$R^{1d2}$ and $R^{1d4}$ are each H or F;
$R^{1d1}$ and $R^{1d3}$ are each independently a member selected from the group of H, —Cl, —F, —Br, —OH, —OMe, —OCF₃, OCHF₂, OCH₂F, —NH₂, —NMe₂, —OCH₂COOEt, —OCH₂COOH, —N(Me)CH₂COOH, —N(Me)COOEt, and,

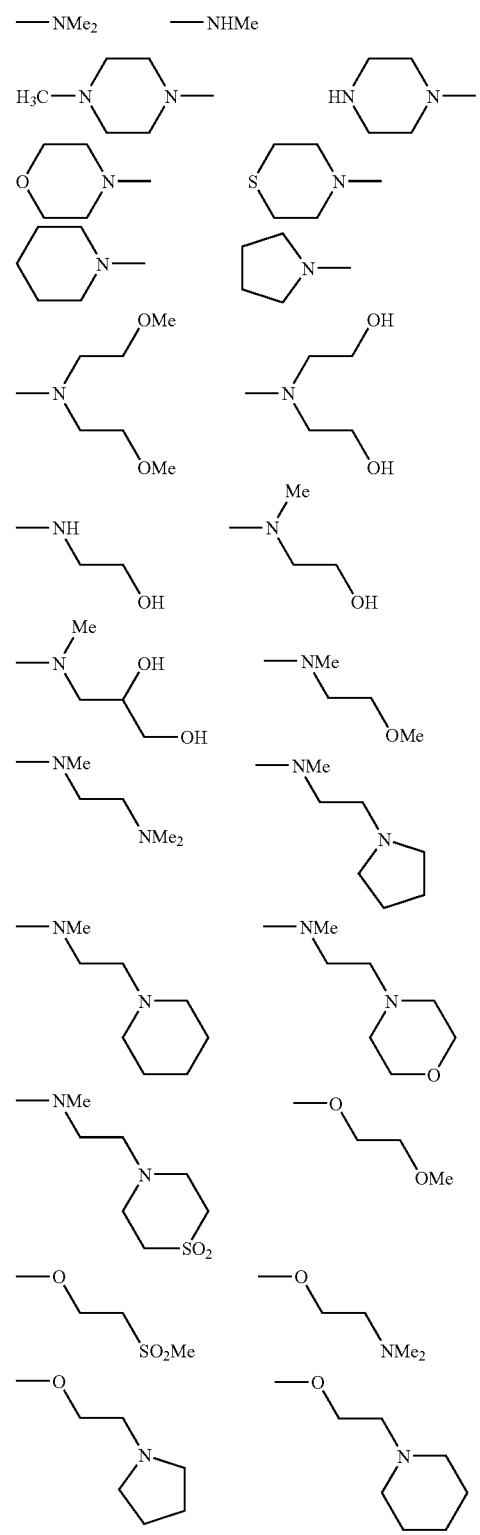

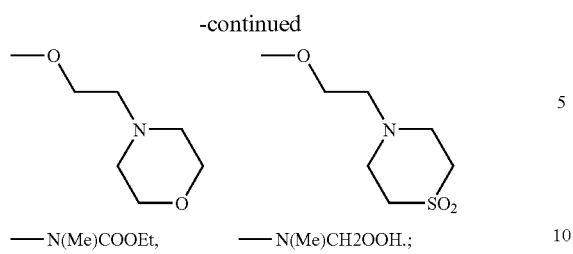

—N(Me)COOEt, —N(Me)CH2OOH.;

$R^{1e}$ is a member selected from the group of —F, —Cl, —Br, —OH, -Me and —OMe;

A-Q is a member selected from the group consisting of:

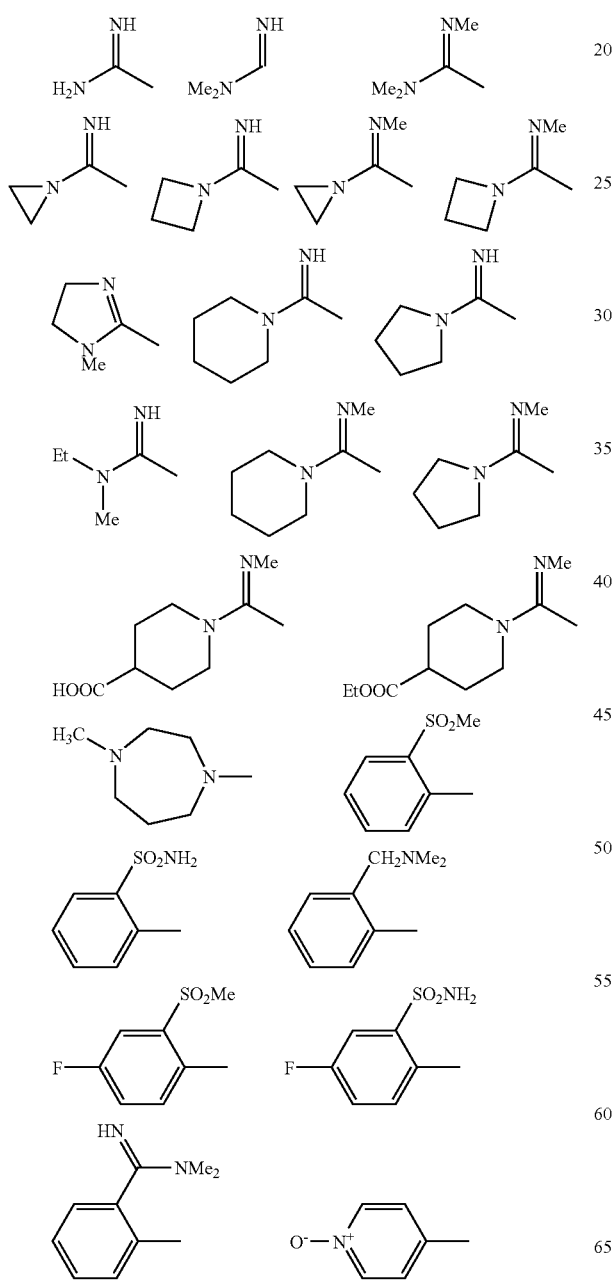

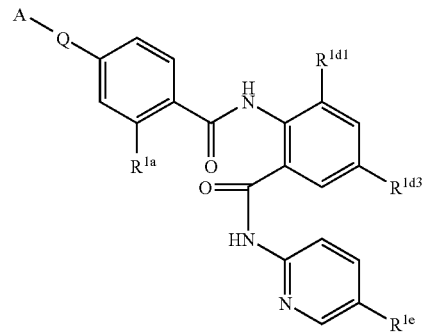

and all pharmaceutically acceptable isomers, salts, hydrates, solvates and prodrug derivatives thereof.

Another preferred embodiment provides a compound of formula VIII having the following structure:

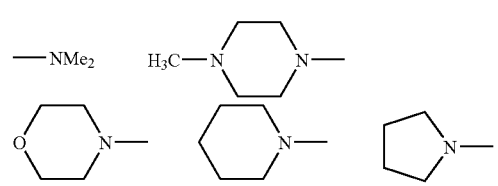

wherein:

$R^{1a}$ is a member selected from the group of H, or —F;

$R^{1d1}$ is each independently a member selected from the group of H, —Cl, —OMe, —NMe$_2$, —OCH$_2$COOEt, —OCH$_2$COOH, —N(Me)CH$_2$COOH, —N(Me)COOEt,

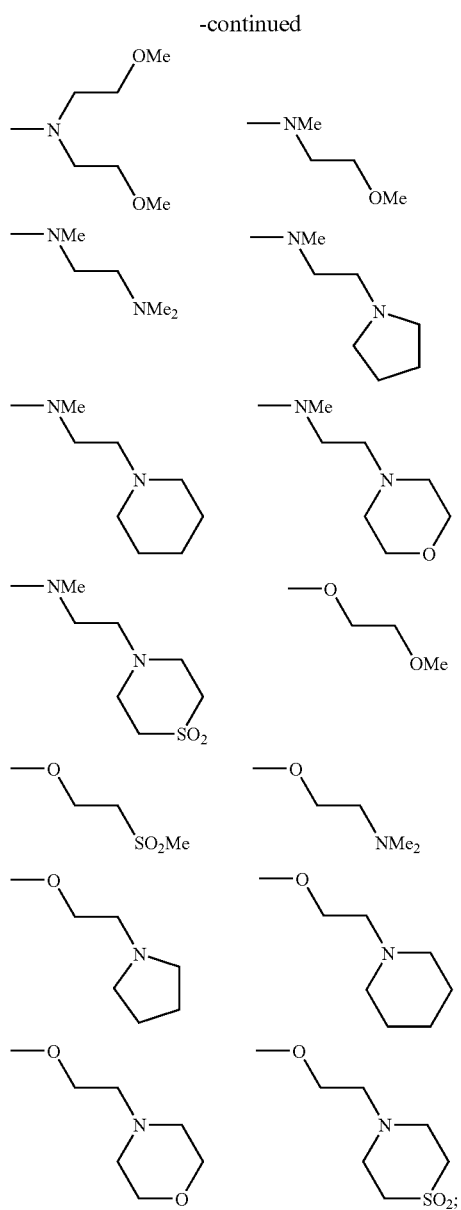

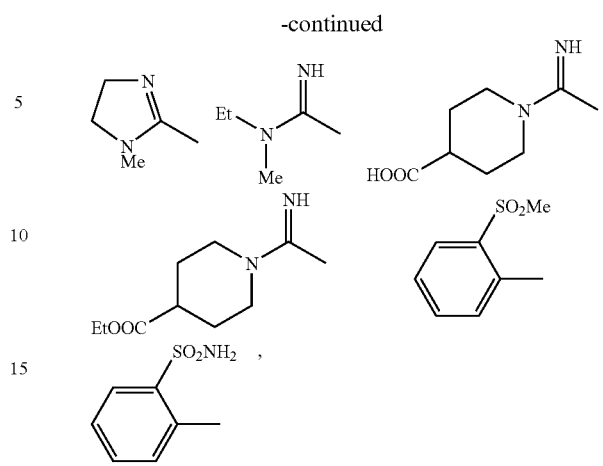

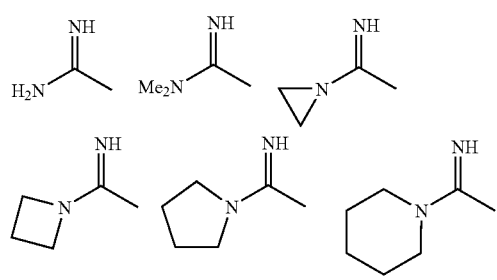

$R^{1d3}$ are independently a member selected from the group of H, —Cl, —Br, —F, and —OMe;

$R^{1e}$ is a member selected from the group of —Cl, and —Br;

A-Q is a member selected from the group consisting of:

and all pharmaceutically acceptable isomers, salts, hydrates, solvates and prodrug derivatives thereof.

Another preferred embodiment according to the present invention provides an individual compound, which is a member selected from the following structures:

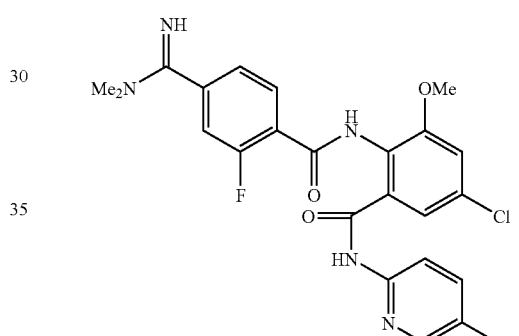

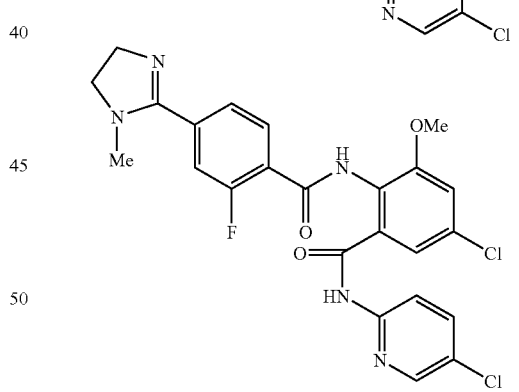

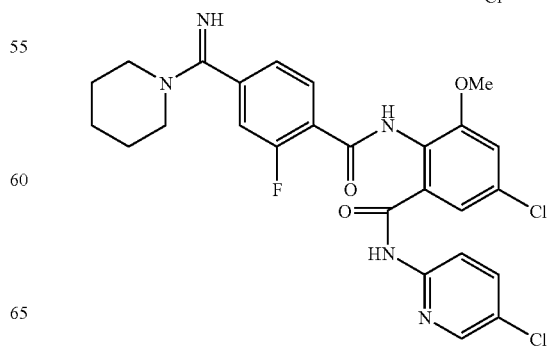

201
-continued
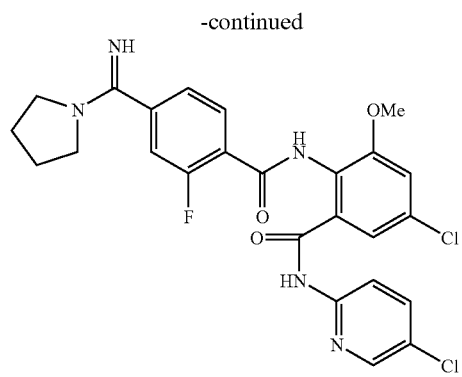
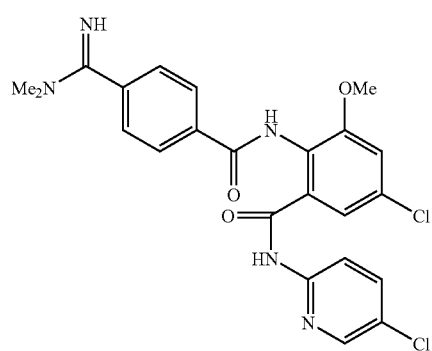
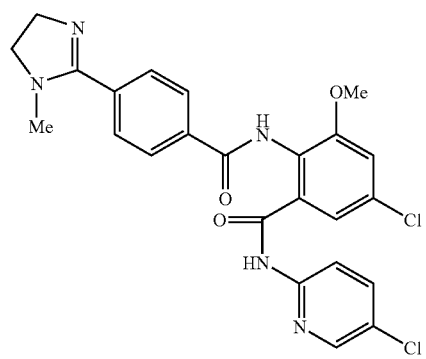
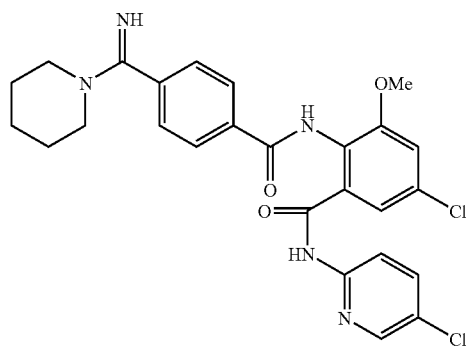
202
-continued
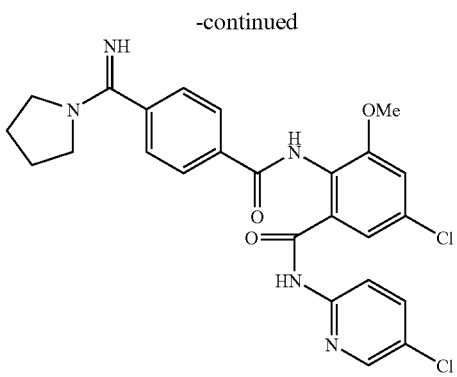
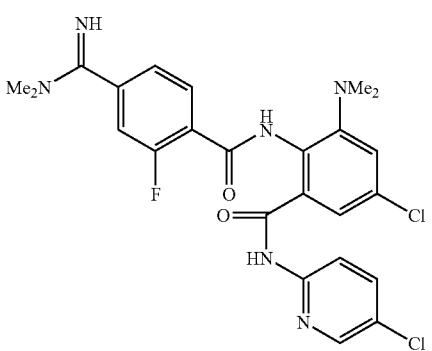
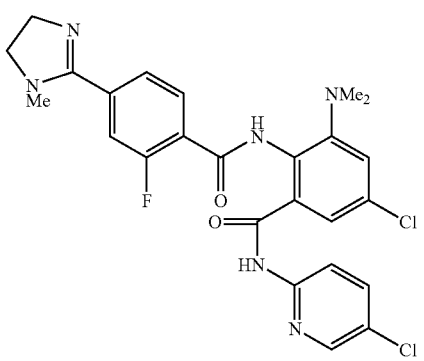
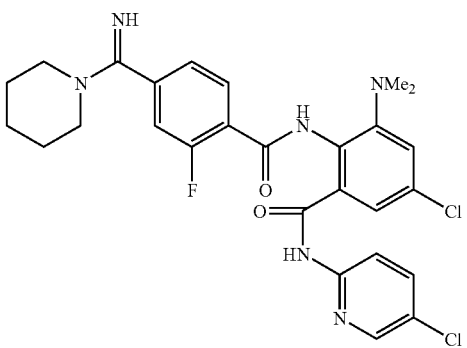

203
-continued
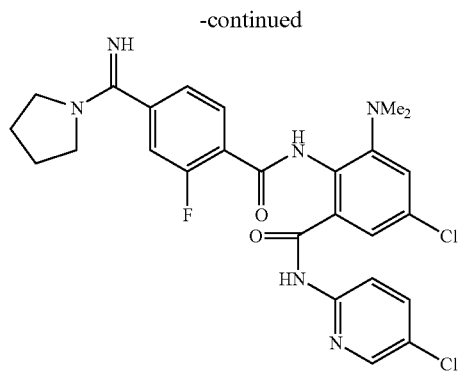
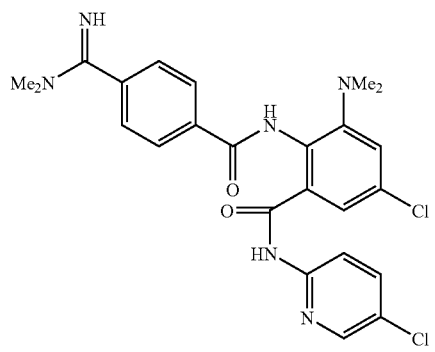
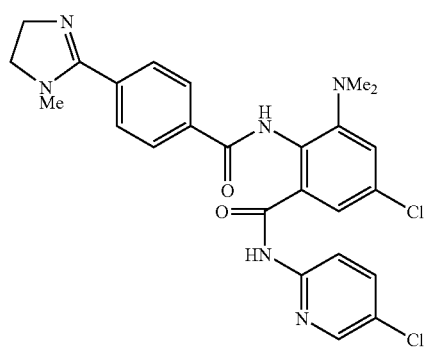
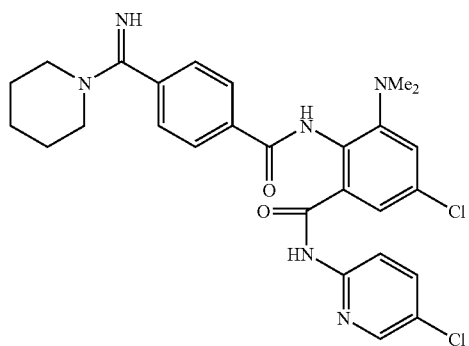
204
-continued
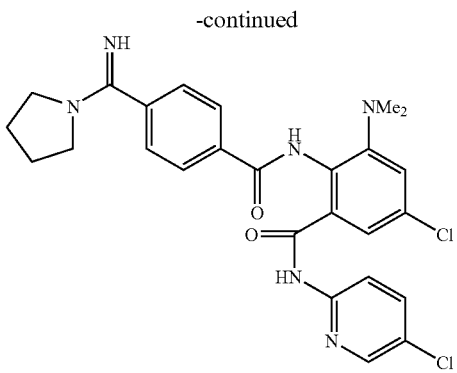
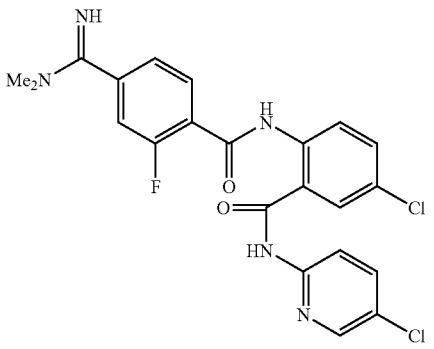
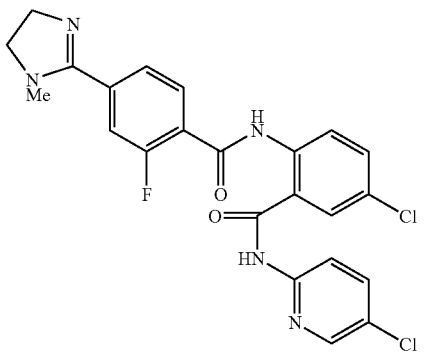
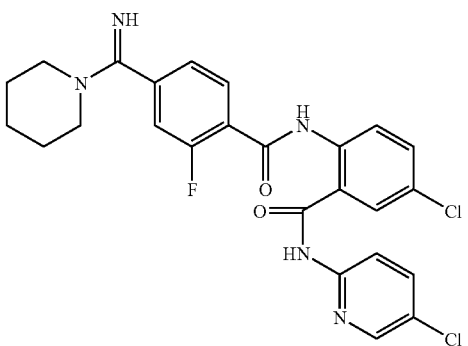

-continued
205
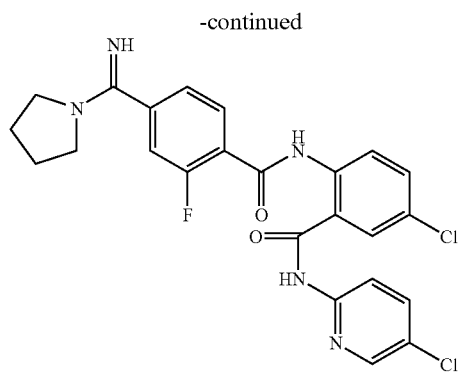
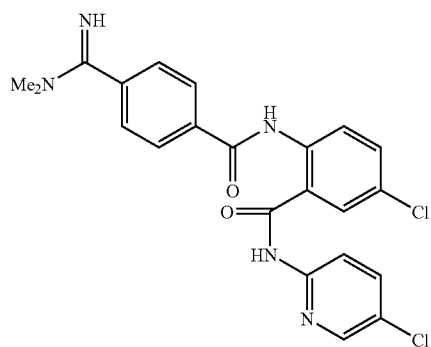
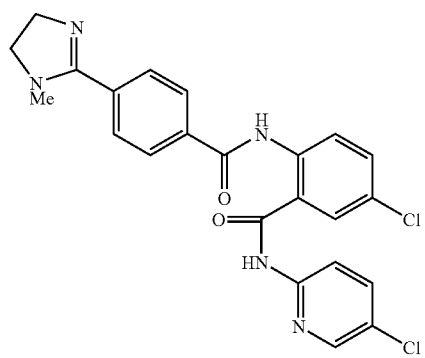
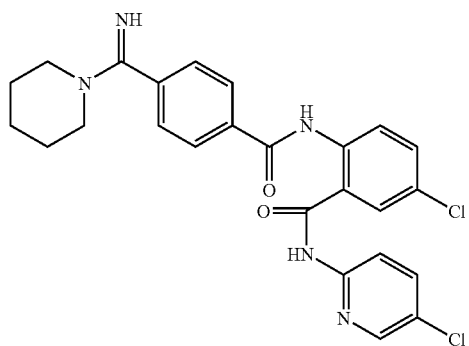
206
-continued
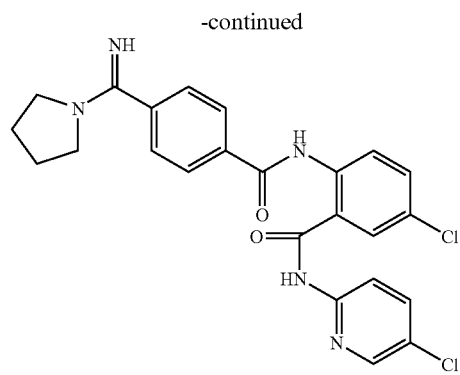
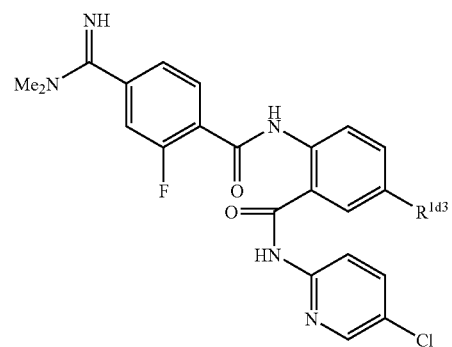
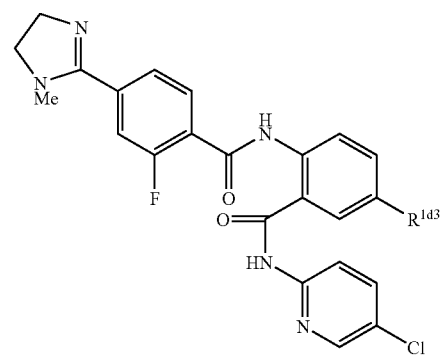
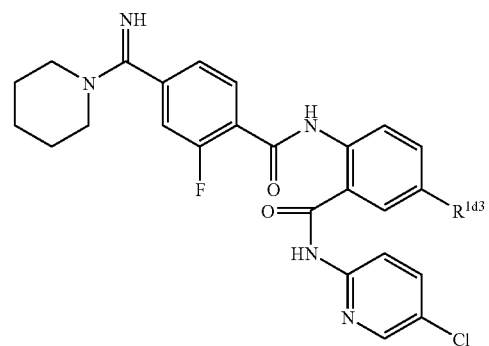

-continued

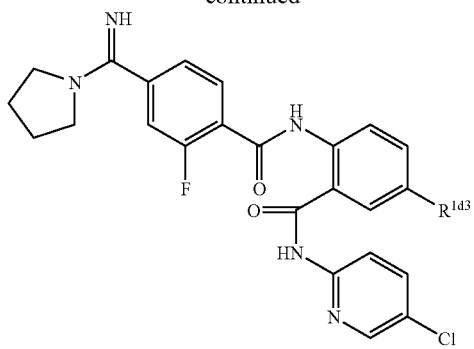

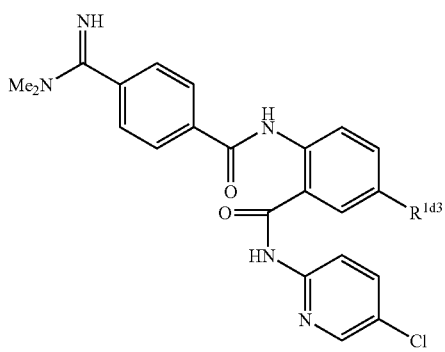

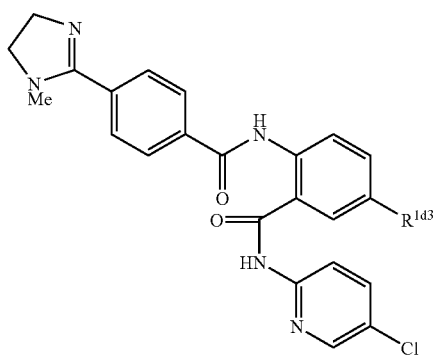

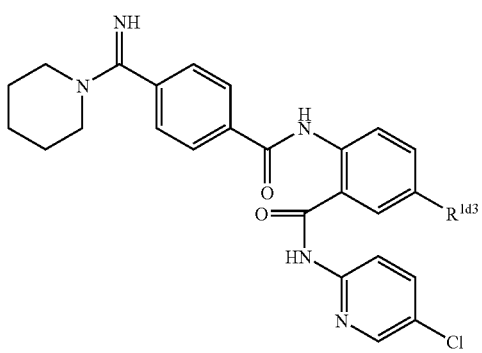

-continued

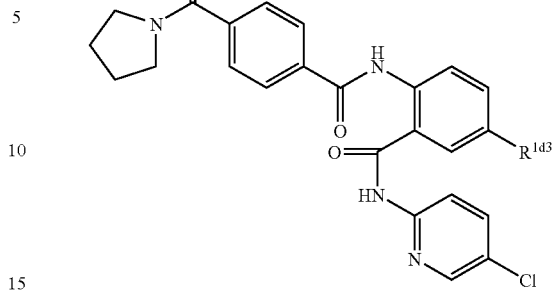

wherein
$R^{1d3}$ is a member selected from the group consisting of:
H, —F, —Cl, —Br, —OMe, —OCF$_3$, —OCF$_2$H, and —OCF$_2$H;

and all pharmaceutically acceptable isomers, salts, hydrates, solvates and prodrug derivatives thereof.

A still further embodiment of the present invention provides a compound according to the formula IX, as follow:

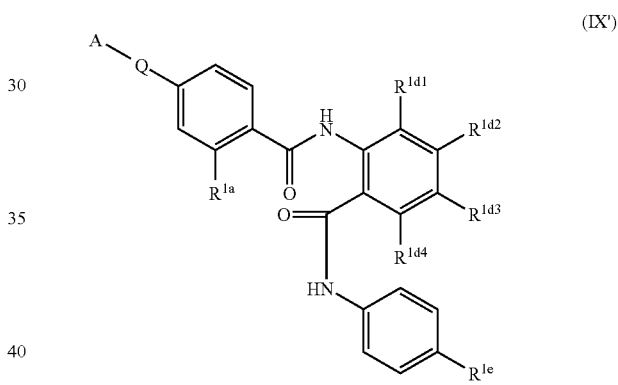

(IX')

wherein:
$R^{1a}$ is a member selected from the group of H, —F, —Cl and Br;
$R^{1d2}$ and $R^{1d4}$ are each H or RF;
$R^{1d1}$ and $R^{1d3}$ are each independently a member selected from the group of H, —Cl, —F, —Br, —OH, —OMe, —OCF$_3$, OCHF$_2$, OCH$_2$F, —NH$_2$, —NMe$_2$, —OCH$_2$COOEt, —OCH$_2$COOH, —N(Me)CH$_2$COOH, —N(Me)COOEt,

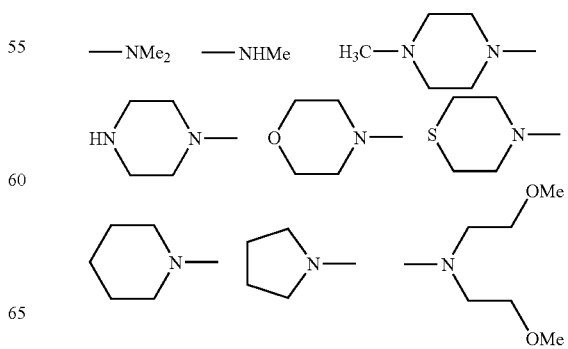

-continued
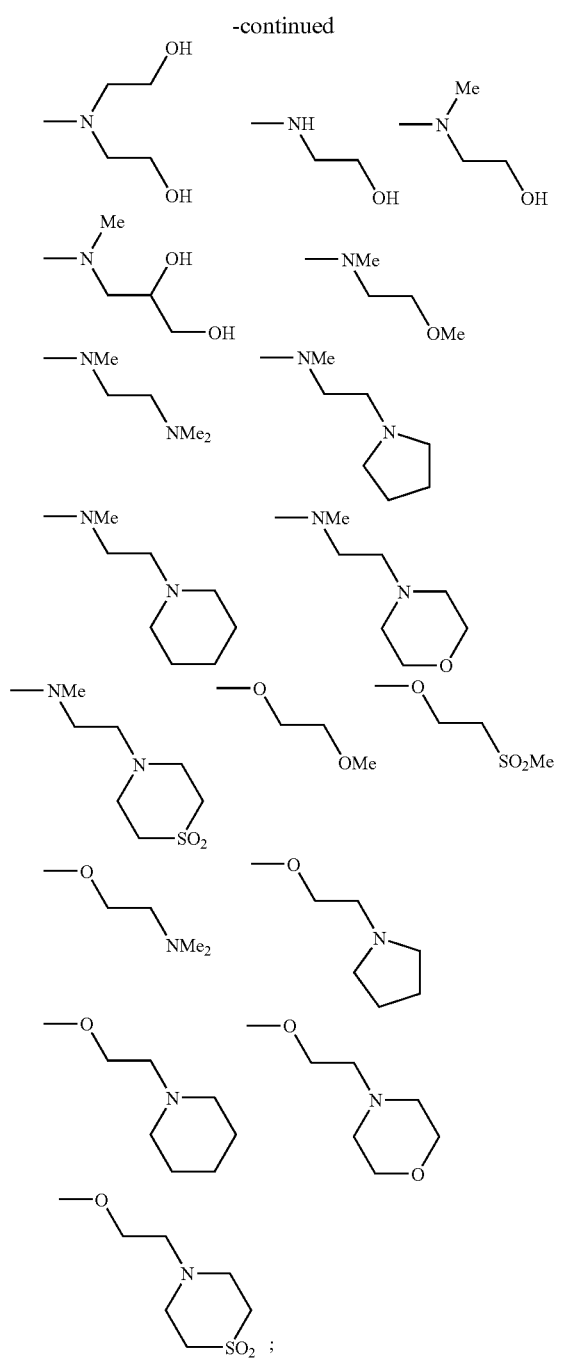
$R^{1e}$ is a member selected from the group of —F, —Cl, —Br, —OH, -Me and —OMe;
A-Q is a member selected from the group consisting of:
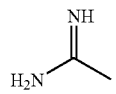 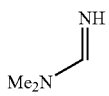 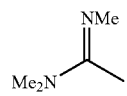
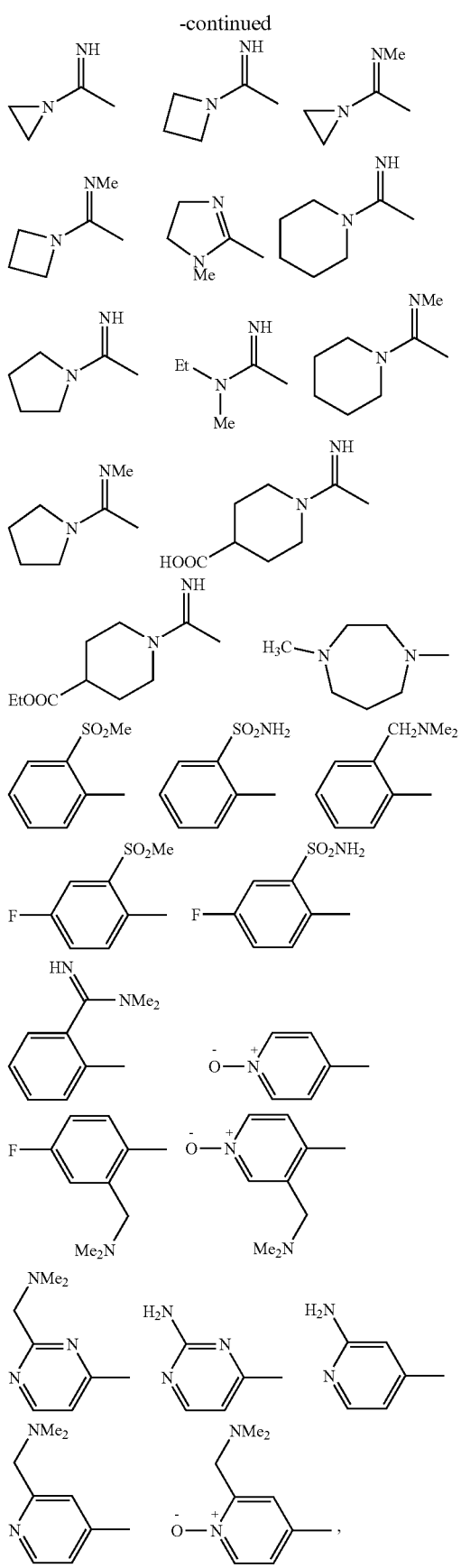

and all pharmaceutically acceptable isomers, salts, hydrates, solvates and prodrug derivatives thereof.

A particularly preferred embodiment of the present invention provides such compounds having the following formula:

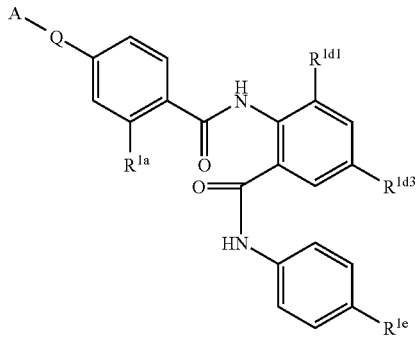

wherein:
R$^{1a}$ is a member selected from the group of H, or —F
R$^{1d1}$ is each independently a member selected from the group of H, —Cl, —OMe, —NMe$_2$, —OCH$_2$COOEt, —OCH$_2$COOH, —N(Me)CH$_2$COOH, —N(Me)COOEt, and,

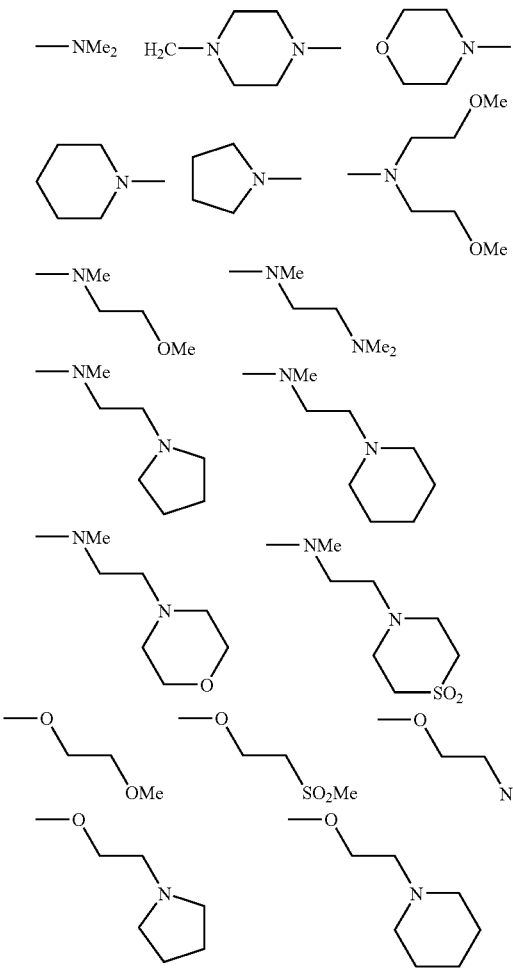

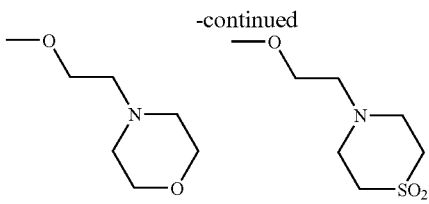

R$^{1d3}$ are independently a member selected from the group of H, —Cl, —Br, —F, and —OMe,
R$^{1e}$ is a member selected from the group of —Cl, and —Br,
A-Q is a member selected from the group consisting of:

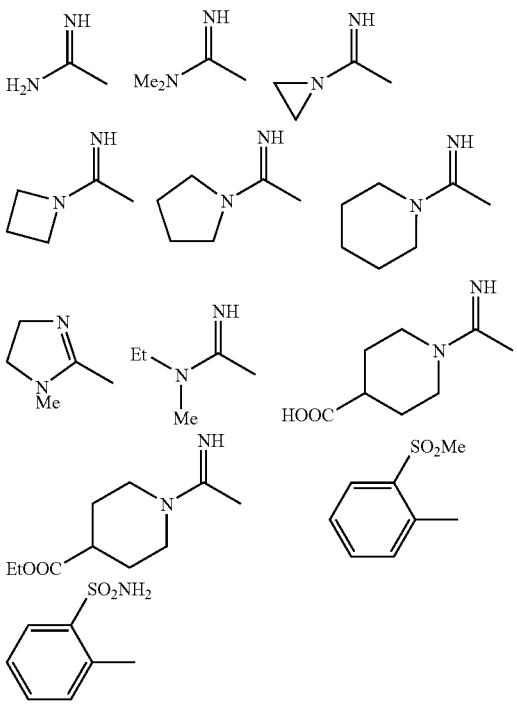

and all pharmaceutically acceptable isomers, salts, hydrates, solvates and prodrug derivatives thereof.

A still further embodiment of the present invention provides an individual compound which is a member selected from the following structures:

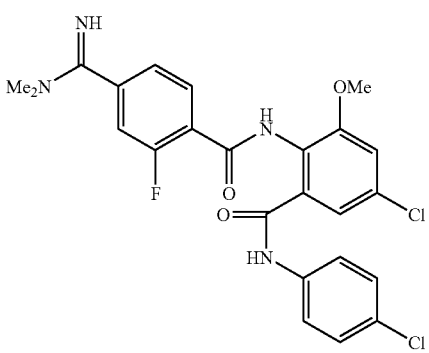

213
-continued
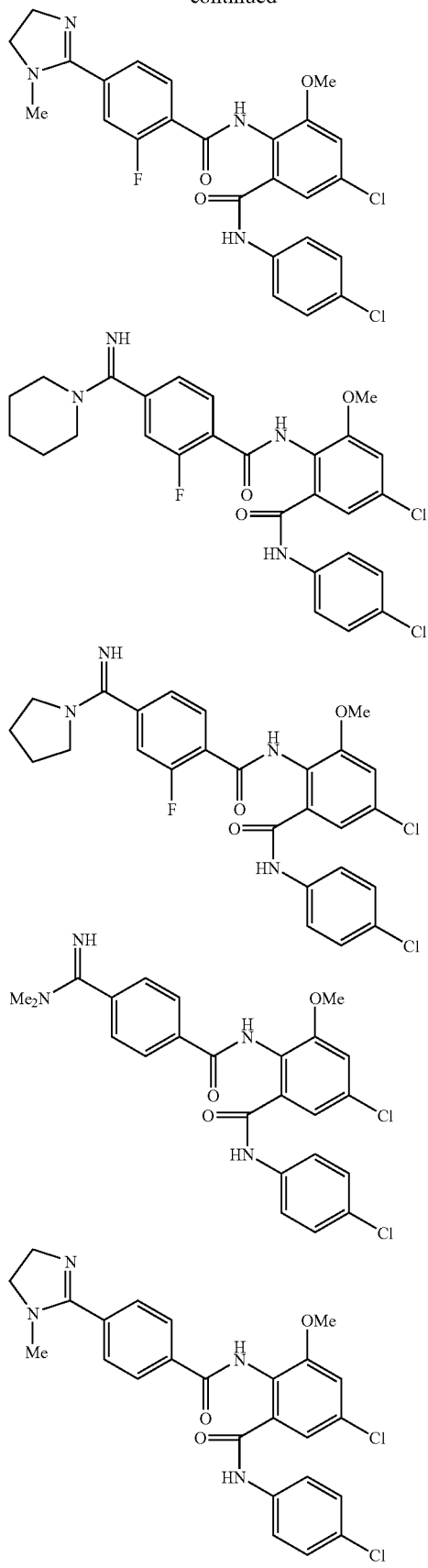
214
-continued
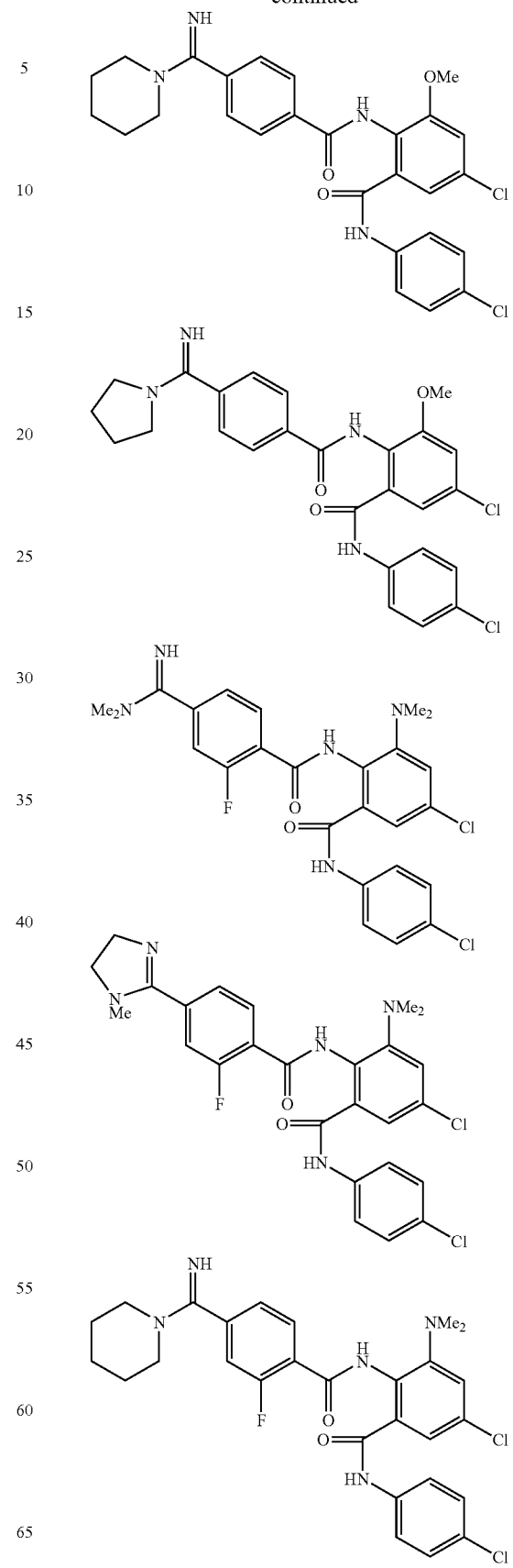

-continued
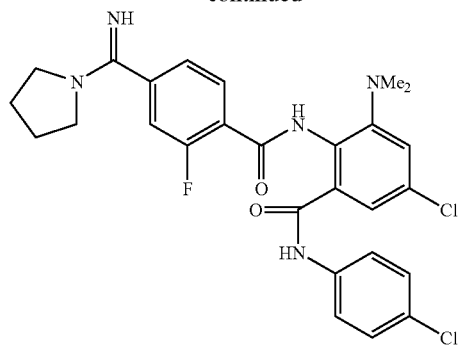
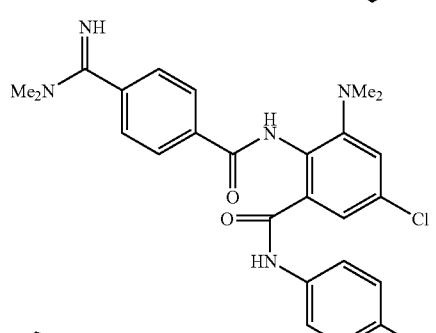
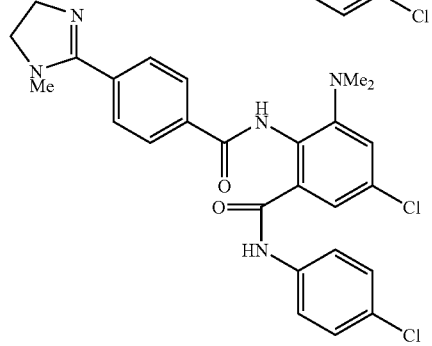
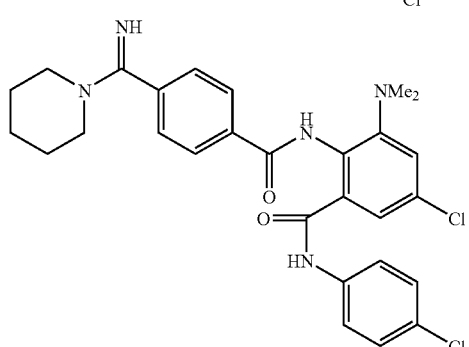
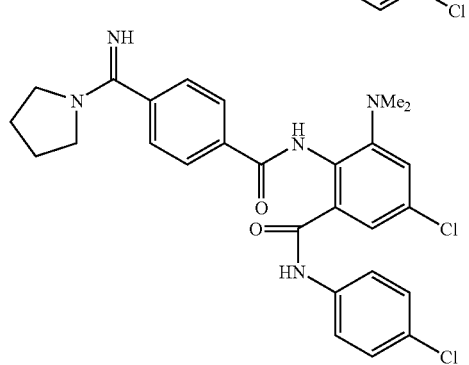
-continued
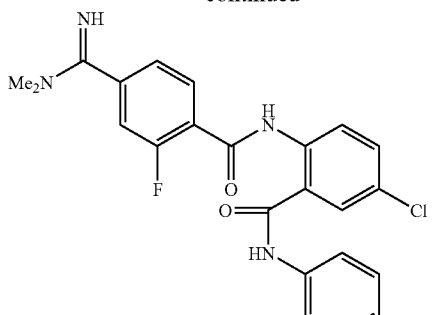
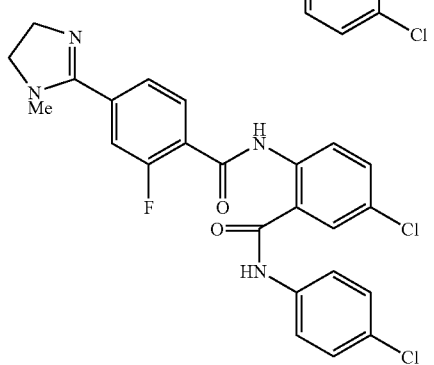
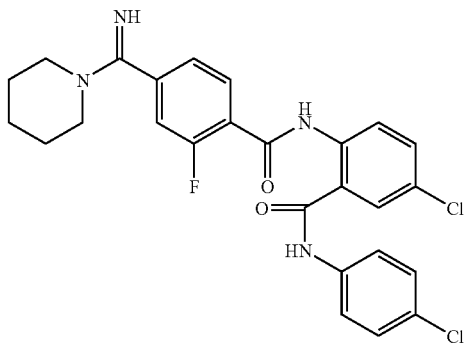
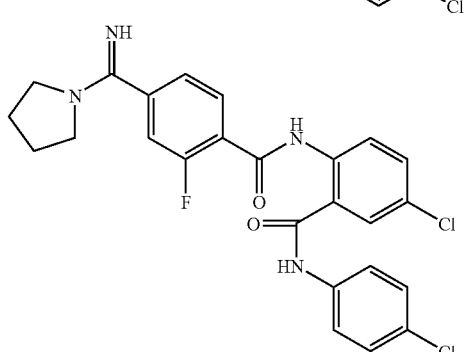
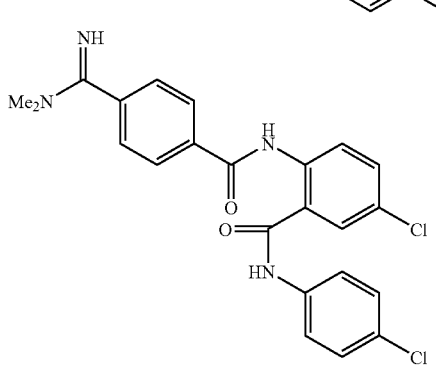

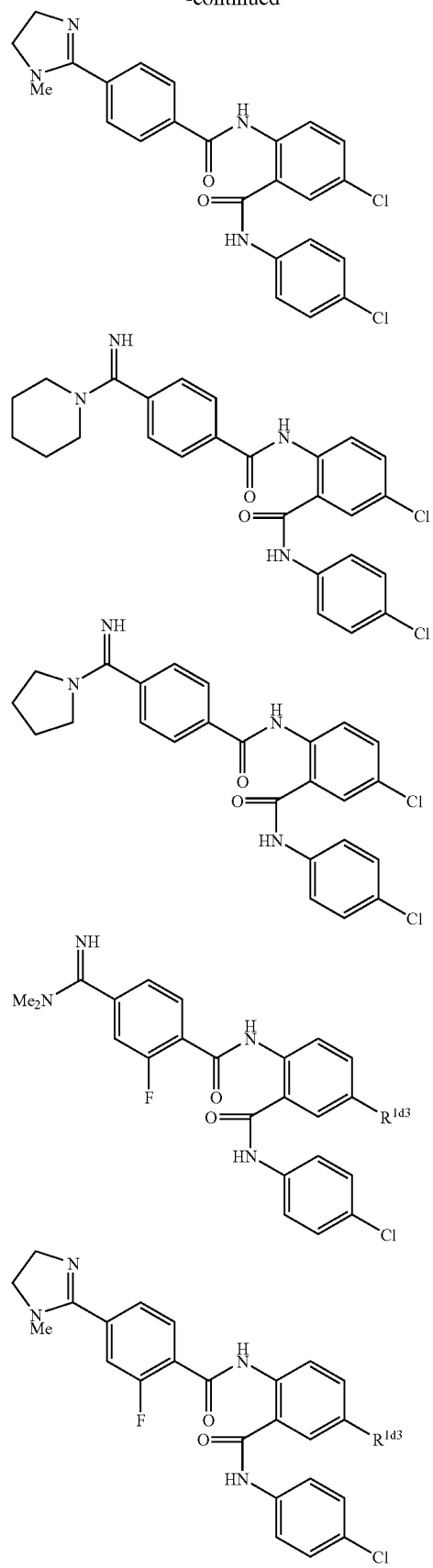
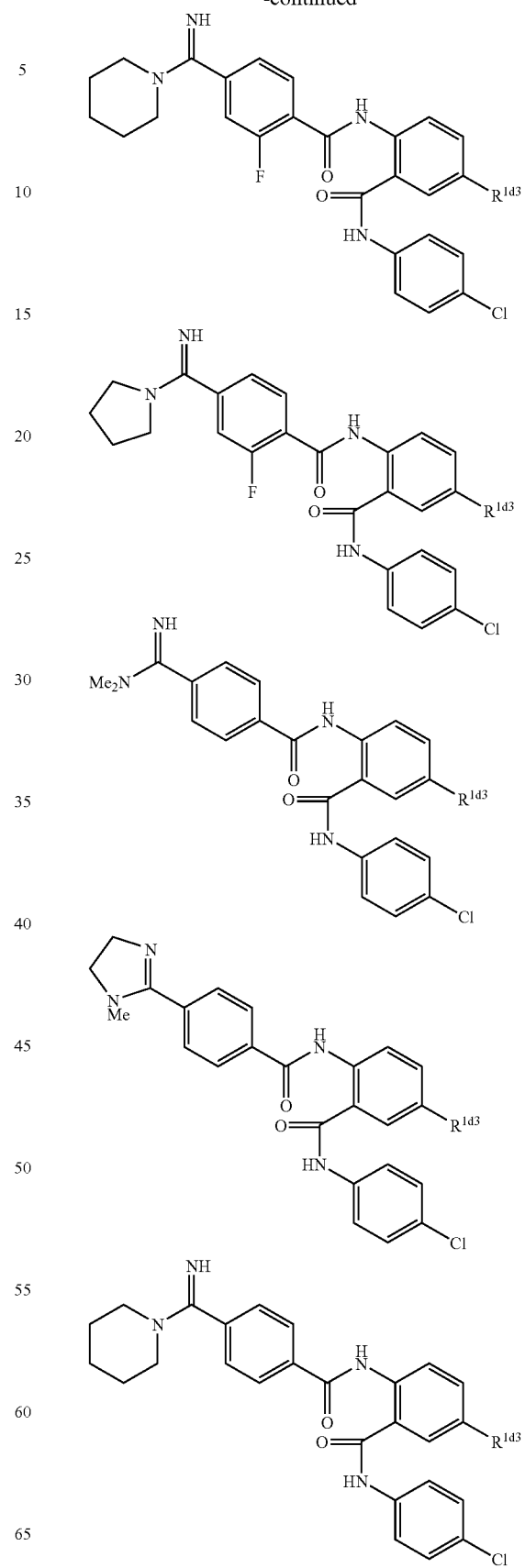

-continued

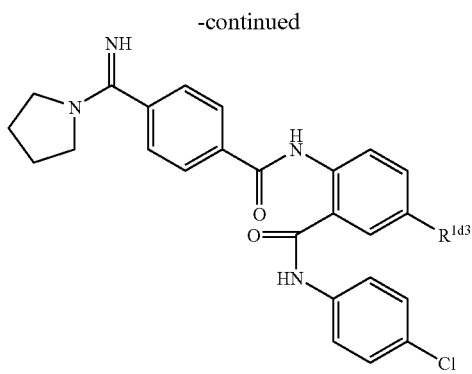

wherein
R$^{1d3}$ is a member selected from the group consisting of:
H, —F, —Cl, —Br, —OMe, —OCF3, —OCF$_2$H, and —OCF$_2$H, and all pharmaceutically acceptable isomers, salts, hydrates, solvates and prodrug derivatives thereof.

Another preferred embodiment of the present invention provides compounds according to the invention as illustrated herein, wherein the A-Q- substituent is an amidinosubstituent, the amine portion of which is a cyclized amine heterocyclic ring, preferably a saturated cyclized amine heterocyclic ring, and the cyclized amine ring is substituted by 1-3 members. Examples of such A-Q substituents include but are not limited to:

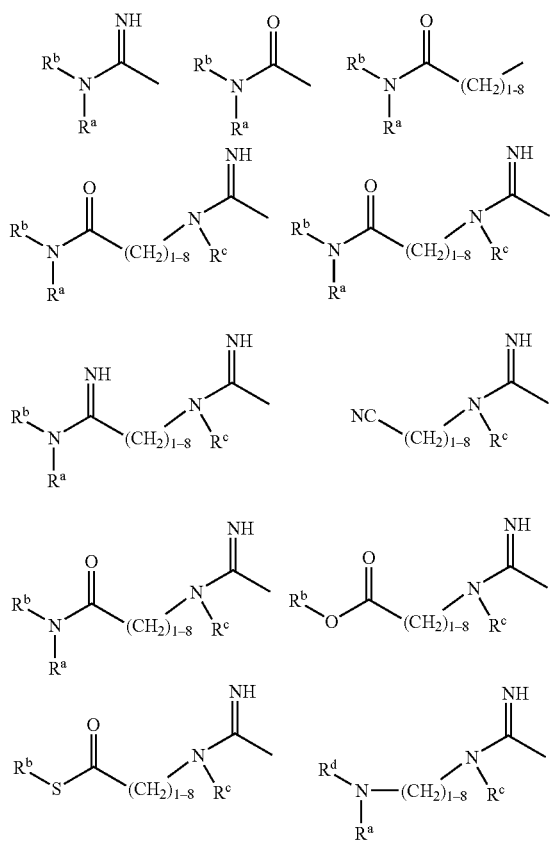

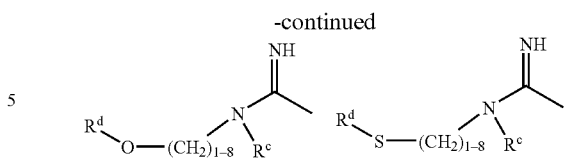

wherein each of R$^a$, R$^b$, R$^c$, R$^d$ and R$^e$ is independently a member selected from the group consisting of C$_1$-C$_8$ alkyl, C$_2$-C$_8$ alkenyl, C$_1$-C$_8$ acyl and C$_1$-C$_8$ acyl C$_1$-C$_8$ alkyl ester, and the R$^a$ and R$^b$ groups together with the nitrogen atom to which they are both attached may be cyclized to form a C$_3$-C$_9$ heterocylic ring having from 1 to 4 additional hetero ring atoms selected from O, N and S, and all pharmaceutically acceptable isomers, salts, hydrates, solvates and prodrug derivatives thereof.

Another preferred embodiment is an embodiment wherein the amidino groups illustrated above as substituents for the cyclized amine heterocyclic ring are instead form an acyclic amidino A-Q group and and all pharmaceutically acceptable isomers, salts, hydrates, solvates and prodrug derivatives thereof.

Such compounds are formed by reacting the appropriate acyclic amine or cyclicsed amine with an amidino group or with a thioimino group wherein the remainder of the structures D-E-G-J-X are defined as in formula I or as in a preferred D-E-G-J-X structure illustrated in a preferred embodiment herein. Other ways to produce such compound structures will be apparent to an ordinary praticitioner in this field upon consideration of the description herein and the illustrated preferred embodiments.

This invention also encompasses all pharmaceutically acceptable isomers, salts, hydrates, solvates, and prodrug derivatives of the preferred compounds. In addition, the preferred compounds can exist in various isomeric and tautomeric forms, and all such forms are meant to be included in the invention, along with pharmaceutically acceptable salts, hydrates, solvates, and prodrug derivatives of such isomers and tautomers.

The compounds of this invention may be isolated as the free acid or base or converted to salts of various inorganic and organic acids and bases. Such salts are within the scope of this invention. Non-toxic and physiologically compatible salts are particularly useful although other less desirable salts may have use in the processes of isolation and purification.

A number of methods are useful for the preparation of the salts described above and are known to those skilled in the art. For example, the free acid or free base form of a compound of one of the formulas above can be reacted with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

Prodrug Derivatives of Compounds

This invention also encompasses prodrug derivatives of the compounds contained herein. The term "prodrug" refers to a pharmacologically inactive derivative of a parent drug molecule that requires biotransformation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active ill vivo, when they undergo solvolysis under physiological conditions or undergo enzymatic degradation. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, Design of Prodrugs, pp. 7-9, 21-24, Elsevier, Amsterdam 1985 and Silverman, The Organic Chemistry of Drug Design and Drug Action, pp. 352-401, Academic Press, San Diego, Calif., 1992). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability.

As mentioned above, the compounds of this invention find utility as therapeutic agents for disease states in mammals which have disorders of coagulation such as in the treatment or prevention of unstable angina, refractory angina, myocardial infarction, transient ischemic attacks, thrombotic stroke, embolic stroke, disseminated intravascular coagulation including the treatment of septic shock, deep venous thrombosis in the prevention of pulmonary embolism or the treatment of reocclusion or restenosis of reperfused coronary arteries. Further, these compounds are useful for the treatment or prophylaxis of those diseases which involve the production and/or action of factor Xa/prothrombinase complex. This includes a number of thrombotic and prothrombotic states in which the coagulation cascade is activated which include but are not limited to, deep venous thrombosis, pulmonary embolism, myocardial infarction, stroke, thromboembolic complications of surgery and peripheral arterial occlusion.

Accordingly, a method for preventing or treating a condition in a mammal characterized by undesired thrombosis comprises administering to the mammal a therapeutically effective amount of a compound of this invention. In addition to the disease states noted above, other diseases treatable or preventable by the administration of compounds of this invention include, without limitation, occlusive coronary thrombus formation resulting from either thrombolytic therapy or percutaneous transluminal coronary angioplasty, thrombus formation in the venous vasculature, disseminated intravascular coagulopathy, a condition wherein there is rapid consumption of coagulation factors and systemic coagulation which results in the formation of life-threatening thrombi occurring throughout the microvasculature leading to widespread organ failure, hemorrhagic stroke, renal dialysis, blood oxygenation, and cardiac catheterization.

The compounds of the invention also find utility in a method for inhibiting the coagulation biological samples, which comprises the administration of a compound of the invention.

The compounds of the present invention may also be used in combination with other therapeutic or diagnostic agents. In certain preferred embodiments, the compounds of this invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of the present invention may act in a synergistic fashion to prevent reocclusion following a successful thrombolytic therapy and/or reduce the time to reperfusion. These compounds may also allow for reduced doses of the thrombolytic agents to be used and therefore minimize potential hemorrhagic side effects. The compounds of this invention can be utilized in vivo, ordinarily in mammals such as primates, (e.g. humans), sheep, horses, cattle, pigs, dogs, cats, rats and mice, or in vitro.

The biological properties of the compounds of the present invention can be readily characterized by methods that are well known in the art, for example by the ill vitro protease activity assays and in vivo studies to evaluate antithrombotic efficacy, and effects on hemostasis and hematological parameters, such as are illustrated in the examples.

Diagnostic applications of the compounds of this invention will typically utilize formulations in the form of solutions or suspensions. In the management of thrombotic disorders the compounds of this invention may be utilized in compositions such as tablets, capsules or elixirs for oral administration, suppositories, sterile solutions or suspensions or injectable administration, and the like, or incorporated into shaped articles. Subjects in need of treatment (typically mammalian) using the compounds of this invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be 3-11, more preferably 5-9 and most preferably 7-8. It will be understood that use of certain of the foregoing excipients, carriers, or stabilizers will result in the formation of cyclic polypeptide salts. While the preferred route of administration is by injection, other methods of administration are also anticipated such as orally, intravenously (bolus and/or infusion), subcutaneously, intramuscularly, colonically, rectally, nasally transdermally or intraperitoneally, employing a variety of dosage forms such as suppositories, implanted pellets or small cylinders, aerosols, oral dosage formulations and topical formulations such as ointments, drops and dermal patches. The compounds of this invention are desirably incorporated into shaped articles such as implants which may employ inert materials such as biodegradable polymers or synthetic silicones, for example, Silastic, silicone rubber or other polymers commercially available.

The compounds of the invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds of this invention may also be delivered by the use of antibodies, antibody fragments, growth factors, hormones, or other targeting moieties, to which the compound molecules are coupled. The compounds of this invention may also be coupled with suitable polymers as targetable drug carriers. Such polymers can include polyvinylpyrrolidinone, pyran copolymer, polyhydroxy-propyl-methacrylamide-phenol, polyhydroxyethyl-aspartamide-phenol, or polyethyleneoxide-polylysine substituted with palmitoyl residues. Furthermore, compounds of the invention may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound of the present invention, individual determinations may be made to determine the optimal dosage required. The range of therapeutically effective dosages will be influenced by the route of administration, the therapeutic objectives and the condition of the patient. For injection by hypodermic needle, it may be assumed the dosage is delivered into the body's fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be readily determined by one skilled in the art. Typically, applications of compound are commenced at lower dosage levels, with dosage levels being increased until the desired effect is achieved.

The compounds of the invention can be administered orally or parenterally in an effective amount within the dosage range of about 0.1 to 100 mg/kg, preferably about 0.5 to 50 mg/kg and more preferably about 1 to 20 mg/kg on a regimen in a single or 2 to 4 divided daily doses and/or continuous infusion.

Typically, about 5 to 500 mg of a compound or mixture of compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

Preparation of Compounds

The compounds of the present invention may be synthesized by either solid or liquid phase methods described and referenced in standard textbooks or by a combination of both methods. These methods are well known in the art. See, Bodanszky, "The Principles of Peptide Synthesis", Hafner, et al., Eds., Springer-Verlag, Berlin, 1984.

Starting materials used in any of these methods are commercially available from chemical vendors such as Aldrich, Sigma, Nova Biochemicals, Bachem Biosciences, and the like, or may be readily synthesized by known procedures.

Reactions are carried out in standard laboratory glassware and reaction vessels under reaction conditions of standard temperature and pressure, except where otherwise indicated.

During the synthesis of these compounds, the functional groups of the amino acid derivatives used in these methods are protected by blocking groups to prevent cross reaction during the coupling procedure. Examples of suitable blocking groups and their use are described in "The Peptides: Analysis, Synthesis, Biology", Academic Press, Vol. 3 (Gross, et al., Eds., 1981) and Vol. 9 (1987), the disclosures of which are incorporated herein by reference.

Compounds according to the invention can be synthesized utilizing procedures well known in the art. The reaction products are isolated and purified by conventional methods, typically by solvent extraction into a compatible solvent. The products may be further purified by column chromatography or other appropriate methods.

Compositions and Formulations

The compounds of this invention may be isolated as the free acid or base or converted to salts of various inorganic and organic acids and bases. Such salts are within the scope of this invention. Non-toxic and physiologically compatible salts are particularly useful although other less desirable salts may have use in the processes of isolation and purification.

A number of methods are useful for the preparation of the salts described above and are known to those skilled in the art. For example, reaction of the free acid or free base form of a compound of the structures recited above with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt or one salt from of the product may be converted to another using the same general process.

Diagnostic applications of the compounds of this invention will typically utilize formulations such as solution or suspension. In the management of thrombotic disorders the compounds of this invention may be utilized in compositions such as tablets, capsules or elixirs for oral administration, suppositories, sterile Solutions or suspensions or injectable administration, and the like, or incorporated into shaped articles. Subjects in need of treatment (typically mammalian) using the compounds of this invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in *Remington's Pharmaceutical Sciences*, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinalpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be between 3 and 11, more preferably from 5 to 9 and most preferably from 7 to 8. It will be understood that use of certain of the foregoing excipients, carriers, or stabilizers will result in the formation of cyclic polypeptide salts. While the preferred route of administration is by injection, other methods of administration are also anticipated such as intravenously (bolus and/or infusion), subcutaneously, intramuscularly, colonically, rectally, nasally or intraperitoneally, employing a variety of dosage forms such as suppositories, implanted pellets or small cylinders, aerosols, oral dosage formulations and topical formulations such as ointments, drops and dermal patches. The compounds of this invention are desirably incorporated into shaped articles such as implants which may employ inert materials such as biodegradable polymers or synthetic silicones, for example, Silastic, silicone rubber or other polymers commercially available.

The compounds of this invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds of this invention may also be delivered by the use of antibodies, antibody fragments, growth factors, hormones, or other targeting moieties, to which the compound molecules are coupled. The compounds of this invention may also be coupled with suitable polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the factor Xa inhibitors of this invention may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound of the present invention, individual determinations may be made to determine the optimal dosage required. The range of therapeutically effective dosages will naturally be influenced by the route of administration, the therapeutic objectives, and the condition of the patient. For injection by hypodermic needle, it may be assumed the dosage is delivered into the body's fluids. For other routes of administration, the absorption efficiency must be individually determined for each inhibitor by, methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved.

A typical dosage might range from about 0.001 mg/kg to about 1000 mg/kg, preferably from about 0.01 mg/kg to about 100 mg/kg, and more preferably from about 0.10 mg/kg to about 20 mg/kg. Advantageously, the compounds of this invention may be administered several times daily, and other dosage regimens may also be useful.

Typically, about 0.5 to 500 mg of a compound or mixture of compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are a binder such as acacia, corn starch or gelatin, and excipient such as microcrystalline cellulose, a disintegrating agent like corn starch or alginic acid, a lubricant such as magnesium stearate, a sweetening agent such as sucrose or lactose, or a flavoring agent. When a dosage form is a capsule, in addition to the above materials it may also contain a liquid carrier such as water, saline, a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

In practicing the methods of this invention, the compounds of this invention may be used alone or in combination, or in combination with other therapeutic or diagnostic agents. In certain preferred embodiments, the compounds of this inventions may be coadministered along with other compounds typically prescribed for these conditions according to generally accepted medical practice, such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of this invention can be utilized in vivo, ordinarily in mammals such as primates, such as humans, sheep, horses, cattle, pigs, dogs, cats, rats and mice, or in vitro.

The preferred compounds of the present invention are characterized by their ability to inhibit thrombus formation with acceptable effects on classical measures of coagulation parameters, platelets and platelet function, and acceptable levels of bleeding complications associated with their use. Conditions characterized by undesired thrombosis would include those involving the arterial and venous vasculature.

With respect to the coronary arterial vasculature, abnormal thrombus formation characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA).

With respect to the venous vasculature, abnormal thrombus formation characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombus formation further characterizes disseminated intravascular coagulopathy commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The compounds of this present invention, selected and used as disclosed herein, are believed to be useful for preventing or treating a condition characterized by undesired thrombosis, such as (a) the treatment or prevention of any thrombotically mediated acute coronary syndrome including myocardial infarction, unstable angina, refractory angina, occlusive coronary thrombus occurring post-thrombolytic therapy or post-coronary angioplasty, (b) the treatment or prevention of any thrombotically mediated cerebrovascular syndrome including embolic stroke, thrombotic stroke or transient ischemic attacks, (c) the treatment or prevention of any thrombotic syndrome occurring in the venous system including deep venous thrombosis or pulmonary embolus occurring either spontaneously or in the setting of malignancy, surgery or trauma, (d) the treatment or prevention of any coagulopathy including disseminated intravascular coagulation (including the setting of septic shock or other infection, surgery, pregnancy, trauma or malignancy and whether associated with multi-organ failure or not), thrombotic thrombocytopenic purpura, thromboangiitis obliterans, or thrombotic disease associated with heparin induced thrombocytopenia, (e) the treatment or prevention of thrombotic complications associated with extracorporeal circulation (e.g. renal dialysis, cardiopulmonary bypass or other oxygenation procedure, plasmapheresis), (f) the treatment or prevention of thrombotic complications associated with instrumentation (e.g. cardiac or other intravascular catheterization, intra-aortic balloon pump, coronary stent or cardiac valve), and (g) those involved with the fitting of prosthetic devices.

Anticoagulant therapy is also useful to prevent coagulation of stored whole blood and to prevent coagulation in other biological samples for testing or storage. Thus the compounds of this invention can be added to or contacted with any medium containing or suspected to contain factor Xa and in which it is desired that blood coagulation be inhibited, e.g., when contacting the mammal's blood with material such as vascular grafts, stents, orthopedic prostheses, cardiac stents, valves and prostheses, extra corporeal circulation systems and the like.

Without further description, it is believed that one of ordinary skill in the art can, using the preceding description and the following illustrative examples, make and utilize the compounds of the present invention and practice the claimed methods.

EXAMPLES

Examples of Chemical Production Process General Reaction Schemes

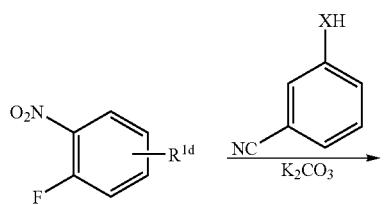

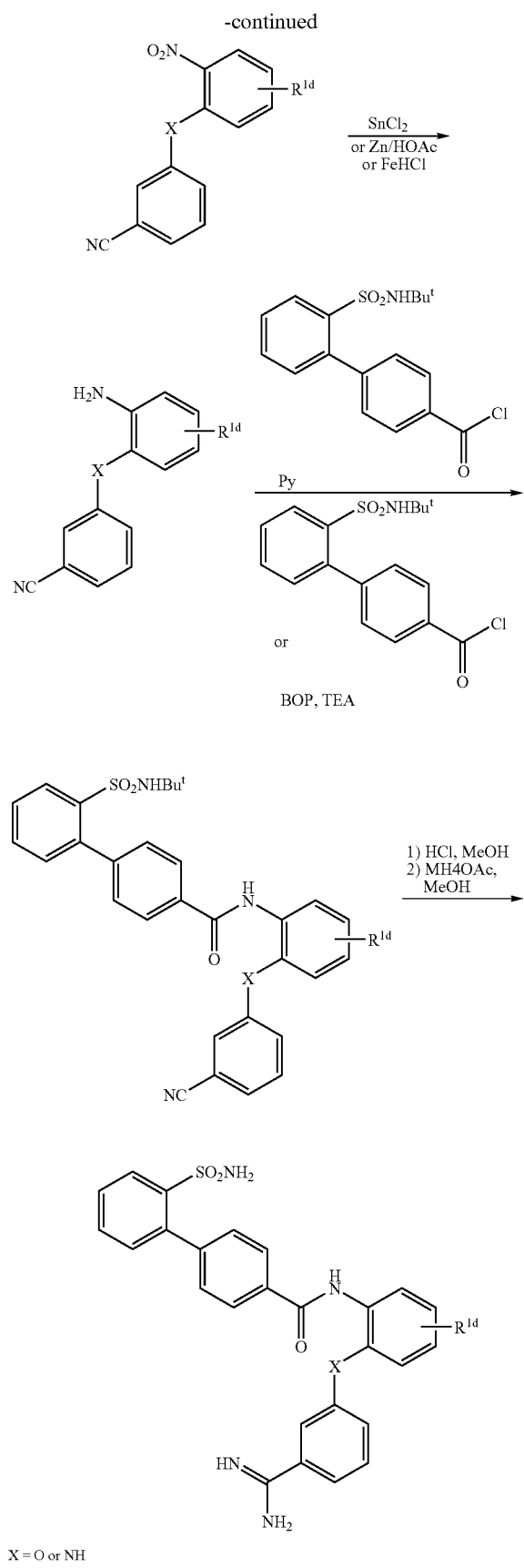
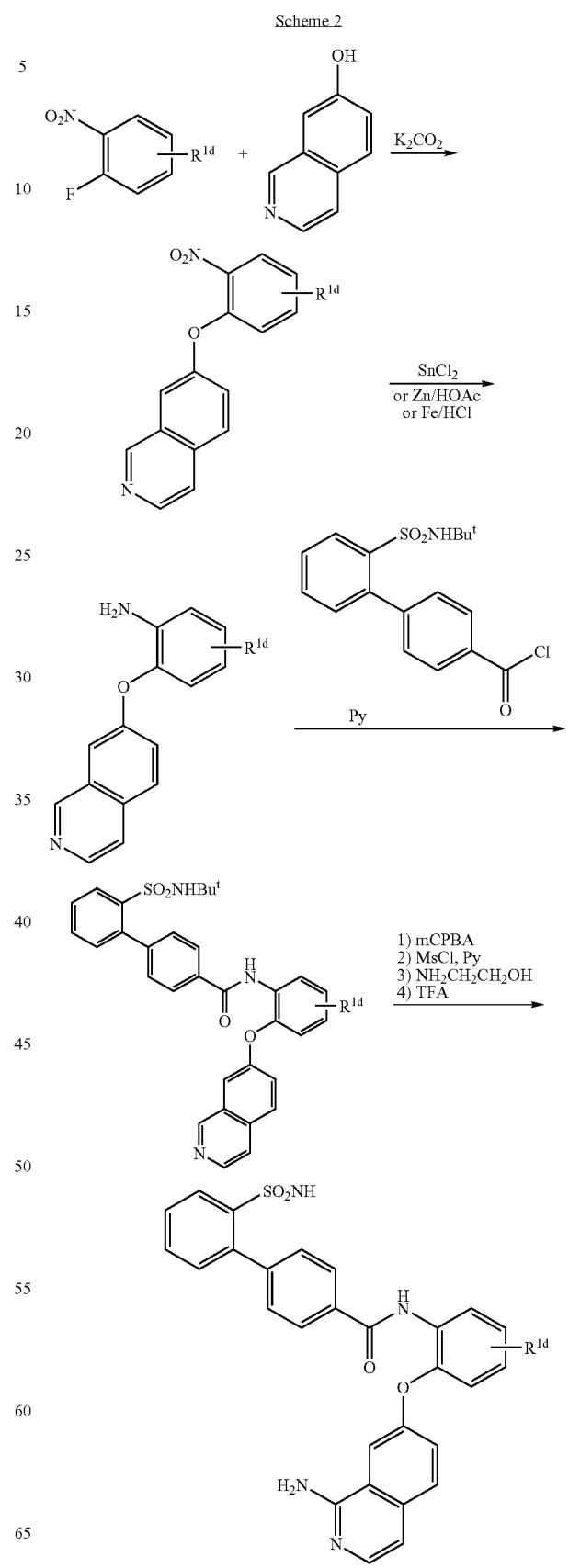

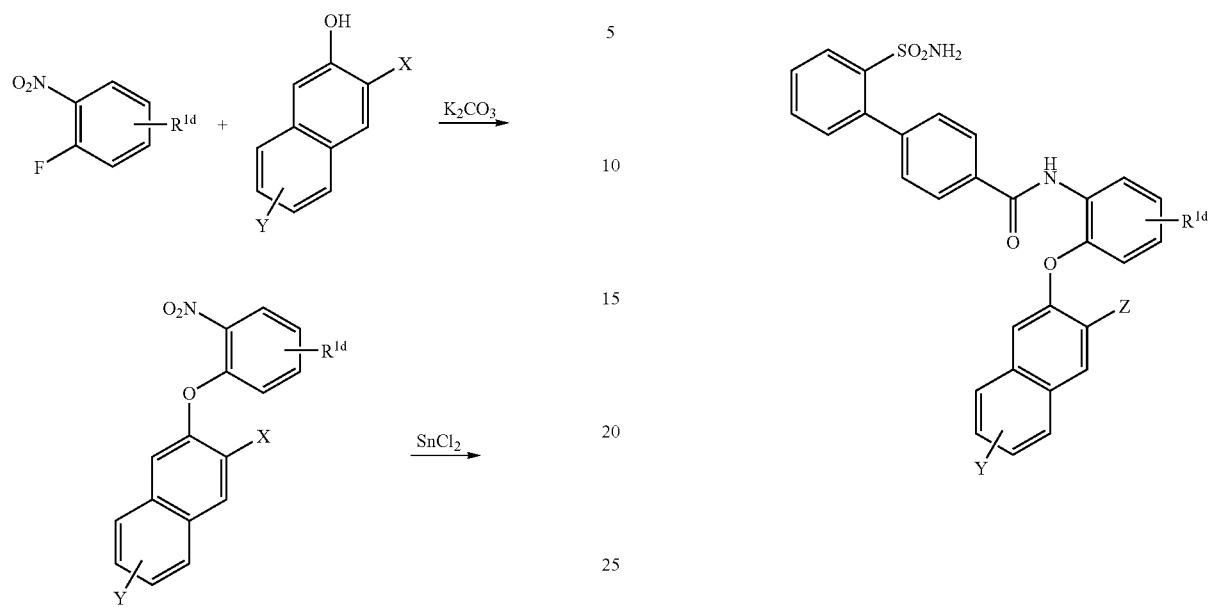
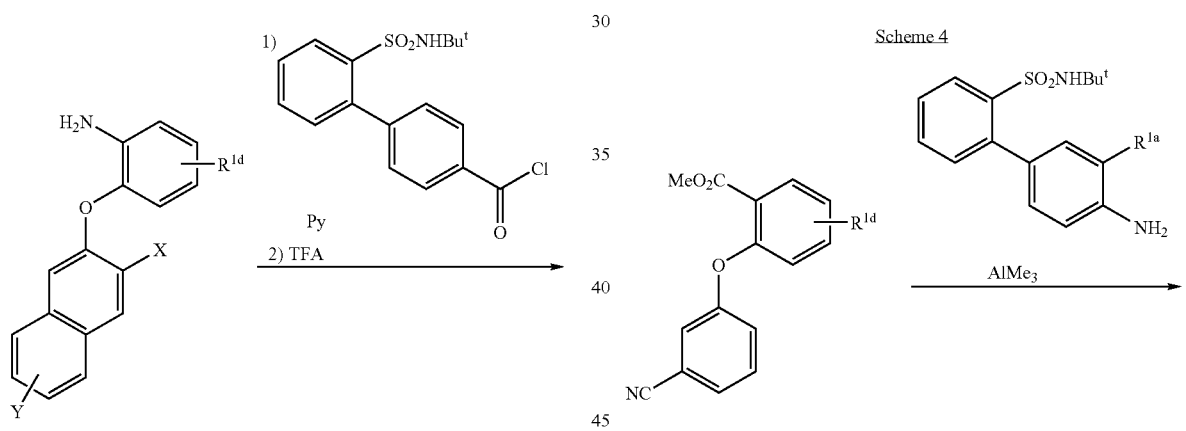
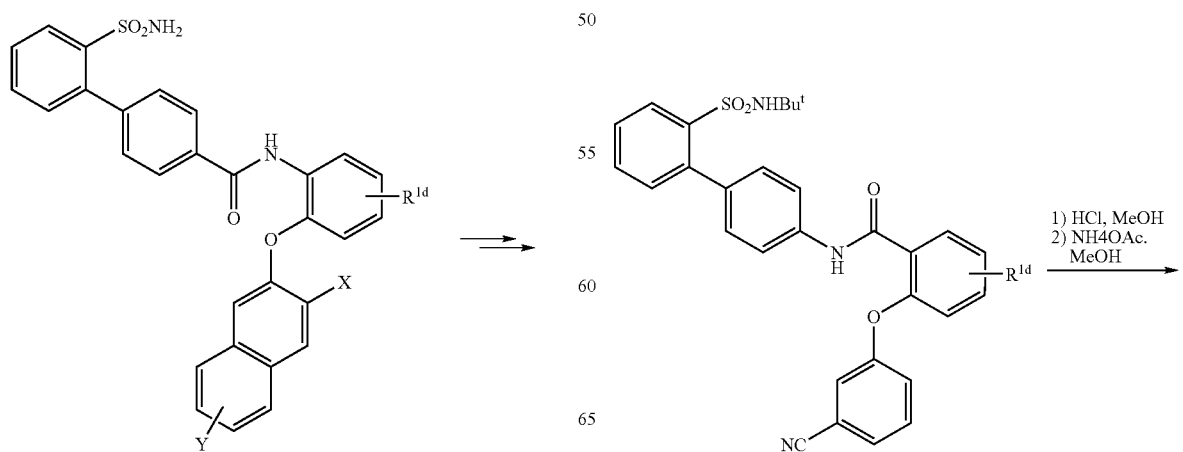

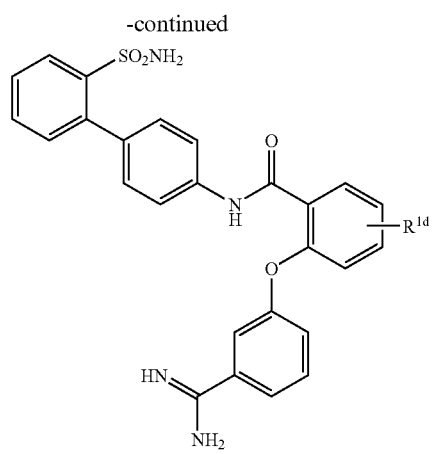
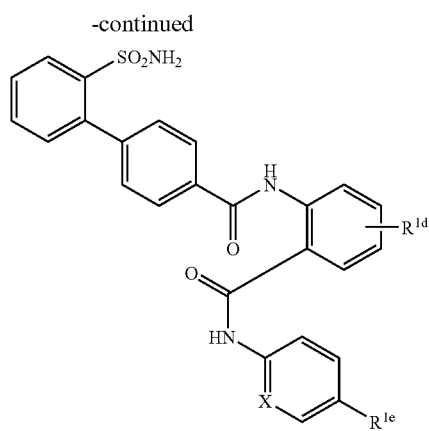
Scheme 5
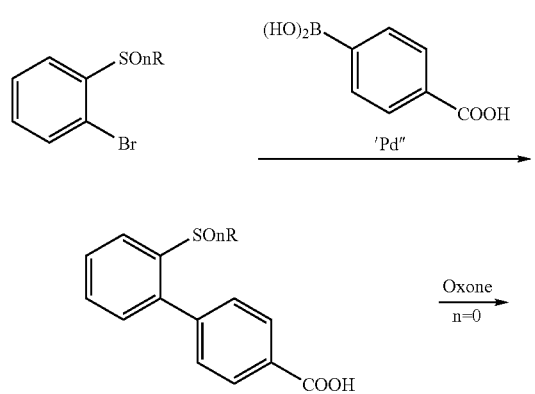
Scheme 6
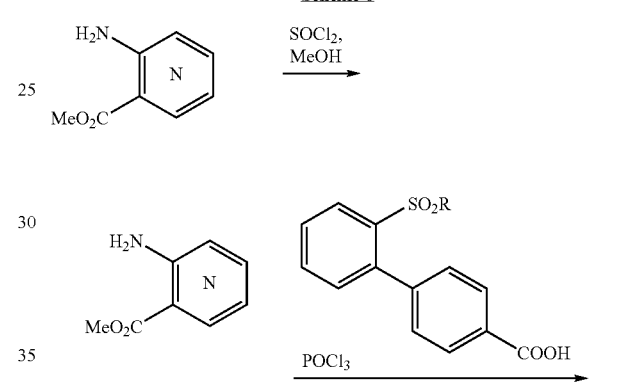
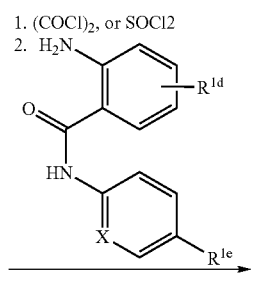

TFA
R=NHBu$^t$

Scheme 7
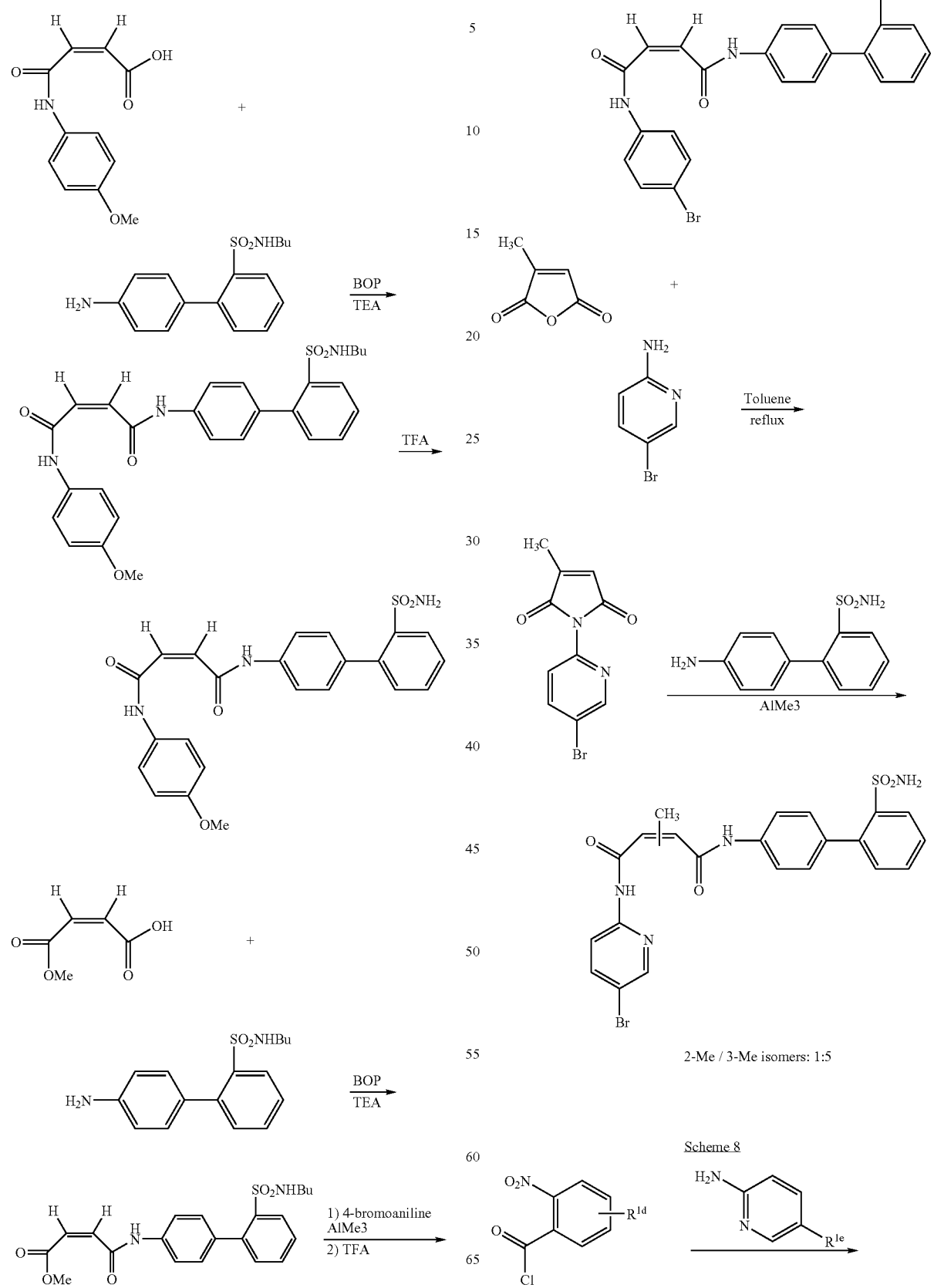
2-Me / 3-Me isomers: 1:5
Scheme 8
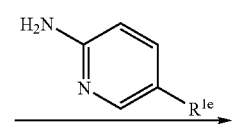

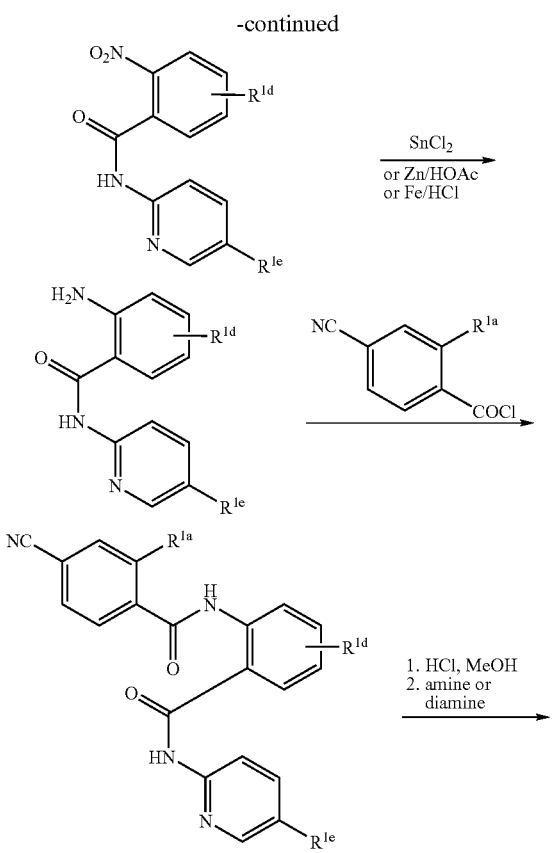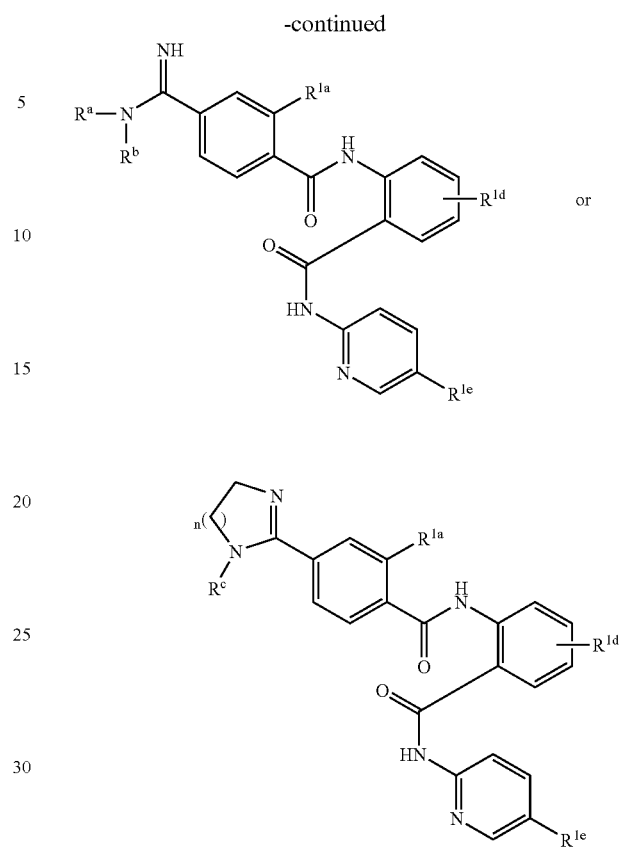
Scheme 9
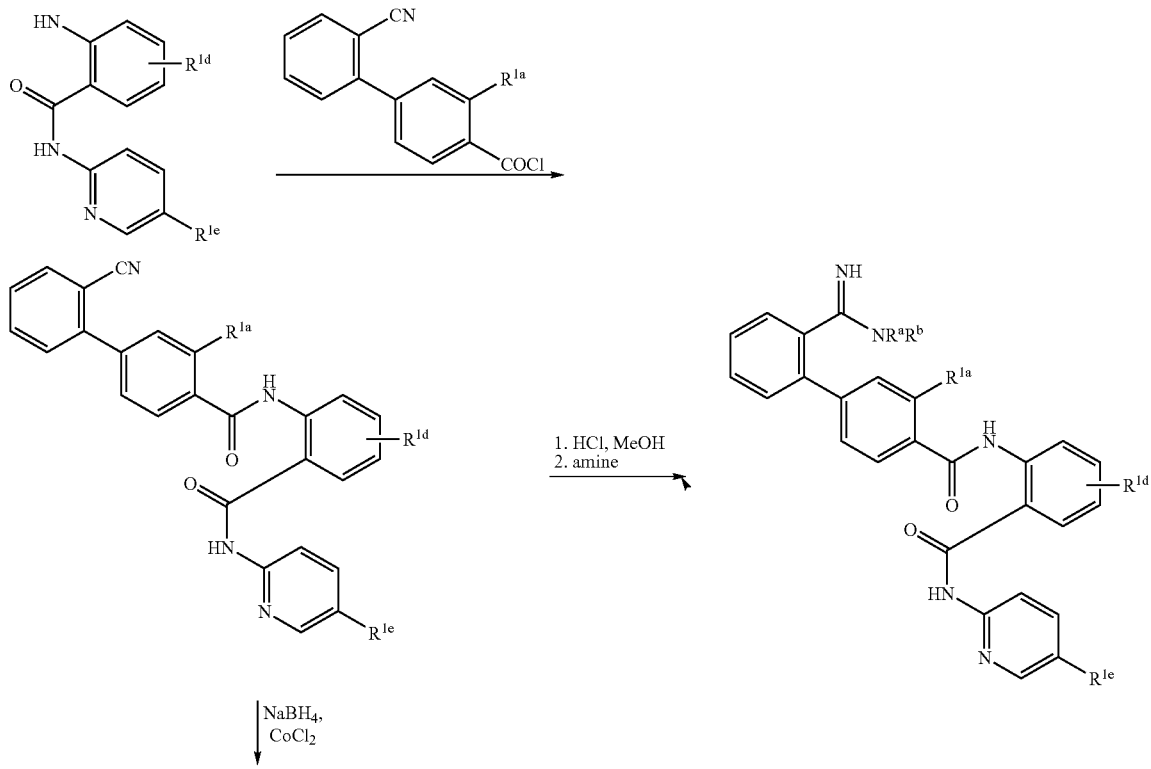

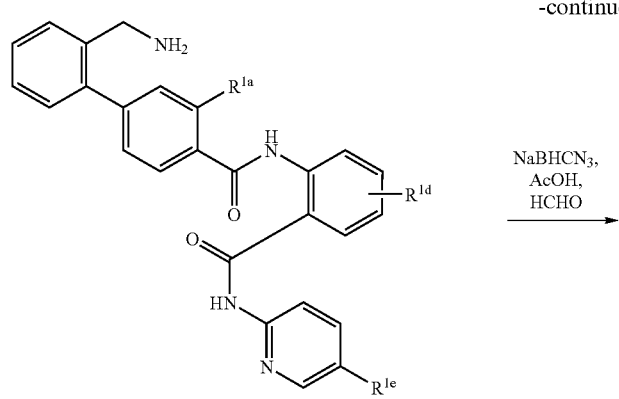
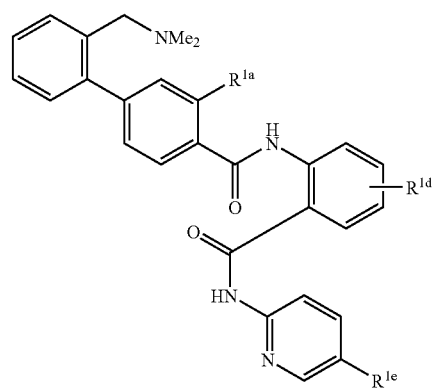
Scheme 10
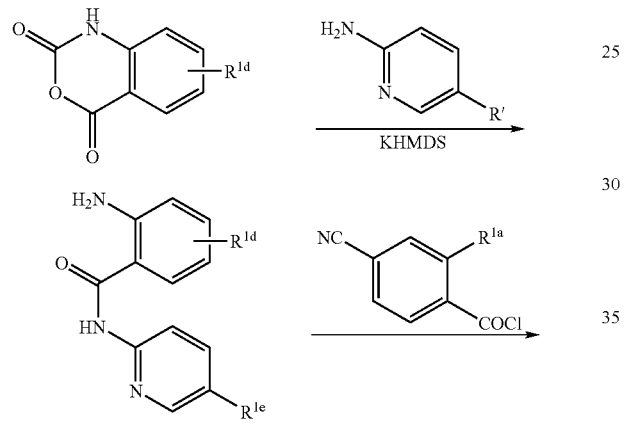
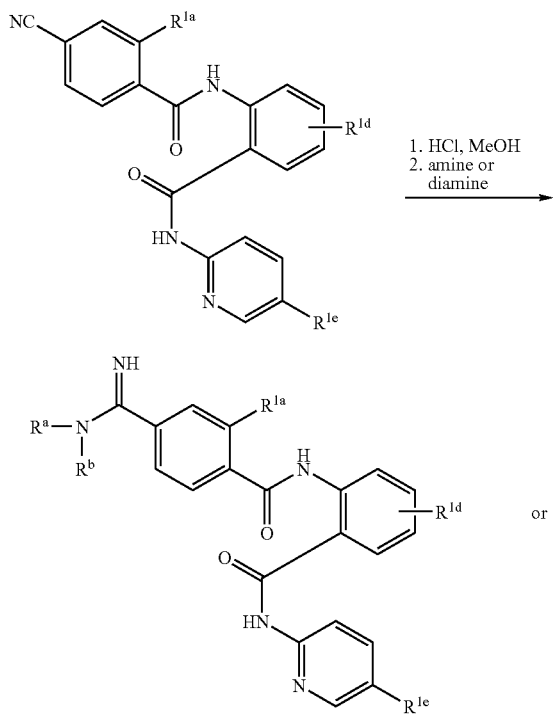
Scheme 11

241 242
-continued
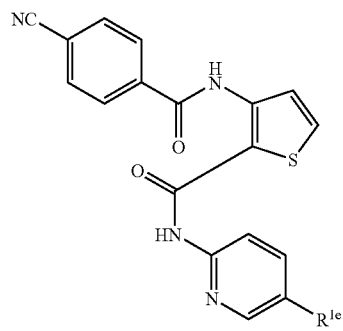
1. HCl, MeOH
2. amine or diamine
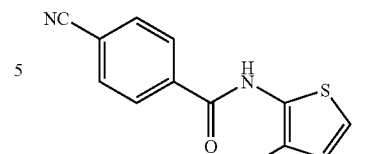
1. HCl, MeOH
2. amine or diamine
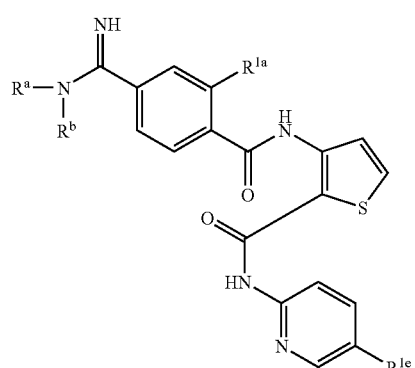
or
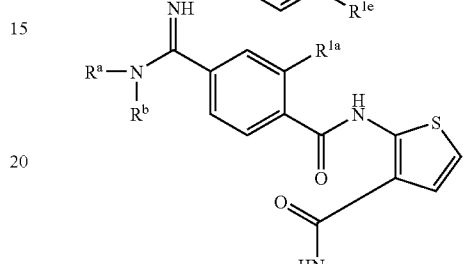
or
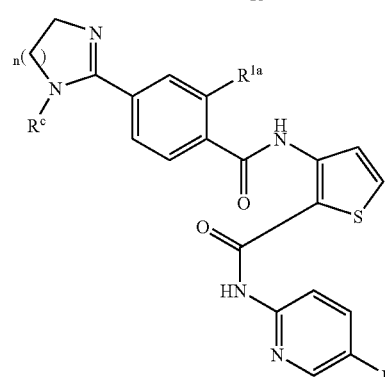
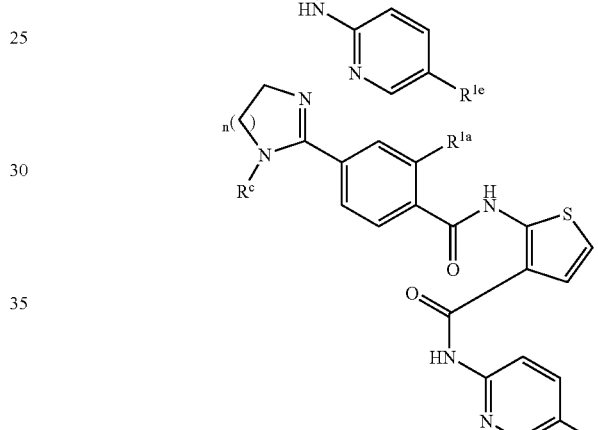
Scheme 12
Scheme 13
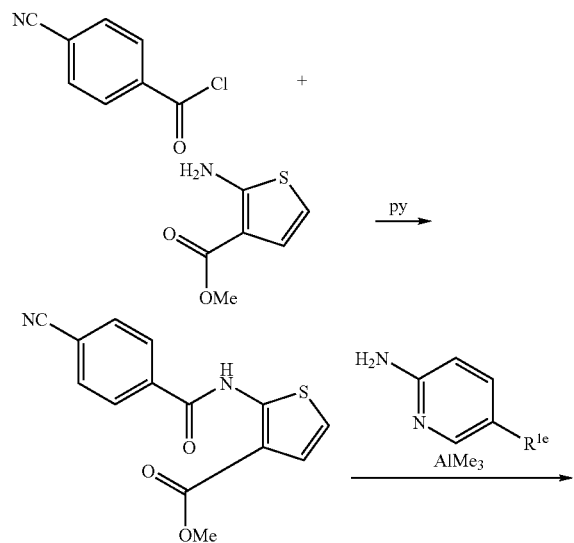
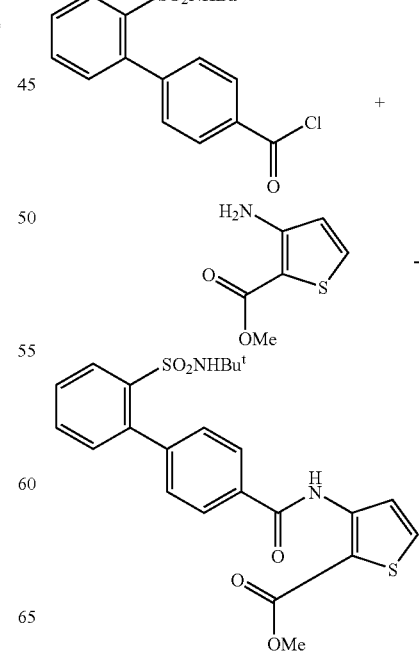

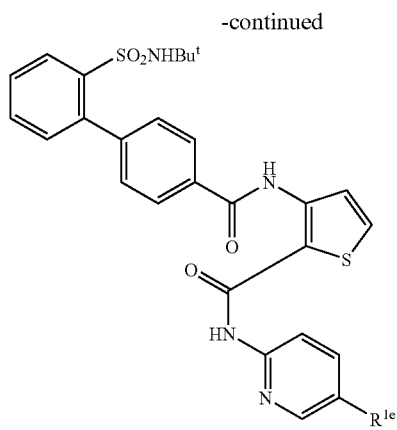
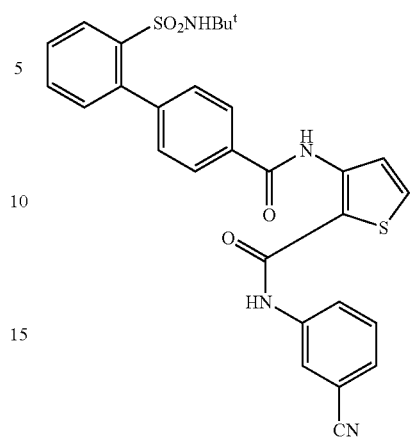
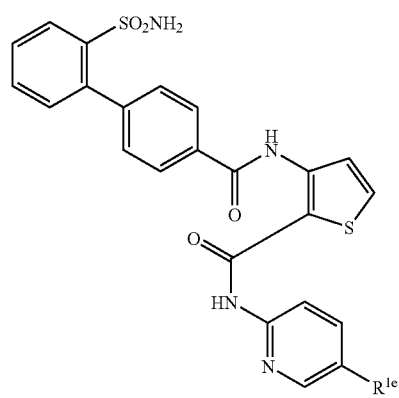
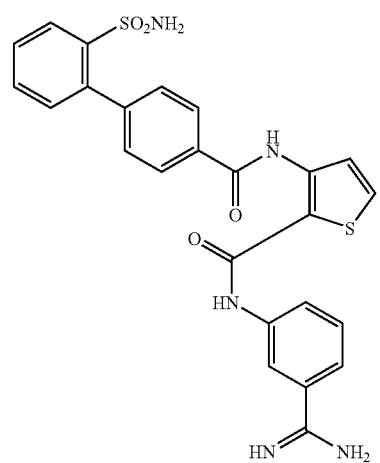
Scheme 14
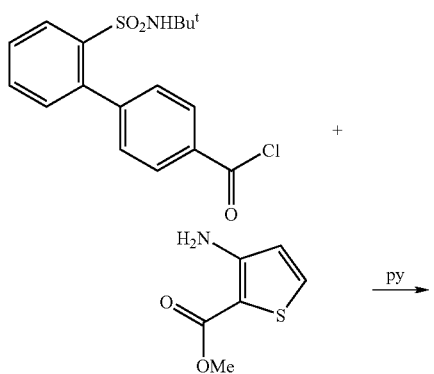
Scheme 15
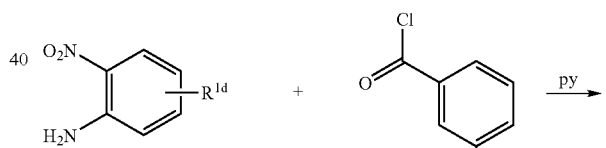
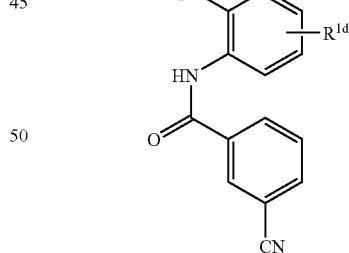
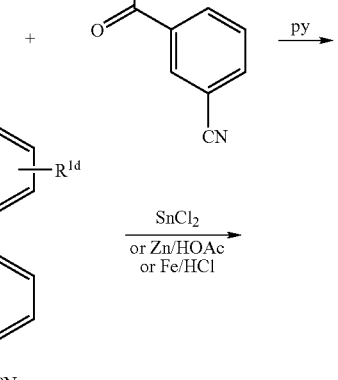
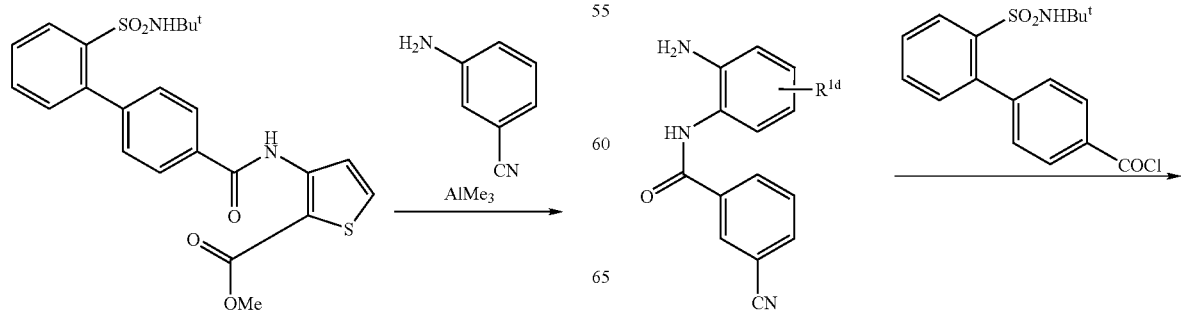

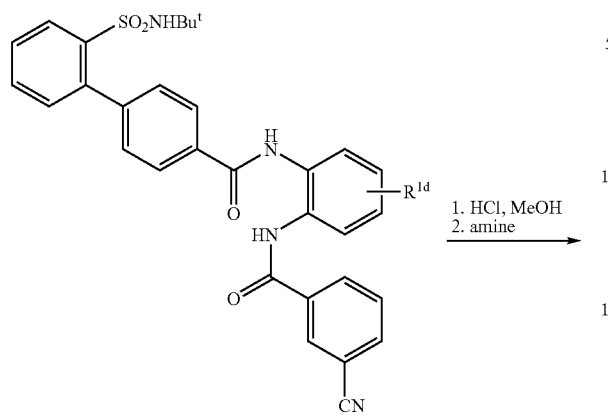
1. HCl, MeOH
2. amine
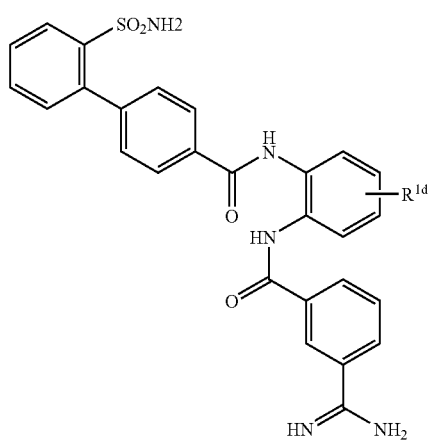
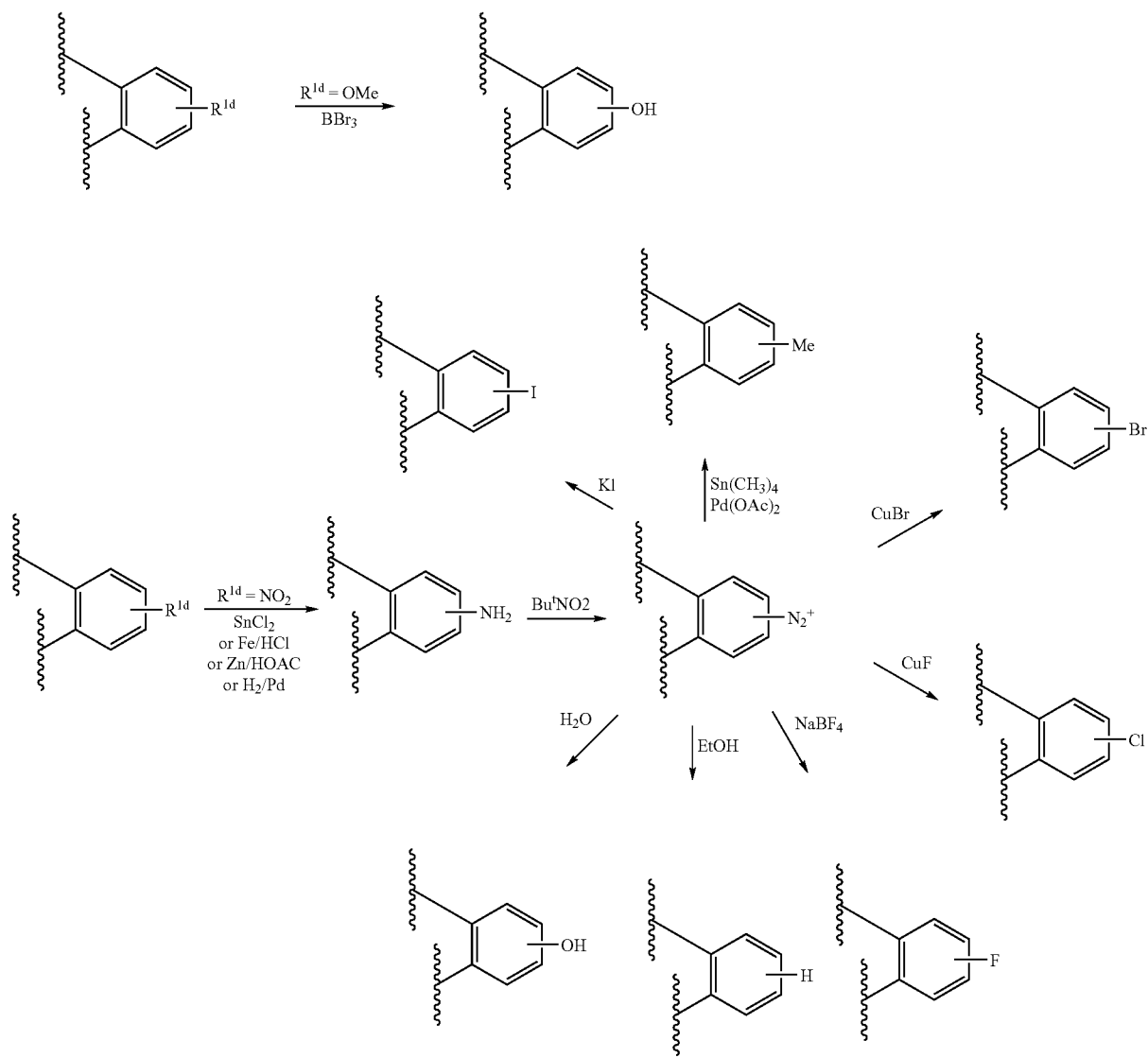

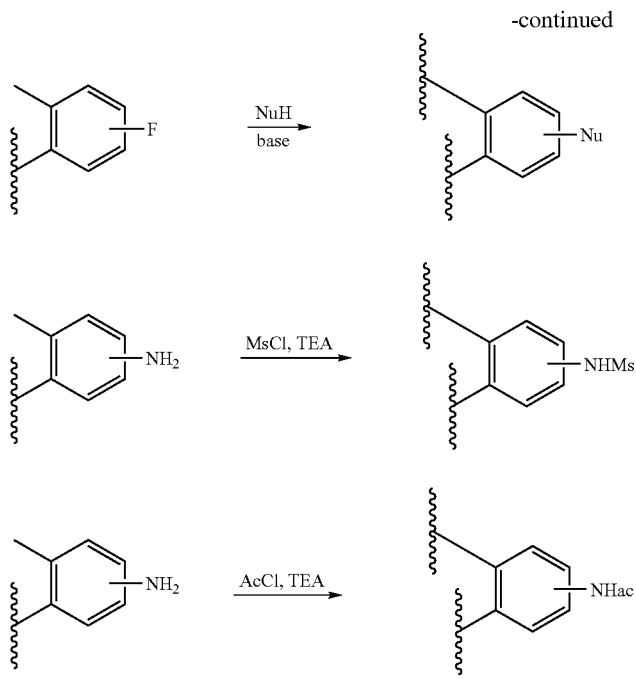

Example 1

N-(5-bromo-2-pyridinyl)-(2-4-[(2-aminosulfonyl)phenyl]phenylcarbonylamino)phenylcarboxamide

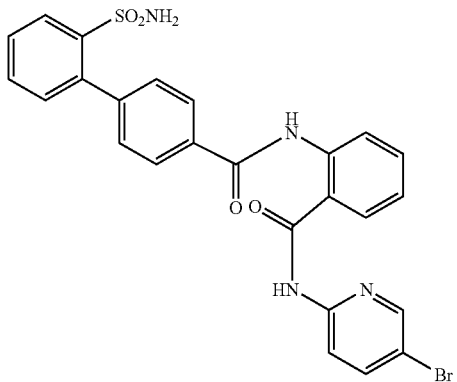

Step 1: A solution of 2-ntrobenzoyl chloride (3.70 g, 20 mmol, 1.0 equiv), 2-amino-5-bromopyridine (3.50 g, 1.0 equiv), pyridine (10 mL) in 25 mL of methylene chloride was stirred overnight. The volatile was evaporated, flash chromatography on silica gel gave N-(5-bromo-2-pyridinyl)-(2-nitro)phenylcarboxamide (5.02 g, 77%). MS found for $C_{12}H_9BrN_3O_3$ (M+H)$^+$: 322.

Step 2: A solution of N-(5-bromo-2-pyridinyl)-(2-nitro)phenylcarboxamide (1.0 g, 3.1 mmol, 1.0 equiv) in 30 mL of EtOAc was treated with $SnCl_2.2H_2O$ (2.80 g, 4 equiv) at reflux for 4 h. The volatile was evaporated and the residue was redissolved in EtOAc, washed with saturated aqueous $NaHCO_3$ and 1N NaOH. The organic layer was dried over $MgSO_4$, filtered and evaporated to N-(5-bromo-2-pyridinyl)-(2-amino)phenylcarboxamide (0.89 g, 98%). MS found for $C_{12}H_{11}BrN_3O$ (M+H)$^+$: 292.

Step 3: A mixture of N-(5-bromo-2-pyridinyl)-(2-amino)phenylcarboxamide (292 mg, 1 mmol, 1.0 equiv), 4-[(2-t-butylaminosulfonyl)phenyl]benzoyl chloride (349 mg, 1 equiv), pyridine (3 mL) in 10 mL of dichloromethane was stirred at rt overnight, washed with $H_2O$. The organic layer was dried over $MgSO_4$, filtered, evaporated and refluxed in 2 mL of trifluoroacetic acid for 30 min. TFA was then evaporated and HPLC (C18 reversed phase) eluting with 0.5% TFA in $H_2O/CH_3CN$ gave N-(5-bromo-2-pyridinyl)-(2-4-[(2-aminosulfonyl)phenyl]phenylcarbonylamino)phenylcarboxamide (470 mg, 85%). MS found for $C_{25}H_{20}BrN_4O_4S$ (M+H)$^+$: 551.

Example 2

N-(5-chloro-2-pyridinyl)-(2-4-[(2-aminosulfonyl)phenyl]phenylcarbonylamino)phenylcarboxamide

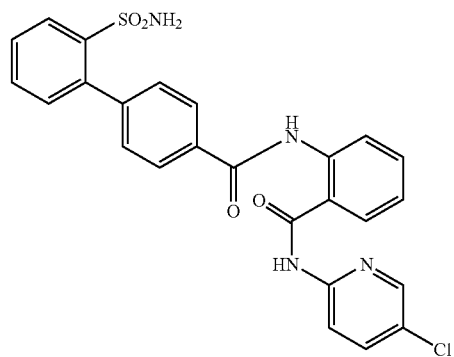

A mixture of N-(5-chloro-2-pyridinyl)-(2-amino)phenylcarboxamide (247 mg, 1 mmol, 1.0 equiv), 4-[(2-t-butylaminosulfonyl)phenyl]benzoyl chloride (349 mg, 1 equiv), pyridine (3 mL) in 10 mL of dichloromethane was stirred at rt overnight, washed with H$_2$O. The organic layer was dried over MgSO$_4$, filtered, evaporated and refluxed in 2 mL of trifluoroacetic acid for 30 min. TFA was then evaporated and HPLC (C18 reversed phase) eluting with 0.5% TFA in H$_2$O/CH$_3$CN gave N-(5-chloro-2-pyridinyl)-(2-4-[(2-aminosulfonyl)phenyl]phenylcarbonylamino)phenylcarboxamide (370 mg, 73%). MS found for C$_{25}$H$_{20}$ClN$_4$O$_4$S (M+H)$^+$: 507.

Example 3

N-(5-bromo-2-pyridinyl)-(2-(4-[(2-methylsulfonyl) phenyl]phenylcarbonyl)amino)phenylcarboxamide

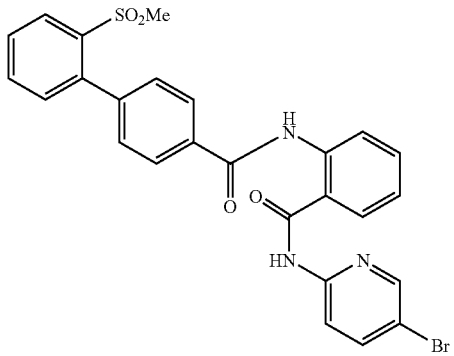

Step 1: To a mixture of 2-bromothioanisole (4.8 g, 23.6 mmol), 4-carboxybenzeneboronic acid (3.92 g, 23.6 mmol) and 2M K$_2$CO$_3$ (35.5 mmol, 71 mmol) in dioxane (20 ml) was added dichlorobis(triphenylphosphine)palladium (II) (415 mg, 0.6 mmol) under Ar. It was refluxed for 2 hrs. After the removal of the solvent, the residue was neutralized by 1N HCl and extracted with dichloromethane. The organic layer was dried over MgSO$_4$ and concentrated in vacuo to give 4-[(2-methylthio)phenyl]benzoic acid (5.9 g, 100%). ES-MS (M+H)$^+$=245.

Step 2: To a solution of 4-[(2-methylthio)phenyl]benzoic acid (3.43 g, 14 mmol) in H$_2$O (10 ml) and acetone (20 ml) was added oxone monopersulfate (34.6 g, 56 mmol). The mixture was stirred at r.t. overnight. After the removal of the solvent, the residue was extracted with ethyl acetate. The organic layer was dried over MgSO$_4$ and concentrated in vacuo to give 2.16 g (63%) 4-[(2-methylsulfonyl)phenyl] benzoic acid. ES-MS (M+H)$^+$=277.

Step 3: To a solution of 4-[(2-methylsulfonyl)phenyl] benzoic acid (552 mg, 2 mmol) in dichloromethane (5 ml) was added oxalyl chloride (350 ul, 4 mmol) and 2 drops of DMF. The mixture was stirred at r.t. for 2 hrs. After the removal of the solvent in vacuo, the residue was dissolved in dichloromethane (5 ml), N-(5-bromo-2-pyridinyl)-(2-amino)phenylcarboxamide (700 mg, 2.4 mmol), pyridine (486 ul, 6 mmol) and catalytic amount of DMAP were added. The mixture was stirred at r.t. overnight. After the removal of the solvent, the residue was purified by flash column (30% ethyl acetate/hexane) and then preparative HPLC to get 41.4 mg (38%) of N-(5-bromo-2-pyridinyl)-(2-(4-[(2-methylsulfonyl)phenyl]phenylcarbonyl)amino) phenylcarboxamide. ES-MS M+=550, (M+2)$^+$=552.

Example 4

N-(5-chloro-2-pyridinyl)-(2-(4-[(2-methylsulfonyl) phenyl]phenylcarbonyl)amino)phenylcarboxamide

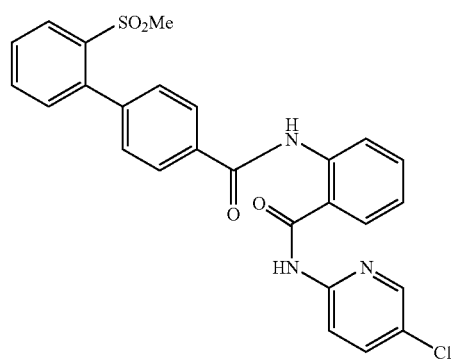

To a solution of 4-[(2-methylsulfonyl)phenyl]benzoic acid (280 mg, 1 mmol) in dichloromethane (5 ml) was added oxalyl chloride (175 ul, 2 mmol) and 2 drops of DMF. The mixture was stirred at r.t. for 2 hrs. After the removal of the solvent in vacuo, the residue was dissolved in dichloromethane (5 ml), N-(5-chloro-2-pyridinyl)-(2-amino)phenylcarboxamide (297 mg, 1.2 mmol), pyridine (243ul, 3 mmol) and catalytic amount of DMAP were added. The mixture was stirred at r.t. overnight. After the removal of the solvent, the residue was purified by flash column (30% ethyl acetate/hexane) and then preparative HPLC to get 95 mg (20%) of N-(5-chloro-2-pyridinyl)-(2-(4-[(2-methylsulfonyl)phenyl]phenylcarbonyl)amino)phenylcarboxamide. ES-MS M+=505.5, (M+2)+=507.5.

Example 5

N-(4-bromo-2-methoxycarbonyphenyl)-(2-(4-[(2-methylsulfonyl)phenyl]phenylcarbonyl)amino)phenylcarboxamide

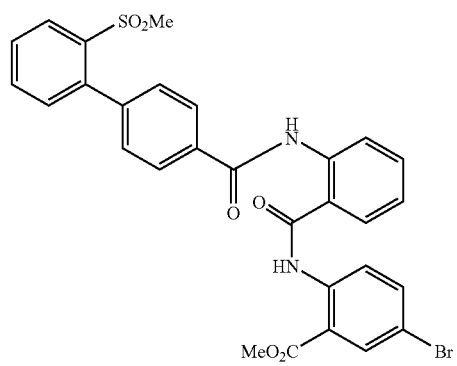

A sample of 4-[(2-methylsulfonyl)phenyl]benzoic acid (280 mg, 1 mmol, 1 equiv) was refluxed with 2 mL of thionyl chloride for 2 h and evaporated. The residue was dissolved in 5 mL of dichloromethane, N-(4-bromo-2-methoxycarbonyphenyl)-(2-amino)phenylcarboxamide (348 mg, 1 equiv), pyridine (3 mL) were added. The mixture was stirred at r.t. overnight. After the removal of the solvent, the residue was purified by flash column to give 480 mg (79%) of N-(4-bromo-2-methoxycarbonylphenyl)-(2-(4-[(2-methylsulfonyl)phenyl]phenylcarbonyl)amino)phenylcarboxamide. MS found for $C_{29}H_{24}BrN_2O_6S$ (M+H)$^+$: 607.

Example 6

N-(4-chloro-2-methoxycarbonylphenyl)-(2-(4-[(2-methylsulfonyl)phenyl]phenylcarbonyl)amino)phenylcarboxamide

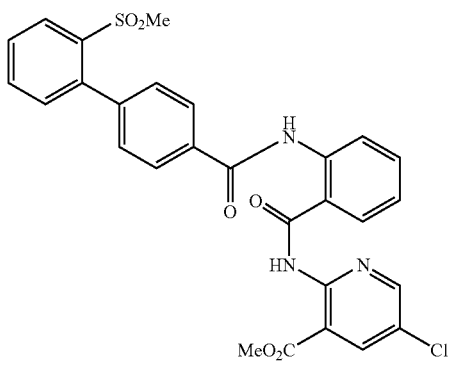

A sample of 4-[(2-methylsulfonyl)phenyl]benzoic acid (280 mg, 1 mmol, 1 equiv) was refluxed with 2 mL of thionyl chloride for 2 h and evaporated. The residue was dissolved in 5 mL of dichloromethane, N-(4-chloro-2-methoxycarbonylphenyl)-(2-amino)phenylcarboxamide (304 mg, 1 equiv), pyridine (3 mL) were added. The mixture was stirred at r.t. overnight. After the removal of the solvent, the residue was purified by flash column to give 479 mg (85%) of N-(4-chloro-2-methoxycarbonylphenyl)-(2-(4-[(2-methylsulfonyl)phenyl]phenylcarbonyl)amino)phenylcarboxamide. MS found for $C_{29}H_{24}ClN_2O_6S$ (M+H)$^+$: 563.

Example 7

N-(5-bromo-2-pyridinyl)-(2-4-[(2-aminosulfonyl)phenyl]phenylcarbonylamino)pyridinyl-3-carboxamide

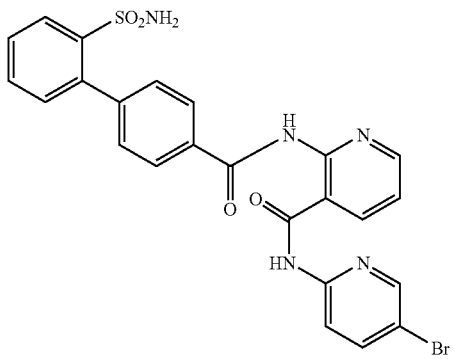

Step 1: A solution of 2-aminopyridine-3-carboxylic acid (138 mg, 1 mmol) in 10 mL of methanol was treated with thionyl chloride in portions until complete reaction. The solvent was evaporated and the residue was dissolved in 10 mL of pyridine. To the solution were added 4-[(2-t-butylaminosulfonyl)phenyl]benzoic acid and POCl$_3$. The resulting mixture was stirred at rt overnight, quenched by slow addition of water, and extracted with EtOAc. The organic layer was dried over MgSO$_4$, filtered and flash chromatographied to give methyl 2-(4-[(2-t-butylaminosulfonyl)phenyl]phenylcarbonyl)aminopyridine-3-carboxylate (243 mg, 52%). MS found for $C_{24}H_{26}N_3O_5S$ (M+H)$^+$: 468.

Step 2: To A solution of 2-amino-5-bromopridine (45 mg, 4.0 equiv) in 5 mL of methylene chloride treated with AlMe$_3$ (2M in hexane, 0.65 mL, 20 equiv) for 30 min was added methyl 2-(4-[(2-t-butylaminosulfonyl)phenyl]phenylcarbonyl)aminopyridine-3-carboxylate (30 mg, 0.064 mmol, 1 equiv). The mixture was stirred at rt overnight, quenched with saturated aqueous potassium sodium tartrate. The organic layer was dried over MgSO$_4$, filtered, evaporated and refluxed in 2 mL of trifluoroacetic acid for 30 min. TFA was then evaporated and HPLC (C18 reversed phase) eluting with 0.5% TFA in H$_2$O/CH$_3$CN gave N-(5-bromo-2-pyridinyl)-(2-4-[(2-aminosulfonyl)phenyl]phenylcarbonylamino)pyridinyl-3-carboxamide (17 mg, 48%). MS found for $C_{24}H_{19}BrN_5O_4S$ (M+H)$^+$: 552.

Example 8

N-(5-chloro-2-pyridinyl)-(2-4-[(2-aminosulfonyl)phenyl phenylcarbonylamino)pyridinyl-3-carboxamide

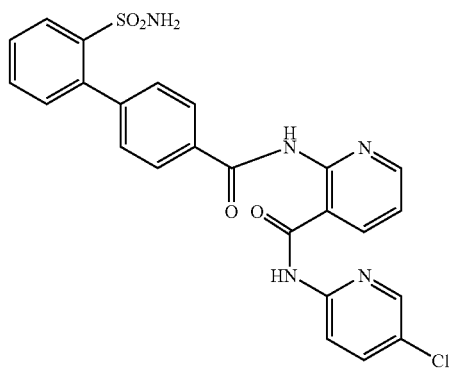

To A solution of 2-amino-5-chloropridine (32 mg, 4.0 equiv) in 5 mL of methylene chloride treated with AlMe$_3$ (2M in hexane, 0.65 mL, 20 equiv) for 30 min was added methyl 2-(4-[(2-t-butylaminosulfonyl)phenyl]phenylcarbonyl)aminopyridine-3-carboxylate (30 mg, 0.064 mmol, 1 equiv). The mixture was stirred at rt overnight, quenched with saturated aqueous potassium sodium tartrate. The organic layer was dried over MgSO$_4$, filtered, evaporated and refluxed in 2 mL of trifluoroacetic acid for 30 min. TFA was then evaporated and HPLC (C18 reversed phase) eluting with 0.5% TFA in H$_2$O/CH$_3$CN gave N-(5-chloro-2-pyridinyl)-(2-4-[(2-aminosulfonyl)phenyl]phenylcarbonylamino)pyridinyl-3-carboxamide (21 mg, 66%). MS found for $C_{24}H_{19}ClN_5O_4S$ (M+H)$^+$: 508.

Example 9

N-(5-bromo-2-pyridinyl)-(3-4-[(2-aminosulfonyl)phenyl]phenylcarbonylamino)pyridinyl-2-carboxamide

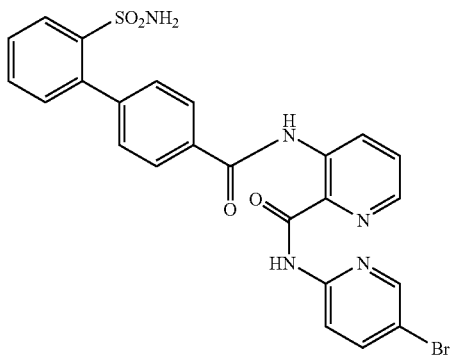

To A solution of 2-amino-5-bromopridine (69.2 mg, 4.0 equiv) in 5 mL of methylene chloride treated with AlMe$_3$ (2M in hexane, 1 mL, 20 equiv) for 30 min was added 3-(4-[(2-t-butylaminosulfonyl)phenyl]phenylcarbonyl)aminopyridine-2-carboxylate (46.7 mg, 1 equiv). The mixture was stirred at rt overnight, quenched with saturated aqueous potassium sodium tartrate. The organic layer was dried over MgSO$_4$, filtered, evaporated and refluxed in 2 mL of trifluoroacetic acid for 30 min. TFA was then evaporated and HPLC (C18 reversed phase) eluting with 0.5% TFA in H$_2$O/CH$_3$CN gave N-(5-bromo-2-pyridinyl)-(3-4-[(2-aminosulfonyl)phenyl]phenylcarbonylamino)pyridinyl-2-carboxamide (29 mg, 53%). MS found for C$_{24}$H$_{19}$BrN$_5$O$_4$S (M+H)$^+$: 552.

Example 10

N-(5-chloro-2-pyridinyl)-(2-4-[(2-aminosulfonyl)phenyl]phenylcarbonylamino)pyridinyl-3-carboxamide

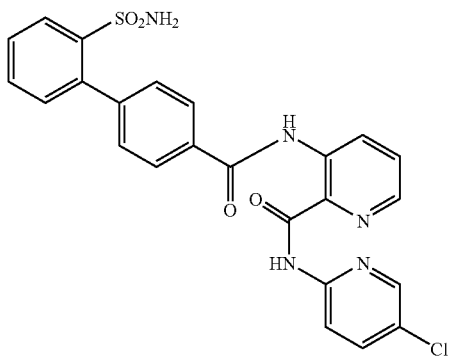

To A solution of 2-amino-5-chloropridine (51.2 mg, 4.0 equiv) in 5 mL of methylene chloride treated with AlMe$_3$ (2M in hexane, 1 mL, 20 equiv) for 30 min was added 3-(4-[(2-t-butylaminosulfonyl)phenyl]phenylcarbonyl)aminopyridine-2-carboxylate (46.7 mg, 0.1 mmol, 1 equiv). The mixture was stirred at rt overnight, quenched with saturated aqueous potassium sodium tartrate. The organic layer was dried over MgSO$_4$, filtered, evaporated and refluxed in 2 mL of trifluoroacetic acid for 30 min. TFA was then evaporated and HPLC (C18 reversed phase) eluting with 0.5% TFA in H$_2$O/CH$_3$CN gave N-(5-chloro-2-pyridinyl)-(2-4-[(2-aminosulfonyl)phenyl]phenylcarbonylamino)pyridinyl-3-carboxamide (33 mg, 64%). MS found for C$_{24}$H$_{19}$ClN$_5$O$_4$S (M+H)$^+$: 508.

Examples 11-14

The following compounds were prepared using the procedure described previously:

Example 11

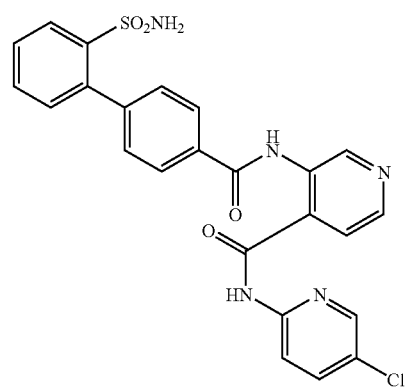

MS (M+H): 508

Example 12

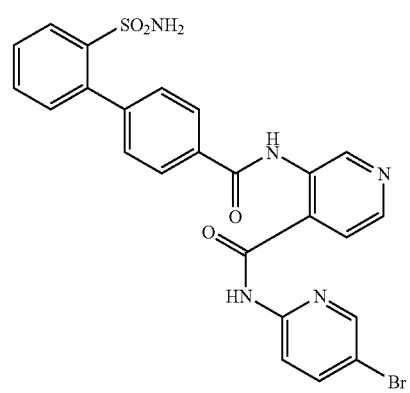

MS (M+H): 552

Example 13

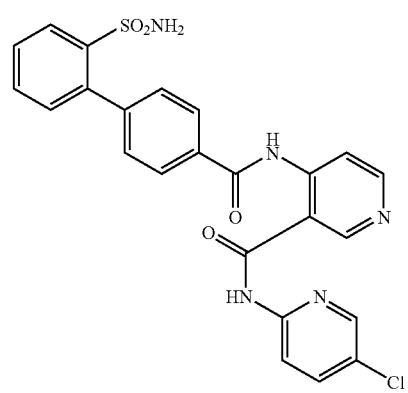

MS (M+H): 508

-continued

Example 14

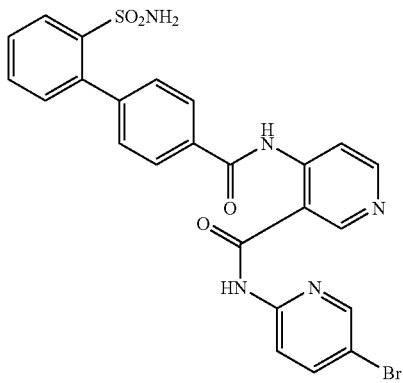

MS (M+H): 552

Example 15

N-(4-bromo-2-nitrophenyl)-(2-(4-[(2-methylsulfonyl)phenyl]phenylcarbonyl)amino)phenylcarboxamide

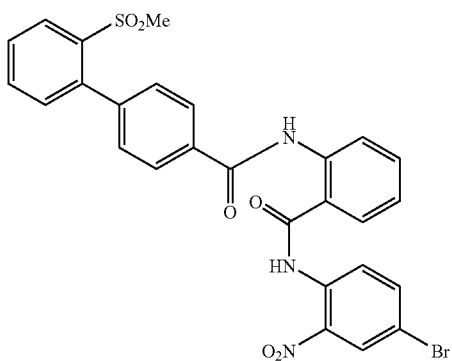

Step 1: A mixture of methyl 2-aminobenzoate (150 mg, 1 mmol, 1.0 equiv), 4-[(2-methylsulfonyl)phenyl]benzoic chloride (294 mg, 1 equiv), pyridine (3 mL) in 10 mL of dichloromethane was stirred at rt overnight, washed with $H_2O$. The organic layer was dried over $MgSO_4$, filtered and evaporated. Flash chromatography on silica gel gave methyl 2-(4-[(2-methylsulfonyl)phenyl]phenylcarbonyl)aminobenzoate (250 mg, 54%). MS found for $C_{25}H_{27}N_2O_5S$ (M+H)$^+$: 467.

Step 2: To a solution of 4-bromo-2-ntroaniline (43.4 mg, 0.2 mmol, 2.0 equiv) in 5 mL of methylene chloride treated with $AlMe_3$ (2M in hexane, 0.3 mL, 6 equiv) for 30 min was added methyl 2-(4-[(2-methylsulfonyl)phenyl]phenylcarbonyl)aminobenzoate (46.6 mg, 1 equiv). The mixture was stirred at rt overnight, quenched with saturated aqueous potassium sodium tartrate. The organic layer was dried over $MgSO_4$, filtered and evaporated. Flash chromatography on silica gel gave N-(4-bromo-2-nitrophenyl)-(2-(4-[(2-methylsulfonyl)phenyl]phenylcarbonyl)amino)phenylcarboxamide (5 mg, 9%). MS found for $C_{27}H_{21}BrN_3O_6S$ (M+H)$^+$: 594.

Example 16

N-(4-methoxyphenyl)-N'-(4-[(2-aminosulfonyl)phenyl]phenyl)-maleamic amide

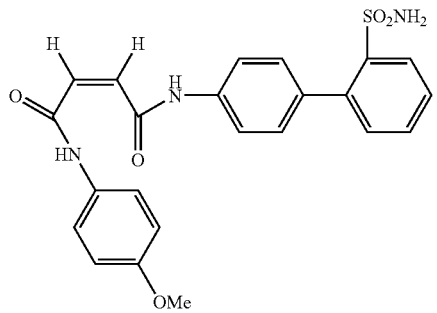

A. Preparation of N-(4-methoxyphenyl)-N'-(4-[(2-tert-butylaminosulfonyl)phenyl]phenyl)-maleamic amide To a solution of commercially available N-(4-methoxyphenyl)maleamic acid (100 mg, 0.452 mmol), triethylamine (0.126 mL, 0.906 mmol) and 4-(2-tert-butylaminosulfonylphenyl)aniline (138 mg, 0.454 mmol) in anhydrous DMF (5 mL), BOP (260 mg, 0.588 mmol) was added. The mixture was stirred at room temperature overnight. Water and EtOAc were added. The organic phase was separated, washed with H2O, then with 5% NaHCO3, dried over Na2SO4, concentrated in vacuo. The residue was purified by HPLC using a gradient of 20% CH3CN in $H_2O$ (containing 0.1% TFA) to 100% CH3CN over 80 min. Fractions containing the desired product were pooled, and lyophilized to give a powder (70 mg, yield: 31%). MS 508 (M+H).

B. Preparation of N-(4-methoxyphenyl)-N'-(4-[(2-aminosulfonyl)phenyl]phenyl)-maleamic amide The compound N-(4-methoxyphenyl)-N'-(4-[(2-tert-butylaminosulfonyl)phenyl]phenyl)-maleamic amide (40 mg, 79 mol) was dissolved in TFA (3 mL). It was allowed to stand at room temperature overnight. TFA was removed in vacuo. The residue was purified by HPLC using a gradient of 5% CH3CN in H2O (containing 0.1% TFA) to 95% CH3CN over 60 min. Fractions containing the desired product were pooled, and lyophilized to give a powder (18 mg, yield: 51%). MS 452 (M+H) and 474 (M+Na). $^1$H NMR (CDCl3) δ 11.40 (br.s, 1H), 10.28 (br.s, 1H), 8.12 (d, 1H, J=8 Hz), 7.72 (d, 2H, J=8 Hz), 7.60-7.20 (m, 9H), 6.86 (AB type, 2H), 6.45 (br.s, 2H), 3.79 (s, 3H).

Example 17

N-(4-bromophenyl)-N'-(4-[(2-aminosulfonyl)phenyl]phenyl)-maleamic amide

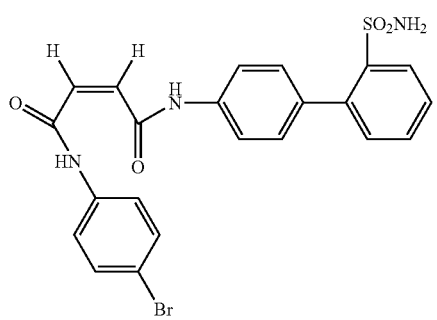

A. Preparation of N-(4-[(2-tert-butylaminosulfonyl)phenyl]phenyl)maleamic methyl ester To a solution of commercially available maleic acid monomethyl ester (277 mg, 2.13 mmol), 4-(2-tert-butylaminosulfonylphenyl)aniline (648 mg, 2.13 mmol) and triethylamine (0.593 mL, 4.26 mmol) in CH$_2$Cl$_2$ (20 mL), BOP (1.13 g, 2.55 mmol) was added. The mixture was stirred at room temperature overnight. More maleic acid monomethyl ester (50 mg, 0.385 mmol) was added. It was stirred for 3 hours. The CH2Cl2 solution was then washed with sat. NaHCO3, 1N HCl and sat. NaCl. The solution was dried over Na2SO4, concentrated in vacuo. The residue was purified by a silica gel column using a gradient of 10-40% EtOAc in hexane as solvents, to give the titled compound (360 mg, yield: 41%). MS 361 (M+H–$^T$Bu) and 439 (M+Na).

B. Preparation of N-(4-bromophenyl)-N'-(4-[(2-aminosulfonyl)phenyl]phenyl)-maleamic amide To a solution of 4-bromoaniline (93 mg, 0.543 mmol) in CH2Cl2 (5 mL) at room temperature, trimethylaluminum (0.82 mL, 2.0 M in hexane, 1.64 mmol) was added dropwise. After the solution was stirred for 30 min at room temperature, compound N-(4-[(2-tert-butylaminosulfonyl)phenyl]phenyl)maleamic methyl ester (113 mg, 0.272 mmol) was added. The mixture was stirred at room temperature for 2 days. The solution was neutralized with 1N HCl to pH 2-3. Water and CH2Cl2 were added, and organic phase was separated, dried over Na2SO4, concentrated in vacuo. The residue was dissolved in TFA (4 mL). It was allowed to stand at room temperature overnight. TFA was removed in vacuo. The residue was purified by HPLC using a gradient of 5% CH3CN in H2O (containing 0.1% TFA) to 95% CH3CN over 60 min. Fractions containing the desired product were pooled, and lyophilized to give a powder (8 mg, yield: 6%). MS 500 and 502 (M+H), 522 and 524 (M+Na). $^1$H NMR (CD3OD) δ 8.09 (d, 1H, J=8 Hz), 7.68 (d, 2H, J=8 Hz), 7.64-7.28 (m, 9H), 6.45 (AB type, 2H).

Examples 18 and 19

Preparation of N$^1$-(5-bromopyridin-2-yl)-N$^4$-(4-[(2-aminosulfonyl)phenyl]phenyl)-2-methylmaleamic amide and N$^1$-(5-bromopyridin-2-yl)-N$^4$-(4-[(2-aminosulfonyl)phenyl]phenyl)-3-methylmaleamic amide

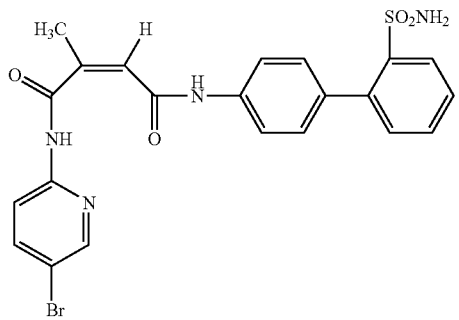

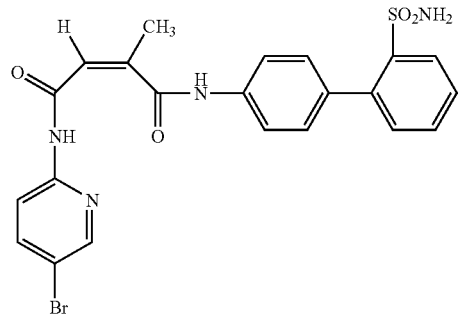

A. Preparation of N-(5-bromopyridin-2-yl)-methylmaleimide

A mixture of citraconic anhydride (1.00 mL, 11.1 mmol) and 2-amino-5-bromopyridine (1.93 g, 11.2 mmol) in toluene (60 mL) was heated to reflux overnight. The solution was cooled down, filtered. The filtrate was concentrated in vacuo to give a solid (2.10 g, yield: 71%). MS 267 and 269 (M+H).

B. Preparation of N$^1$-(5-bromopyridin-2-yl)-N$^4$-(4-[(2-aminosulfonyl)phenyl]phenyl)-2-methylmaleamic amide and N$^{1-}$(5-bromopyridin-2-yl)-N$^4$-(4-[(2-aminosulfonyl)phenyl]phenyl)-3-methylmaleamic amide To the solution of 4-(2-aminosulfonylphenyl)aniline (0.170 g, 0.685 mmol) in CH2Cl2 (10 mL) at room temperature, trimethylaluminum (2.0 M in hexane, 2.00 mL, 4.00 mmol) was added dropwise, during which time, white gel-like precipitates came out the solution. It was stirred for 30 min. A solution of N-(5-bromopyridin-2-yl)-methylmaleimide (0.122 g, 0.457 mmol) in CH2Cl2 (5 mL) was added. It was stirred for 1 hour, during which time the precipitates started to dissolve, and the solution became clear. It was stirred for another 2 hours. 1N HCl was added to neutralize the solution to pH 2-3, which resulted in precipitation. The precipitates were collected by filtration, dried on vacuum. The precipitates (75 mg, yield: 32%) were a mixture of 2-methyl and 3-methylmaleamic amide isomers in a ratio of 1:5. MS 515 and 517 (M+H), 537 and 539 (M+Na).

Example 20

N-(5-bromo-2-pyridinyl)-(2-(4-[(2-aminosulfonyl)phenyl]phenylcarbonyl)amino)-4-nitrophenylcarboxamide

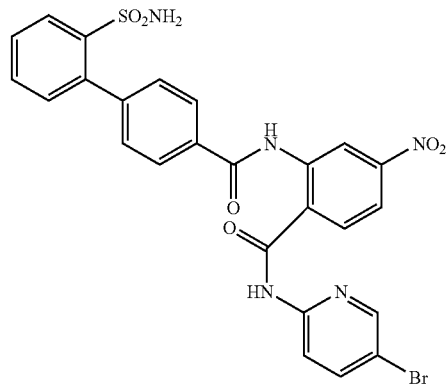

Step 1: A solution of 2-amino-4-nitrobenzoic acid (182 mg, 1 mmol, 1 equiv) in 10 mL of methanol was treated with thionyl chloride in portions until complete reaction. The solvent was evaporated and the residue was dissolved in 10 mL of pyridine. To the solution were added 4-[(2-t-butylaminosulfonyl)phenyl]benzoic acid (330 mg, 1 equiv) and POCl$_3$ (0.93 mL, 10 equiv). The resulting mixture was stirred at rt overnight, quenched by slow addition of water, and extracted with EtOAc. The organic layer was dried over MgSO$_4$, filtered and flash chromatographied to give methyl 2-(4-[(2-t-butylaminosulfonyl)phenyl]phenylcarbonyl)amino-4-nitrobenzoate (430 mg, 84%,). MS found for $C_{25}H_{26}N_3O_7S$ (M+H)$^+$: 512.

Step 2: To A solution of 2-amino-5-bromopridine (135 mg, 4.0 equiv) in 5 mL of methylene chloride treated with AlMe$_3$ (2M in hexane, 1 mL, 10 equiv) for 30 min was added methyl 2-(4-[(2-t-butylaminosulfonyl)phenyl]phenylcarbonyl)amino-4-nitrobenzoate (100 mg, 0.2 mmol, 1 equiv). The mixture was stirred at rt overnight, quenched with saturated aqueous potassium sodium tartrate. The organic layer was dried over MgSO$_4$, filtered, evaporated and refluxed in 2 mL of trifluoroacetic acid for 30 min. TFA was then evaporated and HPLC (C18 reversed phase) eluting with 0.5% TFA in H$_2$O/CH$_3$CN gave N-(5-bromo-2-pyridinyl)-(2-(4-[(2-aminosulfonyl)phenyl]phenylcarbonyl)amino)-4-nitrophenylcarboxamide (42 mg, 36%). MS found for $C_{25}H_{19}BrN_5O_6S$ (M+H)$^+$: 59.6.

Examples 21-23

The following compounds were prepared according to the procedure described previously:

Example 21

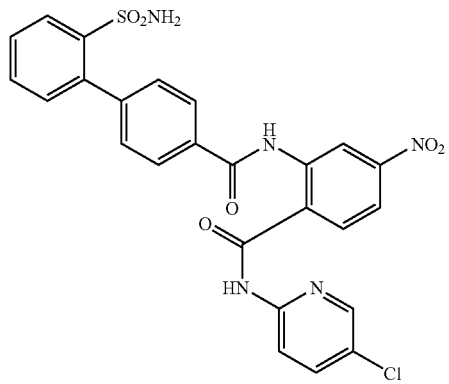

MS (M+H): 552

Example 22

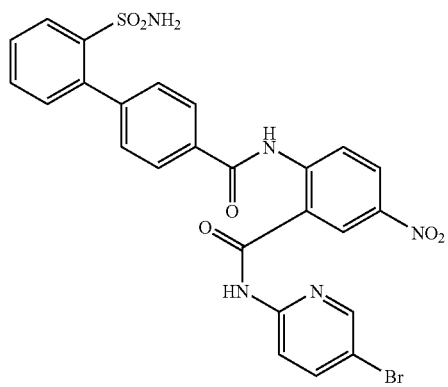

MS (M+H): 596

Example 23

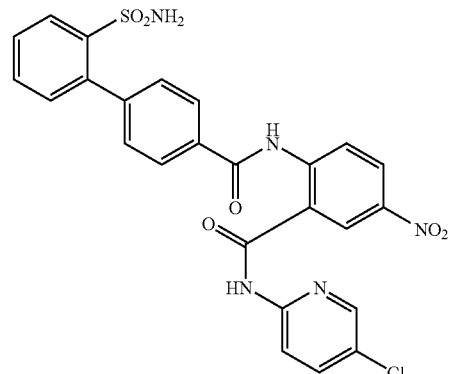

MS (M+H): 552

Example 24

N-(5-bromo-2-pyridinyl)-(2-(4-[(2-aminosulfonyl)phenyl]phenylcarbonyl)amino)-4-aminophenylcarboxamide A solution of N-(5-bromo-2-pyridinyl)-(2-(4-[(2-t-butylsulfonyl)phenyl]phenylcarbonyl)amino)-4-nitrophenylcarboxamide (65 mg, 0.1 mmol, 1 equiv) in 10 mL of EtOAc was treated with SnCl$_2$-2H$_2$O (90 mg, 4 equiv) at reflux for 4 h. The volatile was evaporated and the residue was redissolved in EtOAc, washed with saturated aqueous NaHCO$_3$ and 1N NaOH. The organic layer was dried over MgSO$_4$, filtered and evaporated to give N-(5-bromo-2-pyridinyl)-(2-(4-[(2-t-butylsulfonyl)phenyl]phenylcarbonyl)amino)-4-aminophenyl carboxamide, which was refluxed with 2 mL of TFA for 1 h. After removal of TFA by rotavap, the residue was purified by HPLC (C18 reversed phase) eluting with 0.5% TFA in H$_2$O/CH$_3$CN to give N-(5-bromo-2-pyridinyl)-(2-(4-[(2-aminosulfonyl)phenyl]phenylcarbonyl)amino)-4-aminophenylcarboxamide (47 mg, 84%). MS found for $C_{25}H_{21}BrN_5O_4S$ (M+H)$^+$: 566.

Example 25

N-(5-chloro-2-pyridinyl)-(2-(4-[(2-aminosulfonyl)phenyl]phenylcarbonyl)amino)-4-aminophenylcarboxamide

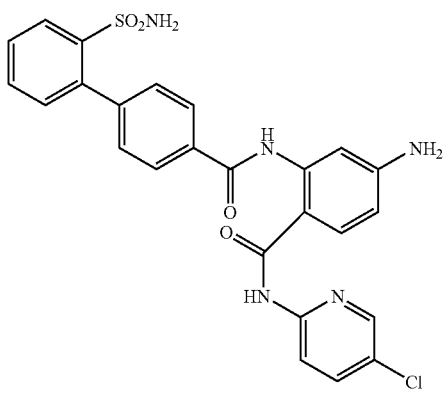

This compound was prepared according to the procedure described in example 50. MS found for $C_{25}H_{21}ClN_5O_4S$ (M+H)$^+$: 522.

Example 26

N-(5-bromo-2-pyridinyl)-(2-(4-[(2-aminosulfonyl)phenyl]phenylcarbonyl)amino)-4-methylsulfonylaminophenylcarboxamide

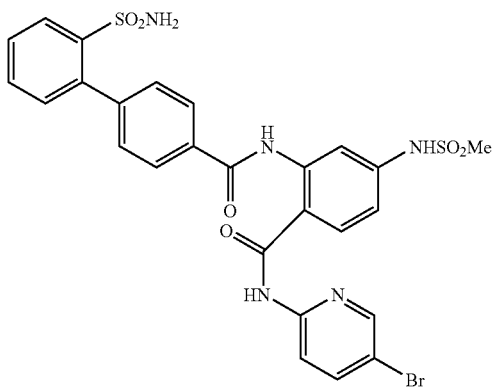

A solution of N-(5-bromo-2-pyridinyl)-(2-(4-[(2-t-butylsulfonyl)phenyl]phenylcarbonyl)amino)-4-aminophenyl carboxamide (62 mg, 0.1 mmol, 1 equiv) in 3 mL of $CH_2Cl_2$ was treated with MsCl (23 mg, 2 equiv) and TEA (0.5 mL) at rt for 4 h. The mixture was washed with water and dried over $MgSO_4$, filtered and evaporated. The residue was refluxed with 2 mL of TFA for 1 h. After removal of TFA by rotavap, the residue was purified by HPLC (C18 reversed phase) eluting with 0.5% TFA in $H_2O/CH_3CN$ to give N-(5-bromo-2-pyridinyl)-(2-(4-[(2-aminosulfonyl)phenyl]phenylcarbonyl)amino)-4-methylsulfonylaminophenylcarboxamide (33 mg, 52%). MS found for $C_{26}H_{23}BrN_5O_6S_2$ (M+H)$^+$: 644.

Example 27

N-(5-chloro-2-pyridinyl)-(2-(4-[(2-aminosulfonyl)phenyl]phenylcarbonyl)amino)-4-methylsulfonylaminophenylcarboxamide

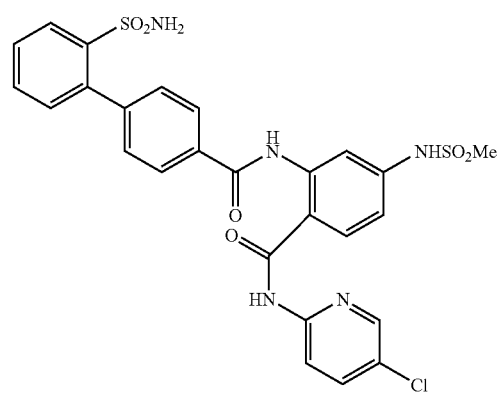

This compound was prepared according to the procedure described in example 53. MS found for $C_{26}U_{23}ClN_5O_6S_2$ (M+H)$^+$: 600.

Example 28

N-(5-bromo-2-pyridinyl)-(2-(4-[(2-aminosulfonyl)phenyl]phenylcarbonyl)amino)-5-aminophenylcarboxamide

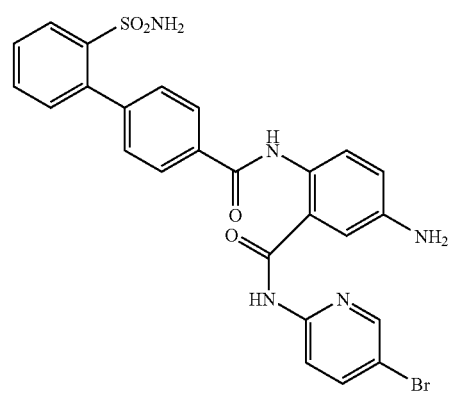

This compound was prepared according to the procedure described in example 50. MS found for $C_{25}H_{21}BrN_5O_4S$ (M+H)$^+$: 566.

Example 29

N-(5-chloro-2-pyridinyl)-(2-(4-[(2-aminosulfonyl)phenyl]phenylcarbonyl)amino)-5-aminophenylcarboxamide

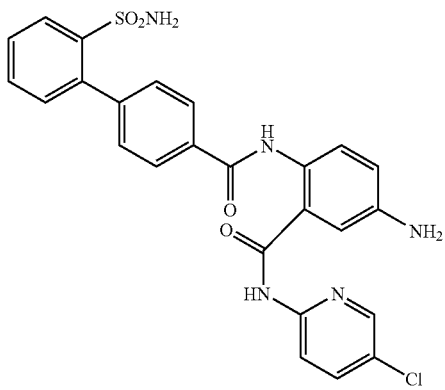

This compound was prepared according to the procedure described in example 50. MS found for $C_{25}H_{21}ClN_5O_4S$ (M+H)$^+$: 522.

Example 30

N-(5-bromo-2-pyridinyl)-(2-(4-amidinophenylcarbonyl)amino)-phenylcarboxamide

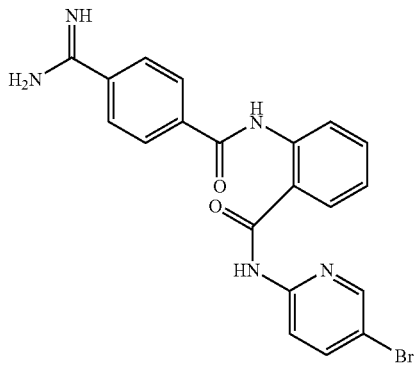

Step 1: A mixture of N-(5-bromo-2-pyridinyl)-(2-amino)phenylcarboxamide (292 mg, 1 mmol, 1.0 equiv), 4-cyano benzoyl chloride (165 mg, 1 equiv), pyridine (3 mL) in 10 mL of dichloromethane was stirred at rt overnight, washed with H$_2$O. The organic layer was dried over MgSO$_4$, filtered, evaporated to give N-(5-bromo-2-pyridinyl)-(2-(4-cyanophenylcarbonyl)amino)-phenylcarboxamide (349 mg, 70%). MS found for $C_{20}H_{14}BrN_4O_2$ (M+H)$^+$: 421.

Step 2: A stream of HCl(g) was bubbled through a 0° C. solution of N-(5-bromo-2-pyridinyl)-(2-(4-cyanophenylcarbonyl)amino)-phenylcarboxamide (49 mg, 0.1 mmol) in 5 mL of methanol until saturation. The mixture was stirred at rt overnight and evaporated. The resulting residue was treated with ammonium acetate (40 mg) in 10 ml methanol at reflux temperature for 2 h. The solvent was removed at reduced pressure and the crude benzamidine was purified by HPLC (C18 reversed phase) eluting with 0.5% TFA in H$_2$O/CH$_3$CN to give N-(5-bromo-2-pyridinyl)-(2-(4-amidinophenylcarbonyl)amino)-phenylcarboxamide (31 mg, 70%). MS found for $C_{20}H_{17}BrN_5O_2$ (M+H)$^+$: 438.

Examples 31-60

The following compounds were prepared according to the procedure described previously

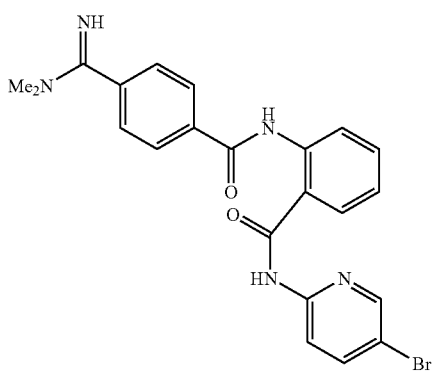

Example 31
MS (M + H): 466

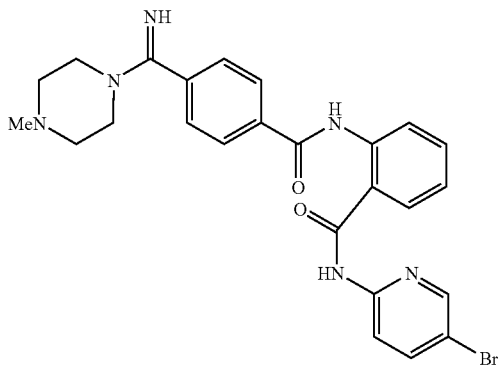

Example 32
MS (M + H): 521

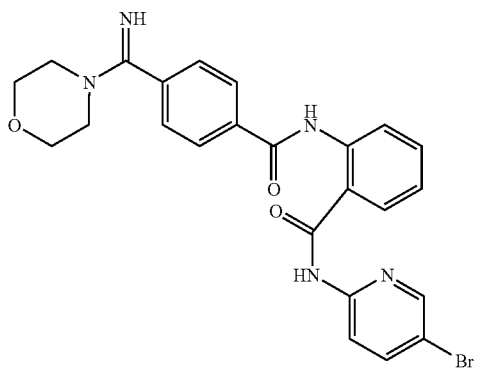

Example 33
MS (M + H): 508

-continued
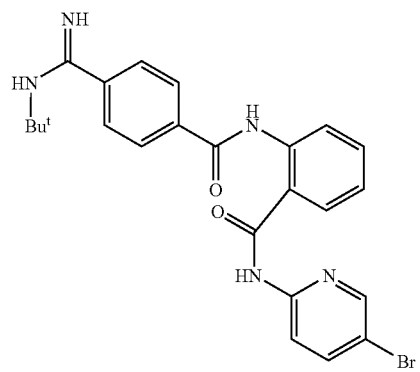
Example 34
MS (M + H): 494
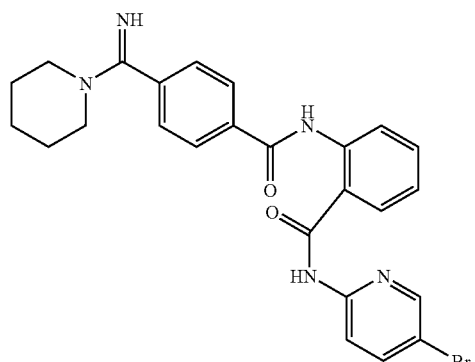
Example 35
MS (M + H): 506
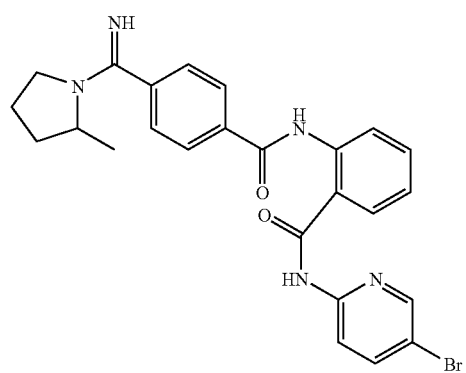
Example 36
MS (M + H): 506
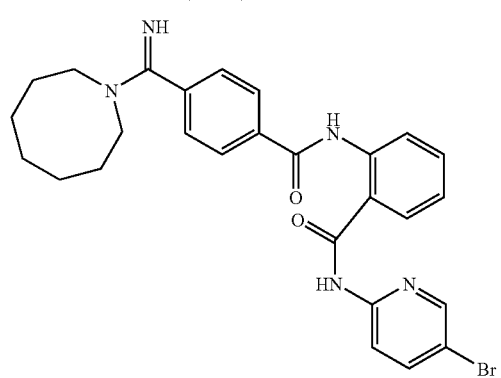
Example 37
MS (M + H): 520
-continued
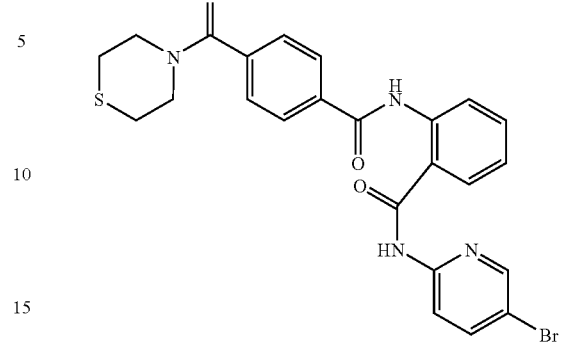
Example 38
MS (M + H): 524

Example 39
MS (M + H): 452
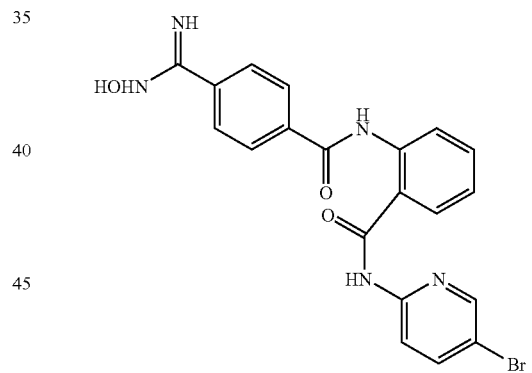
Example 40
MS (M + H): 454
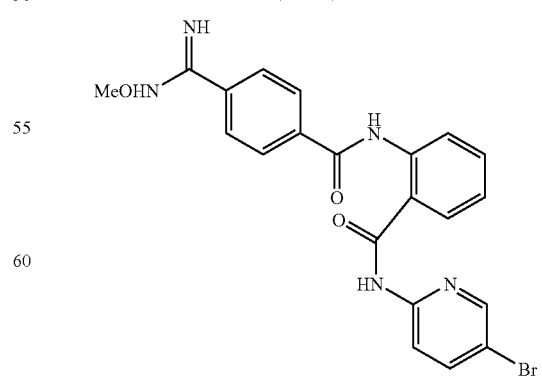
Example 41
MS (M + H): 468

-continued
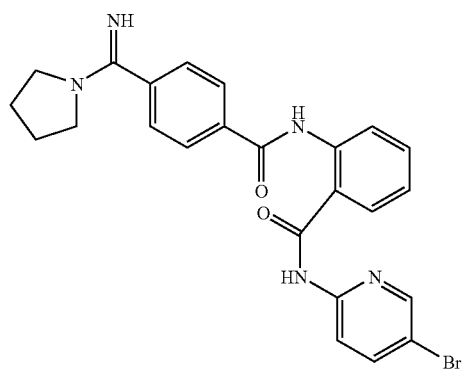
Example 42
MS (M + H): 492
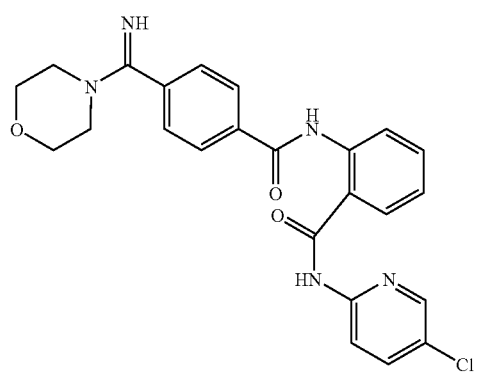
Example 43
MS (M + H): 464
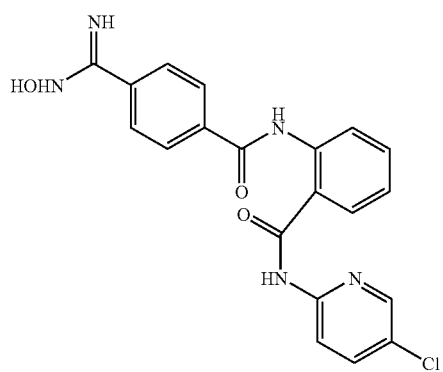
Example 44
MS (M + H): 410
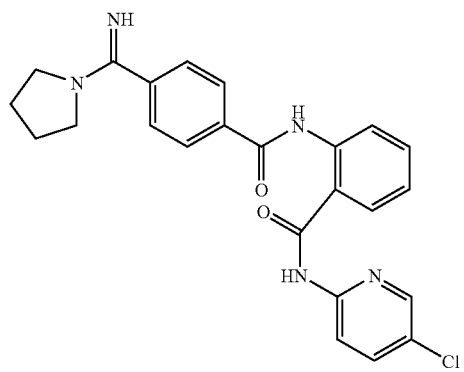
Example 45
MS (M + H): 448
-continued
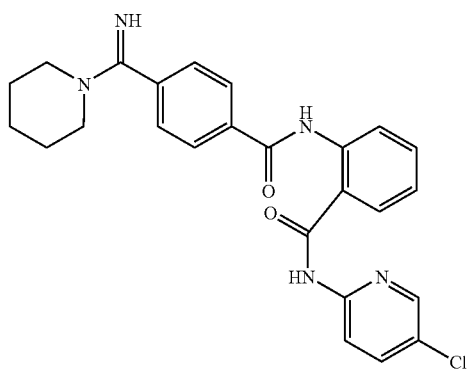
Example 46
MS (M + H): 462
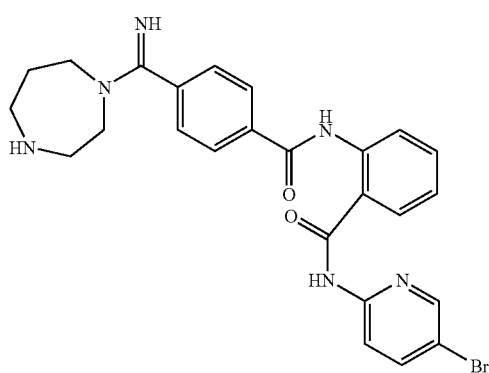
Example 47
MS (M + H): 521
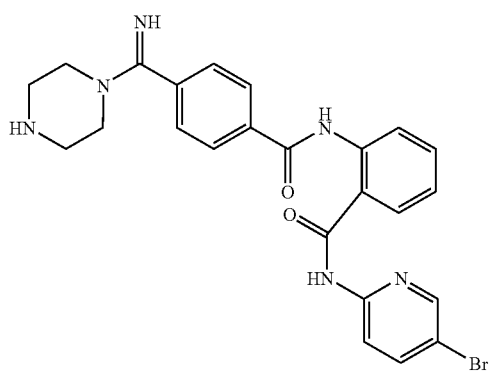
Example 48
MS (M + H): 507
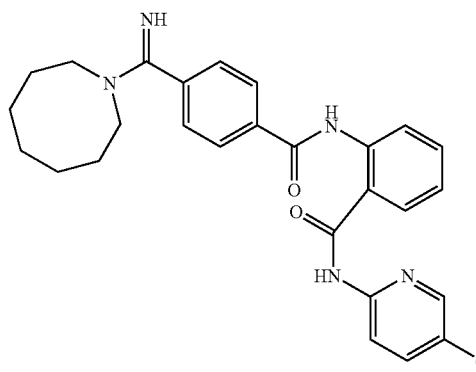
Example 49
MS (M + H): 476

-continued
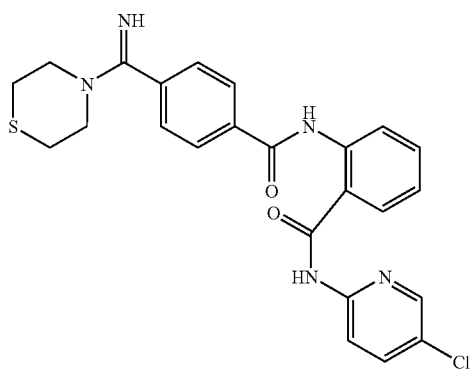
Example 50
MS (M + H): 480
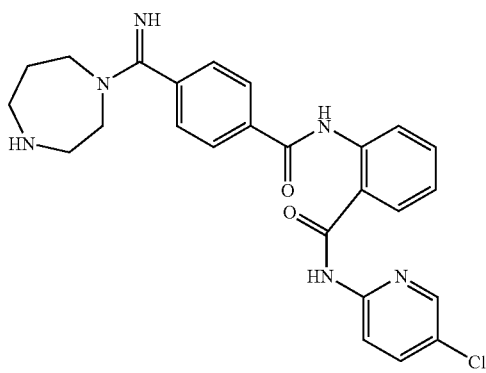
Example 51
MS (M + H): 477
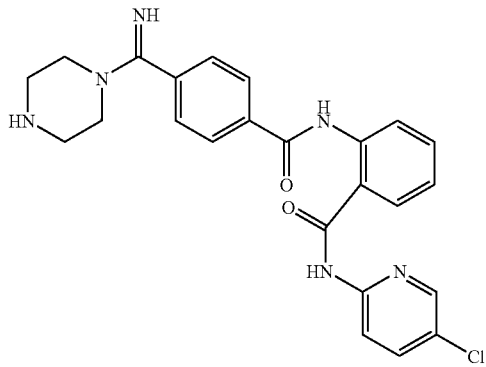
Example 52
MS (M + H): 463
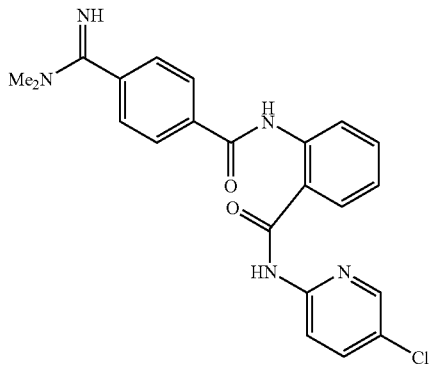
Example 53
MS (M + H): 422
-continued
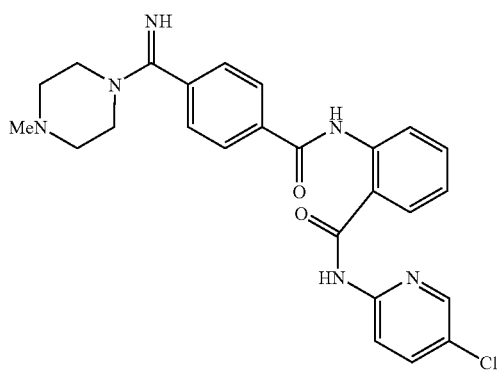
Example 54
MS (M + H): 477
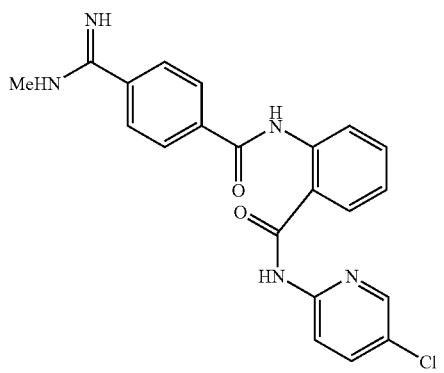
Example 55
MS (M + H): 408
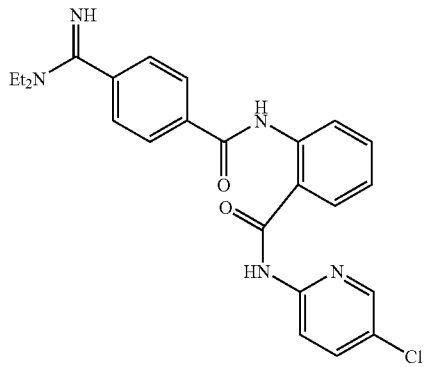
Example 56
MS (M + H): 22
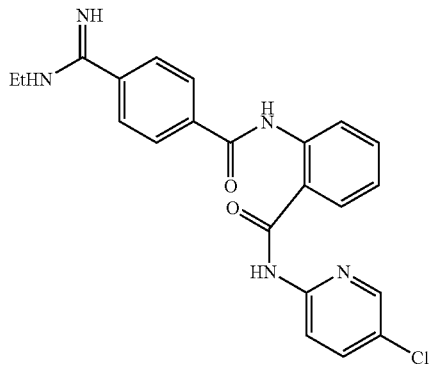
Example 57
MS (M + H): 450

-continued

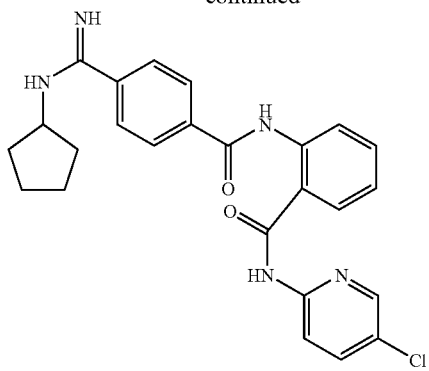

Example 58
MS (M + H): 462

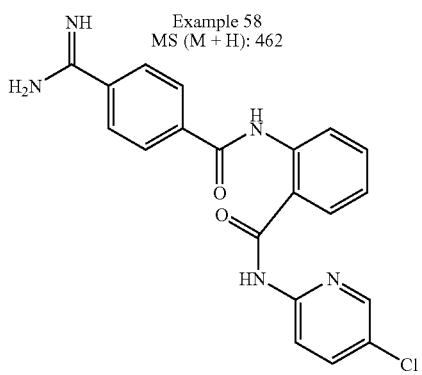

Example 59
MS (M + H): 394

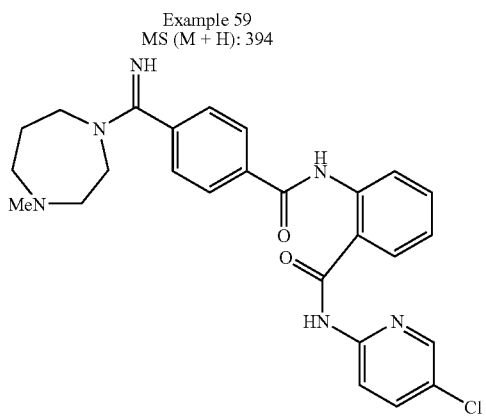

Example 60
MS (M + H): 491

Example 61

N-(5-bromo-2-pyridinyl)-(2-(4-(2-imidazolinyl)phenylcarbonyl)amino)-phenylcarboxamide

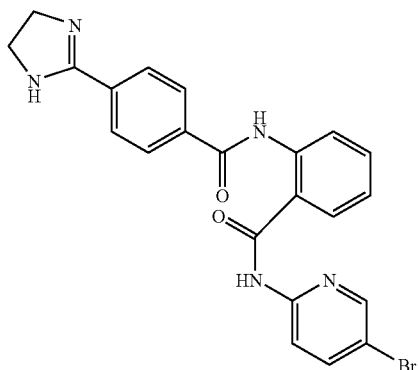

A stream of HCl(g) was bubbled through a 0° C. solution of N-(5-bromo-2-pyridinyl)-(2-(4-cyanophenylcarbonyl)amino)-phenylcarboxamide (49 mg, 0.1 mmol) in 5 mL of methanol until saturation. The mixture was stirred at rt overnight and evaporated. The resulting residue was treated with ethylene diamine (40 mg) in 10 ml methanol at reflux temperature for 2 h. The solvent was removed at reduced pressure and the crude benzamidine was purified by HPLC (C18 reversed phase) eluting with 0.5% TFA in $H_2O$/$CH_3CN$ to give N-(5-bromo-2-pyridinyl)-(2-(4-(2-imidazolinyl)phenylcarbonyl)amino)-phenylcarboxamide (41 mg, 89%). MS found for $C_{22}H_1BrN_5O_2$ (M+H)$^+$: 464.

Examples 62-70

The following compounds were prepared according to the procedure previously described

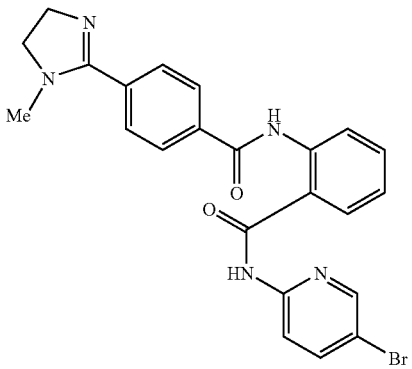

Example 62

MS (M+H): 478

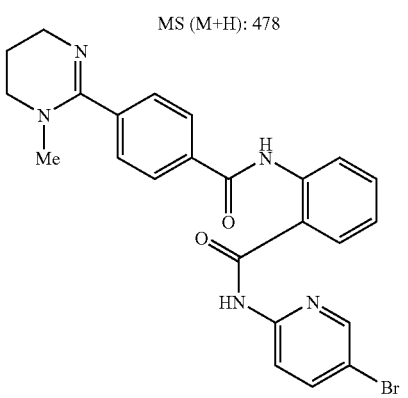

Example 63

MS (M+H): 492

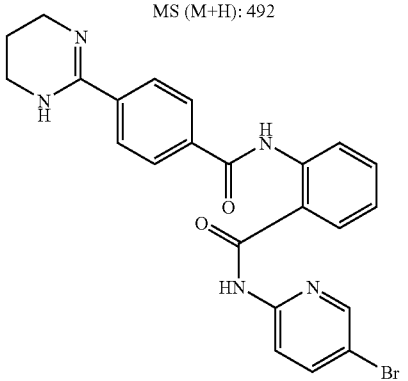

Example 64

MS (M+H): 478

Example 65
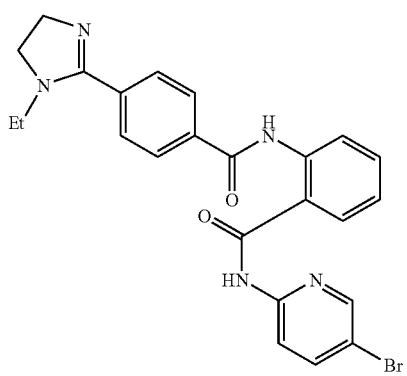
MS (M+H): 492
Example 66
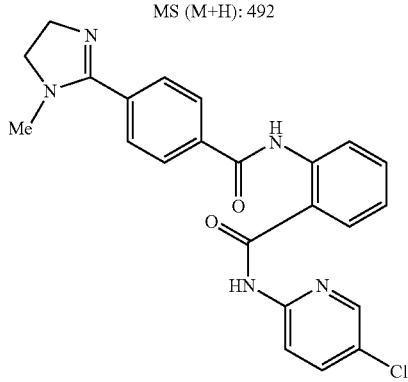
MS (M+H): 434
Example 67
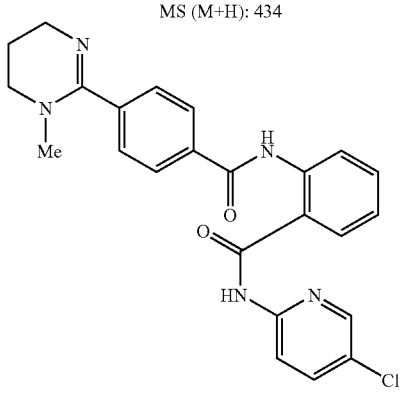
MS (M+H): 448
Example 68
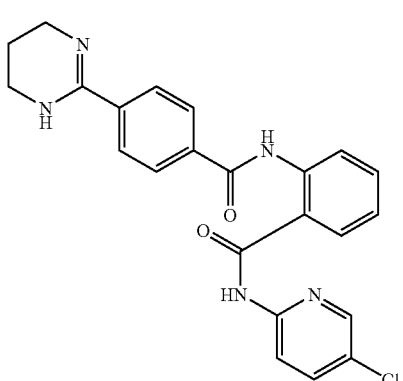
MS (M+H): 434
Example 69
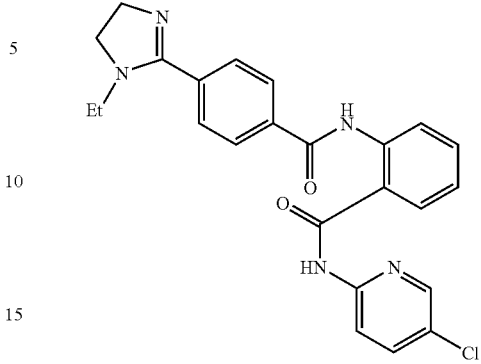
MS (M+H): 448
Example 70
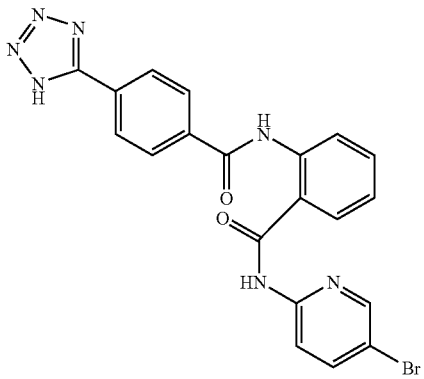
MS (M+H): 420
Example 71
N-(5-bromo-2-pyridinyl)-(2-(4-(5-tetrazolyl)phenyl-carbonyl)amino)-phenylcarboxamide
A mixture of N-(5-bromo-2-pyridinyl)-(2-(4-cyanophenylcarbonyl)amino)-phenylcarboxamide (49 mg, 0.1 mmol) and sodium azide (67 mg, 10 equiv) in 5 mL of DMF was heated at 100¹ C for 24 h. The reaction mixture was diluted with EtOAc, washed with water, dried, filtered and evaporated. The residue was purified by HPLC (C18 reversed phase) eluting with 0.5% TFA in H₂O/CH₃CN to give N-(5-bromo-2-pyridinyl)-(2-(4-(5-tetrazolyl)phenylcarbonyl)amino)-phenylcarboxamide (33 mg, 65%). MS found for $C_{20}H_{15}BrN_7O_2$ (M+H)⁺: 464.

Example 72 and Example 73

N-(5-bromo-2-pyridinyl)-(2-(41-[1,1-doxo(1,4-thiazaperhydroin-4-yl))iminimethylphenylcarbonyl)amino)-phenylcarboxamide and N-(5-bromo-2-pyridinyl)-(2-(4-[1-oxo(1,4-thiazaperhydroin-4-yl))iminimethy]phenylcarbonyl)amino)-phenylcarboxamide

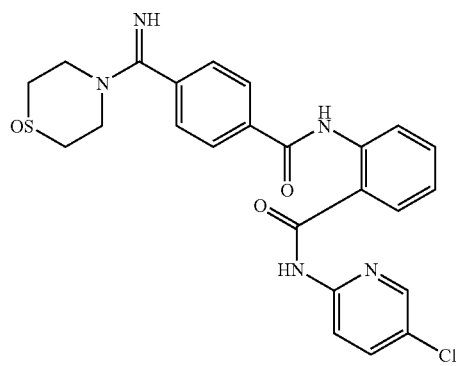

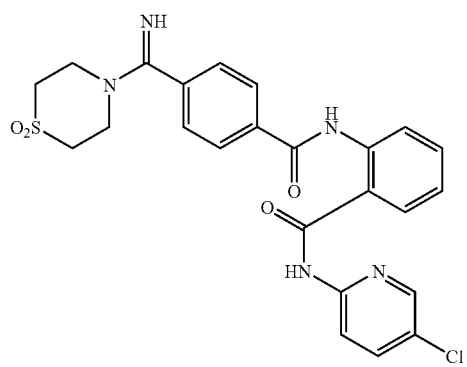

A mixture of N-(5-bromo-2-pyridinyl)-(2-(4-(1,4-thiazaperhydroin-4-yl)iminimethy]phenylcarbonyl)amino)-phenylcarboxamide (48 mg, 0.11 mmol) and and 3 mL of 30% hydrogen doxide was stirred at rt for 12 h. The reaction was quenched with solid Na₂S₂O₃. Purification by HPLC (C18 reversed phase) eluting with 0.5% TFA in H₂O/CH₃CN gave N-(5-bromo-2-pyridinyl)-(2-(4[-[1,1-doxo(1,4-thiazaperhydroin-4-yl))iminimethy]phenylcarbonyl)amino)-phenylcarboxamide (15 mg, 31%), MS found for $C_{24}H_{23}ClN_5O_4S$ (M+H)⁺: 512 and N-(5-bromo-2-pyridinyl)-(2-(4-(1-oxo(1,4-thiazaperhydroin-4-yl))iminimethy]phenylcarbonyl)amino)-phenylcarboxamide (20 mg, 41%). MS found for $C_{24}H)_3ClN_5O_3S$ (M+H)⁺: 496.

Examples 74-79

The following compounds were prepared according to the procedure previously described

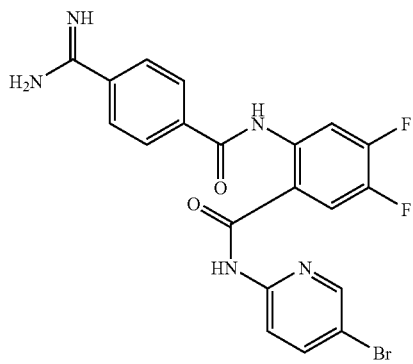

Example 74

MS (M+H): 474

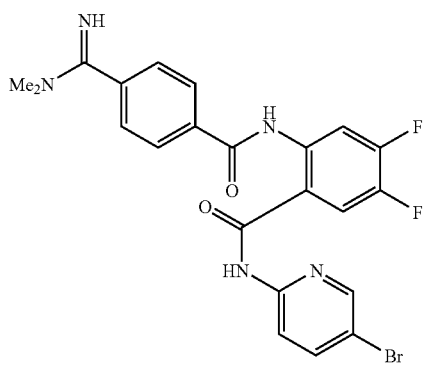

Example 75

MS (M+H): 502

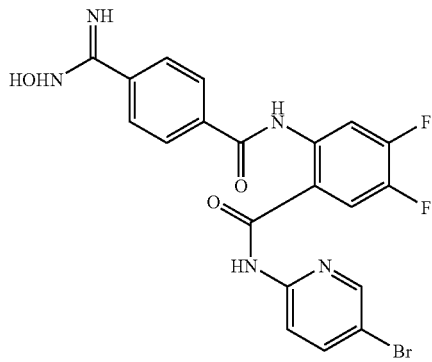

Example 76

MS (M+H): 490

Example 77

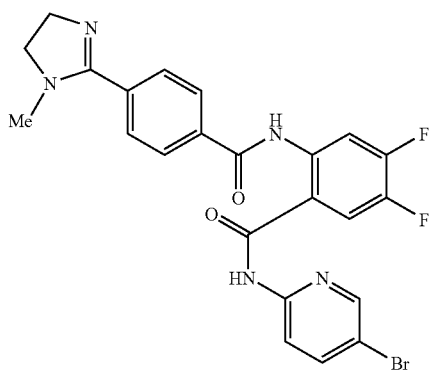

MS (M+H): 514

Example 78

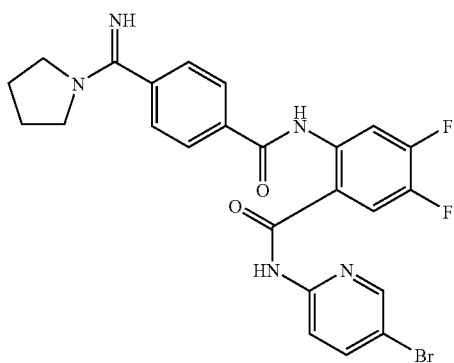

MS (M+H): 528

Example 79

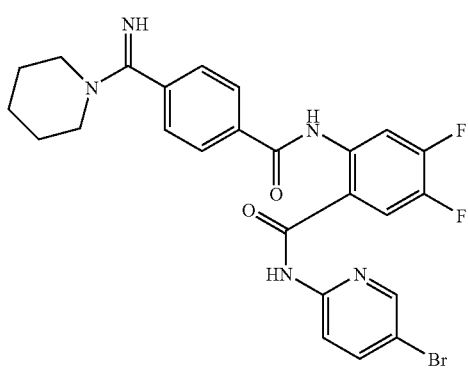

MS (M+H): 542

Example 80

N-(5-bromo-2-pyridinyl)-(2-4-[(2-aminosulfonyl)phenyl]phenylcarbonylamino)-4,5-difluorophenyl-carboxamide

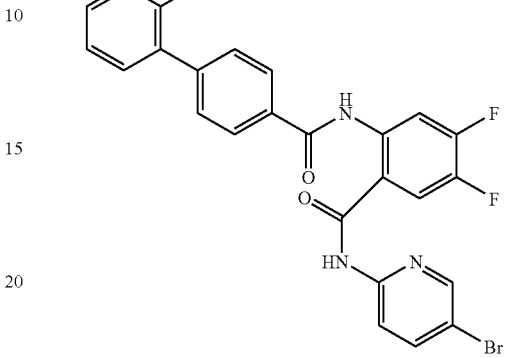

This compound was prepared according to the procedure previously described. MS found for $C_{25}H_{18}BrF_2N_4O_4S$ (M+H)$^+$: 587.

Example 81

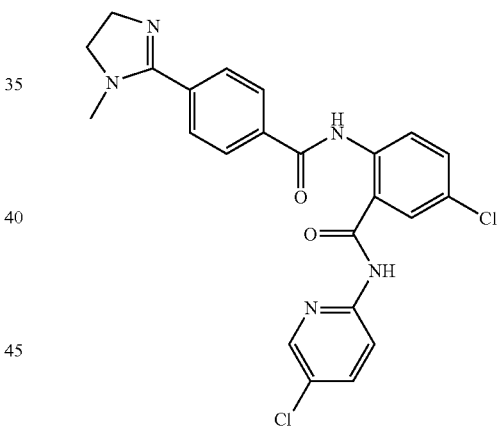

Step 1: To a solution of 2-amino-5-chloropyridine (328 mg, 2.55 mmol) in tetrahydrofuran (5 ml) was 0.5M potassium bis(trimethylsilyl)amide in toluene (10 ml, 5.05 mmol) dropwise at −78° C. After stirred for additional 0.5 hr at −0.78° C., the mixture was added 5-chloroisatoic anhydride (0.5 g, 2.55 mmol) at −78° C. The mixture was warmed up to r.t gradually and stirred overnight. After quenched by saturated ammonium chloride solution, the mixture was extracted by ethyl acetate. The organic layer was dried over magnesium sulfate and concentrated to give (2-amino-5-chlorophenyl)-N-(5-chloro(2-pyridyl))carboxamide (0.71 g. 100%). MS found for C12H9Cl2N3O M$^+$=282, (M+2)$^+$= 284.

Step 2: To a solution of the compound of (2-amino-5-chlorophenyl)-N-(5-chloro(2-pyridyl))carboxamide (0.71 g, 2.52 mmol) in dichloromethane (10ml) was added 3-cyanobenzoyl chloride (417 mg, 2.52 mmol) and pyridine (0.611 ml, 7.55 mmol). The mixture was stirred at r.t.

overnight. The precipitate was filtered and washed with dichloromethane to give N-{4-chloro-2-[N-(5-chloro(2-pyridyl))carbamoyl]phenyl}(4-cyanophenyl)carboxamide as a solid (683 mg, 66%). MS found for C20H12Cl2N4O2 M+=411, (M+2)+=413.

Step 3: To a solution of the compound of N-{4-chloro-2-[N-(5-chloro(2-pyridyl))carbamoyl]phenyl}(4-cyanophenyl)carboxamide (683 mg, 1.66 mmol) in anhydrous pyridine (10 ml) and triethyl amine (1 ml) was saturated with hydrogen sulfide gas at 0° C. The mixture was stirred at r.t. overnight. After the evaporated the solvent, the residue was dissolved in anhydrous acetone (5 ml) and iodomethane (0.1 ml, 16.6 mmol) was added. The mixture was stirred under reflux condition for 2 hrs. After the evaporation of solvent, the residue was dissolved in anhydrous methanol (5 ml) and added a solution of N-methylethylenediamine (0.732 ml, 8.3 mmol) and acetic acid (1.5 ml) in anhydrous methanol (5 ml).The mixture was stirred under reflux condition for 2 hrs. After the evaporation of solvent, the crude residue was purified by RP-HPLC to give N-{4-chloro-2-[N-(5-chloro (2-pyridyl))carbamoyl]phenyl}[4-(1-methyl(2-imidazolin-2-yl))phenyl]carboxamide as a white powder. MS found for C23H19Cl2N5O2 M+=468 (M+2)+=470.

Examples 82-106

The following compounds were prepared according to the procedure previously described

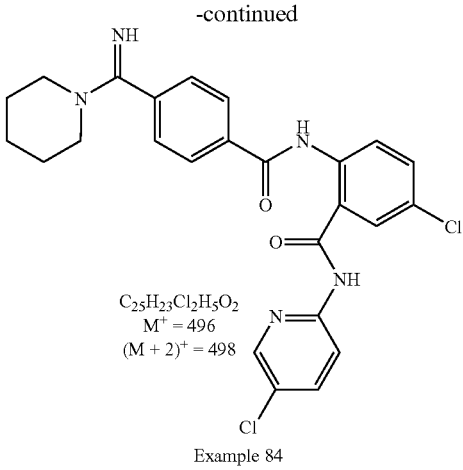

Example 84

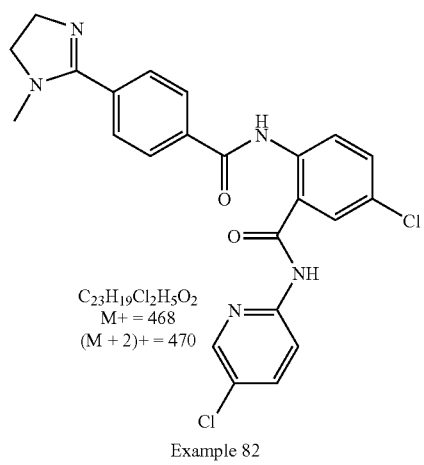

Example 82

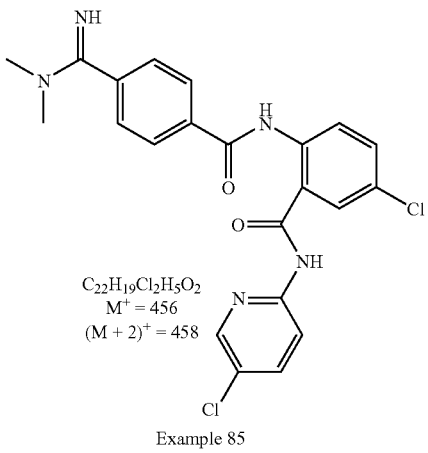

Example 85

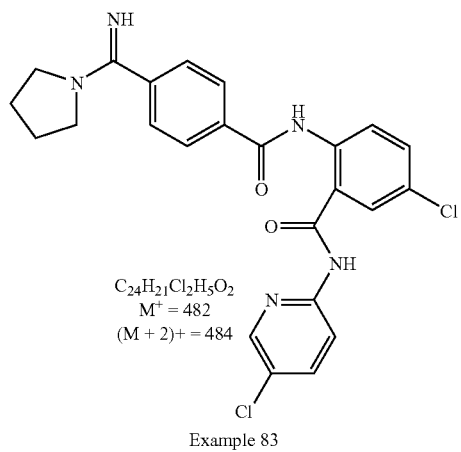

Example 83

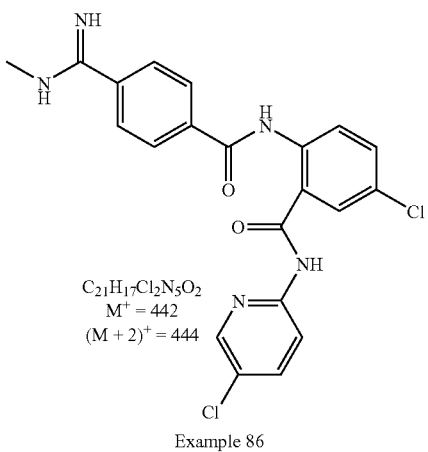

Example 86

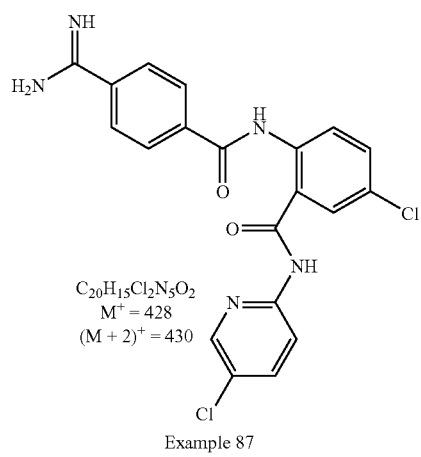
Example 87
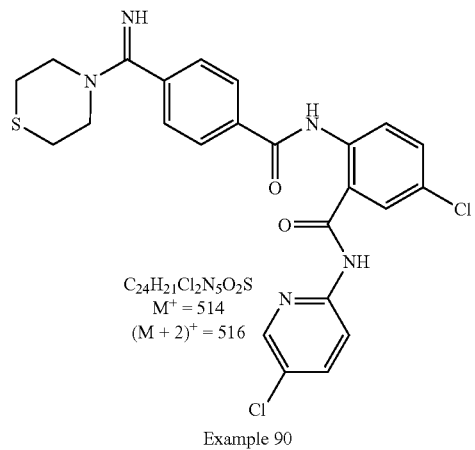
Example 90
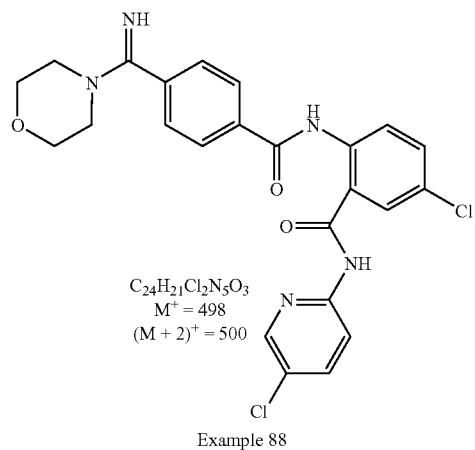
Example 88
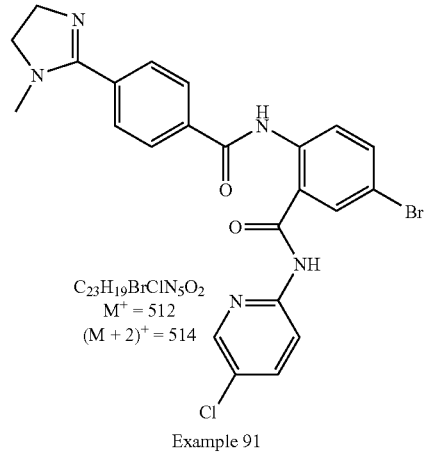
Example 91
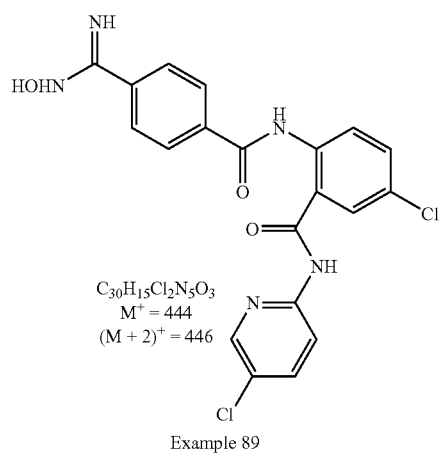
Example 89
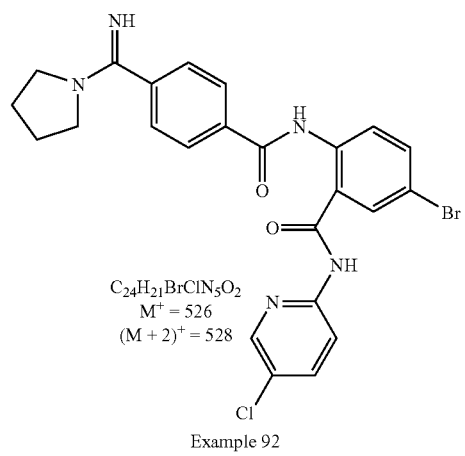
Example 92

-continued
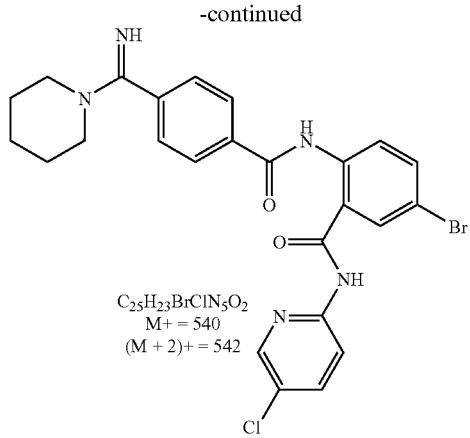
Example 93
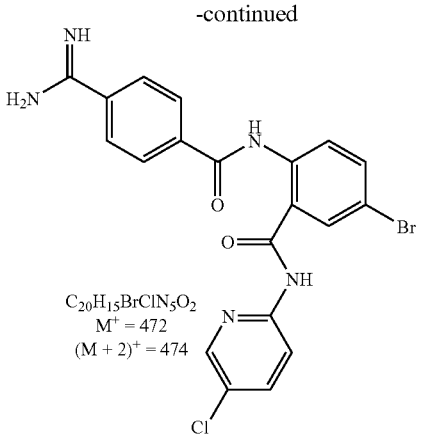
Example 96
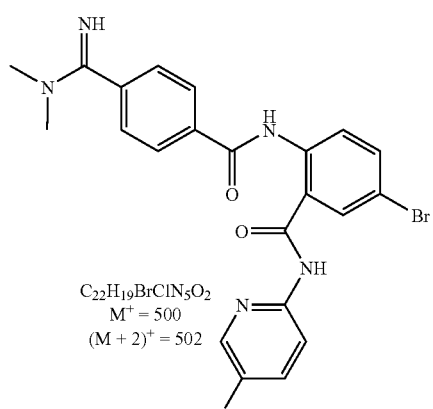
Example 94
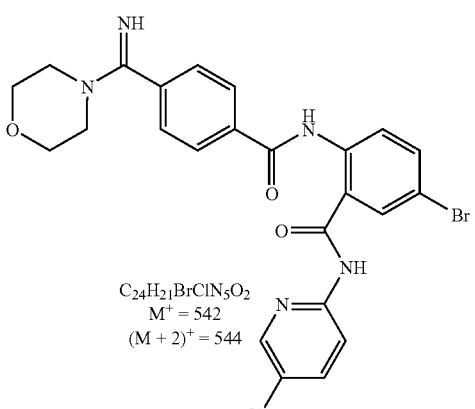
Example 97
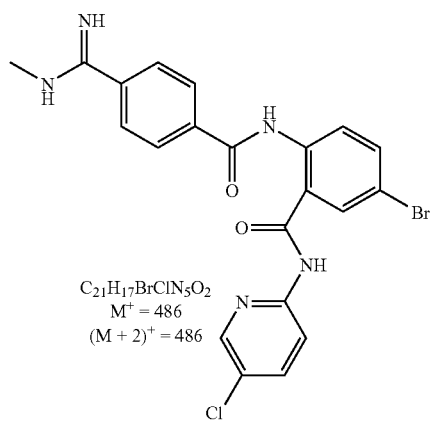
Example 95
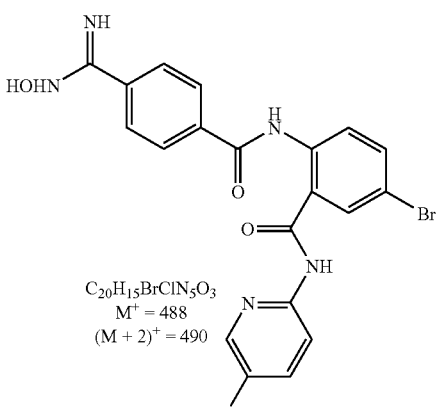
Example 98

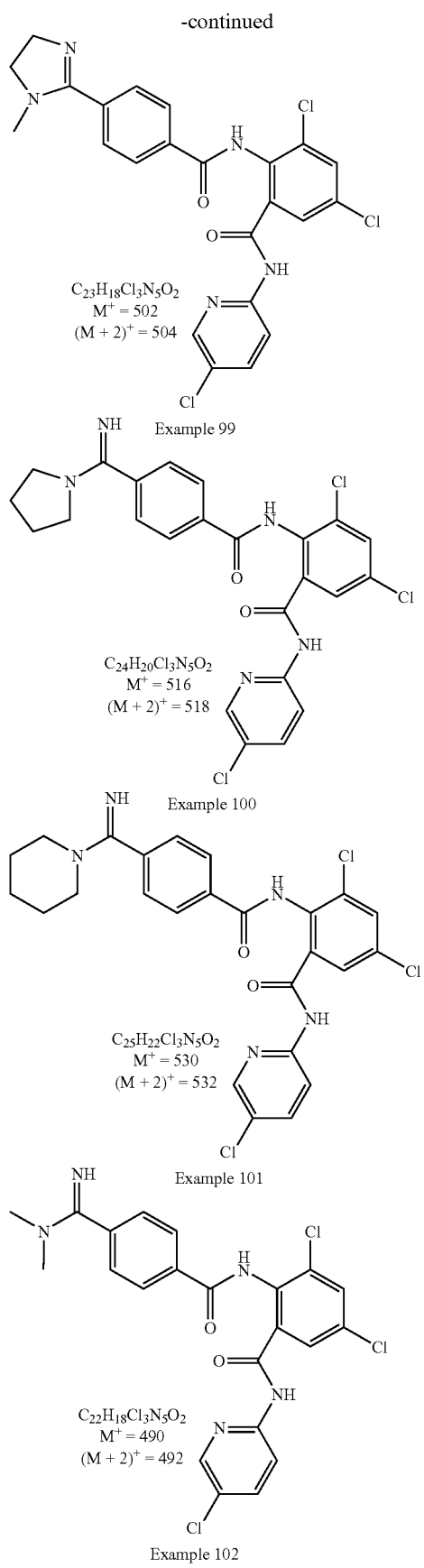
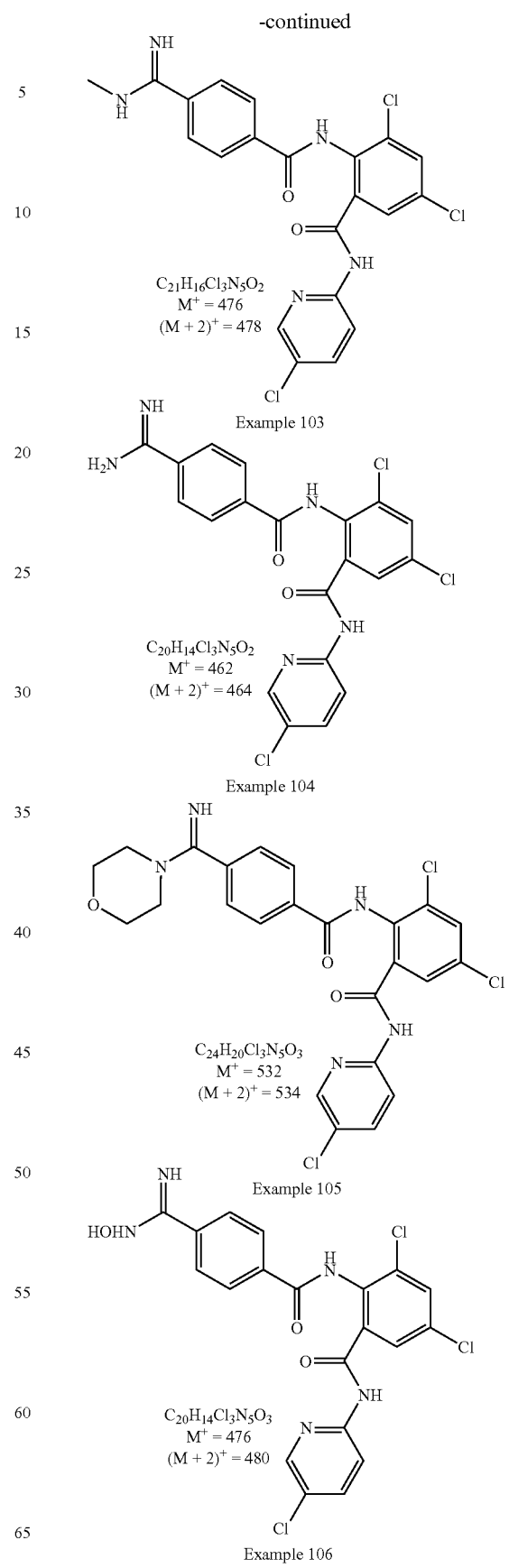

-continued

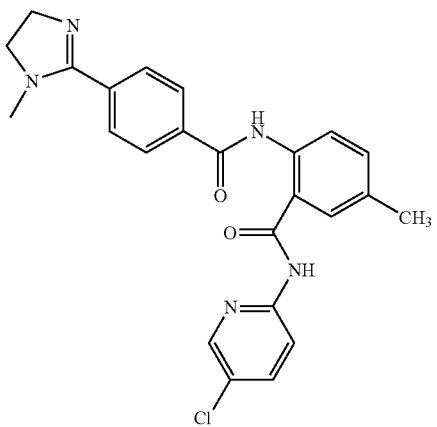

Example 107

Step 1: To a solution of 5-methyl-2-nitrobenzoic acid (1 g, 5.52 mmol) in dichloromethane (5 ml) was added oxalyl chloride (0.964 ml, 11.04 mmol) and a few drops of dimethylformamide. The mixture was stirred at r.t. for 2 hrs. After the evaporation of the solvent, the residue was dissolved in dichloromethane (5 ml). 2-amino-5-chloropyridine (852 mg, 6.62 mmol) and pyridine (1.34 ml, 16.56 mmol) were added to the solution. The mixture was stirred at r.t. overnight. After the evaporation of the solvent, the crude residue was purified by silica gel column chromatography using solvent system 25% ethyl acetate in hexane as eluent to give N-(5-chloro(2-pyridyl))(5-methyl-2-nitrophenyl)carboxamide as a solid (1.48 g, 92%). MS found for $C_{13}H_{10}ClN_3O_3$ $M^+$=291, $(M+2)^+$=293.

Step 2: To a solution of the compound of N-(5-chloro(2-pyridyl))(5-methyl-2-nitrophenyl)carboxamide (1.48 g, 5.1 mmol) in methanol (10 ml) was added 5% Pt/C (1.48 g, 0.19 mmol). The mixture was applied hydrogen balloon at r.t. for 2 hrs. After the filtration by Celite, the filtrate was concentrated to give (2-aminophenyl)-N-(2-pyridyl)carboxamide, C, chloride, N (1.36 g, 100%). MS found for $C_{13}H_{12}ClN_3O$ $M^+$=262, $(M+2)^+$=264.

Step 3: To a solution of the compound of (2-aminophenyl)-N-(2-pyridyl)carboxamide, C, chloride, N (1.36 g, 5.2 mmol) in dichloromethane (10 ml) was added 3-cyanobenzoyl chloride (860 mg, 5.2 mmol) and pyridine (1.26 ml, 15.6 mmol). The mixture was stirred at r.t. overnight. After the evaporation of the solvent, the crude residue was purified by silica gel column chromatography using solvent system 25% ethyl acetate in hexane as eluent to give N-{2-[N-(5-chloro(2-pyridyl))carbamoyl]-4-methylphenyl}(4-cyanophenyl)carboxamide as a solid (830 mg, 41%). MS found for $C_{21}H_{15}ClN_4O_2$ $M^+$=390, $(M+2)^+$=392.

Step 4: To a lotion of the compound of N-{2-[N-(5-chloro(2-pyridyl))carbamoyl]-4-methylphenyl}(4-cyanophenyl)carboxamide (830 mg, 2.1 mmol) in anhydrous methanol (5 ml) and ethyl acetate (10 ml) was saturated with hydrogen chloride gas at 0° C. The mixture was stirred at r.t. overnight. After the evaporated the solvent, the residue was dissolved in anhydrous methanol (5 ml) and N-methylethylenediamine (0.926 ml, 10.5 mmol) was added. The mixture was stirred under reflux condition for 2 hrs. After the evaporation of solvent, the crude residue was purified by RP-HPLC to give N-{2-[N-(5-chloro(2-pyridyl))carbamoyl]-4-methylphenyl}[4-(1-methyl(2-imidazolin-2-yl))phenyl]carboxamide as a white powder. MS found for $C_{24}H_{22}ClN_5O_2$ $M^+$=448, $(M+2)^+$=450.

Examples 108-113

The following compounds were prepared according to the procedure previously described Example 108

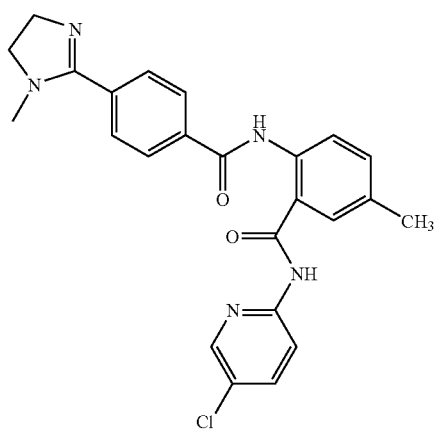

$C_{24}H_{22}ClN_5O_2$
$M^+$ = 448
$(M+2)^+$ = 450

Example 109

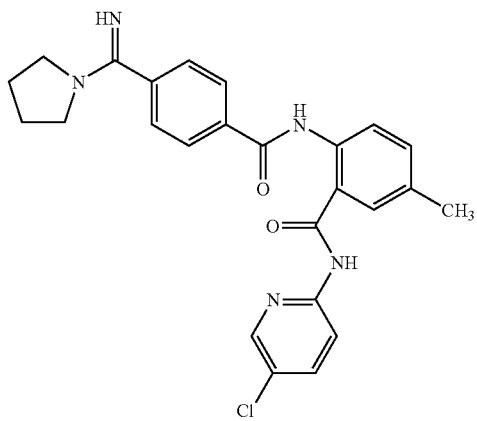

$C_{25}H_{24}ClN_5O_2$
$M^+$ = 462
$(M+2)^+$ = 464

Example 110

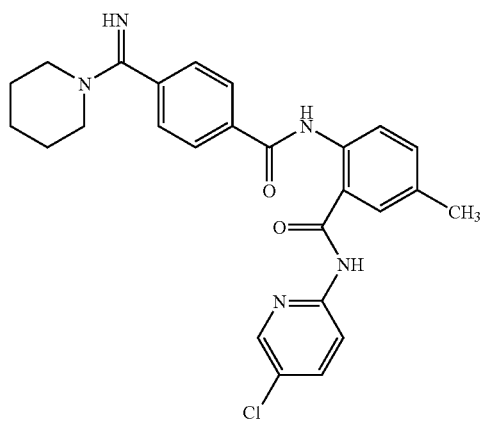

C₂₆H₂₆ClN₅O₂
M⁺ = 476
(M+2)⁺ = 478

Example 111

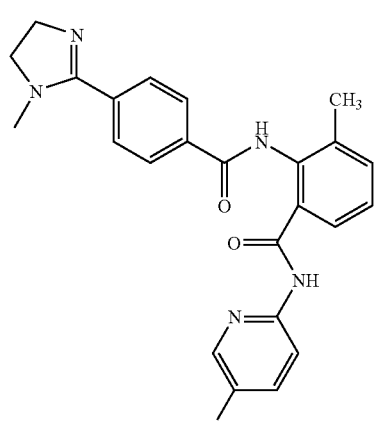

C₂₄H₂₂ClN₅O₂
M⁺ = 448
(M+2)⁺ = 450

Example 112

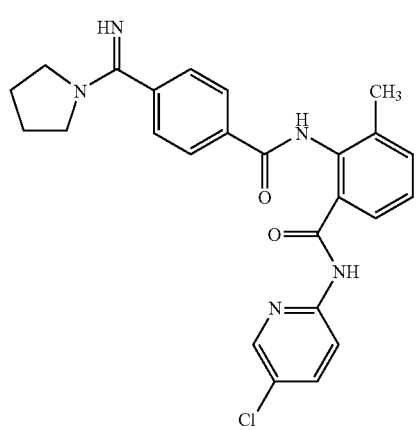

C₂₅H₂₄ClN₅O₂
M⁺ = 462
(M+2)⁺ = 464

Example 113

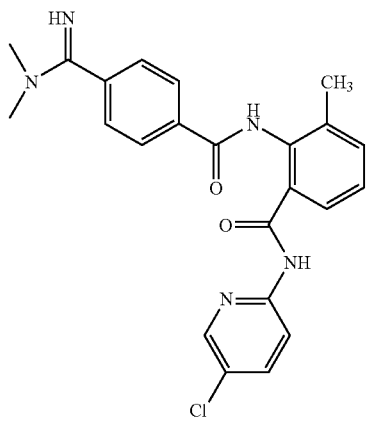

C₂₃H₂₂ClN₅O₂
M⁺ = 436
(M+2)⁺ = 438

Example 114

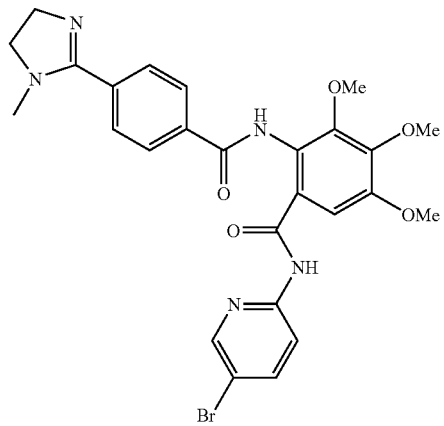

Step 1: To a solution of 3,4,5-trimethoxy-2-nitrobenzoic acid (0.5 g, 1.95 mmol) in dichloromethane (5 ml) was added oxalyl chloride (0.34 ml, 3.9 mmol) and a few drops of dimethylformamide. The mixture was stirred at r.t. for 2 hrs. After the evaporation of the solvent, the residue was dissolved in dichloromethane (5 ml). 2-amino-5-bromopyridine (0.81 g, 4.7 mmol) and pyridine (0.94 ml, 11.7 mmol) were added to the solution. The mixture was stirred at r.t. overnight. After the evaporation of the solvent, the crude residue was purified by silica gel column chromatography using solvent system 25% ethyl acetate in hexane as eluent to give N-(5-bromo(2-pyridyl))(3,4,5-trimethoxy-2-nitrophenyl)carboxamide as a solid (790 mg, 98%). MS found for C15H14BrN3O6 M⁺=412, (M+2)⁺=414.

Step 2: To a solution of the compound of N-(5-bromo(2-pyridyl))(3,4,5-trimethoxy-2-nitrophenyl)carboxamide (790 mg, 1.92 mmol) in ethyl acetate (5 ml) was added tin chloride (II) hydrate (1.73 g, 7.67 mmol). The mixture was stirred under reflux condition for 2 hrs. After filtered by Celite, the filtrate was added 1N sodium hydroxide solution and extracted with ethyl acetate. The organic layer was dried over magnesium sulfate and concentrated to give (2-amino-3,4,5-trimethoxyphenyl)-N-(5-bromo(2-pyridyl))carboxamide (570 mg, 77%). MS found for C15H16BrN3O4 M+=382, (M+2)+=384.

Step 3: To a solution of the compound of (2-amino-3,5-trimethoxyphenyl)-N-(5-bromo(2-pyridyl))carboxamide (570 mg; 1.49 mmol) in dichloromethane (5 ml) was added 3-cyanobenzoyl chloride (247 mg, 1.49 mmol) and pyridine (0.362 ml, 4.48 mmol). The mixture was stirred at r.t. overnight. After the evaporation of the solvent, the crude residue was purified by silica gel column chromatography using solvent system 25% ethyl acetate in hexane as eluent to give N-{6-[N-(5-bromo(2-pyridyl))carbamoyl]-2,3,4-trimethoxyphenyl}(4-cyanophenyl)carboxamide as a solid (680 mg, 69%). MS found for C23H19BrN4O5 M+=511, (M+2)+=513.

Step 4: To a solution of the compound of N-{6-[N-(5-bromo(2-pyridyl))carbamoyl]-2,3,4-trimethoxyphenyl}(4-cyanophenyl)carboxamide (680 mg, 1.33 mmol) in anhydrous methanol (5 ml) and ethyl acetate (10 ml) was saturated with hydrogen chloride gas at 0° C. The mixture was stirred at r.t. overnight. After the evaporated the solvent, the residue was dissolved in anhydrous methanol (5 ml) and N-methylethylenediamine (0.586 ml, 6.65 mmol) was added. The mixture was stirred under reflux condition for 2 hrs. After the evaporation of solvent, the crude residue was purified by RP-HPLC to give N-{6-[N-(5-bromo(2-pyridyl))carbamoyl]-2,3,4-trimethoxyphenyl}[4-(1-methyl(2-imidazolin-2-yl))phenyl]carboxamide as a white powder (240 mg, 32%). MS found for C26H26BrN5O5 M+=568, (M+2)+=570.

Examples 115-118

The following compounds were prepared according to the procedure previously described Example 115

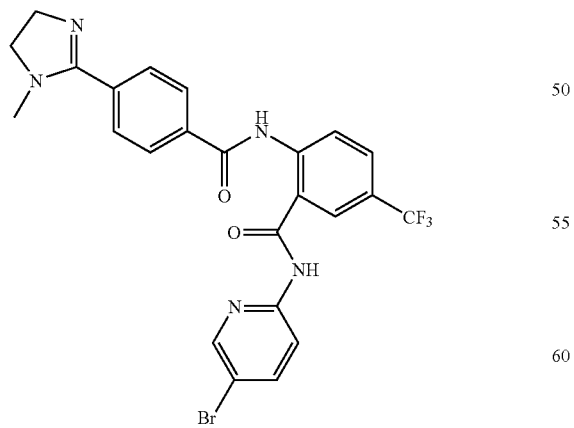

C24H19BrF3N5O2
M+ = 546
(M+2)+ = 548

Example 116

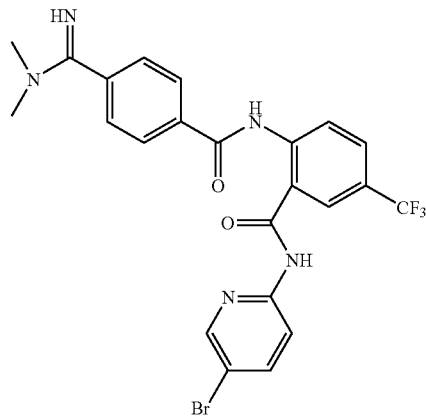

C23H19BrF3N5O2
M+ = 534
(M+2)+ = 536

Example 117

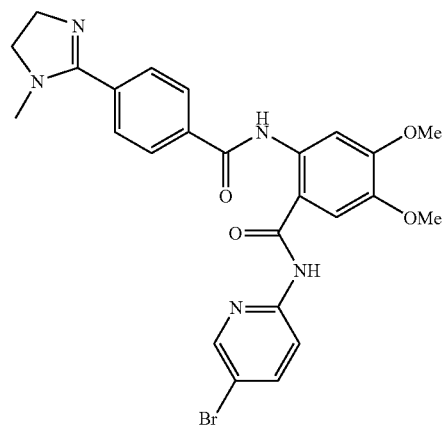

C25H24BrN5O4
M+ = 494
(M+2)+ = 496

Example 118

C24H24BrN5O4
M+ = 482
(M+2)+ = 484

Example 119

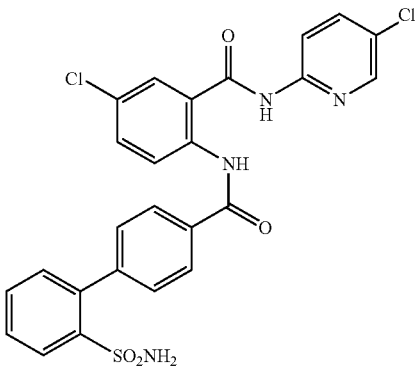

Step 1: To a solution of 4-{2-[((tert-butyl)amino]sulfonyl}phenyl]benzoic acid (167 mg, 0.5 mmol) in dichloromethane (5 ml) was added oxalyl chloride (0.09 ml, 1 mmol) and a few drops of dimethylformamide. The mixture was stirred at r.t. for 2 hrs. After the evaporation of the solvent, the residue was dissolved in dichloromethane (5 ml). The compound of (2-amino-5-chlorophenyl)-N-(5-chloro(2-pyridyl))carboxamide (0.17 g, 0.6 mmol) and pyridine (0.122 ml, 1.5 mmol) were added to the solution. The mixture was stirred at r.t. overnight. The solvent was evaporated to give (2-{[4-(2-{[(tert-butyl)amino]sulfonyl phenyl)phenyl]-carbonylamino}-5-chlorophenyl)-N-(5-chloro(2-pyridyl))carboxamide. MS found for C29H26Cl2N4O4S M+=597, (M+2)+=599.

Step 2: The mixture of the compound of (2-{[4-(2-({[(tert-butyl)amino]sulfonyl}phenyl)phenyl]carbonylamino}-5-chlorophenyl)-N-(5-chloro(2-pyridyl))carboxamide example 12 (0.5 mmol) in trifluoroacetic acid (5 ml) was stirred at r.t. for 5 hrs. After the evaporation of solvent, the crude residue was purified by RP-HPLC to give N-(5-chloro(2-pyridyl))(5-chloro-2-{[4-(2-sulfamoylphenyl)-phenyl]carbonylamino}phenyl)-carboxamide as a white powder (68 mg, 25%). MS found for C25H18Cl2N4O4S M+=541, (M+2)+=543.

Example 120

2-[4-(N-{2-[N-(5-chloro-2-pyridyl)carbamoyl]phenyl}carbamoyl)phenyl]-benzenecarboxamidine

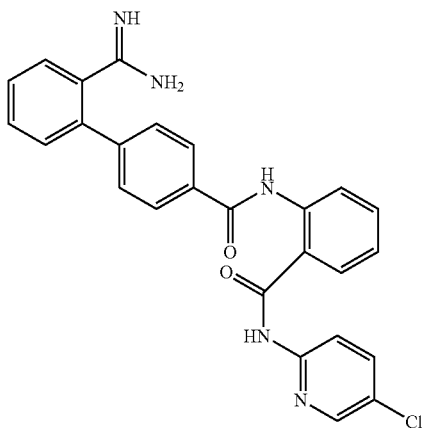

A stream of H₂S (g) was bubbled through a 0° C. solution of N-{2-[N-(5-chloro(2-pyridyl))carbamoyl]phenyl}[4-(2-cyanophenyl)phenyl]carboxamide (100 mg, 0.22 mmol, 1.0 equiv.) in 9 mL pyridine and 1 mL NEt₃ until saturation. The mixture was stirred at rt for 1 day and evaporated. The resulting residue was treated with MeI (94 mg, 0.663 mmol, 3.0 equiv.) in 10 mL acetone at reflux temperature for 1 hr and concentrated to dryness. The resulting residue was treated with a mixture of NH₄OAc (340 mg, 4.42 mmol, 20 equiv.) in 0.5 mL acetic acid and 2 mL methanol at 50° C. for 2 days. The solvent was removed at reduced pressure and the crude benzamidine was purified by HPLC (C18 reversed phase) eluting with 0.1% TFA in H₂O/CH₃CN to give 2-[4-(N-{2-[N-(5-chloro-2-pyridyl)carbamoyl]phenyl}carbamoyl)phenyl]benzenecarboxamidine (15 mg, 15%). MS found for C26H20ClN5O2 (M+H)+: 470.

Example 121

(4-{2-[(dimethylamino)iminomethyl]phenyl}phenyl)-N-{2-[N-(5-chloro(2-pyridyl))carbamoyl]phenyl}carboxamide

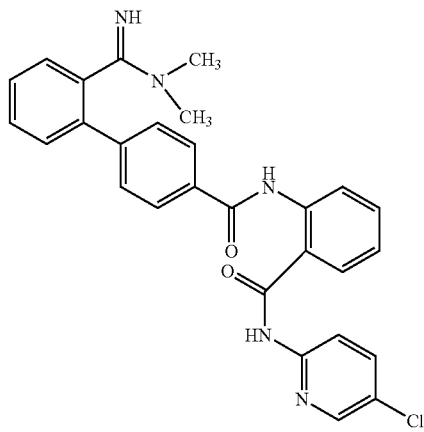

This compound was prepared according to the procedure previously described. MS found for C28H24ClN5O2 (M+H)+: 498.

Example 122

N-{2-[N-(5-chloro(2-pyridyl))carbamoyl]phenyl}{4-[2-((hydroxyamino)iminomethyl)-phenyl]phenyl}carboxamide

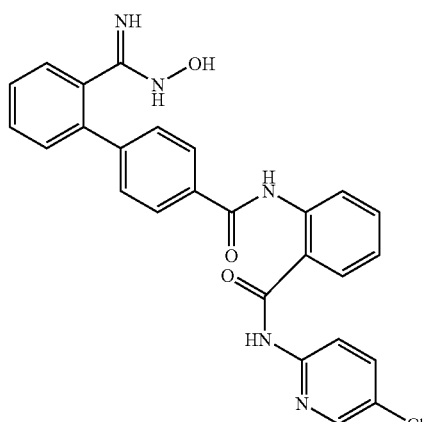

A mixture of N-{2-[N-(5-chloro(2-pyridyl))carbamoyl]phenyl}[4-(2-cyanophenyl)phenyl]carboxamide (14 mg, 0.03 mmol, 1.0 equiv.), hydroxyamine hydrochloride (6.25 mg, 0.09 mmol, 3.0 equiv.) and triethyl amine (0.03 mL, 0.3 mmol, 10.0 equiv.) in ethanol (3 mL) was stirred at rt for 6 days, concentrated and HPLC (C18 reversed phase) eluting with 0.1% TFA in $H_2O/CH_3CN$ to give N-{2-[N-(5-chloro(2-pyridyl))carbamoyl]phenyl}{4-[2-((hydroxyamino)iminomethyl)phenyl]phenyl}carboxamide (4 mg, 27.5%).

MS found for $C_{26}H_{20}ClN_5O_3$ (M+H)$^+$: 486.

Example 123

2-[4-(N-{2-[N-(5-chloro-2-pyridyl)carbamoyl]phenyl}carbamoyl)phenyl]benzamide

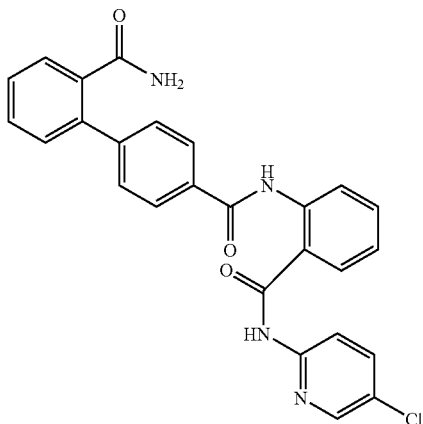

This compound was obtained as one of the side product in Example 122.

MS found for $C_{26}H_{19}ClN_4O_3$ (M+H)$^+$: 471

Example 124

{4-[2-(aminomethyl)phenyl]phenyl}-N-{2-[N-(5-chloro(2-pyridyl))carbamoyl]-phenyl}carboxamide

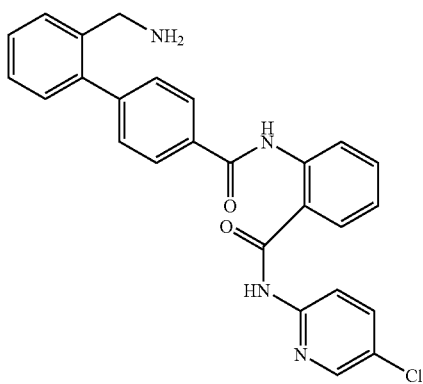

A mixture of N-{2-[N-(5-chloro(2-pyridyl))carbamoyl]phenyl}[4-(2-cyanophenyl)phenyl)carboxamide (200 mg, 0.442 mmol, 1.0 equiv.), cobalt chloride (86 mg, 0.664 mmol, 1.5 equiv.) and sodium borohydride (50 mg, 1.33 mmol, 3.0 equiv.) in DMF (15 mL) was stirred at 0° C. to rt for 3 days. The reaction was quenched with ice cubes, diluted with DCM (100 mL) and filtered through celite. The filtrate was washed with saturated aqueous $NaHCO_3$. The organic layer was dried over $MgSO_4$, filtered, evaporated and HPLC (C18 reversed phase) eluting with 0.1% TFA in $H_2O/CH_3CN$ gave {4-[2-(aminomethyl)phenyl]phenyl}-N-{2-[N-(5-chloro(2-pyridyl))carbamoyl]phenyl}carboxamide (87 mg, 43%). MS found for $C_{26}H_{21}ClN_4O_2$ (M+H)$^+$: 457.

Example 125

[4-(aminomethyl)phenyl]-N-{2-[N-(5-chloro(2-pyridyl))carbamoyl]phenyl}carboxamide

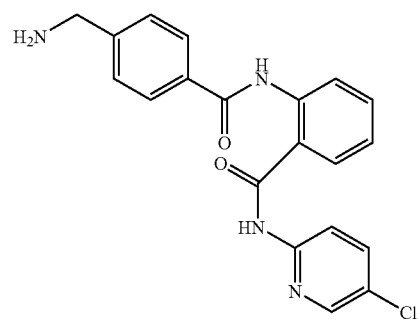

A mixture of N-{2-[N-(5-chloro(2-pyridyl))carbamoyl]phenyl}(4-cyanophenyl)carboxamide (1 g, 2.6 mmol, 1.0 equiv.), cobalt chloride (0.5 g, 3.85 mmol, 1.5 equiv.) and sodium borohydride (0.295 g, 7.8 mmol, 3.0 equiv.) in DMF (20 mL) was stirred at 0° C. to rt for 2.5 hr. The reaction was quenched with ice cubes, diluted with ethyl acetate (100 mL) and filtered through celite. The filtrate was washed with saturated aqueous $NaHCO_3$. The organic layer was dried over $MgSO_4$, filtered, evaporated and HPLC (C18 reversed phase) eluting with 0.1% TFA in $H_2O/CH_3CN$ gave [4-(aminomethyl)phenyl]-N-{2-[N-(5-chloro(2-pyridyl))carbamoyl]phenyl}carboxamide (320 mg, 30%). MS found for $C_{20}H_{17}ClN_4O_2$ (M+H)$^+$: 381.

Example 126

N-{2-[N-(5-chloro(2-pyridyl))carbamoyl]phenyl}{4-[(2-imidazolin-2-ylamino)methyl]-phenyl}carboxamide

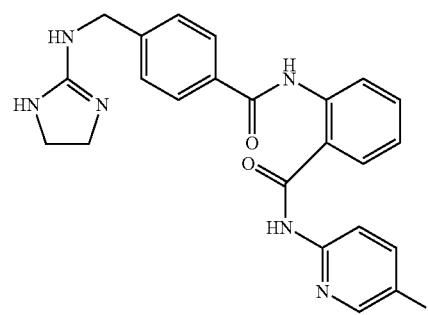

A mixture of [4-(aminomethyl)phenyl]-N-{2-[N-(5-chloro(2-pyridyl))carbamoyl]phenyl}carboxamide (80 mg, 0.21 mmol), 2-methylthio-2-imidazoline hydriodide (77 mg, 0.315 mmol, 1.5 equiv.) and triethyl amine (0.5 mL) in 1 mL DMF was stirred at room temperature overnight, concentrated to dryness and HPLC (C18 reversed phase) eluting with 0.1% TFA in $H_2O/CH_3CN$ gave N-{2-[N-(5-chloro(2-pyridyl))carbamoyl]phenyl}{4-[(2-imidazolin-2-ylamino)methyl]phenyl}carboxamide (13.5 mg, 15%). MS found for $C_{23}H_{21}ClN_6O_2$ (M+H)$^+$: 449.

Example 127

N-{2-[N-(5-chloro(2-pyridyl))carbamoyl]phenyl}(4-{[(1-methyl(2-imidazolin-2-yl))amino]methyl}phenyl)carboxamide

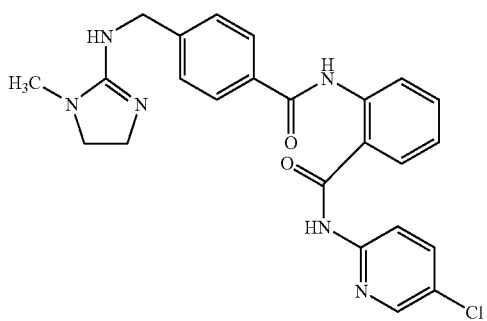

Step 1: To the boiling solution of 2-methylthio-2-imidazoline hydriodide (1 g, 8.4 mmol) in methanol (10 mL) was added MeI (0.78 mL, 12.6 mmol, 1.5 equiv.) dropwise. The reaction mixture was stirred at reflux temperature for 1 hr, concentrated and crystallized with ether to give 1-methyl-2-methylthio-2-imidazoline (1.1 g, 100%).

MS found for $C_5H_{10}N_2S$ (M+H)$^+$: 131.

Step 2: A mixture of [4-(aminomethyl)phenyl]-N-{2-[N-(5-chloro(2-pyridyl))carbamoyl]phenyl}carboxamide (74 mg, 0.195 mmol), 1-methyl-2-methylthio-2-imidazoline (25 mg, 0.195 mmol), NEt3 (2 mL) and pyridine (5 mL) was stirred at 80° C. overnight, concentrated and HPLC (C18 reversed phase)eluting with 0.1% TFA in H2O/CH3CN gave N-{2-[N-(5-chloro(2-pyridyl))carbamoyl]phenyl}(4-{[(1-methyl(2-imidazolin-2-yl))amino]methyl]phenyl)carboxamide (52 mg, 65%). MS found for $C_{24}H_{23}ClN_6O_2$ (M+H)$^+$: 463.

Example 128

N-(5-bromo-2-pyridinyl)-(2-4-[(2-aminosulfonyl)phenyl]phenylcarbonylamino)-5-fluorophenylcarboxamide

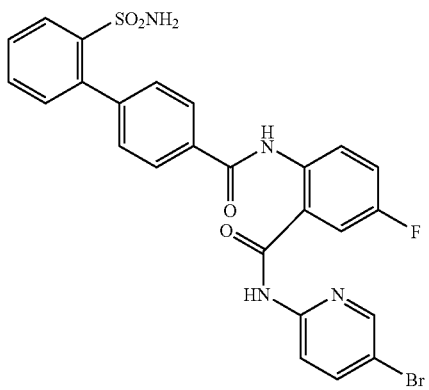

Step 1: A solution of 5-fluoro-2-nitrobenzoic acid (10.0 g, 54 mmol, 1.0 equiv), 2-amino-5-bromopyridine (12.2 g, 1.3 equiv), in 80 mL of pyridine was treated with phosphorous oxychloride (25.3 g, 3.0 equiv) for 30 min. The volatile was evaporated and the residue was redissolved into EtOAc, washed with 1N HCl, saturated aqueous NaHCO₃ and saturated aqueous NaCl. The organic layer was dried over Na₂SO₄, filtered, and evaporated. The volatile was evaporated, and the product was triturated with diethyl ether to give N-(5-bromo-2-pyridinyl)-(2-nitro)-5-fluorophenylcarboxamide (12.5 g, 68%). MS found for $C_{12}H_7BrFN_3O_3$(M+H)$^+$: 340, 342.

Step 2: A solution of N-(5-bromo-2-pyridinyl)-(2-nitro)-5-flurophenylcarboxamide (2.0 g, 5.88 mmol, 1.0 equiv) in 30 mL of EtOAc was treated with SnCl₂2H₂O (5.90 g, 4 equiv) at reflux for 4 h. The volatile was evaporated and the residue was redissolved in EtOAc, washed with saturated aqueous NaHCO₃ and 1N NaOH. The organic layer was dried over MgSO₄, filtered and evaporated to N-(5-bromo-2-pyridinyl)-(2-amino)-5-fluorophenylcarboxamide (1.79 g, 98%). MS found for $C_{12}H_9BrFN_3O$ (M+H)$^+$: 310, 312.

Step 3: A mixture of N-(5-bromo-2-pyridinyl)-(2-amino)-5-fluorophenylcarboxamide (0.310 g, 1 mmol, 1.0 equiv), 4-[(2-t-butylaminosulfonyl)phenyl]benzoyl chloride (0.430 g, 1.3 equiv), pyridine (2 mL) in 10 mL of dichloromethane was stirred at rt overnight The volatile was evaporated and the residue was redissolved into EtOAc, washed with 1N HCl, saturated aqueous NaHCO₃ and saturated aqueous NaCl. The organic layer was dried over Na₂SO₄, filtered, and evaporated. The intermediate was reacted into 5 mL of trifluoroacetic acid at rt overnight. TFA was then evaporated and the product was triturated with diethyl ether, and then with chloroform to give N-(5-bromo-2-pyridinyl)-(2-4-[(2-aminosulfonyl)phenyl]phenylcarbonylamino)-5-fluorophenylcarboxamide (120 mg, 21%). MS found for $C_{25}H_{18}BrFN_4O_4S$ (M+H)$^+$: 569, 571.

Example 129

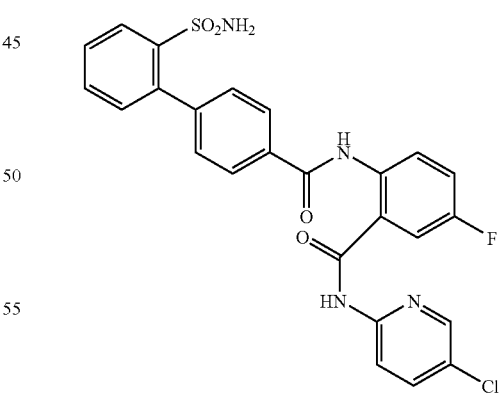

This compound was prepared according to the procedure described in example 2 with the exception of using zinc in acetic acid to reduce nitro-intermediate in step 2. The final product was purified by HPLC (C18 reversed phase) eluting with 0.5% TFA in H₂O/CH₃CN. MS found for $C_{25}H_{18}ClFN_4O_4S$ (M+H)$^+$: 525, 527.

Example 130

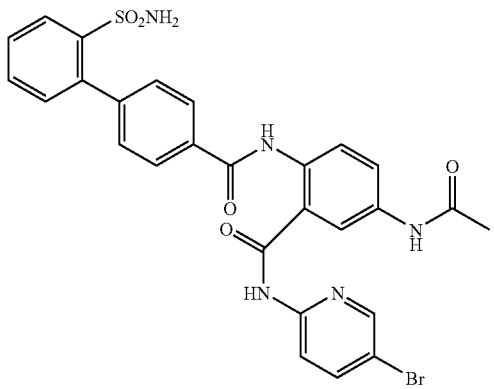

This compound was prepared according to the procedure described in example 2 with the exception of using 5-acetamido-2-nitrobenzoic acid as the starting material in step 1. The final product was purified by HPLC (C18 reversed phase) eluting with 0.5% TFA in $H_2O/CH_3CN$ MS found for $C_{27}H_{22}BrN_5O_5S$ (M+H)$^+$: 608, 610.

Example 131

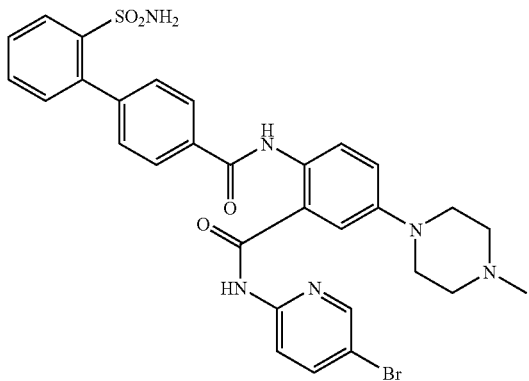

This compound is prepared according to the procedure described in example 2 with the exception of the following step 1b performed on the nitro-intermediate from step 1. The final product was purified by HPLC (C18 reversed phase) eluting with 0.5% TFA in $H_2O/CH_3CN$ MS found for $C_{30}H_{29}BrN_6O_4S$ (M+H)$^+$: 649, 651.

Step 1b: A mixture of N-(5-bromo-2-pyridinyl)-(2-nitro)-5-fluorophenylcarboxamide (0.68 g, 2 mmol, 1.0 equiv), N-methylpiperazine (0.60 g, 3 equiv), and $Cs_2CO_3$ (1.30 g, 2 equiv) in 5 mL of dimethylformamide was stirred at 90° C. overnight. Ethyl acetate was added and washed with $H_2O$. The organic layer was dried over $Na_2SO_4$, filtered, evaporated, purified via flash chromatography on silica gel to give N-(5-bromo-2-pyridinyl)-(2-nitro)-5-(4-N-methylpiperazine)phenylcarboxamide (0.54 g, 65%). MS found for $C_{17}H_{18}BrN_5O_3$ (M+H)$^+$: 419, 421.

Example 132

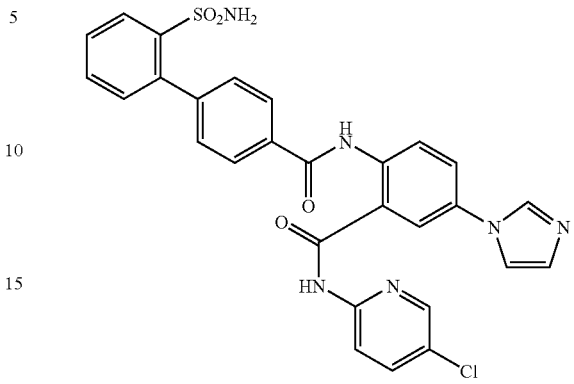

This compound was prepared according to the procedure described in example 5. The final product was purified by HPLC (C18 reversed phase) eluting with 0.5% TFA in $H_2O/CH_3CN$ MS found for $C_2H_{21}ClN_6O_4S$ (M+H)$^+$: 573, 575.

Example 133

N-(5-bromo-2-pyridinyl)-(2-4-[(2-aminosulfonyl)phenyl]phenylaminocarbonylamino)-5-fluorophenyl-carboxamide

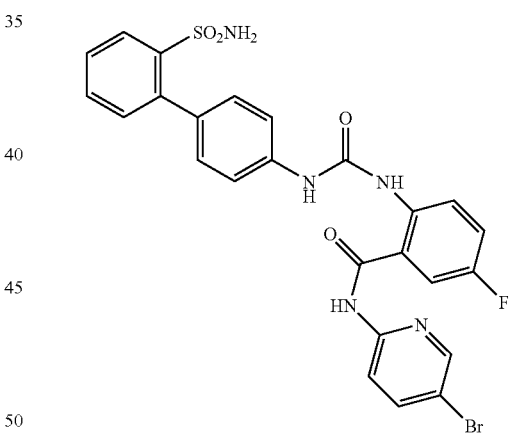

Step 3: A mixture of 4-[(2-t-butylaminosulfonyl)phenyl]phenylamine (0.180 g, 1.2 equiv), N,N'-disuccinimidyl carbonate (0.154 g, 1.2 equiv), 4-methylmorpholine (0.5 mL) in 10 mL of acetonitrile was stirred at rt for 30 min. N-(5-bromo-2-pyridinyl)-(2-amino)-5-fluorophenylcarboxamide (0.155 g, 0.5 mmol, 1.0 equiv) was added and the solution was stirred at rt for 3 hrs. The volatile was evaporated and the residue was redissolved into EtOAc, washed with 1N HCl, saturated aqueous $NaHCO_3$ and saturated aqueous NaCl. The organic layer was dried over $Na_2SO_4$, filtered, and evaporated. The intermediate was reacted into 5 mL of trifluoroacetic acid at rt overnight. TFA was then evaporated and the product was purified by HPLC (C18 reversed phase) eluting with 0.5% TFA in $H_2O/CH_3CN$ to give N-(5-bromo-2-pyridinyl)-(2-4-[(2-aminosulfonyl)phenyl]phenylaminocarbonylamino)-5-fluorophenylcarboxamide (0.053 g, 18%). MS found for $C_{25}H_{19}BrFN_5O_4S$ (M+H)+: 584, 586.

Examples 134-135

N-(5-bromo-2-pyridinyl)-(2-(4-amidinophenylcarbonyl)amino)5-fluorophenylcarboxamide Example 134

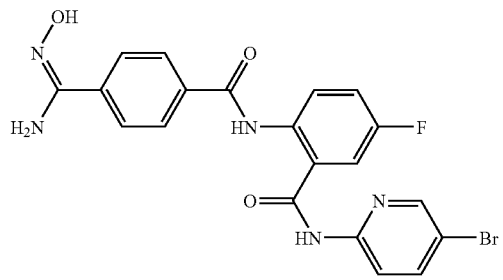

Example 135

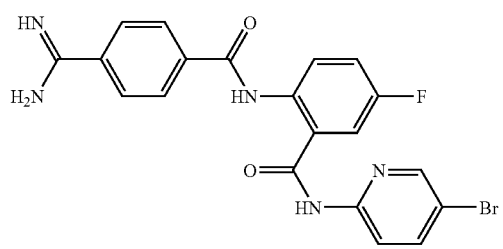

Step 1: A mixture of N-(5-bromo-2-pyridinyl)-(2-amino) 5-fluorophenylcarboxamide (1.24 g, 4 mmol, 1.0 equiv), 4-cyano benzoyl chloride (0.792 g, equiv), and pyridine (3 mL) in 15 mL of dichloromethane was stirred at rt overnight. The volatile was evaporated and the residue was redissolved into EtOAc, washed with 1N HCl, saturated aqueous NaHCO$_3$ and saturated aqueous NaCl. The organic layer was dried over Na$_2$SO$_4$, filtered, and evaporated to give N-(5-bromo-2-pyridinyl)-(2-(4-cyanophenylcarbonyl)amino)5-fluorophenylcarboxamide (1.14 g, 65%). MS found for $C_{20}H_{12}BrFN_4O_2$ (M+H)+: 439, 441.

Step 2: A mixture of N-(5-bromo-2-pyridinyl)-(2-(4-cyanophenylcarbonyl)amino)5-fluorophenylcarboxamide (1.12 g, 2.56 mmol, 1.0 equiv), hydroxylamine-HCl (0.213 g, 1.2 equiv), and triethylamine (1 mL) in 15 mL of ethyl alcohol was stirred at 50° C. overnight. The volatile was evaporated and the residue was redissolved into EtOAc, washed with 1N HCl, saturated aqueous NaHCO$_3$ and saturated aqueous NaCl. The organic layer was dried over Na$_2$SO$_4$, filtered, and evaporated to give N-(5-bromo-2-pyridinyl)-(2-(4-hydroxyamidinophenylcarbonyl)amino)5-fluorophenylcarboxamide (compound Example 194) (0.84 g, 70%). One third of this material was purified by HPLC (C18 reversed phase) eluting with 0.5% TFA in H$_2$O/ CH$_3$CN to yield 0.20 grams (71%). MS found for $C_{20}H_{15}BrFN_5O_3$ (M+H)+: 472, 474.

Step 3: A mixture of N-(5-bromo-2-pyridinyl)-(2-(4-hydroxyamidinophenylcarbonyl)amino)5-fluorophenylcarboxamide (0.56 g, 1.19 mmol, 1.0 equiv) and zinc dust (0.39 g, 5.0 equiv), in 10 mL of acetic acid was stirred at rt for 45 min. The volatile was filtered and evaporated. The residue was purified by HPLC (C18 reversed phase) eluting with 0.5% TFA in H$_2$O/CH$_3$CN give N-(5-bromo-2-pyridinyl)-(2-(4-amidinophenylcarbonyl)amino)5-fluorophenyl-carboxamide (compound Example 195) (0.24 g, 44%).

MS found for $C_{20}H_{15}BrFN_5O_2$ (M+H)+: 456, 458.

Example 136

N-(5-bromo-2-pyridinyl)-(2-(4-(1-methyl-2-imadazolin-2-yl)phenylcarbonyl)amino)5-fluorophenylcarboxamide

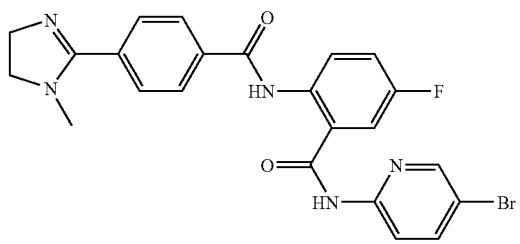

Step 1: A stream of HCl(g) was bubbled through a 0° C. solution of N-(5-bromo-2-pyridinyl)-(2-(4-cyanophenylcarbonyl)amino)5-fluorophenylcarboxamide (1.0 g, 2.3 mmol) in 30 mL of methanol until saturation. The mixture was stirred at rt overnight and evaporated. One-fifth of the resulting residue was treated with (2-aminoethyl)methylamine (0.10 g) in 10 ml methanol at rt overnight. The solvent was removed at reduced pressure and the crude product was purified by HPLC (C18 reversed phase) eluting with 0.5% TFA in H$_2$O/CH$_3$CN to give N-(5-bromo-2-pyridinyl)-(2-(4-(1-methyl-2-imadazolin-2-yl)phenylcarbonyl)amino)5-fluorophenylcarboxamide (0.082 g, 37%). MS found for $C_{23}H_{19}BrFN_5O_2$ (M+H)+: 496, 498.

Examples 137-198

The following compounds were prepared generally according to the procedure described in Example 196.

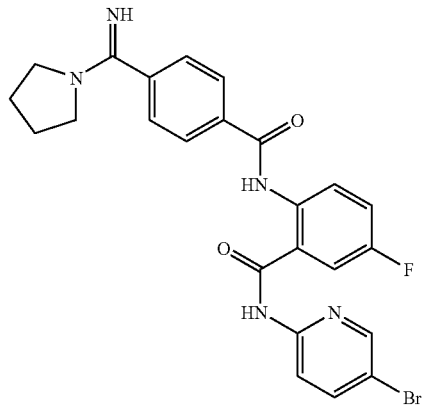

MS (M + H): 510, 512
Example 137

-continued
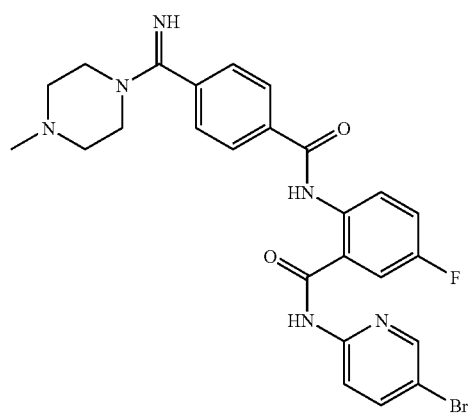
MS (M + H): 539, 541
Example 138
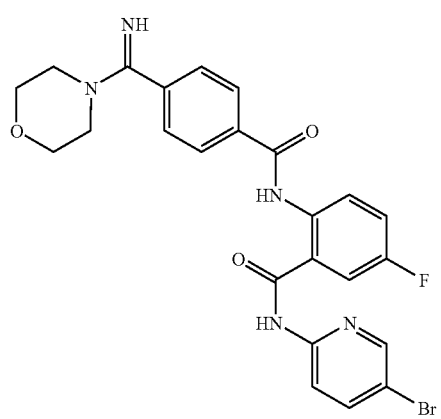
MS (M + H): 526, 528
Example 139
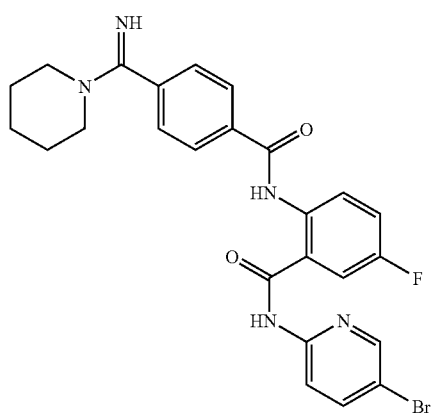
MS (M + H): 524, 526
Example 140
-continued
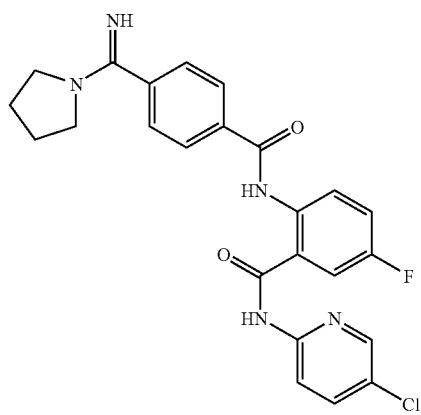
MS (M + H): 466, 468
Example 141
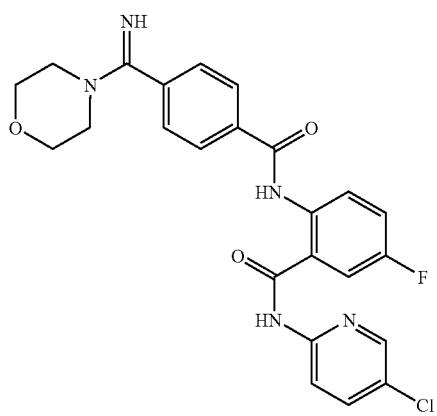
MS (M + H): 440, 442
Example 142
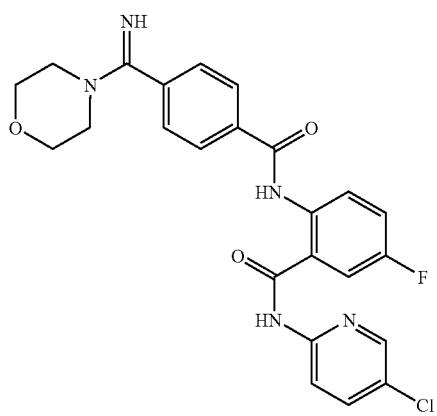
MS (M + H): 482, 484
Example 143

-continued
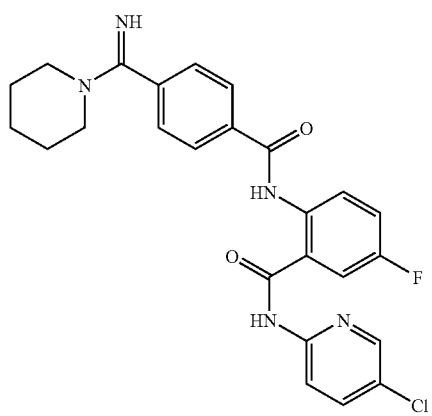
MS (M + H): 480, 482
Example 144
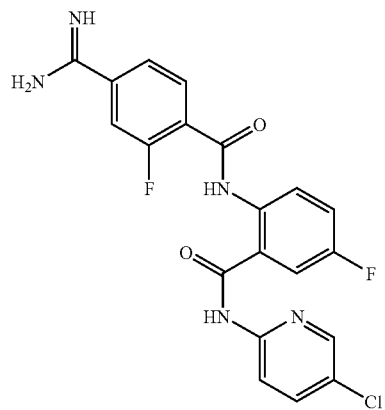
MS (M + H): 430, 432
Example 147
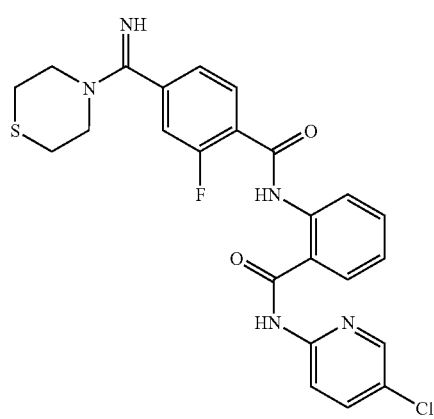
MS (M + H): 498, 500
Example 145
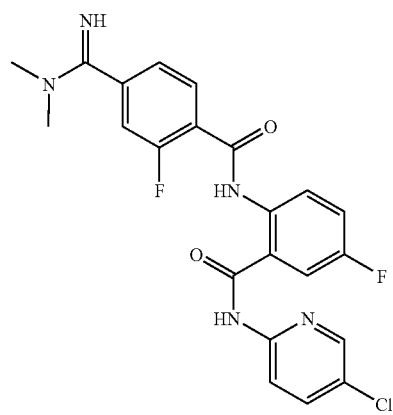
MS (M + H): 458, 460
Example 148
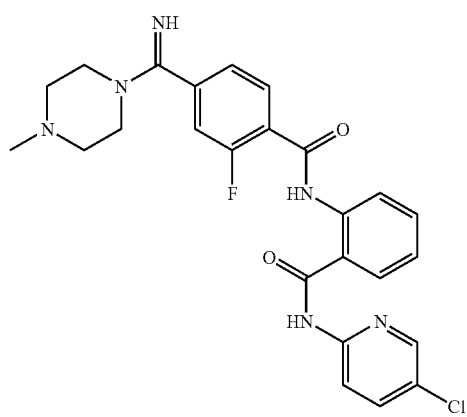
MS (M + H): 495, 497
Example 146
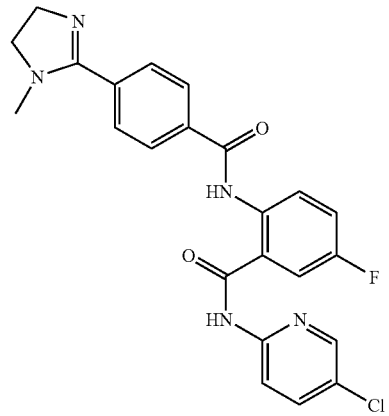
MS (M + H): 452, 454
Example 149

-continued
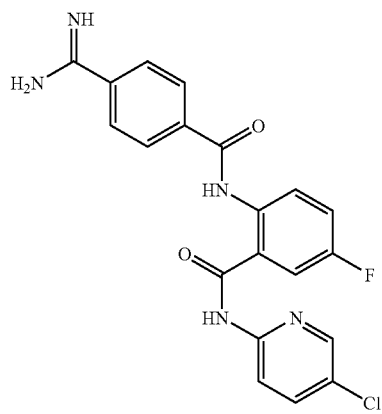
MS (M + H): 412, 414
Example 150
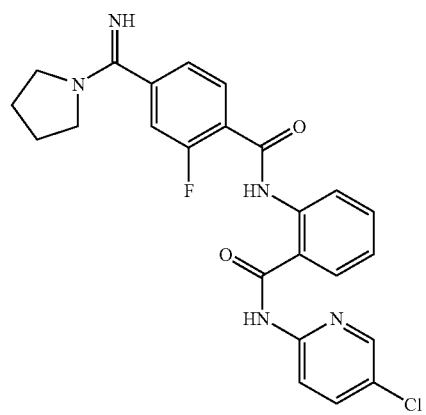
MS (M + H): 466, 468
Example 153
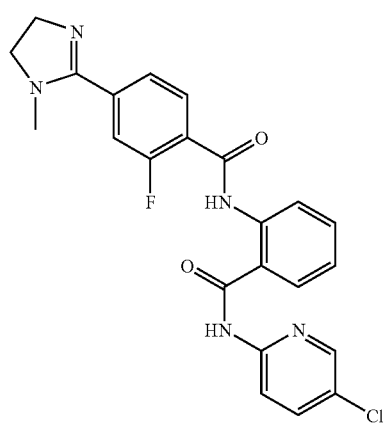
MS (M + H): 452, 454
Example 151
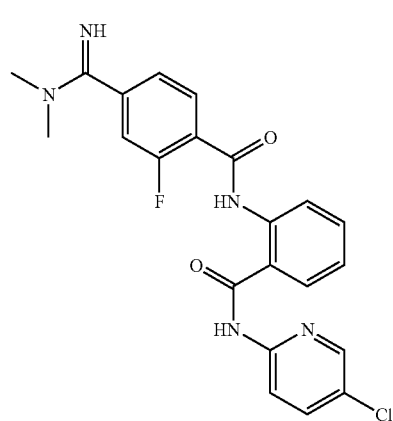
MS (M + H): 440, 442
Example 154
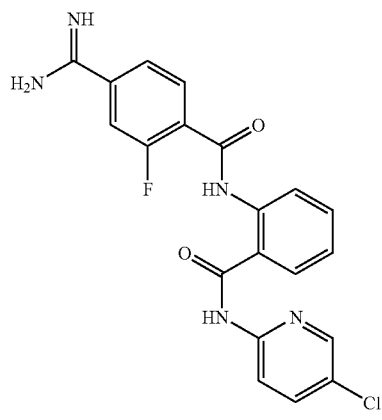
MS (M + H): 412, 414
Example 152
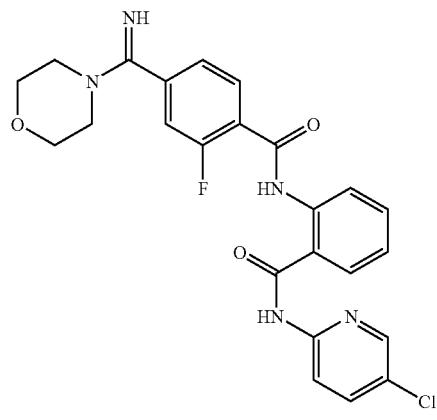
MS (M + H): 482, 484
Example 155

-continued
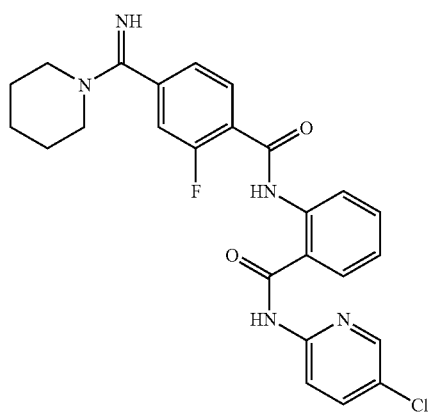
MS (M + H): 480, 482
Example 156
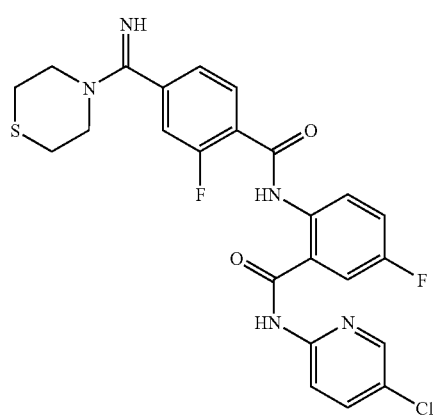
MS (M + H): 516, 518
Example 157
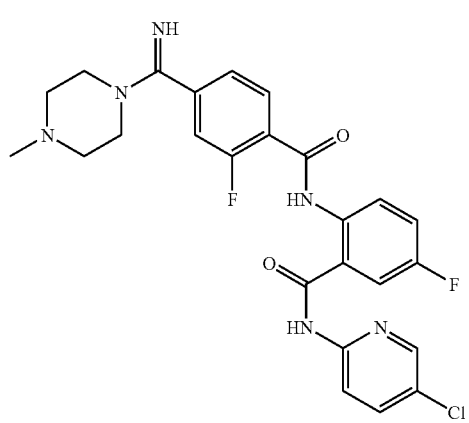
MS (M + H): 513, 515
Example 158
-continued
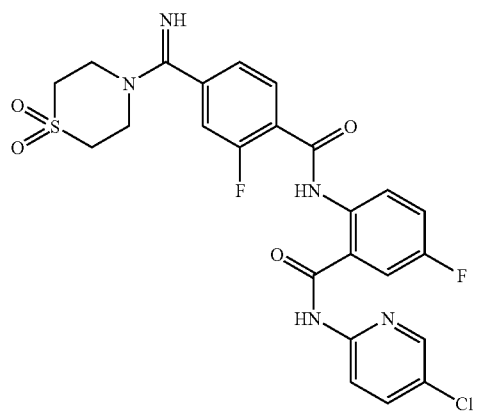
MS (M + H): 548, 550
Example 159
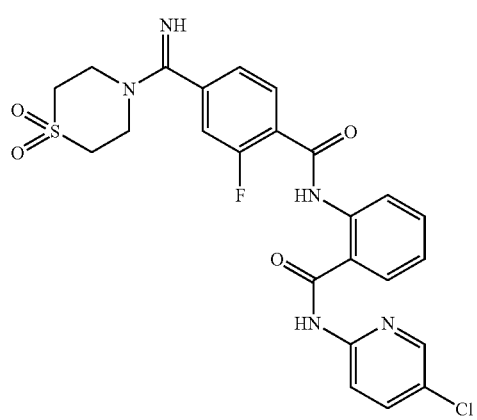
MS (M + H): 530, 532
Example 160
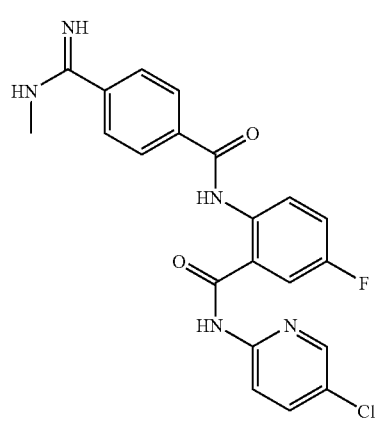
MS (M + H): 426, 428
Example 161

-continued
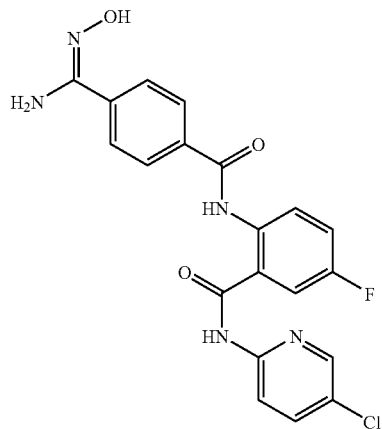
MS (M + H): 428, 430
Example 162
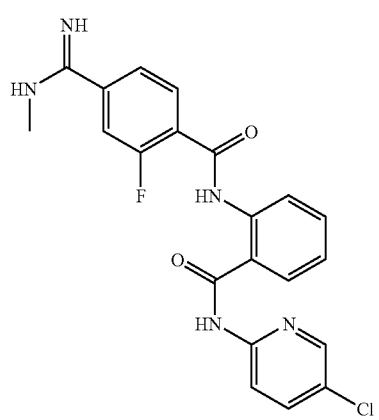
MS (M + H): 426, 428
Example 163
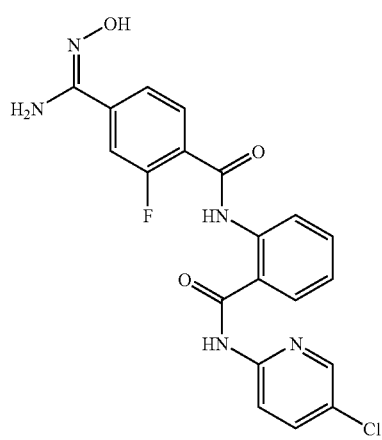
MS (M + H): 428, 430
Example 164
-continued
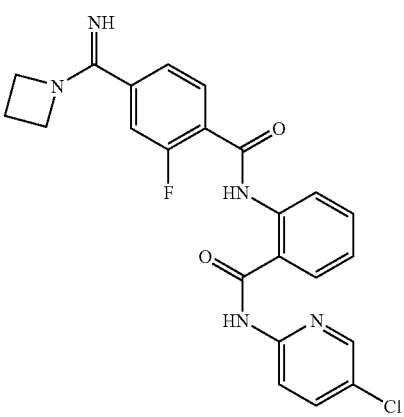
MS (M + H): 452, 454
Example 165
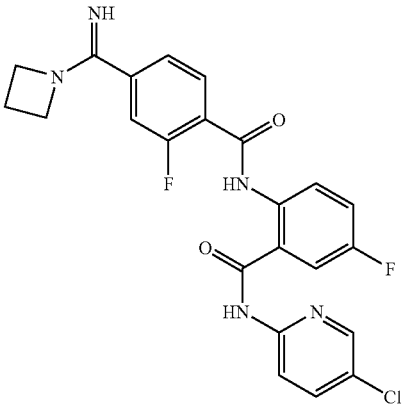
MS (M + H): 470, 472
Example 166
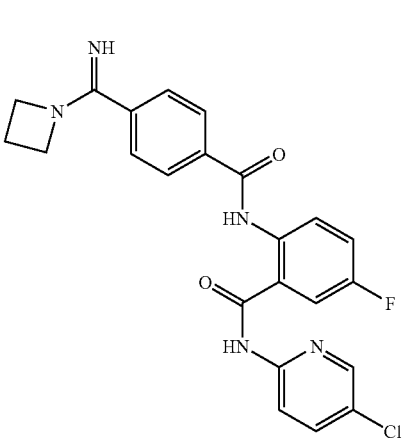
MS (M + H): 452, 454
Example 167

-continued
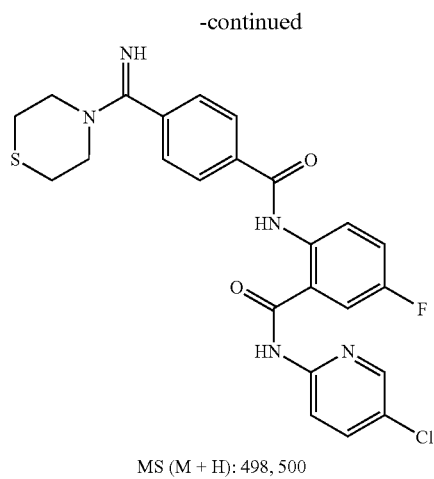
MS (M + H): 498, 500
Example 168
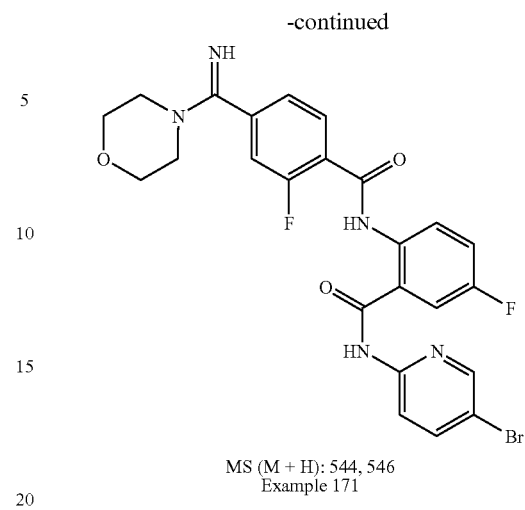
MS (M + H): 544, 546
Example 171
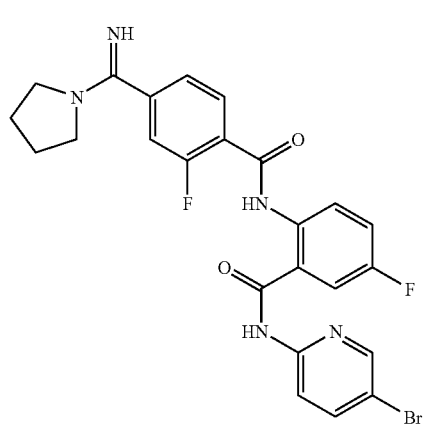
MS (M + H): 528, 530
Example 169
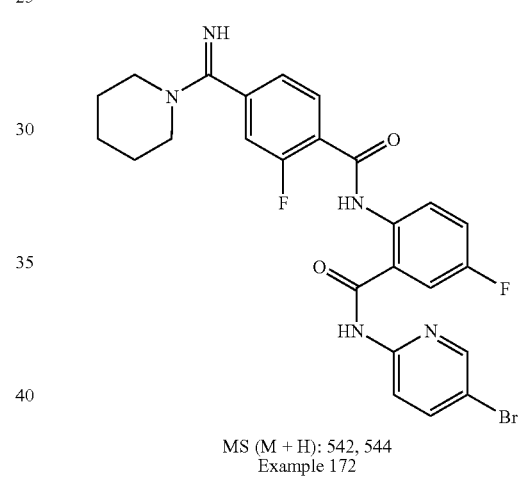
MS (M + H): 542, 544
Example 172
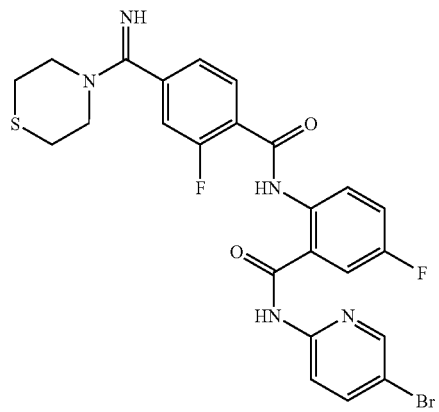
MS (M + H): 560, 562
Example 170
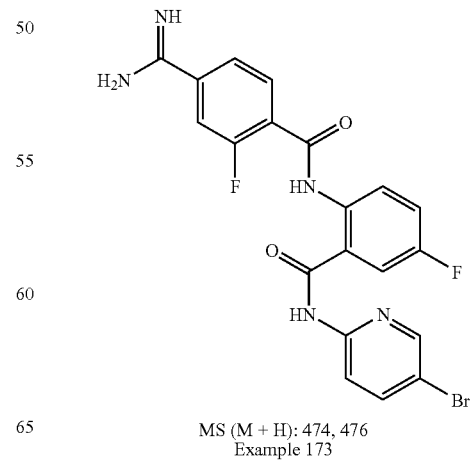
MS (M + H): 474, 476
Example 173

-continued
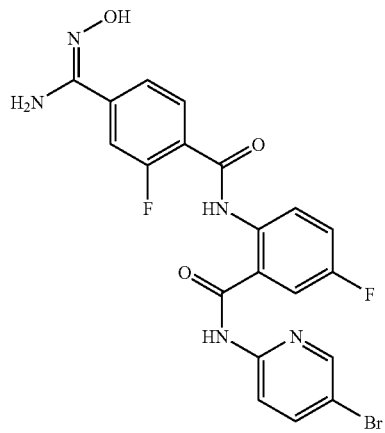
MS (M + H): 490, 492
Example 174
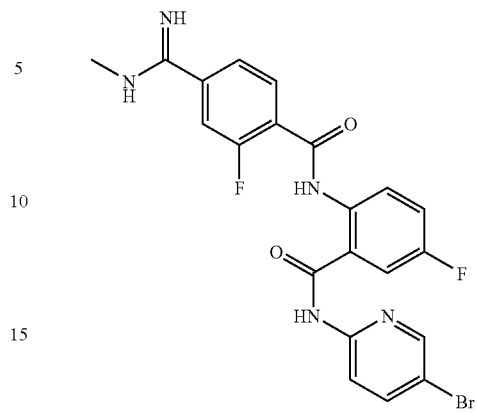
MS (M + H): 488, 490
Example 177
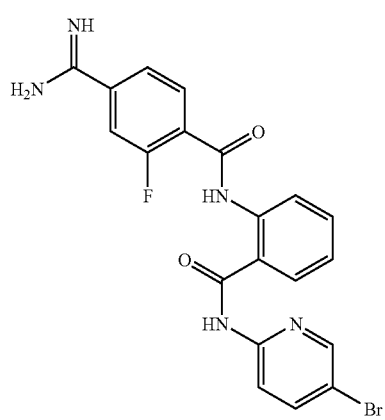
MS (M + H): 456, 458
Example 175
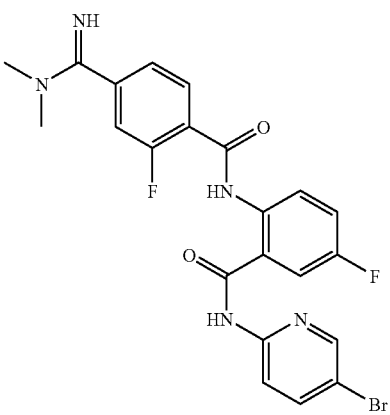
MS (M + H): 502, 504
Example 178
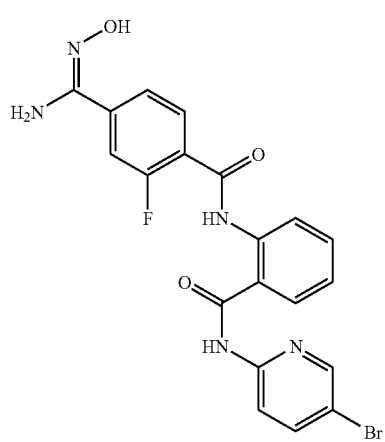
MS (M + H): 472, 474
Example 176
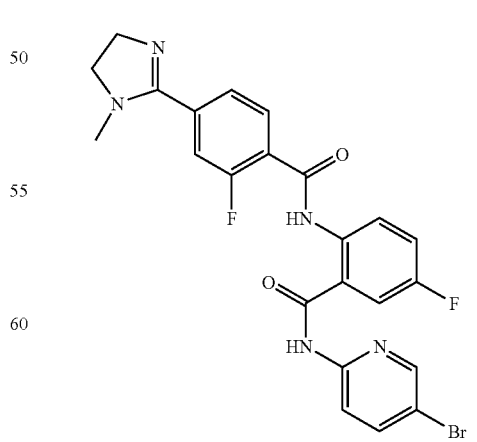
MS (M + H): 514, 516
Example 179

-continued
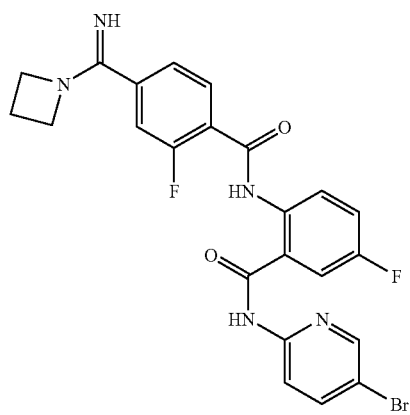
MS (M + H): 514, 516
Example 180
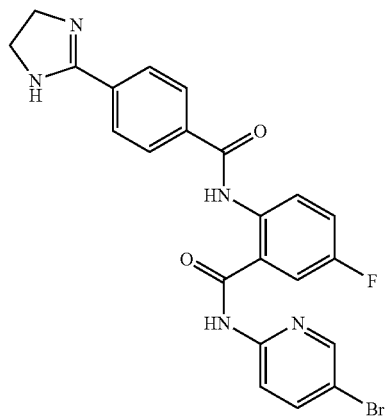
MS (M + H): 482, 484
Example 183
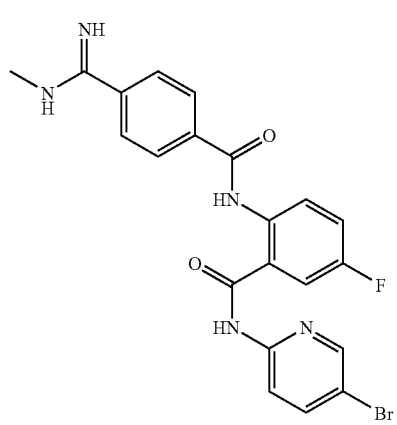
MS (M + H): 470, 472
Example 181
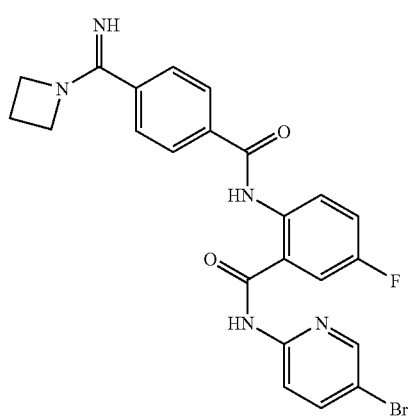
MS (M + H): 496, 498
Example 184
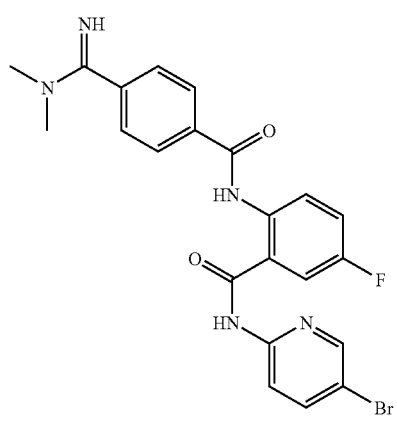
MS (M + H): 484, 486
Example 182
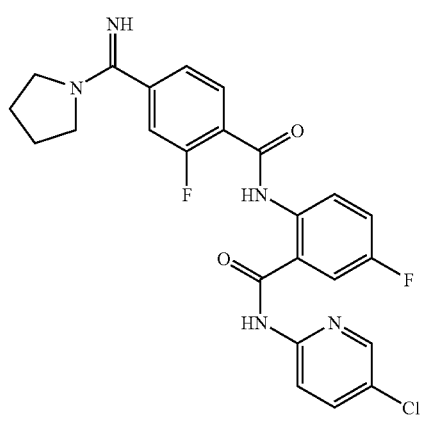
MS (M + H): 484, 486
Example 185

-continued
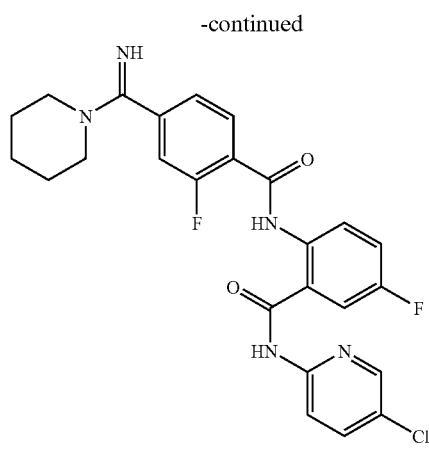
MS (M + H): 498, 500
Example 186
-continued
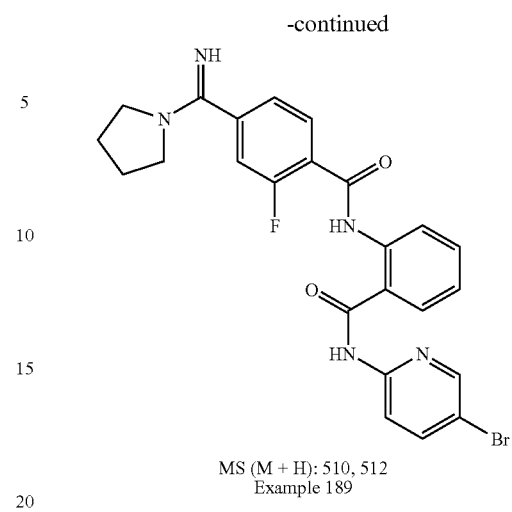
MS (M + H): 510, 512
Example 189
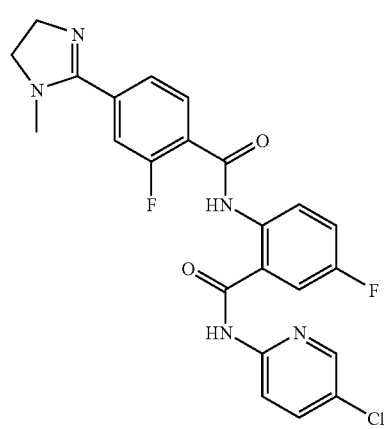
MS (M + H): 470, 472
Example 187
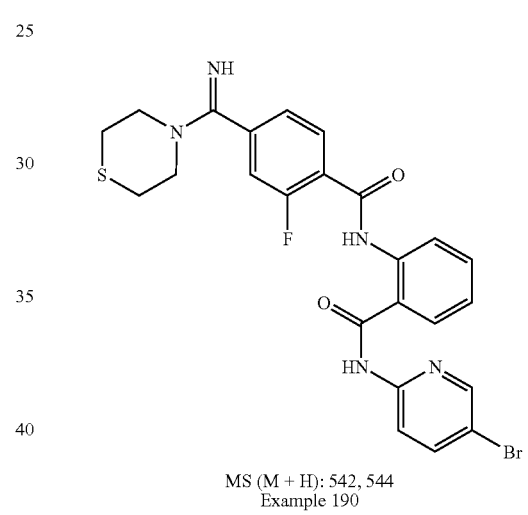
MS (M + H): 542, 544
Example 190
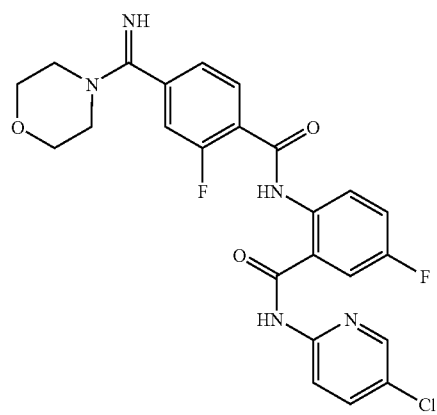
MS (M + H): 500, 502
Example 188
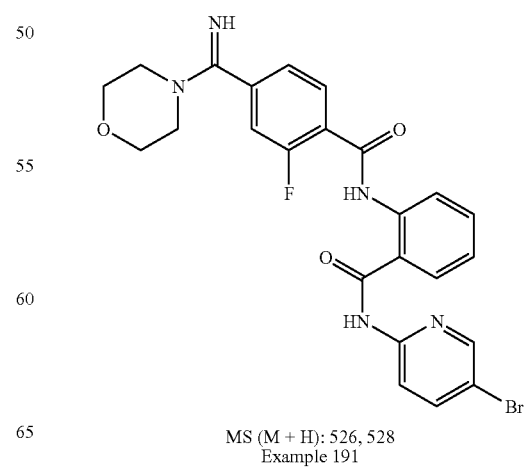
MS (M + H): 526, 528
Example 191

-continued
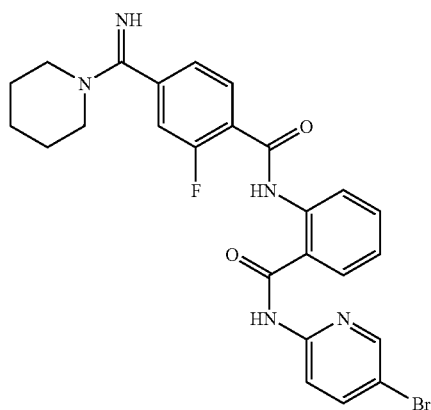
MS (M + H): 524, 526
Example 192
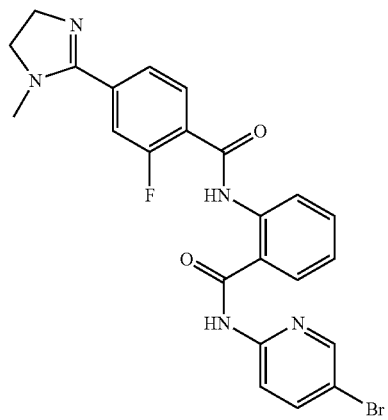
MS (M + H): 496, 498
Example 195
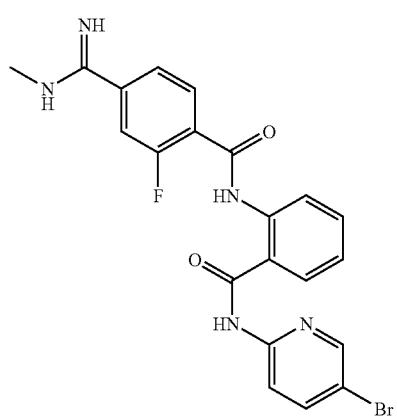
MS (M + H): 470, 472
Example 193
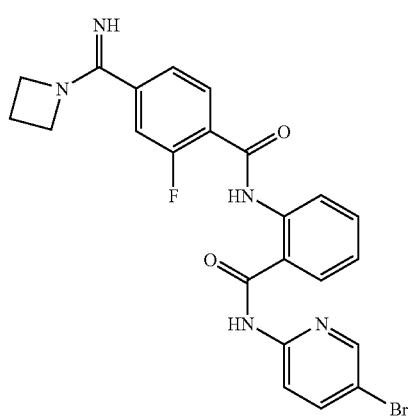
MS (M + H): 496, 498
Example 196
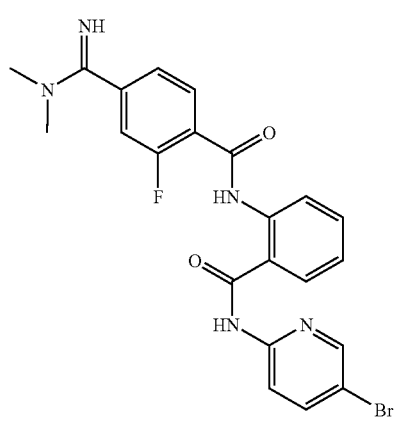
MS (M + H): 484, 486
Example 194
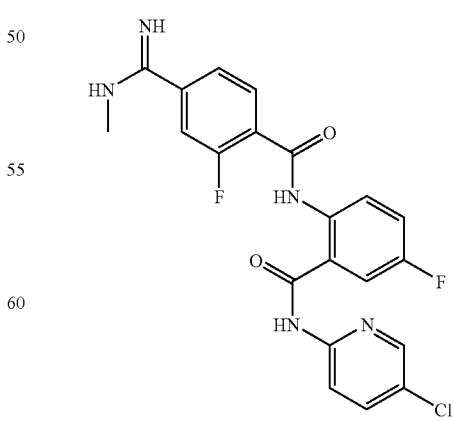
MS (M + H): 444, 446
Example 197

-continued

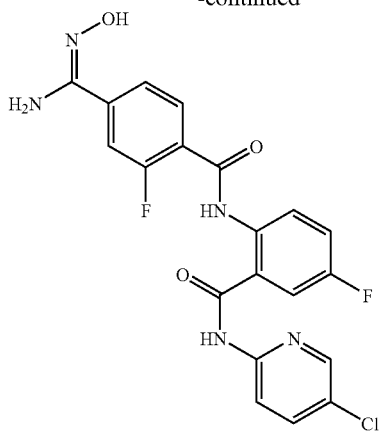

MS (M + H): 446, 448
Example 198

Example 199

N-{2-[N-(5-bromo(2-pyridyl))carbamoyl]-4,5-dimethoxyphenyl}(4-cyanophenyl)carboxamide

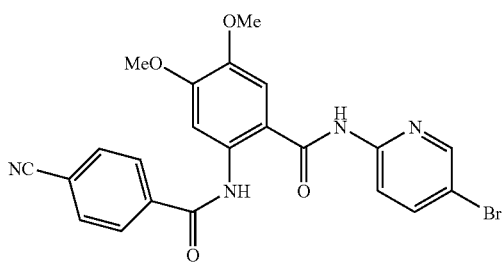

To a solution of 4,5-dimethoxy-2-nitrobenzoic acid (2.2 gm, 10 mmol) and 2-amino-5-bromopyridine (2.4 gm, 14 mmol) in anhydrous pyridine (50 mL) at 0° C. was added $POCl_3$ (1.9 mL, 20 mmol). After stirring at room temperature for 30 min, the reaction was complete. The mixture was concentrated and diluted with EtOAc (200 mL). The organic solution was washed with brine, dried and evaporated to give intermediate compound 1 (3.0 gm, 80%). MS found for $C_{14}H_{12}BrN_3O_5$ (M+H)$^+$: 382.00, 383.95.

A mixture of intermediate compound 1 (320 mg; 0.83 mmol) and $SnCl_2.2H_2O$ (900 mg, 4.0 mmol) in EtOAc (10 mL) was refluxed for 1 hour. Reduction completed. The solid was filtered through a celite bed. The filtrate was diluted with EtOAc (50 mL), and the red solution was washed with 1N aq. NaOH solution (x3) and brine, dried and evaporated to give intermediate compound 2 (230 mg, 78%). MS found for $C_{14}H_{14}BrN_3O_3$ (M+H)$^+$: 352.00, 354.05.

To a solution of intermediate compound 2 (200 mg, 0.57 mmol) in a mixture of pyridine (3 mL) and DCM (10 mL) was added 4-cyanobenzoyl chloride (140 mg, 0.85 mmol). Precipitate formed immediately and the reaction was complete. The solid was collected by filtration and washed with DCM. After drying in vacco, the titled compound was obtained as a yellow solid in 70% yield (190 mg). MS found for $C_{22}H_{17}BrN_4O_4$ (M+H)$^+$: 481.00, 483.00.

Example 200

(4,5-dimethoxy-2-{[4-(1-methyl(2-imidazolin-2-yl))phenyl]carbonylamino}phenyl)-N-(5-bromo(2-pyridyl))carboxamide

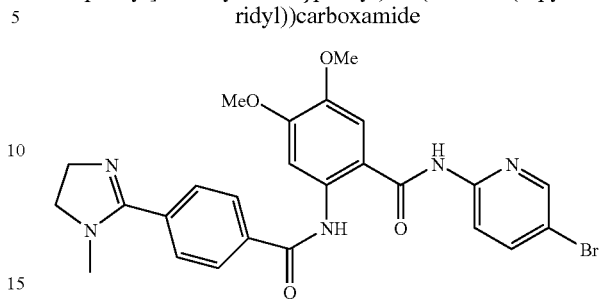

To a solution of compound obtained in Example 259 (100 mg, 0.20 mmol) in 10% $Et_3N$/pyridine (10 mL) at 0° C. was bubbled dry $H_2S$ gas to saturation. The mixture was stirred at ambient temperatures overnight, and the conversion was complete. The solvent was removed to dryness, and the residue was suspended in anhydrous acetone (10 mL), followed by addition of MeI (1 mL). The reaction mixture was refluxed for 1 hour. The solvent was removed by rotary evaporation. To the residue was added anhydrous MeOH (10 mL) and N-methylethylenediamine (1 mL). The resulting mixture was refluxed for 1 hour, concentrated and subjected to RP-HPLC purification to give the title compound. MS found for $C_{25}H_{24}BrN_5O_4$ (M+H)$^+$: 538.1, 540.1.

Example 201

4-(N-{2-[N-(5-bromo(2-pyridyl))carbamoyl]-4,5-dimethoxyphenyl}carbamoyl)-benzenecarboxamidine

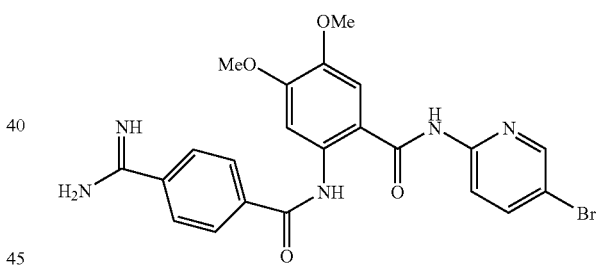

The title compound was obtained according to the procedure previously described. MS found for $C_{22}H_{20}BrN_5O_4$ (M+H)$^+$: 498.1, 500.0.

Example 202

N-(5-chloro(2-pyridyl)){2-[(4-cyanophenyl)carbonylamino]-5-methoxyphenyl}-carboxamide

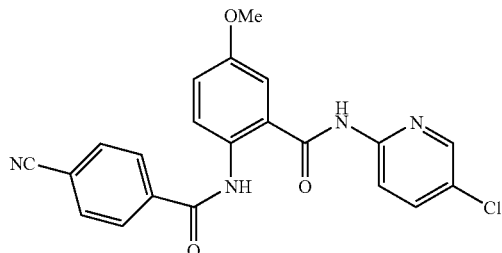

The title compound was obtained according to the procedure previously described. MS found for $C_{21}H_{15}ClN_4O_3$ (M+H)$^+$: 407.0.

Example 203

N-(5-chloro(2-pyridyl))(5-methoxy-2-{[4-(1-methyl (2-imidazolin-2-yl))phenyl]-carbonylamino}phenyl) carboxamide

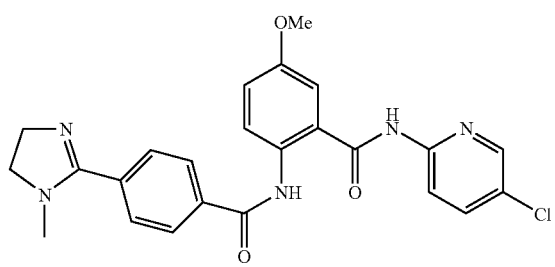

To the suspension of the compound Example 262 (100 mg) in a mixture of anhydrous MeOH (5 mL) and EtOAc (5 mL) at 0° C. was bubbled anhydrous HCl gas to saturation. The mixture was stirred at ambient temperatures overnight. The conversion completed. The solvent was evaporated to dryness. The residue was dissolved in anhydrous MeOH (10 mL), followed by addition of N-methylethylenediamine (1 mL).

The resulting mixture was refluxed for 1 hour, concentrated and subjected to RP-HPLC purification to give the title compound 263. MS found for $C_{24}H_{22}ClN_5O_3$ $(M+H)^+$: 464.

Example 204

4-(N-{2-[N-(5-chloro(2-pyridyl))carbamoyl]-4-methoxyphenyl}carbamoyl)benzene-carboxamidine

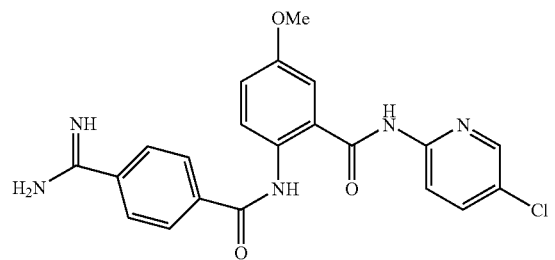

The title compound was obtained according to the procedure previously described. MS found for $C_{21}H_{18}ClN_5O_3$ $(M+H)^+$: 424.

Example 205

N-(5-chloro(2-pyridyl))[2-({4-[imino(methylamino) methyl]phenyl}carbonylamino)-5-methoxyphenyl] carboxamide

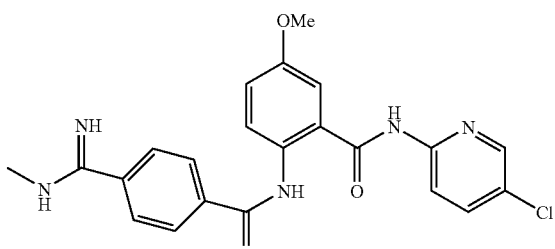

The title compound was obtained according to the procedure previously described. MS found for $C_{22}H_{20}ClN_5O_3$ $(M+H)^+$: 438.

Example 206

[2-({4-[(dimethylamino)iminomethyl] phenyl}carbonylamino)-5-methoxyphenyl]-N-(5-chloro(2-pyridyl))carboxamide

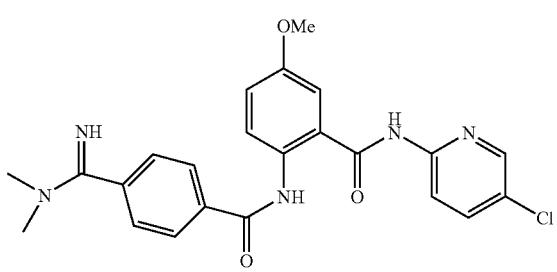

The title compound was obtained according to the procedure previously described. MS found for $C_{23}H_{22}ClN_5O_3$ $(M+H)^+$: 452.

Example 207

N-(5-chloro(2-pyridyl))(2-{[4-(iminopyrrolidinylmethyl)phenyl]carbonylamino}-5-methoxyphenyl) carboxamide

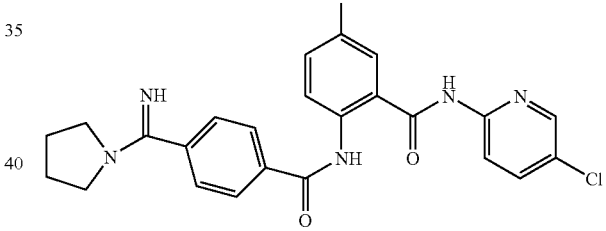

The title compound was obtained according to the procedure previously described. MS found for $C_{25}H_{24}ClN_5O_3$ $(M+H)^+$: 478.

Example 208

N-(5-chloro(2-pyridyl))(2-{[4-(iminopiperidylmethyl)phenyl]carbonylamino}-5-methoxyphenyl) carboxamide

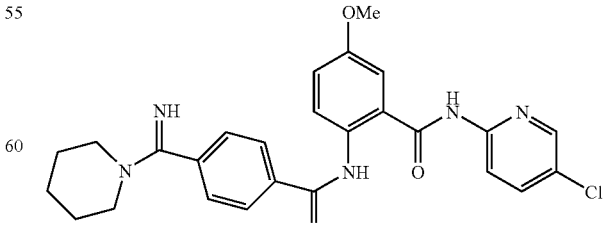

The title compound was obtained according to the procedure previously described. MS found for $C_{26}H_{26}ClN_5O_3$ $(M+H)^+$: 492.

Example 209

N-(5-chloro(2-pyridyl))(2-{[4-(iminomorpholin-4-ylmethyl)phenyl]carbonylamin}-5-methoxyphenyl)carboxamide

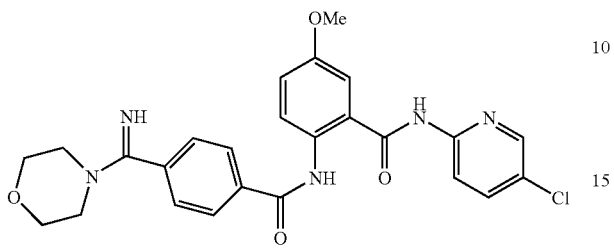

The title compound was obtained according to the procedure previously described. MS found for $C_{25}H_{24}ClN_5O_4$ (M+H)$^+$: 494.1.

Example 210

N-(5-chloro(2-pyridyl))(2-{[4-(imino-1,4-thiazaperhydroin-4-ylmethyl)phenyl]carbonylamino}-5-methoxyphenyl)carboxamide

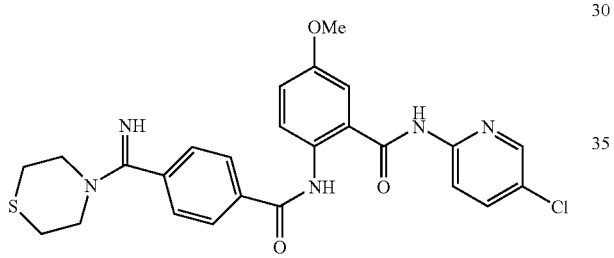

The title compound was obtained according to the procedure previously described. MS found for $C_{25}H_{24}ClN_5O_3S$ (M+H)$^+$: 510.

Example 211

(2-{[4-(amino(hydroxyimino)methyl)phenyl]carbonylamino}-5-methoxyphenyl)-N-(5-chloro(2-pyridyl))carboxamide

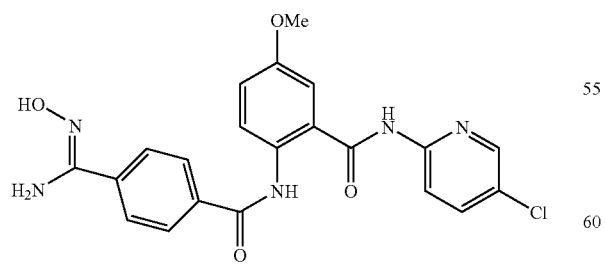

To a suspension of compound N-(5-chloro(2-pyridyl)){2-[(4cyanophenyl)carbonylamino]-5-methoxyphenyl carboxamide (150 mg) in EtOH (10 mL) was added hydroxyamine hydrochloride (80 mg) and Et₃N (200 μL). The mixture was stirred at 60° C. overnight and the reaction was complete. The solvent was evaporated and the crude material was purified by RP-HPLC to give the title compound. MS found for $C_{21}H_{18}ClN_5O_4$ (M+H)$^+$: 440.1.

Example 212

N-(5-bromo(2-pyridyl)){2-[(4-cyanophenyl)carbonylamino]-5-methoxyphenyl}carboxamide

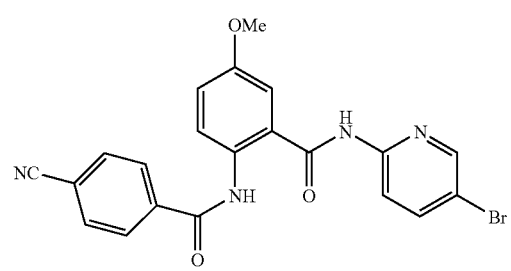

The title compound was obtained according to the procedure previously described. MS found for $C_{21}H_{15}BrN_4O_3$ (M+H)$^+$: 451.00, 453.00.

Example 213

N-(5-bromo(2-pyridyl))(5-methoxy-2-{[4-(1-methyl(2-imidazolin-2-yl))phenyl]carbonylamino}phenyl)carboxamide

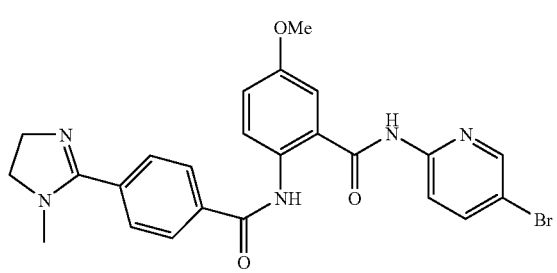

The title compound was obtained according to the procedure previously described. MS found for $C_{24}H_{22}BrN_5O_3$ (M+H)$^+$: 508, 510.

Example 214

4-(N-(2-[N-(5-bromo(2-pyridyl))carbamoyl]-4-methoxyphenyl}carbamoyl)benzenecarboxamidine

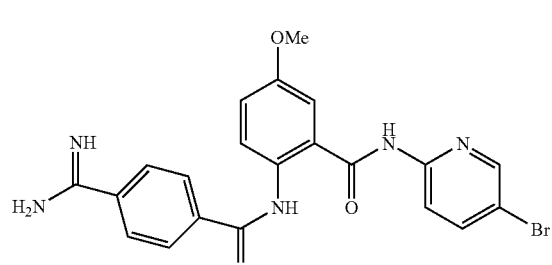

The title compound was obtained according to the procedure previously described. MS found for $C_{21}H_{18}BrN_5O_3$ (M+H)$^+$: 468.05, 470.00.

Example 215

N-(5-bromo(2-pyridyl))[2-({4-[imino(methylamino)methyl]phenyl}carbonylamino)-5-methoxyphenyl]carboxamide

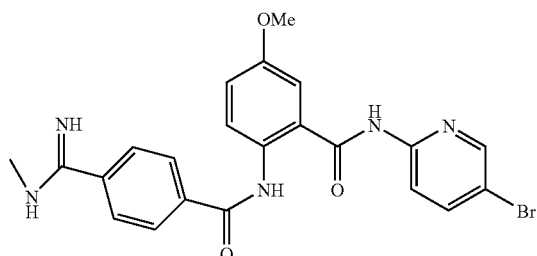

The title compound was obtained according to the procedure previously described. MS found for $C_{22}H_{20}BrN_5O_3$ (M+H)$^+$: 482, 484.

Example 216

[2-({4-[(dimethylamino)iminomethyl]phenyl}carbonylamino)-5-methoxyphenyl]-N-(5 N-(5-bromo(2-pyridyl))carboxamide

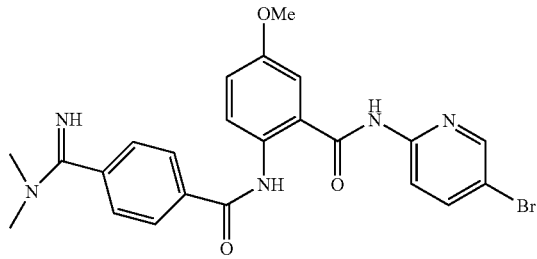

The title compound was obtained according to the procedure previously described. MS found for $C_{23}H_{22}BrN_5O_3$ (M+H)$^+$: 496.1, 498.1.

Example 217

N-(5-chloro(2-pyridyl))(2-{[4-(iminopyrrolidinylmethyl)phenyl carbonylamino}-5-methoxyphenyl)carboxamide

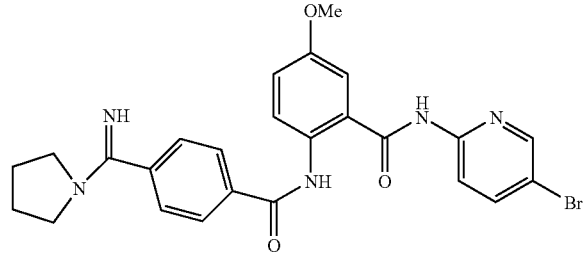

The title compound was obtained according to the procedure previously described. MS found for $C_{25}H_{24}BrN_5O_3$ (M+H)$^+$: 522, 524.

Example 218

N-(N-(5-bromo(2-pyridyl))(2-{[4-(iminopiperidylmethyl)phenyl]carbonylamino}-5-methoxyphenyl)carboxamide

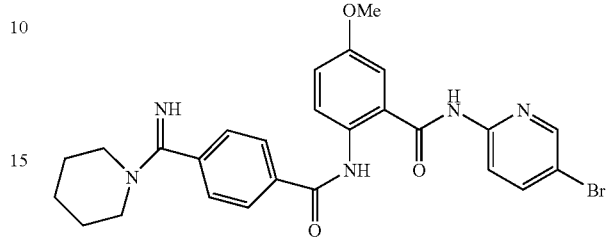

The title compound was obtained according to the procedure previously described. MS found for $C_{26}H_{26}BrN_5O_3$ (M+H)$^+$: 536.1, 538.1.

Example 219

N-(5-bromo(2-pyridyl))(2-{[4-(iminomorpholin-4-ylmethyl)phenyl]carbonylamino}-5-methoxyphenyl)carboxamide

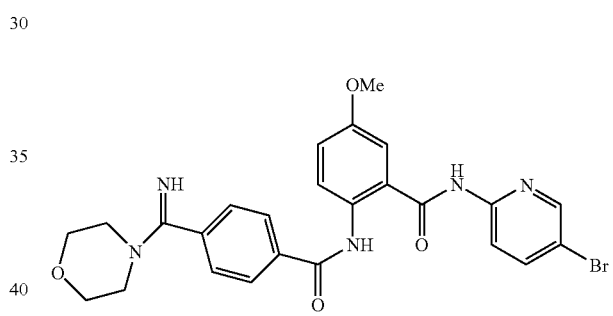

The title compound was obtained according to the procedure previously described. MS found for $C_{25}H_{24}BrN_5O_4$ (M+H)$^+$: 538.1, 540.1.

Example 220

N-(5-bromo(2-pyridyl))(2-{[4-(imino-1,4-thiazaperhydroin-4-ylmethyl)phenyl]carbonylamino}-5-methoxyphenyl)carboxamide

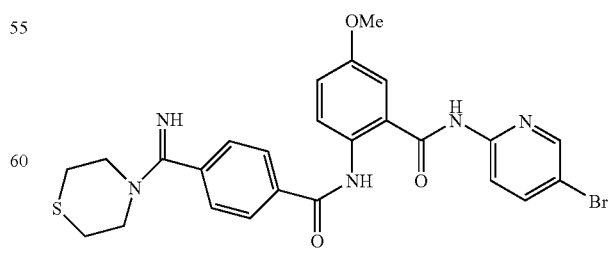

The title compound was obtained according to the procedure previously described. MS found for $C_{25}H_{24}BrN_5O_3S$ (M+H)$^+$: 554.1, 556.05.

Example 221

(2-{[4-(amino(hydroxyimino)methyl)phenyl]carbonylamino}-5-methoxyphenyl)-N-(5-bromo(2-pyridyl))carboxamide

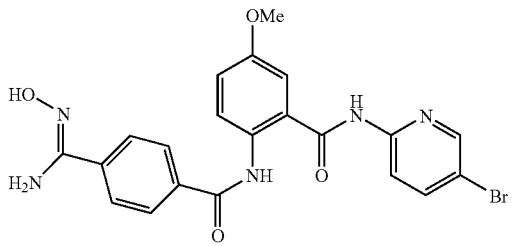

The title compound was obtained according to the procedure previously described. MS found for $C_{21}H_{18}BrN_5O_4$ (M+H)$^+$: 484.1, 486.0.

Example 222

N-(5-chloro(2-pyridyl)){6-[(4-cyanophenyl)carbonylamino]-3-hydroxyphenyl}carboxamide

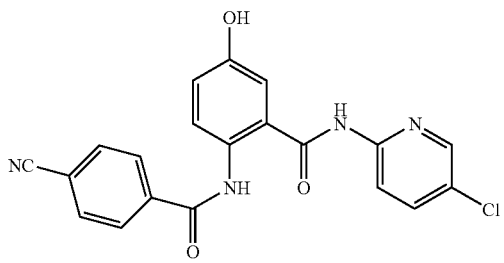

To a suspension of compound N-(5-chloro(2-pyridyl)){2-[(4-cyanophenyl)-carbonylamino]-5-methoxyphenyl}carboxamide (500 mg, 1.2 mmol) in DCM (100 mL) at −78° C. was added BBr$_3$ (2 mL). The mixture was stirred at ambient temperatures for 72 hours. The solid was collected by filtration and was washed by DCM and water, dried under vacuum. The filtrate was concentrated and extracted with EtOAc. The organic extract was washed with brine, dried and evaporated. The resulting solid was combined with the solid obtained from filtration to give the title compound. Total yield is 90% (430 mg). MS found for $C_{20}H_{13}ClN_4O_3$ (M+H)$^+$: 393.0.

Example 223

Ethyl 2-{3-[N-(5-chloro(2-pyridyl))carbamoyl]4-[(4-cyanophenyl)carbonylamino]-phenoxy}acetate

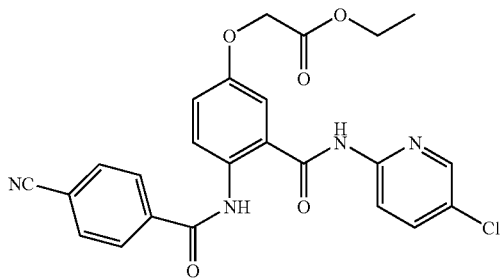

To a mixture of compound N-(5-chloro(2-pyridyl)){6-[(4-cyanophenyl)-carbonylamino]-3-hydroxyphenyl}carboxamide (50 mg, 0.13 mmol) and Cs$_2$CO$_3$ (83 mg, 0.25 mmol) in DMF (1 mL) at room temperature was added ethyl bromoacetate (15 μL, 0.13 mmol). The mixture was stirred for 1 hour before diluted with EtOAc (20 mL) and water (10 mL). The organic layer was washed with brine dried and evaporated to give 70 mg of the crude compound, which was used without farther purification. MS found for $C_{24}H_{19}ClN_4O_5$ (M+H)$^+$: 479.0.

Example 224

Methyl 2-[4-({4-[(dimethylamino)iminomethyl]phenyl}carbonylamino)-3-[N-(5-chloro(2-pyridyl))carbamoyl]phenoxy]acetate

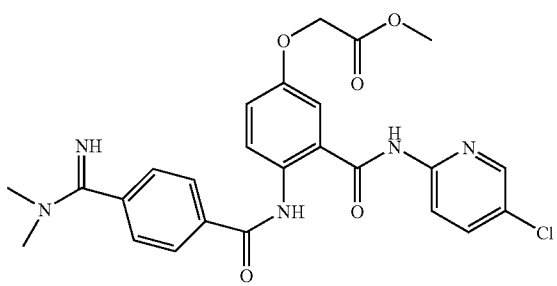

The title compound was obtained according to the procedure previously described. MS found for $C_{25}H_{24}ClN_5O_5$ (M+H)$^+$: 510.1.

Example 225

(6-{[4-(amino(hydroxyimino)methyl)phenyl]carbonylamino}-3-hydroxyphenyl)-N-(5-chloro(2-pyridyl))carboxamide

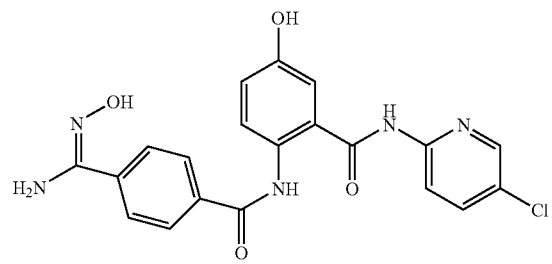

The title compound was obtained according to the procedure previously described. MS found for $C_{20}H_{16}ClN_5O_4$ (M+Na)$^+$: 448.0.

Example 226

4-(N-{2-[N-(5-chloro(2-pyridyl))carbamoyl]4-hydroxyphenyl}carbamoyl)-benzenecarboxamidine

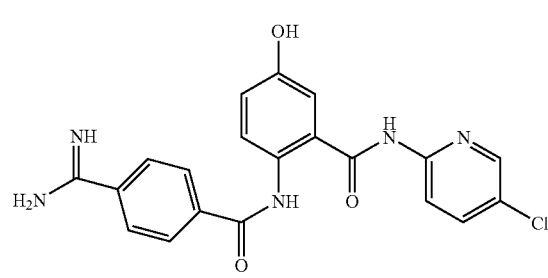

The title compound was obtained according to the procedure previously described. MS found for $C_{20}H_{16}ClN_5O_3$ (M+H)$^+$: 410.1.

Example 227

4-(N-{2-[N-(5-chloro(2-pyridyl))carbamoyl]-4-hydroxyphenyl}carbamoyl)-benzenecarboxamidine

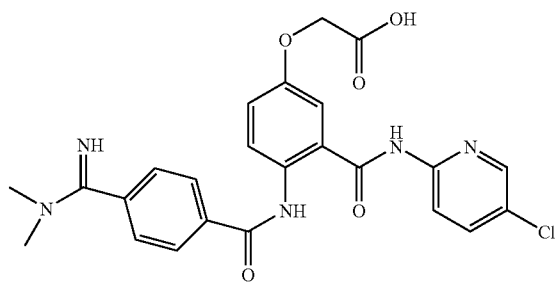

To a solution of Example 284 (10 mg) in MeOH (1 mL) was added 50 µL of 1N aq. LiOH solution. The mixture was stirred for 1 hour and purified by RP-HPLC to give the title compound. MS found for $C_{24}H_{22}ClN_5O_5$ (M+H)$^+$: 496.

Example 228

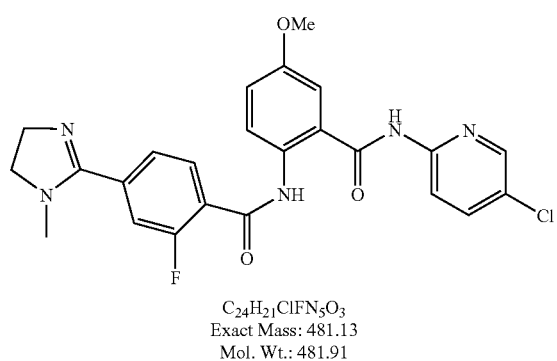

$C_{24}H_{21}ClFN_5O_3$
Exact Mass: 481.13
Mol. Wt.: 481.91

The title compound was synthesized according to the procedure described previously. MS found for $C_{24}H_{21}ClFN_5O_3$: (M+H)$^+$: 482.1.

Example 229

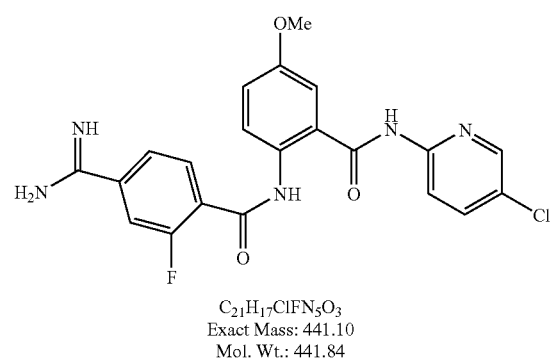

$C_{21}H_{17}ClFN_5O_3$
Exact Mass: 441.10
Mol. Wt.: 441.84

The title compound was synthesized according to the procedure described previously. MS found for $C_{21}H_{17}ClFN_5O_3$: (M+H)$^+$: 442.1.

Example 230

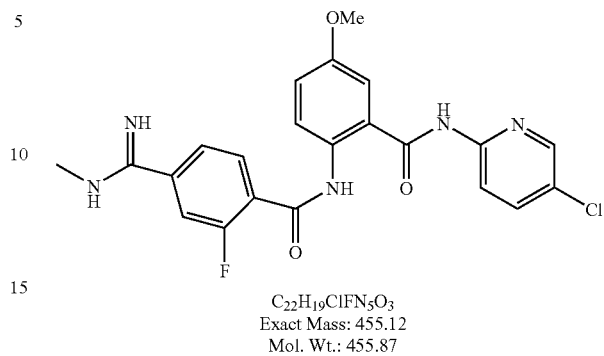

$C_{22}H_{19}ClFN_5O_3$
Exact Mass: 455.12
Mol. Wt.: 455.87

The title compound was synthesized according to the procedure described previously. MS found for $C_{22}H_{19}ClFN_5O_3$: (M+H)$^+$: 456.1.

Example 231

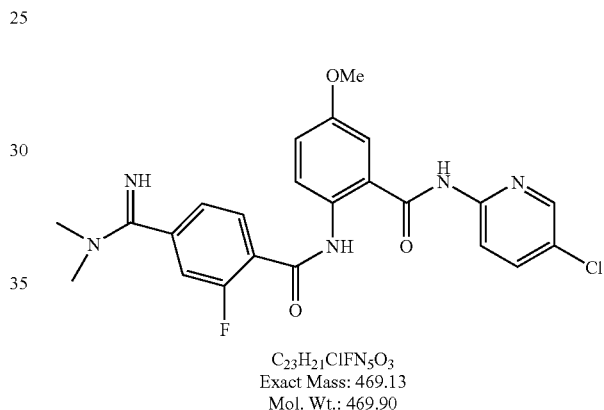

$C_{23}H_{21}ClFN_5O_3$
Exact Mass: 469.13
Mol. Wt.: 469.90

The title compound was synthesized according to the procedure described previously. MS found for $C_{23}H_{21}ClFN_5O_3$: (M+H)$^+$: 470.1.

Example 232

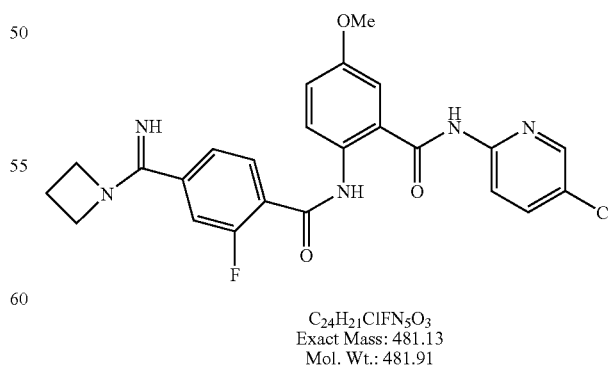

$C_{24}H_{21}ClFN_5O_3$
Exact Mass: 481.13
Mol. Wt.: 481.91

The title compound was synthesized according to the procedure described previously. MS found for $C_{24}H_{21}ClFN_5O_3$: (M+H)$^+$: 482.1.

Example 233

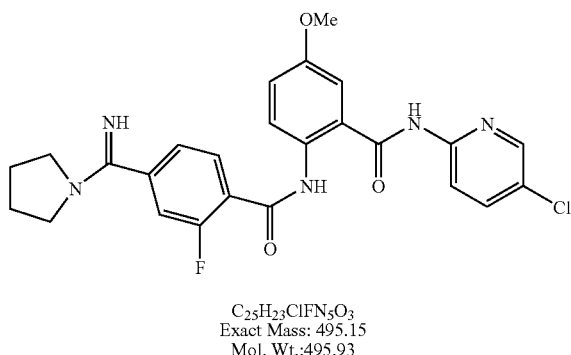

C$_{25}$H$_{23}$ClFN$_5$O$_3$
Exact Mass: 495.15
Mol. Wt.: 495.93

The title compound was synthesized according to the procedure described previously. MS found for C$_{25}$H$_{23}$ClFN$_5$O$_3$: (M+H)$^+$: 496.1.

Example 234

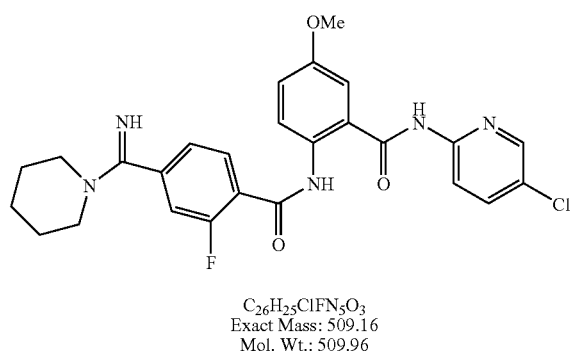

C$_{26}$H$_{25}$ClFN$_5$O$_3$
Exact Mass: 509.16
Mol. Wt.: 509.96

The title compound was synthesized according to the procedure described previously. MS found for C$_{26}$H$_{25}$ClFN$_5$O$_3$: (M+H)$^+$: 510.2.

Example 235

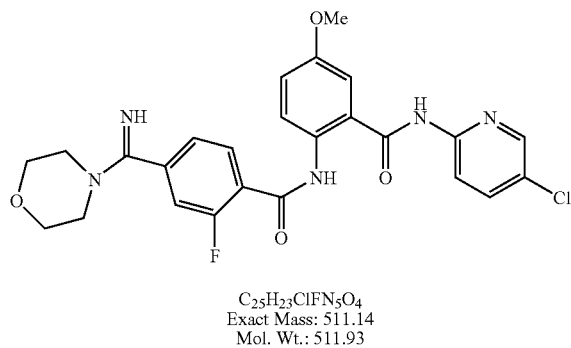

C$_{25}$H$_{23}$ClFN$_5$O$_4$
Exact Mass: 511.14
Mol. Wt.: 511.93

The title compound was synthesized according to the procedure described previously. MS found for C$_{25}$H$_{23}$ClFN$_5$O$_4$: (M+H)$^+$: 512.2.

Example 236

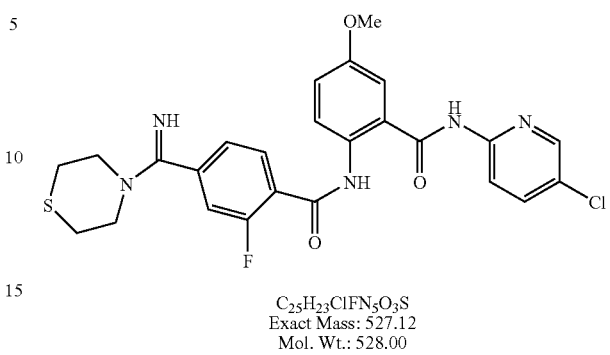

C$_{25}$H$_{23}$ClFN$_5$O$_3$S
Exact Mass: 527.12
Mol. Wt.: 528.00

The title compound was synthesized according to the procedure described previously. MS found for C$_{25}$H$_{23}$ClFN$_5$O$_3$S: (M+H)$^+$: 528.1.

Example 237

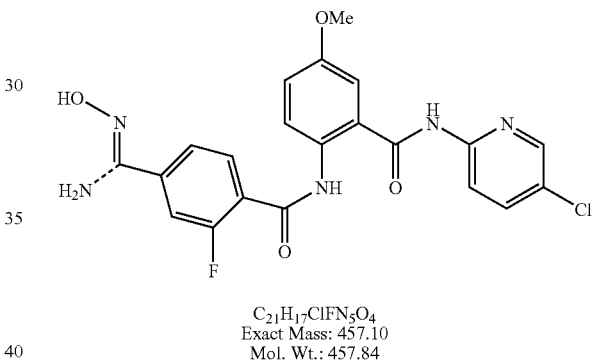

C$_{21}$H$_{17}$ClFN$_5$O$_4$
Exact Mass: 457.10
Mol. Wt.: 457.84

The title compound was synthesized according to the procedure described previously. MS found for C$_{21}$H$_{17}$ClFN$_5$O$_4$: (M+H)$^+$: 458.1.

Example 238

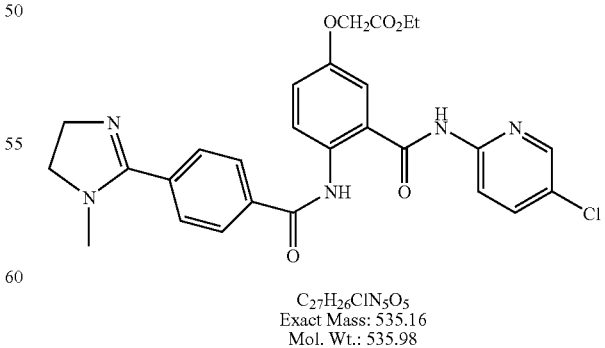

C$_{27}$H$_{26}$ClN$_5$O$_5$
Exact Mass: 535.16
Mol. Wt.: 535.98

The title compound was synthesized according to the procedure described previously. MS found for C$_{27}$H$_{26}$ClN$_5$O$_5$: (M+H)$^+$: 536.1.

Example 239

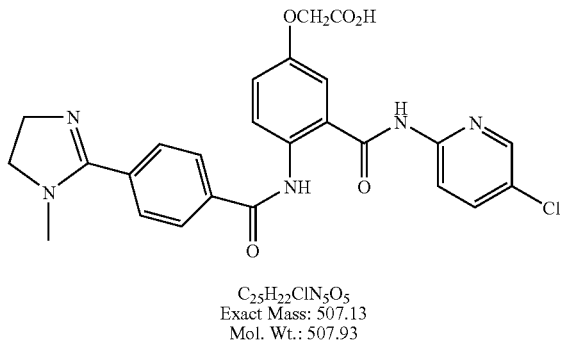

C25H22ClN5O5
Exact Mass: 507.13
Mol. Wt.: 507.93

The title compound was synthesized according to the procedure described previously. MS found for C25H22ClN5O5: (M+H)+: 508.1.

Example 240

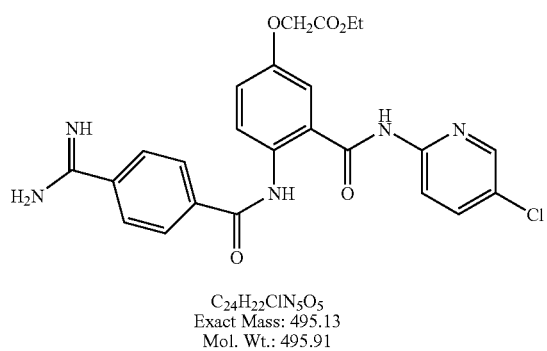

C24H22ClN5O5
Exact Mass: 495.13
Mol. Wt.: 495.91

The title compound was synthesized according to the procedure described previously. MS found for C24H22ClN5O5: (M+H)+: 496.1.

Example 241

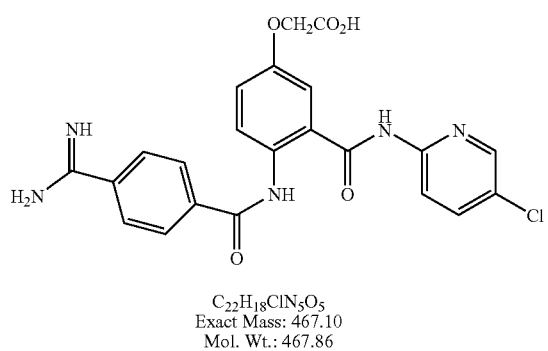

C22H18ClN5O5
Exact Mass: 467.10
Mol. Wt.: 467.86

The title compound was synthesized according to the procedure described previously. MS found for C22H18ClN5O5: (M+H)+: 468.1.

Example 242

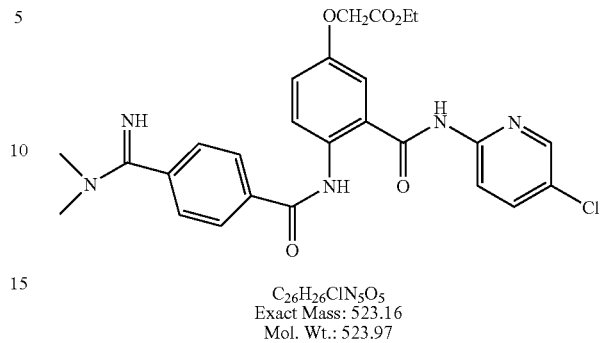

C26H26ClN5O5
Exact Mass: 523.16
Mol. Wt.: 523.97

The title compound was synthesized according to the procedure described previously. MS found for C26H26ClN5O5: (M+H)+: 524.2.

Example 243

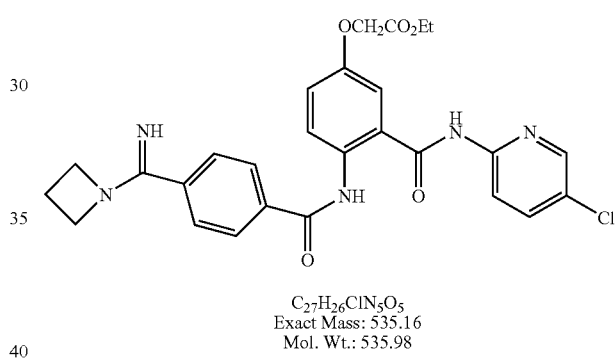

C27H26ClN5O5
Exact Mass: 535.16
Mol. Wt.: 535.98

The title compound was synthesized according to the procedure described previously. MS found for C27H26ClN5O5: (M+H)+: 536.1.

Example 244

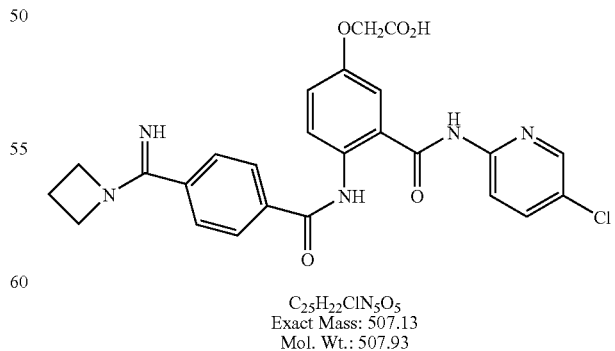

C25H22ClN5O5
Exact Mass: 507.13
Mol. Wt.: 507.93

The title compound was synthesized according to the procedure described previously. MS found for C25H22ClN5O5: (M+H)+: 508.1.

Example 245

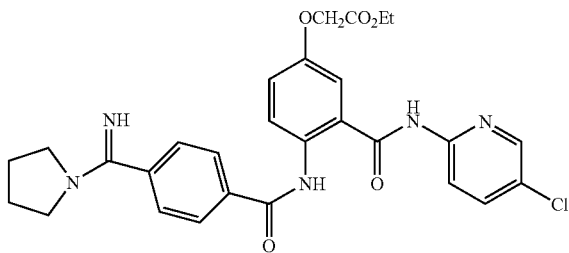

C<sub>28</sub>H<sub>28</sub>ClN<sub>5</sub>O<sub>5</sub>
Exact Mass: 549.18
Mol. Wt.: 550.01

The title compound was synthesized according to the procedure described previously. MS found for $C_{28}H_{28}ClN_5O_5$: $(M+H)^+$: 550.2.

Example 246

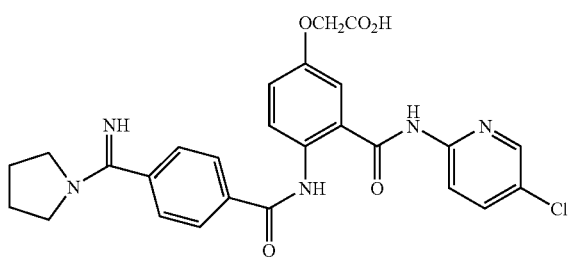

C<sub>26</sub>H<sub>24</sub>ClN<sub>5</sub>O<sub>5</sub>
Exact Mass: 521.15
Mol. Wt.: 521.95

The title compound was synthesized according to the procedure described previously. MS found for $C_{26}H_{24}ClN_5O_5$: $(M+H)^+$: 522.1.

Example 247

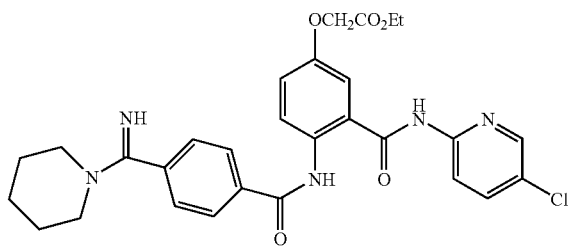

C<sub>29</sub>H<sub>30</sub>ClN<sub>5</sub>O<sub>5</sub>
Exact Mass: 563.19
Mol. Wt.: 564.03

The title compound was synthesized according to the procedure described previously. MS found for $C_{29}H_{30}ClN_5O_5$: $(M+H)^+$: 564.2.

Example 248

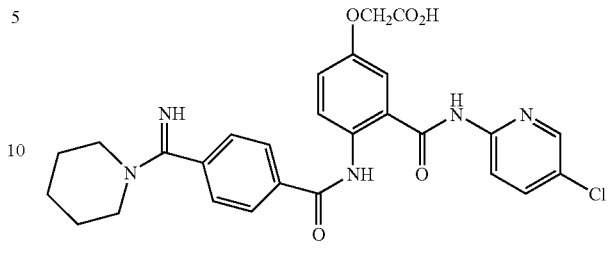

C<sub>27</sub>H<sub>26</sub>ClN<sub>5</sub>O<sub>5</sub>
Exact Mass: 535.16
Mol. Wt.: 535.98

The title compound was synthesized according to the procedure described previously. MS found for $C_{27}H_{26}ClN_5O_5$: $(M+H)^+$: 536.1.

Example 249

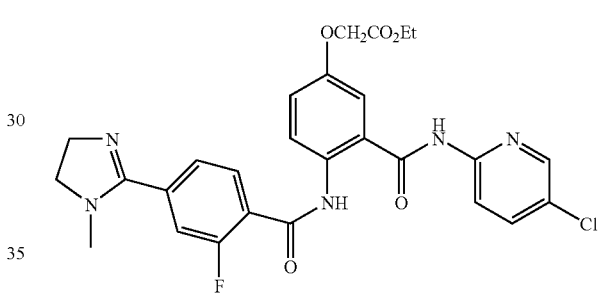

C<sub>27</sub>H<sub>25</sub>ClFN<sub>5</sub>O<sub>5</sub>
Exact Mass: 553.15
Mol. Wt.: 553.97

The title compound was synthesized according to the procedure described previously. MS found for $C_{27}H_{25}ClFN_5O_5$: $(M+H)^+$554.2.

Example 250

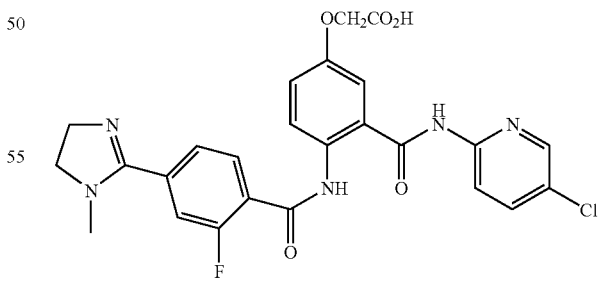

C<sub>25</sub>H<sub>21</sub>ClFN<sub>5</sub>O<sub>5</sub>
Exact Mass: 525.12
Mol. Wt.: 525.92

The title compound was synthesized according to the procedure described previously. MS found for $C_{25}H_{21}ClFN_5O_5$: $(M+H)^+$: 526.1.

Example 251

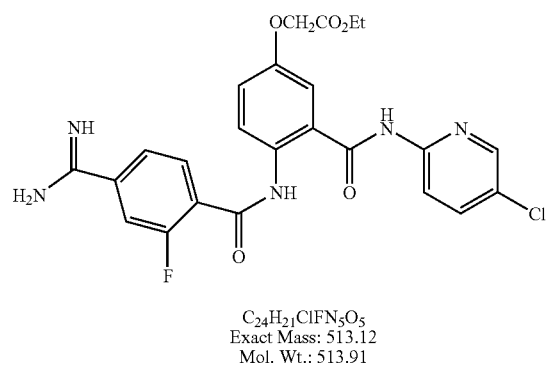

C$_{24}$H$_{21}$ClFN$_5$O$_5$
Exact Mass: 513.12
Mol. Wt.: 513.91

The title compound was synthesized according to the procedure described previously. MS found for C$_{24}$H$_{21}$ClFN$_5$O$_5$: (M+H)$^+$: 514.1.

Example 252

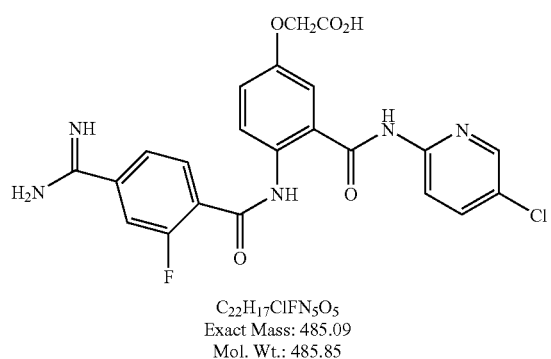

C$_{22}$H$_{17}$ClFN$_5$O$_5$
Exact Mass: 485.09
Mol. Wt.: 485.85

The title compound was synthesized according to the procedure described previously. MS found for C$_{22}$H$_{17}$ClFN$_5$O$_5$: (M+H)$^+$: 486.

Example 253

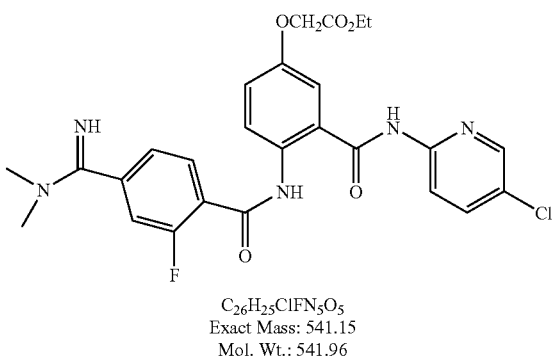

C$_{26}$H$_{25}$ClFN$_5$O$_5$
Exact Mass: 541.15
Mol. Wt.: 541.96

The title compound was synthesized according to the procedure described previously. MS found for C$_{26}$H$_{25}$ClFN$_5$O$_5$: (M+H)$^+$: 542.1.

Example 254

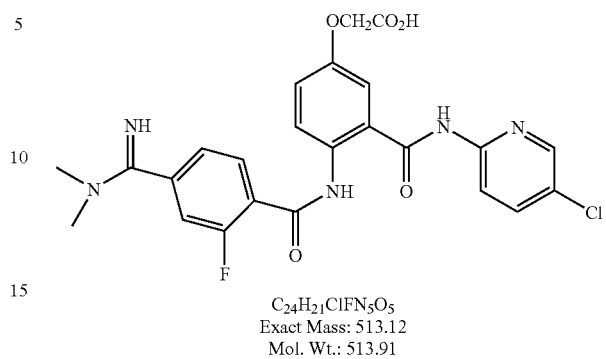

C$_{24}$H$_{21}$ClFN$_5$O$_5$
Exact Mass: 513.12
Mol. Wt.: 513.91

The title compound was synthesized according to the procedure described previously. MS found for C$_{24}$H$_{21}$ClFN$_5$O$_5$: (M+H)$^+$: 514.1.

Example 255

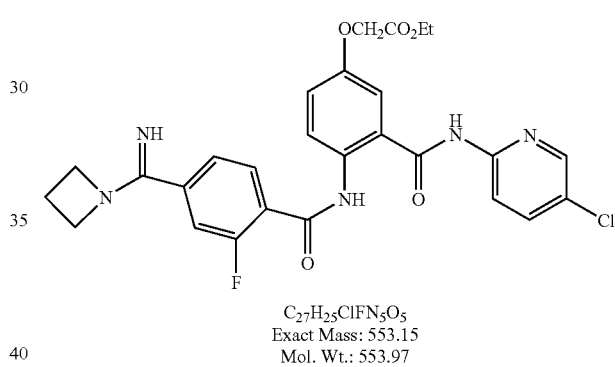

C$_{27}$H$_{25}$ClFN$_5$O$_5$
Exact Mass: 553.15
Mol. Wt.: 553.97

The title compound was synthesized according to the procedure described previously. MS found for C$_{27}$H$_{25}$ClFN$_5$O$_5$: (M+H)$^+$: 554.1.

Example 256

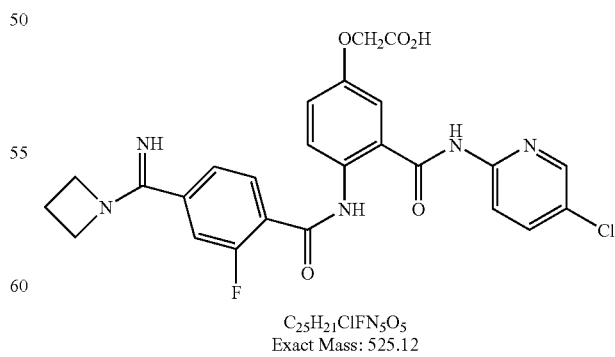

C$_{25}$H$_{21}$ClFN$_5$O$_5$
Exact Mass: 525.12
Mol. Wt.: 525.92

The title compound was synthesized according to the procedure described previously. MS found for C$_{25}$H$_{21}$ClFN$_5$O$_5$: (M+H)$^+$: 526.1.

Example 257

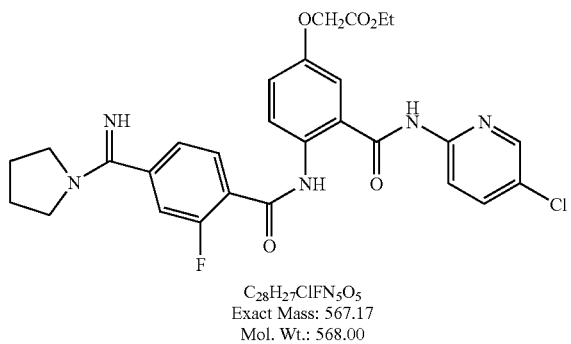

C<sub>28</sub>H<sub>27</sub>ClFN<sub>5</sub>O<sub>5</sub>
Exact Mass: 567.17
Mol. Wt.: 568.00

The title compound was synthesized according to the procedure described previously. MS found for $C_{28}H_{27}ClFN_5O_5$: $(M+H)^+$: 568.1.

Example 258

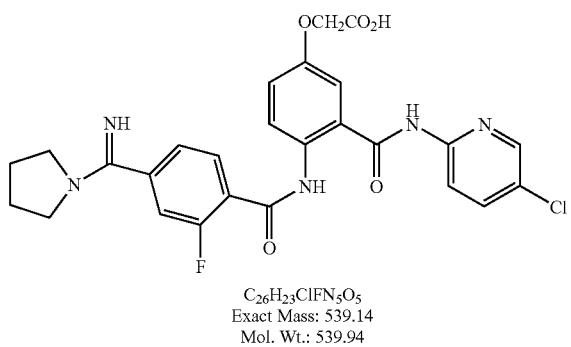

C<sub>26</sub>H<sub>23</sub>ClFN<sub>5</sub>O<sub>5</sub>
Exact Mass: 539.14
Mol. Wt.: 539.94

The title compound was synthesized according to the procedure described previously. MS found for $C_{26}H_{23}ClFN_5O_5$: $(M+H)^+$: 540.1.

Example 259

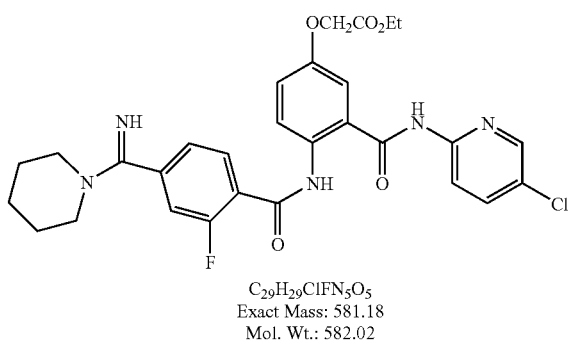

C<sub>29</sub>H<sub>29</sub>ClFN<sub>5</sub>O<sub>5</sub>
Exact Mass: 581.18
Mol. Wt.: 582.02

The title compound was synthesized according to the procedure described previously. MS found for $C_2H_{29}ClFN_5O_5$: $(M+H)^+$: 582.2.

Example 260

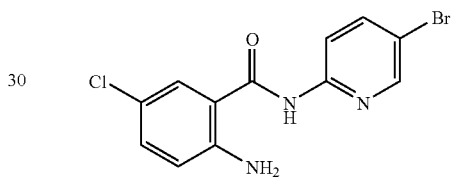

C<sub>27</sub>H<sub>25</sub>ClFN<sub>5</sub>O<sub>5</sub>
Exact Mass: 553.15
Mol. Wt.: 553.97

The title compound was synthesized according to the procedure described previously. MS found for $C_{27}H_{25}ClN_5O_5$: $(M+H)^+$: 554.1.

Example 261

Step 1:

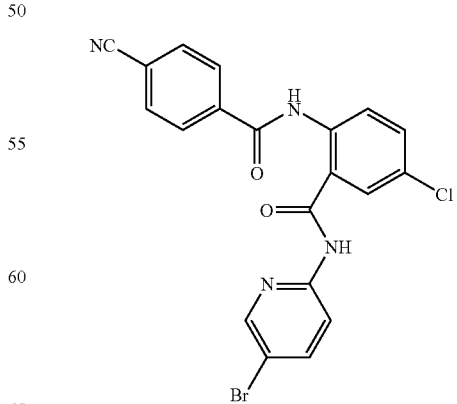

To a solution of 2-amino-5-bromopyridine (882 mg, 5.1 mmol) in tetrahydrofuran (5 ml) was added 0.5M potassium bis(trimethylsilyl)amide in toluene (20 ml, 10.1 mmol) dropwise at −78° C. After stirred for additional 0.5 hr at −78° C., the mixture was added 5-chloroisatoic anhydride (1 g, 5.1 mmol) at −78° C. The mixture was warmed up to r.t gradually and stirred overnight. After concentrated, the crude was washed with saturated ammonium chloride solution and extracted by ethyl acetate. The organic layer was dried over magnesium sulfate and concentrated to give (2-amino-5-bromophenyl)-N-(5-chloro(2-pyridyl))carboxamide as yellow solid (1.54 g, 92%). MS found for C12H9BrClN3O $M^+$=327, $(M+2)^+$=329.

Step 2:

To a solution of the compound of (2-amino-5-bromophenyl)-N-(5-chloro(2-pyridyl))carboxamide (1.33 g, 4.07 mmol) in dichloromethane (10 ml) was added 4-cyanobenzoyl chloride (808 mg, 4.88 mmol) and pyridine (1 ml, 12.21 mmol). The mixture was stirred at r.t. overnight. The precipitate was filtered and washed with a little amount of dichloromethane to give N-{4-chloro-2-[N-(5-bromo(2-pyridyl))carbamoyl]phenyl}(4-cyanophenyl)carboxamide as yellow solid (1.36 g, 73%). MS found for C20H12BrClN4O2 M$^+$=455, (M+2)$^+$=457.

Step 3:

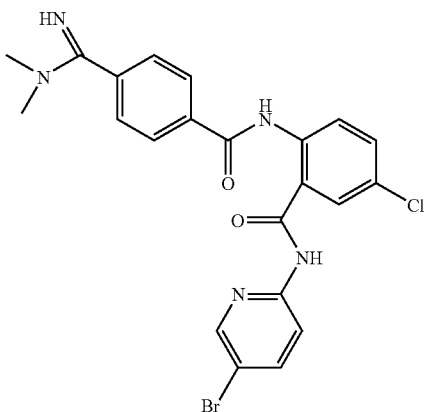

To a solution of the compound of N-{4-chloro-2-[N-(5-bromo(2-pyridyl))carbamoyl]phenyl}(4-cyanophenyl)carboxamide (1.36 g, 3 mmol) in anhydrous pyridine (20 ml) and triethyl amine (2 ml) was saturated with hydrogen sulfide gas at 0° C. The mixture was stirred at r.t. overnight. After concentrated, the residue was dissolved in anhydrous acetone (20 ml) and iodomethane (1.87 ml, 30 mmol) was added. The mixture was refluxed for 2 hrs. After concentrated, the residue was dissolved in anhydrous methanol (20 ml) and a solution of 2M dimethylamine (in THF) (15 ml, 30 mmol) and acetic acid (10 ml) in anhydrous methanol (5 ml) was added. The mixture was refluxed for 2 hrs. After concentrated, the crude residue was purified by RP-HPLC to give target as white solid (750 mg, 50%). MS found C22H19BrClN5O2 M$^+$=500, (M+2)$^+$=502.

Example 262

Step 1:

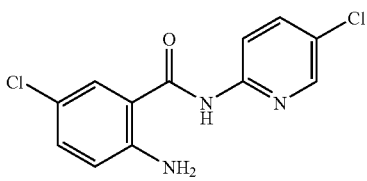

To a solution of 2-amino-5-chloropyridine (787 mg, 6.1 mmol) in tetrahydrofuran (5 ml) was added 0.5M potassium bis(trimethylsilyl)amide in toluene (20 ml, 10.1 mmol) dropwise at −78° C. After stirred for additional 0.5 hr at −78° C., the mixture was added 5-chloroisatoic anhydride (1 g, 5.1 mmol) at −78° C. The mixture was warmed up to r.t gradually and stirred overnight. After concentrated, the crude was washed with saturated ammonium chloride solution and extracted by ethyl acetate. The organic layer was dried over magnesium sulfate and concentrated to give (2-amino-5-chlorophenyl)-N-(5-chloro(2-pyridyl))carboxamide as yellow solid (1.39 g, 99%). MS found for C12H9Cl2N3O M$^+$=282, (M+2)$^+$=284.

Step 2:

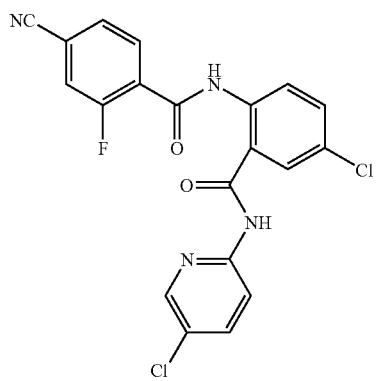

A solution of 2-fluoro-4-cyanobenzoic acid (1 g, 6.06 mmol) in thionyl chloride (5 ml) was refluxed for 2 hr. After concentration, the residue was dissolved in dichloromethane (5 ml). And a solution of the compound of (2-amino-5-chlorophenyl)-N-(5-chloro(2-pyridyl))carboxamide (1.2 g, 4.25 mmol) in dichloromethane (10 ml) and pyridine (1.47 ml, 18.18 mmol) were added. The mixture was stirred at r.t. overnight. The precipitate was filtered and washed with a little amount of dichloromethane to give N-{4-chloro-2-[N-(5-chloro(2-pyridyl))carbamoyl]phenyl}(2-fluoro-4-cyanophenyl)carboxamide (2.03 g, 78%). MS found for C20H11 Cl2FN4O2 M$^+$=429, (M+2)$^+$=431.

Step 3:

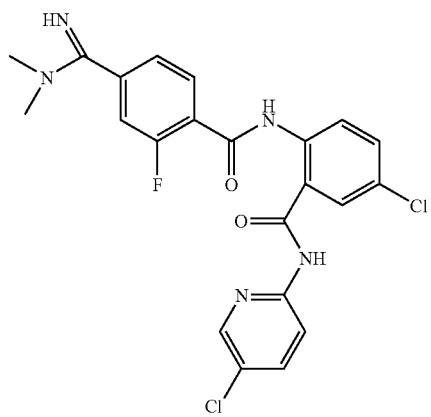

To a solution of the compound of N-{4-chloro-2-[N-(5-chloro(2-pyridyl))carbamoyl]phenyl}(2-fluoro-4-cyanophenyl)carboxamide (3 g, 7 mmol) in anhydrous pyridine (40 ml) and triethyl amine (4 ml) was saturated with hydrogen sulfide gas at 0° C. The mixture was stirred at r.t. overnight. After concentrated, the residue was dissolved in anhydrous acetone (60 ml) and iodomethane (4.36 ml, 70 mmol) was added. The mixture was refluxed for 2 hrs. After concentrated, the residue was dissolved in anhydrous methanol (50 ml) and a solution of 2M dimethylamine (in THF) (35 ml, 70 mmol) and acetic acid (30 ml) in anhydrous methanol (15 ml) was added. The mixture was refluxed for 2 hrs. After concentrated, the crude residue was purified by RP-HPLC to give target as white solid (1.7 g, 50%). MS found C22H18Cl2FN5O2 M$^+$=474, (M+2)$^+$=476.

Examples 263-280
The following compounds were similarly prepared.
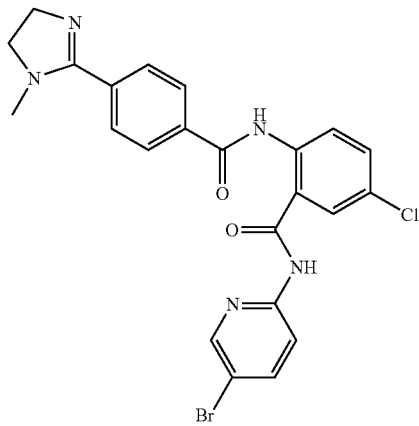
Example 263
M+ = 512
(M + 2)+ = 514
$C_{23}H_{19}BrClN_5O_2$
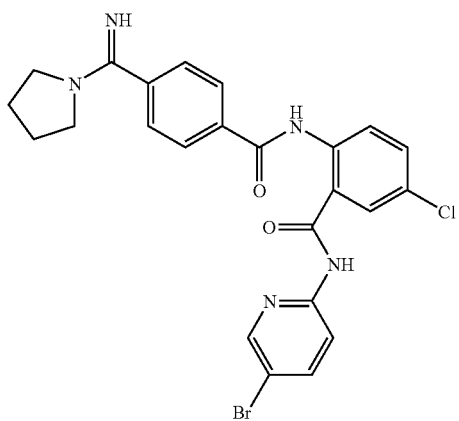
Example 264
$M^+$ = 526
(M + 2)+ = 528
$C_{24}H_{21}BrClN_5O_2$
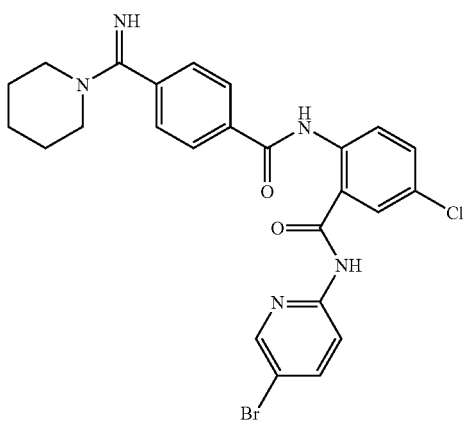
Example 265
$M^+$ = 540
$(M + 2)^+$ = 542
$C_{25}H_{23}BrClN_5O_2$
-continued
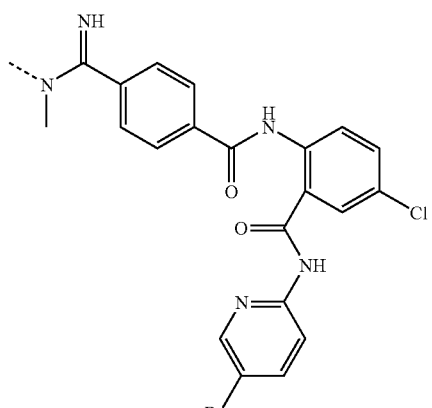
Example 266
$M^+$ = 500
$(M + 2)^+$ = 502
$C_{22}H_{19}BrClN_5O_2$
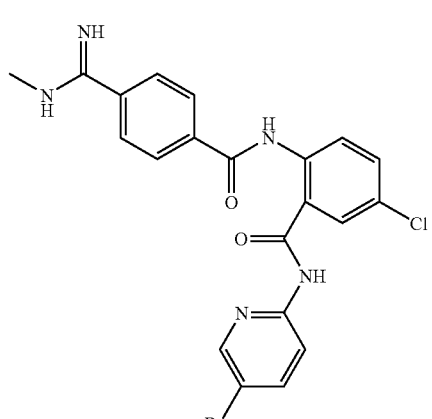
Example 267
$M^+$ = 486
$(M + 2)^+$ = 488
$C_{21}H_{17}BrClN_5O_2$
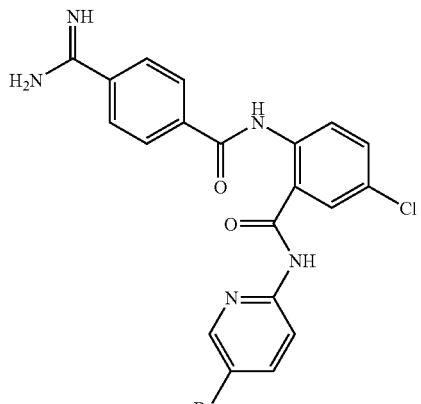
Example 268
$M^+$ = 472
$(M + 2)^+$ = 474
$C_{20}H_{15}BrClN_5O_2$ -continued
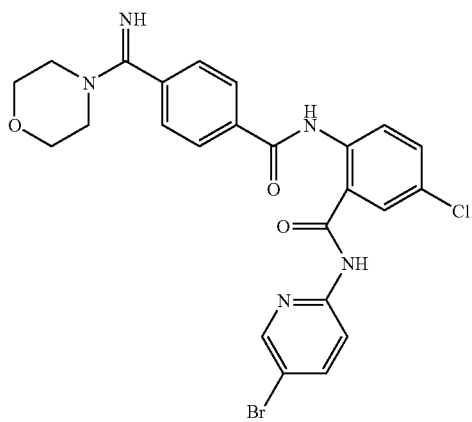
Example 269
M+ = 542
(M + 2)+ = 544
C24H21BrClN5O3
-continued
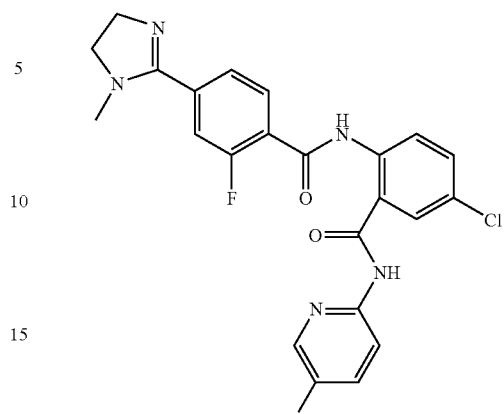
Example 272
M+ = 486
(M + 2)+ = 488
C23H18Cl2FN5O2
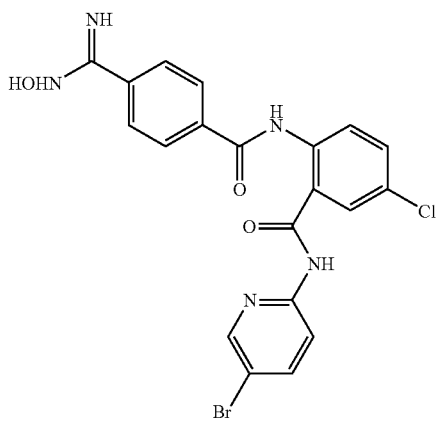
Example 270
M+ = 488
(M + 2)+ = 490
C20H15BrClN5O3
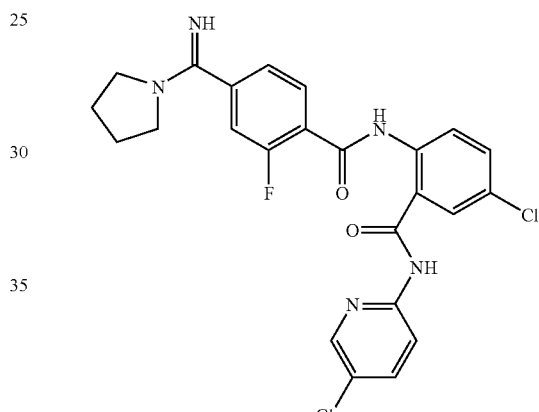
Example 273
M+ = 500
(M + 2)+ = 502
C24H20Cl2FN5O2
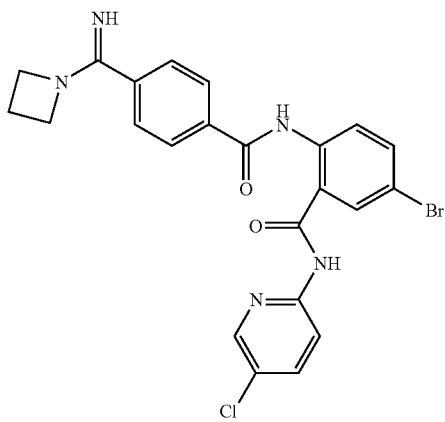
Example 271
M+ = 512
(M + 2)+ = 514
C23H19BrClN5O2
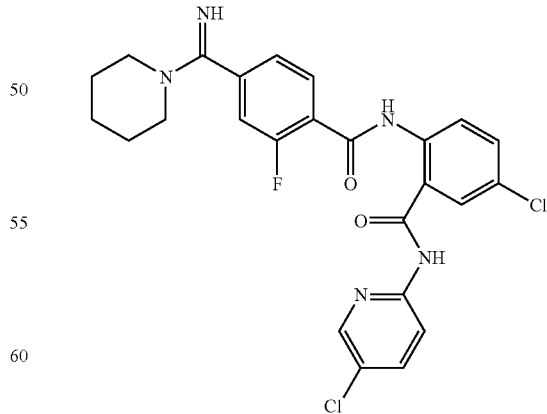
Example 274
M+ = 514
(M + 2)+ = 516
C25H22Cl2FN5O2

-continued
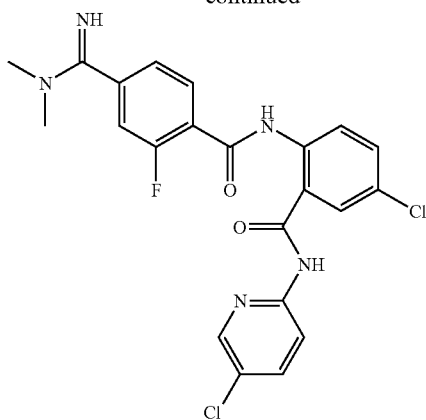
Example 275
M+ = 474
(M + 2)+ = 476
C22H18Cl2FN5O2
-continued
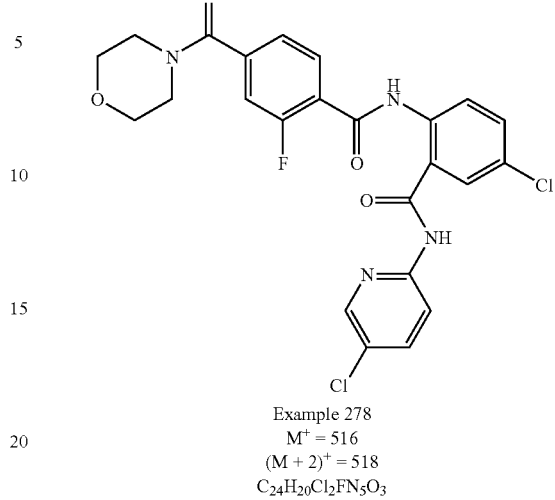
Example 278
M+ = 516
(M + 2)+ = 518
C24H20Cl2FN5O3
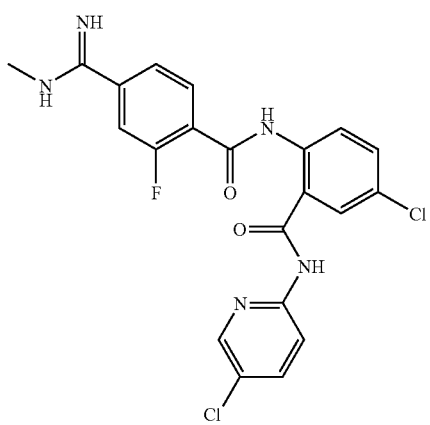
Example 276
M+ = 460
(M + 2)+ = 462
C21H16Cl2FN5O2
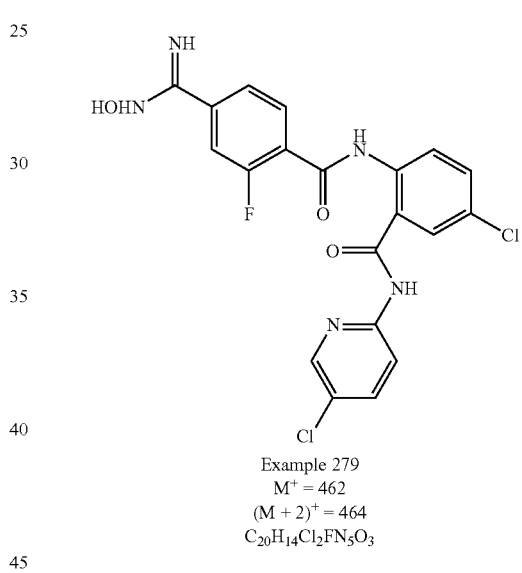
Example 279
M+ = 462
(M + 2)+ = 464
C20H14Cl2FN5O3
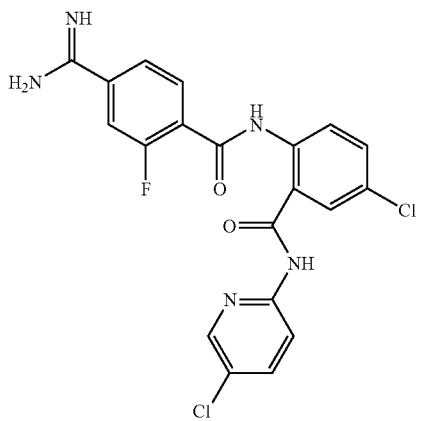
Example 277
M+ = 446
(M + 2)+ = 448
C20H14Cl2FN5O2
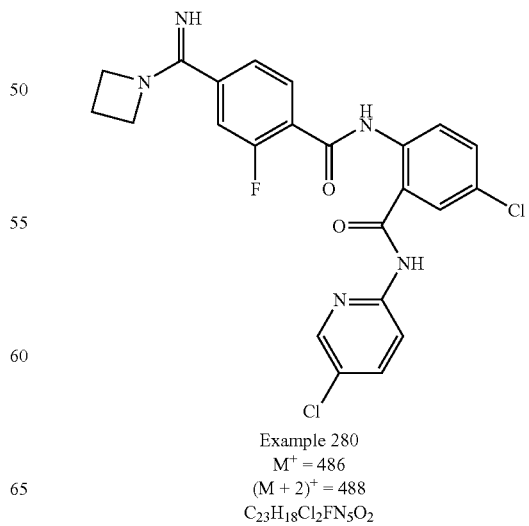
Example 280
M+ = 486
(M + 2)+ = 488
C23H18Cl2FN5O2

Examples 281-287
The following compounds were similarly prepared.
Example 281
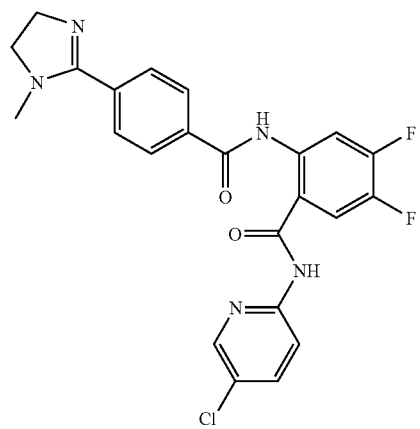
MS (M+H): 470
Example 282
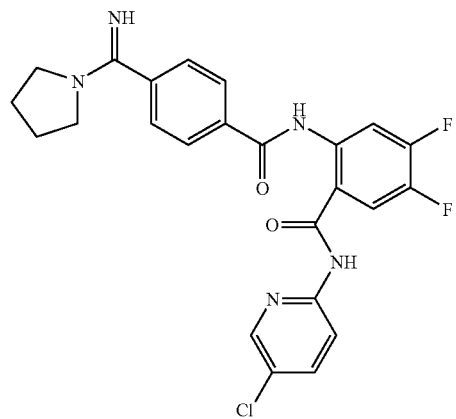
MS (M+H): 484
Example 283
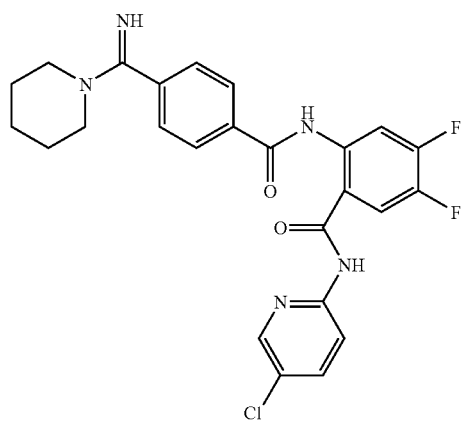
MS (M+H): 496
-continued
Example 284
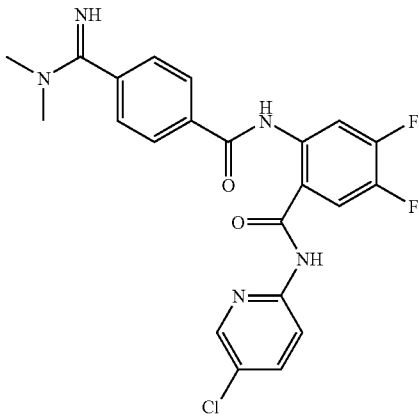
MS (M+H): 458
Example 285
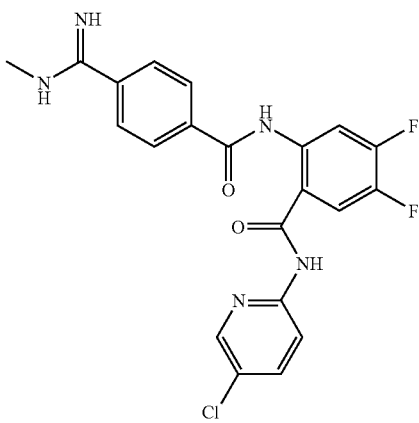
MS (M+H): 444
Example 286
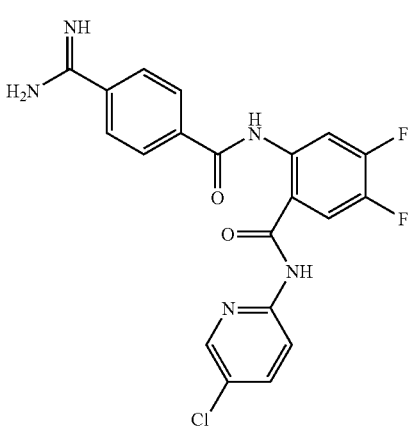
MS (M+H): 430

Example 287

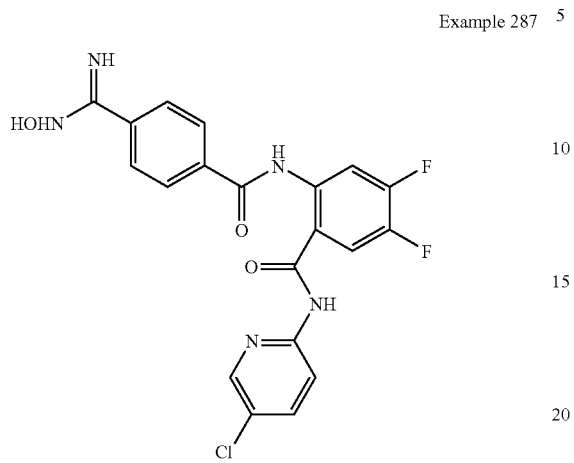

MS (M+H): 446

Example 288

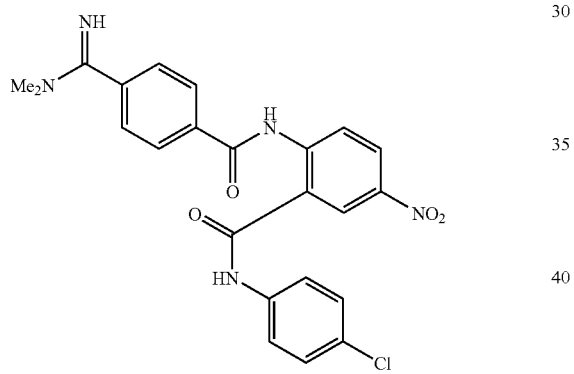

Step 1: A solution of methyl 2-amino-5-nitrobenzoate (1 equiv) and 4-cyanobenzoic acid (1 equiv) in pyridine was treated with $POCl_3$ (1.1 equiv) for 1 h. The resulting mixture was quenched by slow addition of water, and extracted with EtOAc. The organic layer was dried over $MgSO_4$, filtered and flash chromatographied to give the desired product.

Step 2: A solution of 2-amino-5-bromopridine (45 mg, 4.0 equiv) in 5 mL of methylene chloride treated with $AlMe_3$ (2M in hexane, 0.65 mL, 20 equiv) for 30 min was added the compound obtained in step 1 (0.064 mmol, 1 equiv). The mixture was stirred at rt overnight, quenched with saturated aqueous potassium sodium tartrate. The organic layer was dried over $MgSO_4$, filtered, evaporated and purified by column chromatography to give the desired product.

Step 3: The product obtained in step 2 was subjected to standard Pinner conditions to give the title compound after HPLC (C18 reversed phase, eluting with 0.5% TFA in $H_2O/CH_3CN$). MS $(M+H)^+$:467.

Example 289

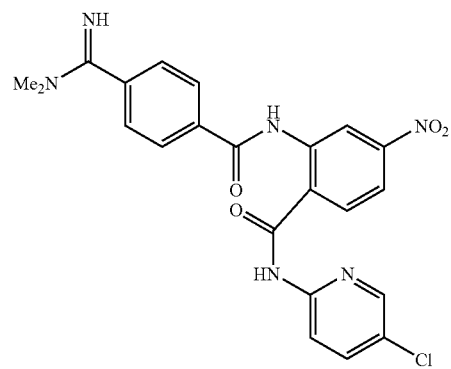

This compound was prepared according to the procedure previously described. MS $(M+H)^+$: 467.

Example 290-302

The following compounds were prepared according to the procedure previously described.

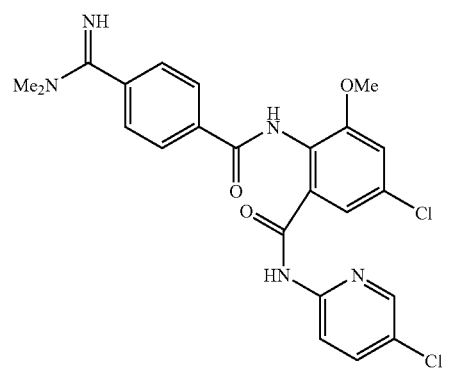

Eample 290
MS (M + H): 486

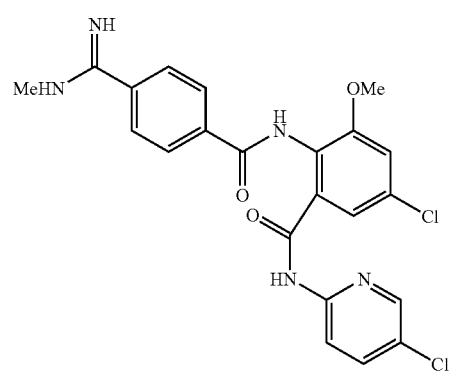

Eample 291
MS (M + H): 472

-continued
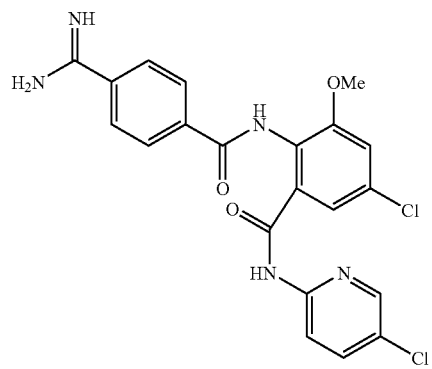
Eample 292
MS (M + H): 458
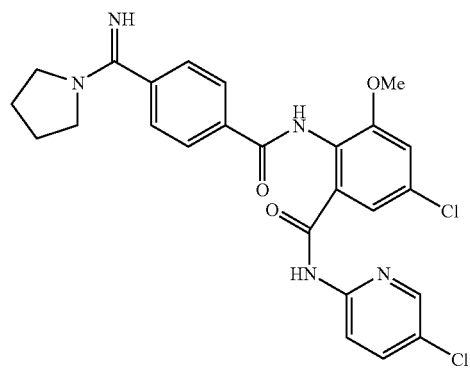
Eample 293
MS (M + H): 512
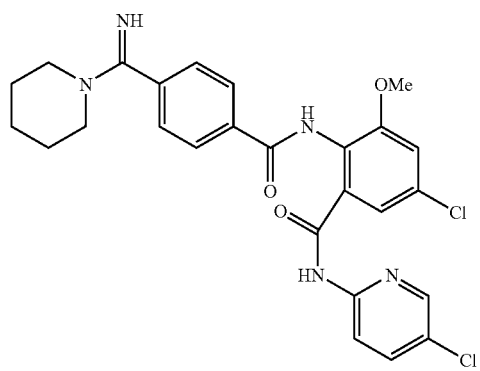
Eample 294
MS (M + H): 526
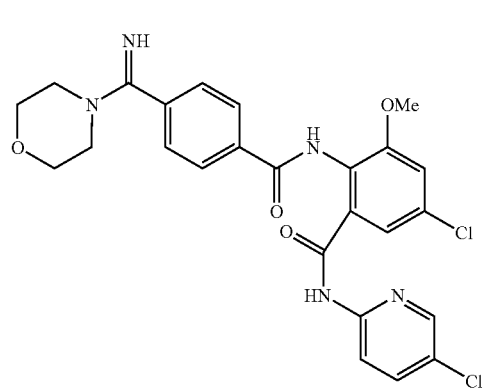
Eample 295
MS (M + H): 528
-continued
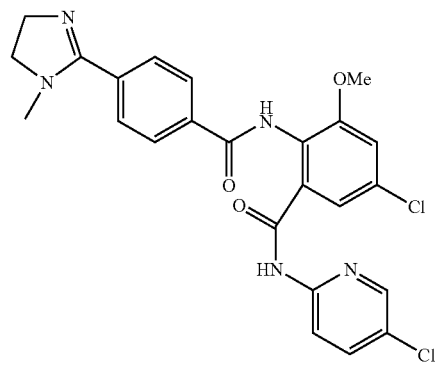
Eample 296
MS (M + H): 498
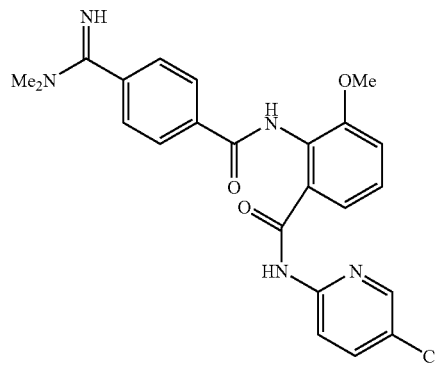
Eample 297
MS (M + H): 452
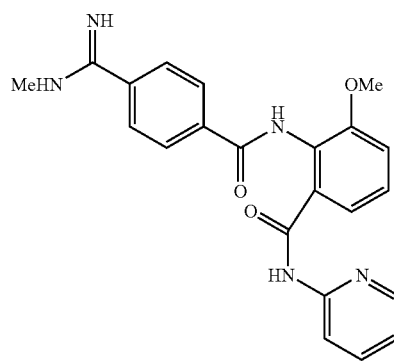
Eample 296
MS (M + H): 438
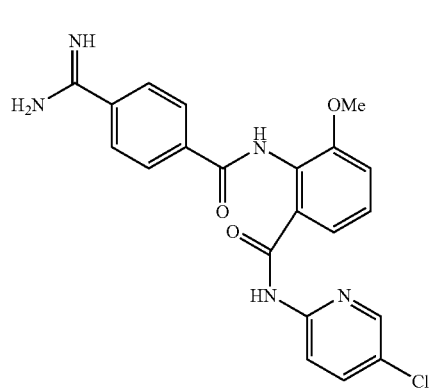
Eample 299
MS (M + H): 424

-continued

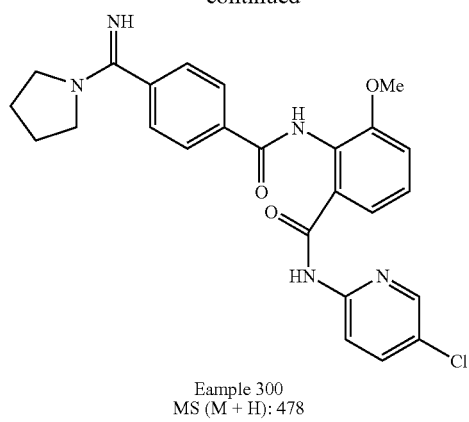

Example 300
MS (M + H): 478

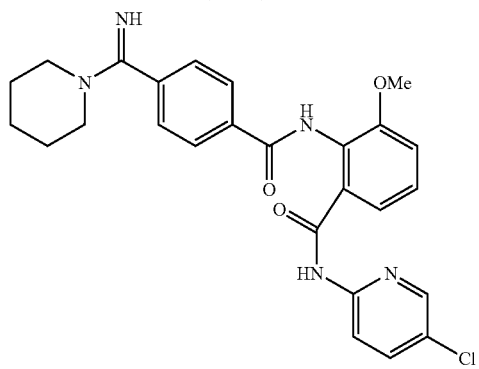

Example 301
MS (M + H): 492

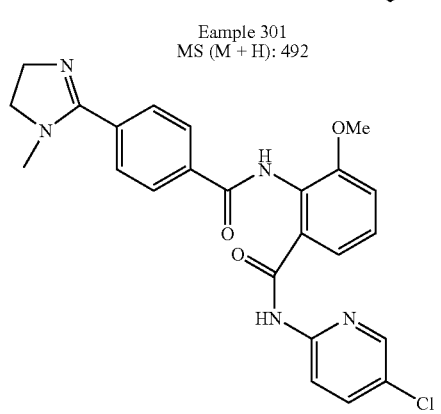

Example 302
MS (M + H): 484

Example 303

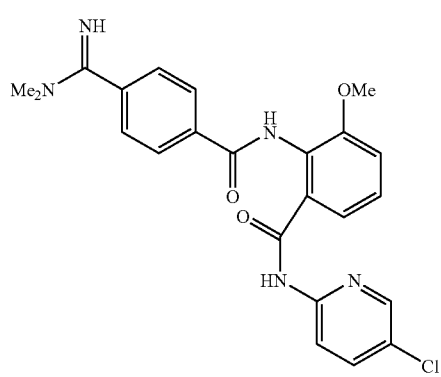

Example 303
MS (M + H): 452

Example 297 (1 equiv) in $CH_2Cl_2$ was treated with $BBr_3$ (4 equiv) overnight, quenched with ice water. HPLC (C18 reversed phase, eluting with 0.5% TFA in $H_2O/CH_3CN$) gave the title compound. MS $(M+H)^+$: 438.

Example 304-308

The following compounds were prepared according to the procedure previously described.

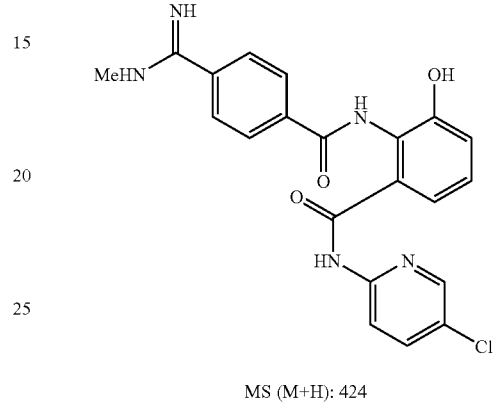

Eample 304

MS (M+H): 424

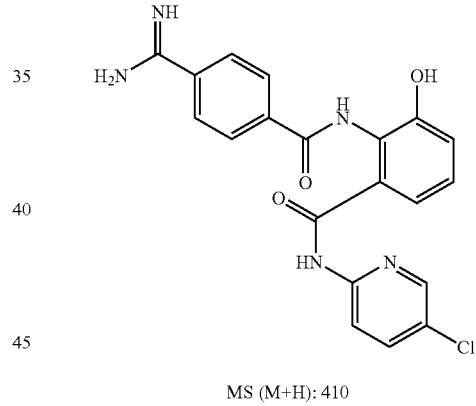

Eample 305

MS (M+H): 410

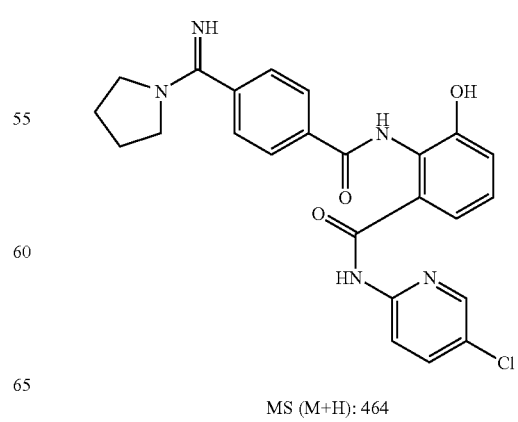

Eample 306

MS (M+H): 464

Eample 307
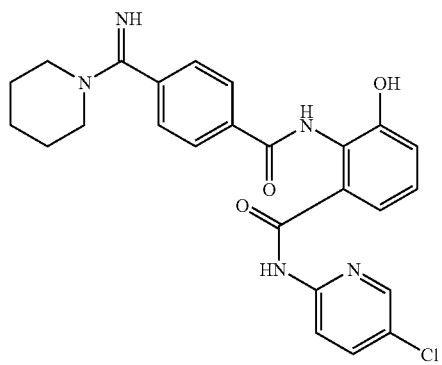
MS (M+H): 478
Eample 308
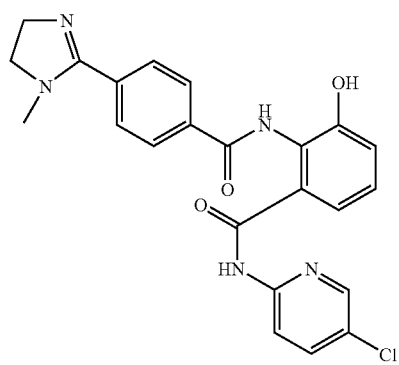
MS (M+H): 470
Example 309
This compound was prepared according to the procedure previously described. MS (M+H)+: 543.
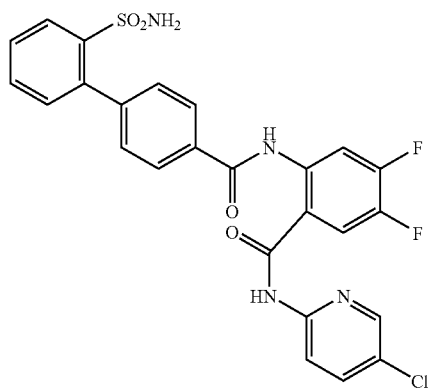
Example 310-315
The following compounds were prepared according to the procedure previously described.
Eample 310
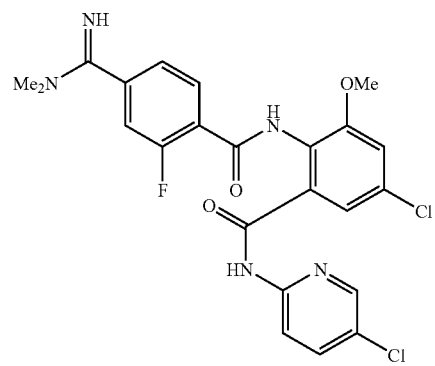
MS (M+H): 504
Eample 311
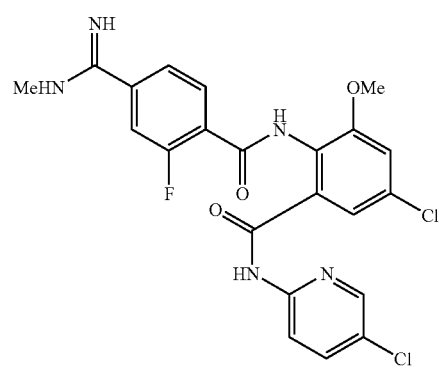
MS (M+H): 490
Eample 312
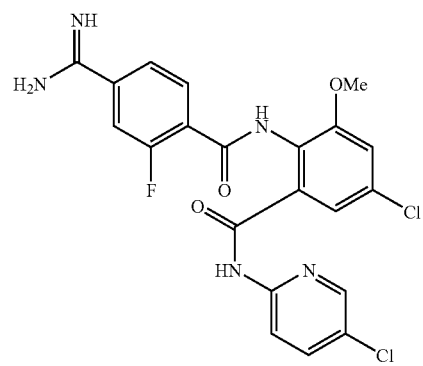
MS (M+H): 476

-continued

Example 313

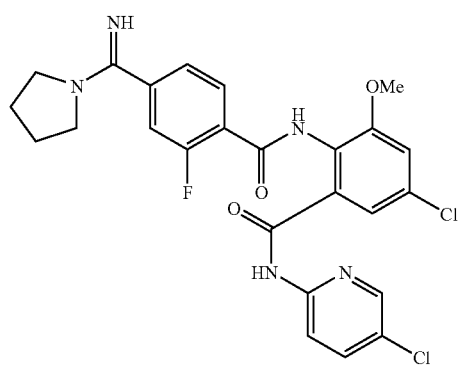

MS (M+H): 530

Example 314

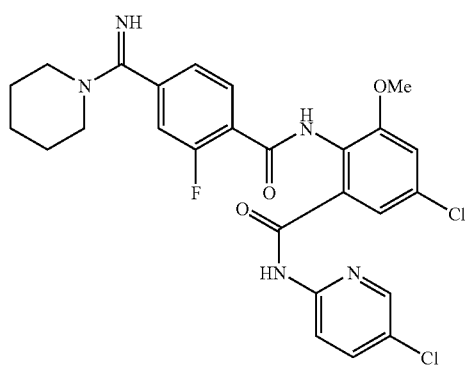

MS (M+H): 544

Example 315

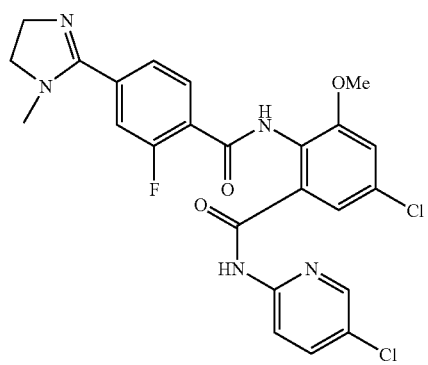

MS (M+H): 516

Example 316

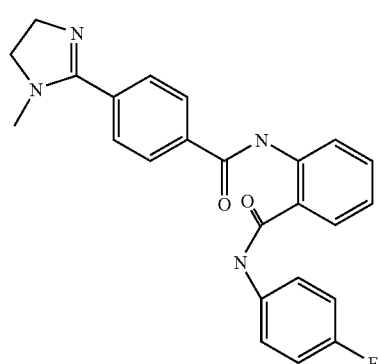

The title compound was synthesized according to the procedure described previously. ES-MS 417(M+1).

Example 317

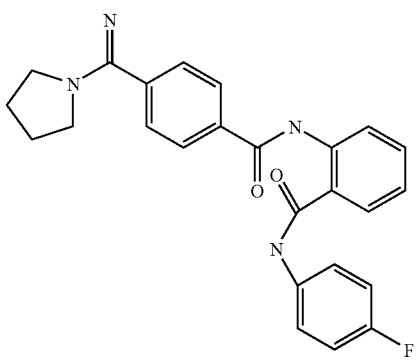

The title compound was synthesized according to the procedure described previously. ES-MS 431 (M+1).

Example 318

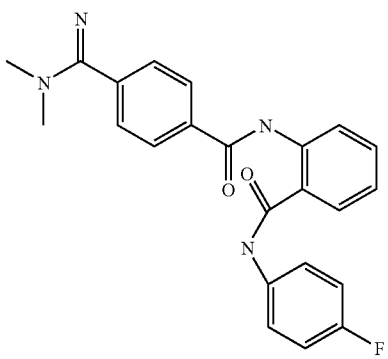

The title compound was synthesized according to the procedure described previously. ES-MS 404(M+1).

Example 319

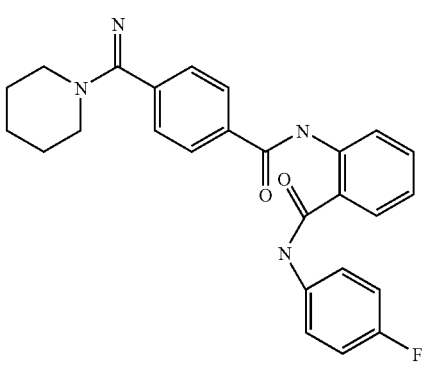

The title compound was synthesized according to the procedure described previously.
ES-MS 445(M+1).

Example 320

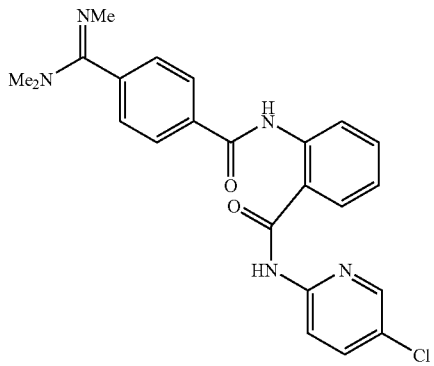

Example 53 (15 mg) was refluxed in pyridine in the presence of 0.1 mL of MeI overnight. The volatile was evaporated and the residue was purified by HPLC to give example 403. MS (M+H): 436.

Examples 321-322

The following compounds were prepared according to the procedure previously described.

Eample 321

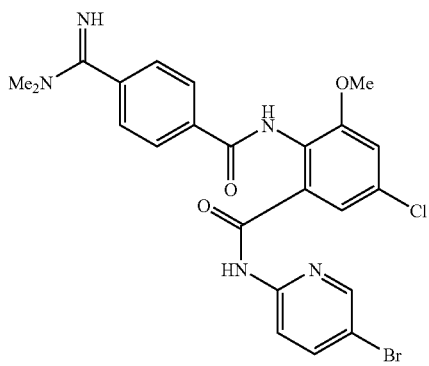

MS (M+H): 530

Eample 322

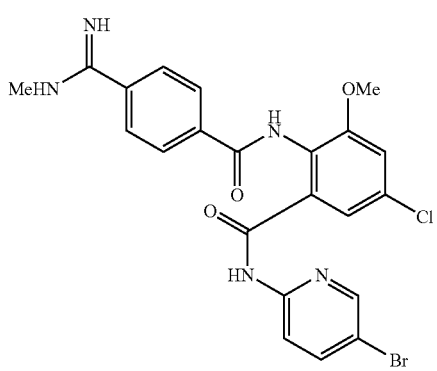

MS (M+H): 516

Example 323

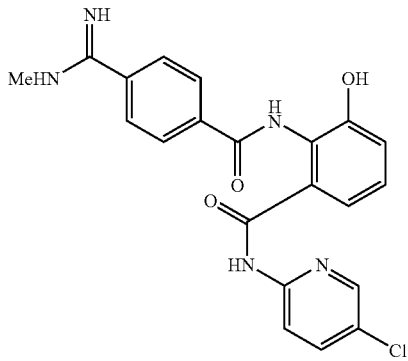

Compound 304 (20 mg) was dissolved in 10 mL of CH$_2$Cl$_2$ and was treated with 2 mL of BBr$_3$ (1N in CH$_2$Cl$_2$) overnight. The reaction was quenched with water and reverse phase HPLC gave the desired product. ES-MS 424 (M+H).

Example 324-336

The following compounds were prepared according to the procedure previously described.

Eample 324

MS (M+H): 472

Eample 325

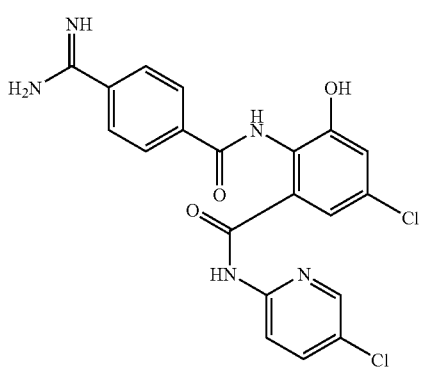

MS (M+H): 444

-continued
Eample 326
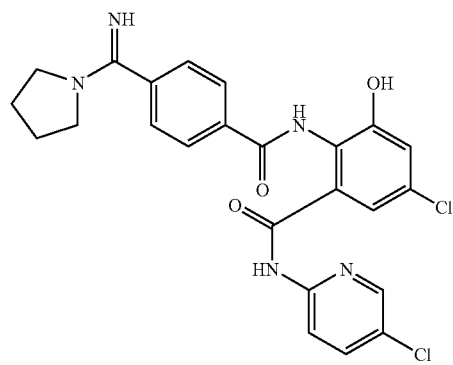
MS (M+H): 498
Eample 327
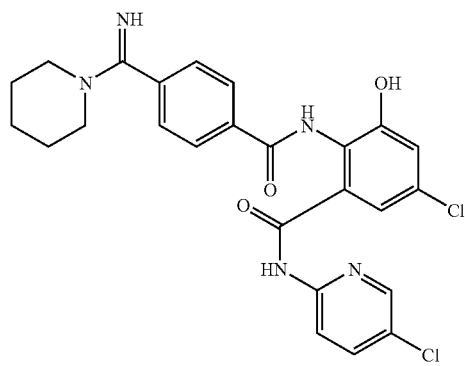
MS (M+H): 512
Eample 328
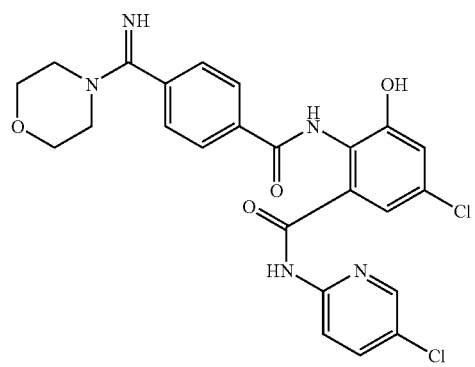
MS (M+H): 514
Eample 329
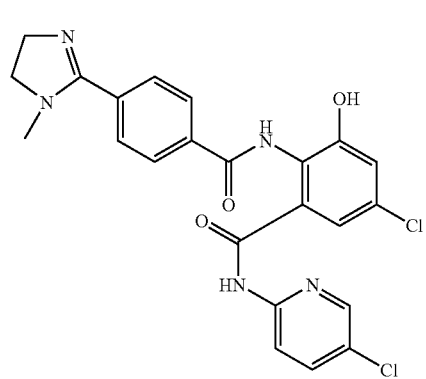
MS (M+H): 484
-continued
Eample 330
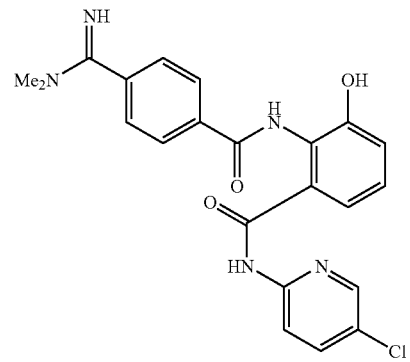
MS (M+H): 438
Eample 331
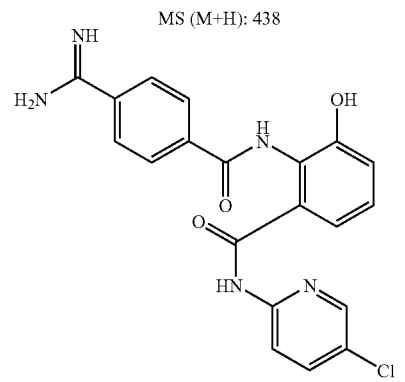
MS (M+H): 410
Eample 332
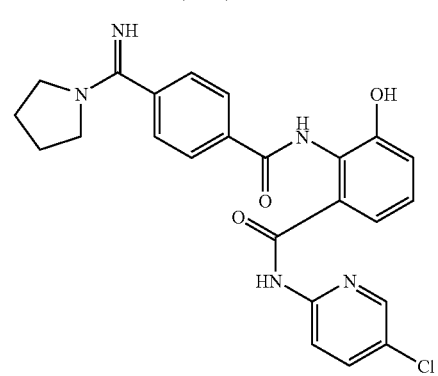
MS (M+H): 464
Eample 333
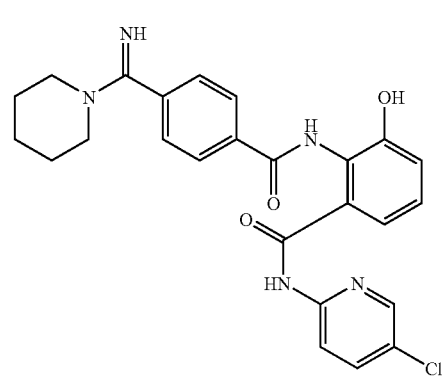
MS (M+H): 478

Example 334
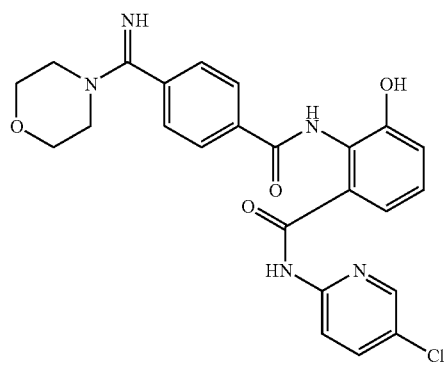
MS (M+H): 480
Example 335
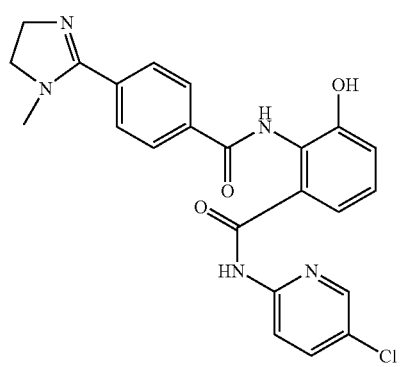
MS (M+H): 450
Example 336
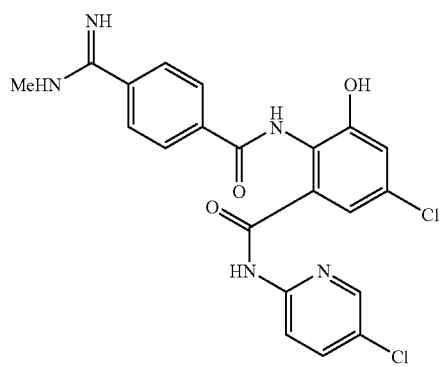
MS (M+H): 458
Example 337-344
The following compounds were prepared according to the procedure previously described.
Example 337
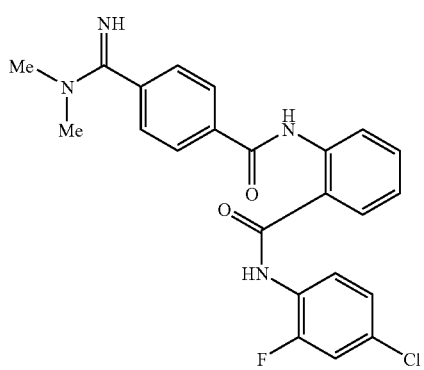
MS (M+H): 439
Example 338
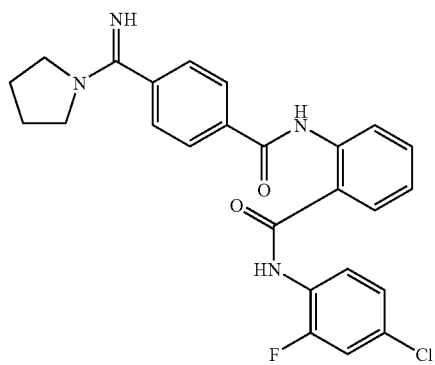
MS (M+H): 465
Example 339
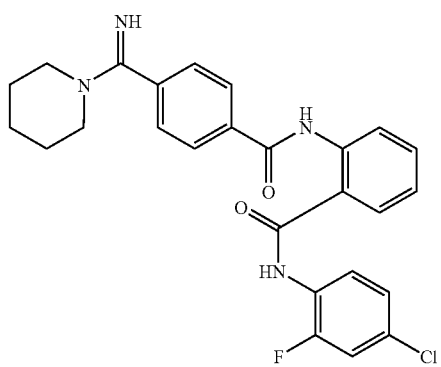
MS (M+H): 479

-continued
Example 340
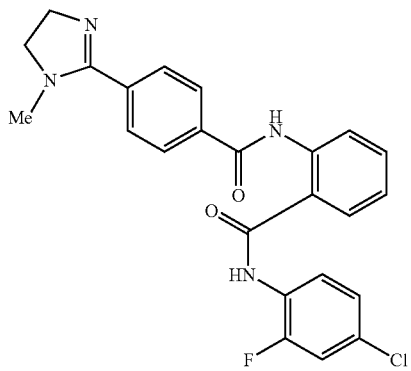
MS (M+H): 451
Example 341
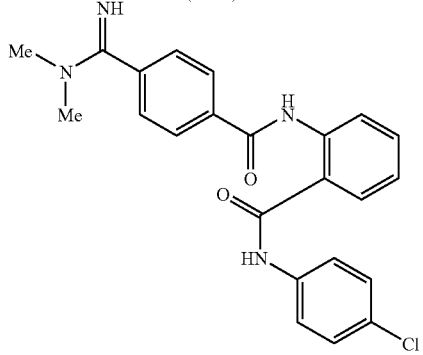
MS (M+H): 421
Example 342
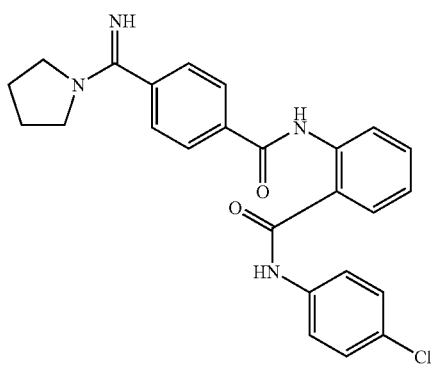
MS (M+H): 447
Example 343
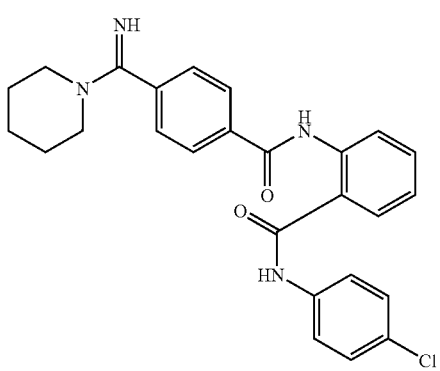
MS (M+H): 461
-continued
Example 344
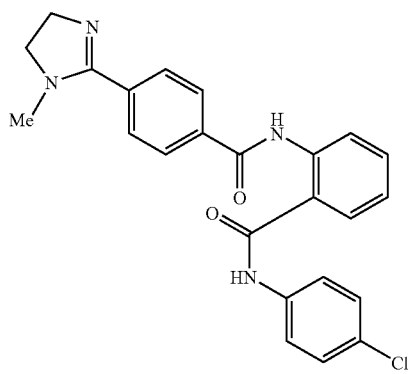
MS (M+H): 433
Example 345-360
The following compounds were prepared according to the procedure previously described.
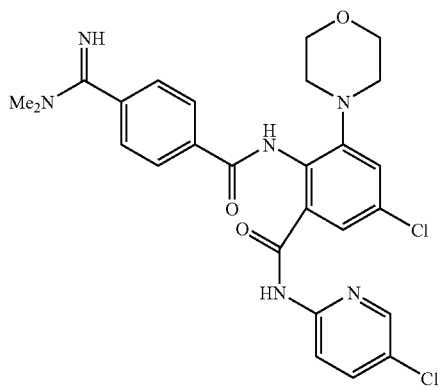
Example 345
MS (M + H): 541
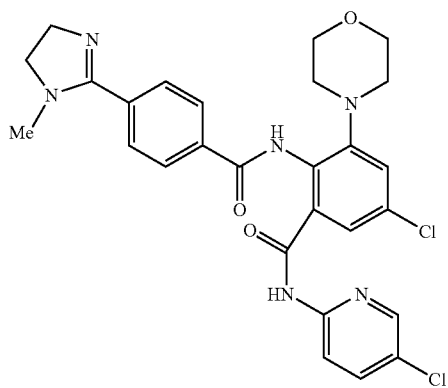
Example 346
MS (M + H): 553

-continued
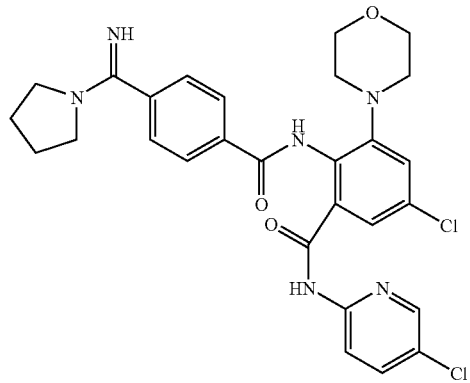
Eample 347
MS (M + H): 567
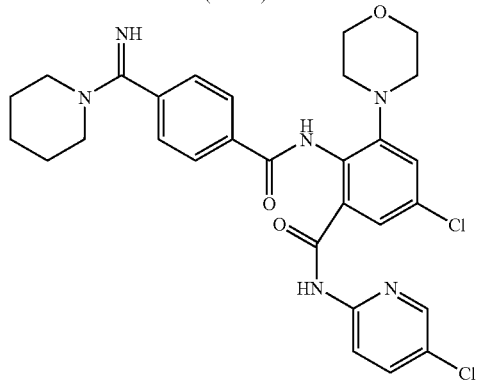
Eample 348
MS (M + H): 581
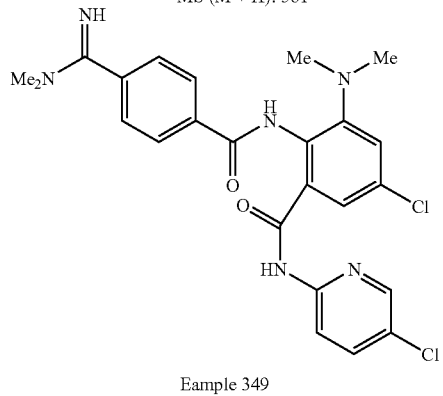
Eample 349
MS (M + H): 499
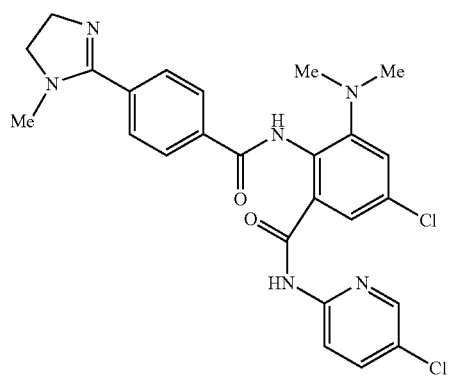
Eample 350
MS (M + H): 511
-continued
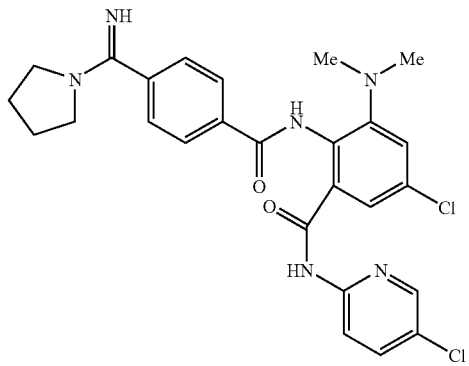
Eample 351
MS (M + H): 525
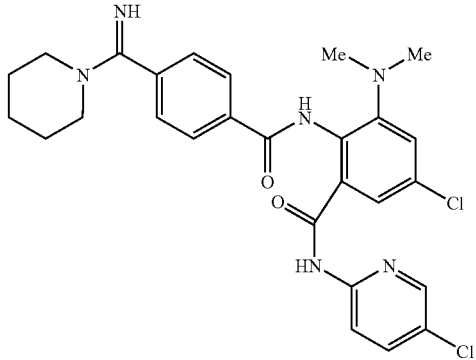
Eample 352
MS (M + H): 539
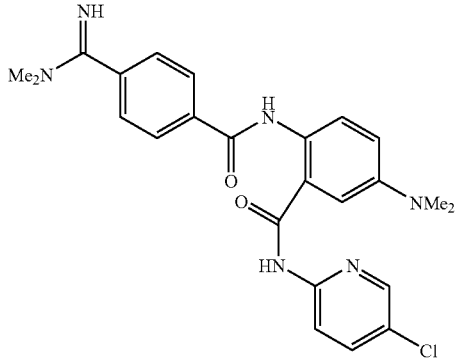
Eample 353
MS (M + H): 499
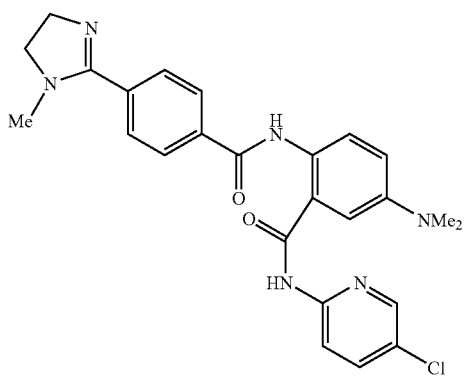
Eample 354
MS (M + H): 511

-continued
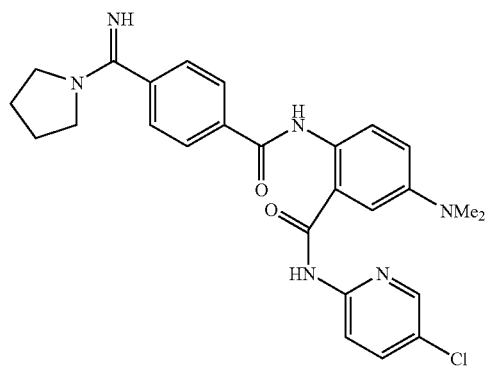
Eample 355
MS (M + H): 525
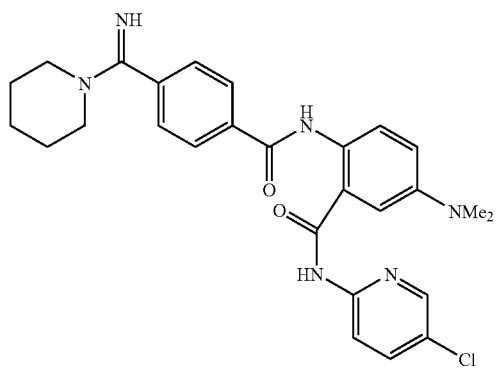
Eample 356
MS (M + H): 539
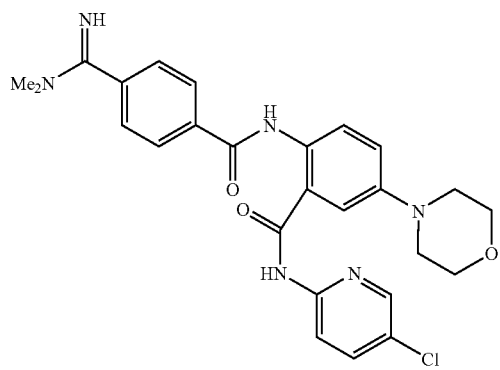
Eample 357
MS (M + H): 541
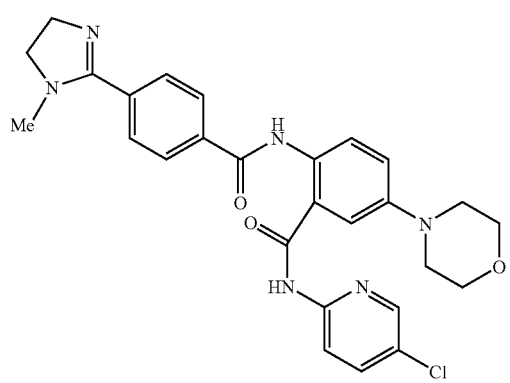
Eample 358
MS (M + H): 553
-continued
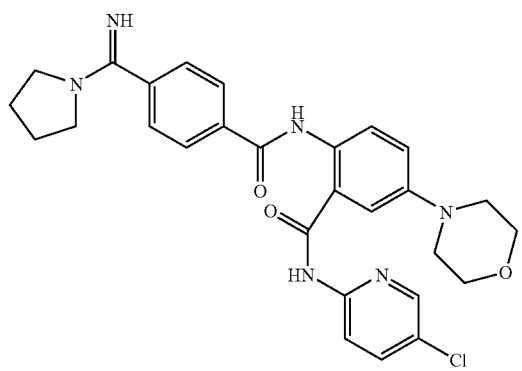
Eample 359
MS (M + H): 567
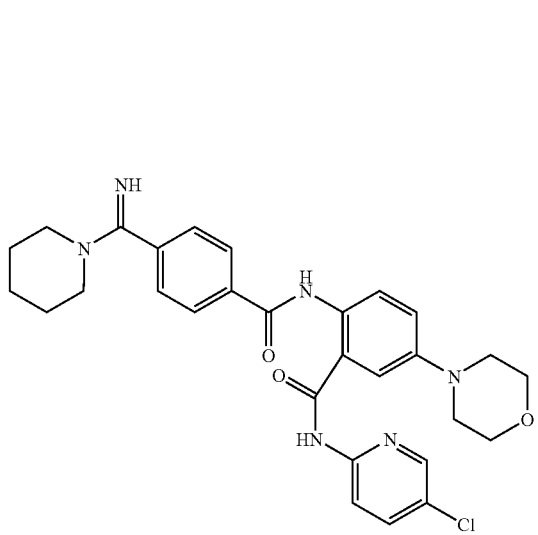
Eample 360
MS (M + H): 581
Example 361-390
The following compounds were prepared according to the procedure previously described.
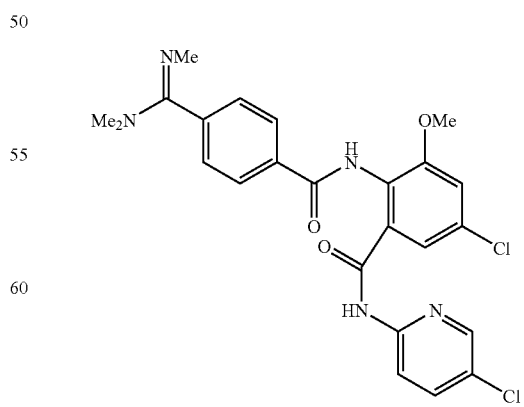
Eample 361
MS (M + H): 500

-continued
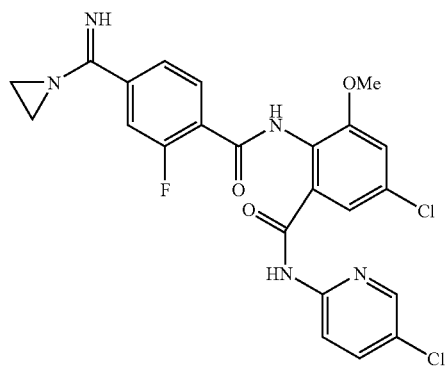
Eample 362
MS (M + H): 502
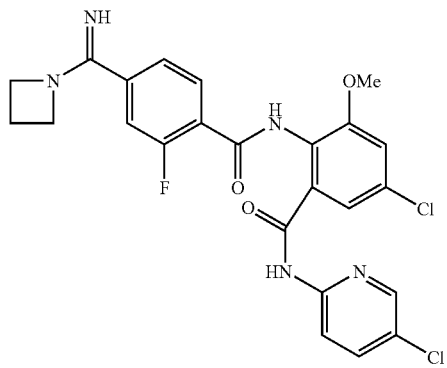
Eample 363
MS (M + H): 514
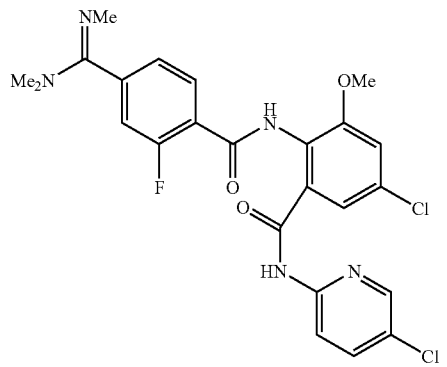
Eample 364
MS (M + H): 512
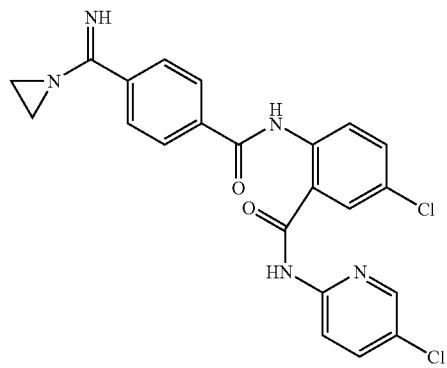
Eample 365
MS (M + H): 454
-continued
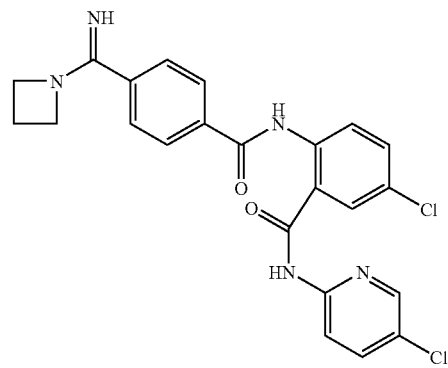
Eample 366
MS (M + H): 468
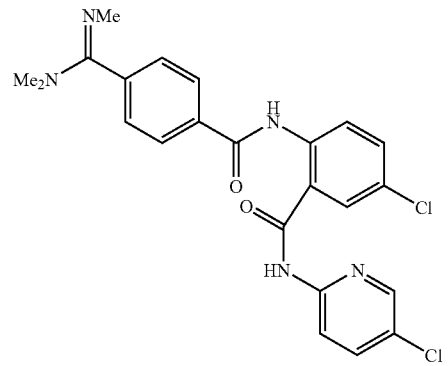
Eample 367
MS (M + H): 466
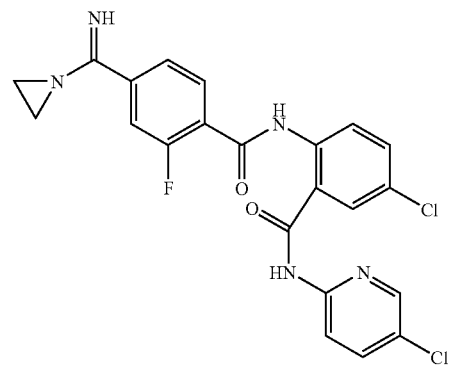
Eample 368
MS (M + H): 472
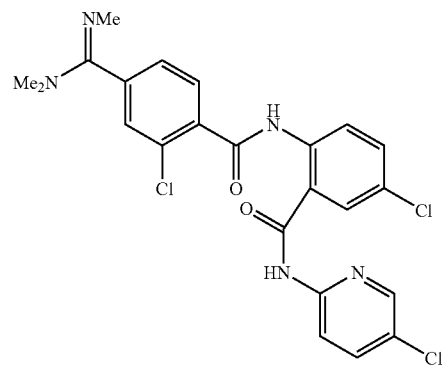
Eample 369
MS (M + H): 504

-continued
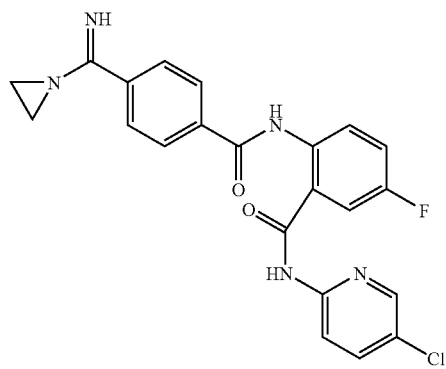
Eample 370
MS (M + H): 438
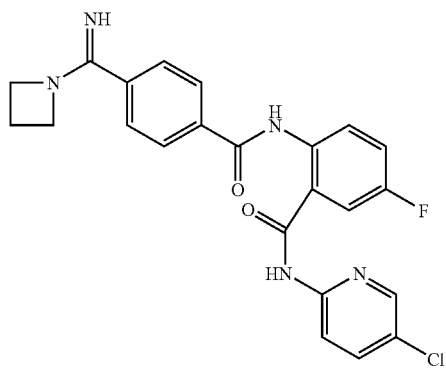
Eample 371
MS (M + H): 452
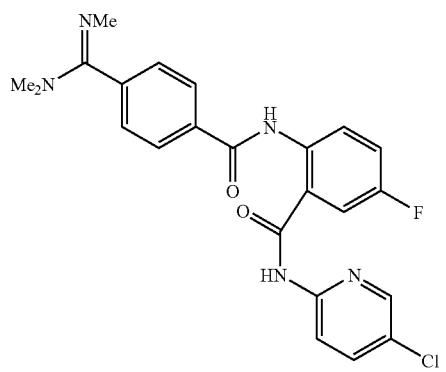
Eample 372
MS (M + H): 450
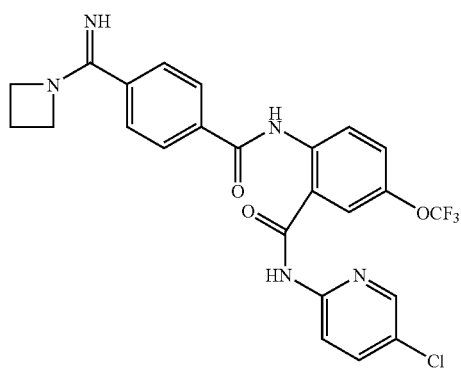
Eample 373
MS (M + H): 518
-continued
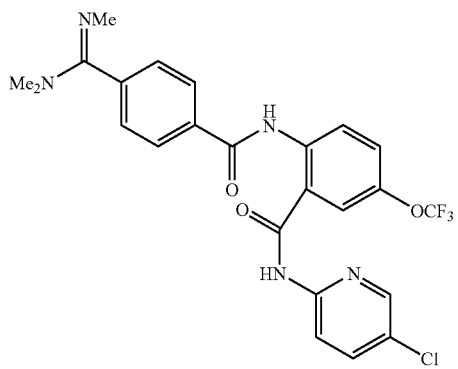
Eample 374
MS (M + H): 516
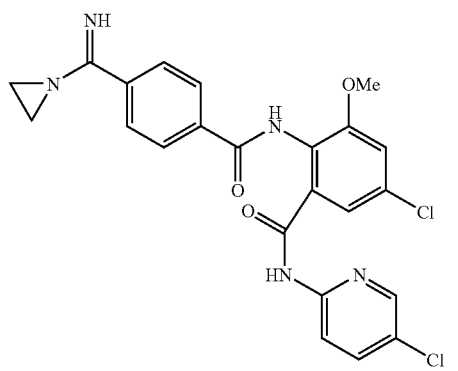
Eample 375
MS (M + H): 484
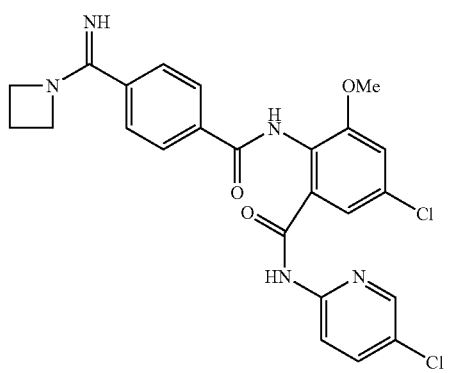
Eample 376
MS (M + H): 498
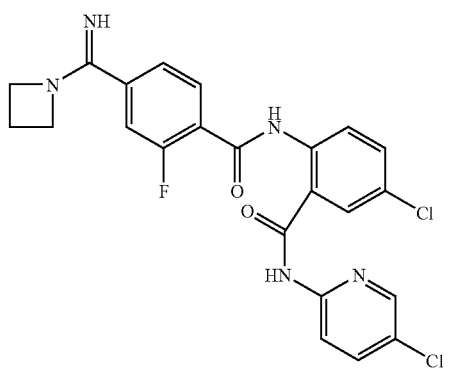
Eample 377
MS (M + H): 486

-continued
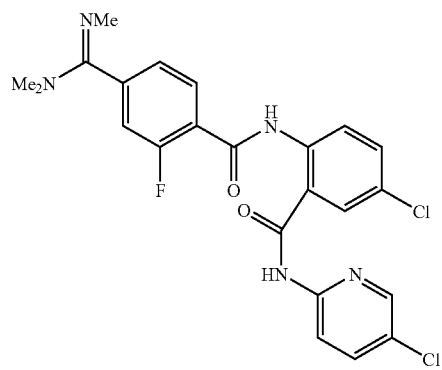
Example 378
MS (M + H): 484
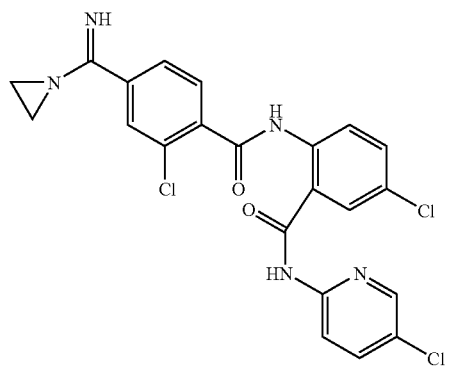
Example 379
MS (M + H): 488
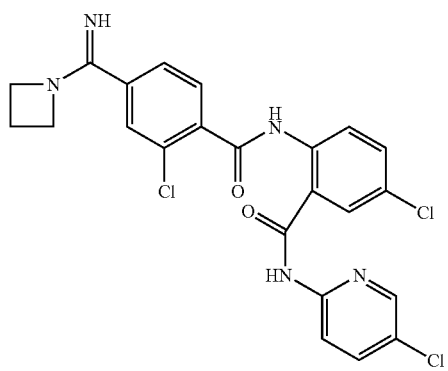
Example 380
MS (M + H): 502
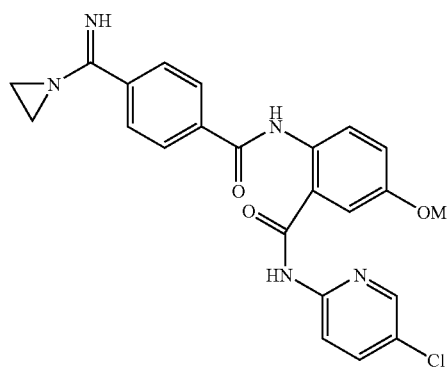
Example 381
MS (M + H): 450
-continued
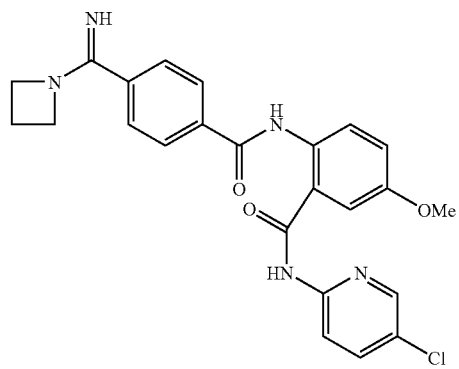
Example 382
MS (M + H): 464
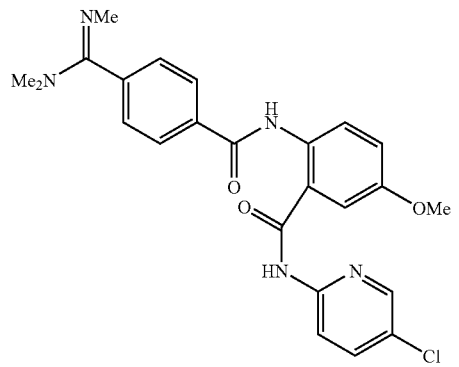
Example 383
MS (M + H): 462
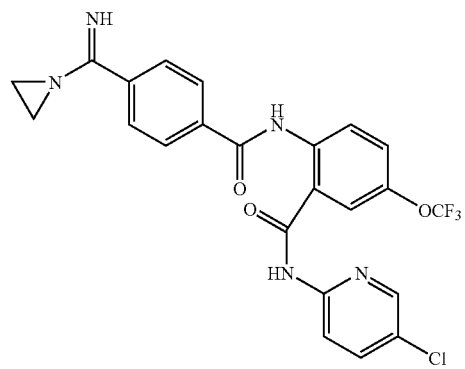
Example 384
MS (M + H): 504
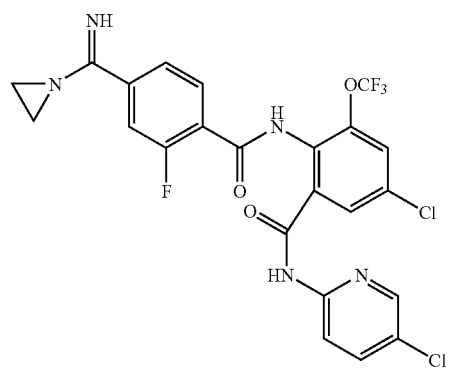
Example 385
MS (M + H): 556

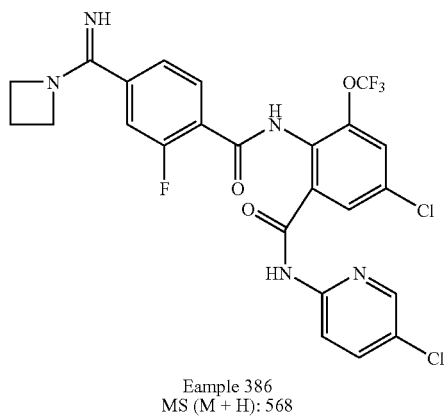
Example 386
MS (M + H): 568
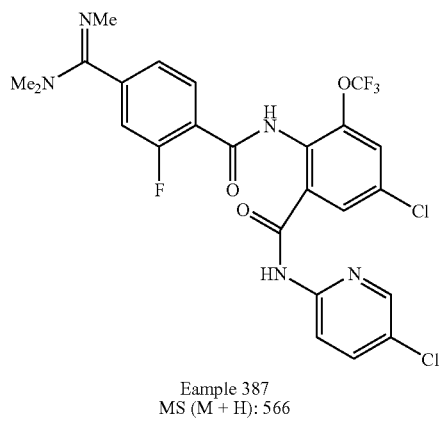
Example 387
MS (M + H): 566
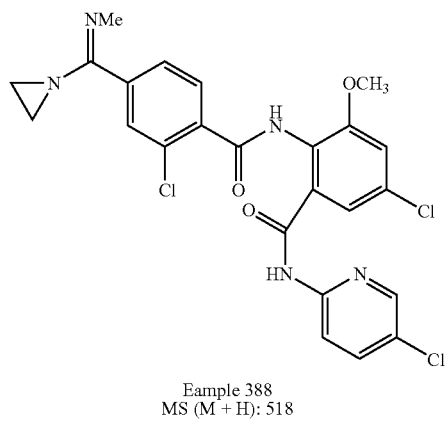
Example 388
MS (M + H): 518
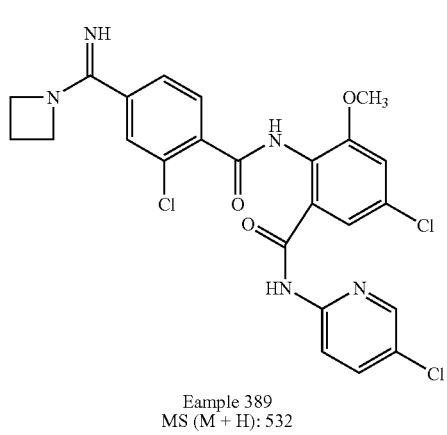
Example 389
MS (M + H): 532
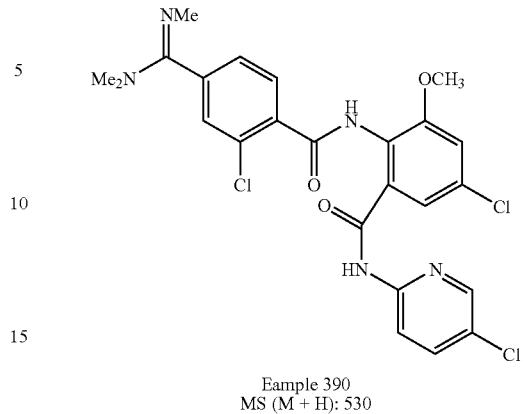
Example 390
MS (M + H): 530
Example 391-398
The following compounds were prepared according to the procedure previously described
Example 391
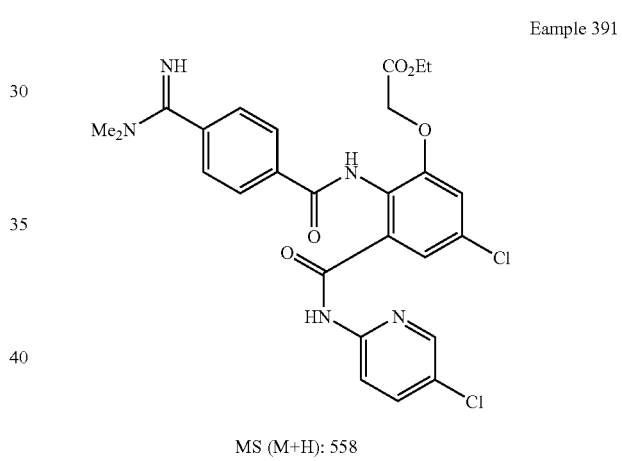
MS (M+H): 558
Example 392
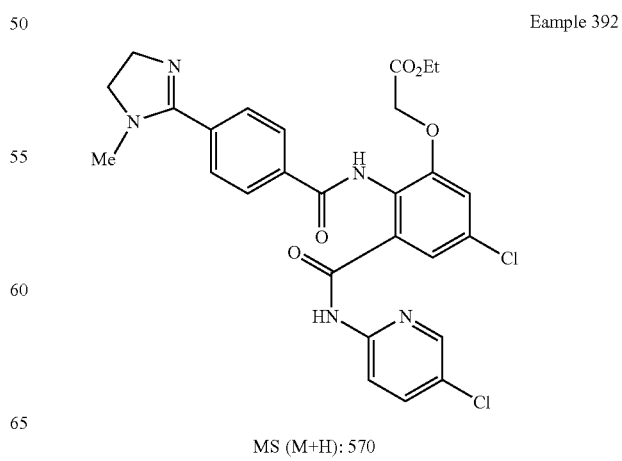
MS (M+H): 570

Example 393

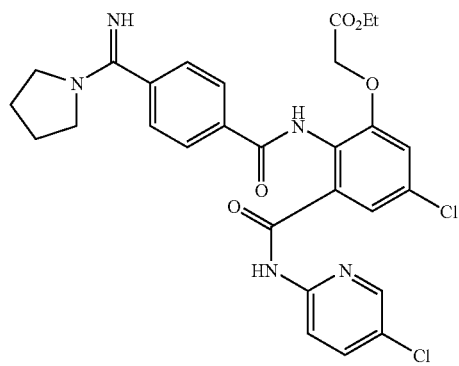

MS (M+H): 584

Example 394

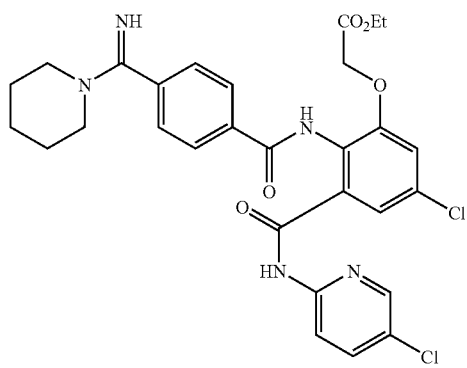

MS (M+H): 598

Example 395

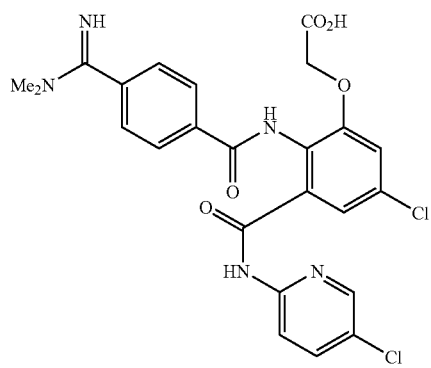

MS (M+H): 530

Example 396

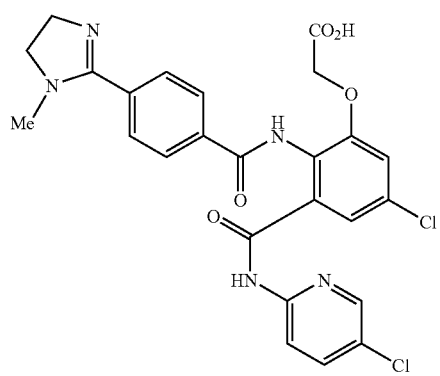

MS (M+H): 542

Example 397

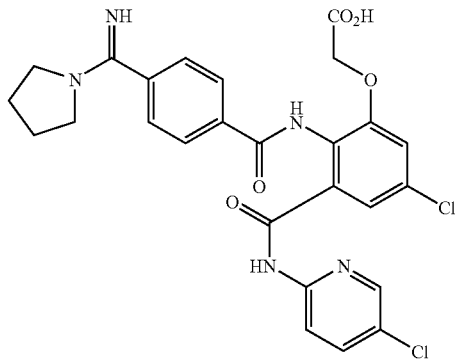

MS (M+H): 556

Example 398

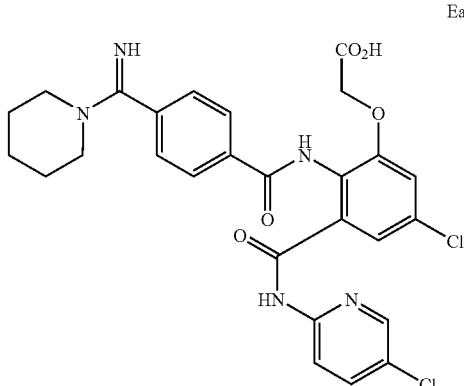

MS (M+H): 570

Example 399

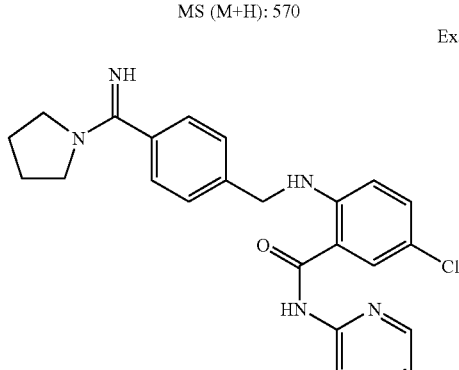

Step 1: A mixture of 4-cyanobenzaldehyde (1 equiv), 4-chloro-2-(5-chloro-2-pyridinyl)amino-carbonyl aniline (1 equiv) and glacial acetic acid (10 equiv) in $CH_2Cl_2$ was stirred at rt for 30 min. $NaBH(OAc)_3$ (3 equiv) was added at once and the mixture was stirred overnight: The reaction was quenched with water and the organic layer was washed with brine and dried over $Na_2SO_4$. Column separation over silica gel gave the desired product.

Step 2: A solution of the compound obtained in step 1 (15 mg) in anhydrous pyridine (10 mL) and triethyl amine (2 mL) was saturated with hydrogen sulfide gas at 0° C. The mixture was stirred at rt overnight. After concentration, the residue was dissolved in anhydrous acetone (10 mL) and iodomethane (1 mL) was added. The mixture was refluxed for 2 hrs. After concentration, the residue was dissolved in anhydrous methanol (5 mL) and a solution of pyrrolidine (0.5 mL) and acetic acid (0.5 mL) in anhydrous methanol (5 ml) was added. The mixture was refluxed for 15 min. After concentrated, the crude residue was purified by RP-HPLC to give target. MS (M+H) 468.

Examples 400-426

The following compounds were prepared according to the procedure previously described.

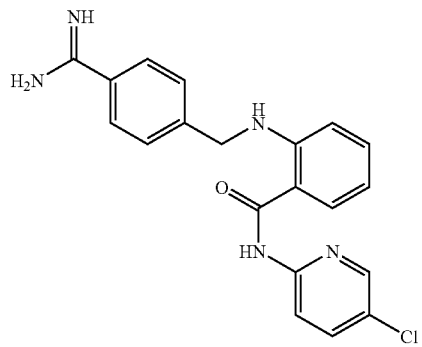

Eample 400
MS (M + H): 414

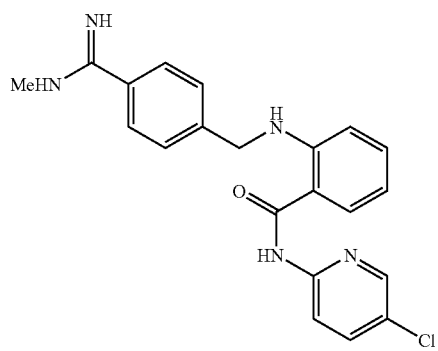

Eample 401
MS (M + H): 428

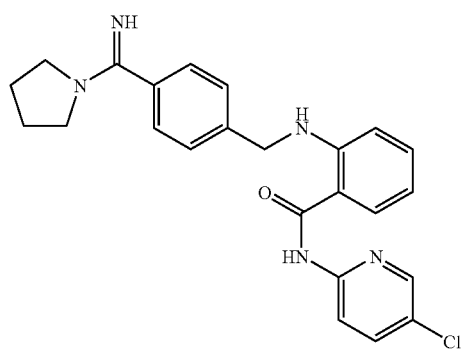

Eample 402
MS (M + H): 468

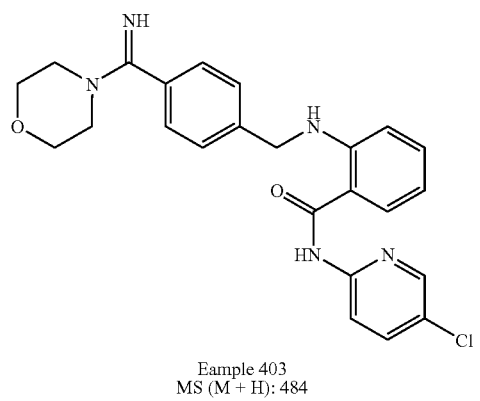

Eample 403
MS (M + H): 484

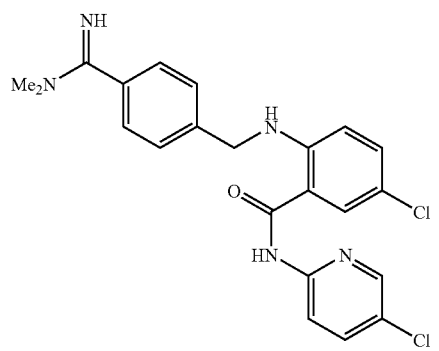

Eample 404
MS (M + H): 442

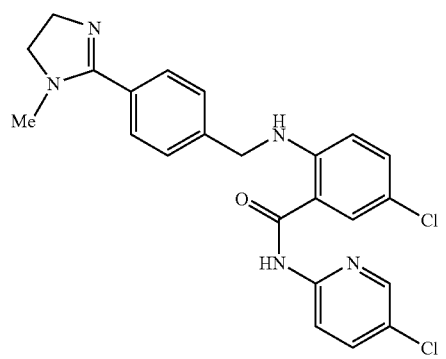

Eample 405
MS (M + H): 428

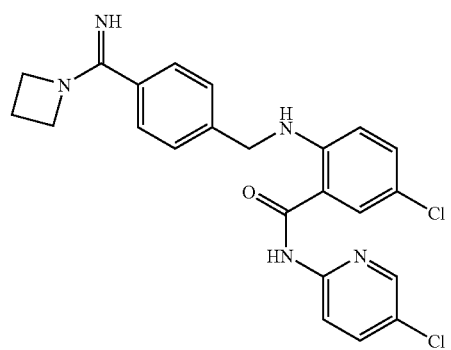

Eample 406
MS (M + H): 468

-continued
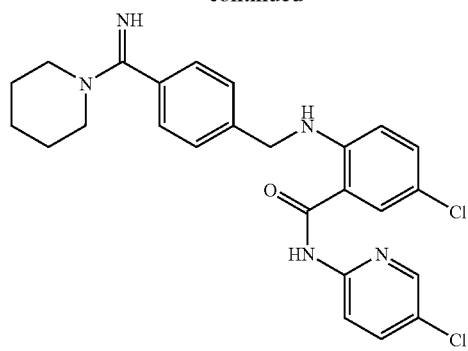
Eample 407
MS (M + H): 484
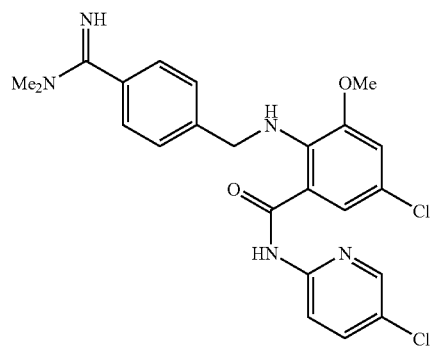
Eample 408
MS (M + H): 472
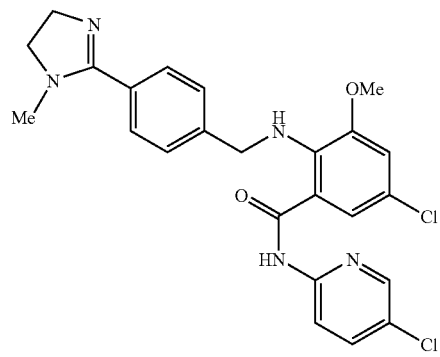
Eample 409
MS (M + H): 484
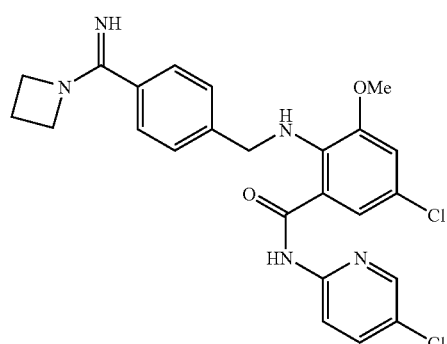
Eample 410
MS (M + H): 484
-continued
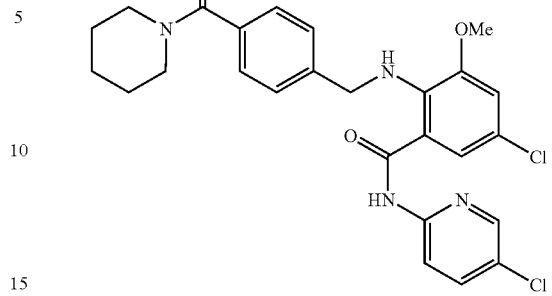
Eample 411
MS (M + H): 512
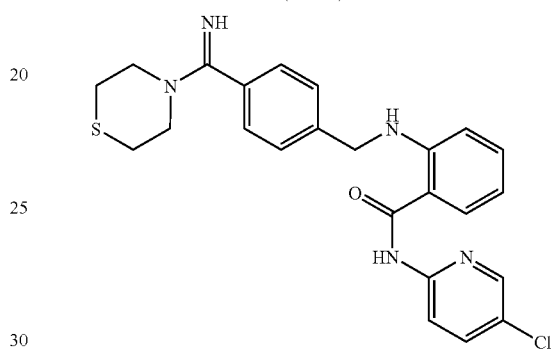
Eample 412
MS (M + H): 530
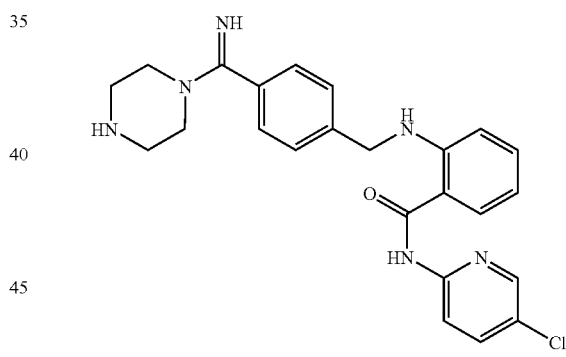
Eample 413
MS (M + H): 513
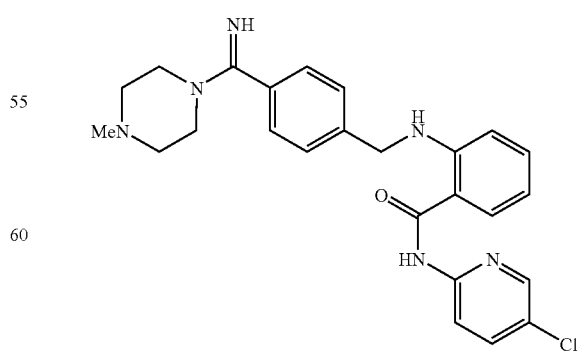
Eample 414
MS (M + H): 527

-continued
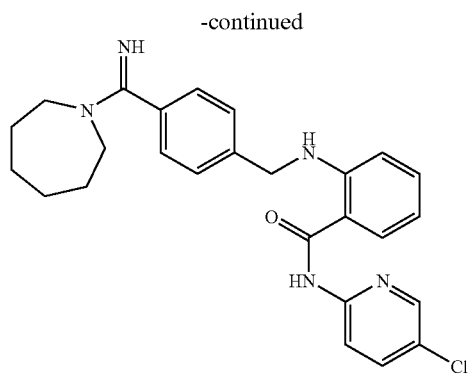
Eample 415
MS (M + H): 526
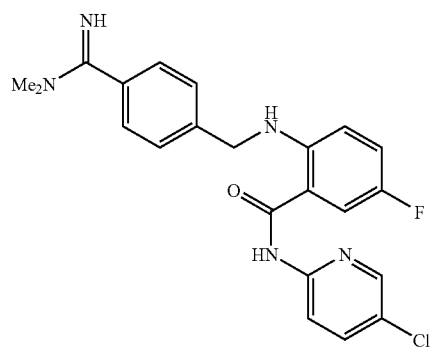
Eample 416
MS (M + H): 426
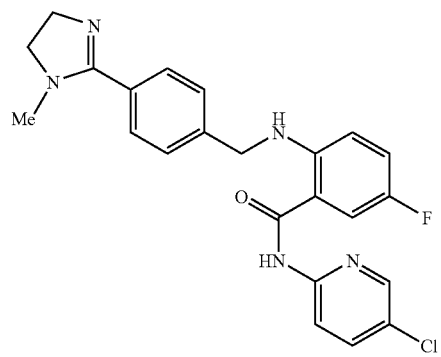
Eample 417
MS (M + H): 438
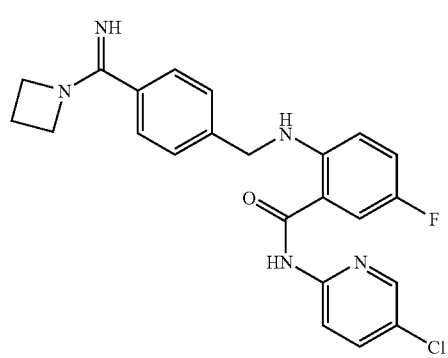
Eample 418
MS (M + H): 438
-continued
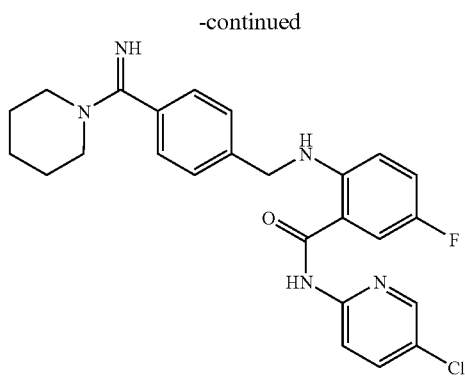
Eample 419
MS (M + H): 466
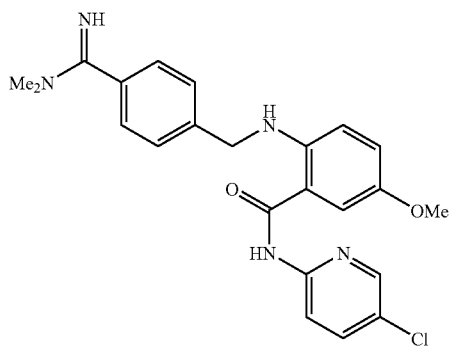
Eample 420
MS (M + H): 438
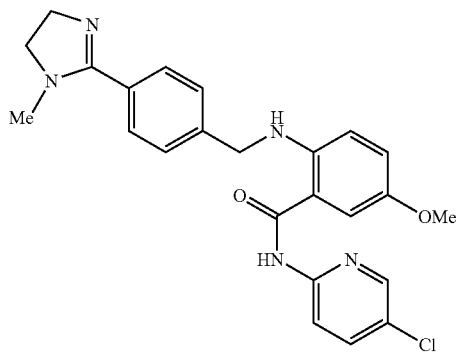
Eample 421
MS (M + H): 450
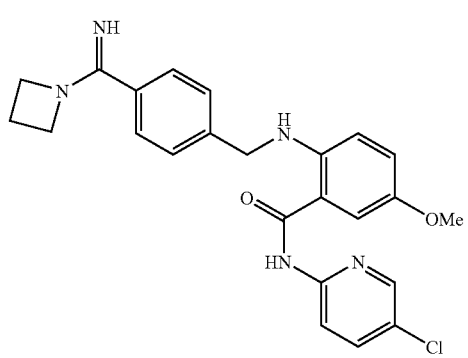
Eample 422
MS (M + H): 450

-continued

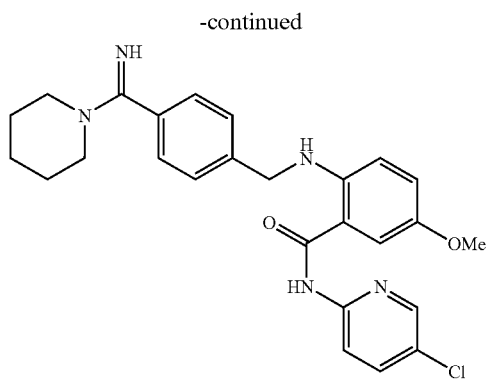

Eample 423
MS (M + H): 478

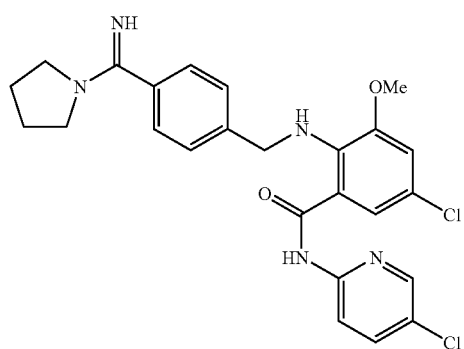

Eample 424
MS (M + H): 498

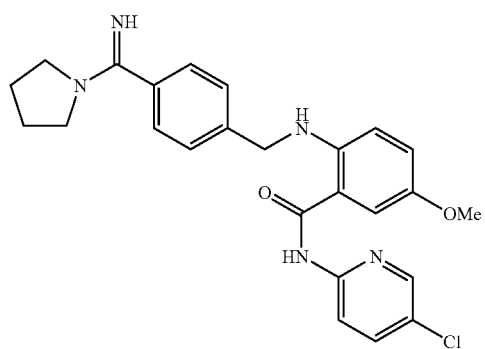

Eample 425
MS (M + H): 464

-continued

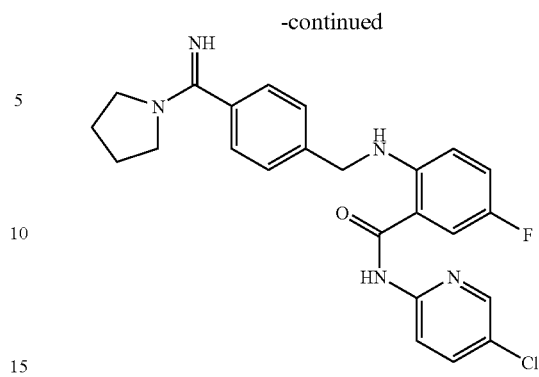

Eample 426
MS (M + H): 448

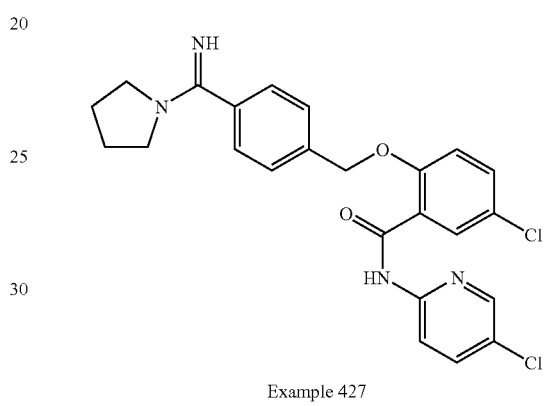

Example 427

Step 1: A mixture of 4-cyanobenzyl bromide (1 equiv), methyl 2-hydroxybenzoate (1 equiv) and cesium carbonate (10 equiv) in DMF was stirred at rt overnight. The mixture was then diluted with EtOAc, washed with water, dried over $Na_2SO_4$, filtered and evaporated to give the product.

Step 2: A solution of the compound obtained in step 1 (1 equiv) in MeOH was treated with 1N LiOH (2.2 equiv) for 1 h. After removal of methanol and acidifying with 1N HCl to PH ~1, the mixture was extracted with EtOAc. The organic layer was dried over $Na_2SO_4$, filtered and evaporated to give the product.

Step 3: A solution of the compound obtained in step 2 (1 equiv) in dichloromethane was treated with oxalyl chloride (3 equiv) and 2 drops of DMF at rt for 3 h. The volatile was evaporated and the residue was redissolved in methylenechloride. To the solution was added 2-amino-5-chloropyridine (1 equiv) and pyridine (5 equiv). The mixture was stirred at rt for 2 h, washed with water, dried over $Na_2SO_4$, filtered and evaporated to give the product.

Step 2: A solution of the compound obtained in step 3 (15 mg) in anhydrous pyridine (10 mL) and triethyl amine (2 mL) was saturated with hydrogen sulfide gas at 0° C. The mixture was stirred at rt overnight. After concentration, the residue was dissolved in anhydrous acetone (10 mL) and iodomethane (1 mL) was added. The mixture was refluxed for 2 hrs. After concentration, the residue was dissolved in anhydrous methanol (5 mL) and a solution of pyrrolidine 0.5 mL) and acetic acid (0.5 mL) in anhydrous methanol (5 ml) was added. The mixture was refluxed for 15 min. After concentrated, the crude residue was purified by RP-HPLC to give target. MS (M+H) 435.

Examples 428-431

The following compounds were similarly prepared.

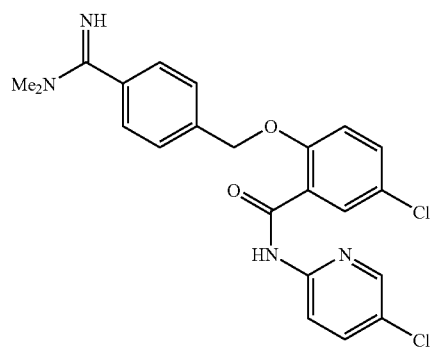

Example 428
MS (M+H): 409

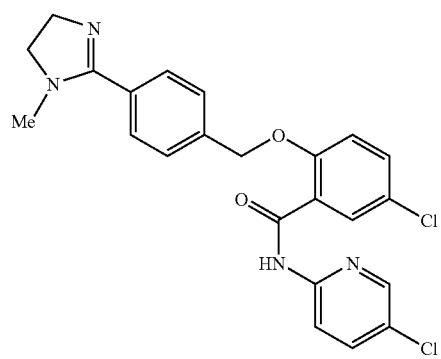

Example 429
MS (M+H): 421

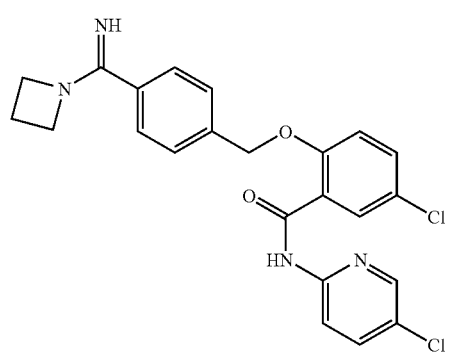

Example 430
MS (M+H): 421

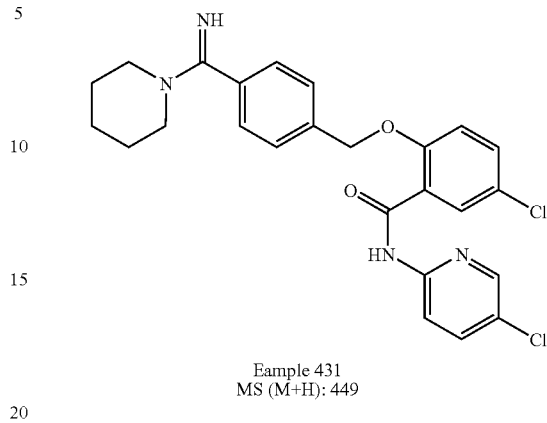

Example 431
MS (M+H): 449

Example 432

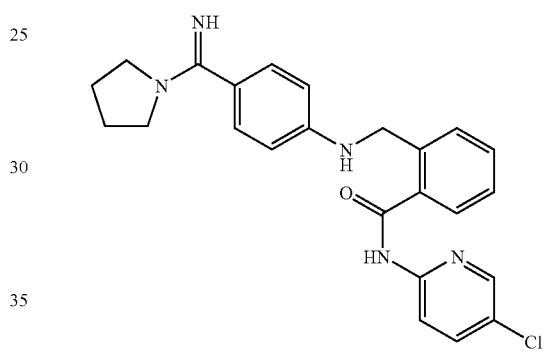

Step 1: A solution of 2-carboxybenzaldehyde (1 equiv) in dichloromethane was treated with oxalyl chloride (3 equiv) and 2 drops of DMF at rt for 3 h. The volatile was evaporated and the residue was redissolved in methylenechloride. To the solution was added 2-amino-5-chloropyridine (1 equiv) and pyridine (5 equiv). The mixture was stirred at rt for 2 h, washed with water, dried over $Na_2SO_4$, filtered and evaporated to give the product.

Step 2: A mixture of the compound obtained in step 1 (1 equiv), 4-cyanoaniline (1 equiv) and glacial acetic acid (10 equiv) in $CH_2Cl_2$ was stirred at rt for 30 min. $NaBH(OAc)_3$ (3 equiv) was added at once and the mixture was stirred overnight. The reaction was quenched with water and the organic layer was washed with brine and dried over $Na_2SO_4$. Column separation over silica gel gave the desired product.

Step 3: A solution of the compound obtained in step 2 (15 mg) in anhydrous pyridine (10 mL) and triethyl amine (2 mL) was saturated with hydrogen sulfide gas at 0° C. The mixture was stirred at rt overnight. After concentration, the residue was dissolved in anhydrous acetone (10 mL) and iodomethane (1 mL) was added. The mixture was refluxed for 2 hrs. After concentration, the residue was dissolved in anhydrous methanol (5 mL) and a solution of pyrrolidine (0.5 mL) and acetic acid (0.5 mL) in anhydrous methanol (5 ml) was added. The mixture was refluxed for 15 min. After concentrated, the crude residue was purified by RP-HPLC to give target. MS (M+H) 434.

Examples 433-437

The following compounds were similarly prepared.

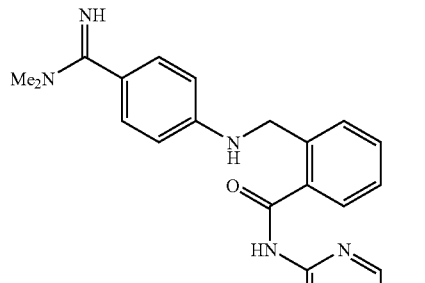

Eample 433
MS (M + H): 408

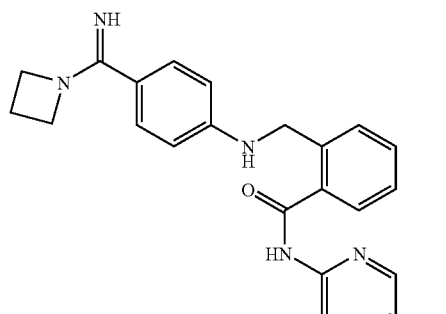

Eample 434
MS (M + H): 420

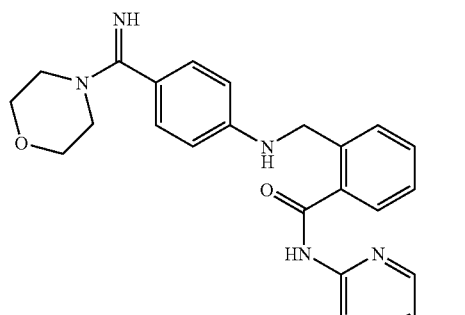

Eample 435
MS (M + H): 450

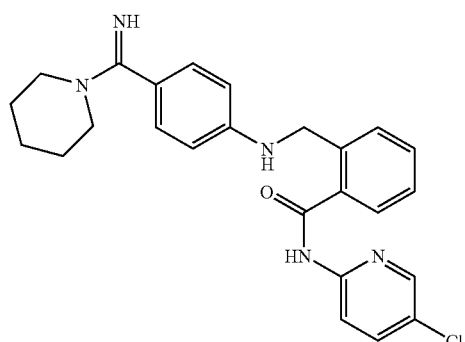

Eample 436
MS (M + H): 448

-continued

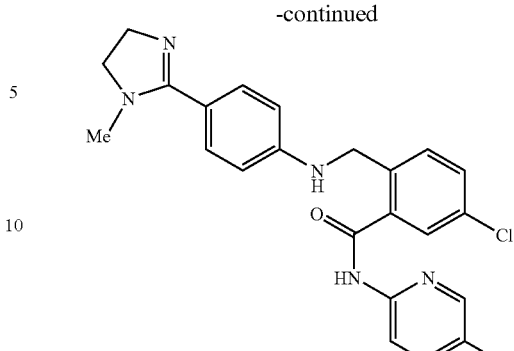

Eample 437
MS (M + H): 420

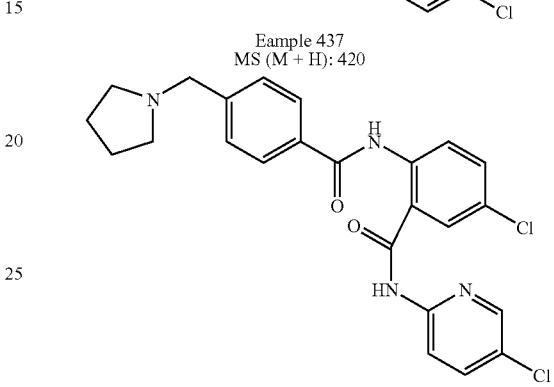

Example 438

Step 1: A mixture of 4-chloromethylbemzoyl chloride (1 equiv), 4-chloro-2-(5-chloro-2-pyridinyl)amino-carbonyl aniline (1 equiv) and pyridine (5 equiv) in $CH_2Cl_2$ was stirred at reflux for 4 h. The reaction was cooled to rt and the organic layer was washed with brine and dried over $Na_2SO_4$. Column separation over silica gel gave the desired product (~20% yield).

Step 2: A solution of the compound obtained in step 1 (15 mg) in DMF (1 mL) was treated with pyrrolidine (1 ml) at rt overnight. After removing the volatile, the crude residue was purified by RP-HPLC to give the target. MS (M+H) 469.

Example 439-458

The following compounds were prepared according to the procedure previously described.

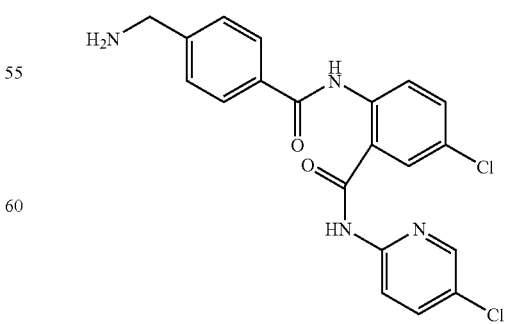

Eample 439
MS (M + H): 415

-continued
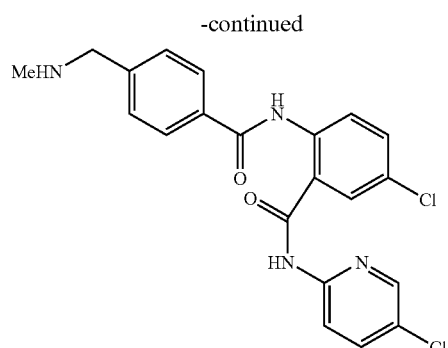
Eample 440
MS (M + H): 429
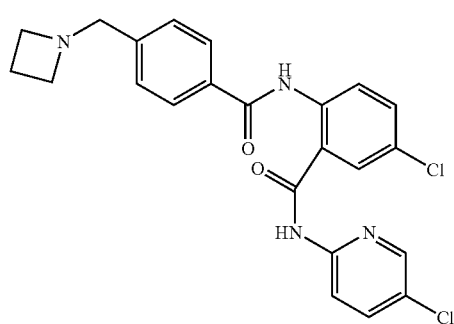
Eample 441
MS (M + H): 455
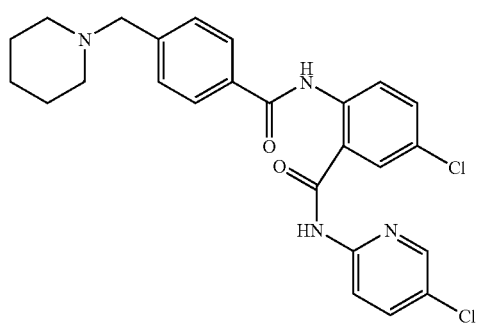
Eample 442
MS (M + H): 483
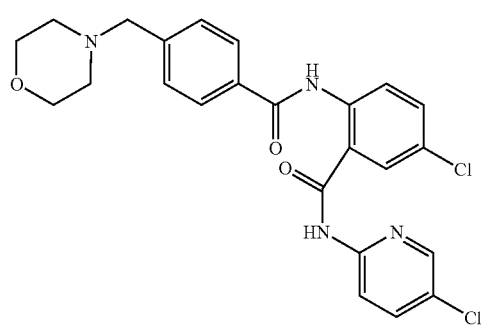
Eample 443
MS (M + H): 485
-continued
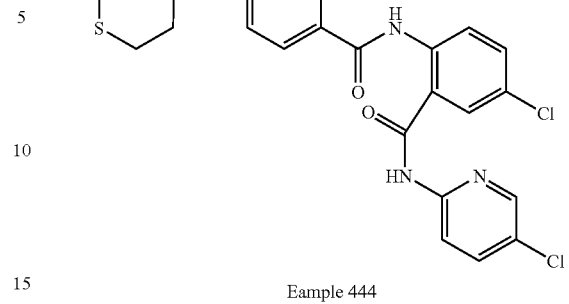
Eample 444
MS (M + H): 501
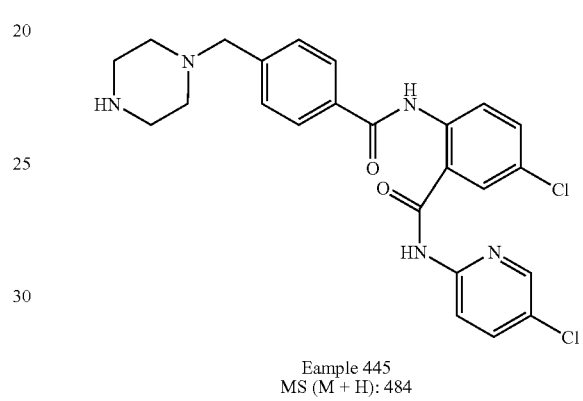
Eample 445
MS (M + H): 484
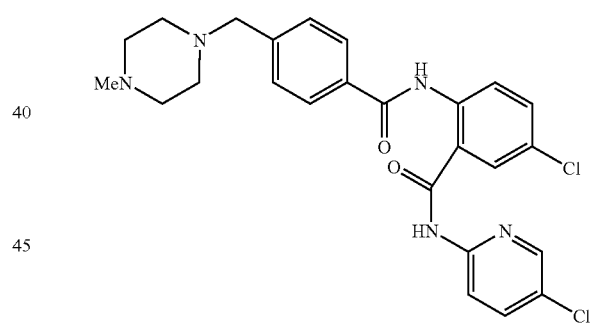
Eample 446
MS (M + H): 498
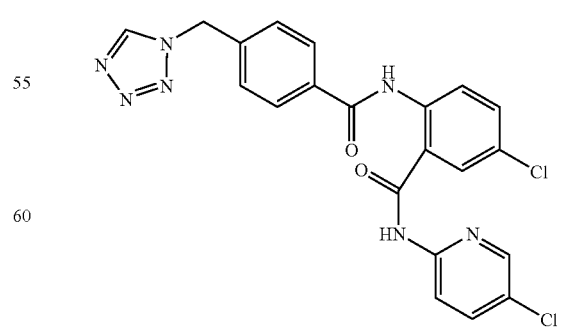
Eample 447
MS (M + H): 468

-continued
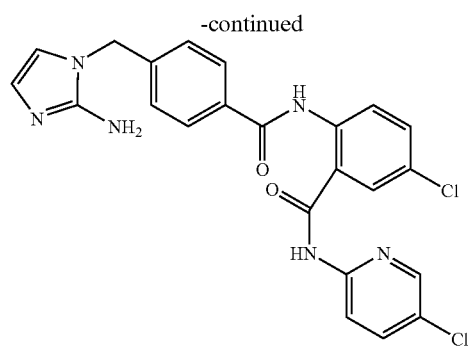
Eample 448
MS (M + H): 481
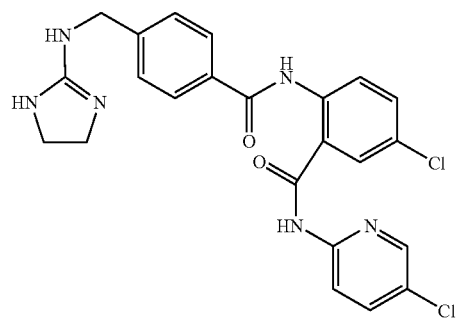
Eample 449
MS (M + H): 483
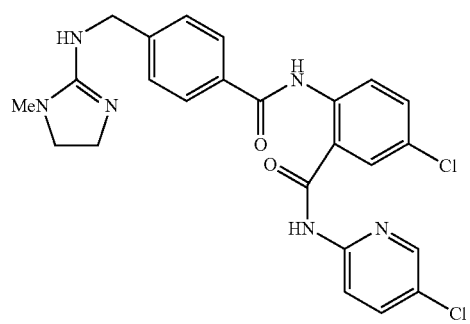
Eample 450
MS (M + H): 497
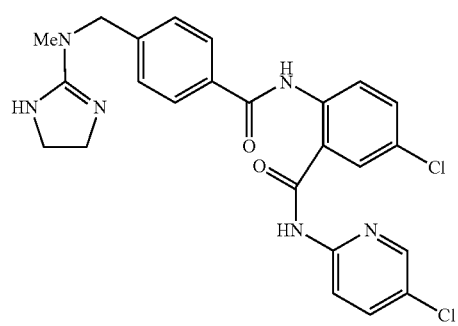
Eample 451
MS (M + H): 497
-continued
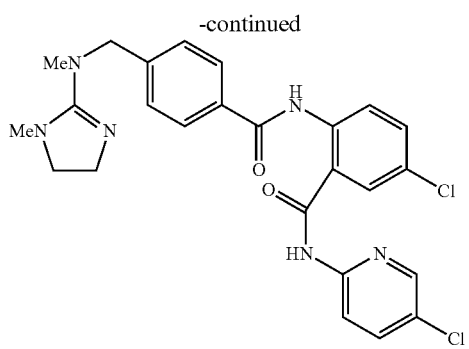
Eample 452
MS (M + H): 511
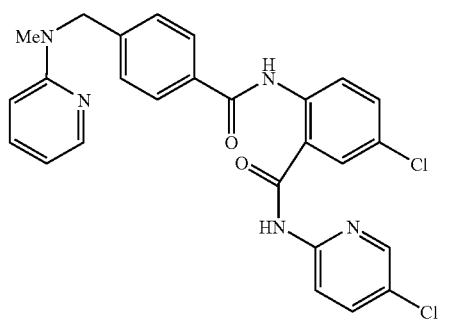
Eample 453
MS (M + H): 506
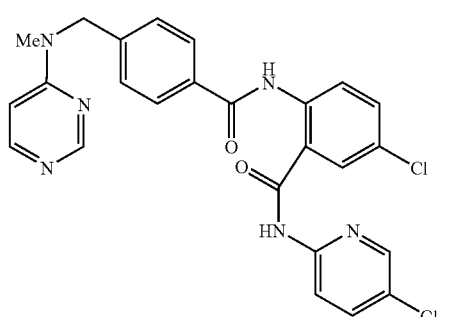
Eample 454
MS (M + H): 507
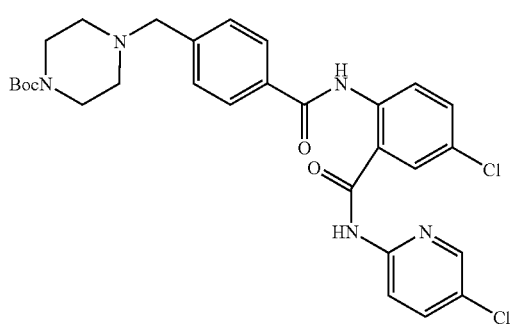
Eample 455
MS (M + H): 539

-continued
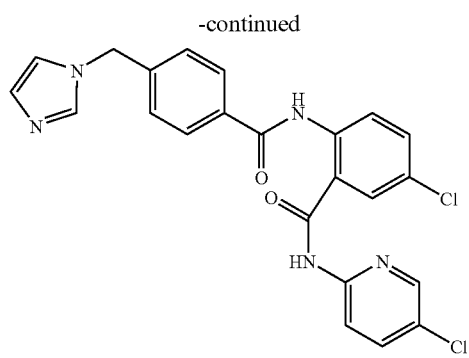
Eample 456
MS (M + H): 466
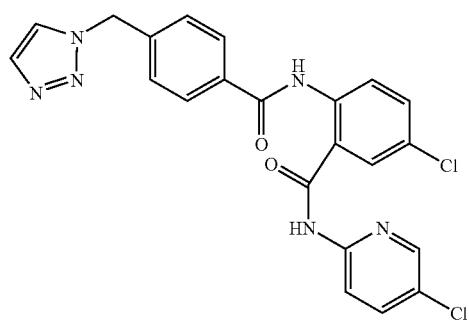
Eample 457
MS (M + H): 467
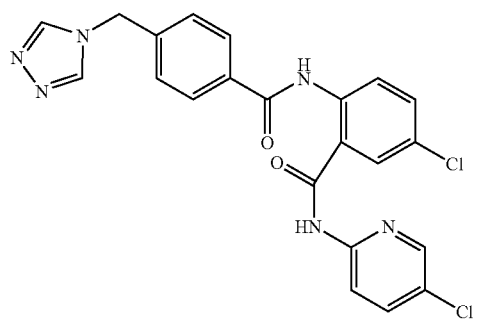
Eample 458
MS (M + H): 467
Example 459-494
The following compounds were prepared according to the procedure previously described.
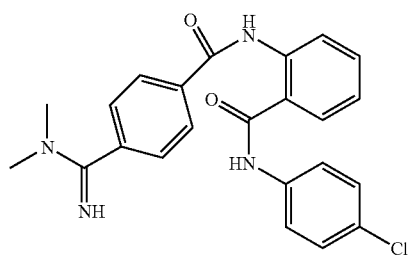
MS 421 (M + H)
-continued
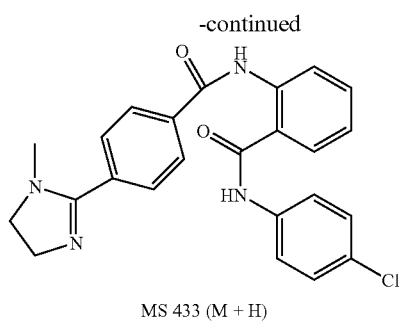
MS 433 (M + H)
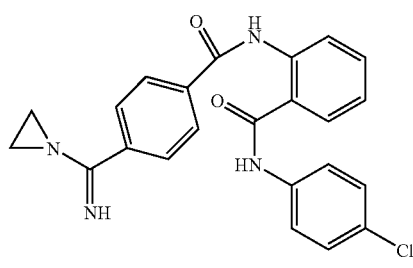
MS 419 (M + H)
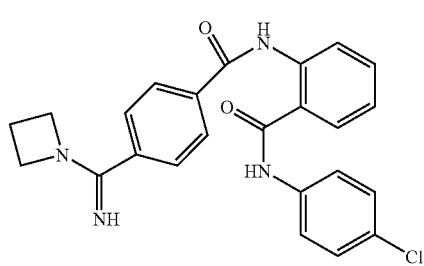
MS 433 (M + H)
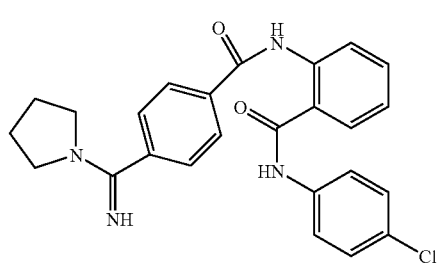
MS 447 (M + H)
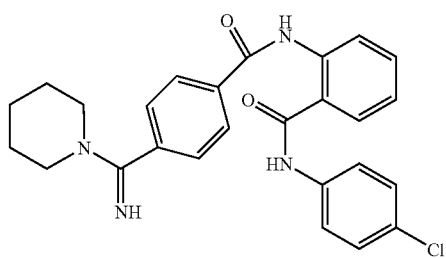
MS 461 (M + H)

-continued
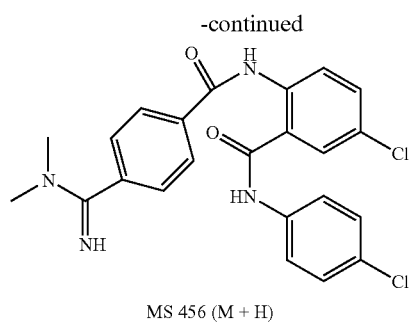
MS 456 (M + H)
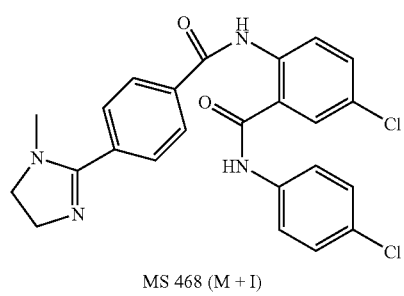
MS 468 (M + I)
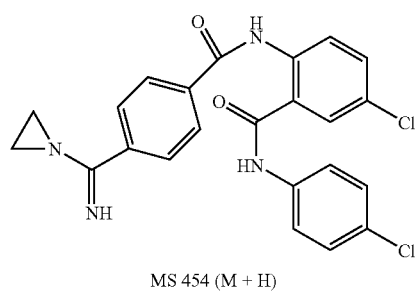
MS 454 (M + H)
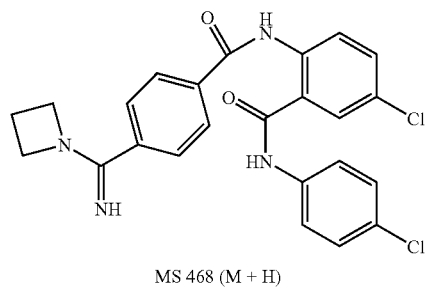
MS 468 (M + H)
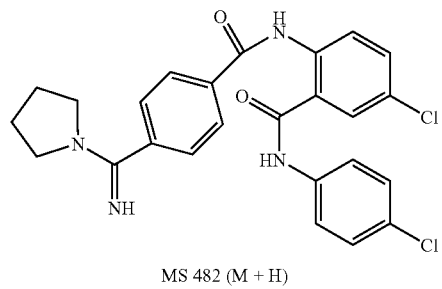
MS 482 (M + H)
-continued
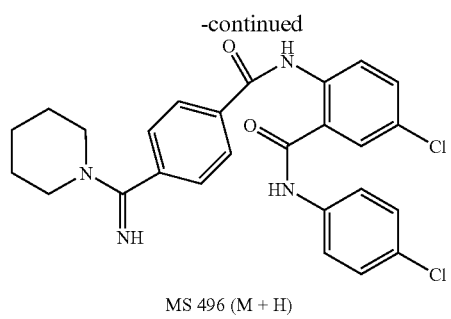
MS 496 (M + H)
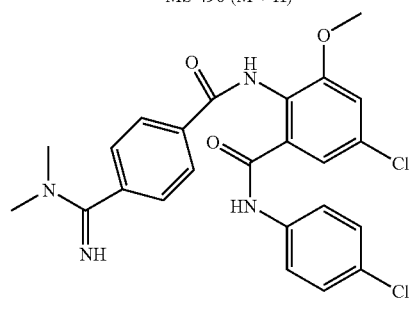
Mol. Wt.: 485.36
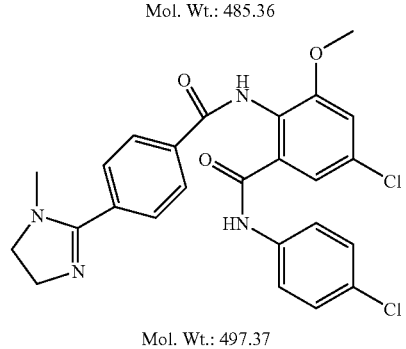
Mol. Wt.: 497.37
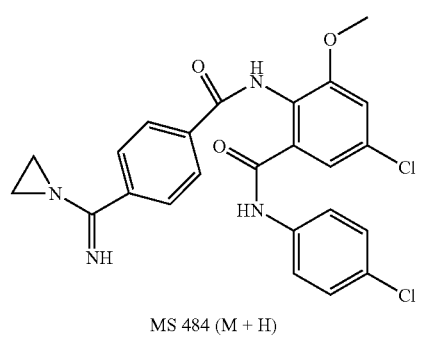
MS 484 (M + H)
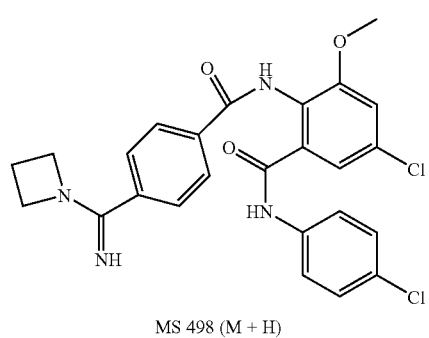
MS 498 (M + H)

-continued
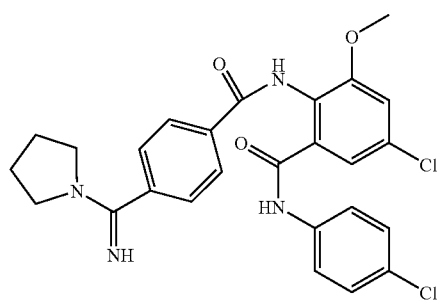
MS 512 (M + H)
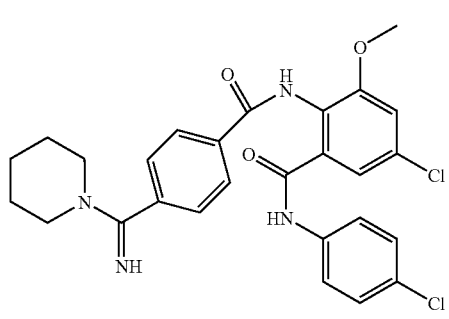
MS 526 (M + H)
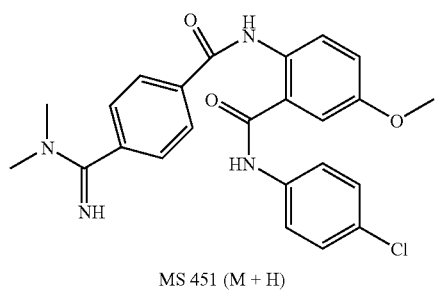
MS 451 (M + H)
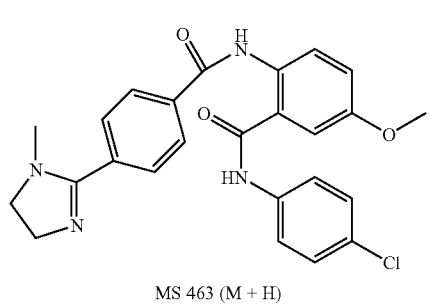
MS 463 (M + H)
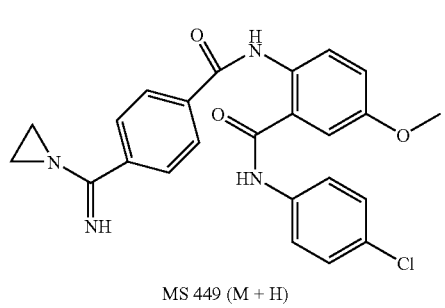
MS 449 (M + H)
-continued
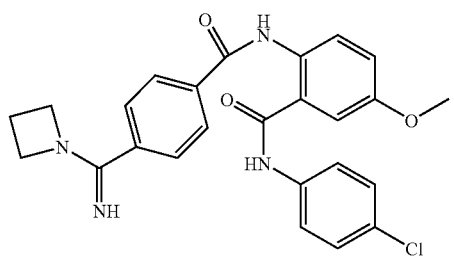
MS 463 (M + H)
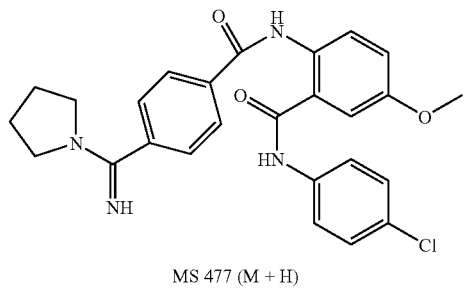
MS 477 (M + H)
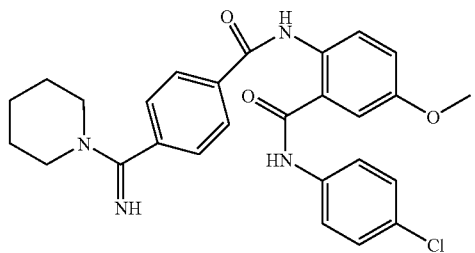
MS 491 (M + H)
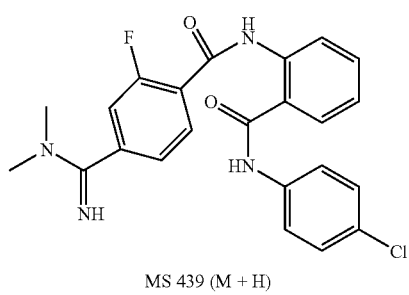
MS 439 (M + H)
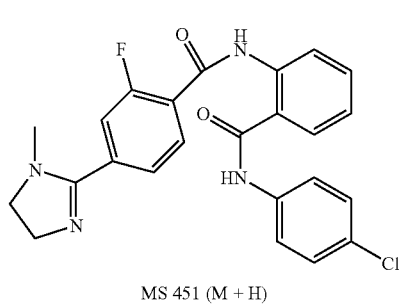
MS 451 (M + H)

-continued
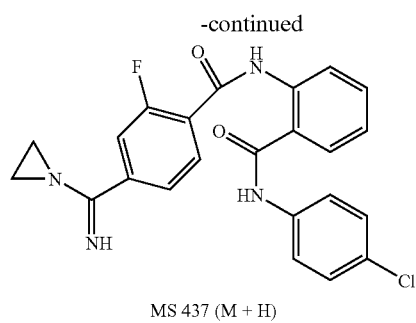
MS 437 (M + H)
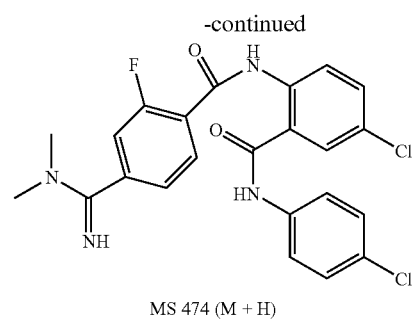
MS 474 (M + H)
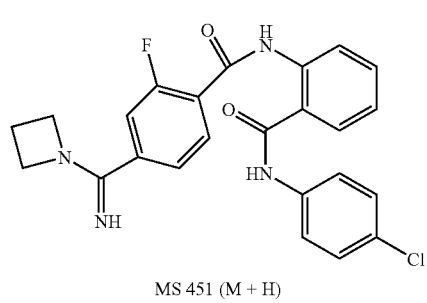
MS 451 (M + H)
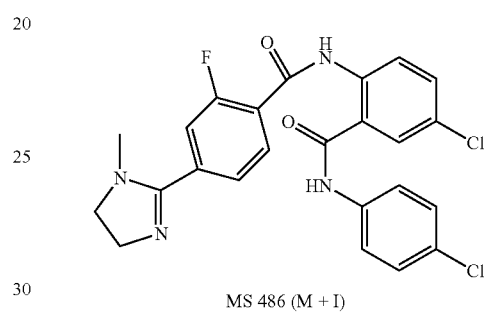
MS 486 (M + I)
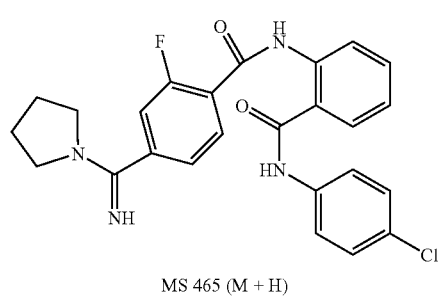
MS 465 (M + H)
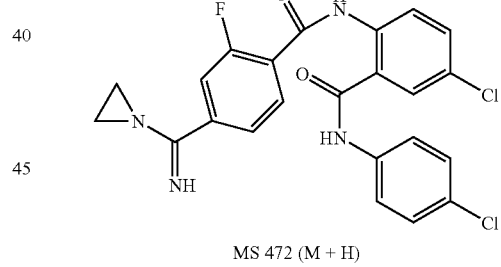
MS 472 (M + H)
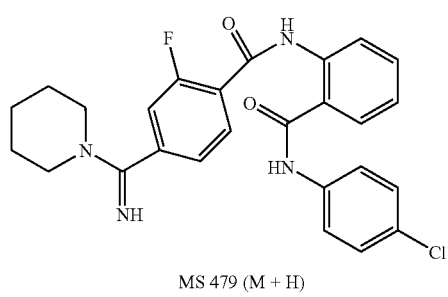
MS 479 (M + H)
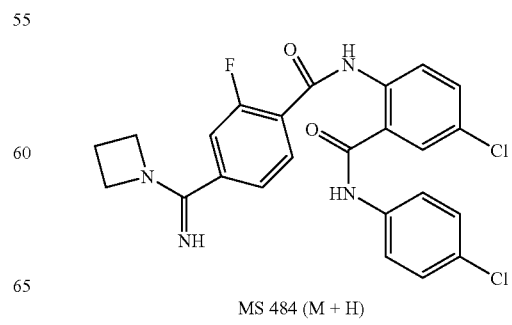
MS 484 (M + H)

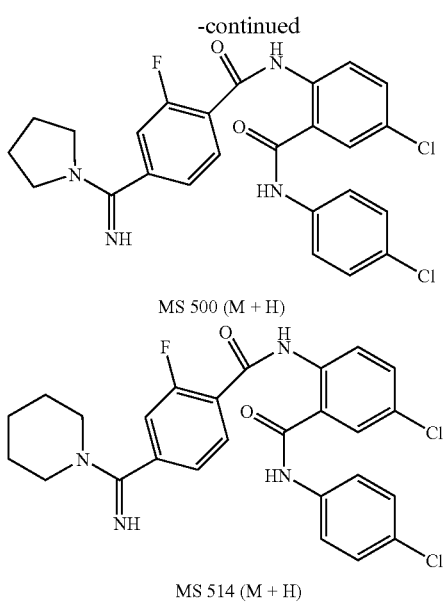

MS 500 (M + H)

MS 514 (M + H)

Example 495

N-{2-[N-(5-chloro(2-pyridyl))carbamoyl](3-thienyl)}(4-(1-methyl(2-imidazolin-2-yl))phenyl]carboxamide

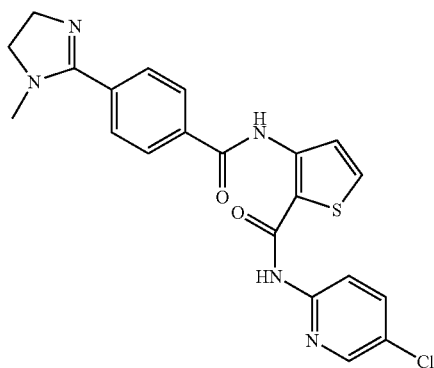

Preparation of methyl 3-[(4-cyanophenyl)carbonylamino]thiophene-2-carboxylate

A mixture of 4-cyanobenzoyl chloride (1.0000 g, 6.4 mmol), methyl 3-aminothiophenecarboxylate (1.0000 g, 6.4 mmol), and triethylamine (1 mL, 7.0 mmol) in dichloromethane was stirred at room temperature for 18 hours. The mixture was poured into a separatory funnel and washed by 1 N HCl. The organic layers were combined, dried over MgSO4, concentrated in vacuo, and chromatographed through a silica gel column to give the title compound 1.6588 g (91%). ES-MS 287 (M+1).

Preparation of N-{2-[N-(5-chloro(2-pyridyl))carbamoyl](3-thienyl)}(4-cyanophenyl)carboxamide A portion of 2-amino-5-chloropyridine (68.6 mg, 0.5 mmol) was treated with AlMe3 (0.8 mL, 1.6 mmol), followed by adding the product from step A (160 mg, 0.5 mmol). The mixture was stirred at room temperature for 18 hours. The excess of AlMe3 was killed by 1N HCl solution. The organic layers were combined, dried over MgSO4, concentrated in vacuo, and chromatographed through a silica gel column to give the title compound 0.1528 g (80%). ES-MS 383 (M+1).

A mixture of the product from step B (0.1528 g, 0.4 mmol) and EtOH saturated with HCl was stirred at room temperature for 18 hours. The solvent was removed by a rotovap. The crude oil was treated with 2 mL N-methylethylenediamine for 2 hours until the reaction was complete. Prep HPLC was used to purity the final product. It gave 0.1537 g (88%). ES-MS 440(M+1).

Example 496

{4-[(dimethylamino)iminomethyl]phenyl}-N-{2-[N-(5-chloro(2-pyridyl))carbamoyl](3-thienyl)}carboxamide

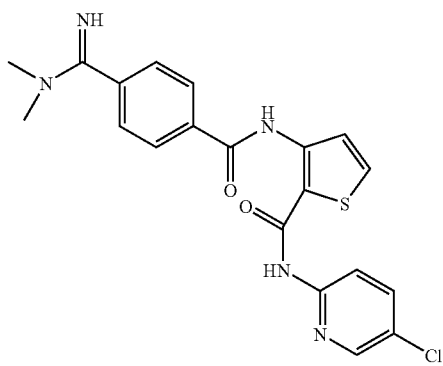

The title compound was obtained according to the procedure previously described. ES-MS 428 (M+1).

Example 497

4-(N-{2-[N-(5-chloro-2-pyridyl)carbamoyl]-3-thienyl)carbamoyl)benzenecarboxamidine

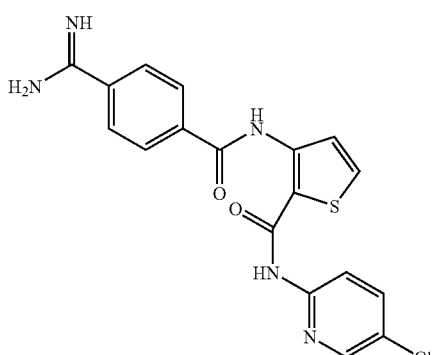

The title compound was obtained according to the procedure previously described. ES-MS 400(M+1).

Example 498

N-{2-[N-(5-chloro(2-pyridyl))carbamoyl](3-thienyl)}[4-(iminopiperidylmethyl)-phenyl]carboxamide

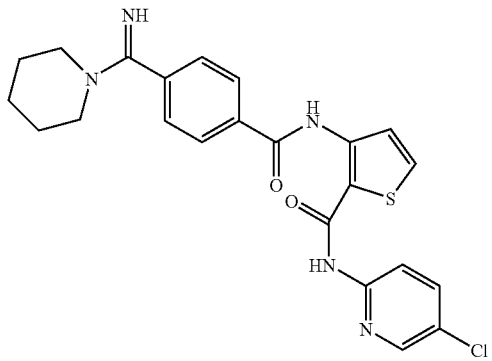

The title compound was obtained according to the procedure previously described. ES-MS 468(M+1).

Example 499

N-{2-[N-(5-chloro(2-pyridyl))carbamoyl](3-thienyl)}[4-(iminopyrrolidinylmethyl)-phenyl]carboxamide

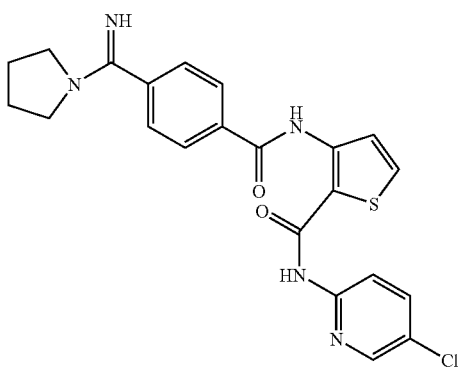

The title compound was obtained according to the procedure previously described. ES-MS 454(M+1).

Example 500

N-{2-[N-(5-chloro(2-pyridyl))carbamoyl](3-thienyl)}[4-(iminomorpholin-4-ylmethyl)phenyl]carboxamide

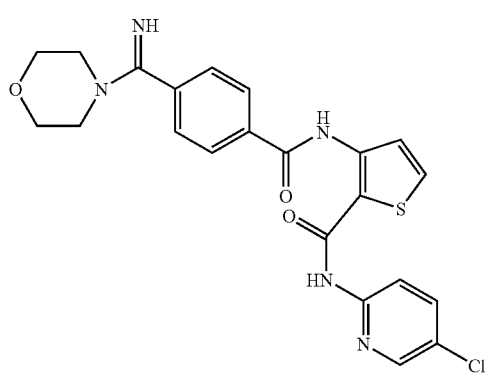

The title compound was obtained according to the procedure previously described. ES-MS 470(M+1).

Example 501

N-{2-[N-(5-chloro(2-pyridyl))carbamoyl](3-thienyl)}[4-(imino-1,4-thiazaperhydroin-4-ylmethyl)phenyl]carboxamide

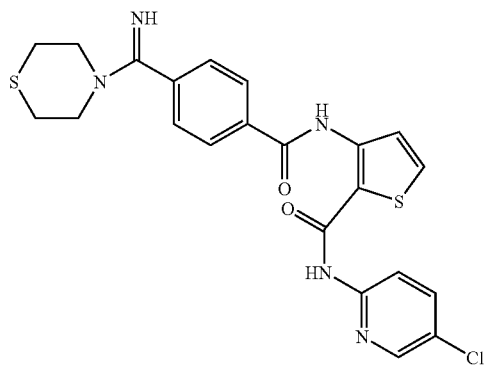

The title compound was obtained according to the procedure previously described. ES-MS 486(M+1).

Example 502

[4-(azaperhydroepinyliminomethyl)phenyl]-N-{2-[N-(5-chloro(2-pyridyl))carbamoyl](3-thienyl)}carboxamide

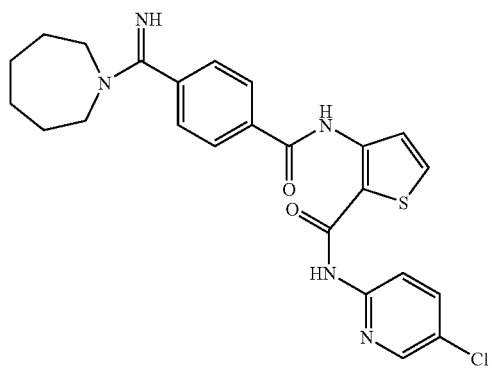

The title compound was obtained according to the procedure previously described. ES-MS 482(M+1).

Example 503

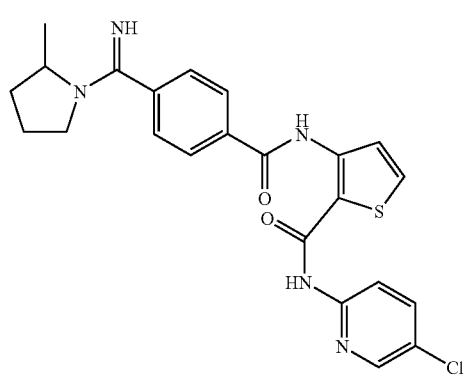

N-{2-[N-(5-chloro(2-pyridyl))carbamoyl](3-thienyl)}{4-[imino(2-methylpyrrolidinyl)methyl]phenyl}carboxamide The title compound was obtained according to the procedure previously described. ES-MS 468(M+1).

Example 504

N-{2-[N-(5-chloro(2-pyridyl))carbamoyl](3-thienyl)}{4-[imino(methylamino)methyl]phenyl}carboxamide

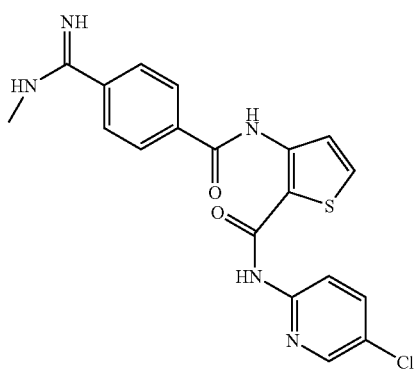

The title compound was obtained according to the procedure previously described.

Example 505

N-{2-[N-(5-chloro(2-pyridyl))carbamoyl](3-thienyl)}[4-(3-methyl(3,4,5,6-tetrahydropyrimidin-2-yl))phenyl]carboxamide

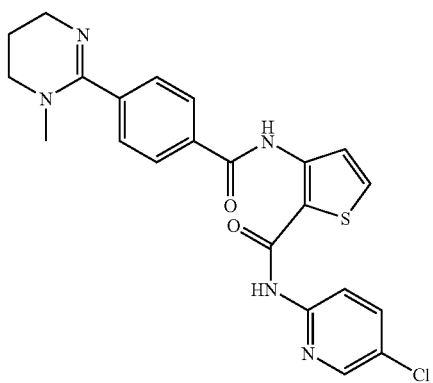

The title compound was obtained according to the procedure previously described. ES-MS 414(M+1).

Example 506

N-{2-[N-(5-chloro(2-pyridyl))carbamoyl](3-thienyl)}[4-((hydroxyamino)iminomethyl)-phenyl]carboxamide

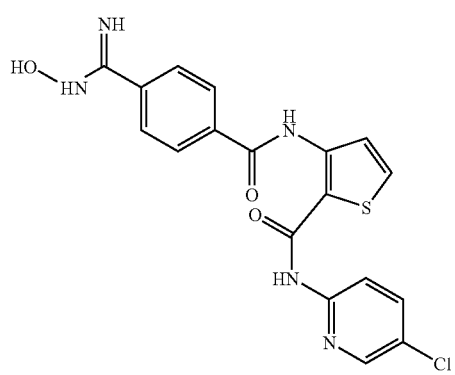

The title compound was obtained according to the procedure previously described. ES-MS 416(M+1).

Example 507

N-(2-[N-(5-bromo(2-pyridyl))carbamoyl(3-thienyl)}[4-(1-methyl(2-imidazolin-2-yl))phenyl]carboxamide

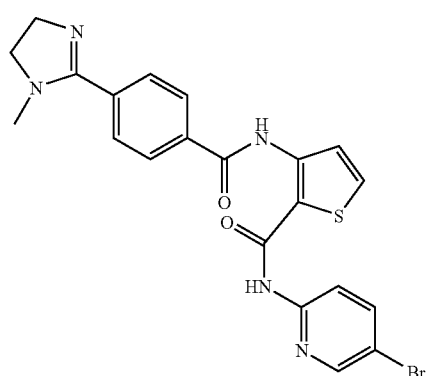

The title compound was obtained according to the procedure previously described. ES-MS 484(M+1).

Example 508

4-(N-{2-[N-(5-bromo-2-pyridyl)carbamoyl]-3-thienyl}carbamoyl)benzenecarboxamidine

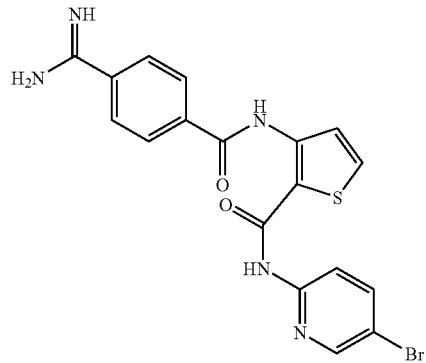

The title compound was obtained according to the procedure previously described. ES-MS 444(M+1).

Example 509

N-{2-[N-(5-bromo(2-pyridyl))carbamoyl](3-thienyl)}[4-(iminopyrrolidinylmethyl)phenyl]carboxamide

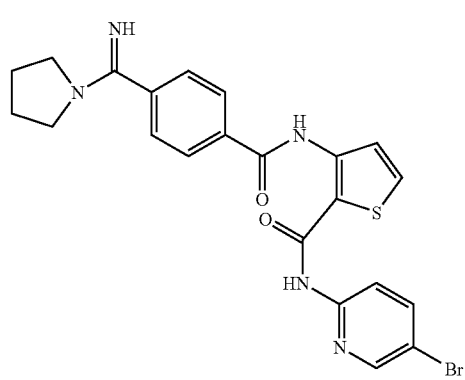

The title compound was obtained according to the procedure previously described. ES-MS 494(M+1).

Example 510

N-{2-[N-(5-bromo(2-pyridyl))carbamoyl](3-thienyl))}[4-(iminopiperidylmethyl)phenyl]carboxamide

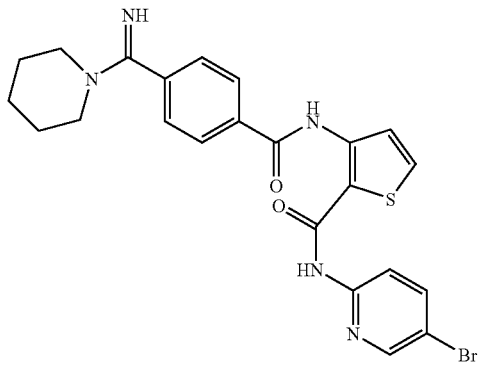

The title compound was obtained according to the procedure previously described. ES-MS 512(M+1).

Example 511

N-{2-[N-(5-bromo(2-pyridyl))carbamoyl](3-thienyl)} [4-(iminomorpholin-4-ylmethyl)phenyl]carboxamide

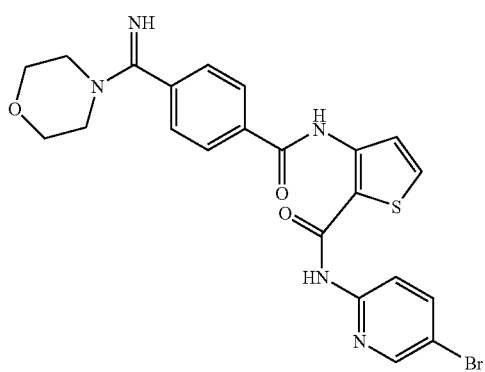

The title compound was obtained according to the procedure previously described. ES-MS 514(M+1).

Example 512

N-{2-[N-(5-bromo(2-pyridyl))carbamoyl](3-thienyl)}[4-(imino-1,4-thiazaperhydroin-4-ylmethyl)phenyl]carboxamide

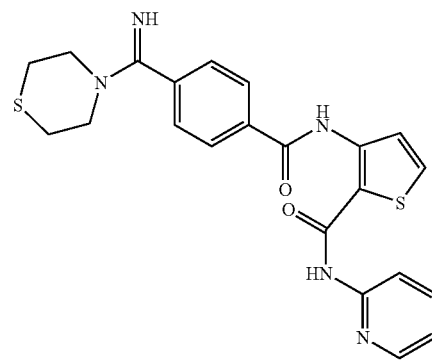

The title compound was obtained according to the procedure previously described. ES-MS 530(M+1).

Example 513

N-{3-1N-(5-chloro(2-pyridyl))carbamoyl](2-thienyl)}[4-(iminopyrrolidinylmethyl)phenyl]carboxamide

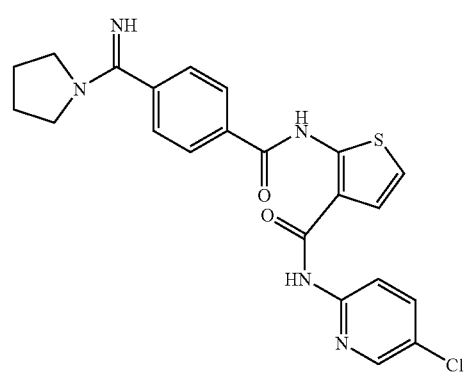

The title compound was obtained according to the procedure previously described. ES-MS 454(M+1).

Example 514
N-{3-[N-(5-chloro(2-pyridyl))carbamoyl](2-thienyl)}[4-(1-methyl(2-imidazolin-2-yl))phenyl]carboxamide
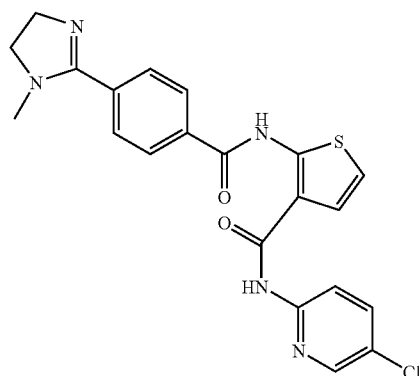
The title compound was obtained according to the procedure previously described. ES-MS 440(M+1).
Examples 515-520
The following examples are prepared according to the procedure previously described.
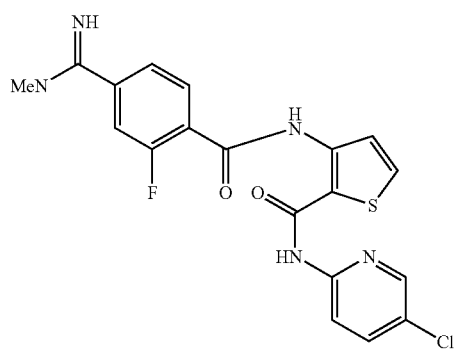
MS (M+H): 446
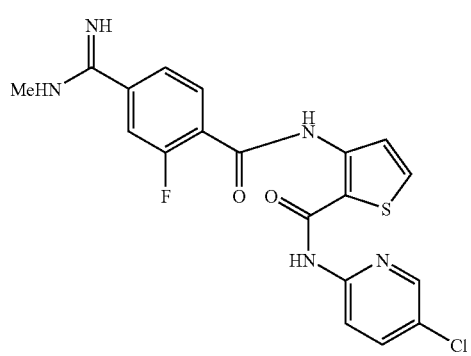
MS (M+H): 432
-continued
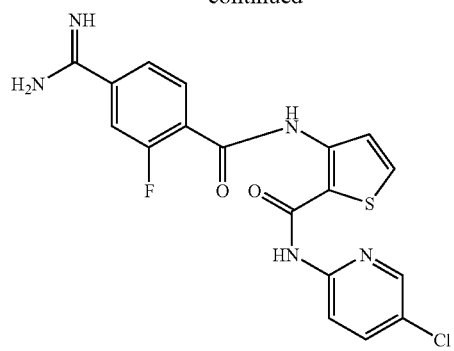
MS (M+H): 418
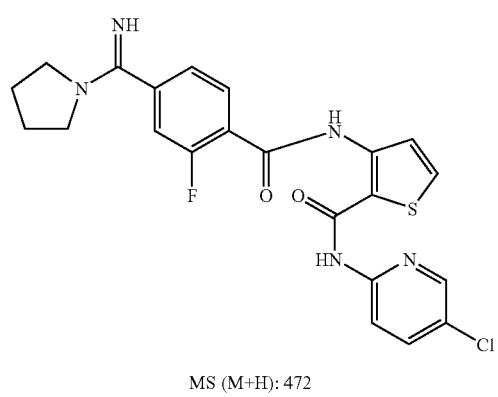
MS (M+H): 472
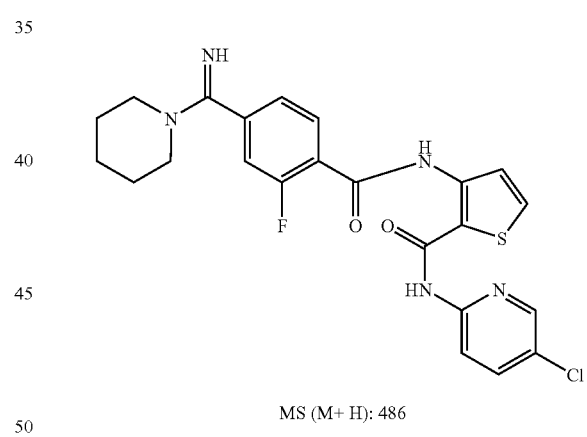
MS (M+H): 486
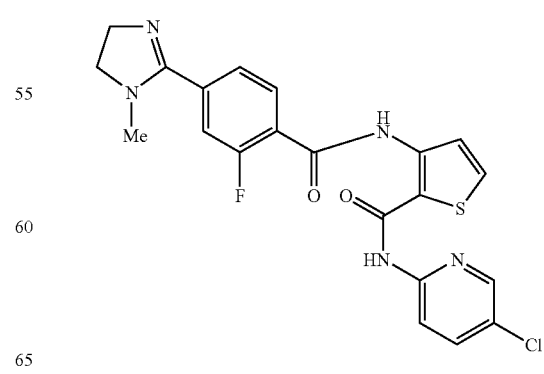
MS (M+H): 458

Example 521

N-{2-[N-(5-chloro(2-pyridyl))carbamoyl](3-thienyl)}[4-(2-sulfamoylphenyl)phenyl]carboxamide

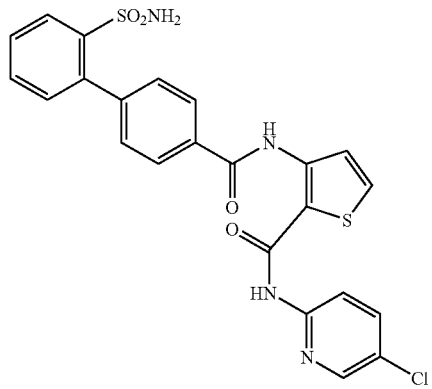

A solution of 4-(2-{[(tert-butyl)amino]sulfonyl}phenyl)benzoyl chloride (1 equiv), 3-amino-2-(4-chloro-2-pyridinyl)aminocarbonyl thiophene (1 equiv), pyridine (5 equiv) in dichloromethane was stirred at rt overnight. The mixture was diluted with dichloromethane, washed with water, dried over Na2SO4, filtered and evaporated. The residue was refluxed with 1 mL of TFA for 2 h. After evaporation, reverse phase HPLC gave the title product. ES-MS 513(M+1).

Example 522

N-{2-[N-(5-bromo(2-pyridyl))carbamoyl](3-thienyl)}[4-(2-sulfamoylphenyl)phenyl]carboxamide

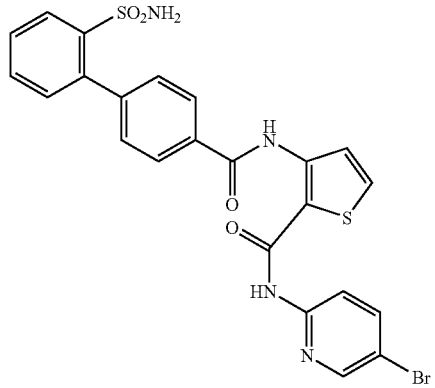

The title compound was obtained according to the procedure previously described. ES-MS 556(M+1).

Example 523

N-(4-methoxyphenyl)-N'-(4-[(2-aminosulfonyl)phenyl]phenyl)-maleamic amide

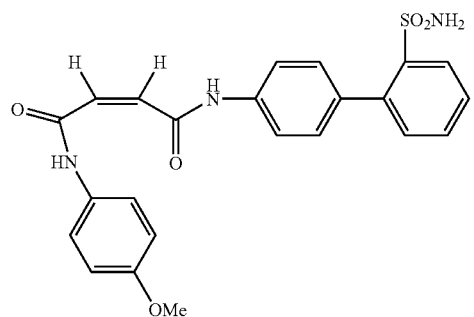

A. Preparation of N-(4-methoxyphenyl)-N'-(4-[(2-tert-butylaminosulfonyl)phenyl]phenyl)-maleamic amide To a solution of commercially available N-(4-methoxyphenyl)maleamic acid (100 mg, 0.452 mmol), triethylamine (0.126 mL, 0.906 mmol) and 4-(2-tert-butylaminosulfonylphenyl)aniline (138 mg, 0.454 mmol) in anhydrous DMF (5 mL), BOP (260 mg, 0.588 mmol) was added. The mixture was stirred at room temperature overnight. Water and EtOAc were added. The organic phase was separated, washed with H2O, then with 5% NaHCO3, dried over Na2SO4, concentrated in vacuo. The residue was purified by HPLC using a gradient of 20% CH3CN in H2O (containing 0.1% TFA) to 100% CH3CN over 80 min. Fractions containing the desired product were pooled, and lyophilized to give a powder (70 mg, yield: 31%). MS 508 (M+H).

B. Preparation of N-(4-methoxyphenyl)-N'-(4-[(2-aminosulfonyl)phenyl]phenyl)-maleamic amide The compound N-(4-methoxyphenyl)-N'-(4-[(2-tert-butylaminosulfonyl)phenyl]phenyl)-maleamic amide (40 mg, 79 mol) was dissolved in TFA (3 mL). It was allowed to stand at room temperature overnight. TFA was removed in vacuo. The residue was purified by HPLC using a gradient of 5% CH3CN in H2O (containing 0.1% TFA) to 95% CH3CN over 60 min. Fractions containing the desired product were pooled, and lyophilized to give a powder (18 mg, yield: 51%). MS 452 (M+H) and 474 (M+Na). $^1$H NMR (CDCl$_3$) δ 11.40 (br.s, 1H), 10.28 (br.s, 1H), 8.12 (d, 1H, J=8 Hz), 7.72 (d, 2H, J=8 Hz), 7.60-7.20 (m, 9H), 6.86 (AB type, 2H), 6.45 (br.s, 2H), 3.79 (s, 3H).

Example 524

N-(4-bromophenyl)-N'-(4-[(2-aminosulfonyl)phenyl]phenyl)-maleamic amide

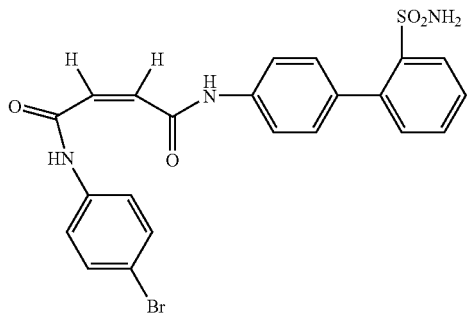

A. Preparation of N-(4-[(2-tert-butylaminosulfonyl)phenyl]phenyl)maleamic methyl ester To a solution of commercially available maleic acid monomethyl ester (277 mg, 2.13 mmol), 4-(2-tert-butylaminosulfonylphenyl)aniline (648 mg, 2.13 mmol) and triethylamine (0.593 mL, 4.26 mmol) in $CH_2Cl_2$ (20 mL), BOP (1.13 g, 2.55 mmol) was added. The mixture was stirred at room temperature overnight. More maleic acid monomethyl ester (50 mg, 0.385 mmol) was added. It was stirred for 3 hours. The CH2Cl2 solution was then washed with sat. NaHCO3, 1N HCl and sat. NaCl. The solution was dried over Na2SO4, concentrated in vacuo. The residue was purified by a silica gel column using a gradient of 10-40% EtOAc in hexane as solvents, to give the titled compound (360 mg, yield: 41%). MS 361 (M+H–$^t$Bu) and 439 (M+Na).

B. Preparation of N-(4-bromophenyl)-N'-(4-[(2-aminosulfonyl)phenyl]phenyl)-maleamic amide To a solution of 4-bromoaniline (93 mg, 0.543 mmol) in $CH_2Cl_2$ (5 mL) at room temperature, trimethylaluminum (0.82 mL, 2.0 M in hexane, 1.64 mmol) was added dropwise. After the solution was stirred for 30 min at room temperature, compound N-(4-[(2-tert-butylaminosulfonyl)phenyl]phenyl)maleamic methyl ester (113 mg, 0.272 mmol) was added. The mixture was stirred at room temperature for 2 days. The solution was neutralized with 1N HCl to pH 2-3. Water and CH2Cl2 were added, and organic phase was separated, dried over Na2SO4, concentrated in vacuo. The residue was dissolved in TFA (4 mL). It was allowed to stand at room temperature overnight. TFA was removed in vacuo. The residue was purified by HPLC using a gradient of 5% CH3CN in $H_2O$ (containing 0.1% TFA) to 95% CH3CN over 60 min. Fractions containing the desired product were pooled, and lyophilized to give a powder (8 mg, yield: 6%). MS 500 and 502 (M+H), 522 and 524 (M+Na). $^1$H NMR (CD$_3$OD) δ 8.09 (d, 1H, J=8 Hz), 7.68 (d, 2H, J=8 Hz), 7.64-7.28 (m, 9H), 6.45 (AB type, 2H).

Examples 525 and 526

Preparation of $N^1$-(5-bromopyridin-2-yl)-$N^4$-(4-[(2-aminosulfonyl)phenyl]phenyl)-2-methylmaleamic amide and $N^1$-(5-bromopyridin-2-yl)-$N^4$-(4-[(2-aminosulfonyl)phenyl]phenyl)-3-methylmaleamic amide

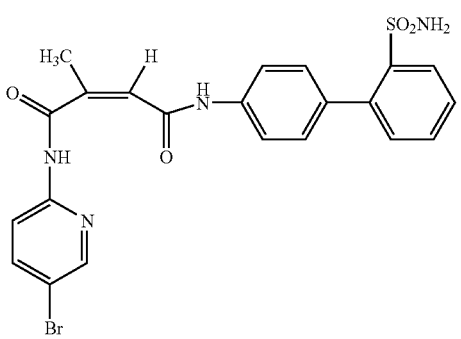

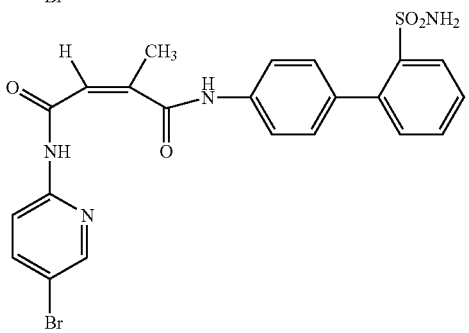

A. Preparation of N-(5-bromopyridin-2-yl)-methylmaleimide

A mixture of citraconic anhydride (1.00 mL, 11.1 mmol) and 2-amino-5-bromopyridine (1.93 g, 11.2 mmol) in toluene (60 mL) was heated to reflux overnight. The solution was cooled down, filtered. The filtrate was concentrated in vacuo to give a solid (2.10 g, yield: 71%). MS 267 and 269 (M+H).

B. Preparation of $N^1$-(5-bromopyridin-2-yl)-$N^4$-(4-[(2-aminosulfonyl)phenyl]phenyl)-2-methylmaleamic amide and $N^1$-(5-bromopyridin-2-yl)-$N^4$-(4-[(2-aminosulfonyl)phenyl]phenyl)-3-methylmaleamic amide To the solution of 4-(2-aminosulfonylphenyl)aniline (0.170 g, 0.685 mmol) in CH2Cl2 (10 mL) at room temperature, trimethylaluminum (2.0 M in hexane, 2.00 mL, 4.00 mmol) was added dropwise, during which time, white gel-like precipitates came out the solution. It was stirred for 30 min. A solution of N-(5-bromopyridin-2-yl)-methylmaleimide (0.122 g, 0.457 mmol) in CH2Cl2 (5 mL) was added. It was stirred for 1 hour, during which time the precipitates started to dissolve, and the solution became clear; It was stirred for another 2 hours. 1N HCl was added to neutralize the solution to pH 2-3, which resulted in precipitation. The precipitates were collected by filtration, dried on vacuum. The precipitates (75 mg, yield: 32%) were a mixture of 2-methyl and 3-methylmaleamic amide isomers in a ratio of 1:5. MS 515 and 517 (M+H), 537 and 539 (M+Na).

Example 527

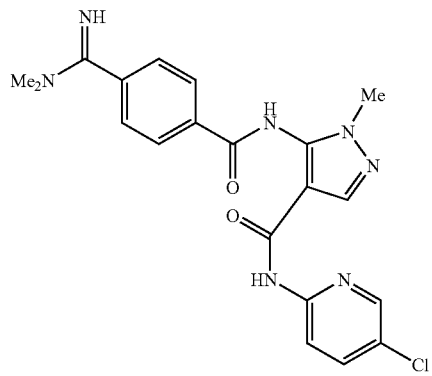

A solution of 3-amino-4-[(5-chloro-2-pyridinyl)aminocarbonyl]pyrazole (1 equiv) and 4-cyanobenzoic acid (1 equiv) in pyridine was treated with POCl₃ (1.1 equiv) for 30 min. The resulting mixture was quenched by slow addition of water, and extracted with CH₂Cl₂ and dried over MgSO₄. After evaporation, the residue was triturated with a small amount of CH₂Cl₂ and EtOAc. The solid on the glass wall was then subjected to standard Pinner conditions to give desired product. MS (M+H)⁺: 426.

Examples 528-538

The following examples were prepared according to the procedure previously described.

Example 539

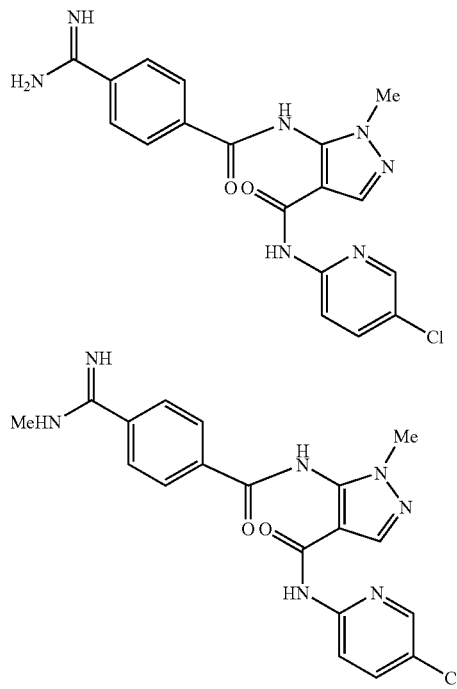

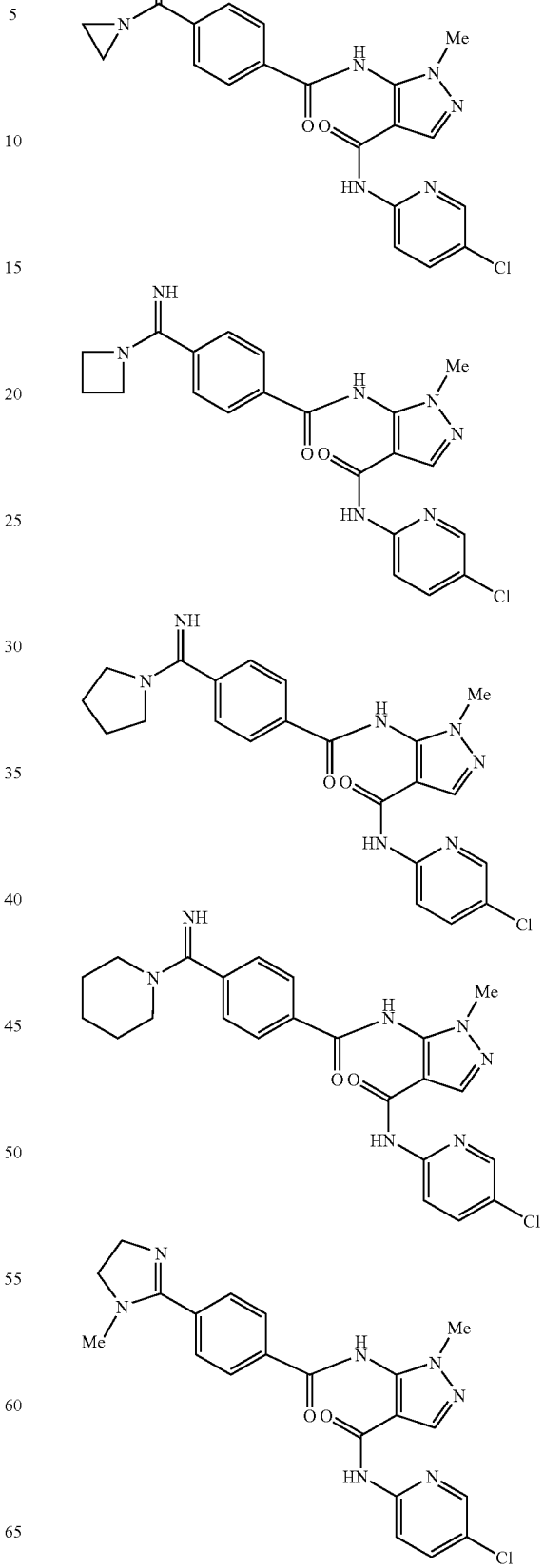

-continued

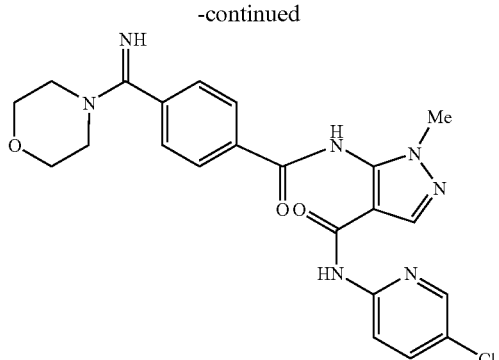

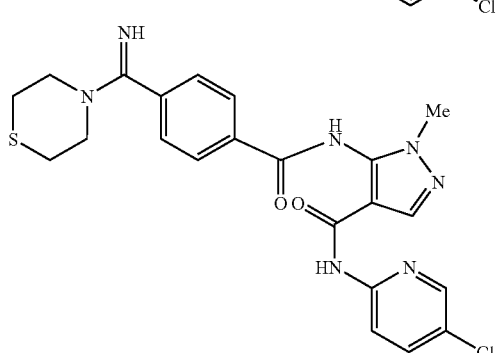

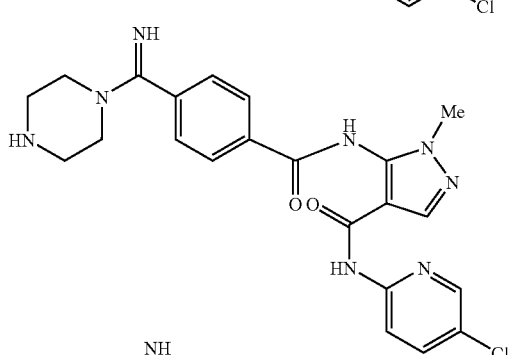

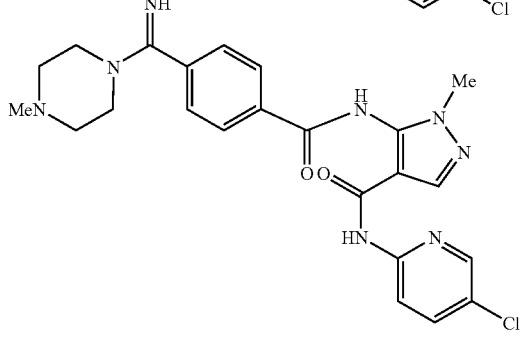

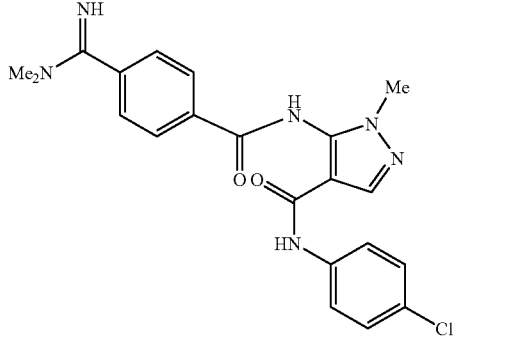

Step 1: A solution of 3-amino-4-ethoxycarbonyl-pyrazole (1 equiv) and 4-cyanobenzoic acid (1 equiv) in pyridine was treated with $POCl_3$ (1.1 equiv) for 1 h. The resulting mixture was quenched by slow addition of water, extracted with $CH_2Cl_2$, dried over $MgSO_4$, and purified by column chromatography to give the desired product.

Step 2: The compound obtained in step 1 (1 equiv) in DMF was treated with NaSMe (10 equiv) at 65° C. overnight. The resulting mixture was quenched by slow addition of water, and acidified with 1 N HCl, extracted with EtOAc, and dried over $MgSO_4$. The acid was reflux in excess $SOCl_2$ for 2 h. The volatile was removed on rotovap, and the residue was redissolved in pyridine, refluxed overnight in the prsence of DMAP (1 equiv) and 4-chloroaniline (10 equiv). The resulting mixture was quenched by slow addition of water, and extracted with $CH_2Cl_2$ and dried over $MgSO_4$. After evaporation, the residue was trituated with a small amount of $CH_2Cl_2$ and EtOAc. The solid on the glass wall was then subjected to standard Pinner conditions to give desired product. MS (M+H)$^+$: 425.

Example 540

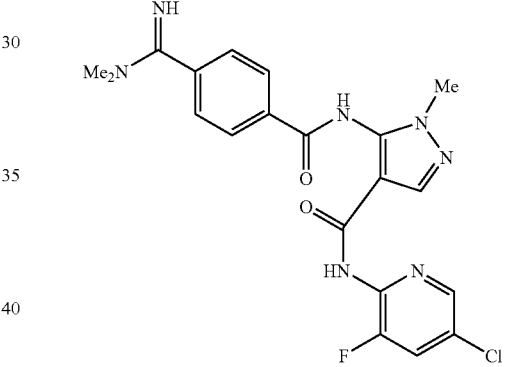

Similarly prepared as Example 350. MS (M+H)$^+$: 443.

Examples 541-551

The following examples were prepared according to the procedure previously described.

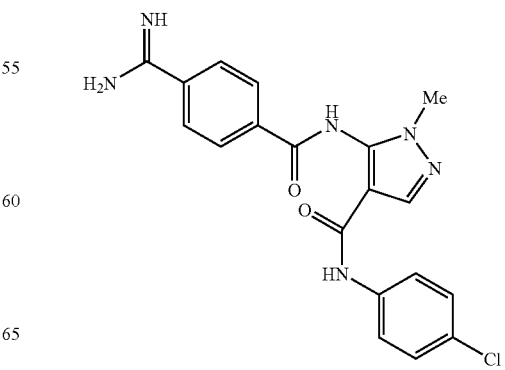

-continued
431
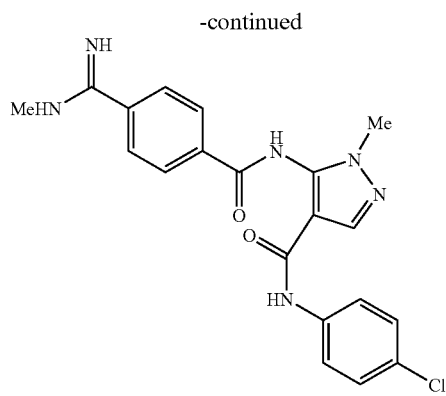
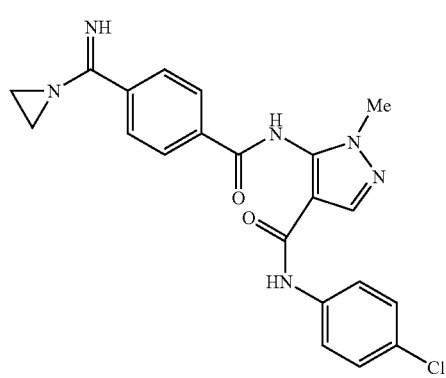
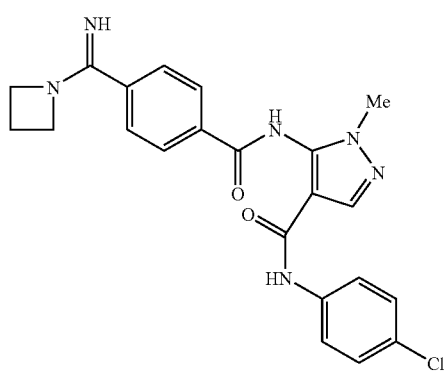
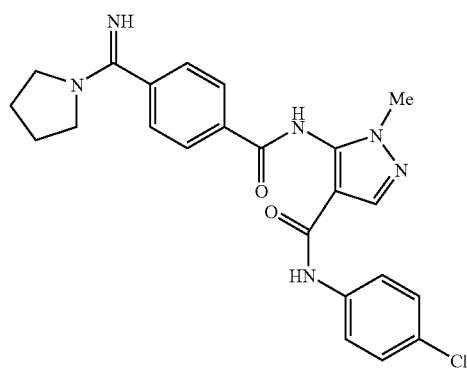
432
-continued
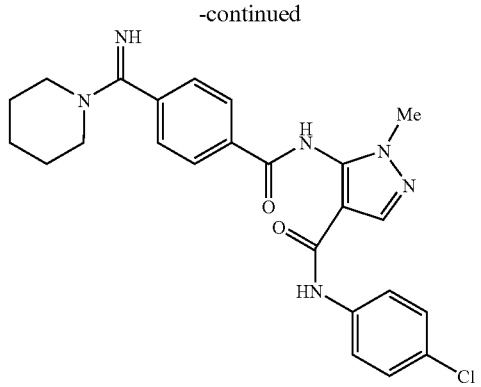
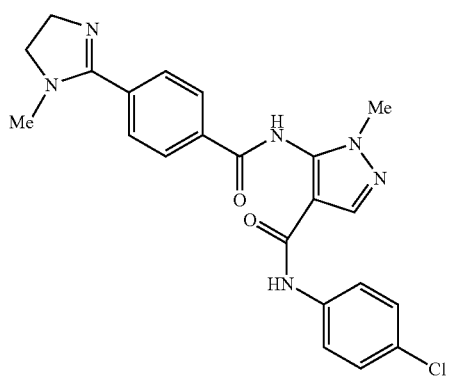
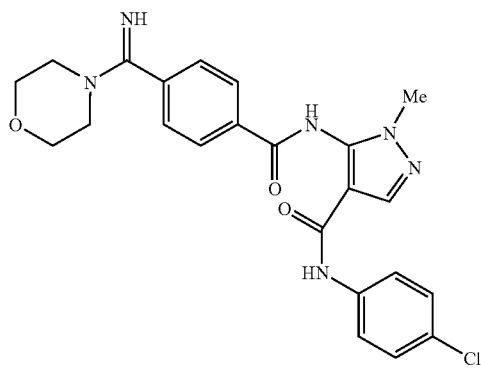
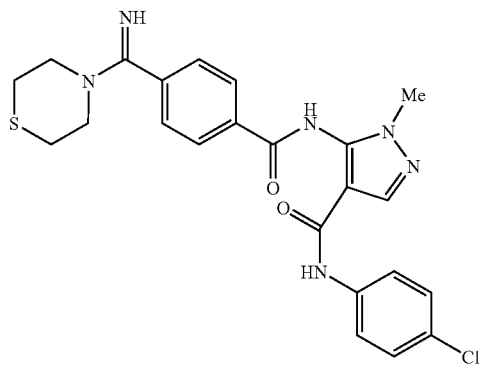

-continued
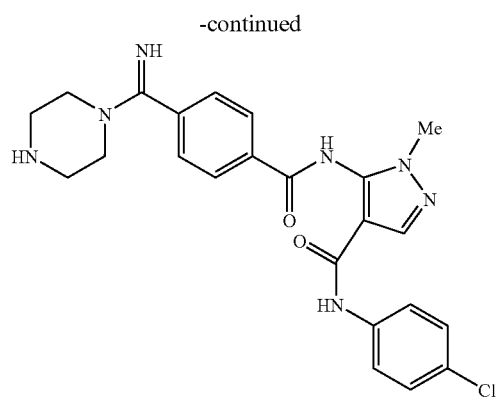
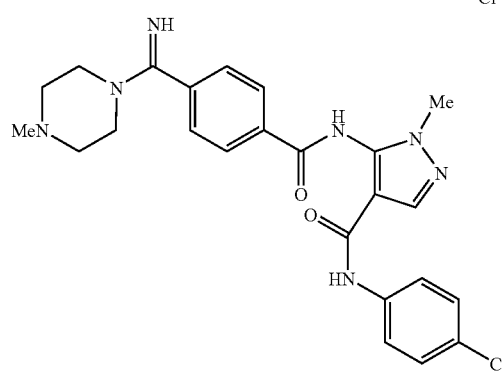
Examples 552-559
The following examples were prepared according to the procedure previously described.
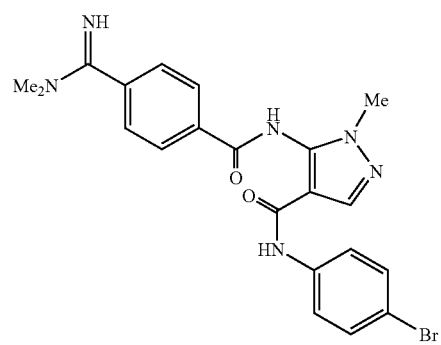
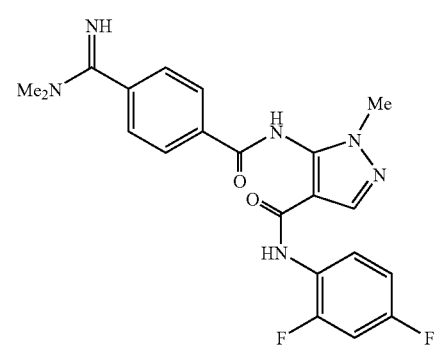
-continued
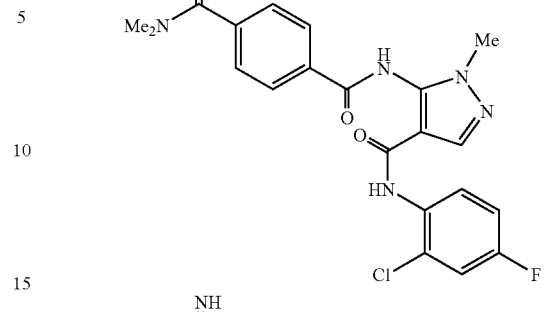
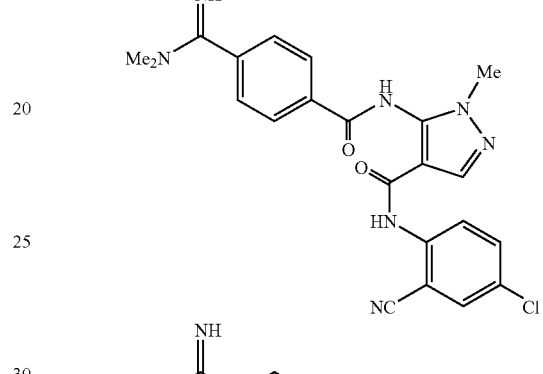
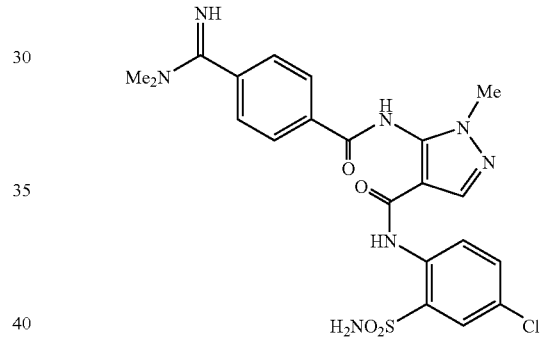
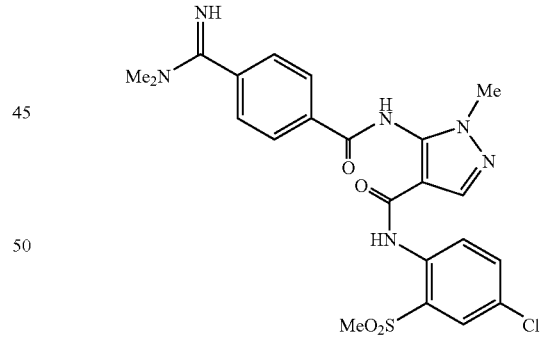
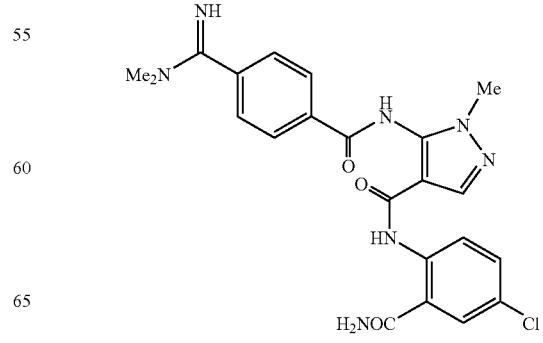

435
-continued
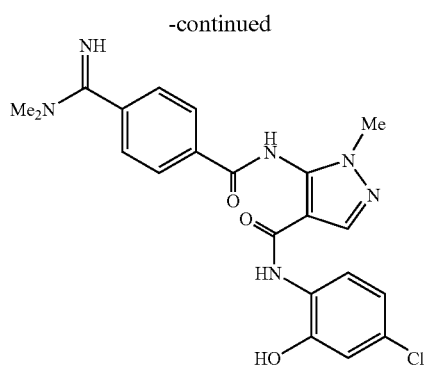
Example 560
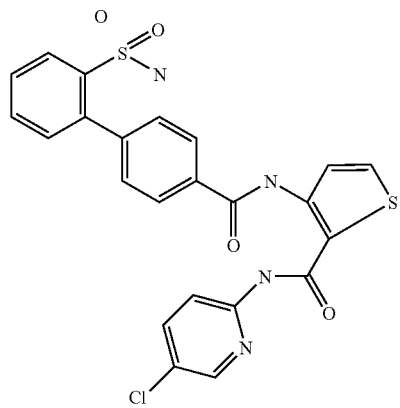
The title compound was synthesized according to the procedure described previously.
ES-MS 514(M+1).
Example 561
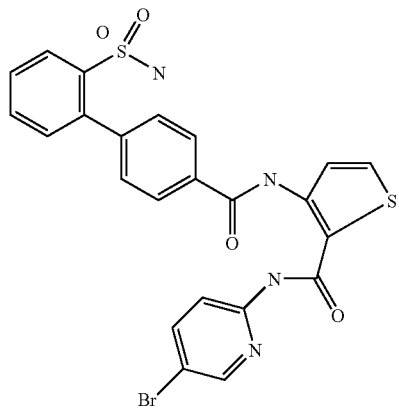
The title compound was synthesized according to the procedure described previously.
ES-MS 558(M+1).
436
Example 562-585
The following compounds were prepared according to the procedure previously described.
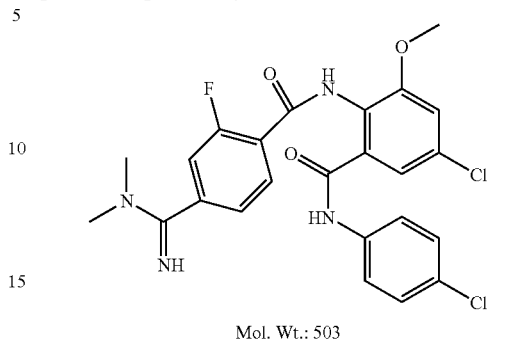
Mol. Wt.: 503
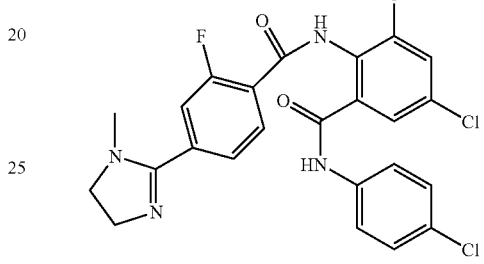
Mol. Wt.: 515
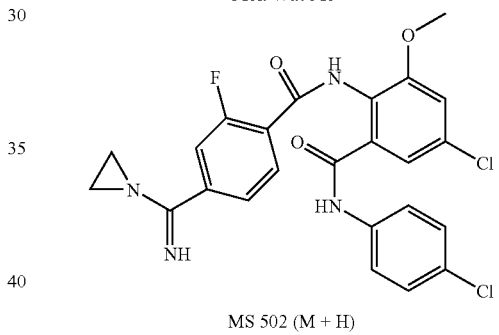
MS 502 (M + H)
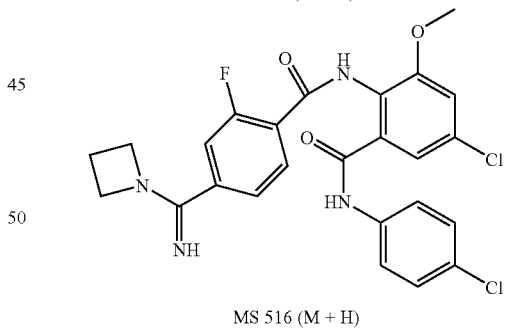
MS 516 (M + H)
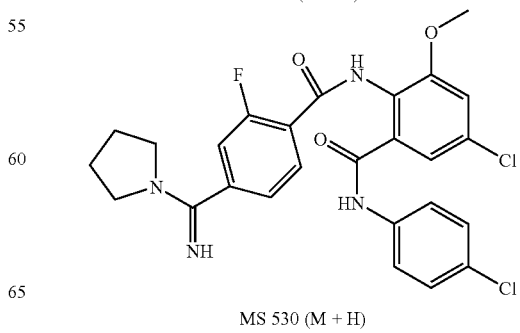
MS 530 (M + H)

-continued
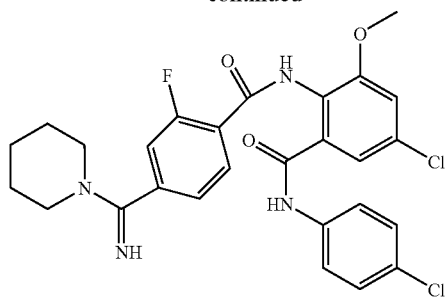
MS 544 (M + H)
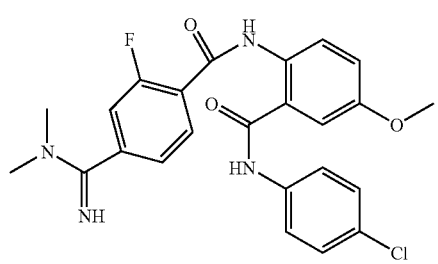
MS 469 (M + H)
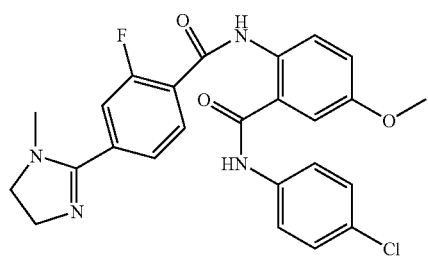
MS 481 (M + H)
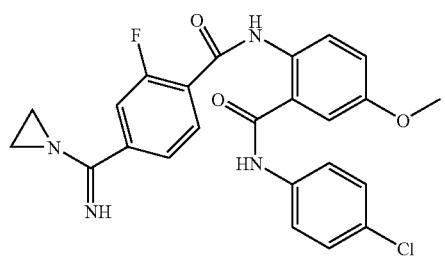
MS 467 (M + H)
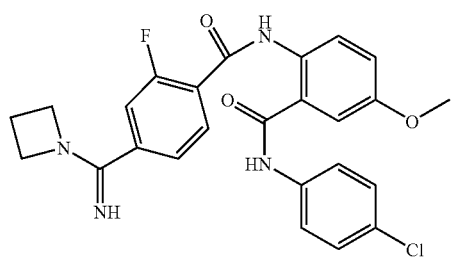
MS 481 (M + H)
-continued
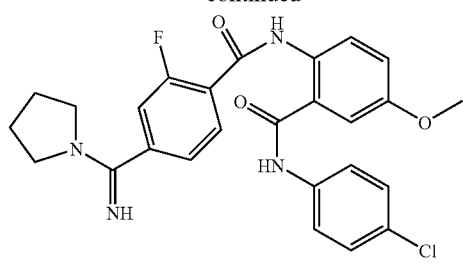
MS 495 (M + H)
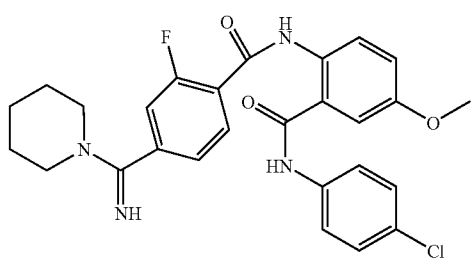
MS 509 (M + H)
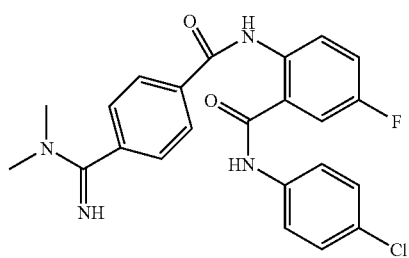
MS 439 (M + H)
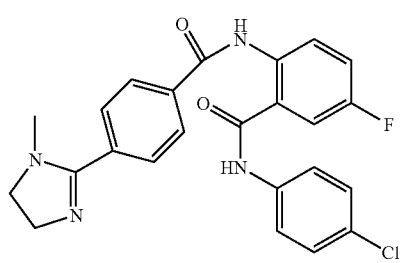
MS 451 (M + H)
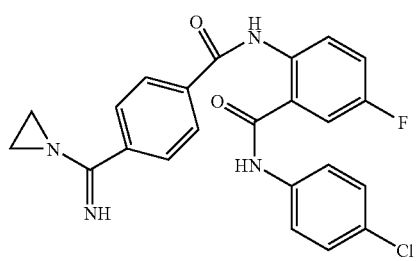
MS 437 (M + H)

-continued
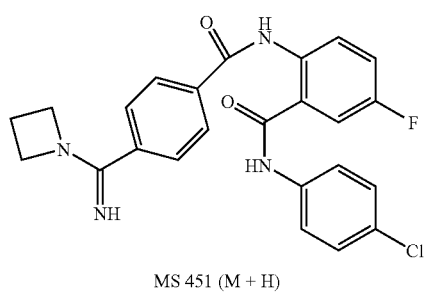
MS 451 (M + H)
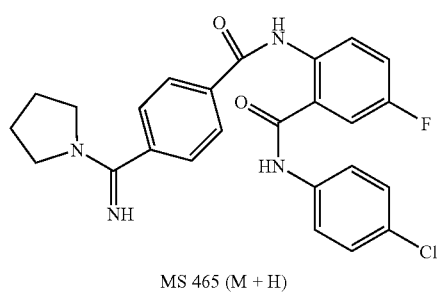
MS 465 (M + H)
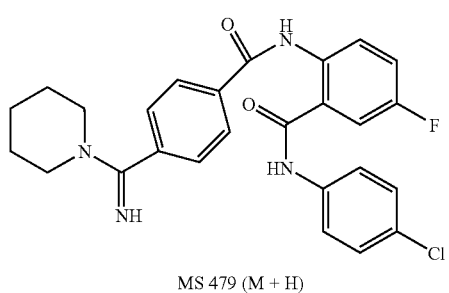
MS 479 (M + H)
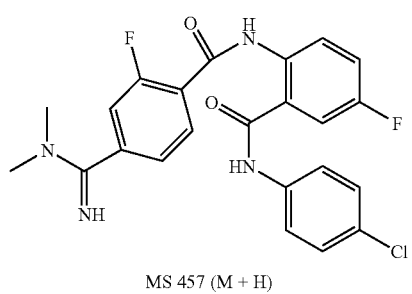
MS 457 (M + H)
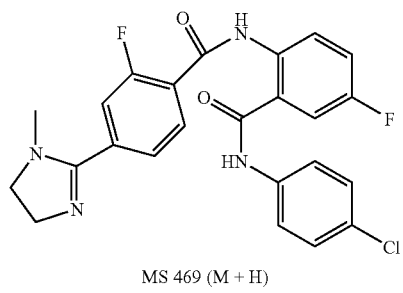
MS 469 (M + H)
-continued
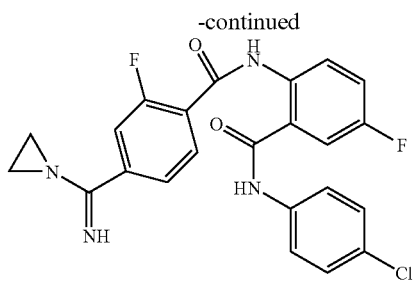
MS 455 (M + H)
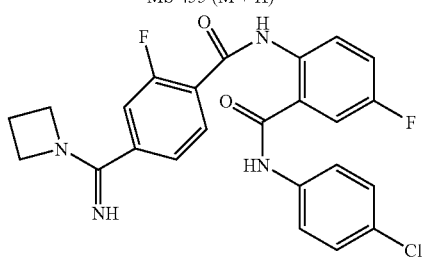
MS 469 (M + H)
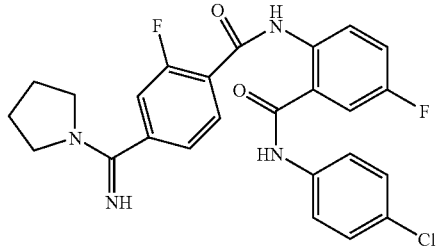
MS 483 (M + H)
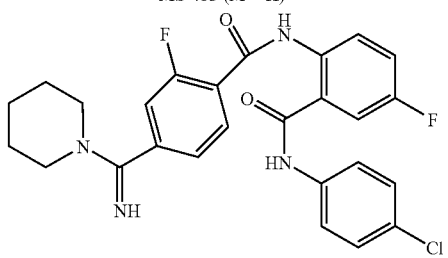
MS 497 (M + H)
Example 586
3-(2-(4-[(2-aminosulfonyl)phenyl]benzoylamino)phenoxy)benzamidine
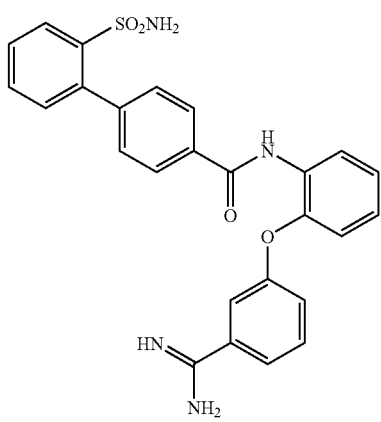

Step 1: To a solution of 2-fluoro nitrobenzene (1.41 g, 10 mmol, 1.0 equiv) and 3-hydroxybenzonitrile (1.19 g, 1.0 equiv) in 10 mL of DMF was added $K_2CO_3$ (2.76 g, 2 equiv). After stirring at 60° C. for 3 h, the mixture was diluted with EtOAc and washed with $H_2O$. The organic layer was dried over $MgSO_4$, filtered and evaporated to give 3-(2-nitrophenoxy)benzonitrile (2.38 g, 99%). MS found for $C_{13}H_9N_2O_3$ (M+H)$^+$: 241.

Step 2: A solution of 3-(2-nitrophenoxy)benzonitrile (1.21 g, 5 mmol, 1.0 equiv) in 30 mL of EtOH was treated with $SnCl_2 2H_2O$ (3.38 g, 3 equiv) at reflux for 4 h. The volatile was evaporated and the residue was redissolved in EtOAc, washed with saturated aqueous $NaHCO_3$ and 1N NaOH. The organic layer was dried over $MgSO_4$, filtered and evaporated to give 3-(2-aminophenoxy)benzonitrile (1.04 g, 99%). MS found for $C_{13}H_{,}N_2O$ (M+H)$^+$: 211.

Step 3: A mixture of 3-(2-aminophenoxy)benzonitrile (210 mg, 1 mmol, 1.0 equiv), 4-[(2-t-butylaminosulfonyl) phenyl]benzoic acid (330 mg, 1 equiv), Bop reagent (880 mg, 2 equiv) and TEA (1.39 mL, 10 equiv) in 3 mL of DMF was stirred at rt overnight. The mixture was diluted with EtOAc, washed with $H_2O$. The organic layer was dried over $MgSO_4$, filtered and evaporated. Flash chromatography on silica gel gave 3-(2-(4-[(2-t-butylaminosulfonyl)phenyl] benzoylamino)phenoxy)benzonitrile (300 mg, 57%). MS found for $C_{30}H_{28}N_3O_4S$ (M+H)$^+$: 526.

Step 4: A stream of HCl(g) was bubbled through a 0° C. solution of 3-(2-(4-[(2-t-butylaminosulfonyl)phenyl]benzoylamino)phenoxy)benzonitrile (53 mg, 0.1 mmol) in 5 mL of methanol until saturation. The mixture was stirred at rt overnight and evaporated. The resulting residue was treated with ammonium acetate (39 mg, 5 equiv) in 10 ml methanol at reflux temperature for 2 h. The solvent was removed at reduced pressure and the crude benzamidine was purified by HPLC (C18 reversed phase) eluting with 0.5% TFA in $H_2O/CH_3CN$ to give 3-(2-(4-[(2-aminosulfonyl)phenyl]benzoylamino) phenoxy)benzamidine (40 mg, 83%). MS found for $C_{26}H_{23}N_4O_4S$ (M+H)$^+$: 487.

Example 587

3-(4-fluoro-2-(4-[(2-aminosulfonyl)phenyl]phenyl-carbonylamino)phenoxy)benzamidine

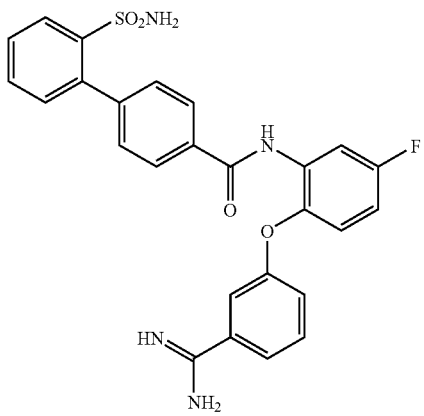

Step 1: A mixture of 3-(2-amino-4-fluorophenoxy)benzonitrile (230 mg, 1 mmol, 1.0 equiv), 4-[(2-t-butylaminosulfonyl)phenyl]benzoic chloride (349 mg, 1 equiv), pyridine (3 mL) in 10 mL of dichloromethane was stirred at rt overnight, washed with $H_2O$. The organic layer was dried over $MgSO_4$, filtered and evaporated. Flash chromatography on silica gel gave 3-(4-fluoro-2-(4-[(2-t-butylaminosulfonyl)phenyl]phenylcarbonylamino)phenoxy)benzonitrile (495 mg, 91%). MS found for $C_{30}H_{27}FN_3O_4S$ (M+H)$^+$: 544.

Step 2: A stream of HCl(g) was bubbled through a 0° C. solution of 3-(4-fluoro-2-(4-[(2-t-butylaminosulfonyl)phenyl]phenylcarbonylamino)phenoxy)benzonitrile (55 mg, 0.1 mmol) in 5 mL of methanol until saturation. The mixture was stirred at rt overnight and evaporated. The resulting residue was treated with ammonium acetate (39 mg, 5 equiv) in 10 ml methanol at reflux temperature for 2 h. The solvent was removed at reduced pressure and the crude benzamidine was purified by HPLC (C18 reversed phase) eluting with 0.5% TFA in $H_2O/CH_3CN$ to give 3-(4-fluoro-2-(4-[(2-aminosulfonyl)phenyl]phenylcarbonylamino)phenoxy)benzamidine (39 mg, 77%). MS found for $C_{26}H_{22}FN_4O_4S$ (M+H)$^+$: 505.

Example 588

3-(4-trifluoromethyl-2-(4-[(2-aminosulfonyl) phenyl]phenylcarbonylamino)phenoxy)benzamidine

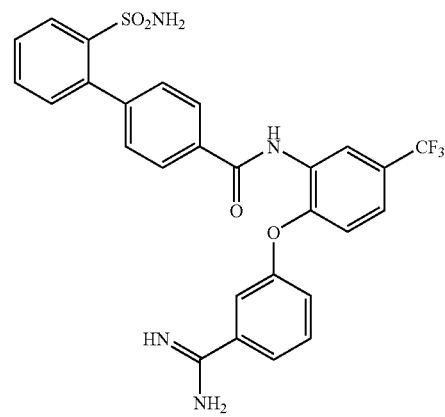

Step 1: A mixture of 3-(2-amino-4-trifluoromethylphenoxy)benzonitrile (280 mg, 1 mmol, 1.0 equiv), 4-[(2-t-butylaminosulfonyl)phenyl]benzoic chloride (349 mg, 1 equiv), pyridine (3 mL) in 10 mL of dichloromethane was stirred at rt overnight, washed with $H_2O$. The organic layer was dried over $MgSO_4$, filtered and evaporated. Flash chromatography on silica gel gave 3-(4-trifluoromethyl-2-(4-[(2-t-butylaminosulfonyl)phenyl]phenylcarbonylamino)phenoxy)benzonitrile (529 mg, 89%). MS found for $C_{31}H_{27}F_3N_3O_4S$ (M+H)$^+$: 594.

Step 2: A stream of HCl(g) was bubbled through a 0° C. solution of 3-(4-trifluoromethyl-2-(4-[(2-t-butylaminosulfonyl)phenyl]phenylcarbonylamino)phenoxy) benzonitrile (59 mg, 0.1 mmol) in 5 mL of methanol until saturation. The mixture was stirred at rt overnight and evaporated. The resulting residue was treated with ammonium acetate (39 mg, 5 equiv) in 10 ml methanol at reflux temperature for 2 h. The solvent was removed at reduced pressure and the crude benzamidine was purified by HPLC (C18 reversed phase) eluting with 0.5% TFA in $HF_2O/CH_3CN$ to give 3-(4-trifluoromethyl-2-(4-[(2-aminosulfonyl)phenyl]phenylcarbonylamino)phenoxy) benzamidine (35 mg, 63%). MS found for $C_{27}H_{22}F_3N_4O_4S$ (M+H)$^+$: 555.

Example 589

3-(4-methylsulfonyl-2-(4-[(2-aminosulfonyl)phenyl]phenylcarbonylamino)phenoxy)benzamidine

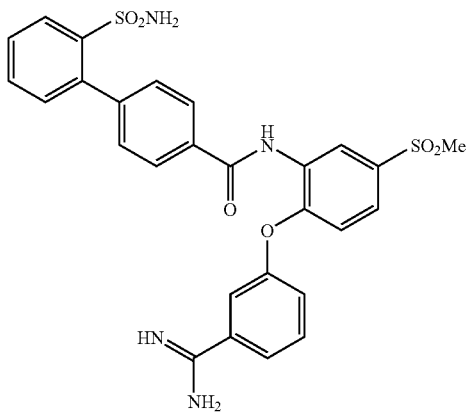

Step 1: A mixture of 3-(2-amino-4-methylsulfonylphenoxy)benzonitrile (290 mg, 1 mmol, 1.0 equiv), 4-[(2-t-butylaminosulfonyl)phenyl]benzoic chloride (349 mg, 1 equiv), pyridine (3 mL) in 10 mL of dichloromethane was stirred at rt overnight, washed with $H_2O$. The organic layer was dried over $MgSO_4$, filtered and evaporated. Flash chromatography on silica gel gave 3-(4-methylsulfonyl-2-(4-[(2-t-butylaminosulfonyl)phenyl]phenylcarbonylamino)phenoxy)benzonitrile (429 mg, 71%). MS found for $C_{31}H_{30}N_3O_6S_2$ (M+H)$^+$: 604.

Step 2: A stream of HCl(g) was bubbled through a 0° C. solution of 3-(4-methylsulfonyl-2-(4-[(2-t-butylaminosulfonyl)phenyl]phenylcarbonylamino)phenoxy) benzonitrile (60 mg, 0.1 mmol) in 5 mL of methanol until saturation. The mixture was stirred at rt overnight and evaporated. The resulting residue was treated with ammonium acetate (39 mg, 5 equiv) in 10 ml methanol at reflux temperature for 2 h. The solvent was removed at reduced pressure and the crude benzamidine was purified by HPLC (C18 reversed phase) eluting with 0.5% TFA in $H_2O/CH_3CN$ to give 3-(4-methylsulfonyl-2-(4-[(2-aminosulfonyl)phenyl]phenylcarbonylamino)phenoxy) benzamidine (27 mg, 47%). MS found for $C_{27}H_{25}N_4O_6S_2$ (M+H)$^+$: 565.

Examples 590-593

The following compounds were prepared using the procedure previously described.

Example 590

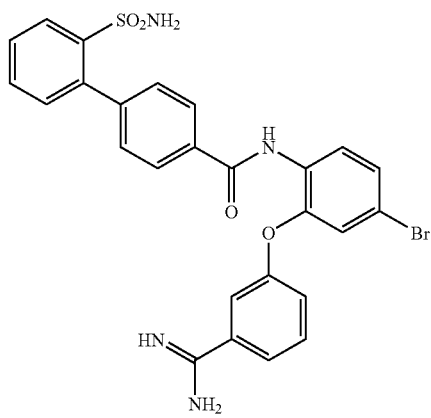

MS (M+H): 565

Example 591

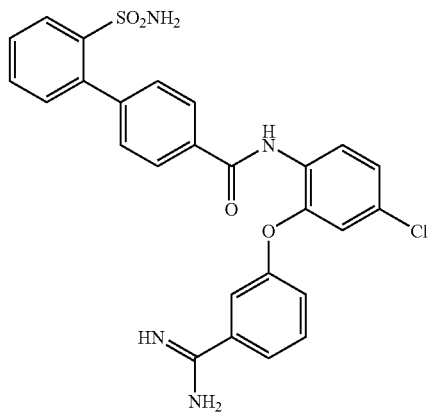

MS (M+H): 521

Example 592

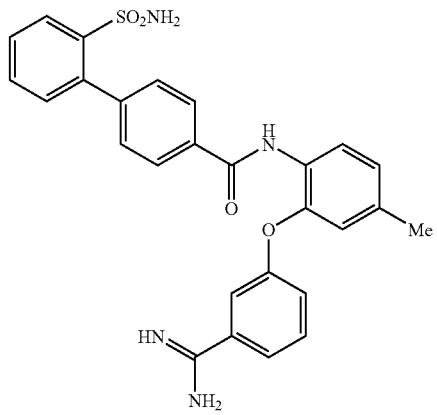

MS (M+H): 501

Example 593

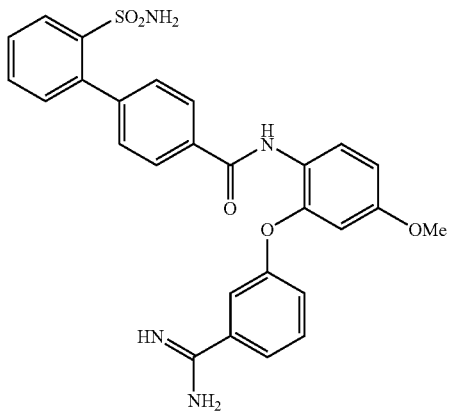

MS (M+H): 517

Example 594

3-(5-hydroxy-2-(4-[(2-aminosulfonyl)phenyl]phenylcarbonylamino)phenoxy)benzamidine

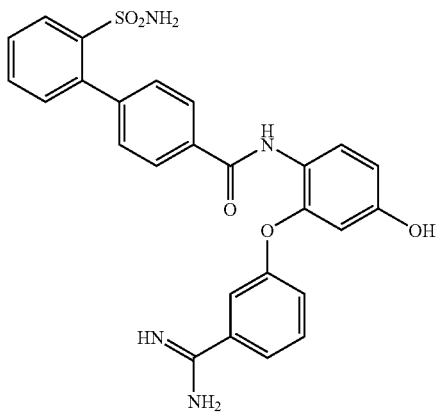

A solution of 3-(5-methoxy-2-(4-[(2-aminosulfonyl)phenyl]phenylcarbonylamino) phenoxy)benzamidine (52 mg, 0.1 mmol, 1 equiv) in 5 mL of methylene chloride was treated with $BBr_3$ (1 M in dichloromethane, 0.5 mL, 5 equiv) overnight. The reaction was quenched with water carefully and after the volatile was evaporated, the aqueous residue was purified by HPLC (C18 reversed phase) eluting with 0.5% TFA in $H_2O/CH_3CN$ to give 3-(5-hydroxy-2-(4-[(2-aminosulfonyl)phenyl]phenylcarbonylamino)phenoxy)benzamidine. (41 mg, 82%). MS found for $C_{26}H_{23}N_4O_6S$ (M+H)$^+$: 503.

Example 595

3-(4-methoxycarbonyl-2-(4-[(2-aminosulfonyl)phenyl]phenylcarbonylamino)phenoxy)benzamidine

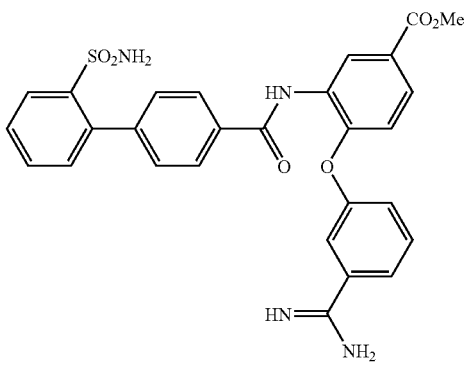

Step 1: A mixture of 3-(2-amino-4-methoxycarbonylphenoxy)benzonitrile (270 mg, 1 mmol, 1.0 equiv), 4-[(2-t-butylaminosulfonyl)phenyl]benzoic chloride (349 mg, 1 equiv), pyridine (3 mL) in 10 mL of dichloromethane was stirred at rt overnight, washed with $H_2O$. The organic layer was dried over $MgSO_4$, filtered and evaporated. Flash chromatography on silica gel gave 3-(4-methoxycarbonyl-2-(4-[(2-t-butylaminosulfonyl)phenyl]phenylcarbonylamino) phenoxy)benzonitrile (502 mg, 86%). MS found for $C_{32}H_{30}N_3O_6S$ (M+H)$^+$: 584.

Step 2: A stream of HCl(g) was bubbled through a 0° C. solution of 3-(4-methoxycarbonyl-2-(4-[(2-t-butylaminosulfonyl)phenyl]phenylcarbonylamino)phenoxy)benzonitrile (58 mg, 0.1 mmol) in 5 mL of methanol until saturation. The mixture was stirred at rt overnight and evaporated. The resulting residue was treated with ammonium acetate (39 mg, 5 equiv) in 10 ml methanol at reflux temperature for 2 h. The solvent was removed at reduced pressure and the crude benzamidine was purified by HPLC (C18 reversed phase) eluting with 0.5% TFA in $H_2O/CH_3CN$ to give 3-(4-methoxycarbonyl-2-(4-[(2-aminosulfonyl)phenyl]phenylcarbonylamino)phenoxy)benzamidine (29.5 mg, 54%). MS found for $C_{28}H_{25}N_4O_6S$ (M+H)$^+$: 545.

Example 596

3-(4-hydroxycarbonyl-2-(4-[(2-aminosulfonyl)phenyl]phenylcarbonylamino)phenoxy)benzamidine

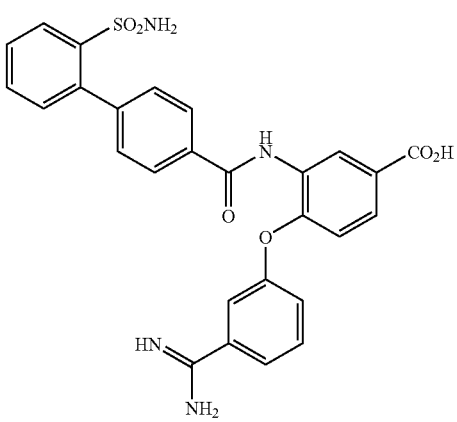

A solution of 3-(4-methoxycarbonyl-2-(4-[(2-aminosulfonyl)phenyl]phenylcarbonylamino)phenoxy)benzamidine (10.9 mg, 0.02 mmol, 1.0 equiv) in 5 mL of methanol was treated with 1N LiOH (2 mL) at rt for 2 h. Methanol was evaporated, the aqueous residue was subjected to HPLC with 0.5% TFA in $H_2O/CH_3CN$ to give 3-(4-hydroxycarbonyl-2-(4-[(2-aminosulfonyl)phenyl]phenylcarbonylamino)phenoxy)benzamidine (8.9 mg, 84%). MS found for $C_{27}H_{23}N_4O_6S$ $(M+H)^+$: 531.

Example 597

3-(2-(4-[(2-aminosulfonyl)phenyl]phenylcarbonylamino)pheylamino)benzamidine

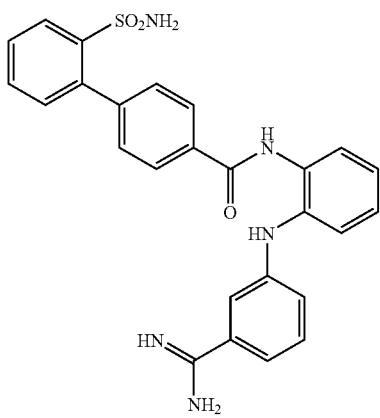

Step 1: A mixture of 3-(2-amino-phenylamino)benzonitrile (196 mg, 1 mmol, 1.0 equiv), 4-[(2-t-butylaminosulfonyl)phenyl]benzoic chloride (349 mg, 1 equiv), pyridine (3 mL) in 10 mL of dichloromethane was stirred at rt overnight, washed with $H_2O$. The organic layer was dried over $MgSO_4$, filtered and evaporated. Flash chromatography on silica gel gave 3-(2-(4-[(2-t-butylaminosulfonyl)phenyl]phenylcarbonylamino)phenylamino)benzonitrile (226 mg, 43%). MS found for $C_{30}H_{29}N_4O_3S$ $(M+H)^+$: 525.

Step 2: A stream of HCl(g) was bubbled through a 0° C. solution of 3-(2-(4-[(2-t-butylaminosulfonyl)phenyl]phenylcarbonylamino)pheylamino)benzonitrile (53 mg, 0.1 mmol) in 5 mL of methanol until saturation. The mixture was stirred at rt overnight and evaporated. The resulting residue was treated with ammonium acetate (39 mg, 5 equiv) in 10 ml methanol at reflux temperature for 2 h. The solvent was removed at reduced pressure and the crude benzamidine was purified by HPLC (C18 reversed phase) eluting with 0.5% TFA in $H_2O/CH_3CN$ to give 3-(2-(4-[(2-aminosulfonyl)phenyl]phenylcarbonylamino)pheylamino)benzamidine (27 mg, 55%). MS found for $C_{26}H_{24}N_5O_3S$ $(M+H)^+$: 486.

Example 598

7-(2-(4-[(2-aminosulfonyl)phenyl benzoylamino)phenoxy)-1-aminoisoquinoline

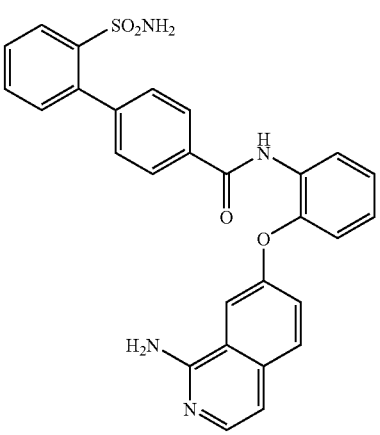

Step 1: A mixture of 7-(2-aminophenoxy)isoquinoline (237 mg, 1 mmol, 1.0 equiv), 4-[(2-t-butylaminosulfonyl)phenyl]benzoic acid (330 mg, 1 equiv), Bop reagent (880 mg, 2 equiv) and TEA (1.39 mL, 10 equiv) in 3 mL of DMF was stirred at rt overnight. The mixture was diluted with EtOAc, washed with $H_2O$. The organic layer was dried over $MgSO_4$, filtered and evaporated. Flash chromatography on silica gel gave 7-(2-(4-[(2-t-butylaminosulfonyl)phenyl]benzoylamino)phenoxy)isoquinoline (469 mg, 85%). MS found for $C_{32}H_{30}N_3O_4S$ $(M+H)^+$: 552.

Step 2: A solution of 7-(2-(4-[(2-t-butylaminosulfonyl)phenyl]benzoylamino)phenoxy) isoquinoline (110 mg, 0.2 mmol, 1 equiv) in 5 mL of acetone was treated with mCPBA (113 mg, 57%, 1.5 equiv) until HPLC showed complete reaction. Acetone was evaporated, the residue was partetioned between methylene chloride and saturated aqueous $NaHCO_3$. The organic layer was dried ove $MgSO_4$ and used in the next step directly.

Step 3: The compound obtained in step 2 in 5 mL of pyridine was treated with tosyl chloride (46 mg, 1.2 equiv) at rt overnight and pyridine was removed under reduced pressure. The residue was reacted with 5 mL of ethanolamine for 12 h, and partitioned between methylene chloride and water. The organic layer was dried over $MgSO_4$, filtered, evaporated and refluxed in 3 mL of trifluoroacetic acid for 30 min. After removing TFA, the crude was purified by HPLC (C18 reversed phase) eluting with 0.5% TFA in $H_2O/CH_3CN$ to give 7-(2-(4-[(2-aminosulfonyl)phenyl]benzoylamino)phenoxy)-1-aminoisoquinoline (43 mg, 42%). MS found for $C_{28}H_{23}N_4O_4S$ $(M+H)^+$: 511.

Example 599

7-(2-(4-[(2-aminosulfonyl)phenyl]benzoylamino)-4-fluorophenoxy)1-aminoisoquinoline

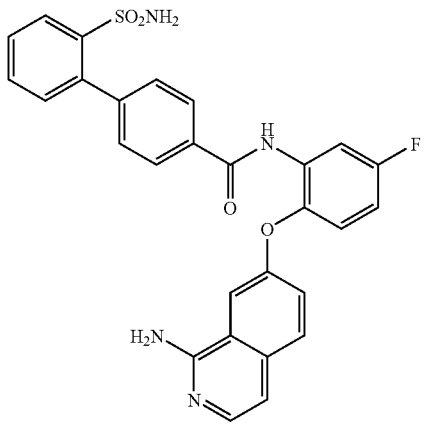

Step 1: A mixture of 7-(2-amino-4-fluorophenoxy)isoquinoline (255 mg, 1 mmol, 1.0 equiv), 4-[(2-t-butylaminosulfonyl)phenyl]benzoic acid (330 mg, 1 equiv), Bop reagent (880 mg, 2 equiv) and TEA (1.39 mL, 10 equiv) in 3 mL of DMF was stirred at rt overnight. The mixture was diluted with EtOAc, washed with $H_2O$. The organic layer was dried over $MgSO_4$, filtered and evaporated. Flash chromatography on silica gel gave 7-(2-(4-[(2-t-butylaminosulfonyl)phenyl]benzoylamino)-4-fluorophenoxy) isoquinoline (467 mg, 82%). MS found for $C_{32}H_{29}FN_3O_4S$ $(M+H)^+$: 570.

Step 2: A solution of 7-(2-(4-[(2-t-butylaminosulfonyl)phenyl]benzoylamino)-4-fluorophenoxy) isoquinoline (114, 0.2 mmol, 1 equiv) in 5 mL of acetone was treated with mCPBA (113 mg, 57%, 1.5 equiv) until HPLC showed complete reaction. Acetone was evaporated, the residue was partetioned between methylene chloride and saturated aqueous $NaHCO_3$. The organic layer was dried ove $MgSO_4$ and used in the next step directly.

Step 3: The compound obtained in step 4 in 5 mL of pyridine was treated with tosyl chloride (46 mg, 1.2 equiv) at rt overnight and pyrine was removed under reduced pressure. The residue was reacted with 5 mL of ethanolamine for 12 h, and partitioned between methylene chloride and water. The organic layer was dried over $MgSO_4$, filtered, evaporated and refluxed in 3 mL of trifluoroacetic acid for 30 min. After removing TFA, the crude was purified by HPLC (C18 reversed phase) eluting with 0.5% TFA in $H_2O/CH_3CN$ to give 7-(2-(4-[(2-aminosulfonyl)phenyl]benzoylamino)-4-fluorophenoxy)1-aminoisoquinoline (77 mg, 50%). MS found for $C_{28}H_{22}FN_4O_4S$ $(M+H)^+$: 529.

Example 600

7-(2-(4-((2-aminosulfonyl)phenyl]benzoylamino)-4-trifluoromethylphenoxy)1-aminoisoquinoline

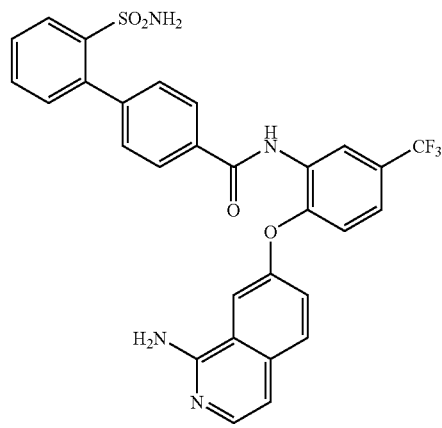

Step 1: A mixture of 7-(2-amino-4-trifluoromethylphenoxy)isoquinoline (305 mg, 1 mmol, 1.0 equiv), 4-[(2-t-butylaminosulfonyl)phenyl]benzoic acid (330 mg, 1 equiv), Bop reagent (880 mg, 2 equiv) and TEA (1.39 mL, 10 equiv) in 3 mL of DMF was stirred at rt overnight. The mixture was diluted with EtOAc, washed with $H_2O$. The organic layer was dried over $MgSO_4$, filtered and evaporated. Flash chromatography on silica gel gave 7-(2-(4-[(2-t-butylaminosulfonyl)phenyl]benzoylamino)-4-trifluoromethylphenoxy) isoquinoline (360 mg, 58%). MS found for $C_{33}H_{29}F_3N_3O_4S$ $(M+H)^+$ 620.

Step 2: A solution of 7-(2-(4-[(2-t-butylaminosulfonyl)phenyl]benzoylamino)-4-trifluoromethylphenoxy) isoquinoline (124 mg, 0.2 mmol, 1 equiv) in 5 mL of acetone was treated with mCPBA (113 mg, 57%, 1.5 equiv) until HPLC showed complete reaction. Acetone was evaporated, the residue was partetioned between methylene chloride and saturated aqueous $NaHCO_3$. The organic layer was dried ove $MgSO_4$ and used in the next step directly.

Step 3: The compound obtained in step 4 in 5 mL of pyridine was treated with tosyl chloride (46 mg, 1.2 equiv) at rt overnight and pyrine was removed under reduced pressure. The residue was reacted with 5 mL of ethanolamine for 12 h, and partitioned between methylene chloride and water. The organic layer was dried ove $MgSO_4$, filtered, evaporated and refluxed in 3 mL of trifluoroacetic acid for 30 min. After removing TFA, the crude was purified by HPLC (C18 reversed phase) eluting with 0.5% TFA in $H_2O/CH_3CN$ to give 7-(2-(4-[(2-aminosulfonyl)phenyl]benzoylamino)-4-trifluoromethylphenoxy)1-aminoisoquinoline (64 mg, 52%). MS found for $C_{29}H_{22}F_3N_4O_4S$ $(M+H)^+$: 579.

Example 601

7-(2-(4-[(2-aminosulfonyl)phenyl]benzoylamino)-4-methylsulfonylphenoxy)1-aminoisoquinoline

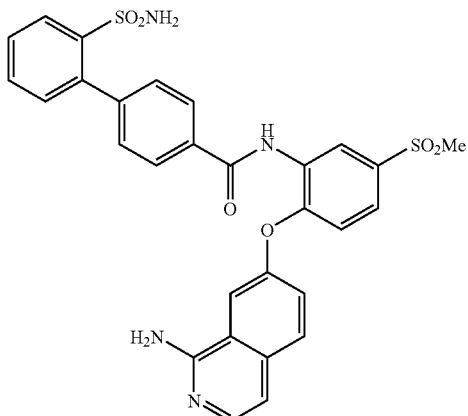

Step 1: A mixture of 7-(2-amino-4-methylsulfonylphenoxy)isoquinoline (315 mg, 1 mmol, 1.0 equiv), 4-[(2-t-butylaminosulfonyl)phenyl]benzoic acid (330 mg, 1 equiv), Bop reagent (880 mg, 2 equiv) and TEA (1.39 mL, 10 equiv) in 3 mL of DMF was stirred at rt overnight. The mixture was diluted with EtOAc, washed with $H_2O$. The organic layer was dried over $MgSO_4$, filtered and evaporated. Flash chromatography on silica gel gave 7-(2-(4-[(2-t-butylaminosulfonyl)phenyl]benzoylamino)-4-methlsulfonylphenoxy) isoquinoline (460 mg, 73%). MS found for $C_{33}H_{32}N_3O_6S_2$ $(M+H)^+$: 630.

Step 2: A solution of 7-(2-(4-[(2-t-butylaminosulfonyl) phenyl]benzoylamino)-4-methlsulfonylphenoxy) isoquinoline (126 mg, 0.2 mmol, 1 equiv) in 5 mL of acetone was treated with mCPBA (113 mg, 57%, 1.5 equiv) until HPLC showed complete reaction. Acetone was evaporated, the residue was partetioned between methylene chloride and saturated aqueous $NaHCO_3$. The organic layer was dried ove $MgSO_4$ and used in the next step directly.

Step 3: The compound obtained in step 4 in 5 mL of pyridine was treated with tosyl chloride (46 mg, 1.2 equiv) at rt overnight and pyrine was removed under reduced pressure. The residue was reacted with 5 mL of ethanolamine for 12 h, and partitioned between methylene chloride and water. The organic layer was dried over $MgSO_4$, filtered, evaporated and refluxed in 3 mL of trifluoroacetic acid for 30 min. After removing TFA, the crude was purified by HPLC (C18 reversed phase) eluting with 0.5% TFA in $H_2O/CH_3CN$ to give 7-(2-(4-[(2-aminosulfonyl)phenyl]benzoylamino)-4-methylsulfonylphenoxy) 1-aminoisoquinoline (94 mg, 80%). MS found for $C_{29}H_{25}N_4O_6S_2$ $(M+H)^+$: 589.

Example 602

3-(2-(4-[(2-aminosulfonyl)phenyl]phenylaminocarbonyl-4-nitrophenoxy)benzamidine

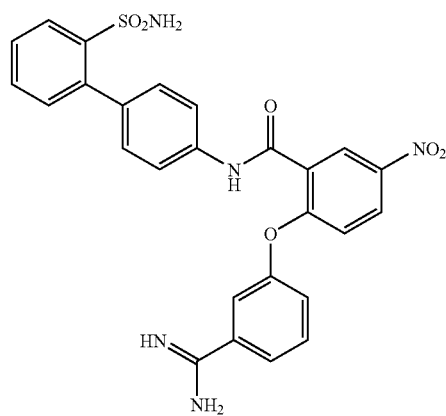

Step 1: A solution of 2-fluoro-5-nitrobenzoic acid (1.85 g, 10 mmol, 1.33 equiv) in thionyl chloride (5 mL) was refluxed for 2 h and evaporated. The residue was redissolved in 20 mL of methylene chloride and to the solution were added 4-[(2-t-butylaminosulfonyl)phenyl]aniline (2.0 g, 1.0 equiv) and 5 mL of pyridine. After stirring at rt overnight, the volatile was evaporated. Flash chromatography on silica gel 1-(4-[(2-t-butylaminosulfonyl)phenyl]phenylaminocarbonyl)-2-fluoro-5-nitrobenzene (2.9 g, 99%). MS found for $C_{23}H_{23}FN_3O_5S$ $(M+H)^+$: 472.

Step 2: To a solution of 1-(4-[(2-t-butylaminosulfonyl)phenyl]phenylaminocarbonyl)-2-fluoro-5-nitrobenzene (1.18 g, 0.25 mmol, 1.0 equiv) and 3-hydroxybenzonitrile (298 mg, 1.0 equiv) in 10 mL of DMF was added $K_2CO_3$ (691 mg, 2 equiv). After stirring at 60° C. for 3 h, the mixture was diluted with EtOAc and washed with $H_2O$. The organic layer was dried over $MgSO_4$, filtered, evaporated and chromatographied to give 3-(2-(4-[(2-t-butylaminosulfonyl)phenyl]phenylaminocarbonyl-4-nitrophenoxy)benzonitrile (950 g, 63%). MS found for $C_{30}H_{27}N_4O_6S$ $(M+H)^+$: 571.

Step 3: A stream of HCl(g) was bubbled through a 0° C. solution of 3-(2-(4-[(2-t-butylaminosulfonyl)phenyl]phenylaminocarbonyl-4-nitrophenoxy)benzonitrile (57 mg, 0.1 mmol) in 5 mL of methanol until saturation. The mixture was stirred at rt overnight and evaporated. The resulting residue was treated with ammonium acetate (39 mg, 5 equiv) in 10 ml methanol at reflux temperature for 2 h. The solvent was removed at reduced pressure and the crude was purified by HPLC (C18 reversed phase) eluting with 0.5% TFA in $H_2O/CH_3CN$ to 3-(2-(4-[(2-aminosulfonyl)phenyl]phenylaminocarbonyl-4-nitrophenoxy)benzamidine (24 mg, 45%). MS found for $C_{26}H_{22}N_5O_6S$ $(M+H)^+$: 532.

Example 603

3-(2-(4-[(2-aminosulfonyl)phenyl]phenylaminocarbonyl-4-aminophenoxy)benzamidine

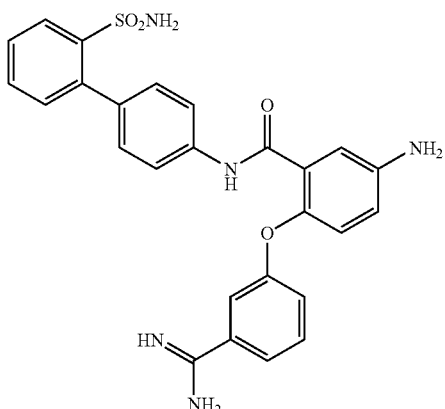

A mixture of 3-(2-(4-[(2-aminosulfonyl)phenyl]phenylaminocarbonyl-4-nitrophenoxy)benzamidine (53 mg, 0.1 mmol, 1 equiv), 5 mL of 1N HCl, 5 mg of Pd/C (10%) in 10 mL of methanol was stirred at rt under 1 atm $H_2$ atomosphere overnight. After filtration through a thin layer of Celite and removal of the volatile, the aqueous residue was purified by HPLC (C18 reversed phase) eluting with 0.5% TFA in $H_2O/CH_3CN$ to 3-(2-(4-[(2-aminosulfonyl)phenyl]phenylaminocarbonyl-4-aminophenoxy)benzamidine (31 mg, 66%). MS found for $C_{26}H_{24}N_5O_4S$ (M+H)$^+$: 502.

Example 604

3-(2-(4-[(2-aminosulfonyl)phenyl]phenylaminocarbonyl-4-chlorophenoxy)benzamidine

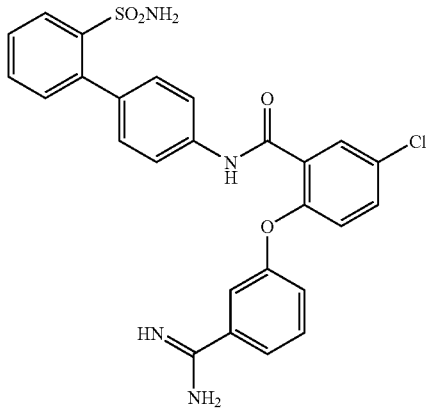

Step 1: A mixture of 3-(2-(4-[(2-t-butylaminosulfonyl)phenyl]phenylaminocarbonyl-4-nitrophenoxy)benzonitrile (570 mg, 1 mmol, 1 equiv) and $SnCl_2.2H_2O$ (677 mg, 3 equiv) in 25 mL of EtOAc was refluxed for 2 h. The reaction was quenched with sat. $NaHCO_3$. The organic layer was separated and dried over $MgSO_4$, filtered and evaporated to give 3-(2-(4-[(2-t-butylaminosulfonyl)phenyl]phenylaminocarbonyl-4-aminophenoxy)benzonitrile (45 mg, 83%). MS found for $C_{30}H_{29}N_4O_4S$ (M+H)$^+$: 541.

Step 2: A mixture of t-BuNO$_2$ (21 mg, 0.1 mmol, 2 equiv), CuCl (20 mg, 2 equiv) in 5 mL of acetonitrile was refluxed for 10 min. To the solution was added 3-(2-(4-[(2-t-butylaminosulfonyl)phenyl]phenylaminocarbonyl-4-aminophenoxy)benzonitrile (54 mg, 0.1 mmol, 1 equiv). The mixture was refluxed for 1 h and evaporated. Flash chromatography with 1:2 EtOAc/hexane to give [(2-t-butylaminosulfonyl)phenyl]phenylaminocarbonyl-4-chlorophenoxy)benzonitrile (43 mg, 77%)MS found for $C_{30}H_{27}ClN_3O_4S$ (M+H)$^+$: 561.

Step 3: A stream of HCl(g) was bubbled through a 0° C. solution of 3-(2-(4-[(2-t-butylaminosulfonyl)phenyl]phenylaminocarbonyl-4-chlorophenoxy)benzonitrile (56 mg, 0.1 mmol) in 5 mL of methanol until saturation. The mixture was stirred at rt overnight and evaporated. The resulting residue was treated with ammonium acetate (40 mg, 5 equiv) in 10 ml methanol at reflux temperature for 2 h. The solvent was removed at reduced pressure and the crude was purified by HPLC (C18 reversed phase) eluting with 0.5% TFA in $H_2O/CH_3CN$ to 3-(2-(4-[(2-aminosulfonyl)phenyl]phenylaminocarbonyl-4-chlorophenoxy)benzamidine (47 mg, 84%). MS found for $C_{20}H_{22}ClN_4O_4S$ (M+H)$^+$: 521.

Example 605

3-(2-(4-[(2-aminosulfonyl)phenyl]phenylaminocarbonyl-4-bromophenoxy)benzamidine

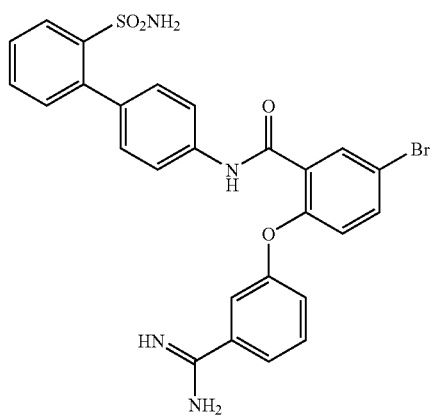

This compound was prepared according to the procedure described in example 19. MS found for $C_{26}H_{22}BrN_4O_4S$ (M+H)$^+$: 565.

Example 606

2-bromo-6-(2-(4-[(2-aminosulfonyl)phenyl]phenyl-carbonylamino)phenoxy naphthalene

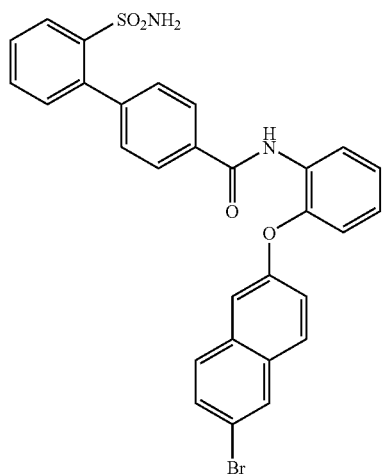

A mixture of 2-bromo-6-(2-aminophenoxy)naphthalene (314 mg, 1 mmol, 1.0 equiv), 4-[(2-t-butylaminosulfonyl)phenyl]benzoyl chloride (349 mg, 1 equiv), pyridine (3 mL) in 10 mL of dichloromethane was stirred at rt overnight, washed with $H_2O$. The organic layer was dried over $MgSO_4$, filtered, evaporated and refluxed in 2 mL of trifluoroacetic acid for 30 min. TFA was then evaporated and HPLC (C18 reversed phase) eluting with 0.5% TFA in $H_2O/CH_3CN$ gave 2-bromo-6-(2-(4-[(2-aminosulfonyl)phenyl]phenylcarbony-lamino)phenoxy naphthalene (378 mg, 66%). MS found for $C_{29}H_{22}BrN_2O_4S$ $(M+H)^+$: 573.

Example 607

3-methoxycarbonyl-2-(4-[(2-aminosulfonyl)phenyl] phenylcarbonylamino)phenoxy naphthalene

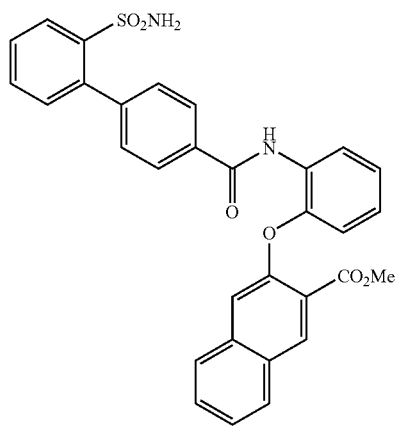

A mixture of 3-methoxycarbonyl-2-(2-aminophenoxy) (294 mg, 1 mmol, 1.0 equiv), 4-[(2-t-butylaminosulfonyl)phenyl]benzoyl chloride (349 mg, 1 equiv), pyridine (3 mL) in 10 mL of dichloromethane was stirred at rt overnight, washed with $H_2O$. The organic layer was dried over $MgSO_4$, filtered, evaporated and refluxed in 2 mL of trifluoroacetic acid for 30 min. TFA was then evaporated and HPLC (C18 reversed phase) eluting with 0.5% TFA in $H_2O/CH_3CN$ gave 3-methoxycarbonyl-2-(4-[(2-aminosulfonyl)phenyl]phenyl-carbonylamino)phenoxy naphthalene (420 mg, 76%). MS found for $C_{31}H_{21}N_2O_6S$ $(M+H)^+$: 553.

Example 608

3-hydroxycarbonyl-2-(4-[(2-aminosulfonyl)phenyl] phenylcarbonylamino)phenoxy naphthalene

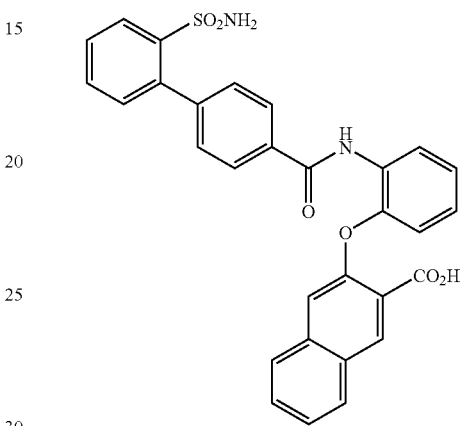

A solution of 3-methoxycarbonyl-2-(4-methylsulfonyl-2-(4-[(2-aminosulfonyl)phenyl]phenylcarbonylamino)phe-noxy)naphthalene (55 mg, 0.1 mmol, 1.0 equiv) in 5 mL of methanol was treated with 1N LiOH (2 mL) at rt for 2 h. Methanol was evaporated, the aqueous residue was subjected to HPLC with 0.5% TFA in $H_2O/CH_3CN$ to give 3-hydroxycarbonyl-2-(4-[(2-aminosulfonyl)phenyl]phenyl-carbonylamino)phenoxy naphthalene (47 mg, 88%). MS found for $C_{30}H_{23}N_2O_6S$ $(M+H)^+$: 539.

Example 609

3-aminocarbonyl-2-(4-[(2-aminosulfonyl)phenyl] phenylcarbonylamino)phenoxy naphthalene

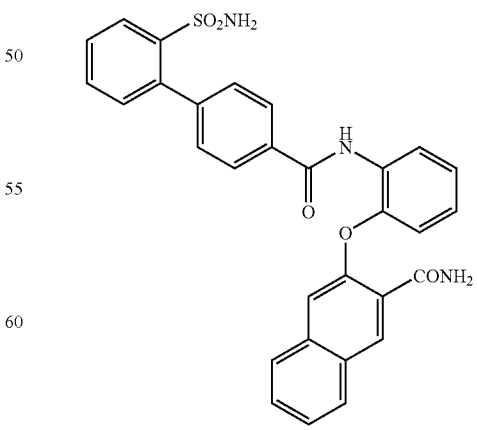

Step 1: A solution of 3-methoxycarbonyl-2-(4-methylsul-fonyl-2-(4-[(2-t-butylaminosulfonyl)phenyl]phenylcarbonylamino)phenoxy)naphthalene (40 mg, 0.066 mmol) in 5 mL of methanol was treated with 1N LiOH (2 mL) at rt for 2 h. Methanol was evaporated, and acidified with 1N HCl until PH~1-2. The product (39 mg, 100%), 3-hydroxycarbonyl-2-(4-methylsulfonyl-2-(4-[(2-t-butylaminosulfonyl)phenyl]phenylcarbonylamino)phenoxy)naphthalene, was extracted with EtOAc, dried over MgSO$_4$, filtered and evaporated. MS found for $C_{34}H_{31}N_2O_6S$ (M+H)$^+$: 595.

Step 2: A solution of 3-hydroxycarbonyl-2-(4-methylsulfonyl-2-(4-[(2-t-butylaminosulfonyl)phenyl]phenylcarbonylamino)phenoxy)naphthalene (39 mg, 0.066 mmol) was refluxed in 3 mL of thionyl chloride for 2 h and evaporated. The residue was then stirred in 5 mL of 2M ammonia in methanol overnight. The volatile was evaporated and the residue was refluxed in 2 mL of trifluoroacetic acid overnight to give the product 3-aminocarbonyl-2-(4-[(2-aminosulfonyl)phenyl]phenylcarbonylamino)phenoxy naphthalene (14 mg, 39%) after HPLC (C18 reversed phase, eluting with 0.5% TFA in H$_2$O/CH$_3$CN). MS found for $C_{30}H_{24}N_3O_5S$ (M+H)$^+$: 538.

Example 610

3-methoxycarbonyl-2-(4-[(2-aminosulfonyl)phenyl]phenylcarbonylamino)phenoxy-6-bromo naphthalene

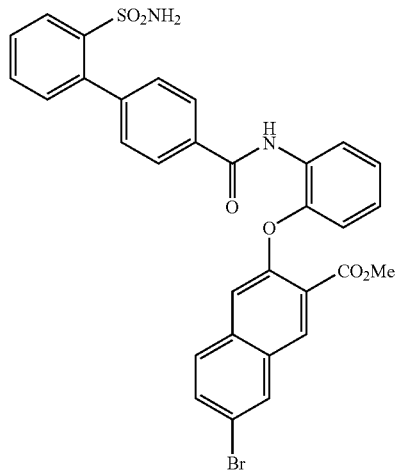

A mixture of 2-(2-aminophenoxy)-3-methoxycarbonyl-6-bromo naphthalene (372 mg, 1 mmol, 1.0 equiv), 4-[(2-t-butylaminosulfonyl)phenyl]benzoyl chloride (349 mg, 1 equiv), pyridine (3 mL) in 10 mL of dichloromethane was stirred at rt overnight, washed with H$_2$O. The organic layer was dried over MgSO$_4$, filtered, evaporated and refluxed in 2 mL of trifluoroacetic acid for 30 min. TFA was then evaporated and HPLC (C18 reversed phase) eluting with 0.5% TFA in H$_2$O/CH$_3$CN gave 3-methoxycarbonyl-2-(4-[(2-aminosulfonyl)phenyl]phenylcarbonylamino)phenoxy-6-bromo naphthalene (423 mg, 67%). MS found for $C_{31}H_{24}BrN_2O_6S$ (M+H)$^+$: 631.

Example 611

3-hydroxycarbonyl-2-(4-[(2-aminosulfonyl)phenyl]phenylcarbonylamino)phenoxy-6-bromo naphthalene

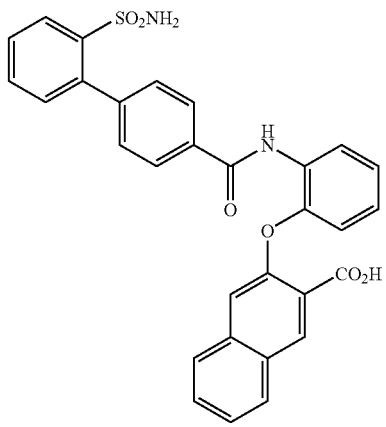

A solution of 3-methoxycarbonyl-2-(4-methylsulfonyl-2-(4-[(2-aminosulfonyl)phenyl]phenylcarbonylamino)phenoxy)-6-bromo naphthalene (63 mg, 0.1 mmol, 1.0 equiv) in 5 mL of methanol was treated with 1N LiOH (2 mL) at rt for 2 h. Methanol was evaporated, the aqueous residue was subjected to HPLC with 0.5% TFA in H$_2$O/CH$_3$CN to give 3-hydroxycarbonyl-2-(4-[(2-aminosulfonyl)phenyl]phenylcarbonylamino)phenoxy-6-bromo naphthalene (47 mg, 78%). MS found for $C_{30}H_{22}BrN_2O_6S$ (M+H)$^+$: 617.

Example 612

3-(2-(4-[(2-aminosulfonyl)phenyl]-2-fluorophenylaminocarbonyl-4-aminophenoxy)benzamidine

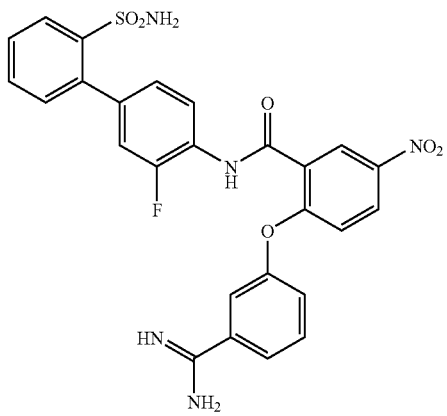

This compound was prepared according to the procedure described in example 17. MS found for MS found for $C_{26}H_{21}FN_5O_6S$ (M+H)$^+$: 550.

Example 613

3-(2-(4-[(2-aminosulfonyl)phenyl]-2-fluorophenylaminocarbonyl-4-aminophenoxy)benzamidine

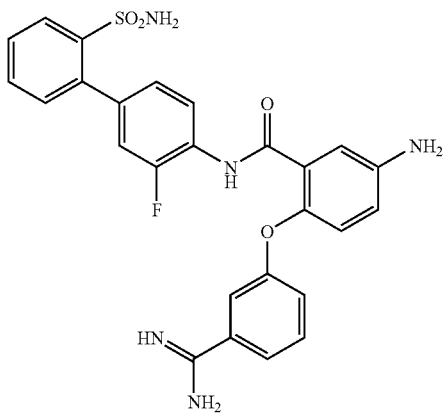

This compound was prepared according to the procedure described in example 18. MS found for $C_{26}H_{23}FN_5O_4S$ (M+H)$^+$: 520.

Example 614

This compound was obtained as a side product in the preparation of example 18. MS (M+H)$^+$: 530.

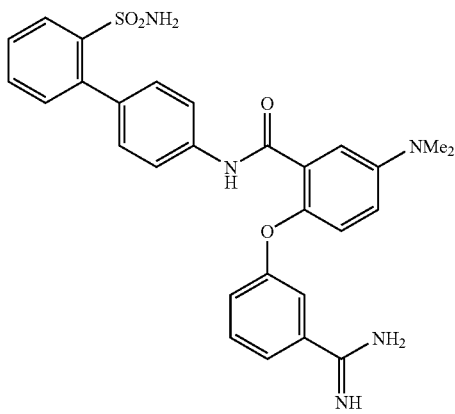

Example 615

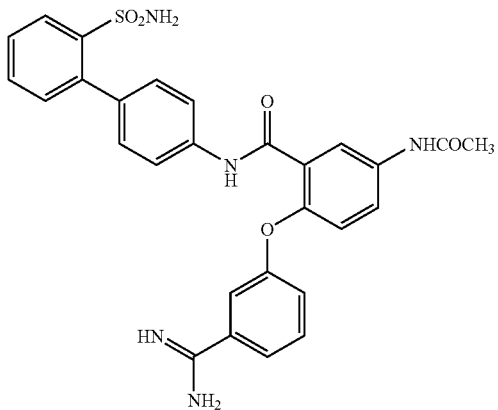

Step 1: A mixure of 3-(2-(4-[(2-t-butylaminosulfonyl)phenyl]phenylaminocarbonyl-4-nitrophenoxy)benzonitrile (1 equiv) and SnCl$_2 \cdot$2H$_2$O (3 equiv) in 15 mL of EtOAc was refluxed for 2 h. The mixture was diluted with EtOAc and washed with saturated aqueous NaHCO3. The organic layer was dried over Na2SO4, filtered and evaporated.

Step 2: The product obtained in step 1 (1 equiv) in 2 mL of pyridine was treated with AcCl (1 equiv) over night. The mixture was diluted with methylene chloride and washed with water. The organic layer was dried over Na$_2$SO$_4$, filtered and evaporated.

Step 3: A stream of HCl(g) was bubbled through a 0° C. solution of the product obtained in step 2 (1 equiv) in 5 mL of methanol until saturation. The mixture was stirred at rt overnight and evaporated. The resulting residue was treated with ammonium (5 equiv) in 10 mL of methanol at reflux temperature for 2 h. The solvent was removed at reduced pressure and the crude was purified by HPLC (C18 reversed phase) eluting with 0.5% TFA in H$_2$O/CH$_3$CN to the title product. MS (M+H)$^+$: 544.

Example 616

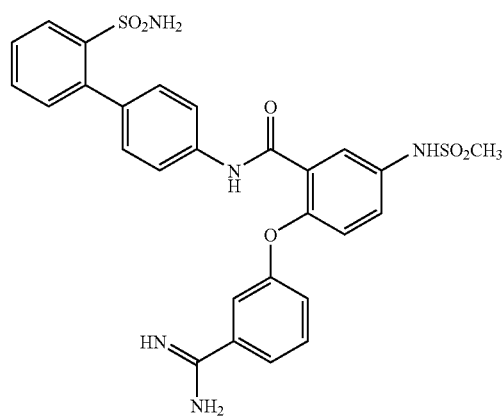

This compound was similarly made as example 30. MS (M+H)$^+$: 580.

Examples 617-624

The following compounds were made according to the methods previously described.

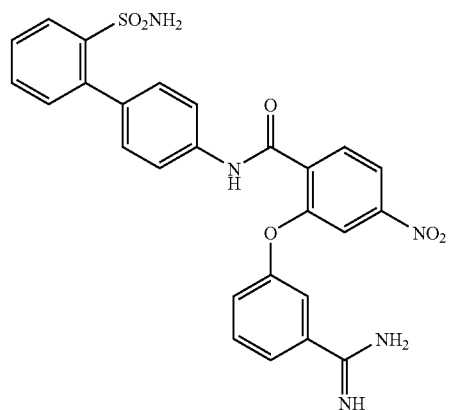

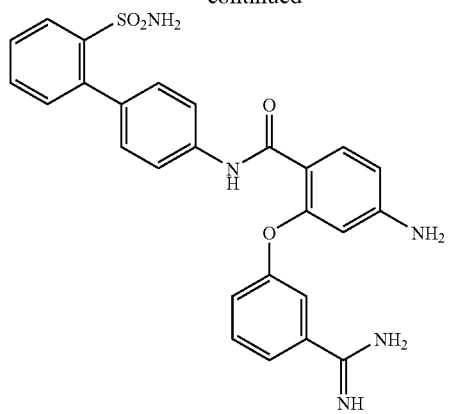
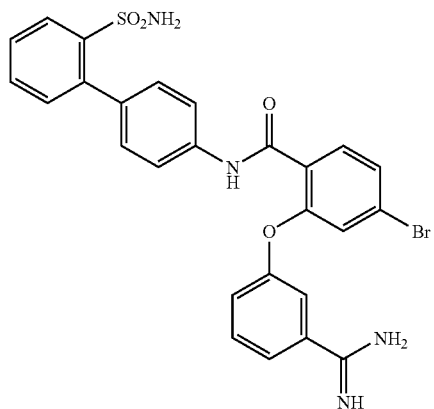
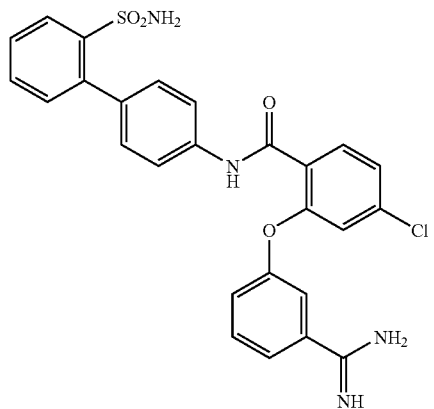
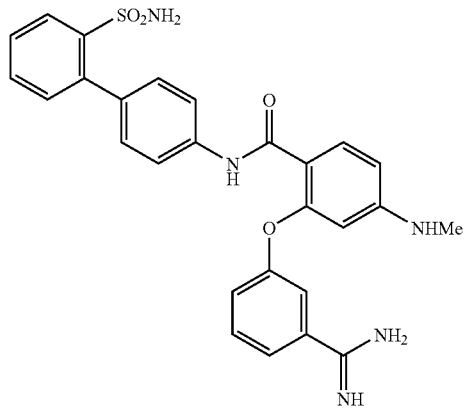
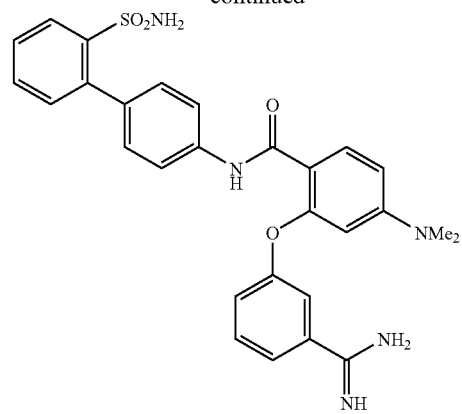
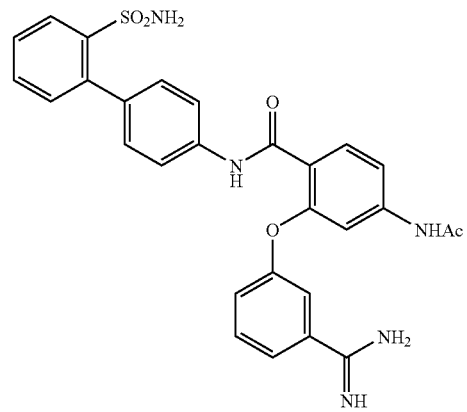
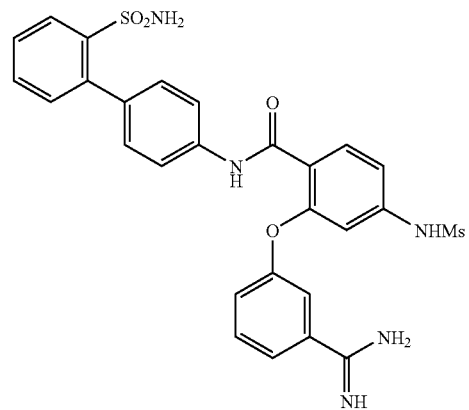
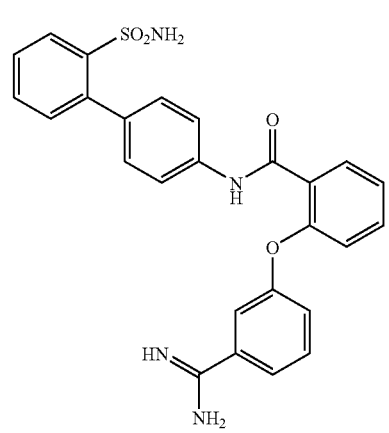
Example 625

A mixture of compound 20 (1 equiv), 5 mL of 1N HCl, 5 mg of Pd/C (10%) in 10 mL of methanol was stirred at rt under 1 atm H$_2$ atomosphere overnight. After filtration through a thin layer of Celite and removal of the volatile, the aqueous residue was purified by HPLC (C18 reversed phase) eluting with 0.5% TFA in H$_2$O/CH$_3$CN to give the title compound. MS (M+H)$^+$: 487.

Examples 626-631

The following compounds were prepared according to the procedure described in the formation of amidines except that NH$_2$OH was used instead of NH$_4$OAc.

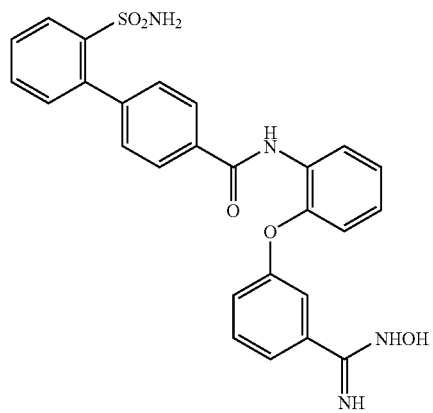

MS (M+H): 502

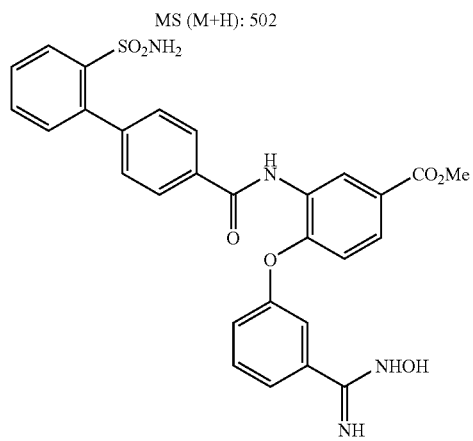

MS (M+H): 560

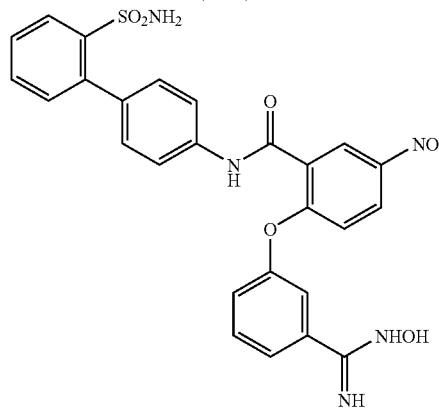

MS (M+H): 547

-continued

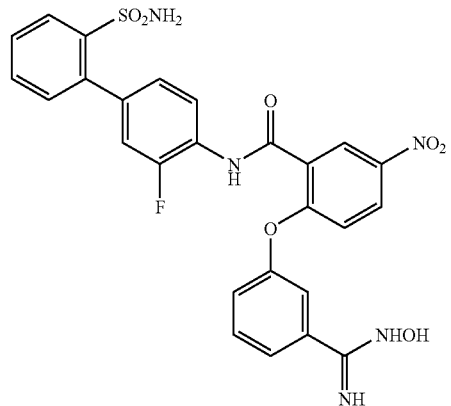

MS (M+H): 547

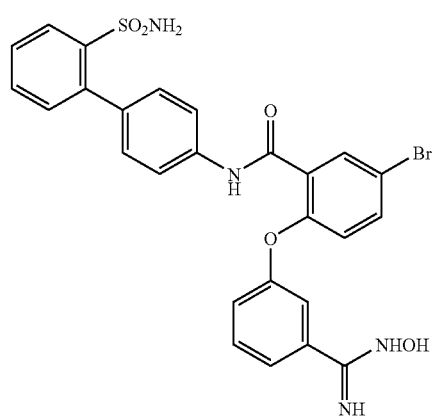

MS (M+H): 581

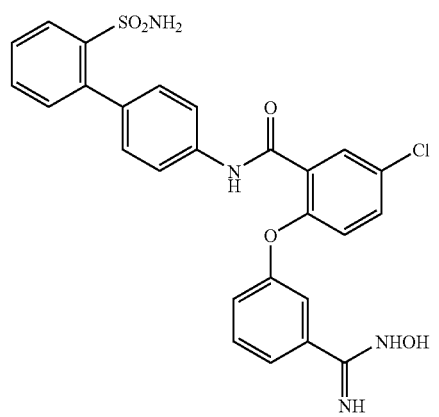

MS (M+H): 537

Example 632

3-(2-(4-[(2-aminosulfonyl)phenyl]benzoylamino)phenoxy)benzylamine

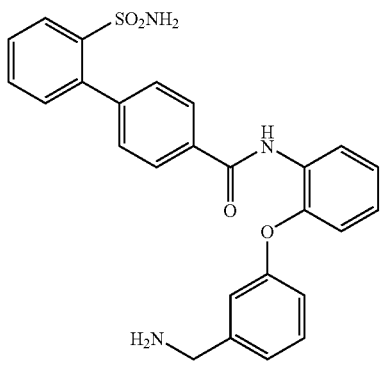

A mixure of 3-(2-(4-[(2-t-butylaminosulfonyl)phenyl]benzoylamino)phenoxy)benzonitrile (25 mg), 5 mL of 1N HCl, 5 mg of Pd/C (10%) in 10 mL of methanol was stirred at rt under 1 atm $H_2$ atmosphere overnight. After filtration through a thin layer of Celite and removal of the volatile, the aqueous residue was dried on vacuum pump and then refluxed with 1 mL of TFA for 2 h, evaporated and purified by HPLC (C18 reversed phase) eluting with 0.5% TFA in $H_2O/CH_3CN$ to give the title compound. MS (M+H)$^+$: 500.

Example 633

3-[(3-{[4-(2-sulfamoylphenyl)phenyl]carbonylamino}-2-thienyl)carbonylamino]benzenecarboxamidine

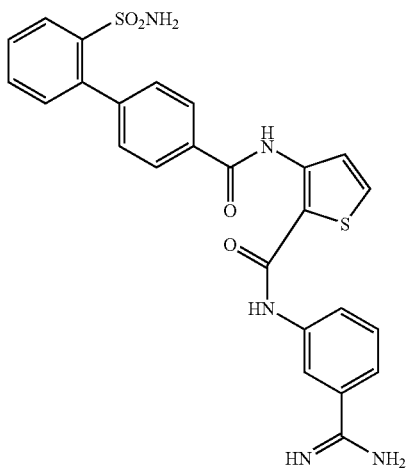

Step 1: A mixture of 3-amino-2-((3-cyanophenyl)aminocarbonyl)thiophene (1 equiv), 4-[(2-t-butylaminosulfonyl)phenyl]benzoyl chloride (1 equiv), pyridine (5 equiv) in 15 mL of dichloromethane was stirred at rt overnight. The mixture was diluted with methylene chloride, washed with $H_2O$. The organic layer was dried over $MgSO_4$, filtered and evaporated.

Step 2: A stream of HCl(g) was bubbled through a 0° C. solution of the compound obtained in step 1 in 5 mL of methanol until saturation. The mixture was stirred at rt overnight and evaporated. The resulting residue was treated with ammonium acetate (5 equiv) in 10 mL of methanol at reflux temperature for 2 h. The solvent was evaporated and the crude benzamidine was purified by HPLC (C18 reversed phase) eluting with 0.5% TFA in $H_2O/CH_3CN$ to give the title compound. ES-MS 520 (M+1).

Example 634

3-[(3-{[4-(2-sulfamoylphenyl)phenyl]carbonylamino}-2-thienyl)carbonylamino]benzenecarboxamidine

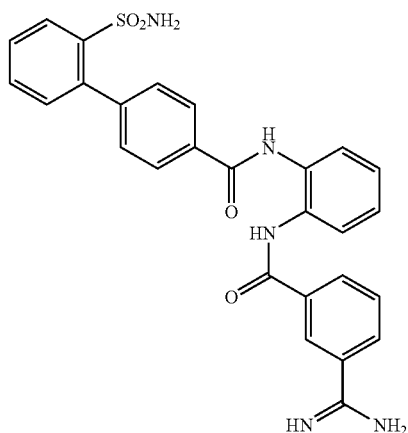

Step 1: A mixture of 2-nitroaniline, 3-cyanobenzoyl chloride (1 equiv), pyridine (5 equiv) in 15 mL of dichloromethane was stirred at rt overnight. The mixture was diluted with methylene chloride, washed with $H_2O$. The organic layer was dried over $MgSO_4$, filtered and evaporated.

Step 2: A mixture of the compound obtained in step 1 (1 equiv) and $SnCl_2 \cdot 2H_2O$ (3 equiv) in 15 mL of EtOAc was refluxed for 2 h. The mixture was diluted with EtOAc and washed with saturated aqueous $NaHCO_3$. The organic layer was dried over $Na_2SO_4$, filtered and evaporated.

Step 3: A mixture of the compound obtained in step 2 (1 equiv), 4-[(2-t-butylaminosulfonyl)phenyl]benzoyl chloride (1 equiv), pyridine (5 equiv) in 15 mL of dichloromethane was stirred at rt overnight. The mixture was diluted with methylene chloride, washed with $H_2O$. The organic layer was dried over $MgSO_4$, filtered and evaporated.

Step 4: A stream of HCl(g) was bubbled through a 0° C. solution of the compound obtained in step 1 in 5 mL of methanol until saturation. The mixture was stirred at rt overnight and evaporated. The resulting residue was treated with ammonium acetate (5 equiv) in 10 mL of methanol at reflux temperature for 2 h. The solvent was evaporated and the crude benzamidine was purified by HPLC (C18 reversed phase) eluting with 0.5% TFA in $H_2O/CH_3CN$ to give the title compound. ES-MS 494 (M+1).

Example 635-640
The following compounds were prepared according to the procedure previously described.
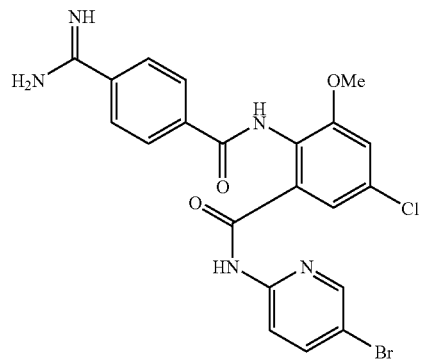
Example 635
MS (M+H): 502
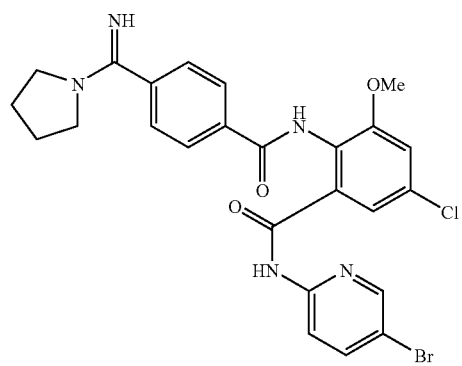
Example 636
MS (M+H): 556
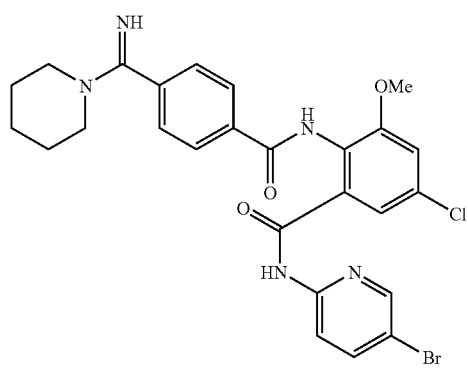
Example 637
MS (M+H): 570
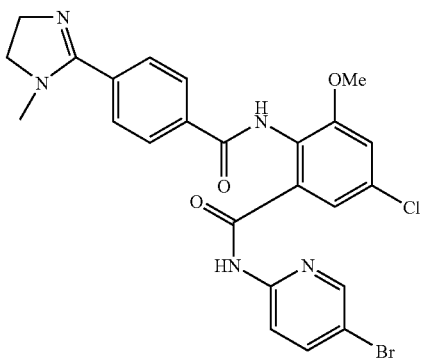
Example 638
MS (M+H): 542
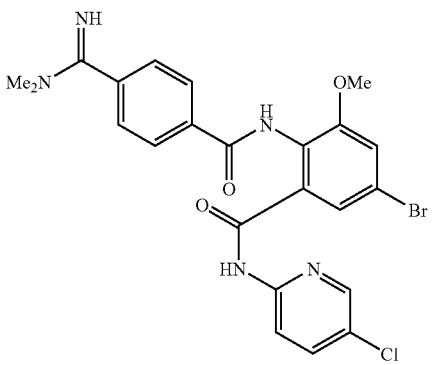
Example 639
MS (M+H): 530
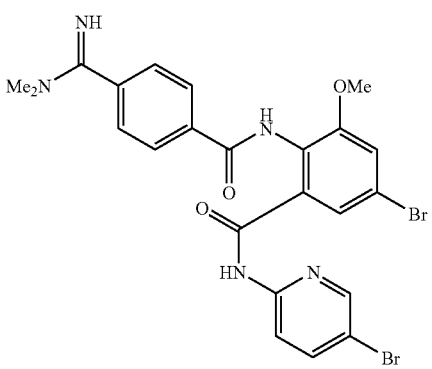
Example 640
MS (M+H): 574

-continued

Example 641

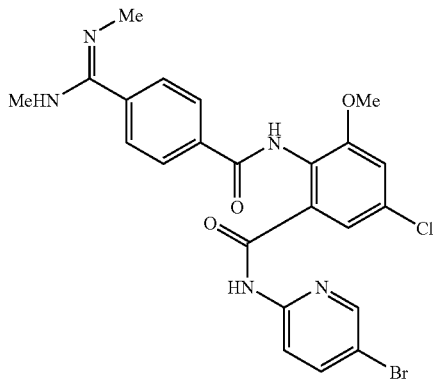

This compound was obtained as a side product in the preparation of Example 322, described earlier, above. ES-MS 530 (M+H).

The above description and illustrative examples show numerous compounds within the formula A-Q-D-E-G-J-X which are potent factor Xa inhibitors. The description and illustrative examples also show the variety of combinations and substituents for each group A, Q, D, E, G, J and X which may be prepared according to the invention and be useful as factor Xa inhibitors. While, for example, compounds having the same A-Q structure but a variety of substituents or D-E-G and/or J-X structures and their substituents are described and shown, the description and illustrative examples are intended to show that compounds of the invention having a different A-Q structure can also have various combinations of D-E-G- and/or J-X structures, even though such compounds may not be illustrated in the examples. In other words, each group within the A-Q-D-E-G-J-X, as each is defined above with their substituents, may be varied and combined to form sub-genuses and compounds of the invention. The description and illustrative examples show such combinations and are not intended to limit the sub-genuses or compounds within the A-Q-D-E-G-J-X genus of the invention.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

What is claimed is:

1. A compound having the following structure:

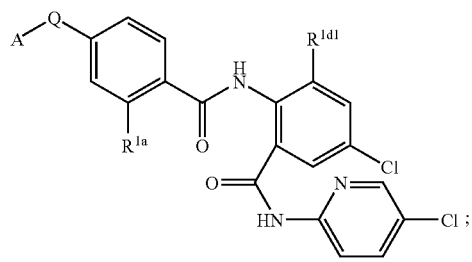

-continued

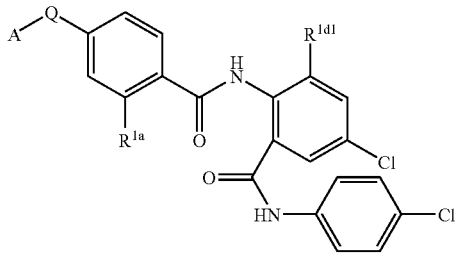

wherein:
$R^{1a}$ is H or F;
$R^{1d1}$ is H or —OMe;
A-Q is a member selected from the group consisting of:

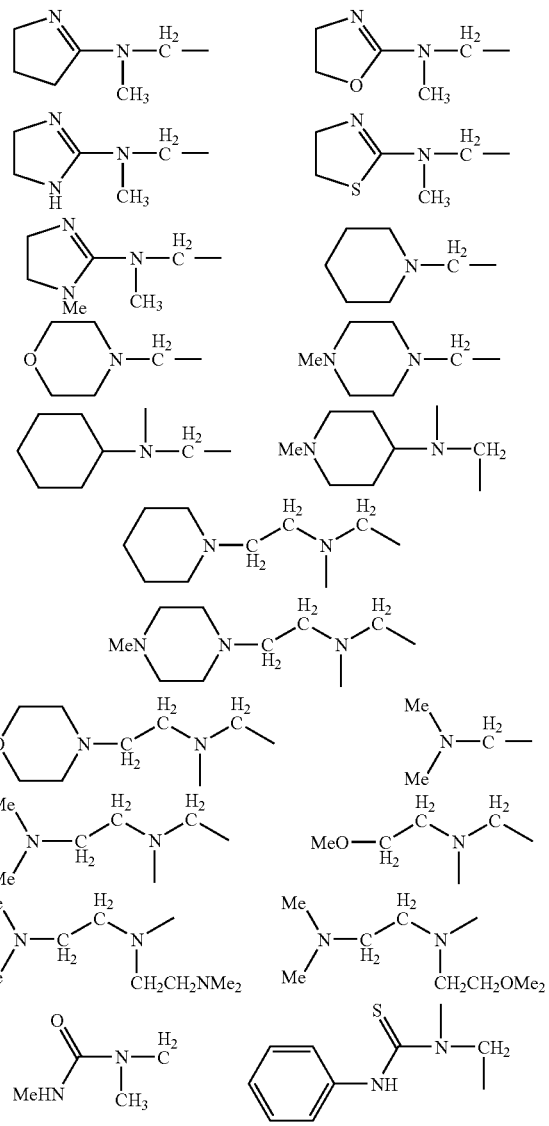

or a pharmaceutically acceptable isomers, salts, hydrates, solvates and prodrug derivatives thereof.

2. A compound of claim 1, wherein $R^{1a}$ is H.
3. A compound of claim 1, wherein $R^{1a}$ is F.

4. A compound of claim 1, wherein $R^{1d1}$ is H.

5. A compound of claim 1, wherein $R^{1d1}$ is —OMe.

6. A compound of claim 1 selected from the group consisting of:

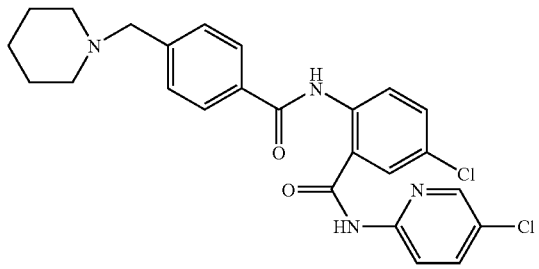

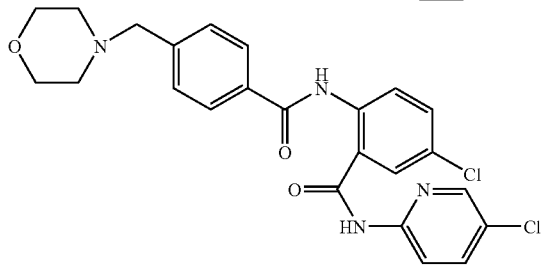

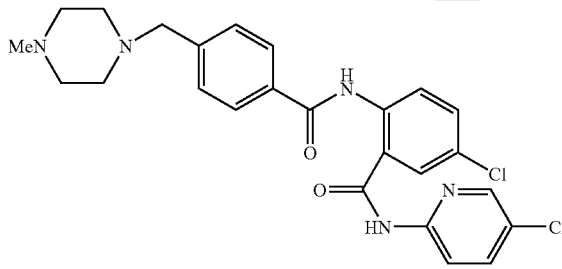

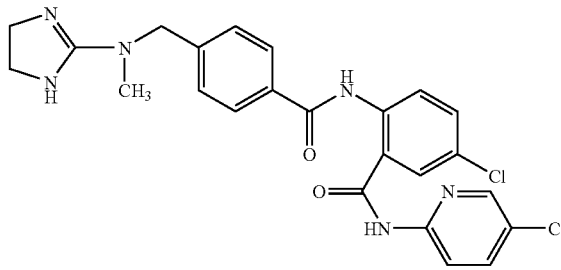

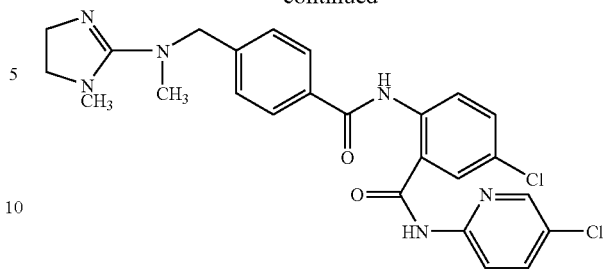

or a pharmaceutically acceptable isomers, salts, hydrates, solvates and prodrug derivatives thereof.

7. A pharmaceutical composition for preventing or treating a condition in a mammal characterized by undesired thrombosis comprising a pharmaceutically acceptable carrier and a pharmaceutically effective amount of a compound of claim 1.

8. A method for preventing or treating a condition in a mammal characterized by undesired thrombosis comprising administering to said mammal a therapeutically effective amount of a compound of claim 1.

9. The method of claim 8, wherein the condition is selected from the group consisting of:
acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation, and thrombotic complications associated with the fitting of prosthetic devices.

10. A method for inhibiting the coagulation of a biological sample, comprising the step of administering a compound of claim 1.

* * * * *